(12) United States Patent
Wang et al.

(10) Patent No.: US 11,001,586 B2
(45) Date of Patent: May 11, 2021

(54) ALKYL PYRROLOPYRIMIDINE ANALOGS AND METHODS OF MAKING AND USING SAME

(71) Applicant: The University of North Carolina at Chapel Hill, Chapel Hill, NC (US)

(72) Inventors: Xiaodong Wang, Chapel Hill, NC (US); Hongchao Zheng, Bethesda, MD (US); Jichen Zhao, Shanghai (CN); Weihe Zhang, Vestavia, AL (US); Stephen V. Frye, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 16/461,300

(22) PCT Filed: Nov. 17, 2017

(86) PCT No.: PCT/US2017/062329
§ 371 (c)(1),
(2) Date: May 15, 2019

(87) PCT Pub. No.: WO2018/094227
PCT Pub. Date: May 24, 2018

(65) Prior Publication Data
US 2020/0062764 A1    Feb. 27, 2020

Related U.S. Application Data

(60) Provisional application No. 62/423,731, filed on Nov. 17, 2016.

(51) Int. Cl.
*C07D 487/04* (2006.01)
*C07D 519/00* (2006.01)
*A61K 31/519* (2006.01)

(52) U.S. Cl.
CPC .......... *C07D 487/04* (2013.01); *A61K 31/519* (2013.01); *C07D 519/00* (2013.01)

(58) Field of Classification Search
CPC ............................ C07D 487/04; A61K 31/519
See application file for complete search history.

(56) References Cited

U.S. PATENT DOCUMENTS

| 8,415,355 B2 | 4/2013 | Brain et al. |
| 8,415,361 B2 | 4/2013 | Lemke et al. |
| 2015/0210702 A1 | 7/2015 | Xu et al. |

FOREIGN PATENT DOCUMENTS

| CN | 2017800831647 | 11/2017 |
| CN | 110177553 A | 8/2019 |
| EP | 17872731.9 | 11/2017 |
| EP | 3541391 | 9/2019 |
| JP | 2019-526553 | 11/2017 |
| JP | 2020-502062 | 1/2020 |
| WO | WO 2011/146313 | 11/2011 |
| WO | WO 2013/052417 | 4/2013 |
| WO | WO 2013/124324 | 8/2013 |
| WO | WO 2014/062774 | 4/2014 |
| WO | WO 2015/157123 | * 10/2015 |
| WO | WO 2015/157123 A1 | 10/2015 |
| WO | PCT/US2017/062329 | 11/2017 |
| WO | WO 2018/094227 | 5/2018 |

OTHER PUBLICATIONS

Lee-Sherick et al., Efficacy of a Mer and Flt3 tyrosine kinase small molecule inhibitor, UNC1666, in acute myeloid leukemia, Oncotarget, vol. 6, No. 9, pp. 6722-6736 (2015).*
Pearce et al., Failure modes in anticancer drug discovery and development, Cancer Drug Design and Discovery Edited by Stephen Neidle, Chapter 18, pp. 424-435 (2008).*
Johnson et al., Relationships between drug activity in NCI preclinical in vitro and in vivo models and early clinical trials, British Journal of Cancer (2001) 64(10): 1424-1431.*
Gura, Systems for identifying New Drugs Are Often Faulty, Cancer Models, Science, vol. 278, No. 5340, pp. 1041-1042, Nov. 1997.*
Acute Leukemia, Merck Manual (Online Edition) 6 pages, pp. 1-6 (2013).*
Simone, Oncology: Introduction, Cecil Textbook of Medicine, 20th Edition, vol. 1, pp. 1004-1010, 1996.*
Douglas, Jr., Introduction to Viral Diseases, Cecil Textbook of Medicine, 20th Edition, vol. 2, pp. 1739-1747, 1996.*
Bosseray et al., PubMed Abstract (Pathol Biol (Paris) 50(8):483-92), 2002.*
Goff, PubMed Abstract (J Gene Med. 3(6):517-28), 2001.*
Razonable et al., PubMed Abstract (Herpes 10(3):60-5), 2003.*
Angelillo-Scherrer et al. (2005) "Role of Gas6 Receptors in Platelet Signaling During Thrombus Stabilization and Implications for Antithrombotic Therapy" *J. Clin. Invest.* 115(2): 237-246.
Bernsmeier et al. (2015) "Patients With Acute-On-Chronic Liver Failure Have Increased Numbers of Regulatory Immune Cells Expressing the Receptor Tyrosine Kinase MERTK" *Gastroenterology* 148(3): 603-615.
Bhattacharayya et al. (2013) "Enveloped Viruses Disable Innate Immune Responses in Dendritic Cells by Direct Activation of TAM Receptors" *Cell Host & Microbe* 14: 136-147.
Brindley, et al. (2011) "Tyrosine Kinase Receptor Axl Enhances Entry of Zaire Ebolavirus Without Direct Interactions With the Viral Glycoprotein" *Virology* 415: 83-84.
Chen, et al. (1997) "Identification of Gas6 as a Ligand for Mer, a Neural Cell Adhesion Molecule Related Receptor Tyrosine Kinase Implicated in Cellular Transformation" Oncogene 14: 2033-2039.

(Continued)

*Primary Examiner* — Deepak R Rao
(74) *Attorney, Agent, or Firm* — Ballard Spahr LLP

(57) ABSTRACT

The present disclosure is concerned with benzo annulene compounds that are capable of inhibiting a Mer tyrosine kinase and/or a Tyro3 tyrosine kinase and methods of treating a bacterial infection, a viral infection, and/or a disorder of uncontrolled cellular proliferation such as, for example, a cancer, using these compounds. This abstract is intended as a scanning tool for purposes of searching in the particular art and is not intended to be limiting of the present invention.

20 Claims, No Drawings

(56) References Cited

OTHER PUBLICATIONS

Chen et al. (2004) "Mer Receptor Tyrosine Kinase Signaling Participates in Platelet Function" *Arterioscler. Thrombosis Vasc. Biol.* 24(6): 1118-1123.

Christoph, et al. (2013) "UNC569, a Novel Small-Molecule Mer Inhibitor With Efficacy Against Acute Lymphoblastic Leukemia in Vitro and in Vivo" *Mol. Cancer Ther.* 12(11): 2367-77.

Cook, et al. (2013) "MerTK Inhibition in Tumor Leukocytes Decreases Tumor Growth and Metastasis" *J. Clin. Invest.* 123: 3231-3242.

Frye, S. "Academic Drug Discovery and Chemical Biology: A Tale of Two Targets," Presentation at Northwestern's 18th Annual Drug Discovery Symposium, Nov. 2013. Posted by Center for Molecular Innovation and Drug Discovery on Dec. 3, 2013. Accessed Jul. 10, 2020 via https://youtu.be/uKznSYBg1Zk.

Lee-Sherick, et al. (2015) "Efficacy of a Mer and Flt3 Tyrosine Kinase Small Molecule Inhibitor, UNC1666, in Acute Myeloid Leukemia" *Octotarget.* 6(9): 6722-36.

Linger, et al. (2013) "Mer Receptor Tyrosine Kinase Is a Therapeutic Target in pre-B-cell Acute Lymphoblastic Leukemia" *Blood* 122: 1599-1609.

Liu, et al. (2012) "Discovery of Novel Small Molecule Mer Kinase Inhibitors for the Treatment of Pediatric Acute Lymphoblastic Leukemia" *ACS Med Chem. Lett* 3(2): 129-134.

Liu, et al. (2013) "UNC1062, a New and Potent Mer Inhibitor" *Eur. J. Med. Chem.* 65: 83-93.

Mercer and Helenius (2008) "Vaccinia Virus Uses Macropinocytosis and Apoptotic Mimicry to Enter Host Cells" *Science* 320: 531-535.

Meertens et al. (2012) "The TIM and TAM Families of Phosphatidylserine Receptors Mediate Dengue Virus Entry" *Cell Host Microbe* 12: 544-557.

Morizono, et al. (2011) "The Soluble Serum Protein Gas6 Bridges Virion Envelope Phosphatidylserine to the TAM Receptor Tyrosine Kinase Axl to Mediate Viral Entry" *Cell Host & Microbe* 9: 286-298.

Morzono and Chen (2014) "Role of Phosphatidylserine Receptors in Enveloped Virus Infection" *J. Virology* 88(8): 4275-4290.

Nomura et al. (2017) "Activated Microglia Desialylate and Phagocytose Cells via Neuraminidase, Galectin-3, and Mer Tyrosine Kinase" *Journal of Immunology*, 198: 4792-4801.

Paolino, et al. (2014) "The E3 Ligase Cbl-b and TAM Receptors Regulate Cancer Metastasis via Natural Killer Cells" *Nature* 507: 508-512.

Petta et al (2016) "MERTK rs4374383 Polymorphism Affects the Severity of Fibrosis in Non-Alcoholic Fatty Liver Disease" *Journal of Hepatology* 64: 682-690.

Schlegal, et al. (2013) "MERTK Receptor Tyrosine Kinase Is a Therapeutic Target in Melanoma" *J. Clin. Invest.* 123(5): 2257-67.

Shimojima, et al. (2006) "Tyro3 Family-Mediated Cell Entry of Ebola and Marburg Viruses" *ournal of Virology*, 10109-10116.

Zhang, et al. (2013) "Pseudo-cyclization Through Intramolecular Hydrogen Bond Enables Discovery of Pyridine Substituted Pyrimidines as New Mer Kinase Inhibitors" *J. Med. Chem.* 56: 9683-9698.

International Search Report and Written Opinion were dated May 24, 2018 by the International Searching Authority for International Application No. PCT/US2017/062329, filed on Nov. 17, 2017 and published as WO 2018/094227 on May 24, 2018 (Applicant—The University of North Carolina at Chapel Hill) (15 Pages).

International Preliminary Report on Patentability dated May 21, 2019 by the International Searching Authority for International Application No. PCT/US2017/062329, filed on Nov. 17, 2017 and published as WO 2018/094227 on May 24, 2018 (Applicant—The University of North Carolina at Chapel Hill) (7 Pages).

U.S. Appl. No. 62/423,731, filed Nov. 17, 2016, Xiaodong Wang, et al. (The University of North Carolina at Chapel Hill).

\* cited by examiner

ALKYL PYRROLOPYRIMIDINE ANALOGS AND METHODS OF MAKING AND USING SAME

CROSS-REFERENCE TO RELATED APPLICATIONS

This Application is a national stage filing under 35 U.S.C. 371 of International Application No. PCT/US2017/062329, filed on Nov. 17, 2017, which claims the benefit of U.S. Provisional Application No. 62/423,731, filed on Nov. 17, 2016, the contents of which are incorporated herein by reference in their entireties.

BACKGROUND

MerTK is a member of a receptor tyrosine kinase (RTK) family known as TAM, which also includes AXL and TYRO3. Each member of the TAM family contains an extracellular domain, a transmembrane domain, and a conserved intracellular kinase domain. The TAM family members undergo ligand-induced homodimerization, followed by catalytic tyrosine kinase activation and intracellular signaling. Cross-phosphorylation has also been demonstrated within this RTK family, suggesting heterodimerization can occur also. These RTKs are widely expressed in many epithelial tissues and in cells of the immune, nervous, and reproductive systems. MerTK was given its name by the Earp laboratory because it was found to be expressed in monocytes and in tissues of epithelial and reproductive tissue.

As described in more detail below, ligand-bound MerTK can complex with phosphatidyl serine and it binds apoptotic cells which triggers ingestion and suppresses inflammatory cytokines. It is aberrantly expressed in certain cancers (e.g., acute leukemia (ALL and AML)) and some solid tumors (e.g., breast cancer, colon cancer, non-small cell lung carcinoma, glioblastoma, and others).

The MerTK ligands include growth arrest-specific 6 protein (GAS6; Chen, et al; Oncogene (1997) 14, 2033-2039), protein-S, tubby and tubby-like protein-1 (TULP), and galectin-3. Several of these ligands are present in serum and expressed locally in a number of tissues. These ligands bind to the extracellular domain of MerTK, resulting in tyrosine kinase activation.

Since the discovery of MerTK in 1994, there has been a growing body of literature that suggest the possibility of MerTK as a druggable target for a number of indications (see, e.g., WO 2013/052417; Frye, S. "Academic Drug Discovery and Chemical Biology," Presentation at Northwestern's 18$^{th}$ Annual Drug Discovery Symposium, November 2013; WO 2011/146313/WO 2014/062774; Liu et al. (2012) *ACS Med Chem. Lett.* 3(2): 129-134; Schlegel et al. (2013) *J. Clin. Invest.* 123(5): 2257-67; Zhang et al. (2013) *J. Med. Chem.* 56: 9683-9692; Liu et al. (2013) *Eur. J. Med. Chem.* 65: 83-93; Christoph et al. (2013) *Mol. Cancer Ther.* 12(11): 2367-77; Linger et al. (2013) *Blood* 122: 1599-1609; Lee-Sherick et al. (2015) *Ocotarget*, Advanced Publications 2015). For example, MerTK is ectopically expressed or overexpressed in a number of hematologic and epithelial malignant cells. Expression of MerTK and GAS6 correlates with poor prognosis and/or chemoresistance in these tumor types.

In 2013 it was determined that MerTK−/− knock-out mice are less susceptible to tumor growth than normal mice (Cook et al. (2013) *J Clin. Invest.* 123: 3231-3242). MerTK is normally expressed in myeloid lineage cells where it acts to suppress pro-inflammatory cytokines following ingestion of apoptotic material. It was found that MerTK−/− leukocytes exhibit lower tumor cell-induced expression of wound healing cytokines (IL-10 and GAS6) and enhanced expression of acute inflammatory cytokines (IL-12 and IL-6). Further, intratumoral CD8+ lymphocytes are increased. The loss of MerTK in the tumor microenvironment in Mer−/− mice slowed the establishment, growth, and metastasis of mammary tumors and melanomas in immune competent, syngeneic mice.

Paolino et al, have reported on the treatment of wild-type NK cells with a newly developed small molecule TAM kinase inhibitor, LDC 1267, that conferred therapeutic potential and efficiently enhanced anti-metastatic NK cell activity in vivo (Paolino et al. (2014) *Nature* 507: 508-512). Oral or intraperitoneal administration using this TAM inhibitor markedly reduced murine mammary cancer and melanoma metastases dependent on NK cells.

TAM receptor tyrosine kinases have been investigated for their involvement in certain infectious diseases. For example, Shimojima et al, reported the involvement of members of the Tyro3 receptor tyrosine kinase family, Ax1, Dkt and MerTK, in the cell entry of filoviruses Ebola virus and Marburg virus, and concluded that each Tyro3 family member is likely a cell entry factor in the infection (Shimokima et al. (2006) *Journal of Virology* p. 10109-10116). Additional diseases for which TAM receptor tyrosine kinases have been studied include, but are not limited to, microbial infections (U.S. Pat. No. 8,415,361), Zaire ebolavirus (Brindley et al. (2011) *Virology* 415: 83-84), vaccinia virus (Morizono et al. (2011) *Cell Host & Microbe* 9: 286-298: Morizono and Chen (2014) *J. Virology* 88(8): 4275-4290; Mercer and Helenius (2008) *Science* 320: 531-535), dengue virus (WO 2013/124324; Bhattacharayya et al. (2013) *Cell Host & Microbe* 14: 136-147; Meertens et al. (2012) *Cell Host Microbe* 12: 544-557). Yellow Fever (WO 2013/124324), West Nile (WO 2013/124324), ebola (Bhattacharayta et al. (2013) *Cell Host & Microbe* 14: 136-147), and HTV (Bhattacharayya et al. (2013) *Cell Host & Microbe* 14: 136-147).

Further, Bernsmeier et al, found that the number of monocytes and macrophages that expressed MerTK was greatly increased in circulation, livers, and lymph nodes of patients with acute-on-chronic liver failure (ACLF) (Bernsmeier et al. (2015) *Gastroenterology* 1-13). Petta et al, found MerTK rs4374383 polymorphism affected the severity of fibrosis in non-alcoholic fatty liver disease (Petta et al (2016) *Journal of Hepatology* 64, 682-690). Nomura et al, found that active microglia releases galectin-3 and a neuraminidase which desialylated microglial and neuron-like PC12 cell surfaces and enable galectin-3 binding to PC 12 cells and their phagocytosis via MerTK, thus protect the brain from excessive inflammation. (Nomura et al. (2017) *Journal of Immunology,* 198, 4792-4801). Addition of a substituted pyrazolopyrimidine, Mer TK inhibitor (see WO 2011/146313, page 25) restored production of inflammatory cytokines.

TAM (Tyro3-Ax1-Mer) receptor tyrosine kinases have also been investigated for their involvement in platelet aggregation. In 2004, Chen et al, observed that MerTK, presumably through activation by its ligand Gas6, participates in the regulation of platelet function in vitro and platelet-dependent thrombosis in vivo (Chen et al. (2004) *Arterioscler. Thrombosis Vase. Biol.* 1118-1123). Chen reported that PtdSer on aggregating platelets activates MerTK, helping to stabilize clot formation. MerTK knockout mice have decreased platelet aggregation while maintaining normal bleeding times and coagulation parameters. Consequently, these mice appear to be protected from thrombosis without concomitant increased spontaneous bleeding. See also, Angelillo-Scherrer et al. (2005) *J Clin. Invest.* 115(2): 237-246).

Despite the involvement of MerTK and Tyro3TK in a variety of disorders and diseases including, but not limited to, cancer, infectious diseases, fibrosis, and thrombosis, potent compounds that selectively target MerTK and/or Tyro3TK have remained elusive. Thus, there remains a need for compounds and compositions capable of targeting these proteins and methods of making and using same.

SUMMARY

In accordance with the purpose(s) of the invention, as embodied and broadly described herein, the invention, in one aspect, relates to alkyl pyrrolopyrimidine compounds useful in the treatment of a variety of disorders and diseases including, but not limited to, disorders of uncontrolled cellular proliferation such as, for example, cancer, infectious diseases, and thrombotic disorders.

The present disclosure relates to compounds having a structure represented by a formula:

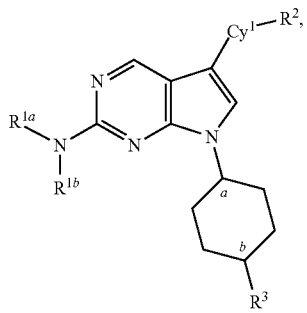

wherein $Cy^1$ is selected from C3-C8 cycloalkyl and C2-C7 heterocycloalkyl, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein $R^{1a}$ is selected from hydrogen, C1-C8 alkyl, and $Cy^2$, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein $Cy^2$, when present, is selected from C3-C9 cycloalkyl, C2-C7 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein $R^{1b}$ is selected from C1-C8 alkyl, $Cy^2$, and (C1-C4 alkyl)$Cy^2$, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein $R^2$ is selected from hydrogen, C1-C4 alkyl, —C(O)$R^{20}$, —C(O)N($R^{22}$)$R^{20}$, —N($R^{22}$)C(O)$R^{20}$, —SO$_2$N($R^{22}$)$R^{21}$, —N($R^{22}$)SO$_2R^{21}$, —SO$_2R^{21}$, and —(CH$_2$)$_n$Cy$^3$; wherein n is selected from 0, 1, 2, 3, and 4; wherein each of $R^{20}$ and $R^{21}$, when present, is selected from C1-C4 alkyl, —(CH$_2$)$_q$OR$^{30}$, and $Cy^4$; wherein q is selected from 0, 1, 2, 3, and 4; wherein $R^{30}$, when present, is selected from hydrogen and C1-C4 alkyl; wherein $Cy^4$, when present, is selected from C3-C8 cycloalkyl, C2-C7 heterocycloalkyl, C5-C6 aryl, and C3-C5 heteroaryl and substituted with 0, 1, 2, or 3 groups independently selected from halogen, —NH$_2$, C1-C4 alkyl, C1-C4 haloalkyl, C1-C4 alkoxy, C1-C4 hydroxyalkyl, C1-C4 alkylamino, (C1-C4)(C1-C4) dialkylamino, and (C1-C4 alkyl)NR$^{40a}$R$^{40b}$; wherein each of $R^{40a}$ and $R^{40b}$, when present, is independently selected from hydrogen and C1-C4 alkyl; wherein $R^{22}$, when present, is selected from hydrogen and C1-C4 alkyl; wherein $Cy^3$, when present, is selected from C3-C8 cycloalkyl, C2-C7 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; and wherein $R^3$ is selected from —(CH$_2$)$_p$OH and —(CH$_2$)$_p$NHR$^{23}$; wherein p is selected from 0, 1, and 2; and wherein $R^{23}$, when present, is selected from hydrogen and C1-C4 alkyl, provided that when $R^2$ is hydrogen or C1-C4 alkyl, then $Cy^1$ is a structure:

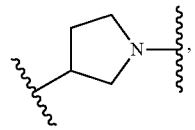

provided that when $R^2$ is C1-C4 alkyl, then $R^{1b}$ is selected from $Cy^2$ and (C1-C4 alkyl)$Cy^2$, or a pharmaceutically acceptable salt thereof.

Also disclosed are compounds having a structure represented by a formula:

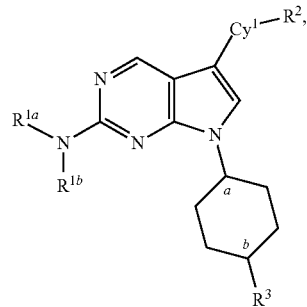

wherein $Cy^1$ is selected from C3-C8 cycloalkyl and C2-C7 heterocycloalkyl, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein $R^{1a}$ is selected from hydrogen, C1-C8 alkyl, and $Cy^2$, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein $Cy^2$, when present, is selected from C3-C8 cycloalkyl, C2-C7 heterocycloalkyl. C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein $R^{1b}$ is selected from C1-C8 alkyl and $Cy^2$, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein $R^2$ is selected from —C(O)$R^2$, —C(O)N($R^{22}$)$R^{20}$, —N($R^{22}$)C(O)$R^{20}$, —SO$_2$N($R^{22}$)$R^{21}$, —N($R^{22}$)SO$_2R^{21}$, —SO$_2R^{21}$, and —(CH$_2$)$_n$Cy$^3$; wherein n is selected from 0, 1, 2, 3, and 4; wherein each of $R^{20}$ and $R^{21}$, when present, is selected from C1-C4 alkyl, —$(CH_2)_qOR^{30}$, and $Cy^4$; wherein q is selected from 0, 1, 2, 3, and 4; wherein $R^{30}$, when present, is selected from hydrogen and C1-C4 alkyl; wherein $Cy^4$, when present, is selected from C3-C8 cycloalkyl, C2-C7 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein $R^{22}$, when present, is selected from hydrogen and C1-C4 alkyl; wherein $Cy^3$, when present, is selected from C3-C8 cycloalkyl, C2-C7 heterocycloalkyl. C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; and wherein $R^3$ is selected from —$(CH_2)_pOH$ and —$(CH_2)_pNHR^{23}$; wherein p is selected from 0, 1, or 2; and wherein $R^{23}$, when present, is selected from hydrogen and C1-C4 alkyl, or a pharmaceutically acceptable salt thereof.

Also disclosed are compounds having a structure selected from:

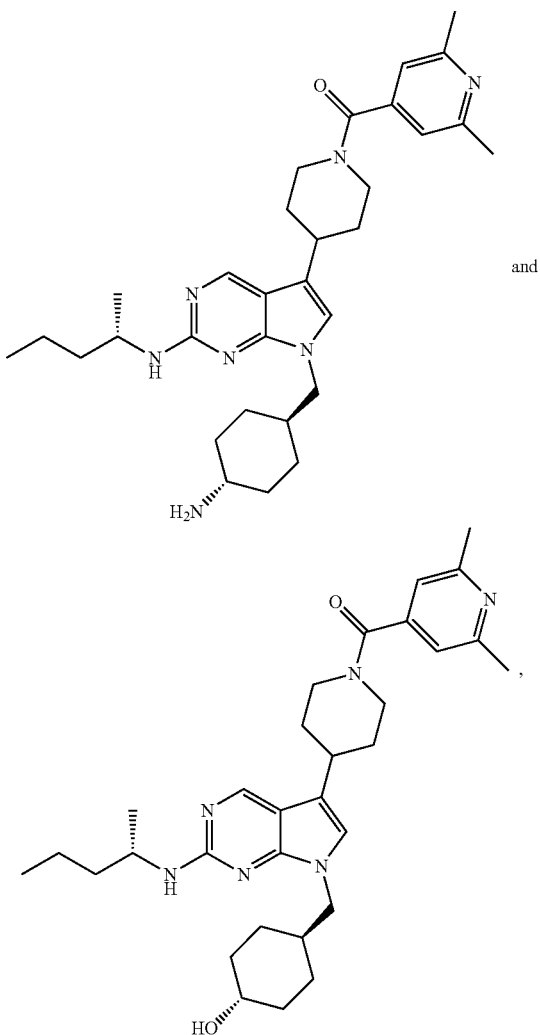

or a pharmaceutically acceptable salt thereof.

Also disclosed are pharmaceutical compositions comprising a therapeutically effective amount of at least one disclosed compound, and a pharmaceutically acceptable carrier.

Also disclosed are methods for the treatment of a disorder associated with Mer tyrosine kinase dysfunction and/or Tyro3 tyrosine kinase dysfunction in a subject, the method comprising the step of administering to the subject an effective amount of at least one disclosed compound, thereby treating the disorder.

Also disclosed are methods for the treatment of an infection in a subject, the method comprising the step of administering to the subject an effective amount of at least one disclosed compound, thereby treating the infection.

Also disclosed are methods for inhibiting a Mer tyrosine kinase in at least one cell, the method comprising the step of contacting the at least one cell with an effective amount of at least one disclosed compound, thereby treating the infection.

Also disclosed are methods for inhibiting a Tyro3 tyrosine kinase in at least one cell, the method comprising the step of contacting the at least one cell with an effective amount of at least one disclosed compound, thereby treating the infection.

Also disclosed are uses of a disclosed compound in immunostimulatory therapy.

Also disclosed are uses of a disclosed compound in immunomodulatory therapy.

Also disclosed are kits comprising at least one disclosed compound and one or more of: (a) at least one agent known to increase Mer tyrosine kinase activity; (b) at least one agent known to increase Tyro3 tyrosine kinase activity; (c) at least one agent known to treat a disorder of uncontrolled cellular proliferation; (d) at least one agent known to a bacterial infection; (e) at least one antiviral agent; (f) instructions for treating a disorder associated with Mer tyrosine kinase dysfunction; (g) instructions for treating a disorder associated with Tyro3 tyrosine kinase dysfunction; (h) instructions for treating a disorder of uncontrolled cellular proliferation; or (i) instructions for treating an infection.

Still other objects and advantages of the present disclosure will become readily apparent by those skilled in the art from the following detailed description, wherein it is shown and described only the preferred aspects, simply by way of illustration of the best mode. As will be realized, the disclosure is capable of other and different aspects, and its several details are capable of modifications in various obvious respects, without departing from the disclosure. Accordingly, the description is to be regarded as illustrative in nature and not as restrictive.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. DEFINITIONS

Listed below are definitions of various terms used to describe this invention. These definitions apply to the terms as they are used throughout this specification, unless otherwise limited in specific instances, either individually or as part of a larger group.

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" mean that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig, or rodent. The term does not denote a particular age or sex. Thus, adult and newborn subjects, as well as fetuses, whether male or female, are intended to be covered. In one aspect, the subject is a mammal. A patient refers to a subject afflicted with a viral infection. The term "patient" includes human and veterinary subjects. In some aspects of the disclosed methods, the subject has been diagnosed with a need for treatment of one or more viral infections prior to the administering step. In various aspects, the one or more disorders is selected from chikungunya, Venezuelan equine encephalitis, dengue, influenza, and zika.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development: or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit, or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. In some aspects of the disclosed methods, the subject has been diagnosed with a need for treatment of a viral infection prior to the administering step. As used herein, the phrase "identified to be in need of treatment for a disorder," or the like, refers to selection of a subject based upon need for treatment of the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically: that is, administered to treat an existing disease or condition. In further various aspects, a preparation can be administered prophylactically; that is, administered for prevention of a disease or condition.

The term "treating" refers to relieving the disease, disorder, or condition, i.e., causing regression of the disease, disorder, and/or condition. The term "preventing" refers to preventing a disease, disorder, or condition from occurring in a human or an animal that may be predisposed to the disease, disorder and/or condition, but has not yet been diagnosed as having it; and/or inhibiting the disease, disorder, or condition, i.e., arresting its development.

The term "contacting" as used herein refers to bringing a disclosed compound and a cell, target receptor, or other biological entity together in such a manner that the compound can affect the activity of the target (e.g., receptor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder: the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "$EC_{90}$," is intended to refer to the concentration of a substance (e.g., a compound or a drug) that is required for 90% inhibition of a biological process, or component of a process, including a protein, subunit, organelle, ribonucleoprotein, etc. In one aspect, an $EC_{90}$ can refer to the concentration of a substance that is required for 90% inhibition in vivo, as further defined elsewhere herein.

The term "comprising" (and its grammatical variations) as used herein is used in the inclusive sense of "having" or "including" and not in the exclusive sense of "consisting of."

The compounds according to this disclosure may form prodrugs at hydroxyl or amino functionalities using alkoxy, amino acids, etc., groups as the prodrug forming moieties. For instance, the hydroxymethyl position may form mono-, di- or triphosphates and again these phosphates can form prodrugs. Preparations of such prodrug derivatives are discussed in various literature sources (examples are: Alexander et al., J. Med. Chem. 1988, 31, 318; Aligas-Martin et al., PCT WO 2000/041531, p. 30). The nitrogen function converted in preparing these derivatives is one (or more) of the nitrogen atoms of a compound of the disclosure.

"Derivatives" of the compounds disclosed herein are pharmaceutically acceptable salts, prodrugs, deuterated forms, radio-actively labeled forms, isomers, solvates and combinations thereof. The "combinations" mentioned in this context are refer to derivatives falling within at least two of the groups: pharmaceutically acceptable salts, prodrugs, deuterated forms, radio-actively labeled forms, isomers, and solvates. Examples of radio-actively labeled forms include compounds labeled with tritium, phosphorous-32, iodine-129, carbon-11, fluorine-18, and the like.

"Pharmaceutically acceptable salts" refer to derivatives of the disclosed compounds wherein the parent compound is modified by making acid or base salts thereof. The compounds of this disclosure form acid addition salts with a wide variety of organic and inorganic acids and include the physiologically acceptable salts which are often used in pharmaceutical chemistry. Such salts are also part of this disclosure. Typical inorganic acids used to form such salts include hydrochloric, hydrobromic, hydroiodic, nitric, sulfuric, phosphoric, hypophosphoric acid, and the like. Salts derived from organic acids, such as aliphatic mono- and dicarboxylic acids, phenyl substituted alkanoic acids, hydroxyalkanoic and hydroxyalkandioic acids, aromatic acids, aliphatic and aromatic sulfonic acids may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toleunesulfonate, xylenesulfonate, tartarate, and the like.

It is understood that the compounds of the present disclosure relate to all optical isomers and stereo-isomers at the various possible atoms of the molecule, unless specified otherwise. Compounds may be separated or prepared as their pure enantiomers or diasteriomers by crystallization, chromatography or synthesis.

The term "leaving group" refers to an atom (or a group of atoms) with electron withdrawing ability that can be displaced as a stable species, taking with it the bonding electrons. Examples of suitable leaving groups include sulfonate esters, including triflate, mesylate, tosylate, brosylate, and halides.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

The term "polyalkylene group" as used herein is a group having two or more CH$_2$ groups linked to one another. The polyalkylene group can be represented by the formula —(CH$_2$)$_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —OA$^1$ where A$^1$ is alkyl or cycloalkyl as defined above. "Alkoxy" also includes polymers of alkoxy groups as just described; that is, an alkoxy can be a polyether such as —OA$^1$–OA$^2$ or —OA$^1$—(OA$^2$)$_a$-OA$^3$, where "a" is an integer of from 1 to 200 and A$^1$, A$^2$, and A$^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —NA$^1$A$^2$, where A$^1$ and A$^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be an optionally substituted alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an optionally substituted alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an optionally substituted alkyl, cycloalkyl, alkenyl, cycloalkenyl, alkynyl, cycloalkynyl, aryl, or heteroaryl group described herein. The term "polyether" as used herein is represented by the formula -(A$^1$O-A$^3$O)$_a$—, where A$^1$ and A$^2$ can be, independently, an optionally substituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "hydroxyl" as used herein is represented by the formula —OH.

The term "ketone" as used herein is represented by the formula $A^1C(O)A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —$SiA^1A^2A^3$, where $A^1$, $A^2$, and $A^3$ can be, independently, hydrogen or an optionally substituted alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an optionally substituted alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an optionally substituted alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^4$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —$O(CH_2)_{0-4}R°$, —$O—(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with $R°$; —$(CH_2)_{0-4}O(CH_2)_{0-4}Ph$ which may be substituted with $R°$; —CH=CHPh, which may be substituted with $R°$; —$(CH_2)_{0-4}O(CH_2)_{0-4}$-pyridyl which may be substituted with $R°$; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR—$, $SC(S)SR°$; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —C(NOR)R; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; $SiR°$; —($C_{1-4}$ straight or branched alkylene)O—$N(R°)_2$; or —($C_{1-4}$ straight or branched alkylene)C(O)O—$N(R°)_2$, wherein each $R°$ may be substituted as defined below and is independently hydrogen, $C_{1-6}$ aliphatic, —$CH_2Ph$, —$O(CH_2)_{0-4}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R°$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R°$ (or the ring formed by taking two independent occurrences of $R°$ together with their intervening atoms), are independently halogen, —(CH$_2$)$_{0-2}$R˙, -(haloR˙), —(CH$_2$)$_{0-2}$OH, —(CH$_2$)$_{0-2}$OR˙, —(CH$_2$)$_{0-2}$CH(OR˙)$_2$; —O(haloR˙), —CN, —N$_3$, —(CH$_2$)$_{0-2}$C(O)R˙, —(CH$_2$)$_{0-2}$C(O)OH, —(CH$_2$)$_{0-2}$C(O)OR˙, —(CH$_2$)$_{0-2}$SR˙, —(CH$_2$)$_{0-2}$SH, —(CH$_2$)$_{0-2}$NH$_2$, —(CH$_2$)$_{0-2}$NHR˙, —(CH$_2$)$_{0-2}$NR˙$_2$, —NO$_2$, —SiR˙$_3$, —OSiR˙$_3$, —C(O)SR, —(C$_{1-4}$ straight or branched alkylene)C(O)OR˙, or —SSR˙ wherein each R˙ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R˙, -(haloR˙), —OH, —OR˙, —O(haloR˙), —CN, —C(O)OH, —C(O)OR˙, —NH$_2$, —NHR˙, —NR˙$_2$, or —NO$_2$, wherein each R˙ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R˙, -(haloR˙), —OH, —OR˙, —O(haloR˙), —CN, —C(O)OH, —C(O)OR˙, —NH$_2$, —NHR˙, —NR˙$_2$, or —NO$_2$, wherein each R˙ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

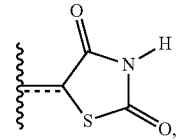

regardless of whether thiazolidinedione is used to prepare the compound. In some aspects the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some aspects, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

When the disclosed compounds contain one chiral center, the compounds exist in two enantiomeric forms. Unless specifically stated to the contrary, a disclosed compound includes both enantiomers and mixtures of enantiomers, such as the specific 50:50 mixture referred to as a racemic mixture. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step can liberate the desired enantiomeric form. Alternatively, specific enantiomers can be synthesized by asymmetric synthesis using optically active reagents, substrates, catalysts or solvents, or by converting one enantiomer into the other by asymmetric transformation.

Designation of a specific absolute configuration at a chiral carbon in a disclosed compound is understood to mean that the designated enantiomeric form of the compounds can be provided in enantiomeric excess (e.e.). Enantiomeric excess, as used herein, is the presence of a particular enantiomer at greater than 50%, for example, greater than 60% greater than 70%, greater than 75%, greater than 80%, greater than 85%, greater than 90%, greater than 95%, greater than 98%, or greater than 99%. In one aspect, the designated enantiomer is substantially free from the other enantiomer. For example, the "R" forms of the compounds can be substantially free from the "S" forms of the compounds and are, thus, in enantiomeric excess of the "S" forms. Conversely, "S" forms of the compounds can be substantially free of "R" forms of the compounds and are, thus, in enantiomeric excess of the "R" forms.

When a disclosed compound has two or more chiral carbons, it can have more than two optical isomers and can exist in diastereoisomeric forms. For example, when there are two chiral carbons, the compound can have up to four optical isomers and two pairs of enantiomers ((S,S)/(R,R) and (R,S)/(S,R)). The pairs of enantiomers (e.g., (S,S)/(R, R)) are mirror image stereoisomers of one another. The stereoisomers that are not mirror-images (e.g., (S,S) and (R,S)) are diastereomers. The diastereoisomeric pairs can be separated by methods known to those skilled in the art, for example chromatography or crystallization and the individual enantiomers within each pair may be separated as described above. Unless otherwise specifically excluded, a disclosed compound includes each diastereoisomer of such compounds and mixtures thereof.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Tritiated, i.e., H, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. "Solvates" refers to the compound formed by the interaction of a solvent and a solute and includes hydrates. Solvates are usually crystalline solid adducts containing solvent molecules within the crystal structure, in either stoichiometric or nonstoichiometric proportions. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et, al., The Royal Society of Chemistry, 1889-1896, 2004. Examples of co-crystals include p-toluenesulfonic acid and benzenesulfonic acid.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

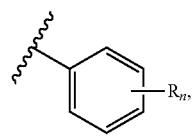

which is understood to be equivalent to a formula:

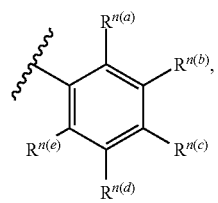

wherein n is typically an integer. That is, $R^n$ is understood to represent five independent substituents, $R^{n(a)}$, $R^{n(b)}$, $R^{n(c)}$, $R^{n(d)}$, $R^{n(e)}$. In each such case, each of the five $R^n$ can be hydrogen or a recited substituent. By "independent substituents," it is meant that each R substituent can be independently defined. For example, if in one instance $R^{n(a)}$ is halogen, then $R^{n(b)}$ is not necessarily halogen in that instance.

In some yet further aspects, a structure of a compound can be represented by a formula:

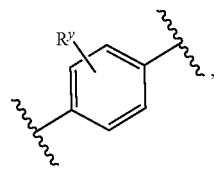

wherein $R^y$ represents, for example, 0-2 independent substituents selected from $A^1$, $A^2$, and $A^3$, which is understood to be equivalent to the groups of formulae:

wherein $R^y$ represents 0 independent substituents

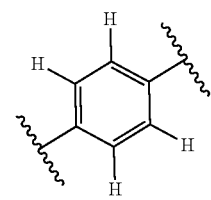

wherein $R^y$ represents 1 independent substituent

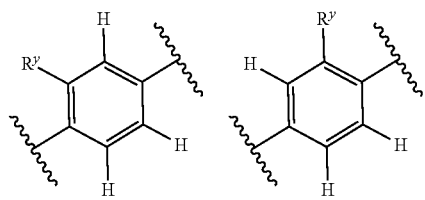

-continued

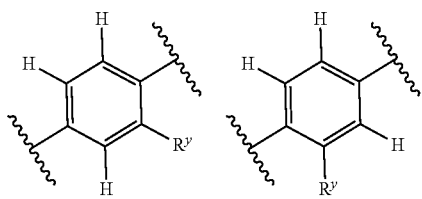

wherein $R^y$ represents 2 independent substituents

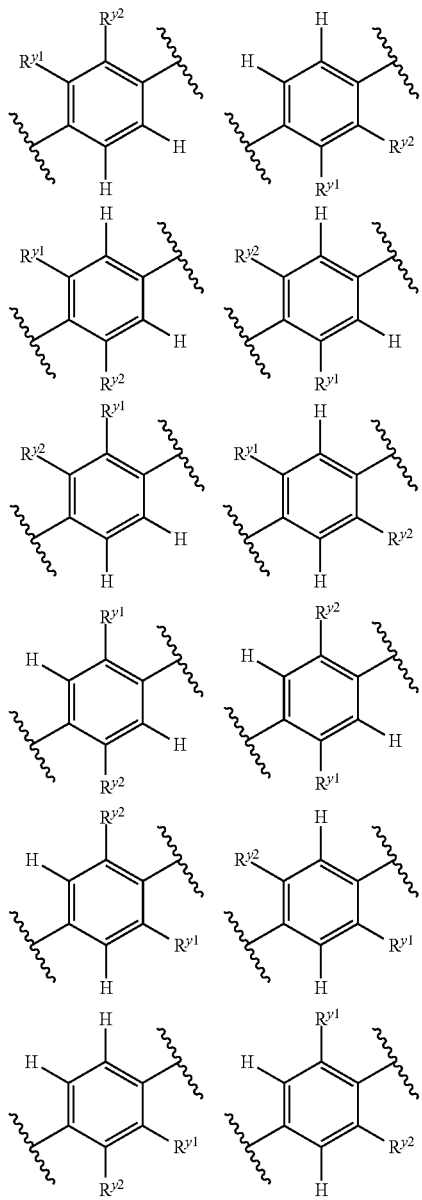

Again, by "independent substituents," it is meant that each R substituent can be independently defined. For example, if in one instance $R^{y1}$ is $A^1$, then $R^{y2}$ is not necessarily $A^1$ in that instance.

In some further aspects, a structure of a compound can be represented by a formula,

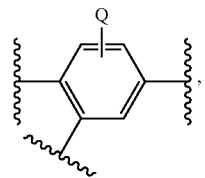

wherein, for example, Q comprises three substituents independently selected from hydrogen and A, which is understood to be equivalent to a formula:

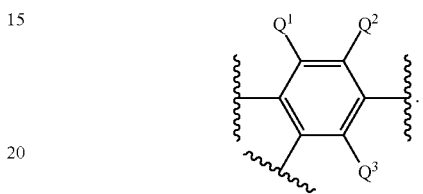

Again, by "independent substituents." it is meant that each Q substituent is independently defined as hydrogen or A, which is understood to be equivalent to the groups of formulae:

wherein Q comprises three substituents independently selected from H and A

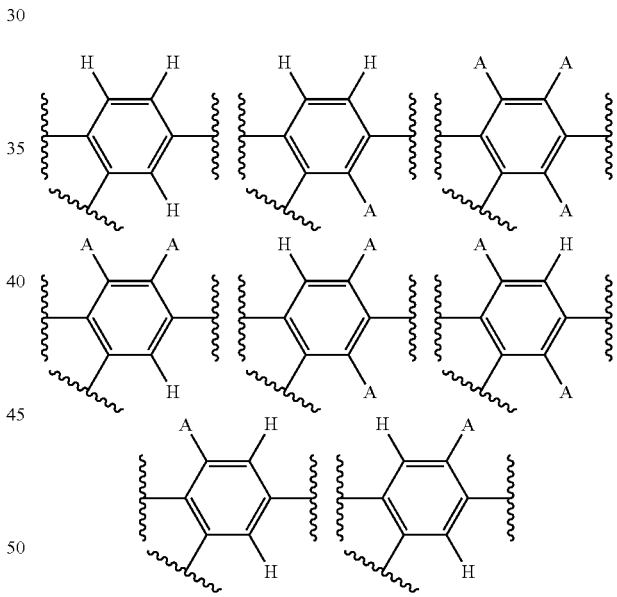

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis. Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989);

Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of aspects described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc, of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific aspect or combination of aspects of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. COMPOUNDS

In one aspect, the invention relates to compounds useful in treating a variety of disorders and diseases including, but not limited to, disorders of uncontrolled cellular proliferation such as, for example, cancer, infectious diseases, and thrombosis.

In a further aspect, the disclosed compounds exhibit antiviral activity.

In a further aspect, the disclosed compounds exhibit antibacterial activity.

In a further aspect, the compounds of the invention are useful in inhibiting viral and/or bacterial activity in a mammal. In a still further aspect, the compounds of the invention are useful in inhibiting viral and/or bacterial activity in at least one cell.

In a further aspect, the compounds of the invention are useful in inhibiting a Mer tyrosine kinase in at least one cell. In a still further aspect, the compounds of the invention are useful in inhibiting a Tyro3 tyrosine kinase in at least one cell.

In a further aspect, the compounds of the invention are useful in the treatment of a disorder associated with Mer tyrosine kinase dysfunction and/or Tyro3 tyrosine kinase dysfunction in a subject. In a still further aspect, the compounds of the invention are useful in the treatment of a disorder associated with Mer tyrosine kinase dysfunction in a subject. In yet a further aspect, the compounds of the invention are useful in the treatment of a disorder associated with Tyro3 tyrosine kinase dysfunction in a subject.

In a further aspect, the compounds of the invention are useful in immunostimulatory therapy.

In a further aspect, the compounds of the invention are useful in immunomodulaton therapy.

In a further aspect, the compounds of the invention are useful in the treatment of viral and/or bacterial disorders, as further described herein. In a still further aspect, the compounds of the invention are useful in the treatment of a cancer, as further described herein. In yet a further aspect, the compounds of the invention are useful in the treatment of thrombosis, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, disclosed are compounds having a structure represented by a formula:

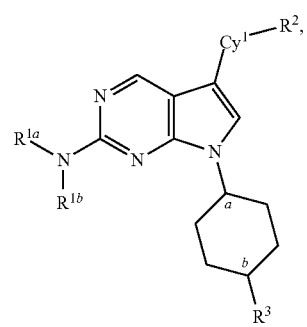

wherein $Cy^1$ is selected from C3-C8 cycloalkyl and C2-C7 heterocycloalkyl, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein $R^{1a}$ is selected from hydrogen, C1-C8 alkyl, and $Cy^2$, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-

C4) dialkylamino; wherein Cy$^2$, when present, is selected from C3-C9 cycloalkyl, C2-C7 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein R$^{1b}$ is selected from C1-C8 alkyl, Cy$^2$, and (C1-C4 alkyl)Cy$^2$, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein R$^2$ is selected from hydrogen, C1-C4 alkyl, —C(O)R$^{20}$, —C(O)N(R$^{22}$)R$^{20}$, —N(R$^{22}$)C(O)R$^{20}$, —SO$_2$N(R$^{22}$)R$^{20}$, —N(R$^{22}$)SO$_2$R$^{21}$, —SO$_2$R$^{21}$, and —(CH$_2$)$_n$Cy$^3$; wherein n is selected from 0, 1, 2, 3, and 4; wherein each of R$^2$ and R$^{21}$, when present, is selected from C1-C4 alkyl, —(CH$_2$)$_q$OR$^{20}$, and Cy$^4$; wherein q is selected from 0, 1, 2, 3, and 4; wherein R$^{30}$, when present, is selected from hydrogen and C1-C4 alkyl; wherein Cy$^4$, when present, is selected from C3-C8 cycloalkyl, C2-C7 heterocycloalkyl, C5-C6 aryl, and C3-C5 heteroaryl and substituted with 0, 1, 2, or 3 groups independently selected from halogen, —NH$_2$, C1-C4 alkyl, C1-C4 haloalkyl, C1-C4 alkoxy, C1-C4 hydroxyalkyl, C1-C4 alkylamino, (C1-C4)(C1-C4) dialkylamino, and (C1-C4 alkyl)NR$^{40a}$R$^{40b}$; wherein each of R$^{40a}$ and R$^{40b}$, when present, is independently selected from hydrogen and C1-C4 alkyl; wherein R$^{22}$, when present, is selected from hydrogen and C1-C4 alkyl; wherein Cy$^3$, when present, is selected from C3-C8 cycloalkyl, C2-C7 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; and wherein R$^3$ is selected from —(CH$_2$)$_p$OH and —(CH$_2$)$_p$NHR$^{23}$; wherein p is selected from 0, 1, and 2; and wherein R$^{23}$, when present, is selected from hydrogen and C1-C4 alkyl, provided that when R$^2$ is hydrogen or C1-C4 alkyl, then Cy$^1$ is a structure:

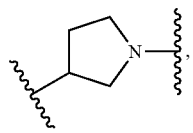 [SMILES: *C1CCN(*)C1]

or
provided that when R$^2$ is C1-C4 alkyl, then R$^{1b}$ is selected from Cy$^2$ and (C1-C4 alkyl)Cy$^2$, or a pharmaceutically acceptable salt thereof.

In one aspect, disclosed are compounds having a structure represented by a formula:

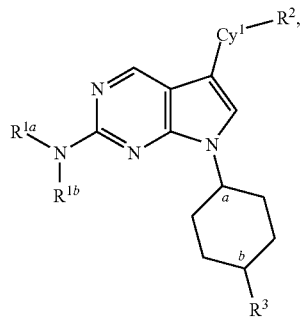

wherein Cy$^1$ is selected from C3-C8 cycloalkyl and C2-C7 heterocycloalkyl, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein R$^{1a}$ is selected from hydrogen, C1-C8 alkyl, and Cy$^2$, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein Cy$^2$, when present, is selected from C3-C8 cycloalkyl, C2-C7 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein R$^{1b}$ is selected from C1-C8 alkyl and Cy$^2$, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein R$^2$ is selected from —C(O)R$^2$, —C(O)N(R$^{22}$)R$^{20}$, —N(R$^{22}$)C(O)R$^{20}$, —SO$_2$N(R$^{22}$)R$^{21}$, —N(R$^2$)SO$_2$R$^{21}$, —SO$_2$R$^{21}$, and —(CH$_2$)$_n$Cy$^3$; wherein n is selected from 0, 1, 2, 3, and 4; wherein each of R$^{20}$ and R$^{21}$, when present, is selected from C1-C4 alkyl, —(CH$_2$)$_q$OR$^{30}$, and Cy$^4$; wherein q is selected from 0, 1, 2, 3, and 4; wherein R$^{30}$, when present, is selected from hydrogen and C1-C4 alkyl; wherein Cy$^4$, when present, is selected from C3-C8 cycloalkyl, C2-C7 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein R$^{22}$, when present, is selected from hydrogen and C1-C4 alkyl; wherein Cy$^3$, when present, is selected from C3-C8 cycloalkyl, C2-C7 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; and wherein R$^3$ is selected from —(CH$_2$)$_p$OH and —(CH$_2$)$_p$NHR$^{23}$; wherein p is selected from 0, 1, or 2; and wherein R$^{23}$, when present, is selected from hydrogen and C1-C4 alkyl, or a pharmaceutically acceptable salt thereof.

In one aspect, disclosed are compounds having a structure selected from:

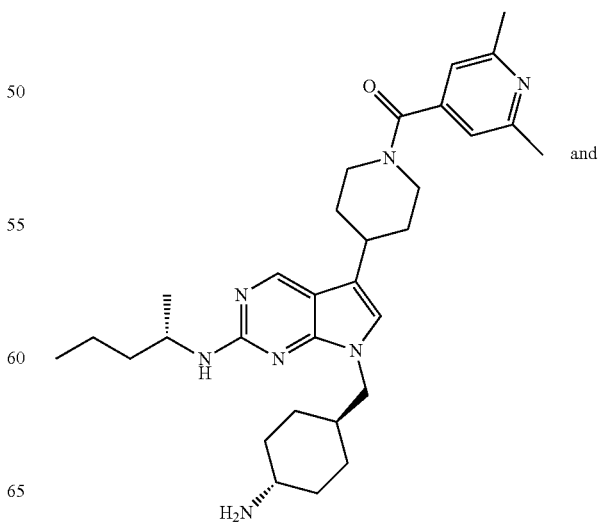

and

-continued
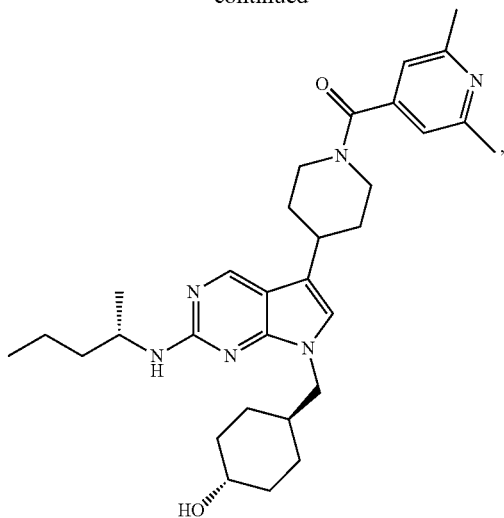
or a pharmaceutically acceptable salt thereof.
In a further aspect, the compound has a structure:
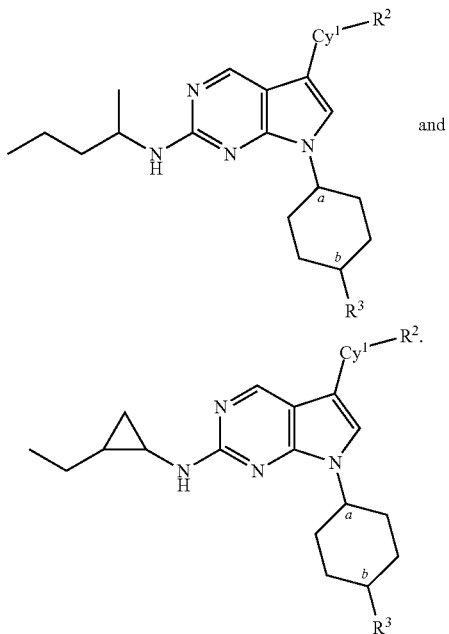
In a further aspect, the compound has a structure:
In a further aspect, the compound has a structure selected from:
In a further aspect, the compound has a structure selected from:

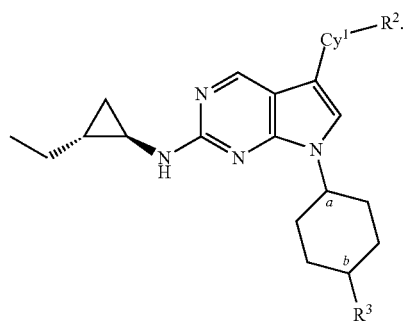
In a further aspect, the compound has a structure:
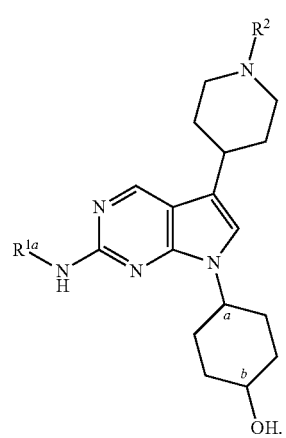
In a further aspect, the compound has a structure selected from:
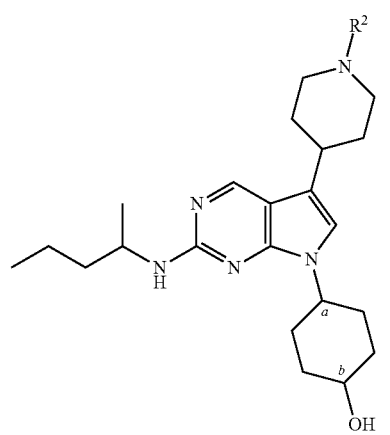
and
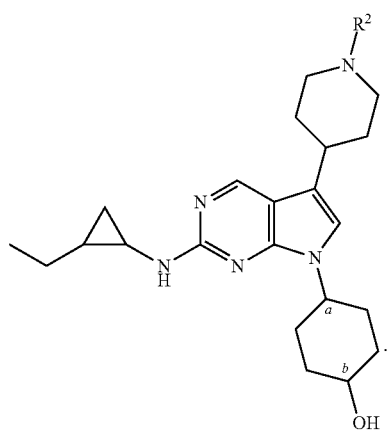
In a further aspect, the compound has a structure selected from:
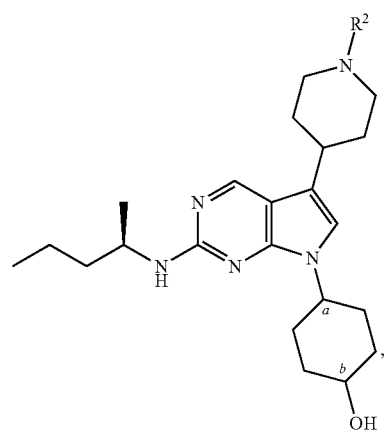
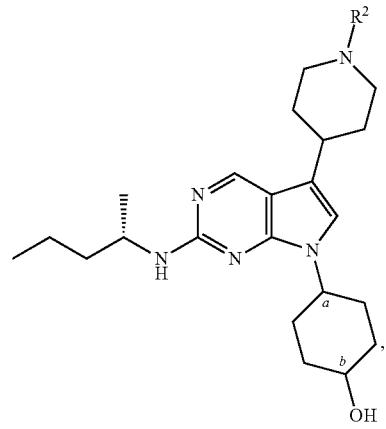

-continued
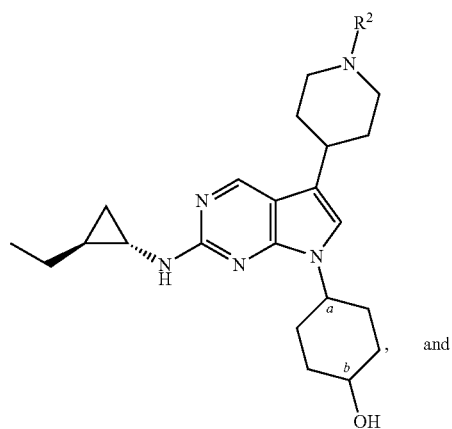, and
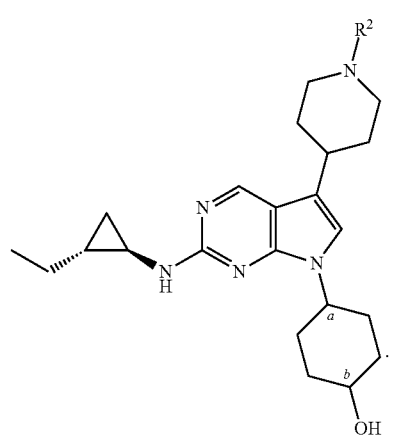.
In a further aspect, the compound has a structure:
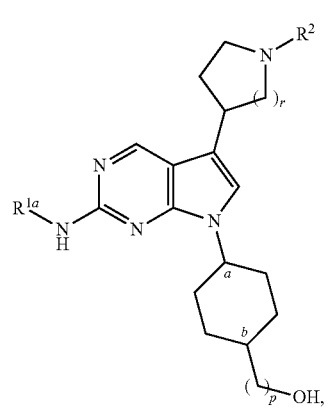
wherein r is selected from 0 and 1.
In a further aspect, the compound is selected from:
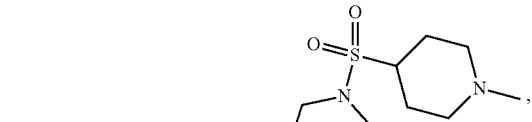
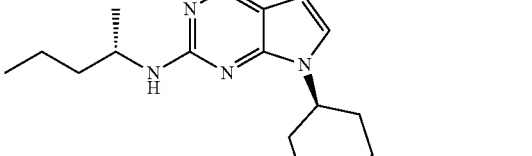
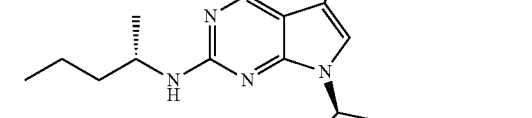
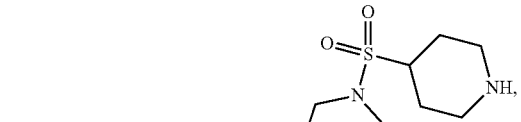
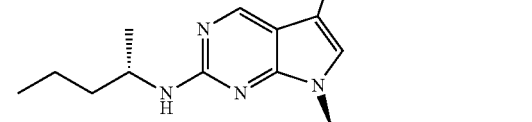
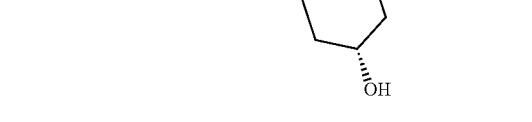

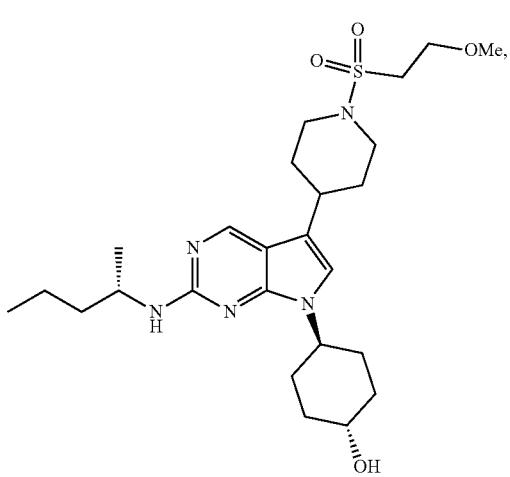
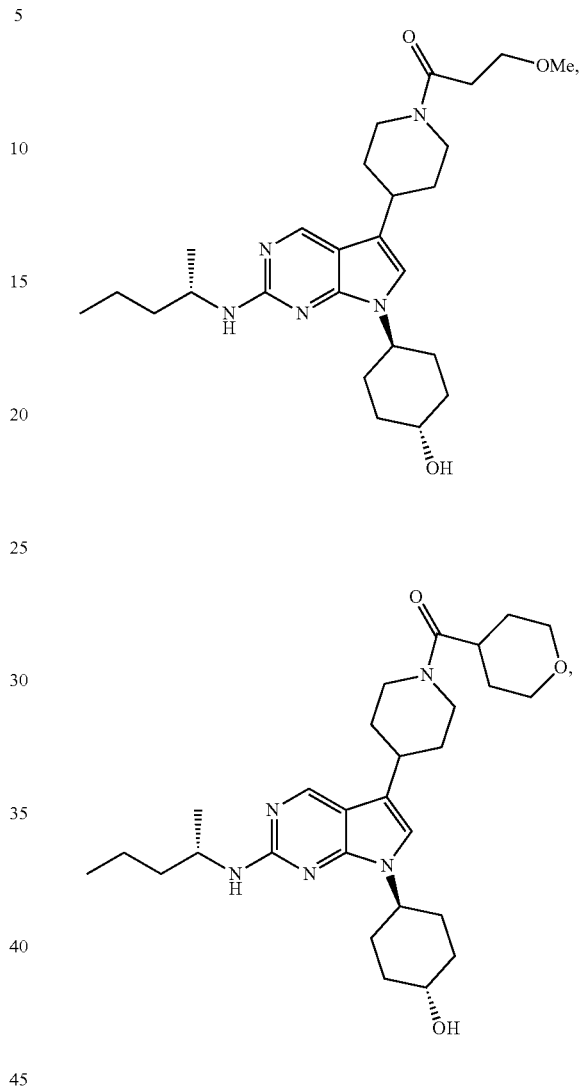
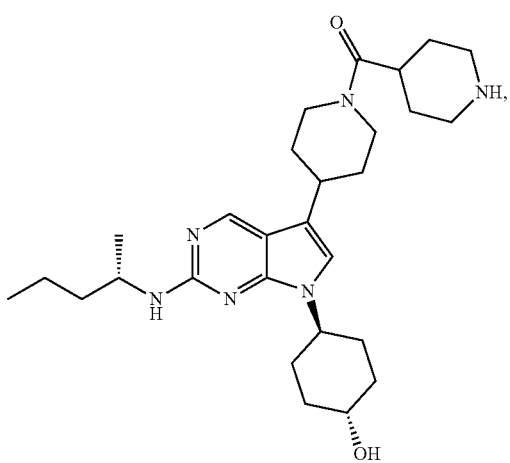
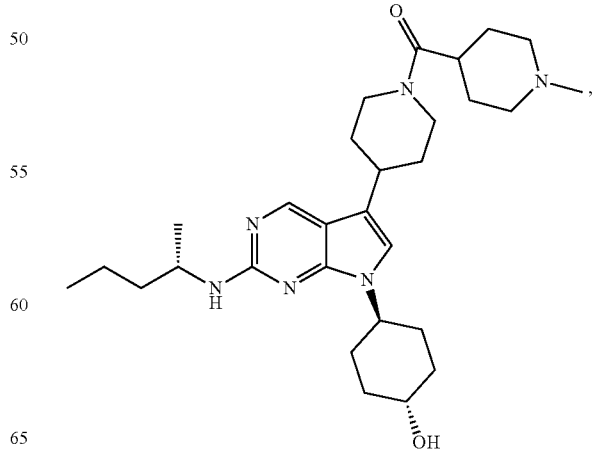

37
-continued
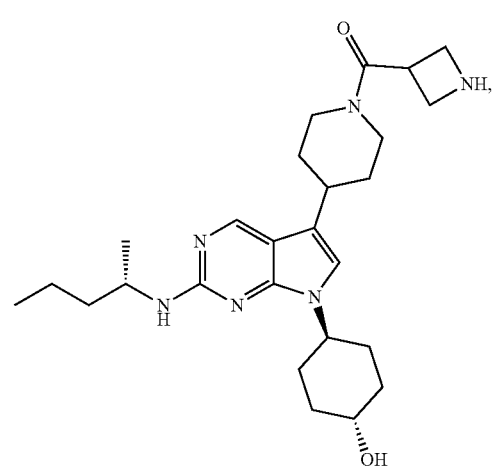
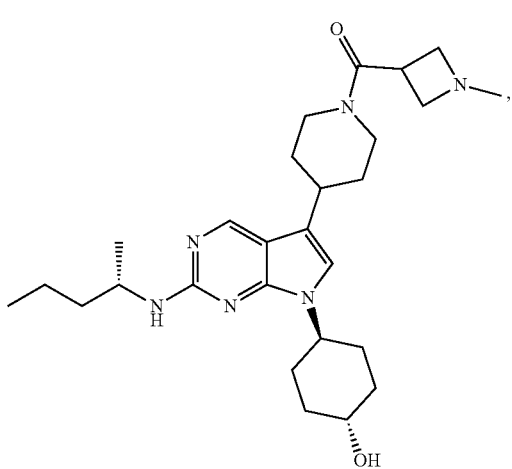
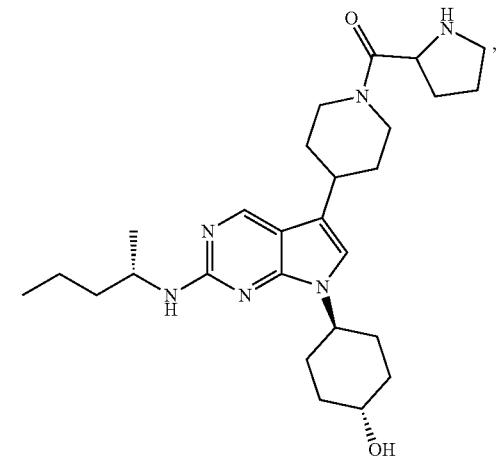
38
-continued
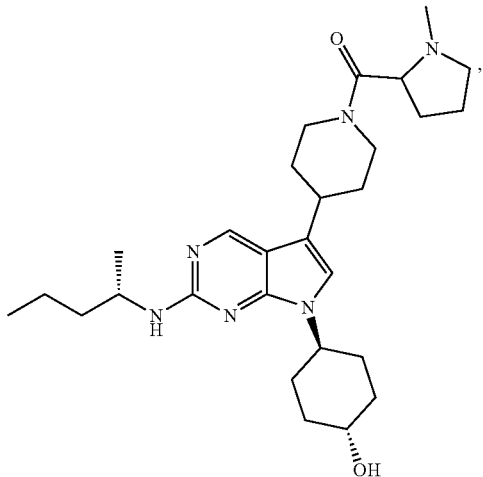
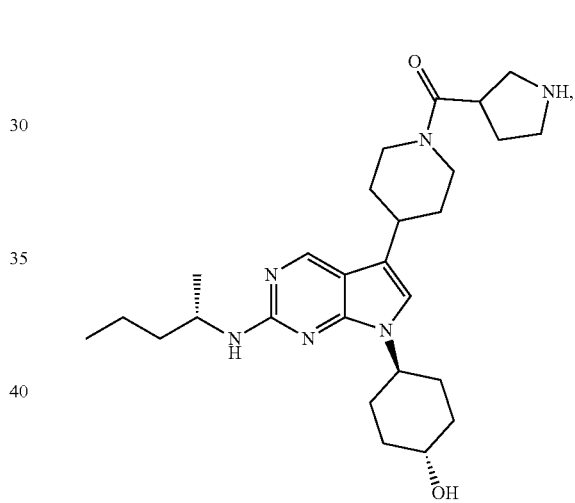
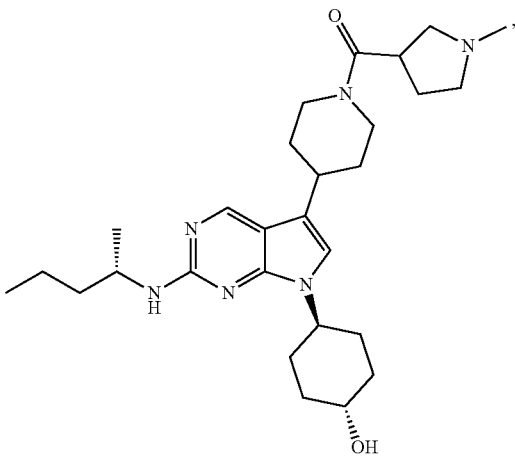

39
-continued
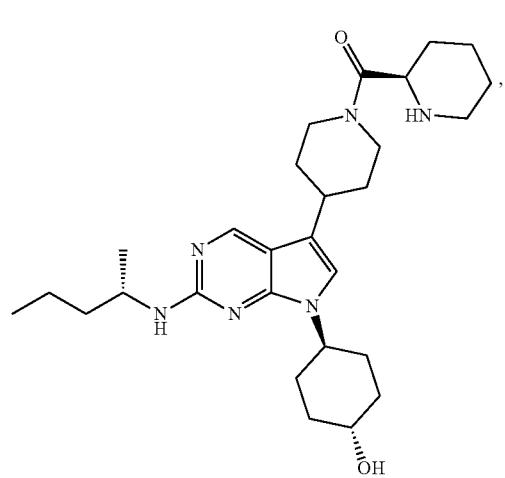
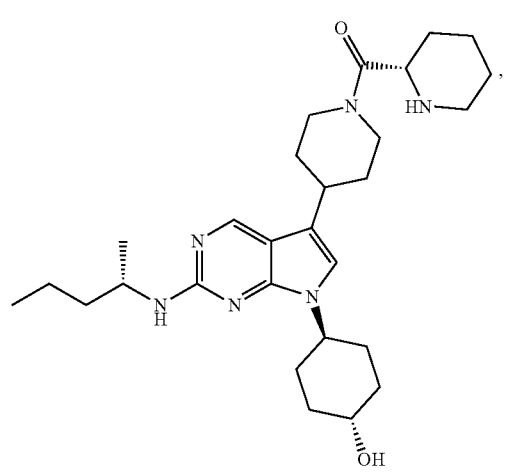
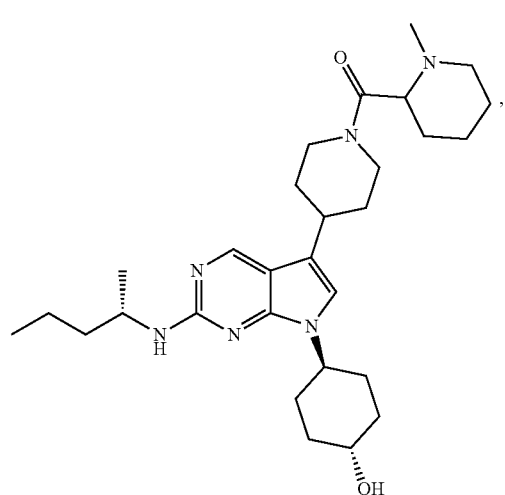
40
-continued
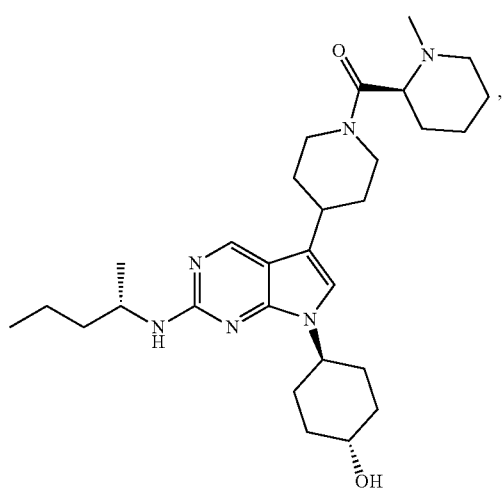
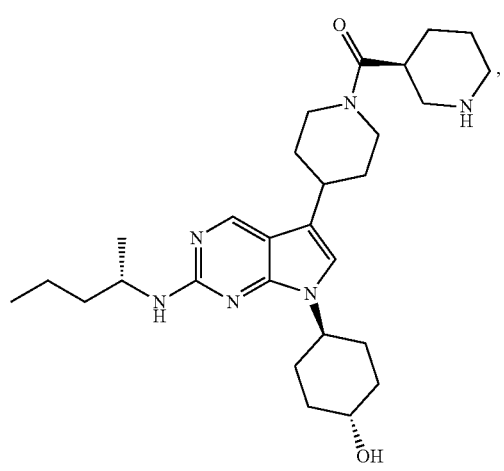
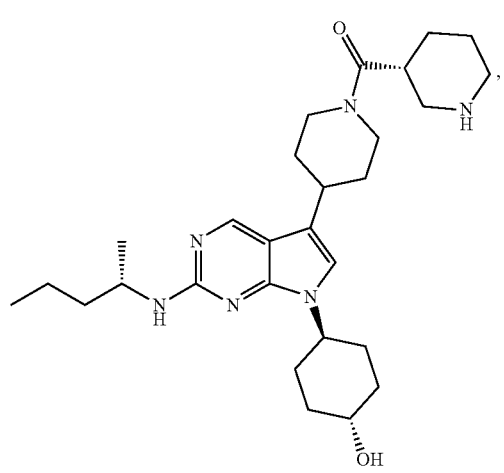

41
-continued
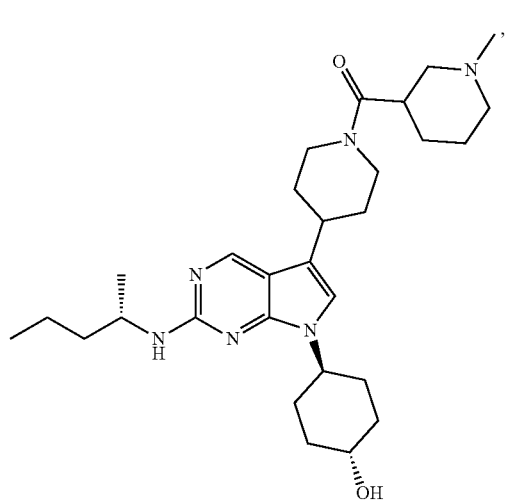
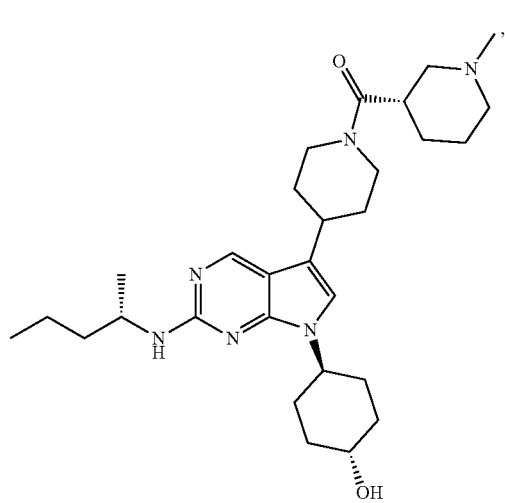
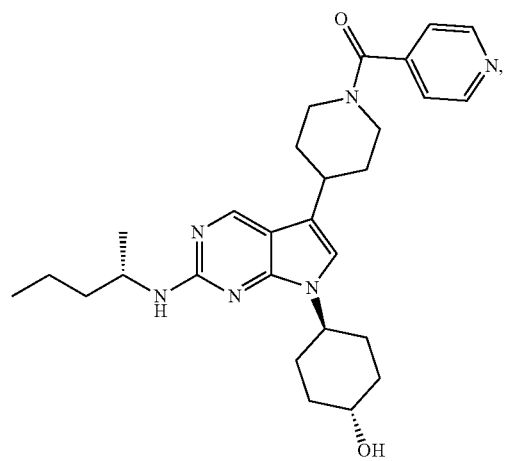
42
-continued
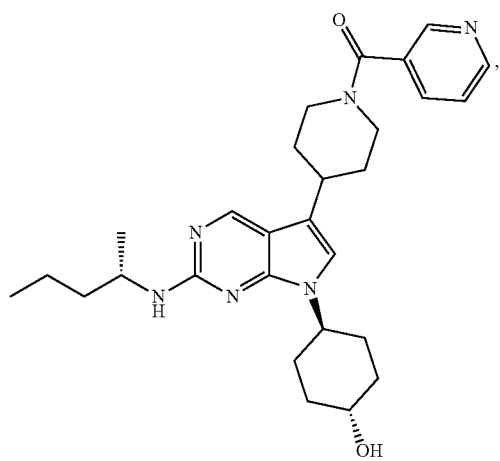
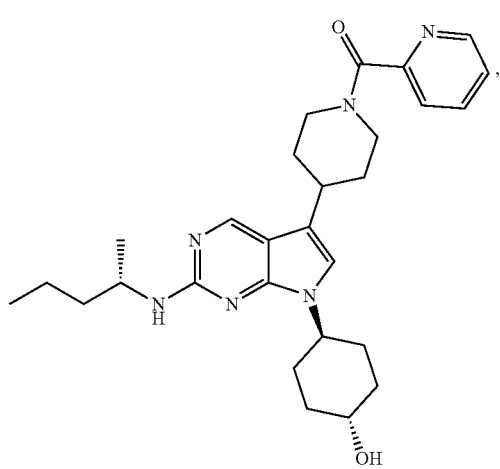
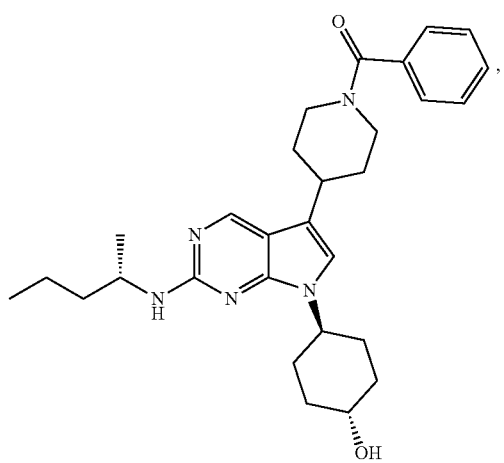

-continued
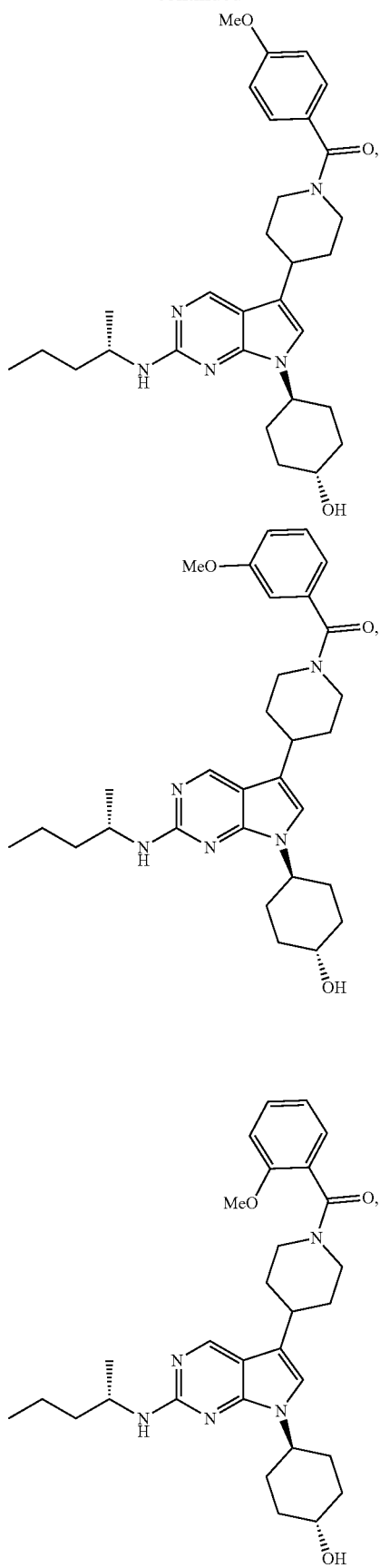
-continued
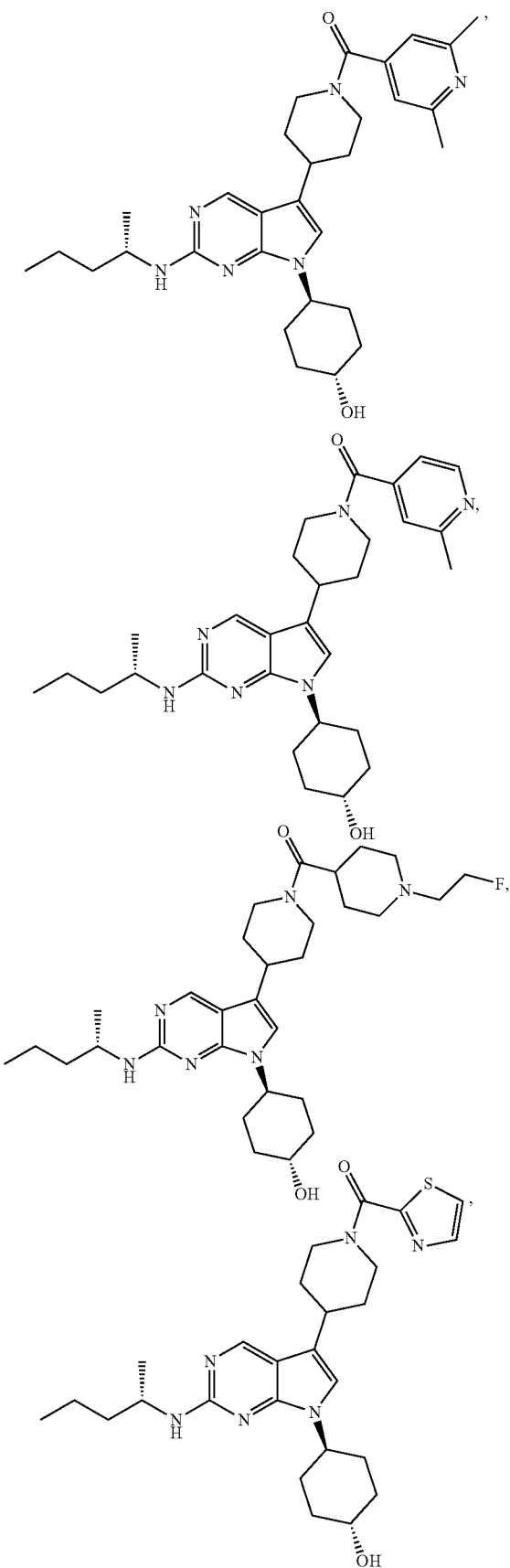

45
-continued
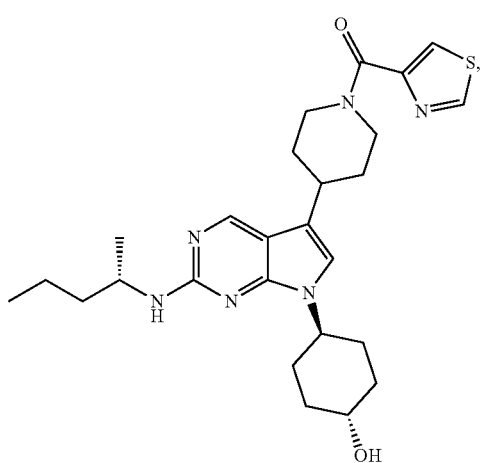
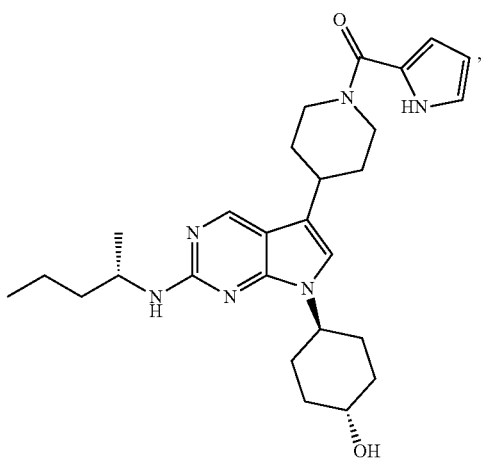
46
-continued
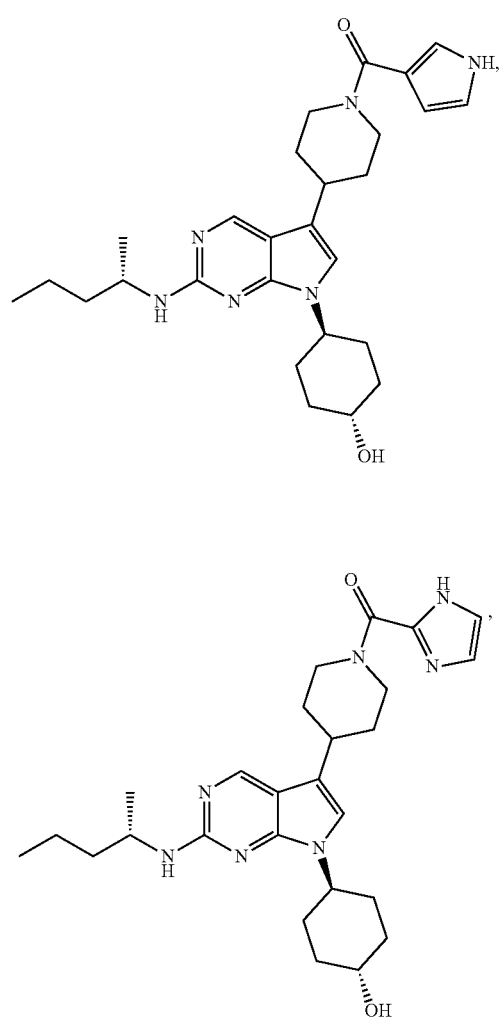
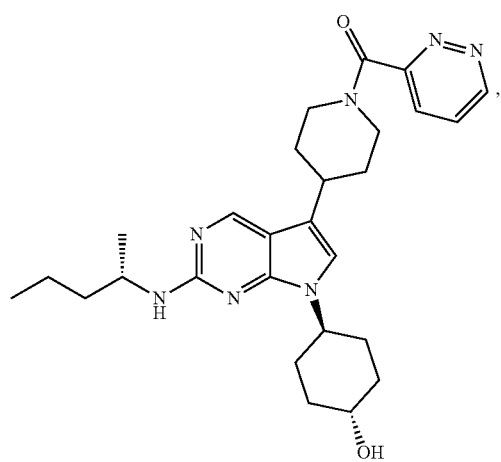

47
-continued
48
-continued
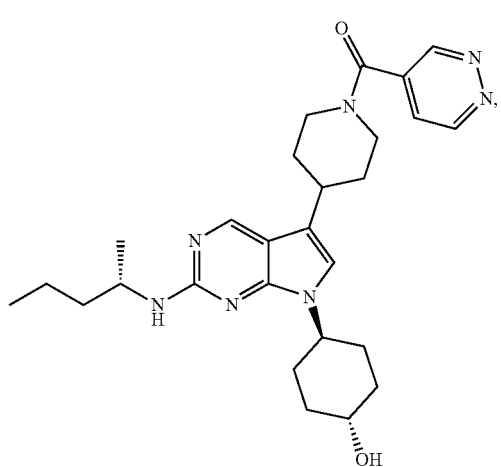
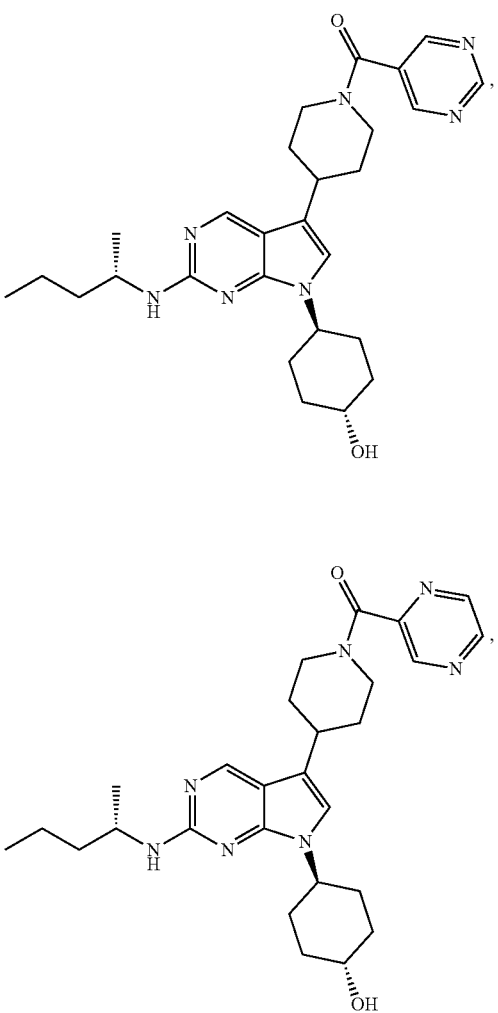
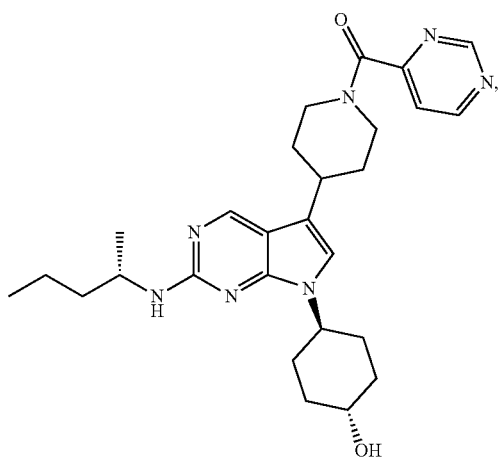

49
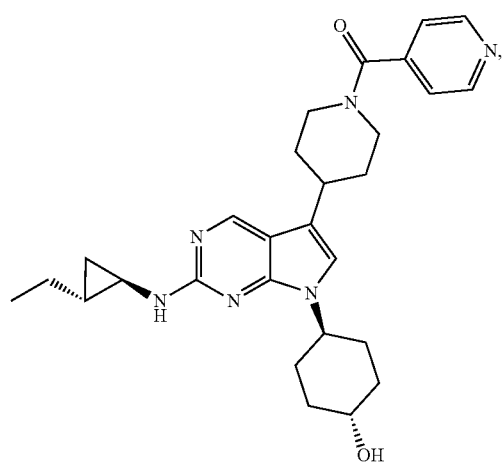
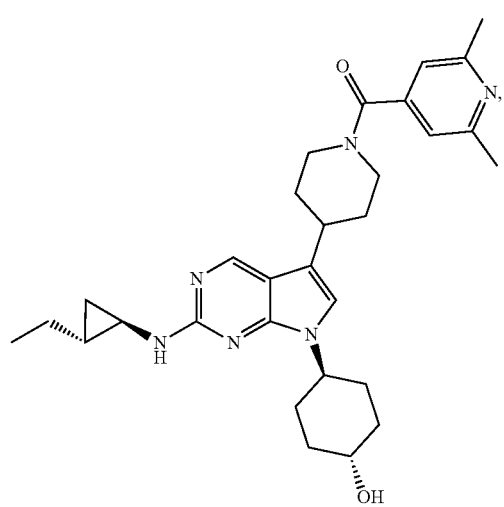
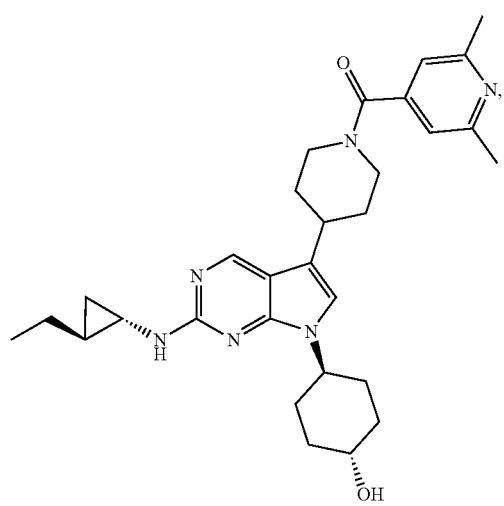
50
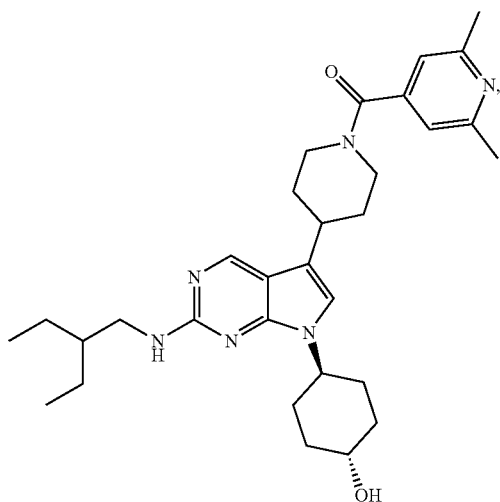
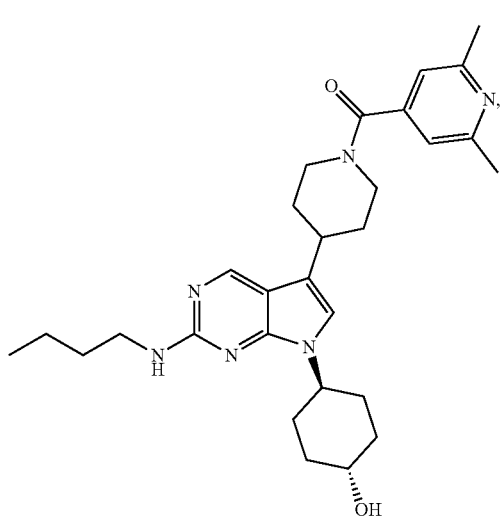
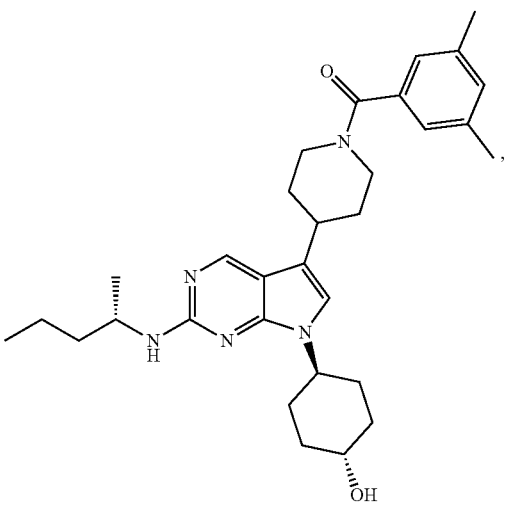

51
-continued
52
-continued
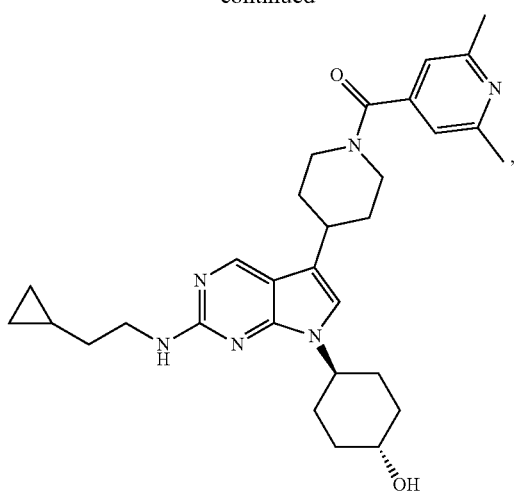
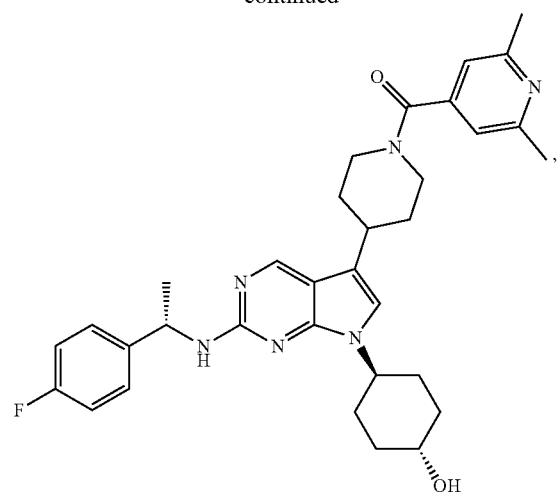

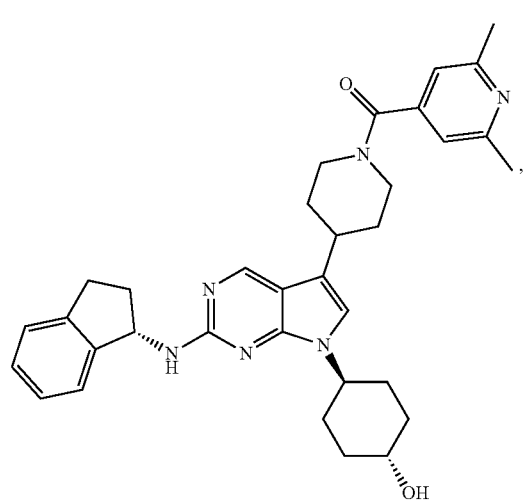

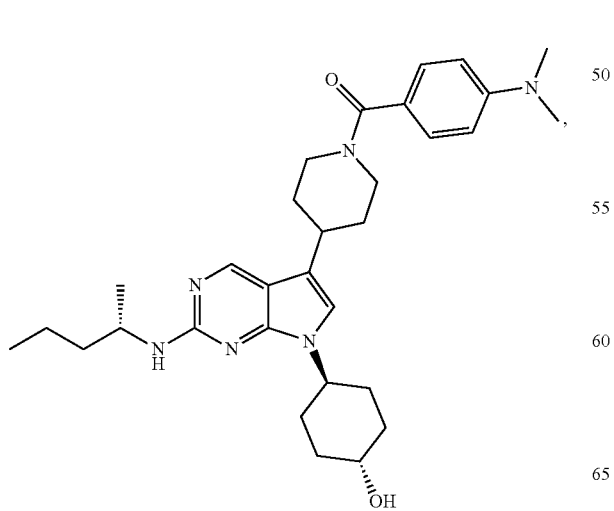
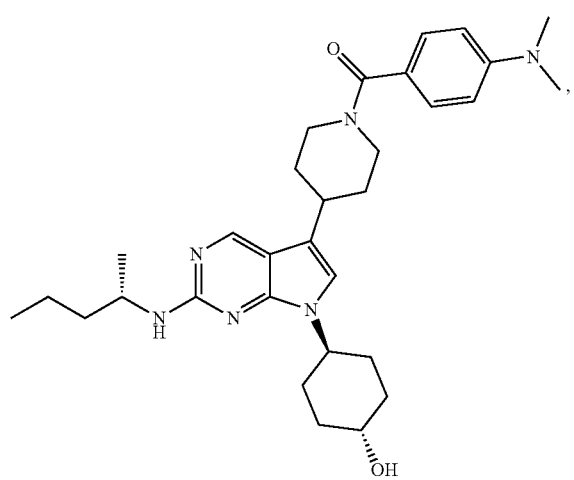
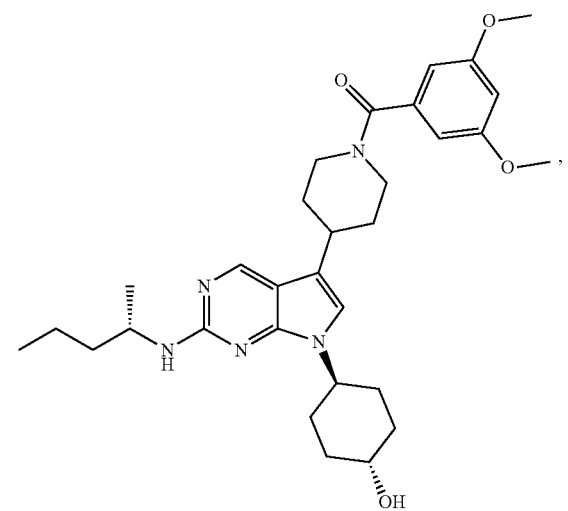

55
-continued
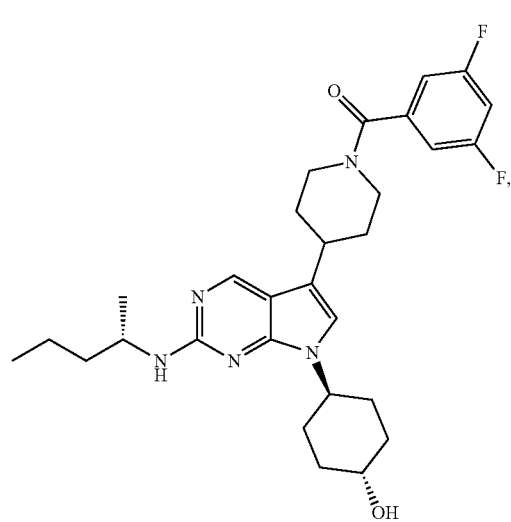
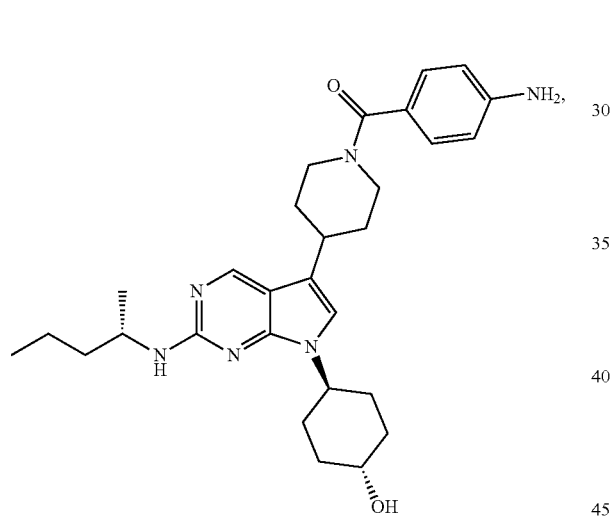
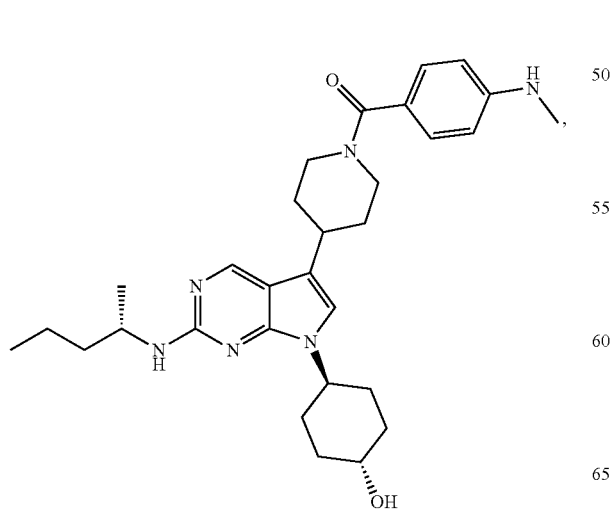
56
-continued
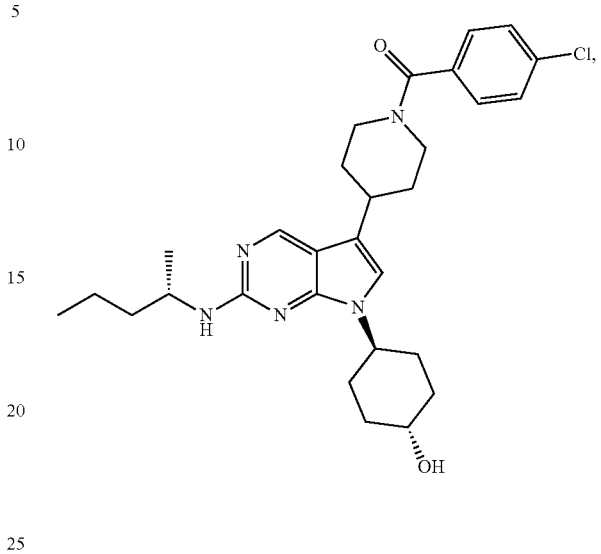
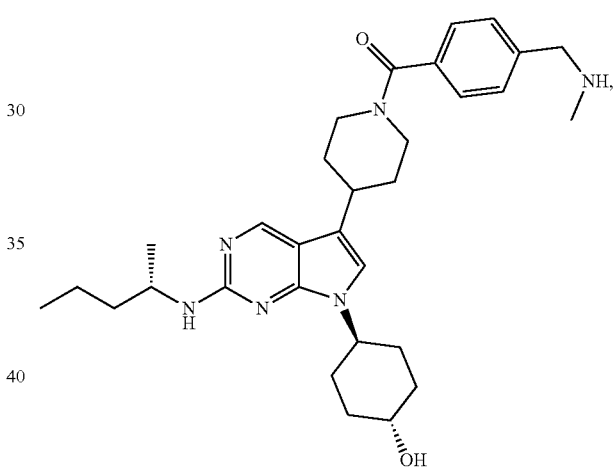
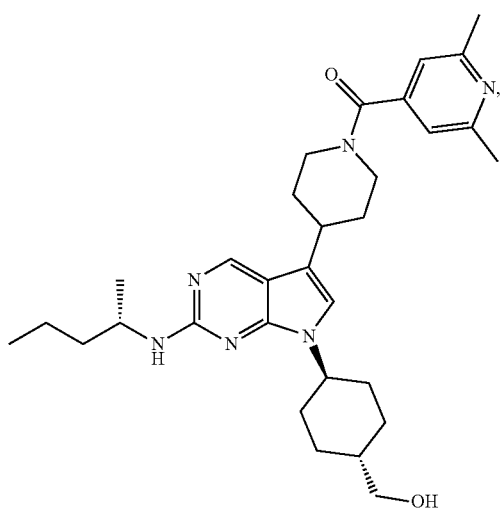

57
-continued
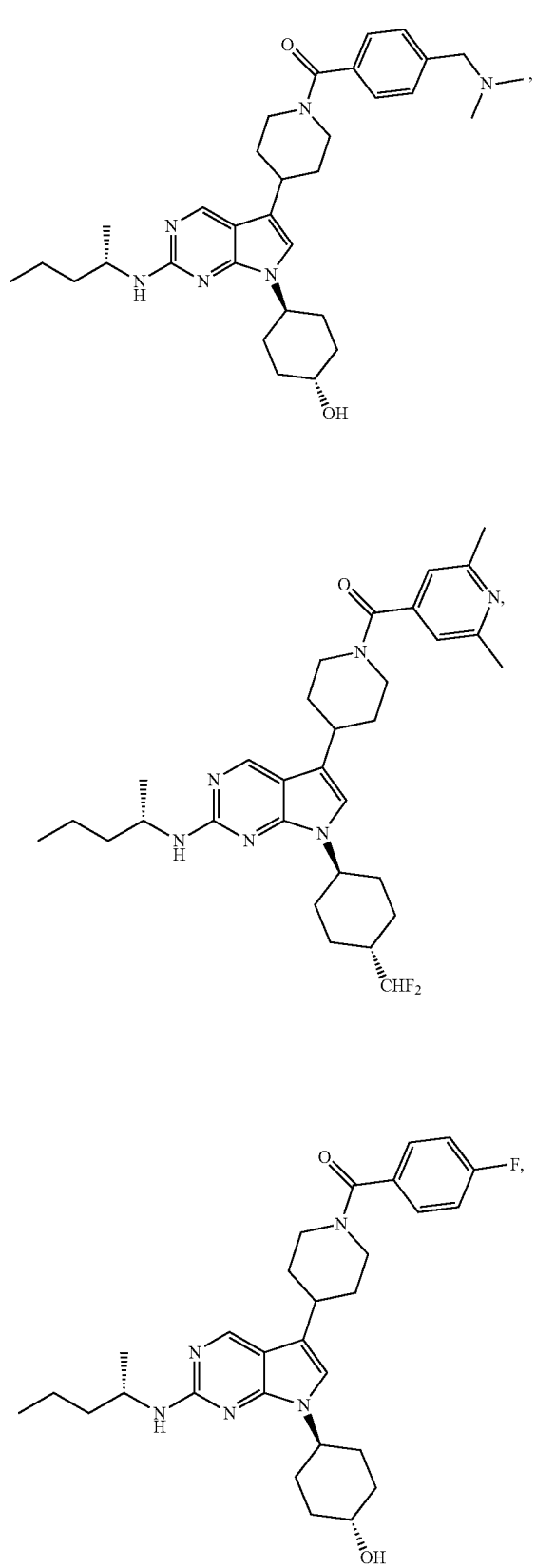
58
-continued
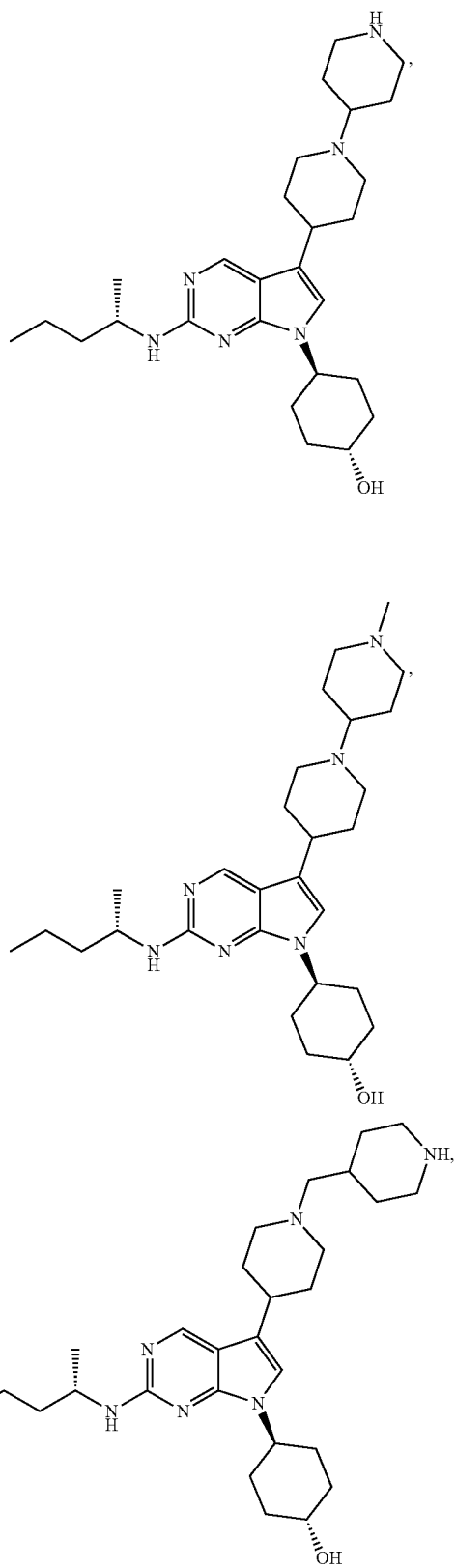

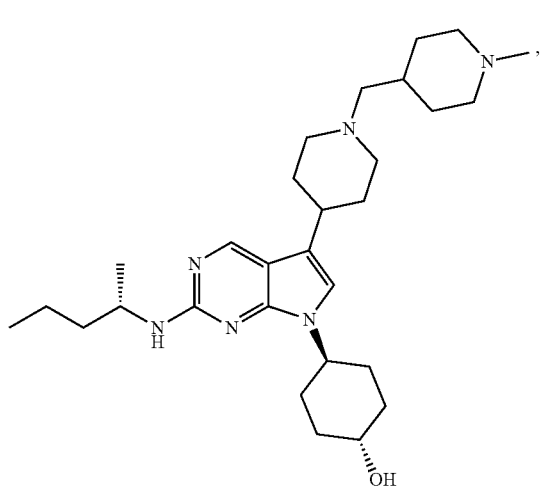
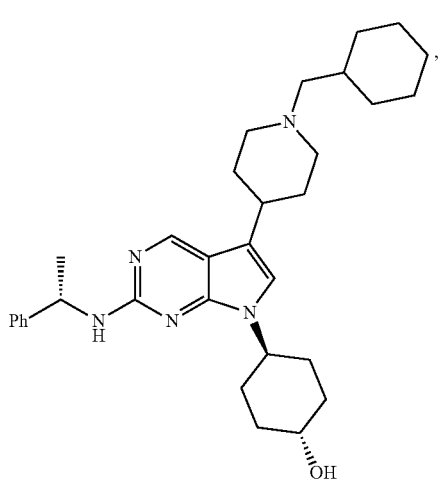
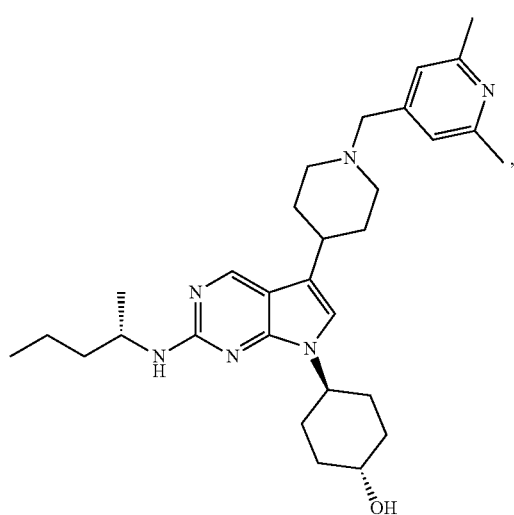
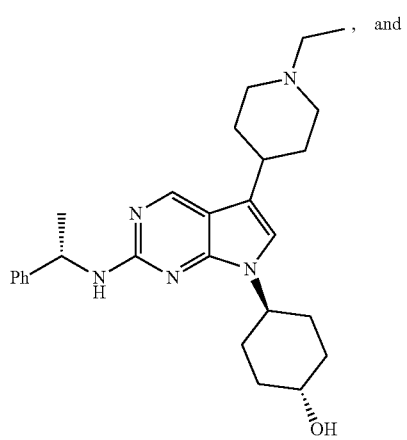
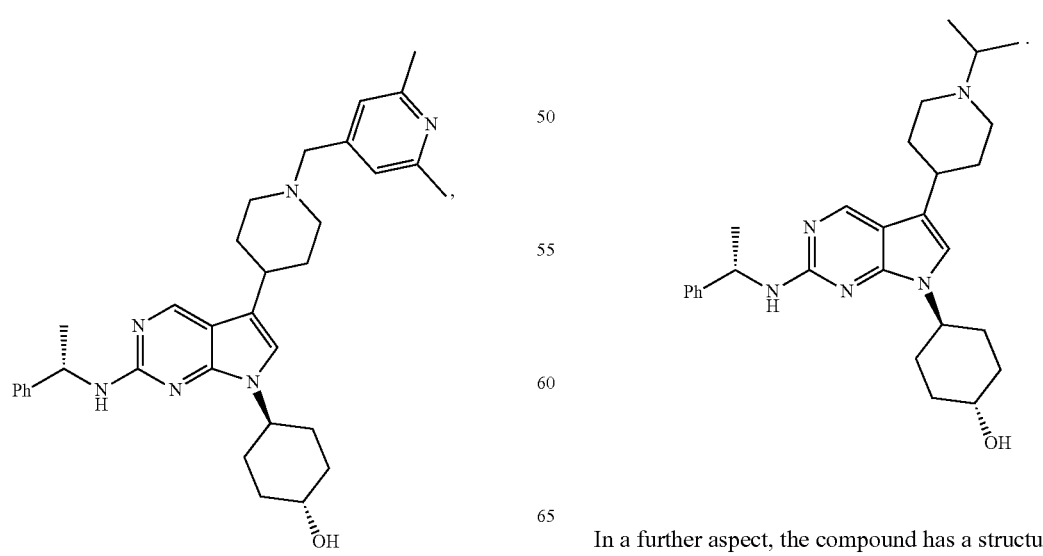
In a further aspect, the compound has a structure selected from:

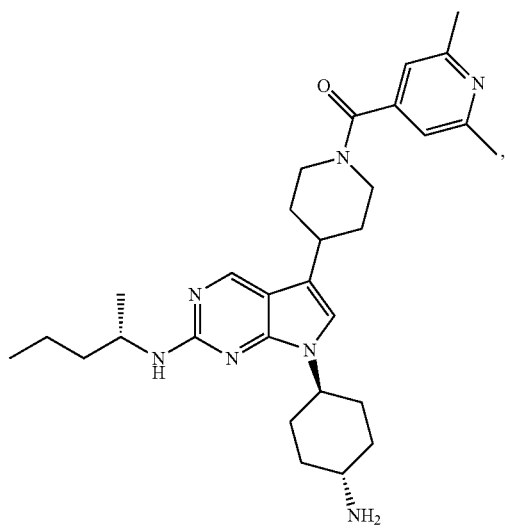

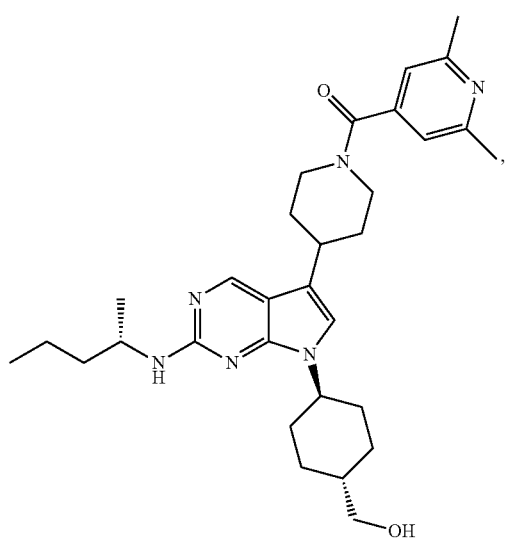

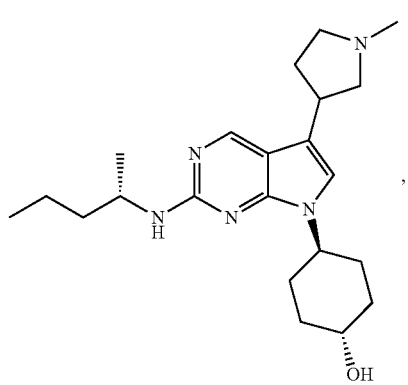

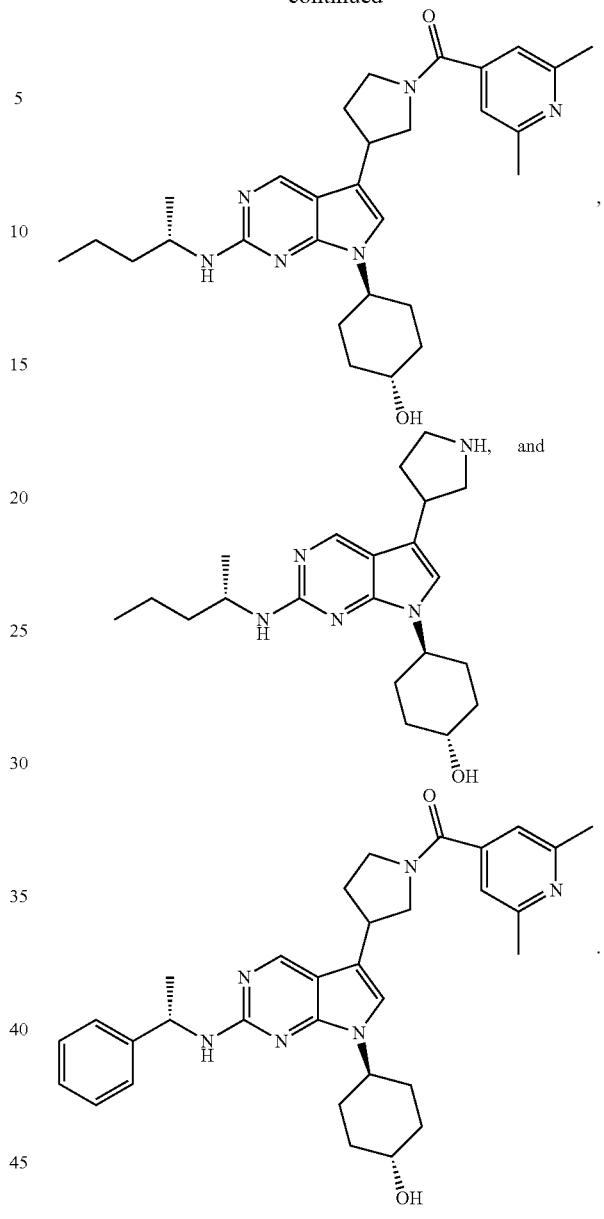

In a further aspect, the substituents on the carbons marked "a" and "b" are in a cis configuration. In a still further aspect, the substituents on the carbons marked "a" and "b" are in a trans configuration.

In one aspect, n is selected from 0, 1, 2, 3, and 4. In a further aspect, n is selected from 0, 1, 2, and 3. In a still further aspect, n is selected from 0, 1, and 2. In yet a further aspect, n is selected from 0 and 1. In an even further aspect, n is 0. In a still further aspect, n is 1. In yet a further aspect, n is 2. In an even further aspect, n is 3. In a still further aspect, n is 4.

In one aspect, q is selected from 0, 1, 2, 3, and 4. In a further aspect, q is selected from 0, 1, 2, and 3. In a still further aspect, q is selected from 0, 1, and 2. In yet a further aspect, q is selected from 0 and 1. In an even further aspect, q is 0. In a still further aspect, q is 1. In yet a further aspect, q is 2. In an even further aspect, q is 3. In a still further aspect, q is 4.

In one aspect, p is selected from 0, 1, and 2. In a further aspect, p is selected from 0 and 1. In a still further aspect, p is selected from 1 and 2. In yet a further aspect, p is 0. In an even further aspect, p is 1. In a still further aspect, p is 2.

In one aspect, r is selected from 0 and 1. In a further aspect, r is 0. In a still further aspect, r is 1.

a. $R^{1A}$ Groups

In one aspect, $R^{1a}$ is selected from hydrogen, C1-C8 alkyl, and $Cy^2$, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a further aspect, $R^{1a}$ is hydrogen.

In a further aspect, $R^{1a}$ is selected from hydrogen, C1-C8 alkyl, and $Cy^2$, and substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $R^{1a}$ is selected from hydrogen, C1-C8 alkyl, and $Cy^2$, and substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $R^{1a}$ is selected from hydrogen, C1-C8 alkyl, and $Cy^2$, and monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $R^{1a}$ is selected from hydrogen, C1-C8 alkyl, and $Cy^2$, and unsubstituted.

In various further aspects, $R^{1a}$ is selected from C1-C8 alkyl and $Cy^2$, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a further aspect, $R^{1a}$ is selected from C1-C8 alkyl and $Cy^2$, and substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $R^{1a}$ is selected from C1-C8 alkyl and $Cy^2$, and substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $R^{1a}$ is selected from C1-C8 alkyl and $Cy^2$, and monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $R^{1a}$ is selected from C1-C8 alkyl and $Cy^2$, and unsubstituted.

In various further aspects, $R^{1a}$ is selected from C1-C4 alkyl and $Cy^2$, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a further aspect, $R^{1a}$ is selected from C1-C4 alkyl and $Cy^2$, and substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $R^{1a}$ is selected from C1-C4 alkyl and $Cy^2$, and substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $R^{1a}$ is selected from C1-C4 alkyl and $Cy^2$, and monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $R^{1a}$ is selected from C1-C4 alkyl and $Cy^2$, and unsubstituted.

In various further aspects, $R^{1a}$ is C1-C8 alkyl substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a further aspect, $R^{1a}$ is C1-C8 alkyl substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $R^{1a}$ is C1-C8 alkyl substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $R^{1a}$ is C1-C8 alkyl monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $R^{1a}$ is unsubstituted C1-C8 alkyl.

In various further aspects, $R^{1a}$ is C1-C4 alkyl substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a further aspect, $R^{1a}$ is C1-C4 alkyl substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $R^{1a}$ is C1-C4 alkyl substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $R^{1a}$ is C1-C4 alkyl monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $R^{1a}$ is unsubstituted C1-C4 alkyl.

In various aspects, $R^{1a}$ is C1-C8 alkyl substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a further aspect, $R^{1a}$ is C1-C8 alkyl substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $R^{1a}$ is C1-C8 alkyl substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $R^{1a}$ is C1-C8 alkyl monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $R^{1a}$ is unsubstituted C1-C8 alkyl.

In various aspects, $R^{1a}$ is C1-C8 alkyl monosubstituted with a C1-C4 alkyl. In a further aspect, $R^{1a}$ is C1-C4 alkyl monosubstituted with a C1-C4 alkyl. In a still further aspect, $R^{1a}$ is selected from methyl, ethyl, n-propyl, and i-propyl, and monosubstituted with a C1-C4 alkyl. In yet a further aspect, $R^{1a}$ is n-butyl monosubstituted with a C1-C4 alkyl.

In various aspects, $R^{1a}$ is C1-C8 alkyl monosubstituted with a methyl group. In a further aspect, $R^{1a}$ is C1-C4 alkyl monosubstituted with a methyl group. In a still further aspect, $R^{1a}$ is selected from methyl, ethyl, n-propyl, and i-propyl, and monosubstituted with a methyl group. In yet a further aspect, $R^{1a}$ is n-butyl monosubstituted with a methyl group.

In various further aspects, $R^{1a}$ is selected from methyl, ethyl, n-propyl, and i-propyl, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a further aspect, $R^{1a}$ is selected from methyl, ethyl, n-propyl, and i-propyl, and substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $R^{1a}$ is selected from methyl, ethyl, n-propyl, and i-propyl, and substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $R^{1a}$ is selected from methyl, ethyl, n-propyl, and i-propyl, and monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $R^{1a}$ is selected from methyl, ethyl, n-propyl, and i-propyl, and unsubstituted.

In various aspects, $R^{1a}$ is $Cy^2$ substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a further aspect. $R^{1a}$ is $Cy^2$ substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $R^{1a}$ is $Cy^2$ substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect. $R^{1a}$ is $Cy^2$ monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $R^{1a}$ is unsubstituted $Cy^2$.

In various aspects, $R^{1a}$ is cyclopropyl substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a further aspect, $R^{1a}$ is cyclopropyl substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $R^{1a}$ is cyclopropyl substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $R^{1a}$ is cyclopropyl monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $R^{1a}$ is unsubstituted cyclopropyl.

In various aspects, $R^{1a}$ is $Cy^2$ monosubstituted with a C1-C4 alkyl. In a further aspect, $R^{1a}$ is cyclopropyl monosubstituted with a C1-C4 alkyl.

In various aspects, $R^{1a}$ is $Cy^2$ monosubstituted with an ethyl group. In a further aspect. $R^{1a}$ is cyclopropyl monosubstituted with an ethyl group.

b. $R^{1B}$ Groups

In one aspect, $R^{1b}$ is selected from C1-C8 alkyl, $Cy^2$, and (C1-C4 alkyl)$Cy^2$, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a further aspect, $R^{1b}$ is selected from C1-C8 alkyl, $Cy^2$, and (C1-C4 alkyl)$Cy^2$, and substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $R^{1b}$ is selected from C1-C8 alkyl, $Cy^2$, and (C1-C4 alkyl)$Cy^2$, and substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect. $R^{1b}$ is selected from C1-C8 alkyl, $Cy^2$, and (C1-C4 alkyl)$Cy^2$, and monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $R^{1b}$ is selected from C1-C8 alkyl, $Cy^2$, and (C1-C4 alkyl)$Cy^2$, and unsubstituted.

In one aspect, $R^{1b}$ is selected from C1-C8 alkyl and $Cy^2$, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a further aspect, $R^{1b}$ is selected from C1-C8 alkyl and $Cy^2$, and substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $R^{1b}$ is selected from C1-C8 alkyl and $Cy^2$, and substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $R^{1b}$ is selected from C1-C8 alkyl and $Cy^2$, and monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $R^{1b}$ is selected from C1-C8 alkyl and $Cy^2$, and unsubstituted.

In a further aspect, $R^{1b}$ is selected from C1-C4 alkyl and $Cy^2$, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $R^{1b}$ is selected from methyl, ethyl, n-propyl, i-propyl, and $Cy^2$, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $R^{1b}$ is selected methyl, ethyl, and $Cy^2$, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $R^{1b}$ is selected from ethyl and $Cy^2$, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $R^{1b}$ is selected from methyl and $Cy^2$, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino.

In a further aspect, $R^{1b}$ is C1-C8 alkyl substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $R^{1b}$ is C1-C8 alkyl substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-

C4) dialkylamino. In yet a further aspect, $R^{1b}$ is C1-C8 alkyl substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect. $R^{1b}$ is C1-C8 alkyl monosubstituted with a group selected from halogen. C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $R^{1b}$ is unsubstituted C1-C8 alkyl.

In a further aspect, $R^{1b}$ is C1-C4 alkyl substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $R^{1b}$ is C1-C4 alkyl substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect. $R^{1b}$ is C1-C4 alkyl substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $R^{1b}$ is C1-C4 alkyl monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $R^{1b}$ is unsubstituted C1-C4 alkyl.

In a further aspect, $R^{1b}$ is selected from methyl, ethyl, n-propyl, and i-propyl, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $R^{1b}$ is selected from methyl, ethyl, n-propyl, and i-propyl, and substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $R^{1b}$ is selected from methyl, ethyl, n-propyl, and i-propyl, and substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $R^{1b}$ is selected from methyl, ethyl, n-propyl, and i-propyl, and monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect. $R^{1b}$ is selected from methyl, ethyl, n-propyl, and i-propyl, and unsubstituted.

In various aspects, $R^{1b}$ is C1-C8 alkyl monosubstituted with a C1-C4 alkyl. In a further aspect, $R^{1b}$ is C1-C4 alkyl monosubstituted with a C1-C4 alkyl. In a still further aspect. $R^{1b}$ is selected from methyl, ethyl, n-propyl, and i-propyl, and monosubstituted with a C1-C4 alkyl. In yet a further aspect, $R^{1b}$ is n-butyl monosubstituted with a C1-C4 alkyl.

In various aspects, $R^{1b}$ is C1-C8 alkyl monosubstituted with a methyl group. In a further aspect, $R^{1b}$ is C1-C4 alkyl monosubstituted with a methyl group. In a still further aspect. $R^{1b}$ is selected from methyl, ethyl, n-propyl, and i-propyl, and monosubstituted with a methyl group. In yet a further aspect, $R^{1b}$ is n-butyl monosubstituted with a methyl group.

In a further aspect, $R^{1b}$ is selected from $Cy^2$ and (C1-C4 alkyl)$Cy^2$ and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $R^{1b}$ is selected from $Cy^2$ and (C1-C4 alkyl)$Cy^2$ and substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $R^{1b}$ is selected from $Cy^2$ and (C1-C4 alkyl)$Cy^2$ and substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $R^{1b}$ is selected from $Cy^2$ and (C1-C4 alkyl)$Cy^2$ and monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $R^{1b}$ is selected from $Cy^2$ and (C1-C4 alkyl)$Cy^2$ and unsubstituted.

In a further aspect, $R^{1b}$ is $Cy^2$ substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $R^{1b}$ is $Cy^2$ substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $R^{1b}$ is $Cy^2$ substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $R^{1b}$ is $Cy^2$ monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $R^{1b}$ is unsubstituted $Cy^2$.

In a further aspect, $R^{1b}$ is cyclopropyl substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $R^{1b}$ is cyclopropyl substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $R^{1b}$ is cyclopropyl substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $R^{1b}$ is cyclopropyl monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $R^{1b}$ is unsubstituted cyclopropyl.

In various aspects, $R^{1b}$ is $Cy^2$ monosubstituted with a C1-C4 alkyl. In a further aspect. $R^{1b}$ is cyclopropyl monosubstituted with a C1-C4 alkyl.

In various aspects, $R^{1b}$ is $Cy^2$ monosubstituted with an ethyl group. In a further aspect, $R^{1b}$ is cyclopropyl monosubstituted with an ethyl group.

In a further aspect, $R^{1b}$ is (C1-C4 alkyl)$Cy^2$ substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $R^{1b}$ is (C1-C4 alkyl)$Cy^2$ substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $R^{1b}$ is (C1-C4 alkyl)$Cy^2$ substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $R^{1b}$ is (C1-C4 alkyl)$Cy^2$ monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $R^{1b}$ is unsubstituted (C1-C4 alkyl)$Cy^2$.

In a further aspect, $R^{1b}$ is C1-C8 alkyl.

In a further aspect, $R^{1b}$ is a structure:

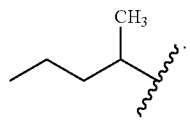 [SMILES: *C(C)CCC]

In a further aspect, $R^{1b}$ is a structure selected from:

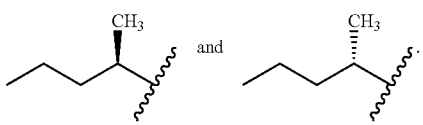

In a further aspect, $R^{1b}$ is a structure:

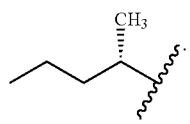

In a further aspect, $R^{1b}$ is a structure:

In a further aspect, $R^{1b}$ is a structure selected from:

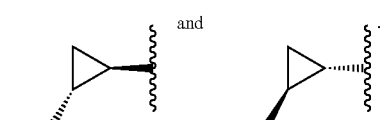

In a further aspect, $R^{1b}$ is a structure selected from:

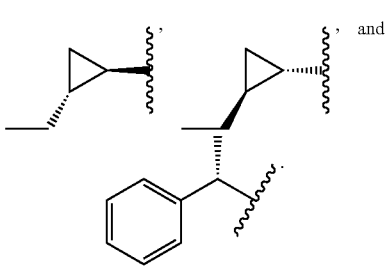

c. $R^2$ Groups

In one aspect, $R^2$ is selected from hydrogen, C1-C4 alkyl, —C(O)$R^{20}$, —C(O)N($R^{22}$)$R^{20}$, —N(R)C(O)$R^{20}$, —SO$_2$N($R^{22}$)$R^{21}$, —N($R^{22}$)SO$_2R^{21}$, —SO$_2R^{21}$, and —(CH$_2$)$_n$Cy$^3$. In a further aspect, $R^2$ is hydrogen.

In one aspect, $R^2$ is selected from —C(O)$R^{20}$, —C(O)N($R^{22}$)$R^{20}$, —N($R^{22}$)C(O)$R^{20}$, —SO$_2$N($R^{22}$)$R^{21}$, —N($R^{22}$)SO$_2R^{21}$, —SO$_2R^{21}$, and —(CH$_2$)$_n$Cy$^3$.

In a further aspect, $R^2$ is selected from —C(O)$R^{20}$, —C(O)N($R^{22}$)$R^{20}$, —SO$_2$N($R^{22}$)$R^{21}$, —SO$_2R^{21}$, and —(CH$_2$)$_n$Cy$^3$. In a still further aspect, $R^2$ is selected from —C(O)$R^{20}$, —C(O)N($R^{22}$)$R^{20}$, —SO$_2R^{21}$, and —(CH$_2$)$_n$Cy$^3$. In yet a further aspect, $R^2$ is selected from —C(O)$R^{20}$, —SO$_2R^{21}$, and —(CH$_2$)Cy$^3$. In an even further aspect, $R^2$ is selected from —C(O)N($R^{22}$)$R^{20}$, —SO$_2$N($R^{22}$)$R^{21}$, and —(CH$_2$)$_n$Cy$^3$. In a still further aspect, $R^2$ is —C(O)N($R^{22}$)$R^{20}$. In yet a further aspect, $R^2$ is —SO$_2$N($R^{22}$)$R^{21}$. In an even further aspect, $R^2$ is —(CH$_2$)$_n$Cy$^3$.

In a further aspect, $R^2$ is selected from —C(O)$R^{20}$, —N($R^{22}$)C(O)$R^{20}$, —N($R^{22}$)SO$_2R^{21}$, —SO$_2R^{21}$, and —(CH$_2$)Cy$^3$. In a still further aspect, $R^2$ is selected from —N($R^{22}$)C(O)$R^{20}$, —N($R^{22}$)SO$_2R^{21}$, and —(CH$_2$)$_n$Cy$^3$. In yet a further aspect, $R^2$ is —N($R^{22}$)C(O)$R^{20}$. In an even further aspect, $R^2$ is —N($R^{22}$)SO$_2R^{21}$.

In a further aspect, $R^2$ is selected from —C(O)$R^{20}$ and —SO$_2R^{21}$. In a still further aspect, $R^2$ is —C(O)$R^{20}$. In yet a further aspect, $R^2$ is —SO$_2R^{21}$.

In a further aspect, $R^2$ is selected form hydrogen and C1-C4 alkyl. In a still further aspect, $R^2$ is selected from hydrogen, methyl, ethyl, n-propyl, and i-propyl. In yet a further aspect, $R^2$ is selected from hydrogen, methyl, and ethyl. In an even further aspect, $R^2$ is selected from hydrogen and ethyl. In a still further aspect, $R^2$ is selected from hydrogen and methyl.

In a further aspect, $R^2$ is selected from methyl, ethyl, n-propyl, i-propyl, n-butyl, i-butyl, s-butyl, and t-butyl. In a still further aspect, $R^2$ is selected from methyl, ethyl, n-propyl, and i-propyl. In yet a further aspect, $R^2$ is selected from methyl and ethyl. In an even further aspect, $R^2$ is ethyl. In a still further aspect, $R^2$ is methyl.

d. $R^3$ Groups

In one aspect, $R^3$ is selected from —(CH$_2$)$_p$OH and —(CH$_2$)$_p$NHR$^{23}$. In a further aspect, $R^3$ is —(CH$_2$)$_p$OH. In a still further aspect, $R^3$ is —(CH$_2$)$_p$NHR$^{23}$.

In a further aspect, $R^3$ is selected from —CH$_2$OH and —CH$_2$NHR$^{23}$. In a still further aspect, $R^3$ is —CH$_2$OH. In yet a further aspect, $R^3$ is —CH$_2$NHR$^{23}$.

In a further aspect, $R^3$ is selected from —OH and —NHR$^{23}$. In a still further aspect, $R^3$ is —OH. In yet a further aspect, $R^3$ is —NHR$^{23}$.

e. $R^{20}$ and $R^{21}$ Groups

In one aspect, each of $R^{20}$ and $R^{21}$, when present, is selected from C1-C4 alkyl, —(CH$_2$)$_q$OR$^{30}$, and Cy$^4$. In a further aspect, each of $R^{20}$ and $R^{21}$, when present, is Cy$^4$.

In a further aspect, each of $R^2$ and $R^{20}$, when present, is selected from methyl, ethyl, n-propyl, i-propyl, n-butyl, s-butyl, i-butyl, and t-butyl. In a still further aspect, each of $R^{20}$ and $R^{21}$, when present, is selected from methyl, ethyl, n-propyl, and i-propyl. In yet a further aspect, each of $R^{20}$ and $R^{21}$, when present, is selected from methyl and ethyl. In an even further aspect, each of $R^{20}$ and $R^{21}$, when present, is ethyl. In a still further aspect, each of $R^{20}$ and $R^{21}$, when present, is methyl.

In a further aspect, each of $R^{20}$ and $R^{21}$, when present, is —(CH$_2$)$_q$OR$^{30}$. In a still further aspect, each of $R^{20}$ and $R^{21}$, when present, is —(CH$_2$)$_3$OR$^{30}$. In yet a further aspect, each of $R^{20}$ and $R^{21}$, when present, is —$(CH_2)_2OR^{30}$. In an even further aspect, each of $R^{20}$ and $R^{21}$, when present, is —$CH_2OR^{30}$. In a still further aspect, each of $R^{20}$ and $R^{21}$, when present, is —$OR^{30}$.

In a further aspect, each of $R^{20}$ and $R^{21}$, when present, is —$(CH_2)_qOH$. In a still further aspect, each of $R^{20}$ and $R^{21}$, when present, is —$(CH_2)_3OH$. In yet a further aspect, each of $R^{20}$ and $R^{21}$, when present, is —$(CH_2)_2OH$. In an even further aspect, each of $R^{20}$ and $R^{21}$, when present, is —$CH_2OH$. In a still further aspect, each of $R^{20}$ and $R^{21}$, when present, is —OH.

f. $R^2$ Groups

In one aspect, $R^{22}$, when present, is selected from hydrogen and C1-C4 alkyl. In a further aspect, $R^{22}$, when present, is hydrogen.

In a further aspect, $R^{22}$, when present, is selected from hydrogen, methyl, ethyl, n-propyl, and i-propyl. In a still further aspect, $R^{22}$, when present, is selected from hydrogen, methyl, and ethyl. In yet a further aspect. $R^{22}$, when present, is selected from hydrogen and ethyl. In an even further aspect, $R^{22}$, when present, is selected from hydrogen and methyl.

In a further aspect, $R^{22}$, when present, is C1-C4 alkyl. In a still further aspect, $R^{22}$, when present, is selected from methyl, ethyl, n-propyl, and i-propyl. In yet a further aspect, $R^{22}$, when present, is selected from methyl and ethyl. In an even further aspect, $R^{22}$, when present, is ethyl. In a still further aspect, R, when present, is methyl.

g. $R^2$ Groups

In one aspect, $R^{23}$, when present, is selected from hydrogen and C1-C4 alkyl. In a further aspect, $R^{23}$, when present, is hydrogen.

In a further aspect, $R^{23}$, when present, is selected from hydrogen, methyl, ethyl, n-propyl, and i-propyl. In a still further aspect, $R^{23}$, when present, is selected from hydrogen, methyl, and ethyl. In yet a further aspect, $R^{23}$, when present, is selected from hydrogen and ethyl. In an even further aspect, $R^{23}$, when present, is selected from hydrogen and methyl.

In a further aspect, $R^{23}$, when present, is C1-C4 alkyl. In a still further aspect, $R^{23}$, when present, is selected from methyl, ethyl, n-propyl, and i-propyl. In yet a further aspect, $R^{23}$, when present, is selected from methyl and ethyl. In an even further aspect, $R^{23}$, when present, is ethyl. In a still further aspect, $R^{23}$, when present, is methyl.

h. $R^{30}$ Groups

In one aspect, $R^{30}$, when present, is selected from hydrogen and C1-C4 alkyl. In a further aspect, $R^{30}$, when present, is hydrogen.

In a further aspect, $R^{30}$, when present, is selected from hydrogen, methyl, ethyl, n-propyl, and i-propyl. In a still further aspect, $R^{30}$, when present, is selected from hydrogen, methyl, and ethyl. In yet a further aspect. $R^{30}$, when present, is selected from hydrogen and ethyl. In an even further aspect, $R^{30}$, when present, is selected from hydrogen and methyl.

In a further aspect, $R^{30}$, when present, is C1-C4 alkyl. In a still further aspect, $R^{30}$, when present, is selected from methyl, ethyl, n-propyl, and i-propyl. In yet a further aspect, $R^{30}$, when present, is selected from methyl and ethyl. In an even further aspect, $R^{30}$, when present, is ethyl. In a still further aspect, $R^{30}$, when present, is methyl.

i. $R^{40A}$ and $R^{40B}$ Groups

In one aspect, each of $R^{40a}$ and $R^{40b}$, when present, is independently selected from hydrogen and C1-C4 alkyl. In a further aspect, each of $R^{40a}$ and $R^{40b}$, when present, is hydrogen.

In a further aspect, each of $R^{40a}$ and $R^{40b}$, when present, is independently selected from hydrogen, methyl, ethyl, n-propyl, and i-propyl. In a still further aspect, each of $R^{41a}$ and $R^{40b}$, when present, is independently selected from hydrogen, methyl, and ethyl. In yet a further aspect, each of $R^{40a}$ and $R^{40b}$, when present, is independently selected from hydrogen and ethyl. In an even further aspect, each of $R^{40a}$ and $R^{40b}$, when present, is independently selected from hydrogen and methyl.

In a further aspect, each of $R^{40a}$ and $R^{40b}$, when present, is independently C1-C4 alkyl. In a still further aspect, each of $R^{40a}$ and $R^{40b}$, when present, is independently selected from methyl, ethyl, n-propyl, and i-propyl. In yet a further aspect, each of $R^{40a}$ and $R^{40b}$, when present, is independently selected from methyl and ethyl. In an even further aspect, each of $R^{40a}$ and $R^{40b}$, when present, is methyl.

j. $Cy^1$ Groups

In one aspect, $Cy^1$ is selected from C3-C8 cycloalkyl and C2-C7 heterocycloalkyl, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a further aspect. $Cy^1$ is selected from C3-C8 cycloalkyl and C2-C7 heterocycloalkyl, and substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^1$ is selected from C3-C8 cycloalkyl and C2-C7 heterocycloalkyl, and substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $Cy^1$ is selected from C3-C8 cycloalkyl and C2-C7 heterocycloalkyl, and monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $Cy^1$ is selected from C3-C8 cycloalkyl and C2-C7 heterocycloalkyl, and unsubstituted.

In a further aspect, $Cy^1$ is C3-C8 cycloalkyl substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^1$ is C3-C8 cycloalkyl substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $Cy^1$ is C3-C8 cycloalkyl substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $Cy^1$ is C3-C8 cycloalkyl monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^1$ is unsubstituted C3-C8 cycloalkyl.

In a further aspect, $Cy^1$ is C2-C7 heterocycloalkyl substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^1$ is C2-C7 heterocycloalkyl substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $Cy^1$ is C2-C7 heterocycloalkyl substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $Cy^1$ is C2-C7 heterocycloalkyl monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^1$ is unsubstituted C2-C7 heterocycloalkyl.

In a further aspect, $Cy^1$ is piperidinyl substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^1$ is piperidinyl substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $Cy^1$ is piperidinyl substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $Cy^1$ is piperidinyl monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^1$ is unsubstituted piperidinyl.

In a further aspect, $Cy^1$ is tetrahydro-2H-pyranyl substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^1$ is tetrahydro-2H-pyranyl substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $Cy^1$ is tetrahydro-2H-pyranyl substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $Cy^1$ is tetrahydro-2H-pyranyl monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^1$ is unsubstituted tetrahydro-2H-pyranyl.

In a further aspect, $Cy^1$ is a structure selected from:

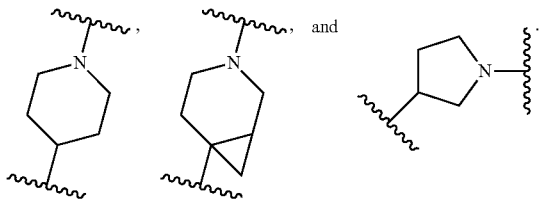 [SMILES: *C1CCN(*)CC1 ; *N1CCC2(*)CC2C1 ; *C1CCN(*)C1]

In a further aspect, $Cy^1$ is a structure selected from:

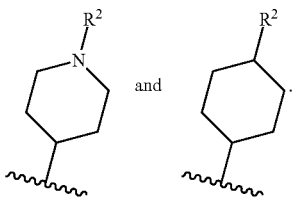

In a further aspect, $Cy^1$ is a structure selected from:

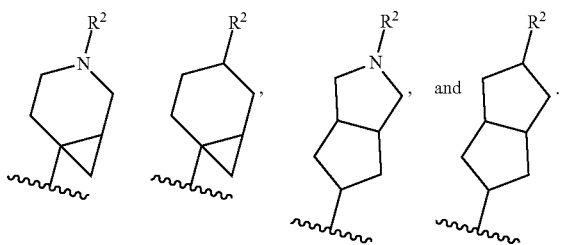

k. $Cy^2$ Groups

In one aspect, $Cy^2$, when present, is selected from C3-C9 cycloalkyl, C2-C7 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a further aspect, $Cy^2$, when present, is selected from C3-C9 cycloalkyl, C2-C7 heterocycloalkyl, C5-C6 aryl, and C4-C5 heteroaryl and substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^2$, when present, is selected from C3-C9 cycloalkyl, C2-C7 heterocycloalkyl, C5-C6 aryl, and C4-C5 heteroaryl and substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $Cy^2$, when present, is selected from C3-C9 cycloalkyl, C2-C7 heterocycloalkyl, C5-C6 aryl, and C4-C5 heteroaryl and monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $Cy^2$, when present, is selected from C3-C9 cycloalkyl, C2-C7 heterocycloalkyl, C5-C6 aryl, and C4-C5 heteroaryl and unsubstituted.

In one aspect, $Cy^2$, when present, is selected from C3-C8 cycloalkyl, C2-C7 heterocycloalkyl. C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^2$, when present, is selected from C3-C8 cycloalkyl, C2-C7 heterocycloalkyl, C5-C6 aryl, and C4-C5 heteroaryl and substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $Cy^2$, when present, is selected from C3-C8 cycloalkyl, C2-C7 heterocycloalkyl, C5-C6 aryl, and C4-C5 heteroaryl and substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $Cy^2$, when present, is selected from C3-C8 cycloalkyl, C2-C7 heterocycloalkyl, C5-C6 aryl, and C4-C5 heteroaryl and monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^2$, when present, is selected from C3-C8 cycloalkyl, C2-C7 heterocycloalkyl, C5-C6 aryl, and C4-C5 heteroaryl and unsubstituted.

In a further aspect, $Cy^2$, when present, is selected from C3-C8 cycloalkyl and C2-C7 heterocycloalkyl, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^2$, when present, is selected from C3-C8 cycloalkyl and C2-C7 heterocycloalkyl, and substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $Cy^2$, when present, is selected from C3-C8 cycloalkyl and C2-C7 heterocycloalkyl, and substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $Cy^2$, when present, is selected from C3-C8 cycloalkyl and C2-C7 heterocycloalkyl, and monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^2$, when present, is selected from C3-C8 cycloalkyl and C2-C7 heterocycloalkyl, and unsubstituted.

In a further aspect, $Cy^2$, when present, is C3-C9 cycloalkyl substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^2$, when present, is C3-C9 cycloalkyl substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $Cy^2$, when present, is C3-C9 cycloalkyl substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $Cy^2$, when present, is C3-C9 cycloalkyl monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^2$, when present, is unsubstituted C3-C9 cycloalkyl.

In a further aspect, $Cy^2$, when present, is C3-C8 cycloalkyl substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect. $Cy^2$, when present, is C3-C8 cycloalkyl substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $Cy^2$, when present, is C3-C8 cycloalkyl substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $Cy^2$, when present, is C3-C8 cycloalkyl monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^2$, when present, is unsubstituted C3-C8 cycloalkyl.

In a further aspect, $Cy^2$, when present, is cyclopropyl substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^2$, when present, is cyclopropyl substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $Cy^2$, when present, is cyclopropyl substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $Cy^2$, when present, is cyclopropyl monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^2$, when present, is unsubstituted cyclopropyl.

In various aspects. $Cy^2$ is C3-C8 cycloalkyl monosubstituted with a C1-C4 alkyl. In a further aspect. $Cy^2$ is cyclopropyl monosubstituted with a C1-C4 alkyl.

In various aspects, $Cy^2$ is C3-C8 cycloalkyl monosubstituted with an ethyl group. In a further aspect, $Cy^2$ is cyclopropyl monosubstituted with an ethyl group.

In a further aspect, $Cy^2$, when present, is C2-C7 heterocycloalkyl substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^2$, when present, is C2-C7 heterocycloalkyl substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $Cy^2$, when present, is C2-C7 heterocycloalkyl substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $Cy^2$, when present, is C2-C7 heterocycloalkyl monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^2$, when present, is unsubstituted C2-C7 heterocycloalkyl.

In a further aspect, $Cy^2$, when present, is selected from azetidine, aziridine, oxetane, oxirane, piperidine, pyrrolidine, tetrahydro-2H-pyran, tetrahydro-2H-thiopyran, tetrahydrofuran, tetrahydrothiophene, thietane, thiirane, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^2$, when present, is selected from azetidine, aziridine, oxetane, oxirane, piperidine, pyrrolidine, tetrahydro-2H-pyran, tetrahydro-2H-thiopyran, tetrahydrofuran, tetrahydrothiophene, thietane, thiirane, and substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, Cy$^2$, when present, is selected from azetidine, aziridine, oxetane, oxirane, piperidine, pyrrolidine, tetrahydro-2H-pyran, tetrahydro-2H-thiopyran, tetrahydrofuran, tetrahydrothiophene, thietane, thiirane, and substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, Cy$^2$, when present, is selected from azetidine, aziridine, oxetane, oxirane, piperidine, pyrrolidine, tetrahydro-2H-pyran, tetrahydro-2H-thiopyran, tetrahydrofuran, tetrahydrothiophene, thietane, thiirane, and monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, Cy$^2$, when present, is selected from azetidine, aziridine, oxetane, oxirane, piperidine, pyrrolidine, tetrahydro-2H-pyran, tetrahydro-2H-thiopyran, tetrahydrofuran, tetrahydrothiophene, thietane, thiirane, and unsubstituted.

In a further aspect, Cy$^2$, when present, is selected from C5-C6 aryl and C4-C5 heteroaryl and substituted with 0, 1, 2, or 3 groups independently selected from halogen. C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, Cy$^2$, when present, is selected from C5-C6 aryl and C4-C5 heteroaryl and substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, Cy$^2$, when present, is selected from C5-C6 aryl and C4-C5 heteroaryl and substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, Cy$^2$, when present, is selected from C5-C6 aryl and C4-C5 heteroaryl and monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, Cy$^2$, when present, is selected from C5-C6 aryl and C4-C5 heteroaryl and unsubstituted.

In a further aspect, Cy$^2$, when present, is C5-C6 aryl substituted with 0, 1, 2, or 3 groups independently selected from halogen, C1-C4 alkyl, C1-C4 haloalkyl, C1-C4 alkoxy. C1-C4 hydroxyalkyl, C1-C4 alkylamino, and (C1-C4)(C1-C4) dialkylamino. In a still further aspect, Cy$^2$, when present, is C5-C6 aryl substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, Cy$^2$, when present, is C5-C6 aryl substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, Cy$^2$, when present, is C5-C6 aryl monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, Cy$^2$, when present, is unsubstituted C5-C6 aryl.

In a further aspect, Cy$^2$, when present, is phenyl substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, Cy$^2$, when present, is phenyl substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, Cy$^2$, when present, is phenyl substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, Cy$^2$, when present, is phenyl monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, Cy$^2$, when present, is unsubstituted phenyl.

In a further aspect, Cy$^2$, when present, is C4-C5 heteroaryl substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, Cy$^2$, when present, is C4-C5 heteroaryl substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, Cy$^2$, when present, is C4-C5 heteroaryl substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, Cy$^2$, when present, is C4-C5 heteroaryl monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, Cy$^2$, when present, is unsubstituted C4-C5 heteroaryl.

In a further aspect, Cy$^2$, when present, is selected from 1H-pyrrole, furan, pyridine, and thiophene, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, Cy$^2$, when present, is selected from 1H-pyrrole, furan, pyridine, and thiophene, and substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect. Cy$^2$, when present, is selected from 1H-pyrrole, furan, pyridine, and thiophene, and substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, Cy$^2$, when present, is selected from 1H-pyrrole, furan, pyridine, and thiophene, and monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, Cy$^2$, when present, is selected from 1H-pyrrole, furan, pyridine, and thiophene, and unsubstituted.

I. Cy$^3$ Groups

In one aspect, Cy$^3$, when present, is selected from C3-C8 cycloalkyl, C2-C7 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, Cy$^3$, when present, is selected from C3-C8 cycloalkyl, C2-C7 heterocycloalkyl. C5-C6 aryl, and C4-C5 heteroaryl and substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect. Cy$^3$, when present, is selected from C3-C8 cycloalkyl, C2-C7 heterocycloalkyl, C5-C6 aryl, and C4-C5 heteroaryl and substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $Cy^3$, when present, is selected from C3-C8 cycloalkyl, C2-C7 heterocycloalkyl, C5-C6 aryl, and C4-C5 heteroaryl and monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^3$, when present, is selected from C3-C8 cycloalkyl, C2-C7 heterocycloalkyl, C5-C6 aryl, and C4-C5 heteroaryl and unsubstituted.

In a further aspect, $Cy^3$, when present, is selected from C3-C8 cycloalkyl and C2-C7 heterocycloalkyl, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^3$, when present, is selected from C3-C8 cycloalkyl and C2-C7 heterocycloalkyl, and substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $Cy^3$, when present, is selected from C3-C8 cycloalkyl and C2-C7 heterocycloalkyl, and substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $Cy^3$, when present, is selected from C3-C8 cycloalkyl and C2-C7 heterocycloalkyl, and monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^3$, when present, is selected from C3-C8 cycloalkyl and C2-C7 heterocycloalkyl, and unsubstituted.

In a further aspect, $Cy^3$, when present, is C3-C8 cycloalkyl substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^3$, when present, is C3-C8 cycloalkyl substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $Cy^3$, when present, is C3-C8 cycloalkyl substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $Cy^3$, when present, is C3-C8 cycloalkyl monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^3$, when present, is unsubstituted C3-C8 cycloalkyl.

In a further aspect, $Cy^3$, when present, is C2-C7 heterocycloalkyl substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^3$, when present, is C2-C7 heterocycloalkyl substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $Cy^3$, when present, is C2-C7 heterocycloalkyl substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $Cy^3$, when present, is C2-C7 heterocycloalkyl monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^3$, when present, is unsubstituted C2-C7 heterocycloalkyl.

In a further aspect, $Cy^3$, when present, is pyridinyl substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^3$, when present, is pyridinyl substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect. $Cy^3$, when present, is pyridinyl substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $Cy^3$, when present, is pyridinyl monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^3$, when present, is unsubstituted pyridinyl.

In a further aspect, $Cy^3$, when present, is selected from C5-C6 aryl and C4-C5 heteroaryl and substituted with 0, 1, 2, or 3 groups independently selected from halogen. C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^3$, when present, is selected from C5-C6 aryl and C4-C5 heteroaryl and substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $Cy^3$, when present, is selected from C5-C6 aryl and C4-C5 heteroaryl and substituted with 0 or 1 group selected from halogen, C1-C4 alkyl, C1-C4 haloalkyl, C1-C4 alkoxy, C1-C4 hydroxyalkyl. C1-C4 alkylamino, and (C1-C4)(C1-C4) dialkylamino. In an even further aspect, $Cy^3$, when present, is selected from C5-C6 aryl and C4-C5 heteroaryl and monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^3$, when present, is selected from C5-C6 aryl and C4-C5 heteroaryl and unsubstituted.

In a further aspect, $Cy^3$, when present, is C5-C6 aryl substituted with 0, 1, 2, or 3 groups independently selected from halogen, C1-C4 alkyl, C1-C4 haloalkyl, C1-C4 alkoxy. C1-C4 hydroxyalkyl, C1-C4 alkylamino, and (C1-C4)(C1-C4) dialkylamino. In a still further aspect, $Cy^3$, when present, is C5-C6 aryl substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $Cy^3$, when present, is C5-C6 aryl substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $Cy^3$, when present, is C5-C6 aryl monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^3$, when present, is unsubstituted C5-C6 aryl.

In a further aspect, $Cy^3$, when present, is phenyl substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^3$, when present, is phenyl substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $Cy^3$, when present, is phenyl substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $Cy^3$, when present, is phenyl monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect. $Cy^3$, when present, is unsubstituted phenyl.

In a further aspect, $Cy^3$, when present, is C4-C5 heteroaryl substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^3$, when present, is C4-C5 heteroaryl substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $Cy^3$, when present, is C4-C5 heteroaryl substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $Cy^3$, when present, is C4-C5 heteroaryl monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^3$, when present, is unsubstituted C4-C5 heteroaryl.

In a further aspect, $Cy^3$, when present, is selected from 1H-pyrrole, furan, pyridine, and thiophene, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^3$, when present, is selected from 1H-pyrrole, furan, pyridine, and thiophene, and substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $Cy^3$, when present, is selected from 1H-pyrrole, furan, pyridine, and thiophene, and substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $Cy^3$, when present, is selected from 1H-pyrrole, furan, pyridine, and thiophene, and monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^3$, when present, is selected from 1H-pyrrole, furan, pyridine, and thiophene, and unsubstituted.

m. $Cy^4$ Groups

In one aspect, $Cy^4$, when present, is selected from C3-C8 cycloalkyl, C2-C7 heterocycloalkyl, C5-C6 aryl, and C3-C5 heteroaryl and substituted with 0, 1, 2, or 3 groups independently selected from halogen, —$NH_2$, C1-C4 alkyl, C1-C4 haloalkyl, C1-C4 alkoxy, C1-C4 hydroxyalkyl, C1-C4 alkylamino, (C1-C4)(C1-C4) dialkylamino, and (C1-C4 alkyl)$NR^{40a}R^{40b}$. In a further aspect, $Cy^4$, when present, is selected from C3-C8 cycloalkyl, C2-C7 heterocycloalkyl, C5-C6 aryl, and C3-C5 heteroaryl and substituted with 0, 1, or 2 groups independently selected from halogen, —$NH_2$, C1-C4 alkyl, C1-C4 haloalkyl, C1-C4 alkoxy, C1-C4 hydroxyalkyl, C1-C4 alkylamino, (C1-C4)(C1-C4) dialkylamino, and (C1-C4 alkyl)$NR^{40a}R^{40b}$. In a still further aspect, $Cy^4$, when present, is selected from C3-C8 cycloalkyl, C2-C7 heterocycloalkyl, C5-C6 aryl, and C3-C5 heteroaryl and substituted with 0 or 1 group selected from halogen, —$NH_2$, C1-C4 alkyl, C1-C4 haloalkyl, C1-C4 alkoxy, C1-C4 hydroxyalkyl, C1-C4 alkylamino. (C1-C4)(C1-C4) dialkylamino, and (C1-C4 alkyl)$NR^{40a}R^{40b}$. In yet a further aspect, $Cy^4$, when present, is selected from C3-C8 cycloalkyl, C2-C7 heterocycloalkyl, C5-C6 aryl, and C3-C5 heteroaryl and monosubstituted with a group selected from halogen, —$NH_2$, C1-C4 alkyl, C1-C4 haloalkyl, C1-C4 alkoxy, C1-C4 hydroxyalkyl, C1-C4 alkylamino, (C1-C4)(C1-C4) dialkylamino, and (C1-C4 alkyl)$NR^{40a}R^{40b}$. In an even further aspect, $Cy^4$, when present, is selected from C3-C8 cycloalkyl, C2-C7 heterocycloalkyl, C5-C6 aryl, and C3-C5 heteroaryl and unsubstituted.

In one aspect, $Cy^4$, when present, is selected from C3-C8 cycloalkyl, C2-C7 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^4$, when present, is selected from C3-C8 cycloalkyl, C2-C7 heterocycloalkyl, C5-C6 aryl, and C4-C5 heteroaryl and substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $Cy^4$, when present, is selected from C3-C8 cycloalkyl, C2-C7 heterocycloalkyl, C5-C6 aryl, and C4-C5 heteroaryl and substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $Cy^4$, when present, is selected from C3-C8 cycloalkyl, C2-C7 heterocycloalkyl, C5-C6 aryl, and C4-C5 heteroaryl and monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^4$, when present, is selected from C3-C8 cycloalkyl. C2-C7 heterocycloalkyl, C5-C6 aryl, and C4-C5 heteroaryl and unsubstituted.

In a further aspect, $Cy^4$, when present, is selected from C3-C8 cycloalkyl and C2-C7 heterocycloalkyl, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^4$, when present, is selected from C3-C8 cycloalkyl and C2-C7 heterocycloalkyl, and substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $Cy^4$, when present, is selected from C3-C8 cycloalkyl and C2-C7 heterocycloalkyl, and substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $Cy^4$, when present, is selected from C3-C8 cycloalkyl and C2-C7 heterocycloalkyl, and monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect. $Cy^4$, when present, is selected from C3-C8 cycloalkyl and C2-C7 heterocycloalkyl, and unsubstituted.

In a further aspect, $Cy^4$, when present, is C3-C8 cycloalkyl substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^4$, when present, is C3-C8 cycloalkyl substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $Cy^4$, when present, is C3-C8 cycloalkyl substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $Cy^4$, when present, is C3-C8 cycloalkyl monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^4$, when present, is unsubstituted C3-C8 cycloalkyl.

In a further aspect, $Cy^4$, when present, is cyclopropyl substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect. $Cy^4$, when present, is cyclopropyl substituted with 0, 1, or 2 groups independently selected from halogen, C1-C4 alkyl, C1-C4 haloalkyl, C1-C4 alkoxy, C1-C4 hydroxyalkyl. C1-C4 alkylamino, and (C1-C4)(C1-C4) dialkylamino. In yet a further aspect, $Cy^4$, when present, is cyclopropyl substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $Cy^4$, when present, is cyclopropyl monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^4$, when present, is unsubstituted cyclopropyl.

In various aspects, $Cy^4$ is C3-C8 cycloalkyl monosubstituted with a C1-C4 alkyl. In a further aspect, $Cy^4$ is cyclopropyl monosubstituted with a C1-C4 alkyl.

In various aspects, $Cy^4$ is C3-C8 cycloalkyl monosubstituted with an ethyl group. In a further aspect, $Cy^4$ is cyclopropyl monosubstituted with an ethyl group.

In a further aspect, $Cy^4$, when present, is C2-C7 heterocycloalkyl substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^4$, when present, is C2-C7 heterocycloalkyl substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $Cy^4$, when present, is C2-C7 heterocycloalkyl substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $Cy^4$, when present, is C2-C7 heterocycloalkyl monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^4$, when present, is unsubstituted C2-C7 heterocycloalkyl.

In a further aspect, $Cy^4$, when present, is selected from azetidine, aziridine, oxetane, oxirane, piperidine, pyrrolidine, tetrahydro-2H-pyran, tetrahydro-2H-thiopyran, tetrahydrofuran, tetrahydrothiophene, thietane, thiirane, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect. $Cy^4$, when present, is selected from azetidine, aziridine, oxetane, oxirane, piperidine, pyrrolidine, tetrahydro-2H-pyran, tetrahydro-2H-thiopyran, tetrahydrofuran, tetrahydrothiophene, thietane, thiirane, and substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $Cy^4$, when present, is selected from azetidine, aziridine, oxetane, oxirane, piperidine, pyrrolidine, tetrahydro-2H-pyran, tetrahydro-2H-thiopyran, tetrahydrofuran, tetrahydrothiophene, thietane, thiirane, and substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $Cy^4$, when present, is selected from azetidine, aziridine, oxetane, oxirane, piperidine, pyrrolidine, tetrahydro-2H-pyran, tetrahydro-2H-thiopyran, tetrahydrofuran, tetrahydrothiophene, thietane, thiirane, and monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^4$, when present, is selected from azetidine, aziridine, oxetane, oxirane, piperidine, pyrrolidine, tetrahydro-2H-pyran, tetrahydro-2H-thiopyran, tetrahydrofuran, tetrahydrothiophene, thietane, thiirane, and unsubstituted.

In a further aspect, $Cy^4$, when present, is selected from C5-C6 aryl and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^4$, when present, is selected from C5-C6 aryl and C4-C5 heteroaryl and substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, $Cy^4$, when present, is selected from C5-C6 aryl and C4-C5 heteroaryl and substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, $Cy^4$, when present, is selected from C5-C6 aryl and C4-C5 heteroaryl and monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^4$, when present, is selected from C5-C6 aryl and C4-C5 heteroaryl and unsubstituted.

In a further aspect, $Cy^4$, when present, is C5-C6 aryl substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, $Cy^4$, when present, is C5-C6 aryl substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, Cy⁴, when present, is C5-C6 aryl substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, Cy⁴, when present, is C5-C6 aryl monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, Cy⁴, when present, is unsubstituted C5-C6 aryl.

In a further aspect, Cy⁴, when present, is phenyl substituted with 0, 1, 2, or 3 groups independently selected from halogen, C1-C4 alkyl, C1-C4 haloalkyl, C1-C4 alkoxy. C1-C4 hydroxyalkyl, C1-C4 alkylamino, and (C1-C4)(C1-C4) dialkylamino. In a still further aspect, Cy⁴, when present, is phenyl substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, Cy⁴, when present, is phenyl substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect. Cy⁴, when present, is phenyl monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, Cy⁴, when present, is unsubstituted phenyl.

In a further aspect, Cy⁴, when present, is C4-C5 heteroaryl substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect. Cy⁴, when present, is C4-C5 heteroaryl substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, Cy⁴, when present, is C4-C5 heteroaryl substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, Cy⁴, when present, is C4-C5 heteroaryl monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, Cy⁴, when present, is unsubstituted C4-C5 heteroaryl.

In a further aspect, Cy⁴, when present, is selected from 1H-pyrrole, furan, pyridine, and thiophene, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect, Cy⁴, when present, is selected from 1H-pyrrole, furan, pyridine, and thiophene, and substituted with 0, 1, or 2 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In yet a further aspect, Cy⁴, when present, is selected from 1H-pyrrole, furan, pyridine, and thiophene, and substituted with 0 or 1 group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In an even further aspect, Cy⁴, when present, is selected from 1H-pyrrole, furan, pyridine, and thiophene, and monosubstituted with a group selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino. In a still further aspect. Cy⁴, when present, is selected from 1H-pyrrole, furan, pyridine, and thiophene, and unsubstituted.

2. Example Compounds

In one aspect, a compound can be present as one or more of the following structures:

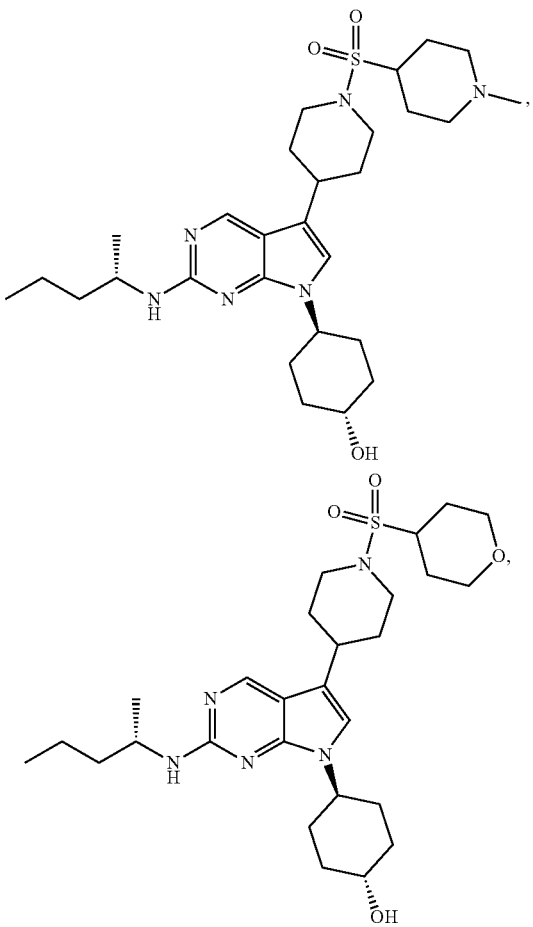

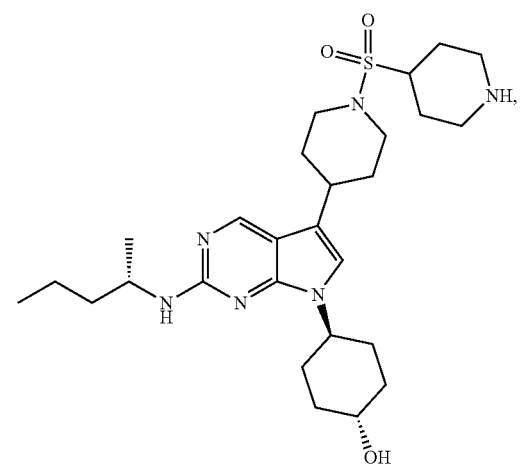

87
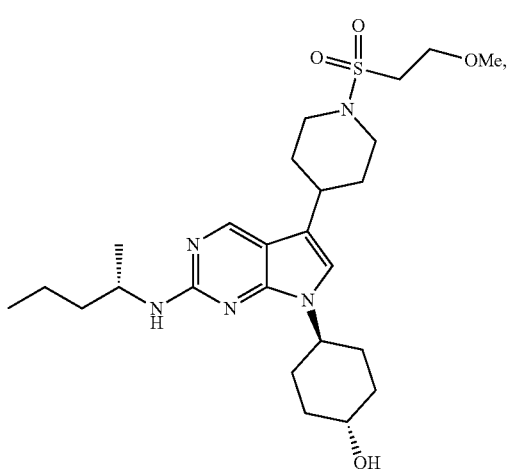
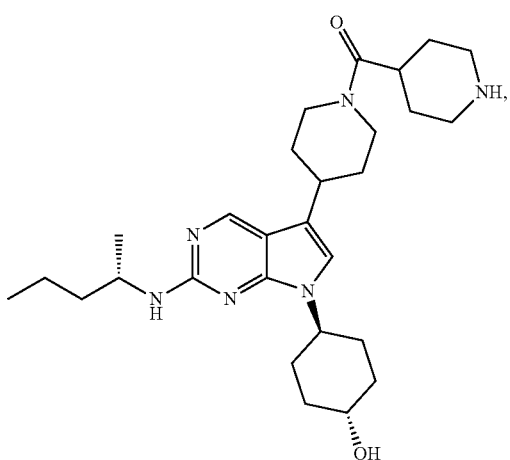
88
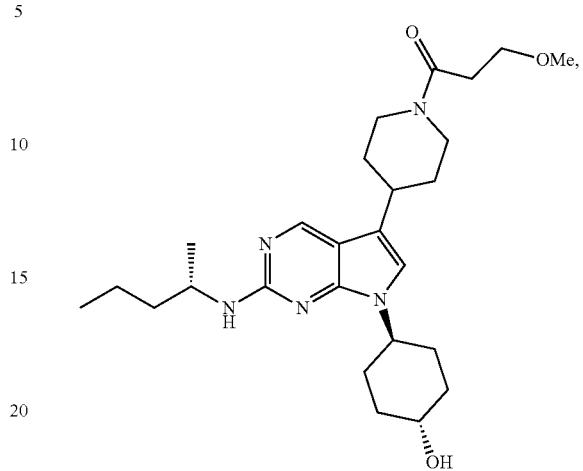
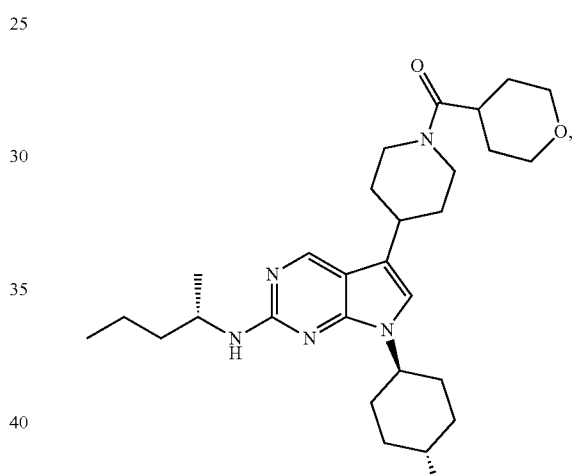
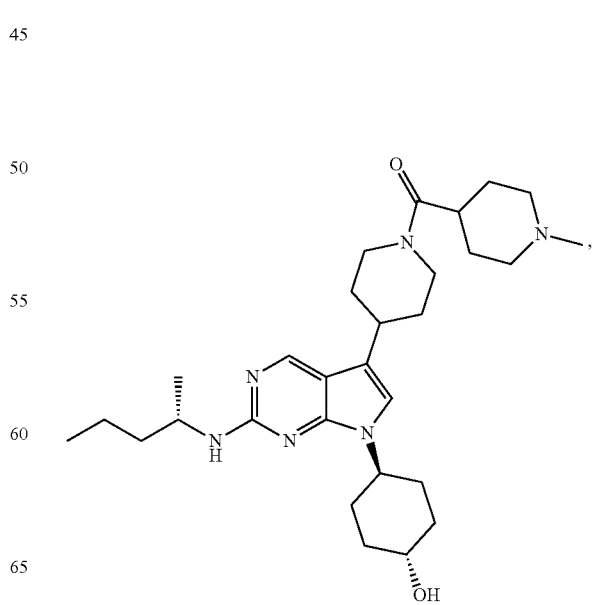

89
-continued
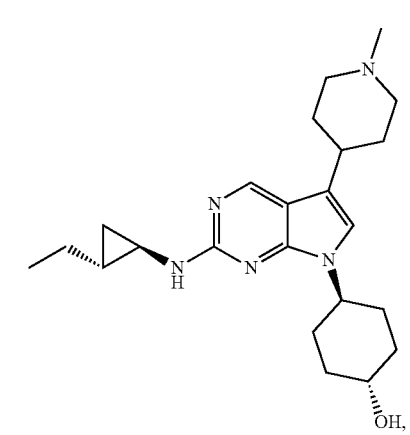
90
-continued
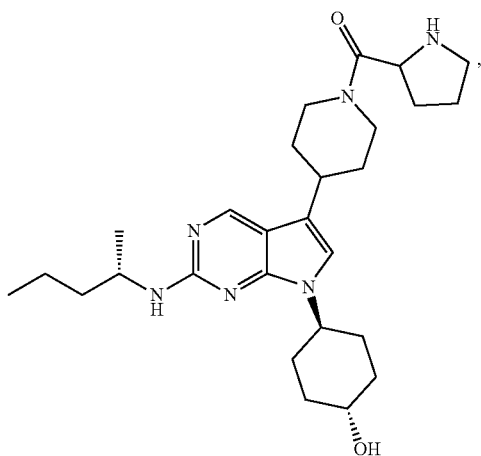
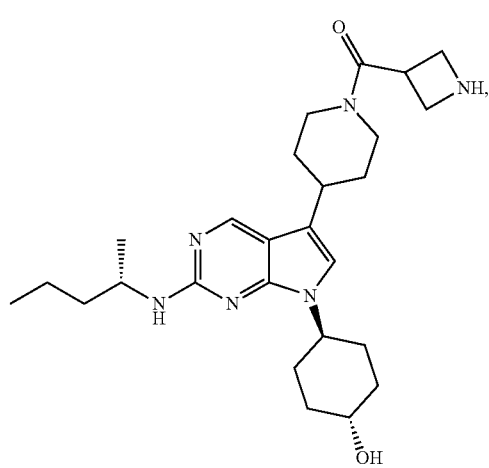
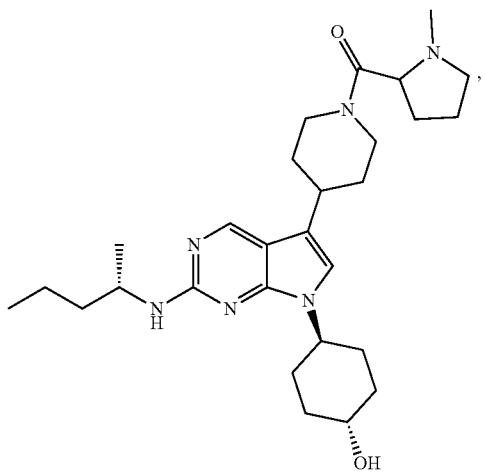
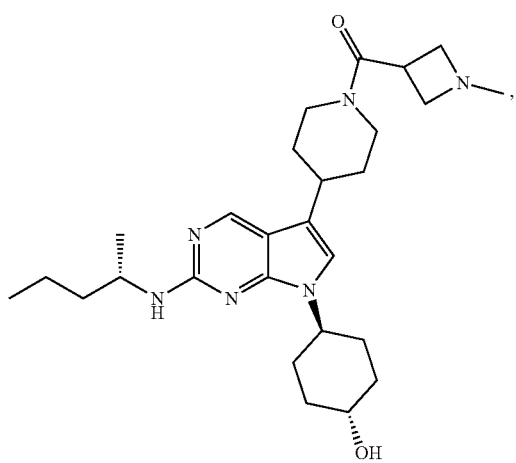

91
-continued
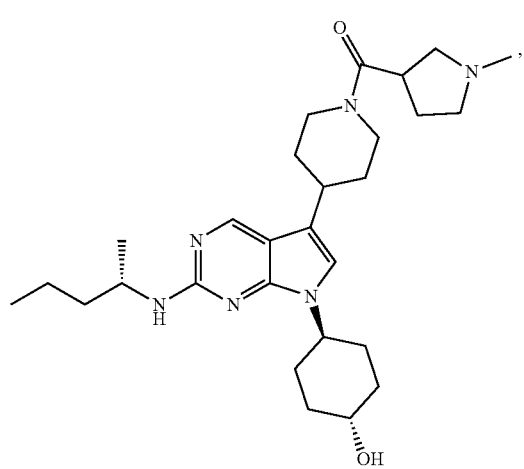
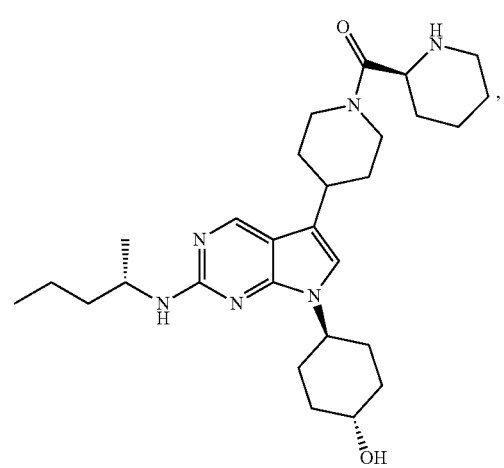
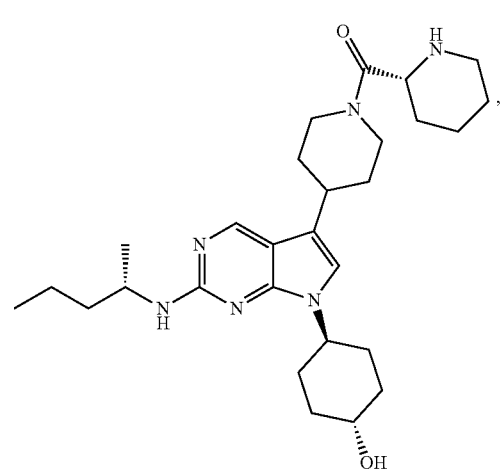
92
-continued
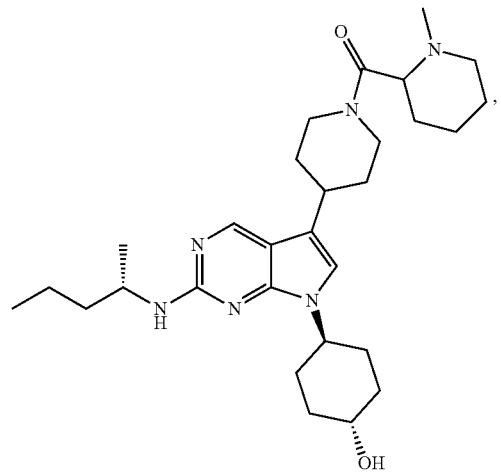
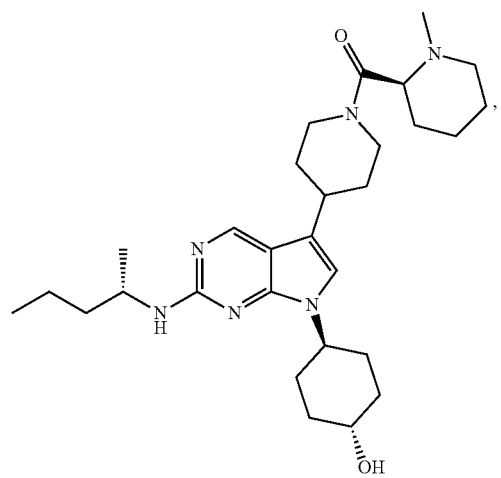
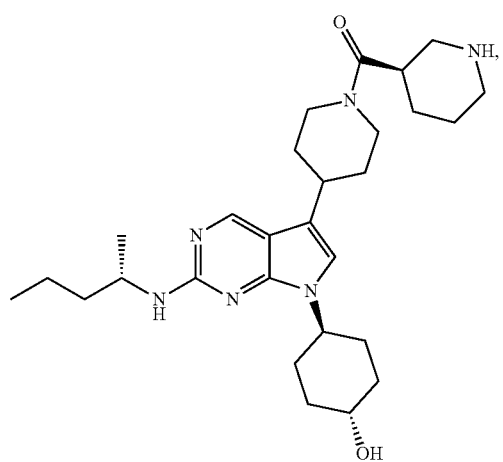

93
-continued
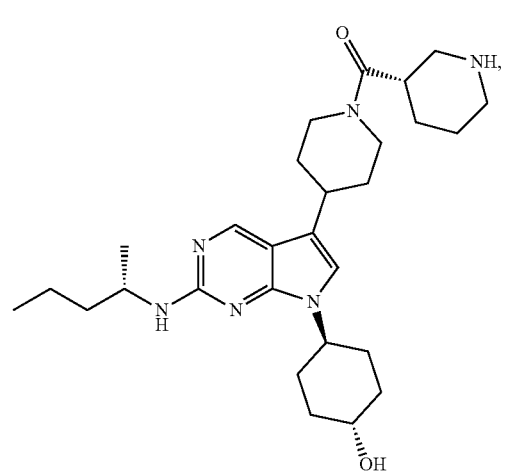
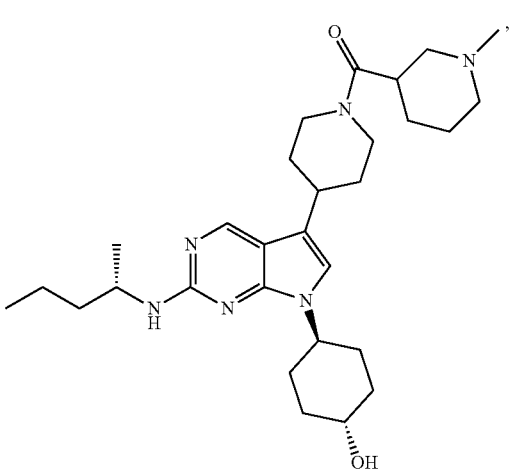
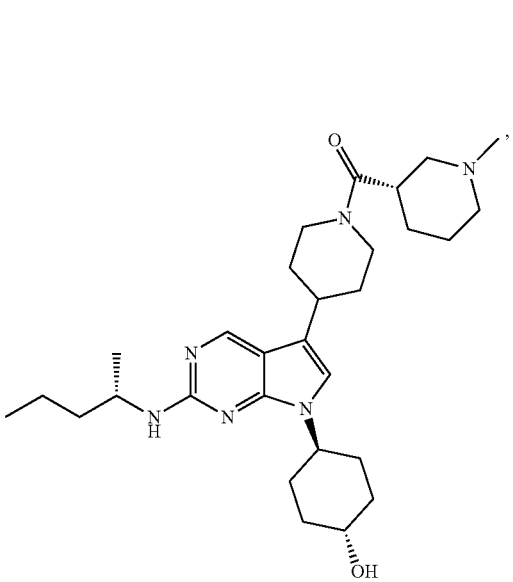
94
-continued
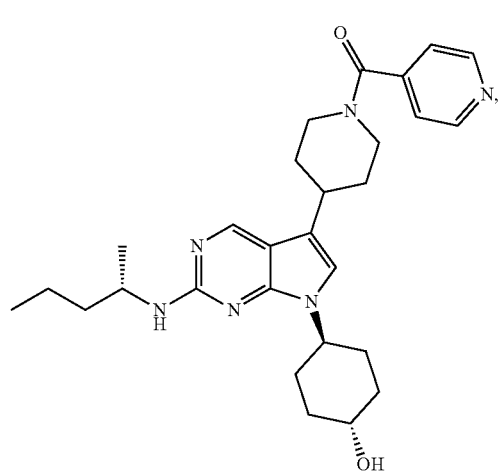
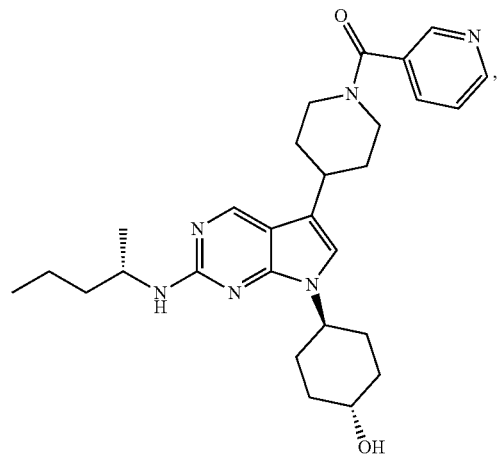
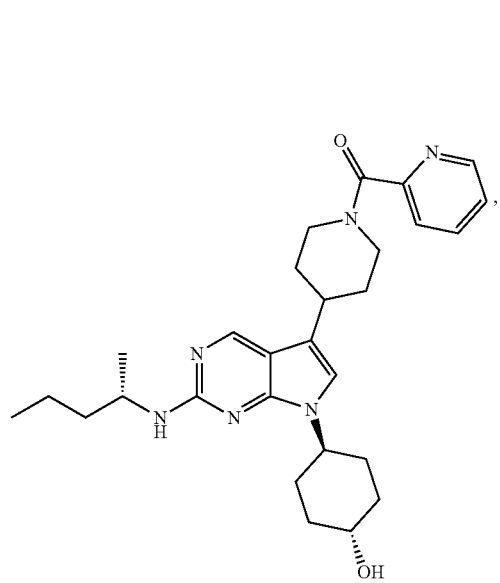

95
-continued
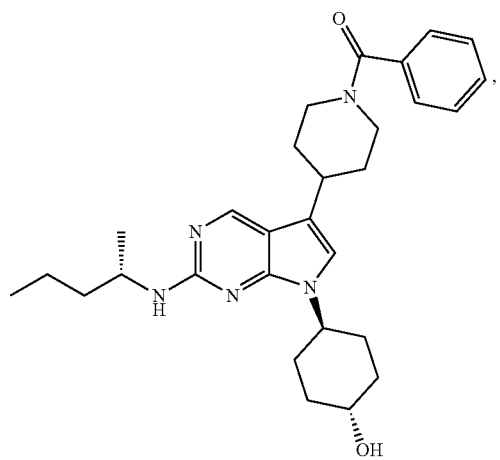
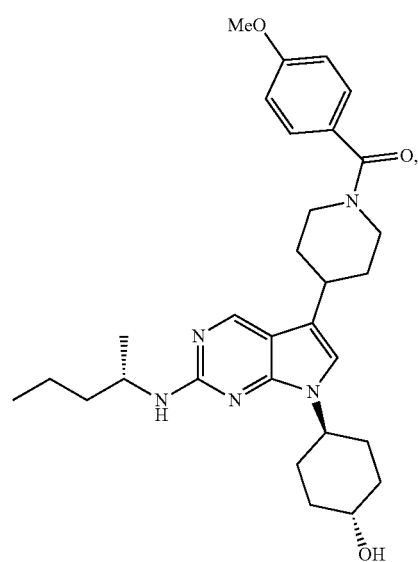
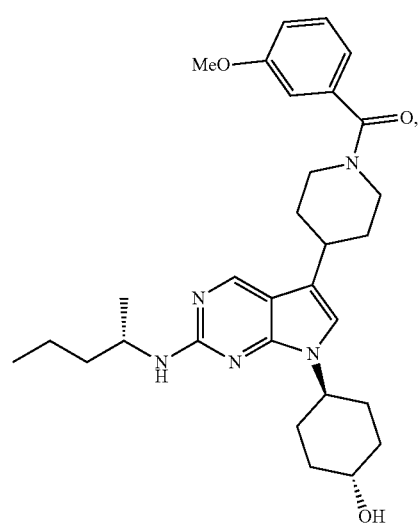
96
-continued
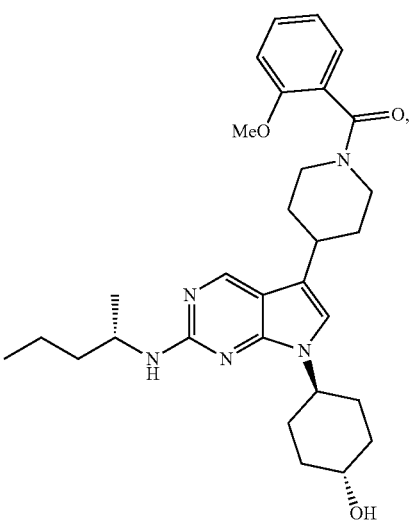
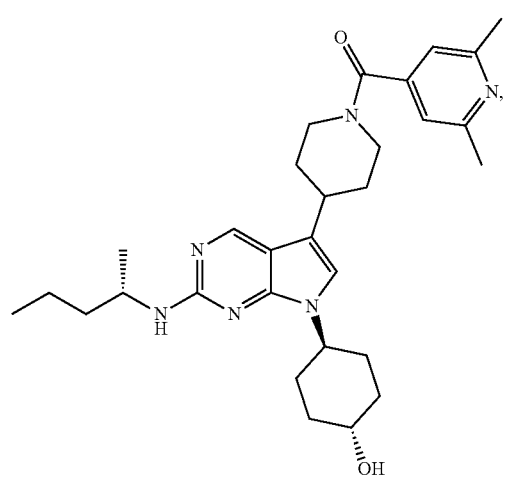
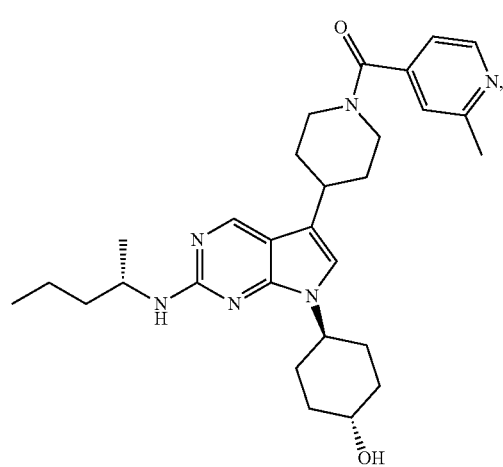

97
-continued
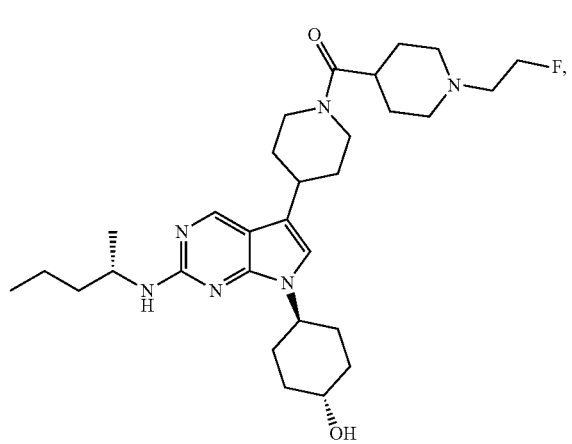
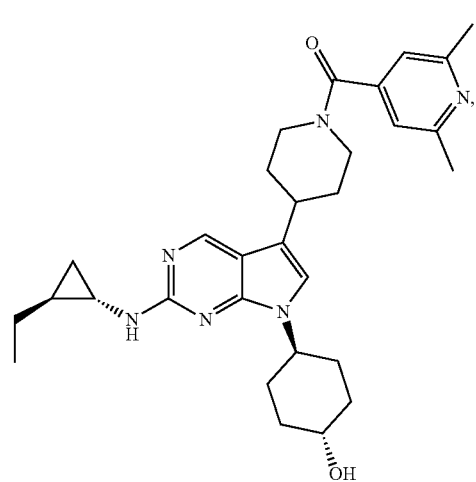
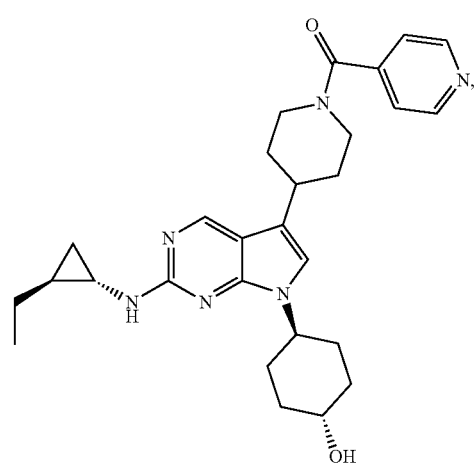
98
-continued
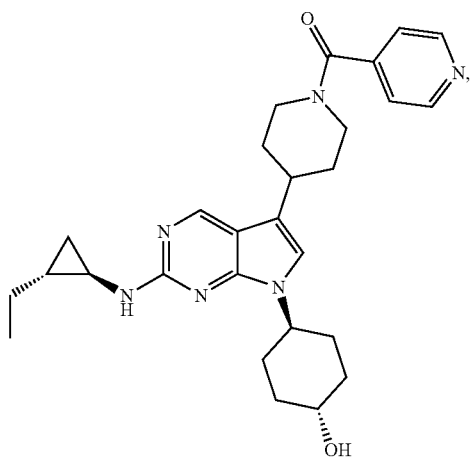
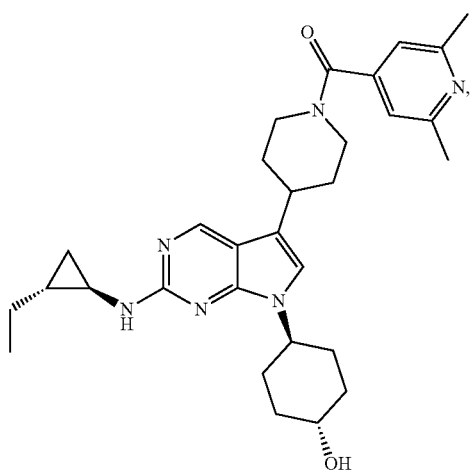
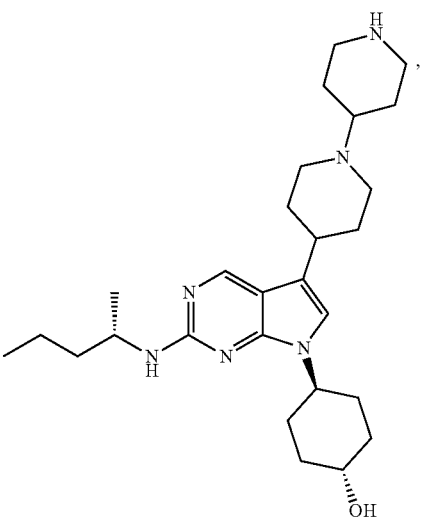

-continued
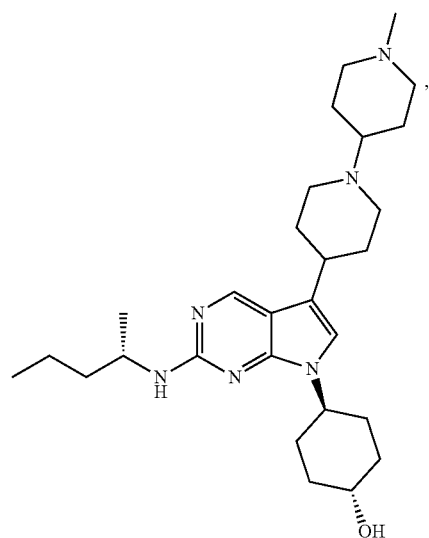
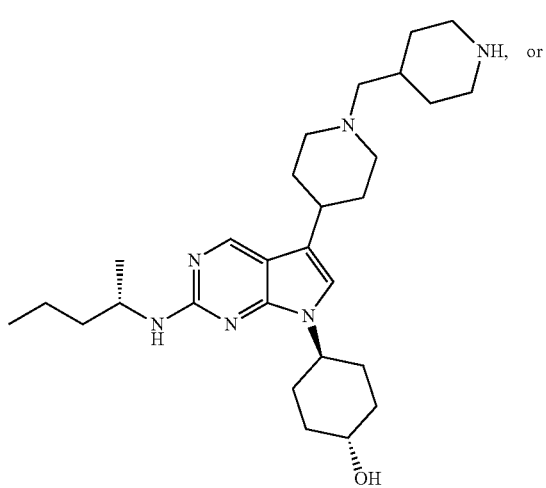
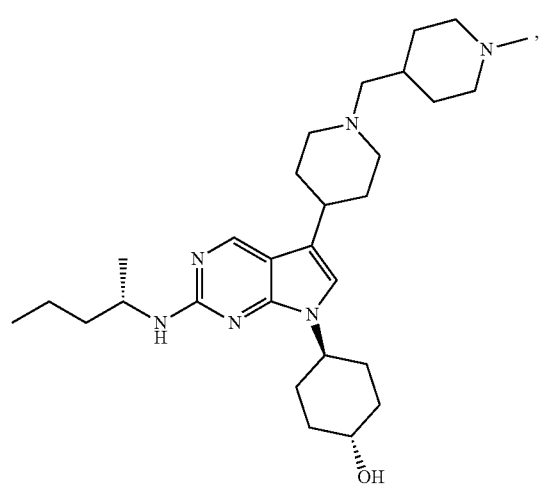 [SMILES: CCC[C@H](C)Nc1ncc2c(C3CCN(CC4CCN(C)CC4)CC3)cn([C@H]3CC[C@H](O)CC3)c2n1]
or a pharmaceutically acceptable salt thereof.
In one aspect, a compound can be present as one or more of the following structures:
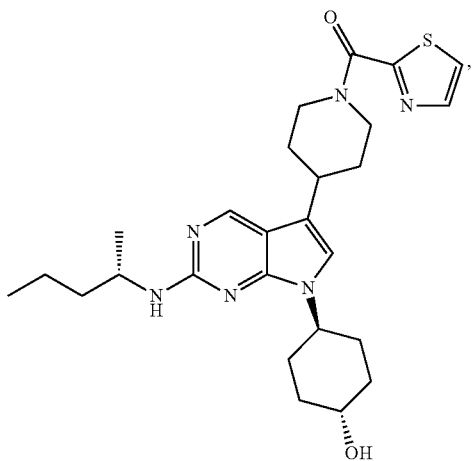
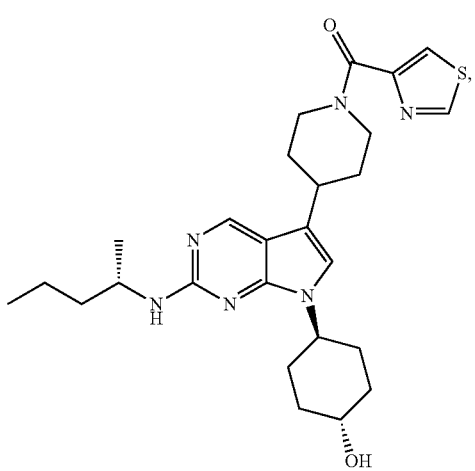
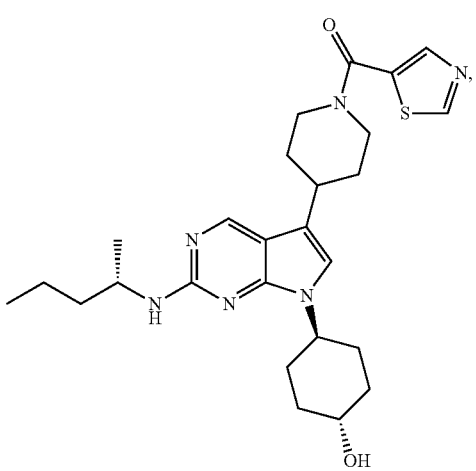

101
-continued
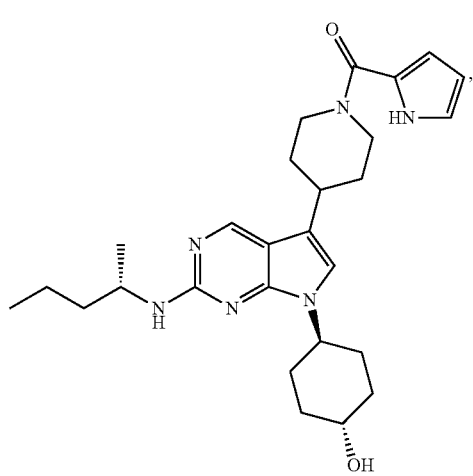
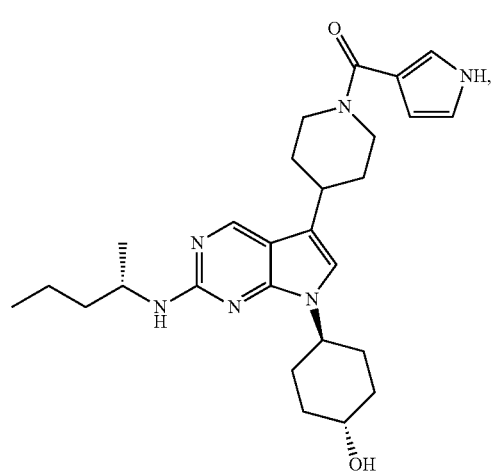
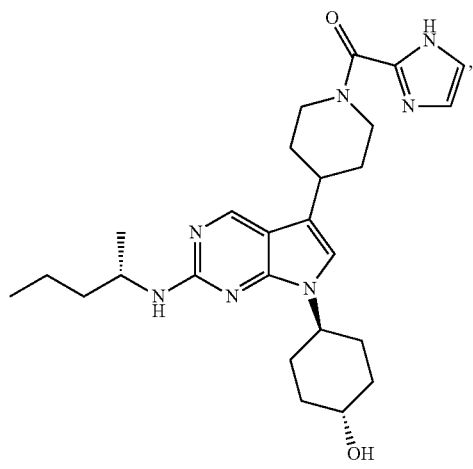
102
-continued
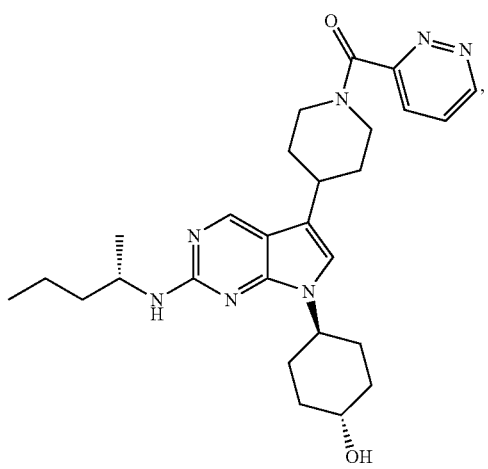
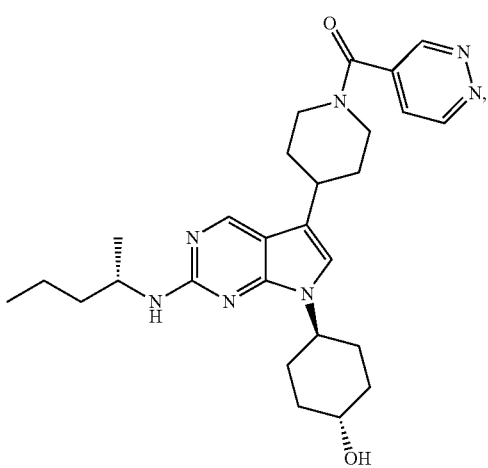
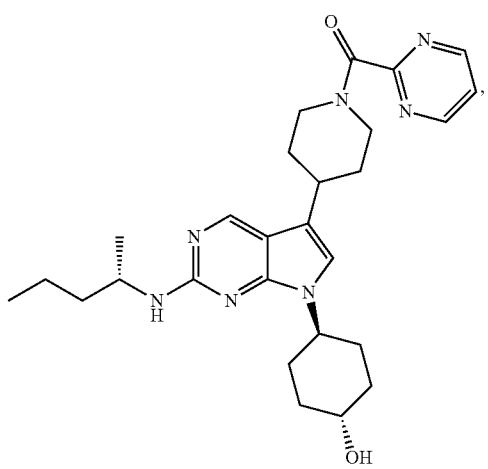

103
-continued
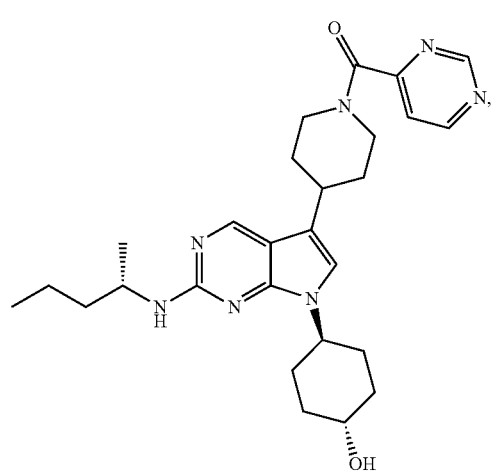
104
-continued
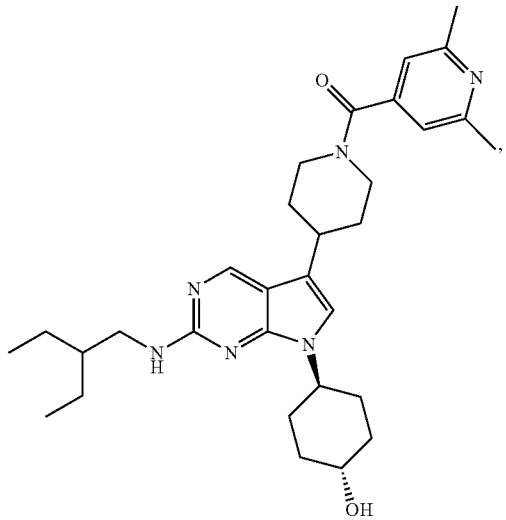

105
-continued
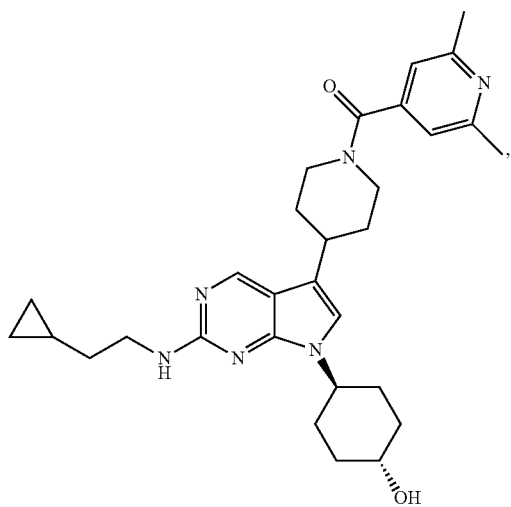
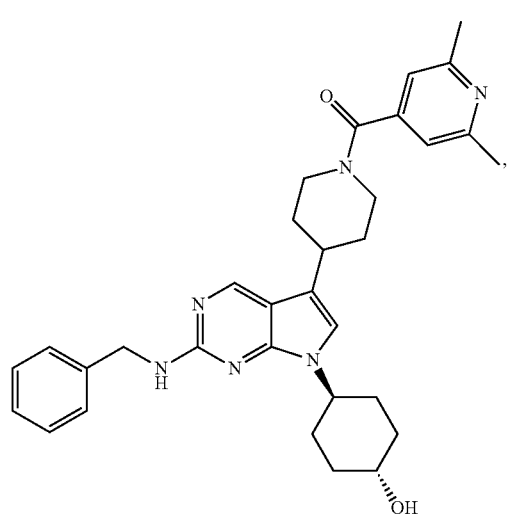
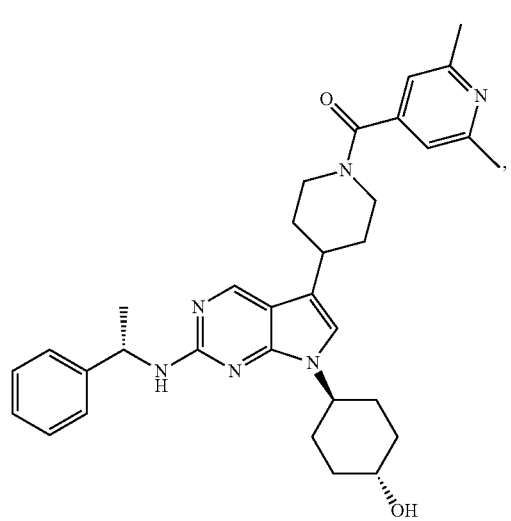
106
-continued
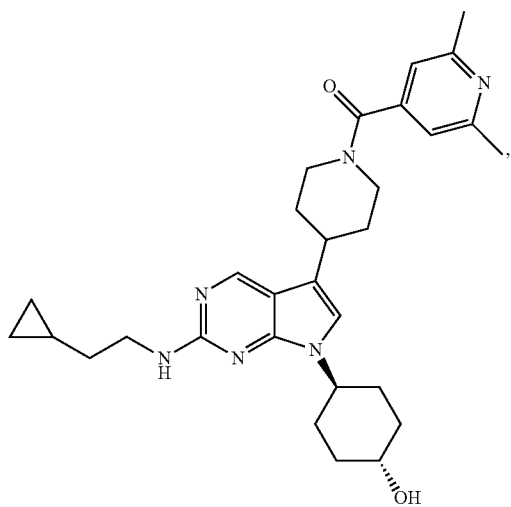
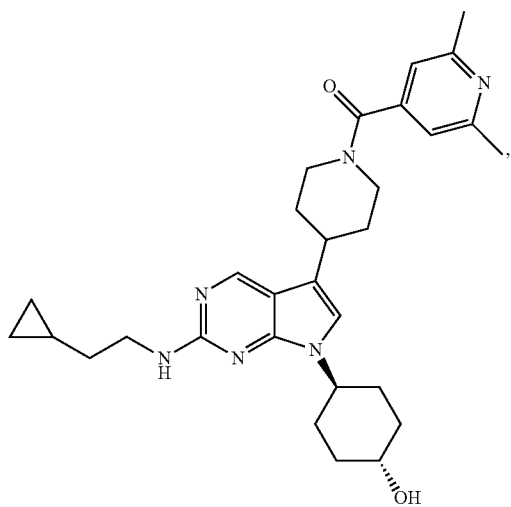
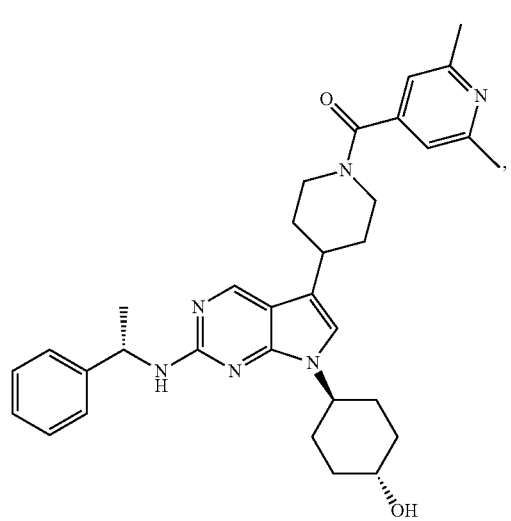

107
-continued
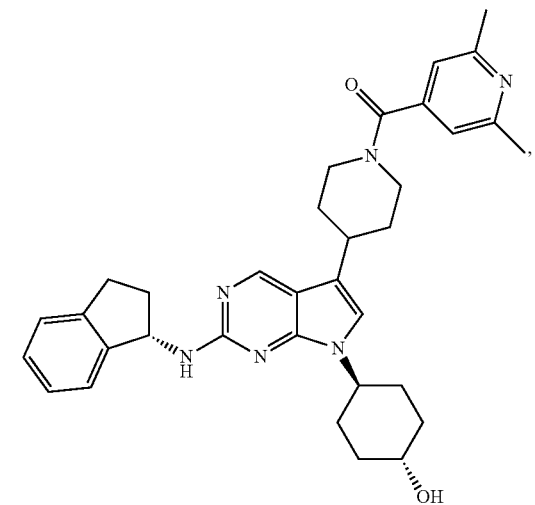
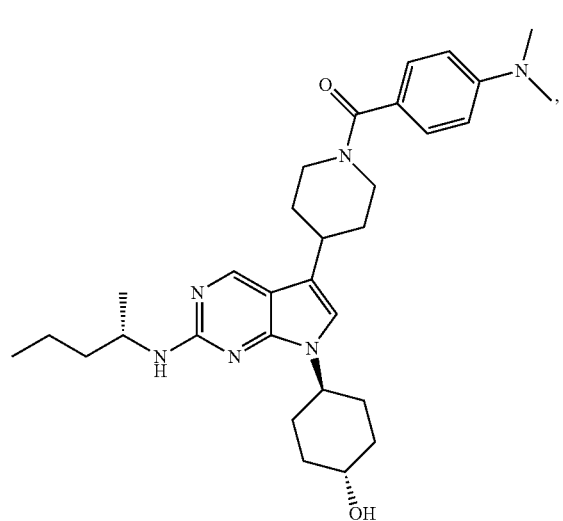
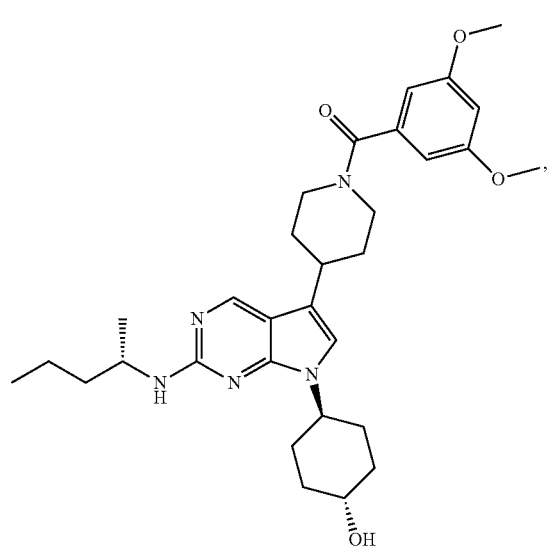
108
-continued
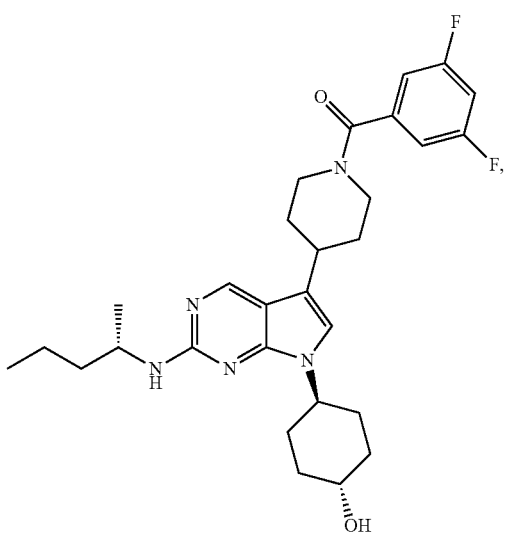
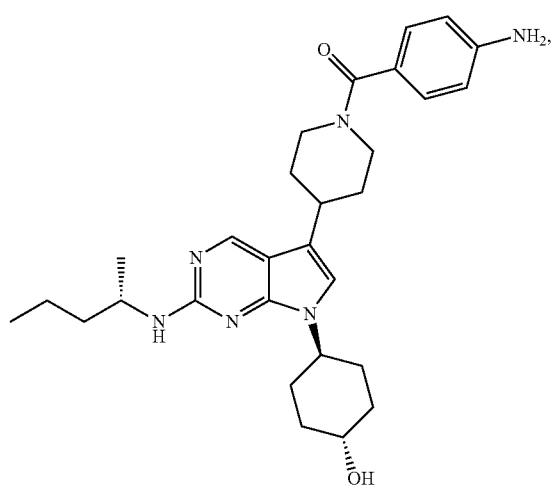
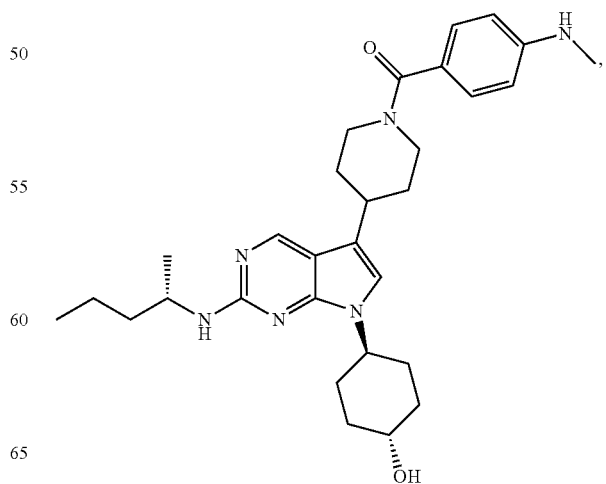

109
-continued
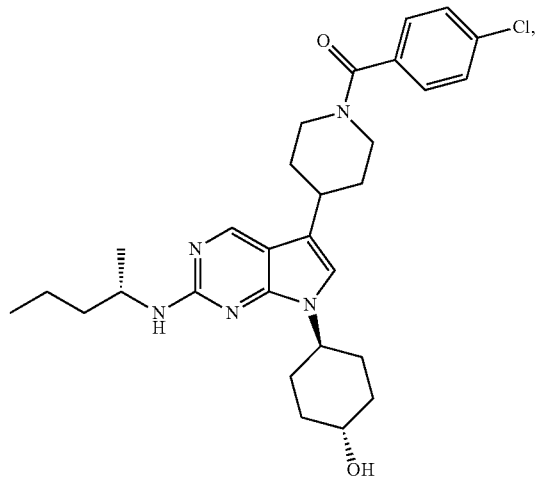
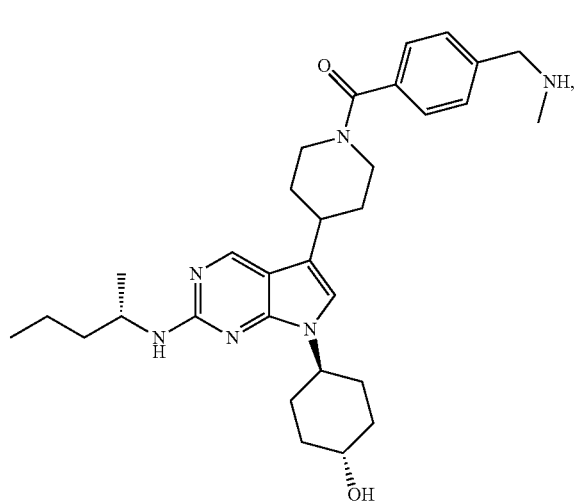
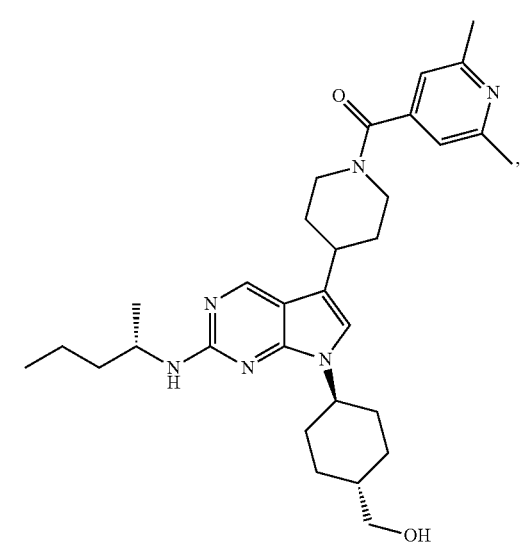
110
-continued
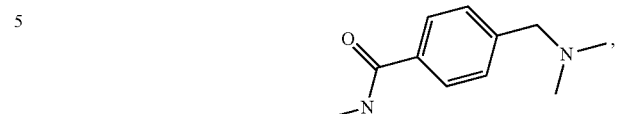
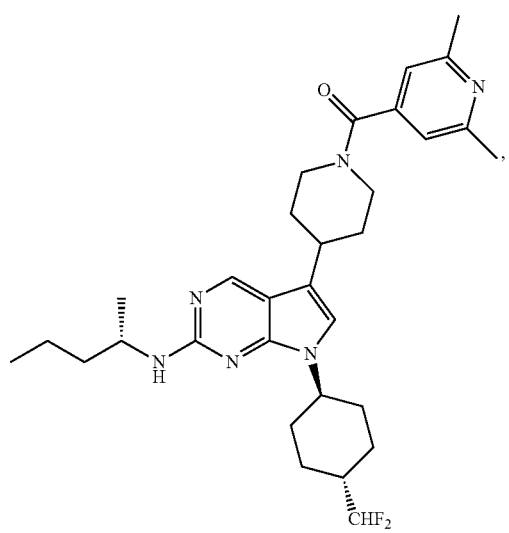
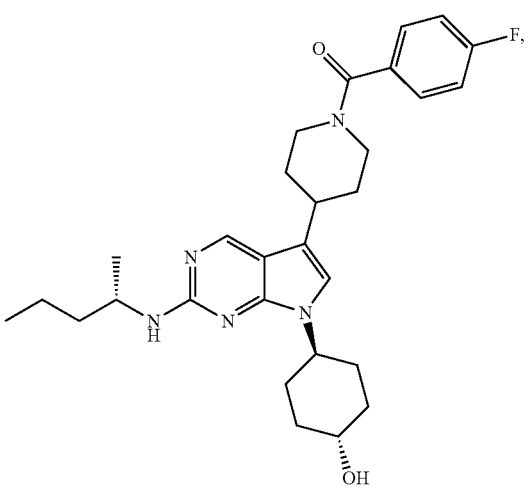

-continued
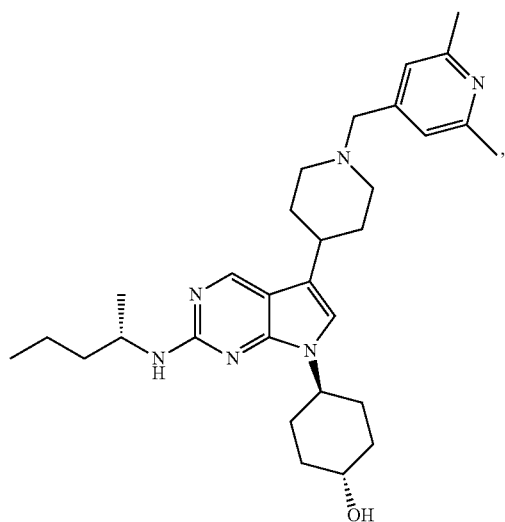
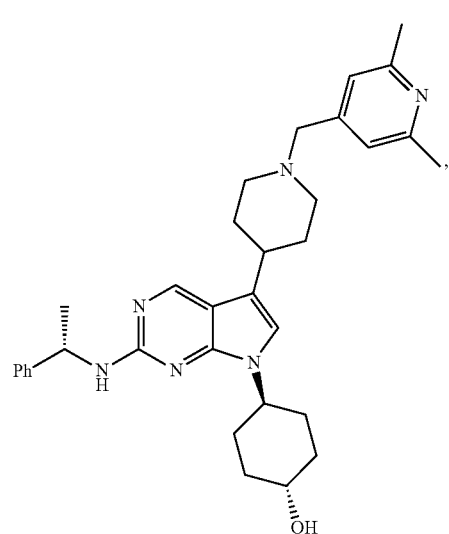
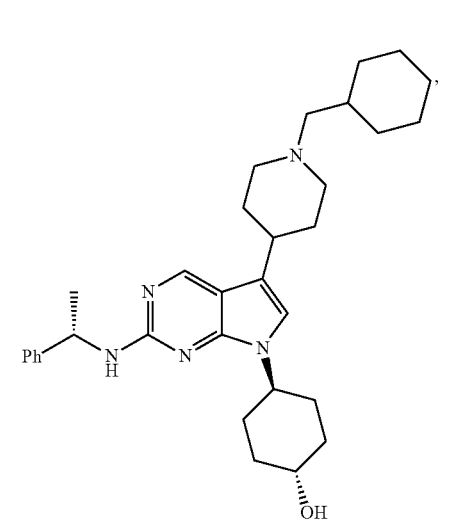
-continued
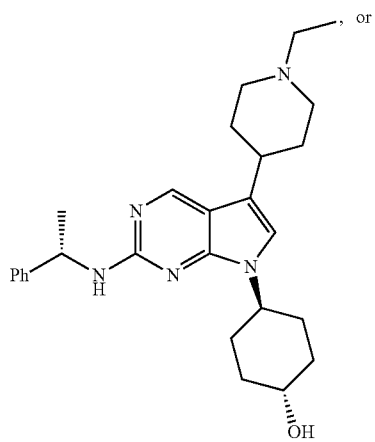
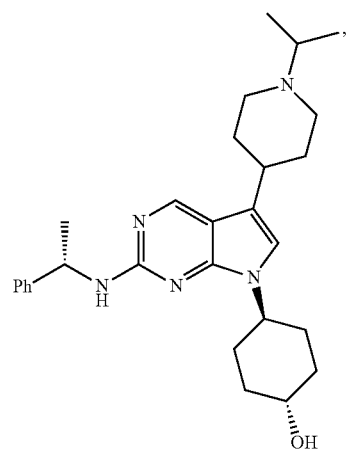
or a pharmaceutically acceptable salt thereof.
In one aspect, a compound can be present as one or more of the following structures:
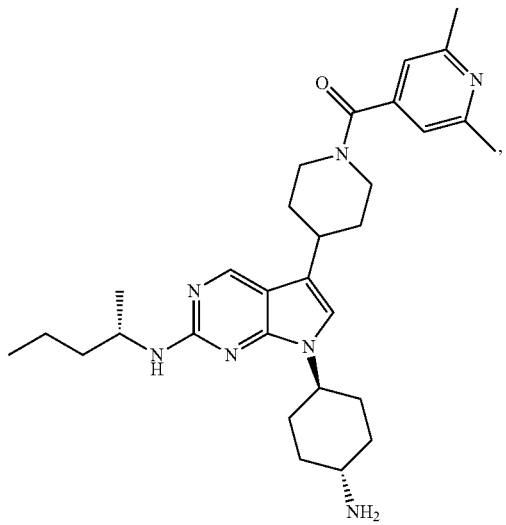

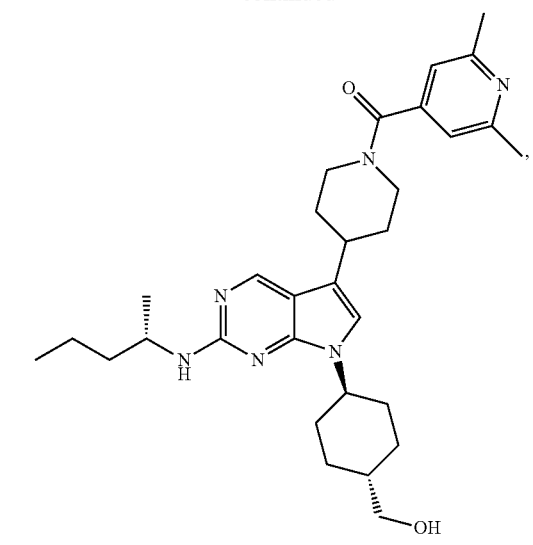
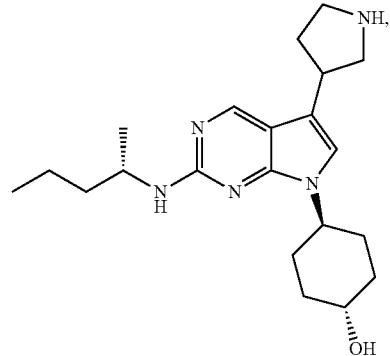
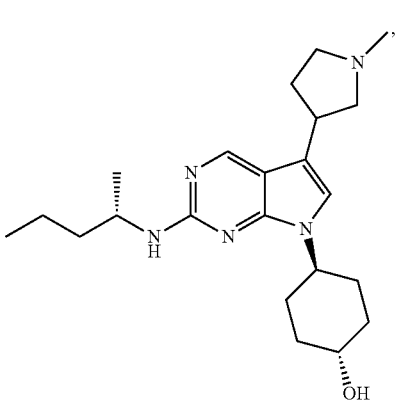
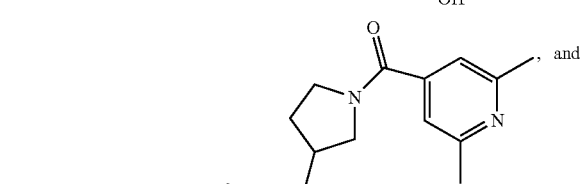
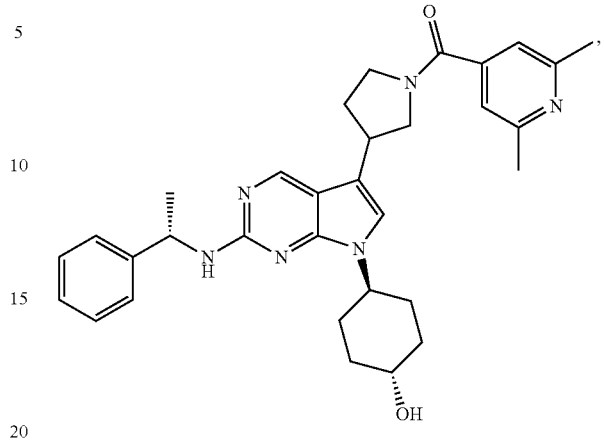
or a pharmaceutically acceptable salt thereof.
In one aspect, a compound can be present as one or more of the following structures:
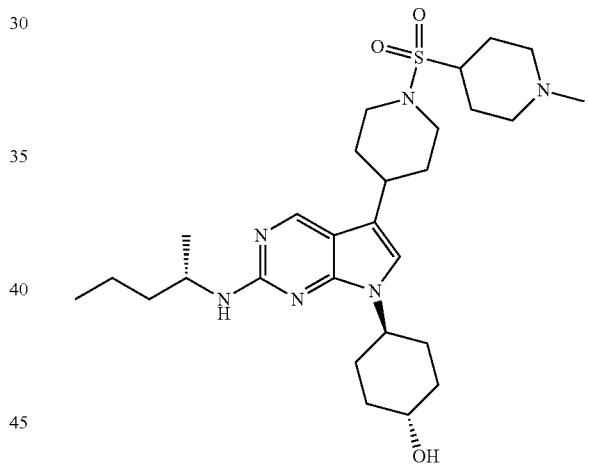
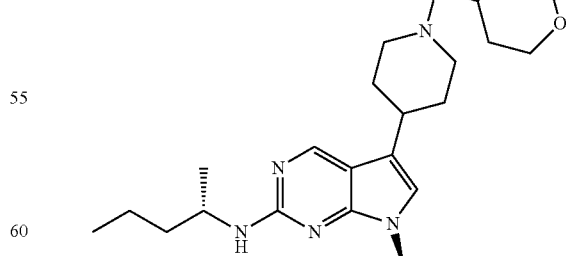

115
-continued
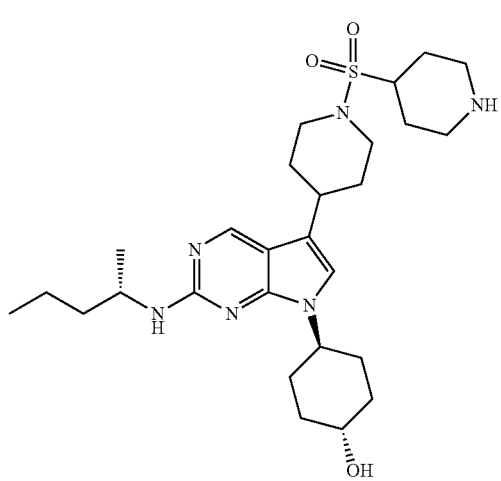
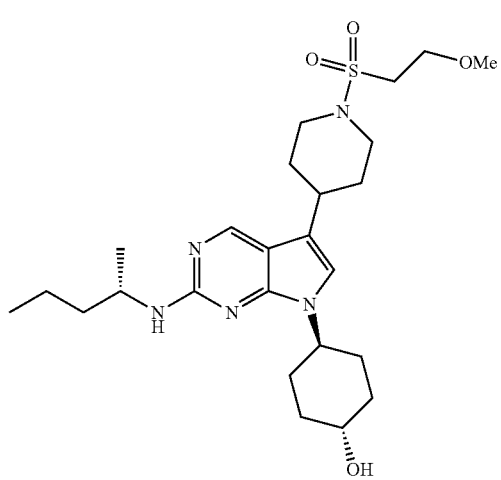
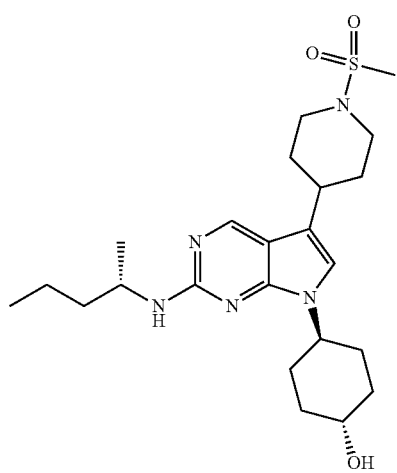
116
-continued
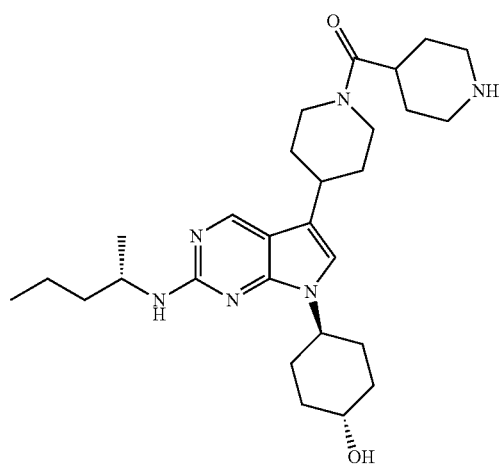
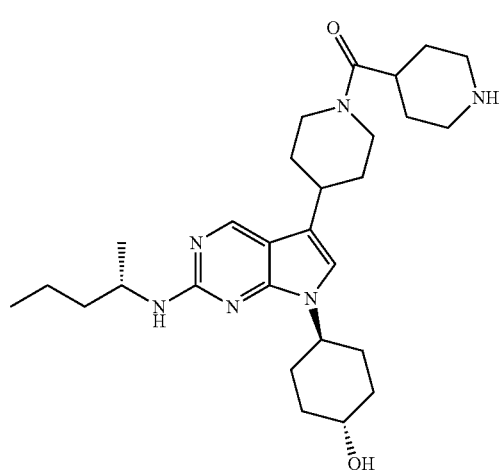

117
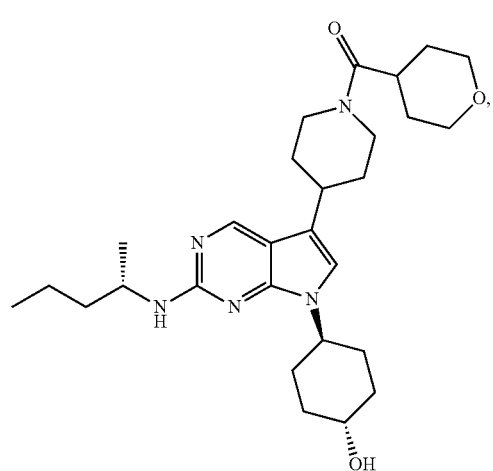
118
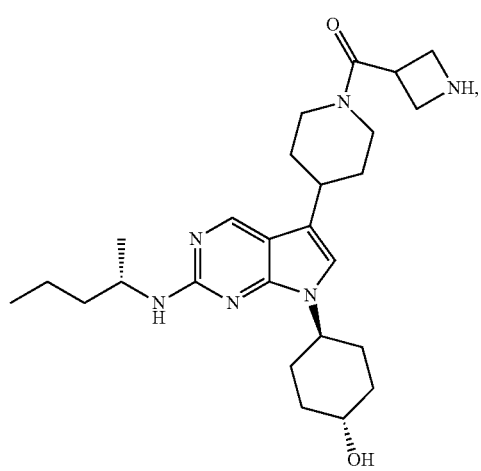

119
-continued
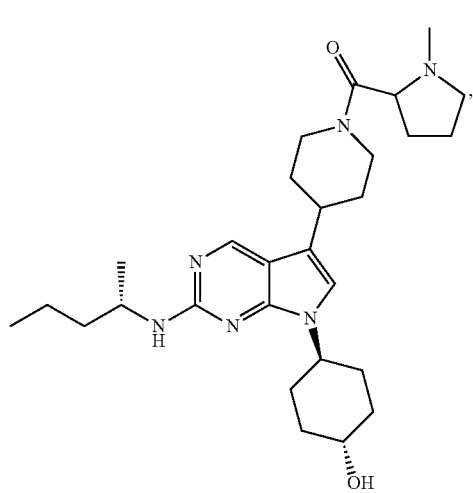
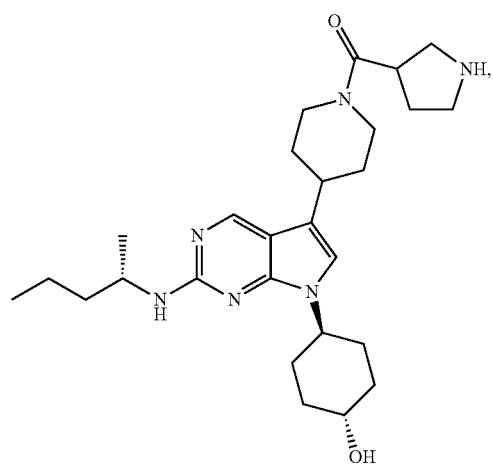
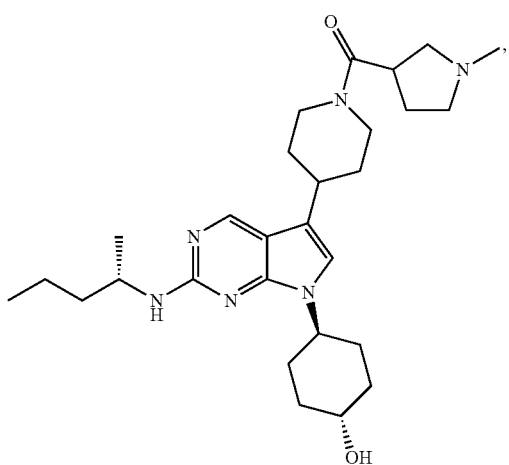
120
-continued
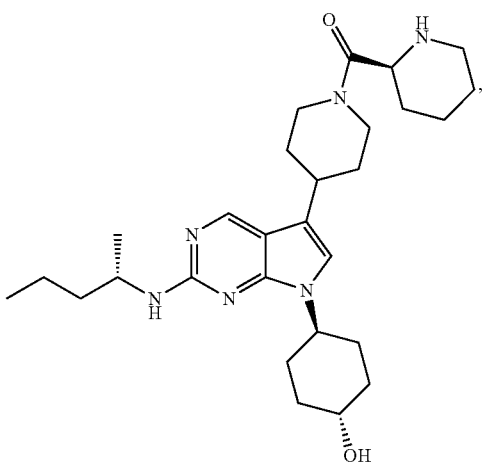
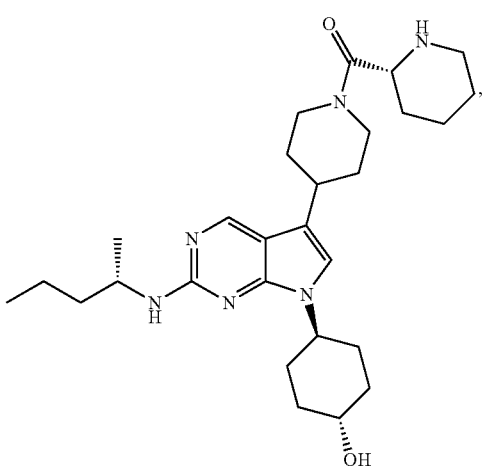
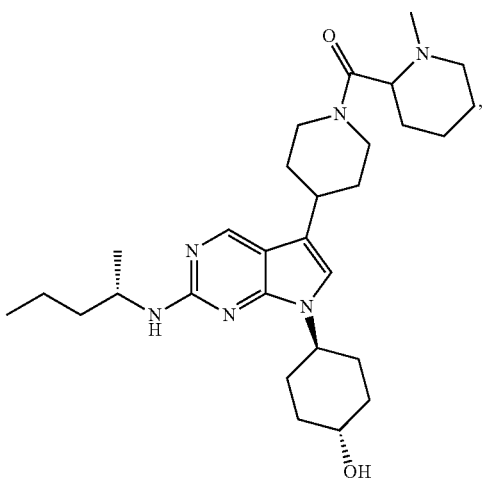

121
-continued
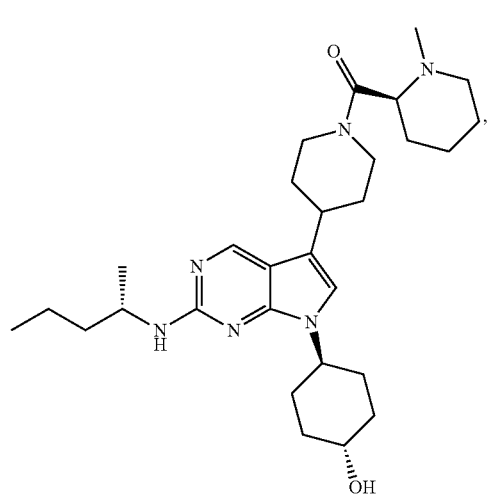
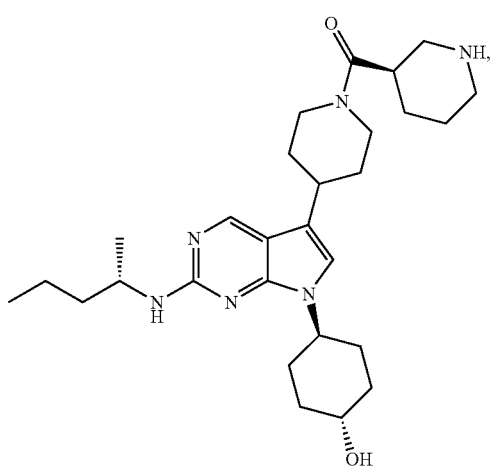
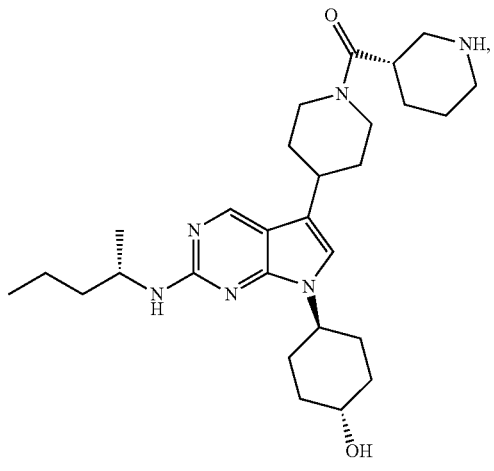
122
-continued
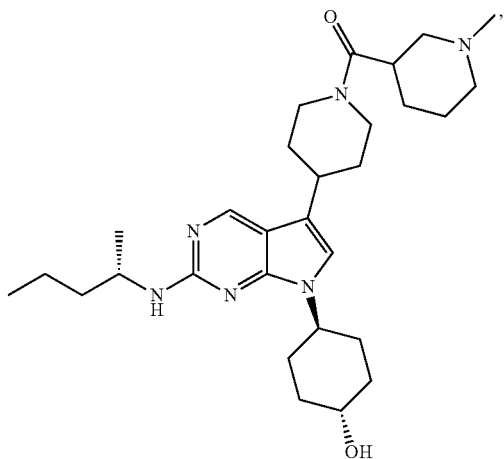
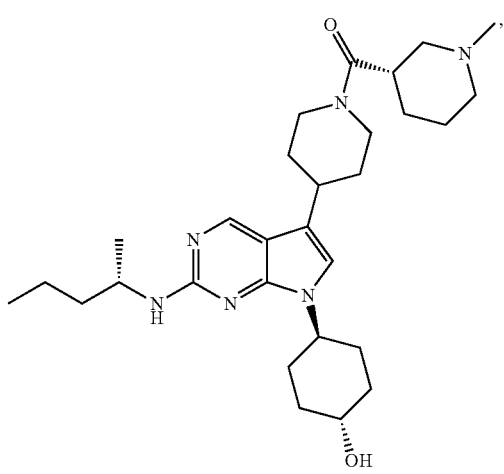
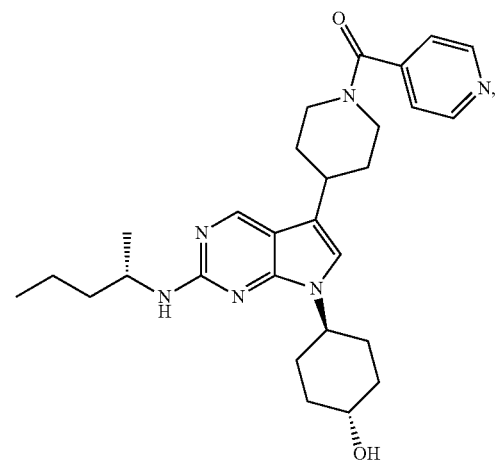

123
-continued
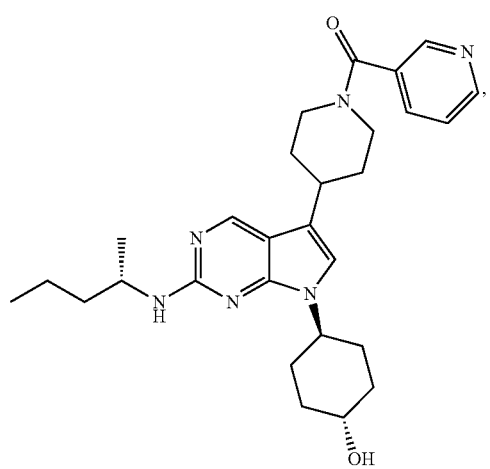
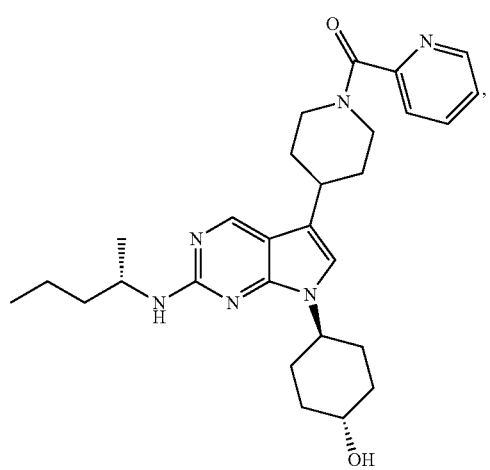
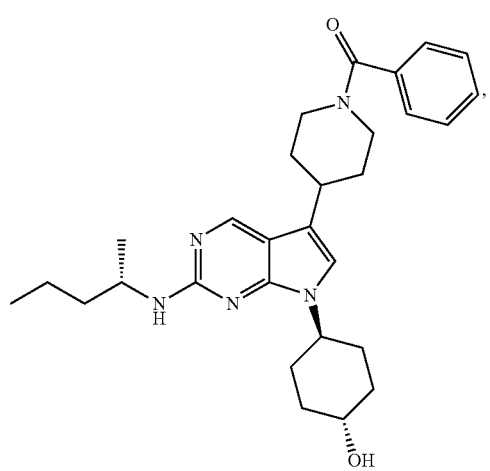
124
-continued
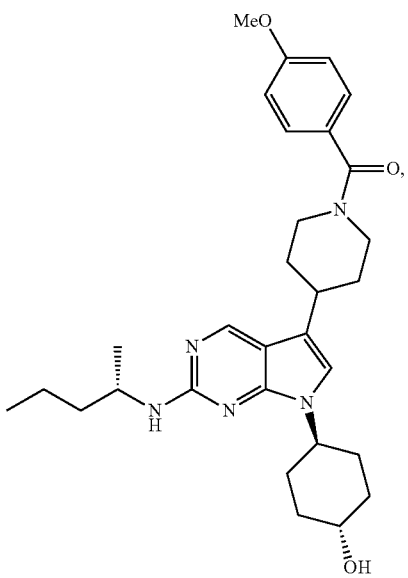
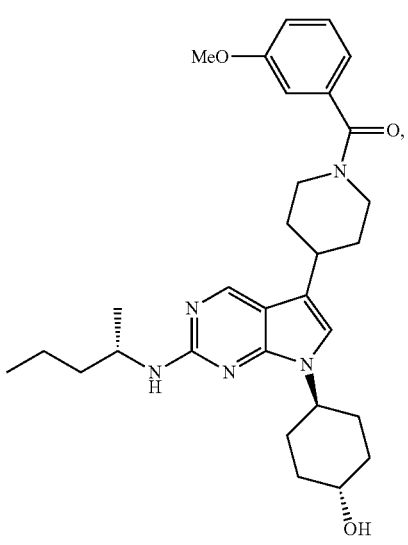

125
-continued
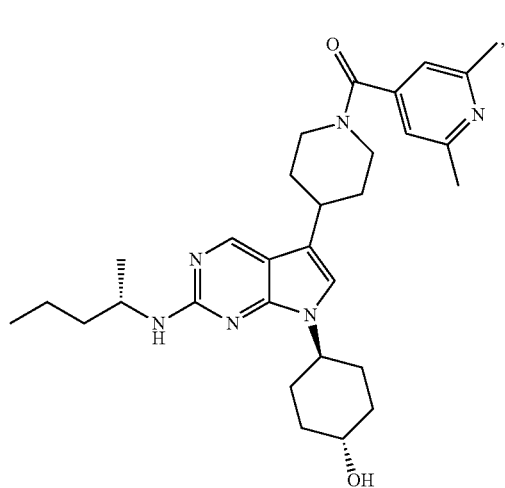
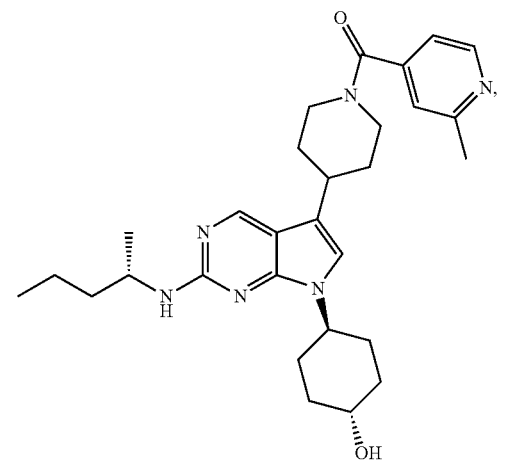
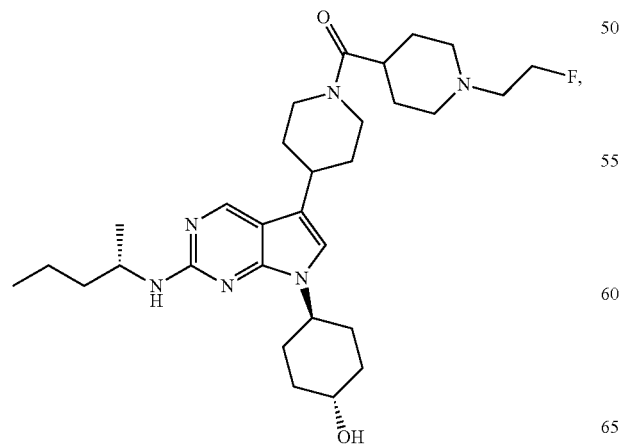
126
-continued
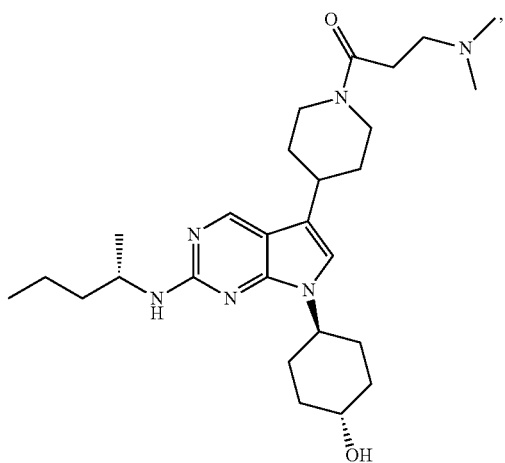
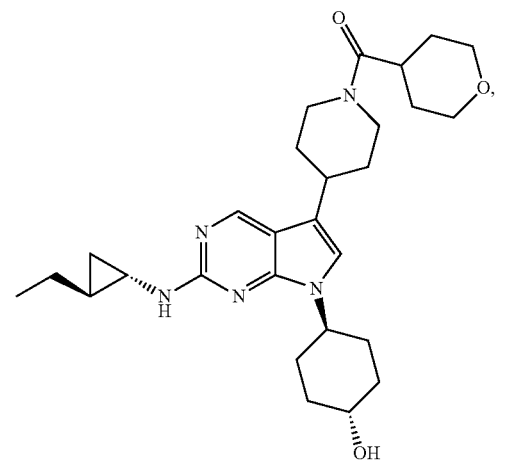
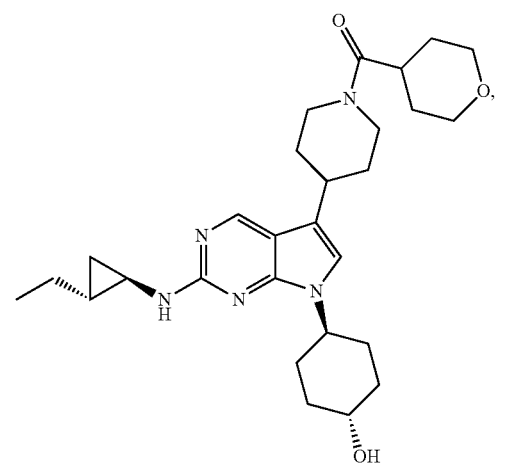

127
-continued
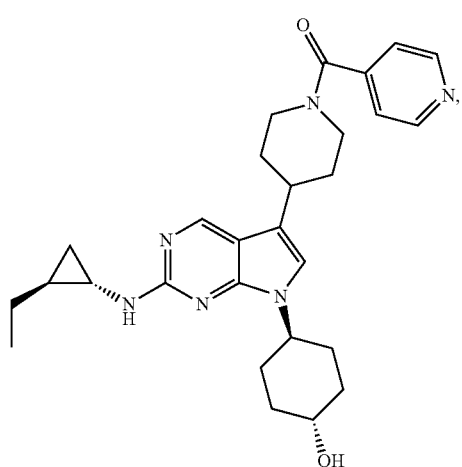
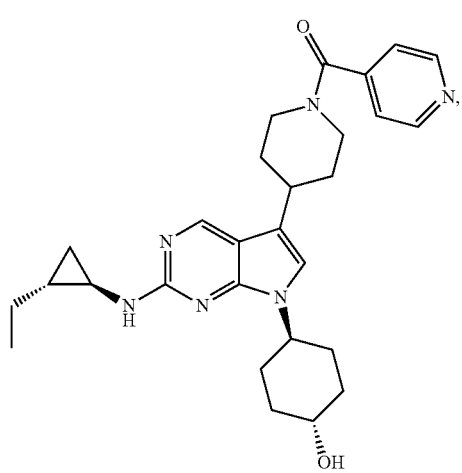
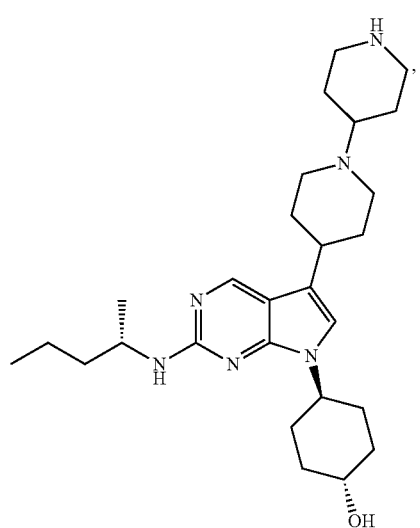
128
-continued
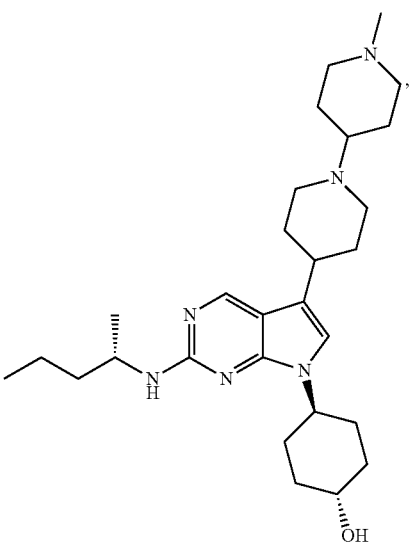
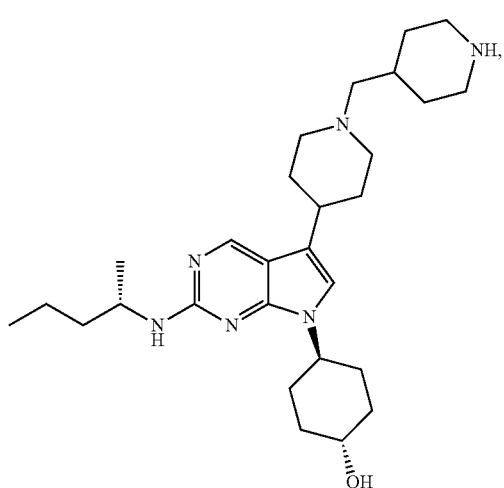
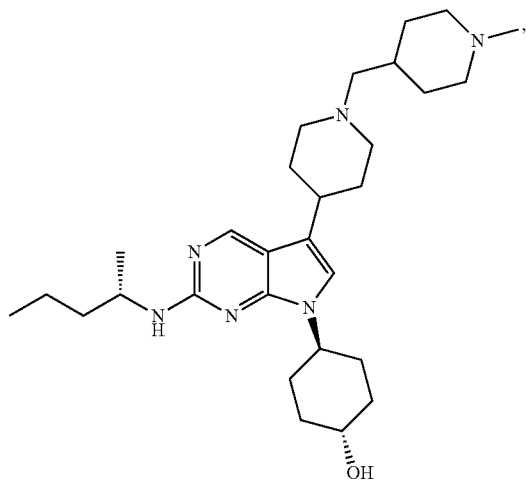

129
-continued
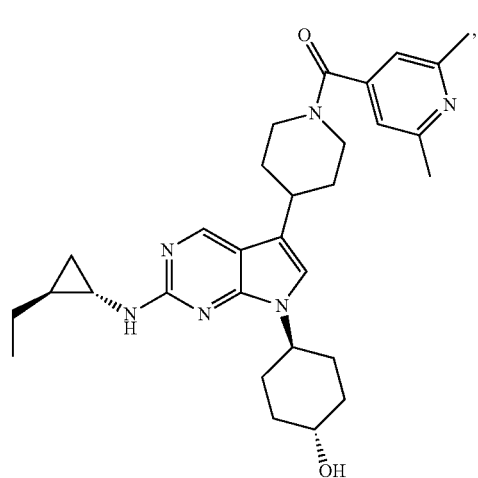
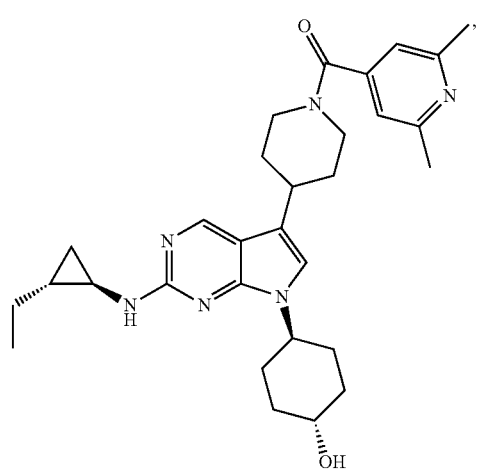
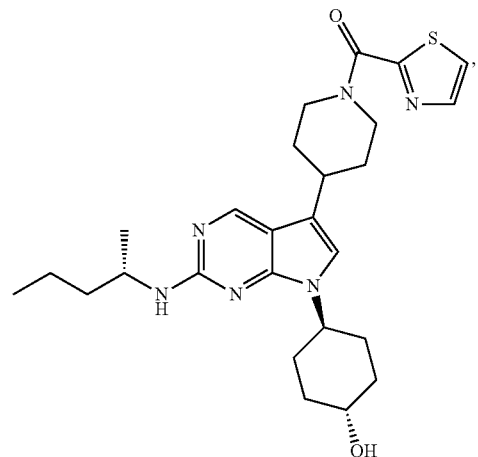
130
-continued
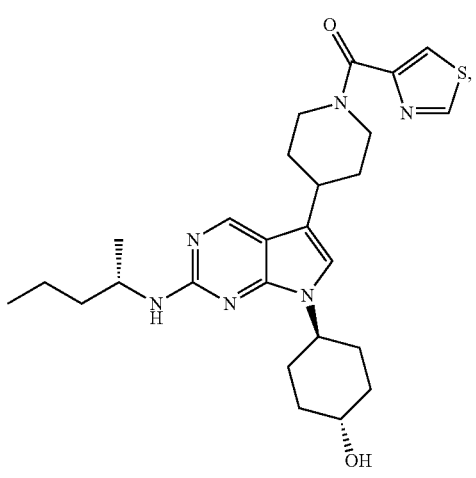
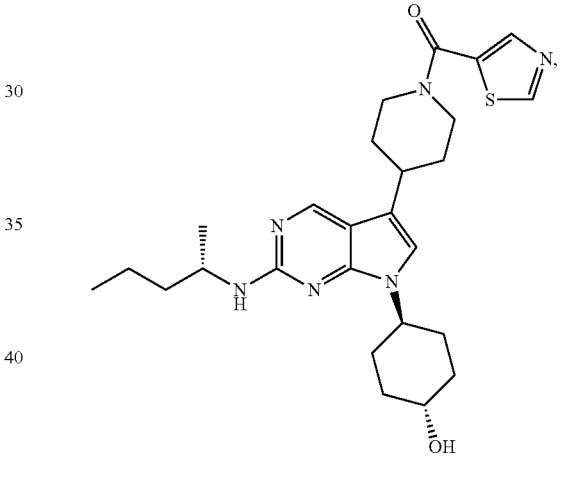
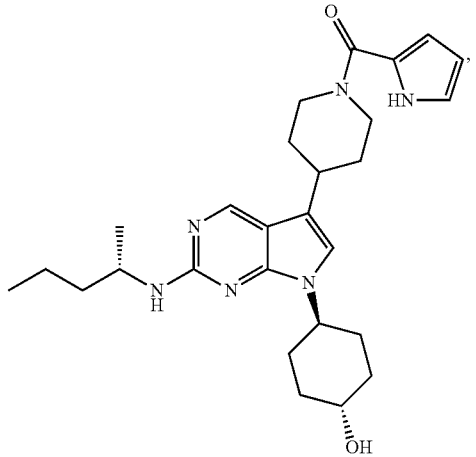

131
-continued
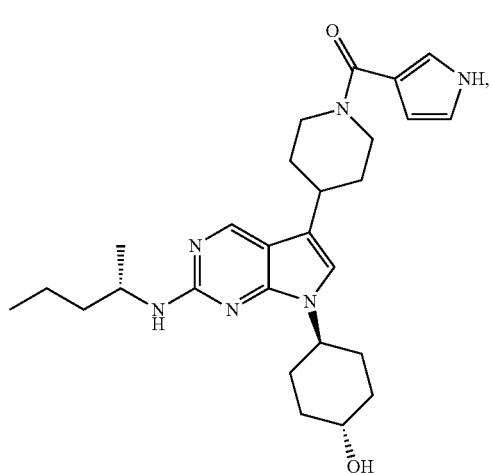
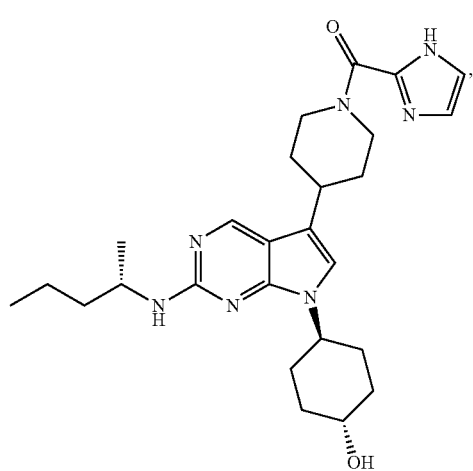
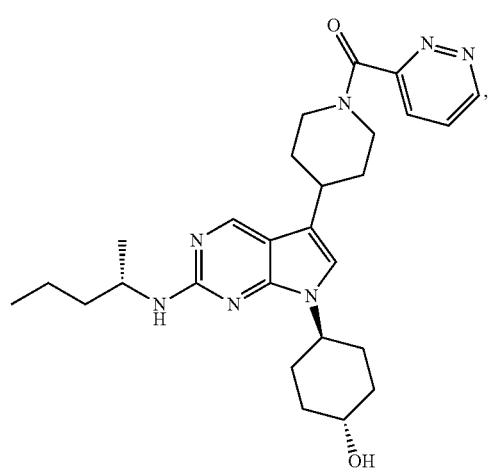
132
-continued
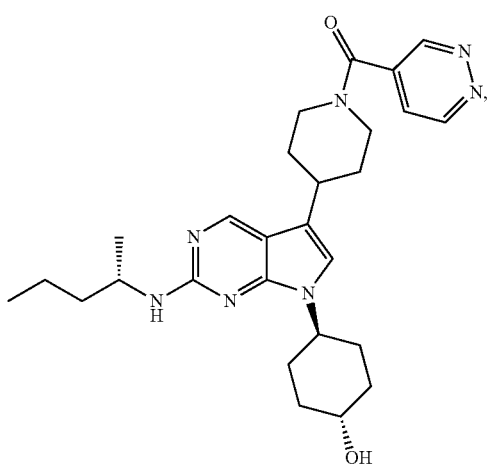
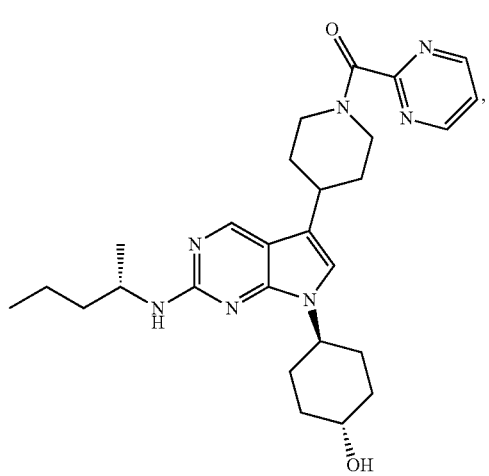
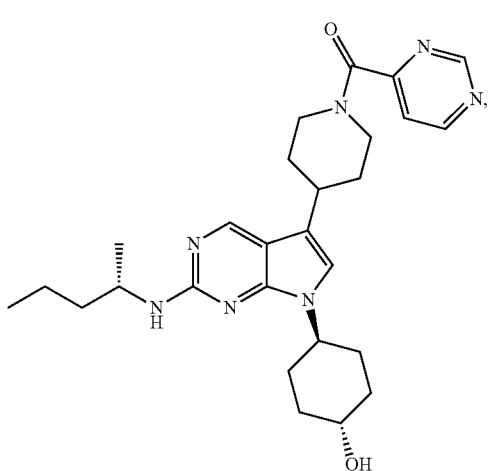

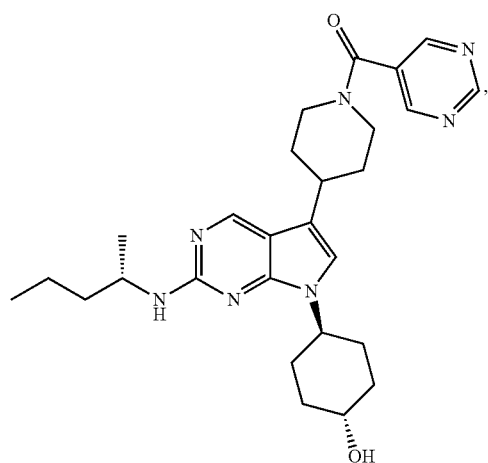
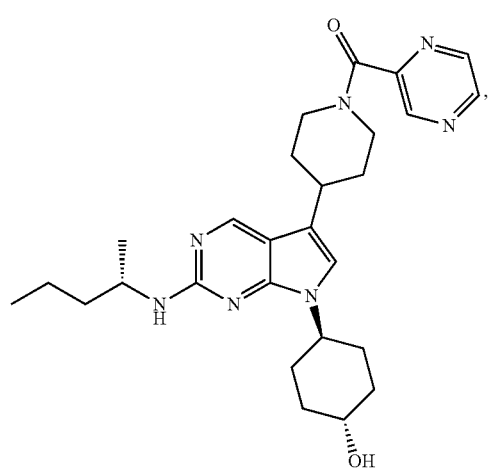
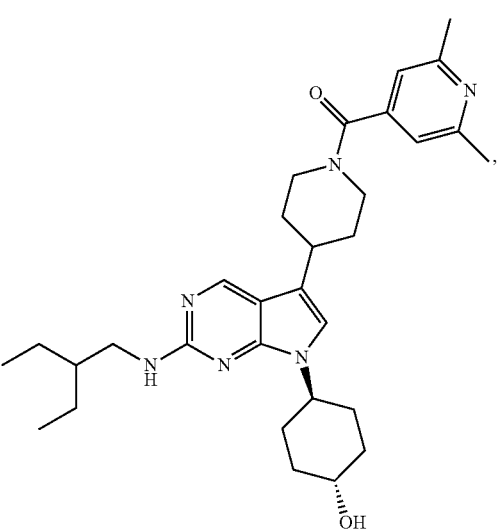
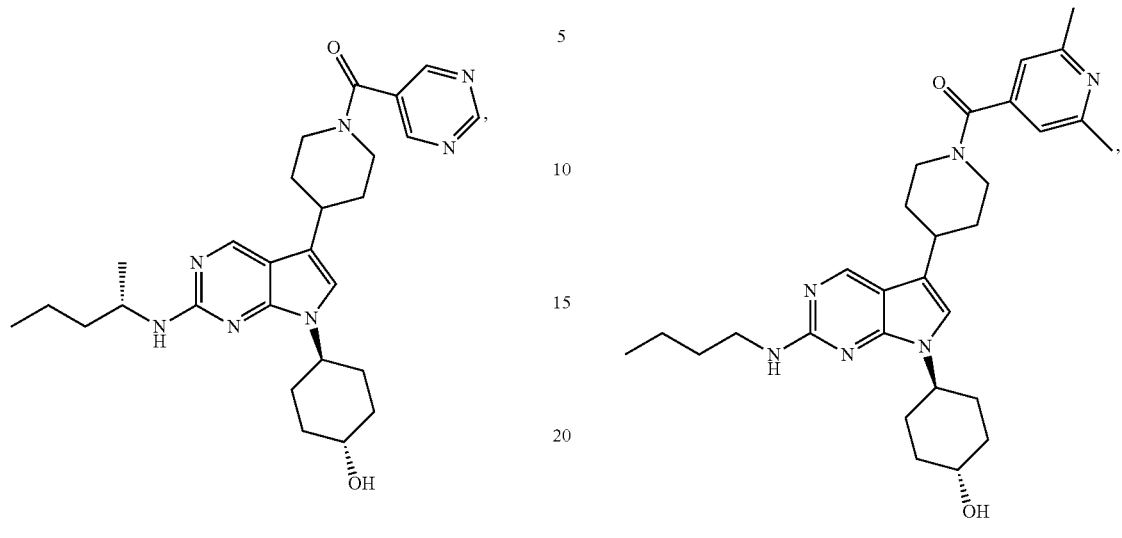
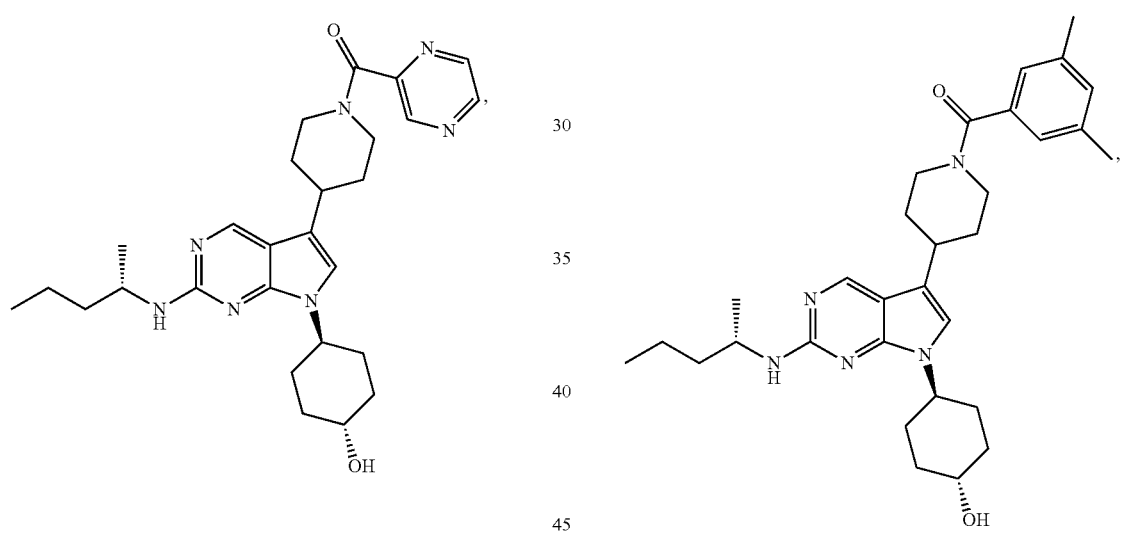
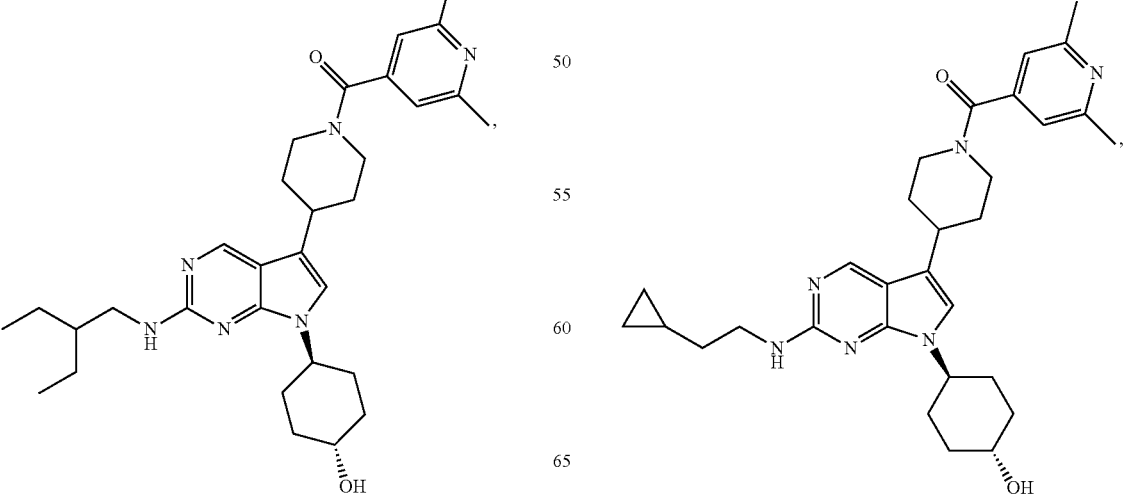

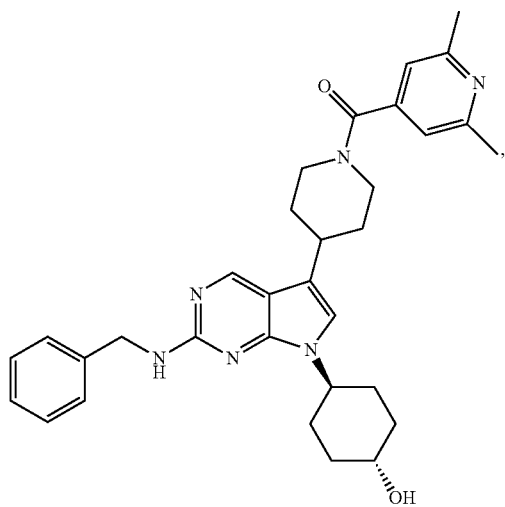
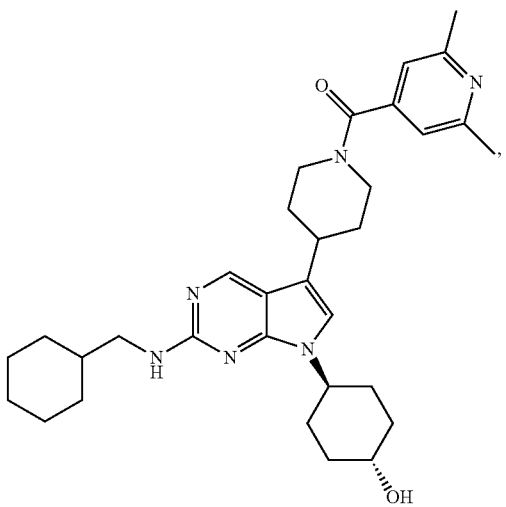

137
-continued
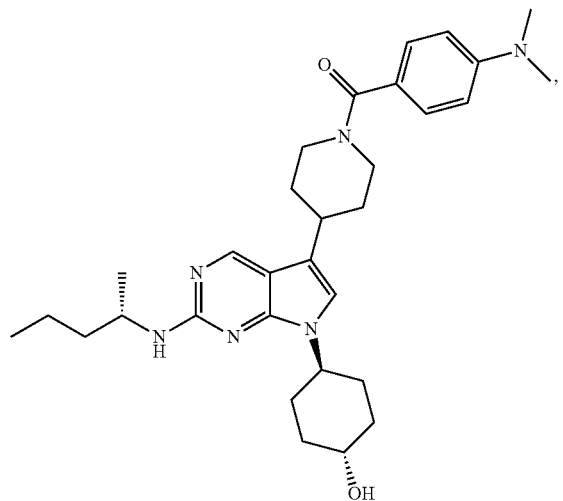
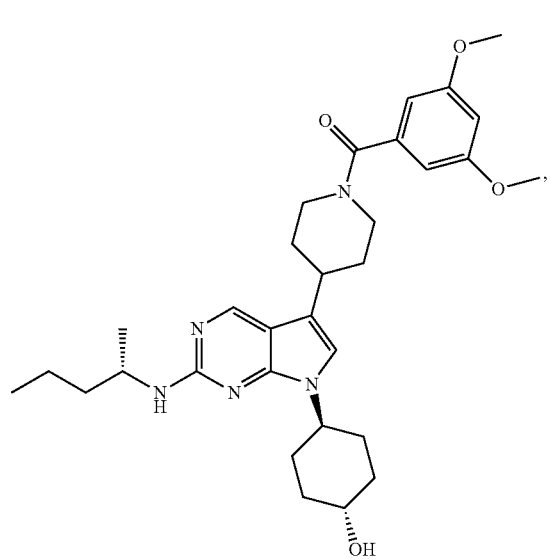
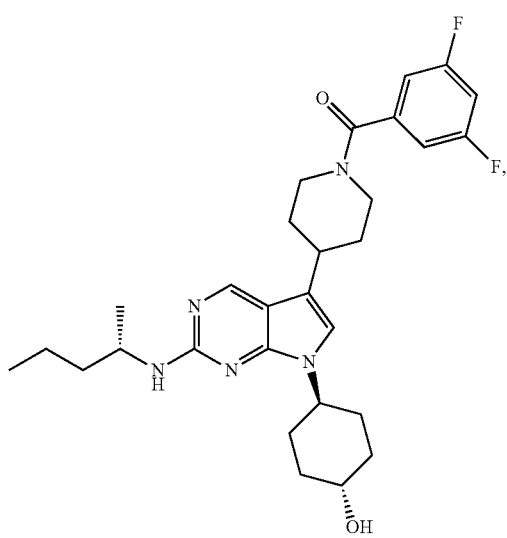
138
-continued
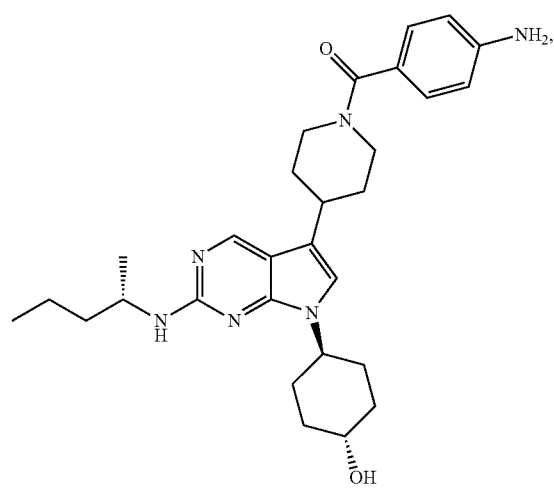
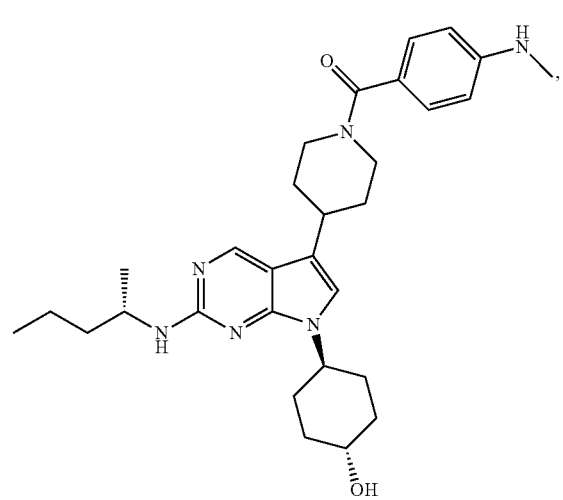
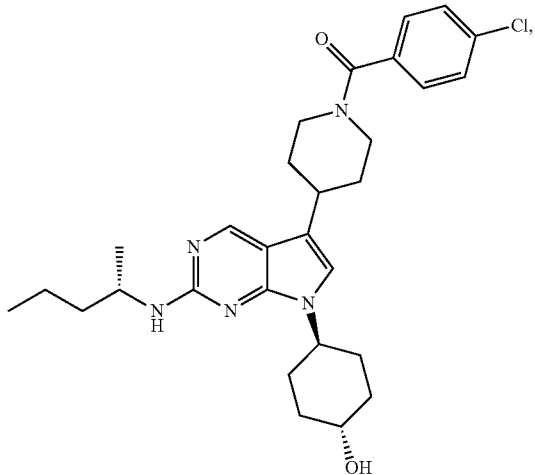

-continued
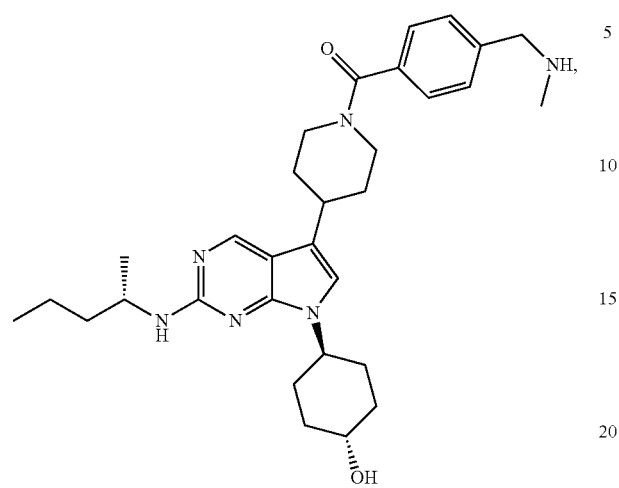
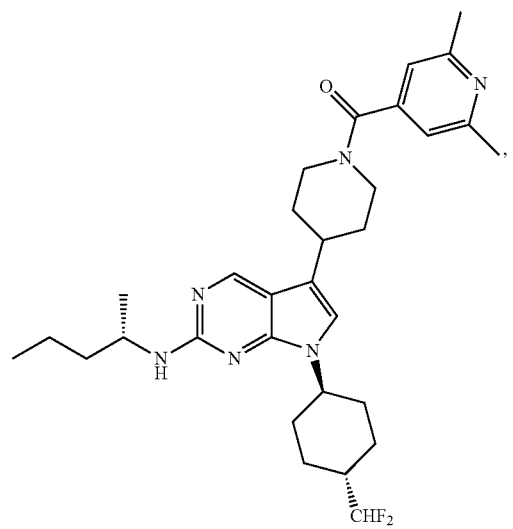
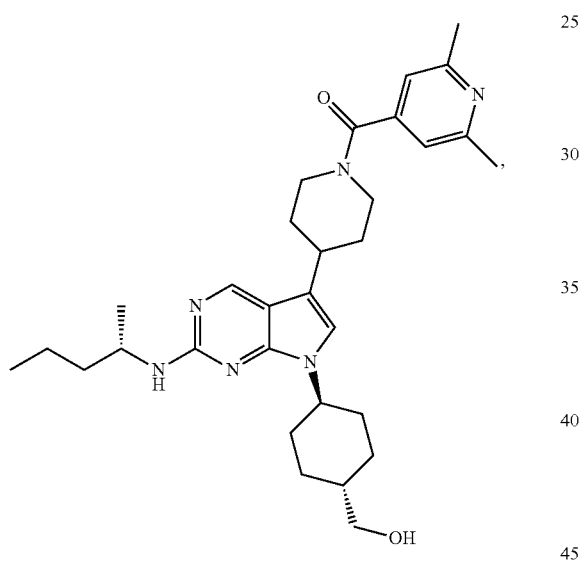
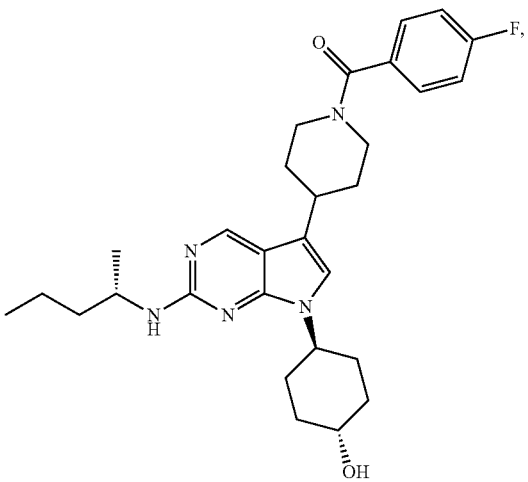
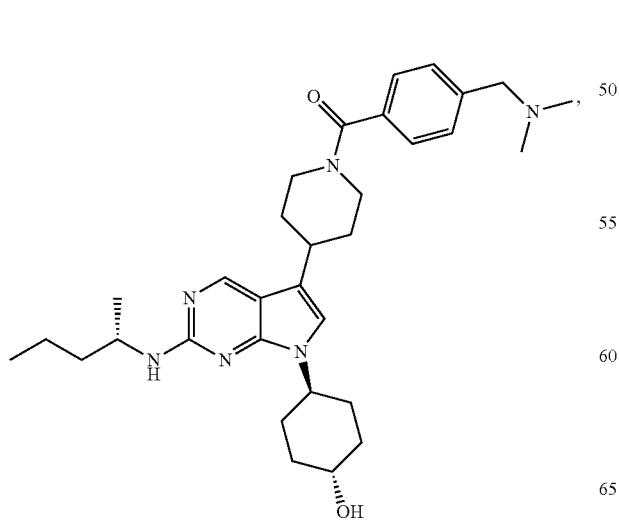
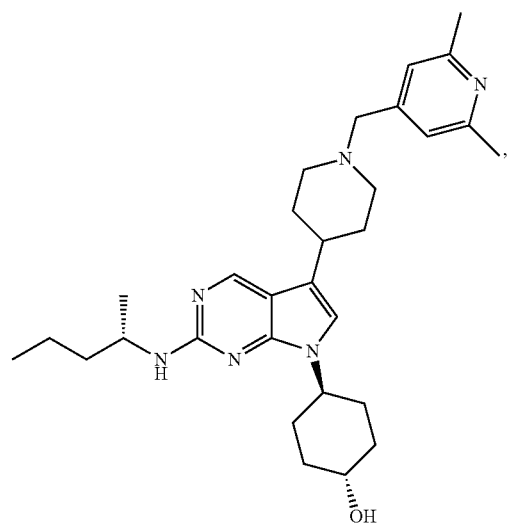

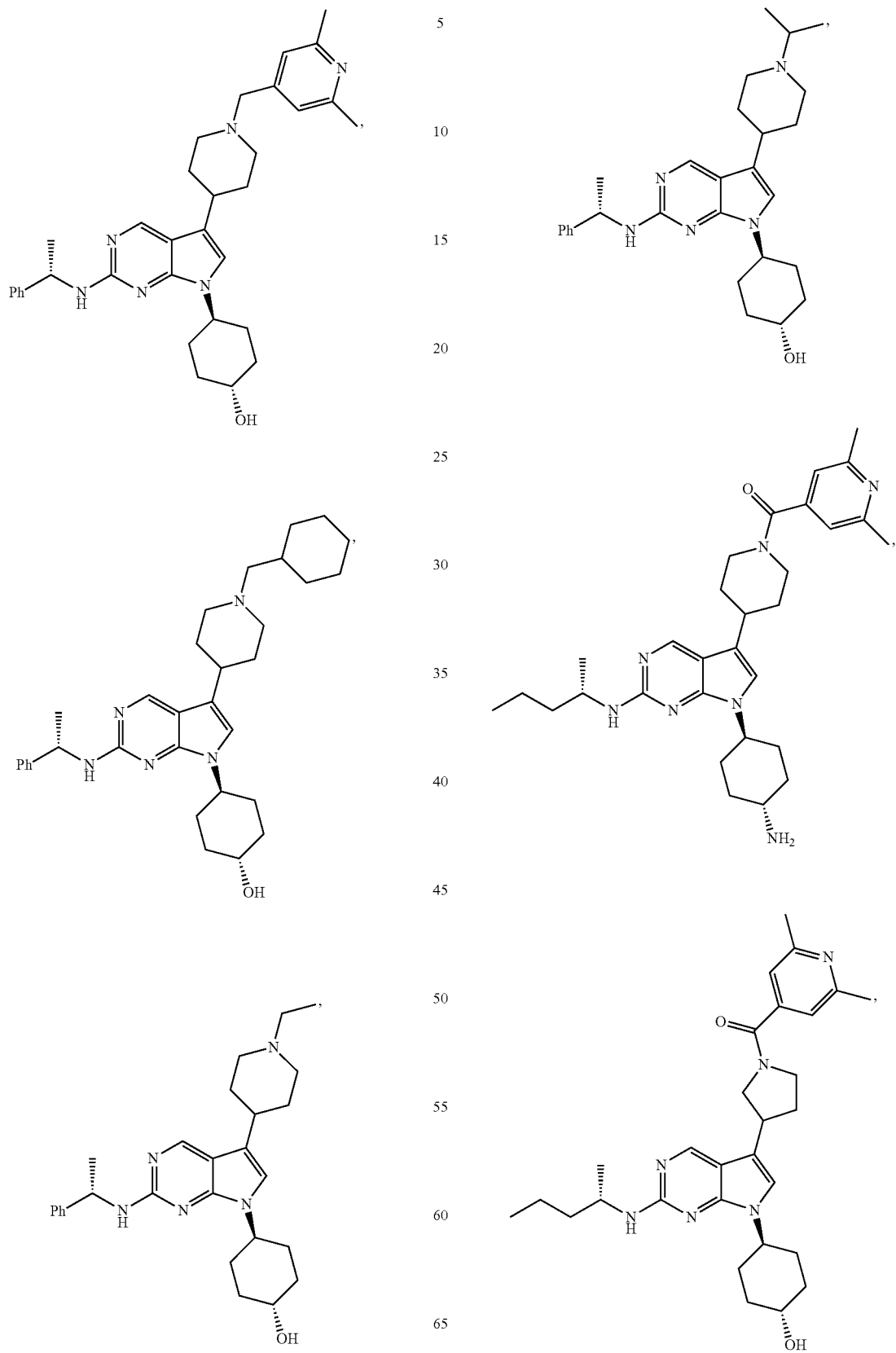

143
-continued
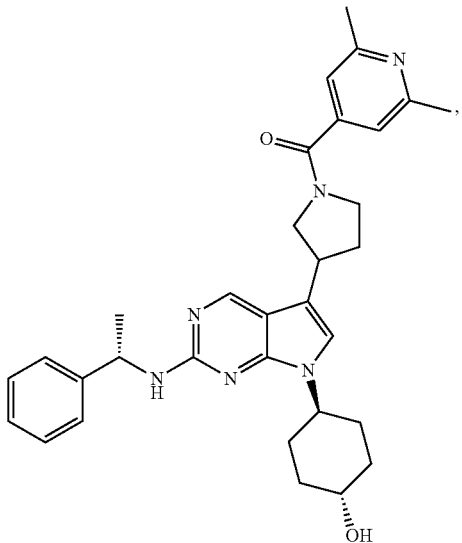
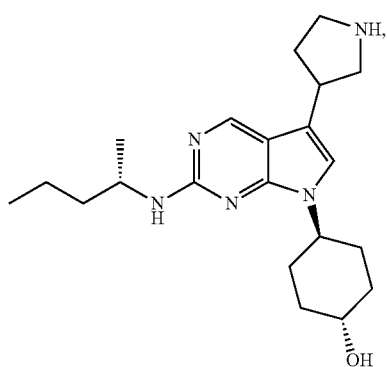
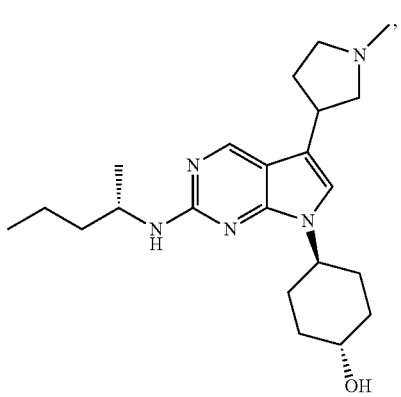
144
-continued
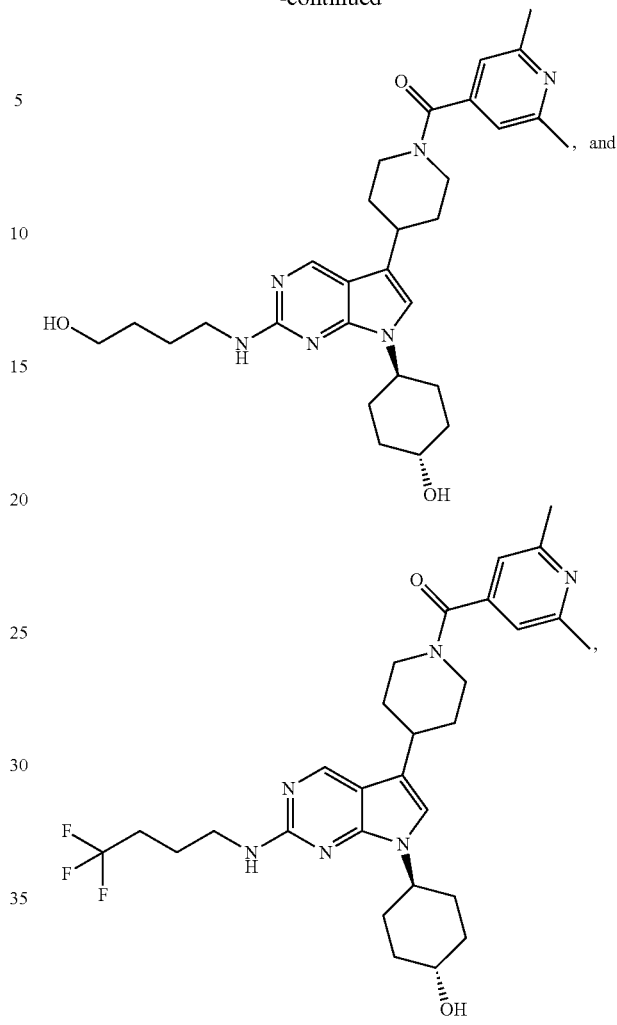
or a pharmaceutically acceptable salt thereof.
In one aspect, a compound can be present as one or more of the following structures:
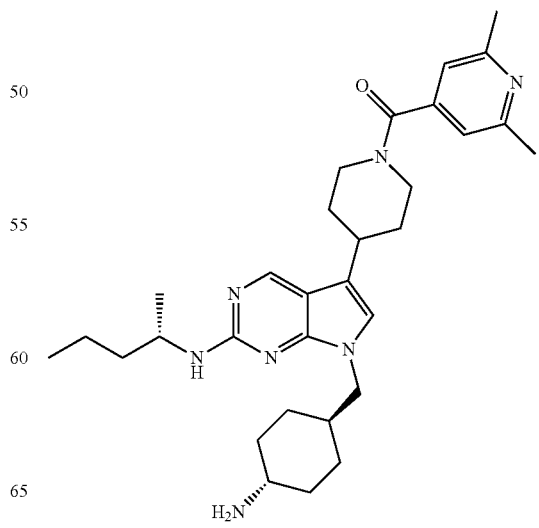
and

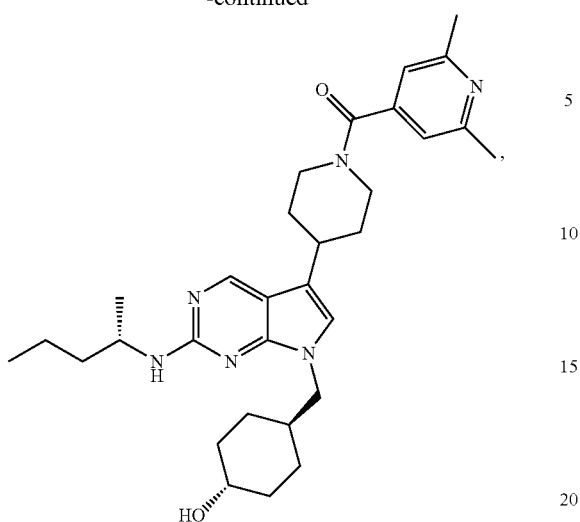

or a pharmaceutically acceptable salt thereof.

In one aspect, a compound can be present as the following structure:

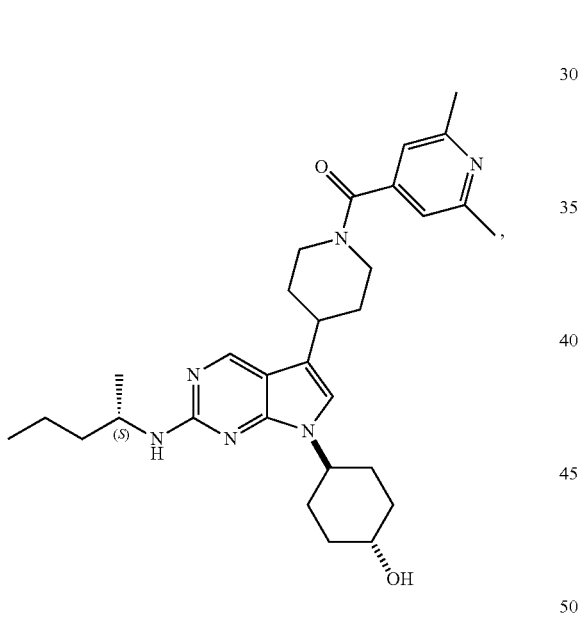

or a pharmaceutically acceptable salt thereof.

3. Prophetic Compound Examples

The following compound examples are prophetic, and can be prepared using the synthesis methods described herein above and other general methods as needed as would be known to one skilled in the art. It is anticipated that the prophetic compounds would be useful in treating a variety of disorders and diseases including, but not limited to, disorders of uncontrolled cellular proliferation such as, for example, cancer, infectious diseases, and thrombosis, and such activity can be determined using the assay methods described herein.

In one aspect, a compound can be selected from:

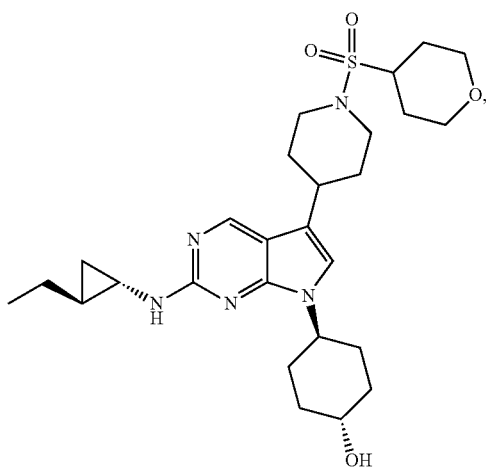

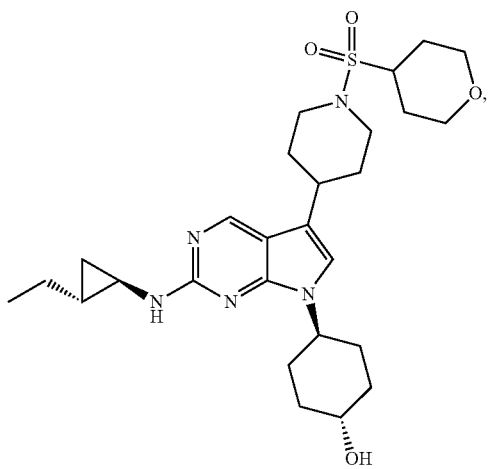

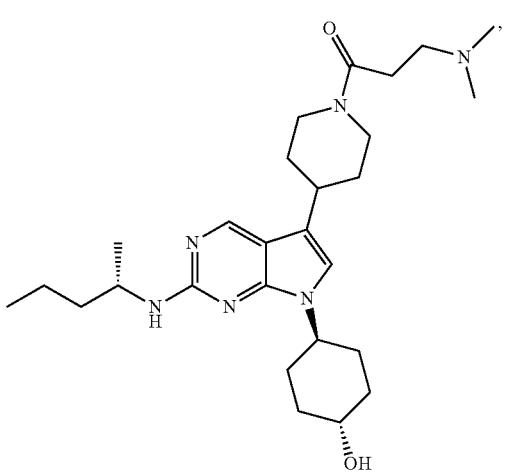

147
-continued
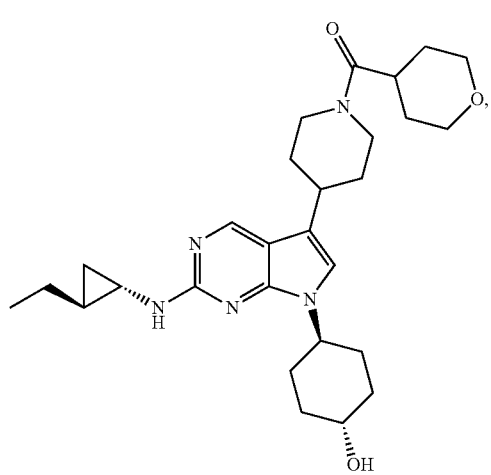
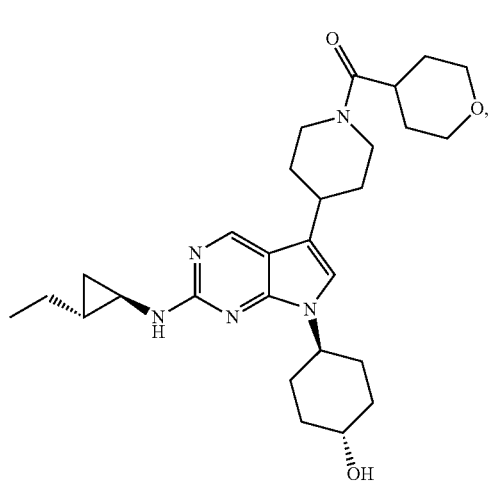
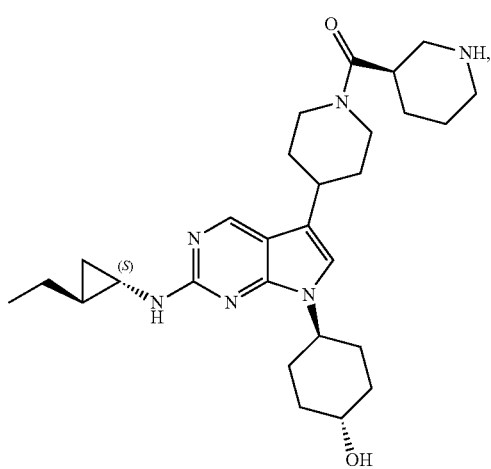
148
-continued
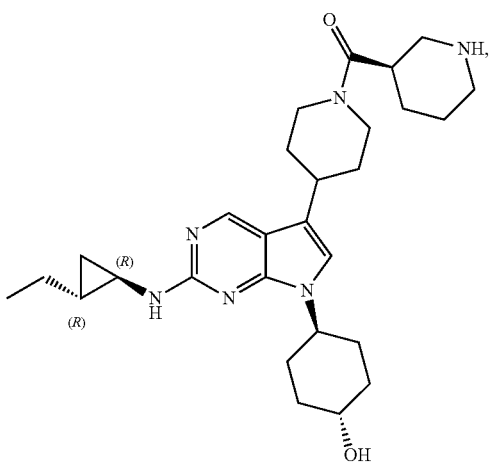
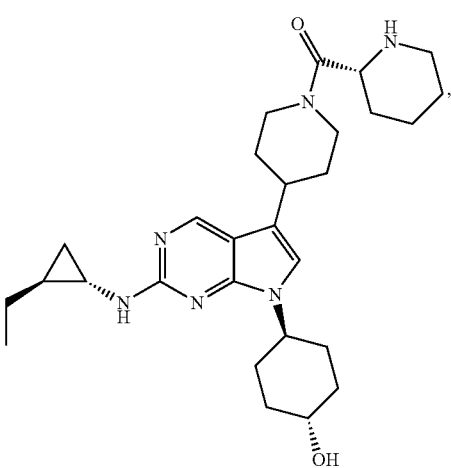
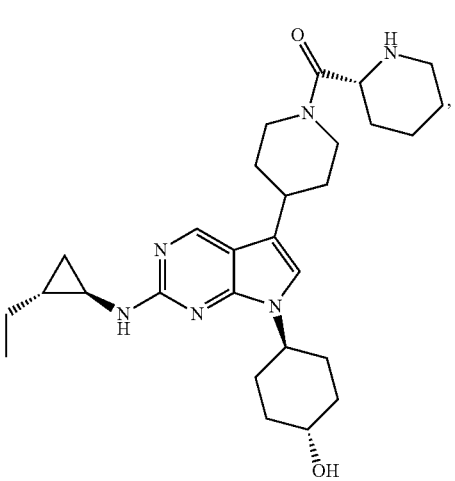

149
-continued
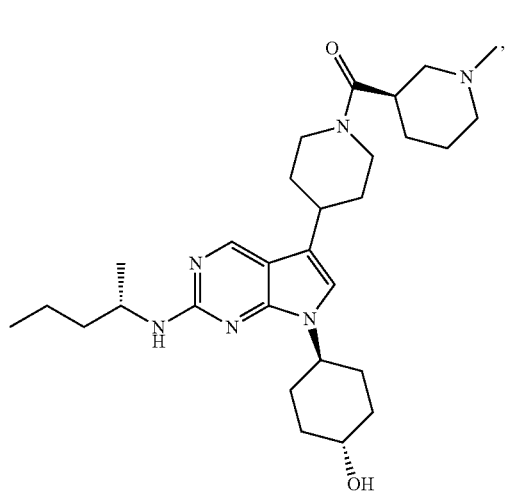
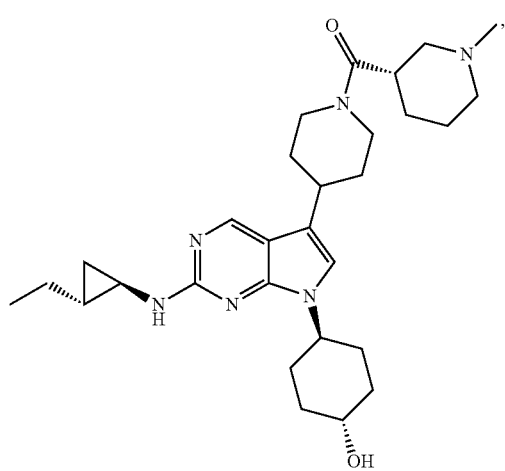
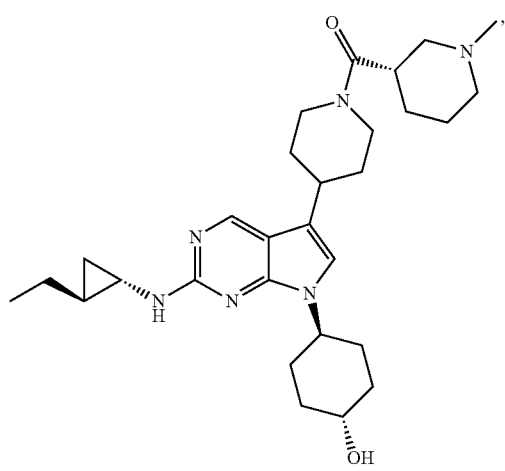
150
-continued
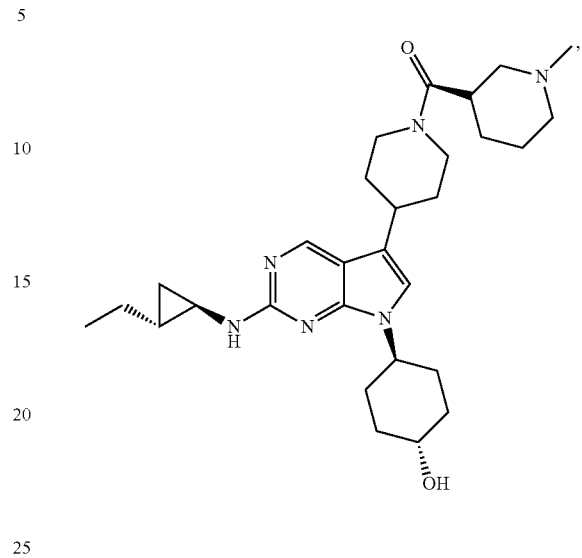
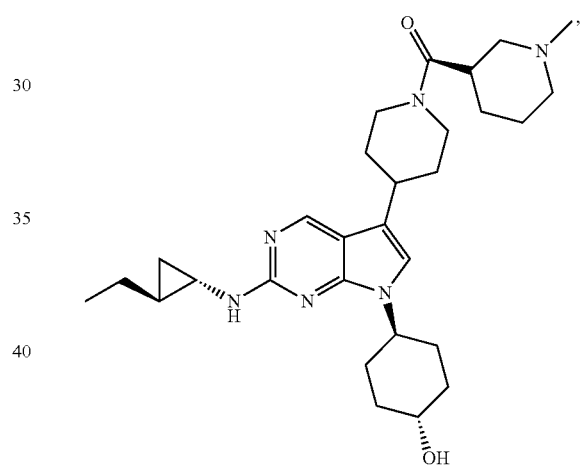
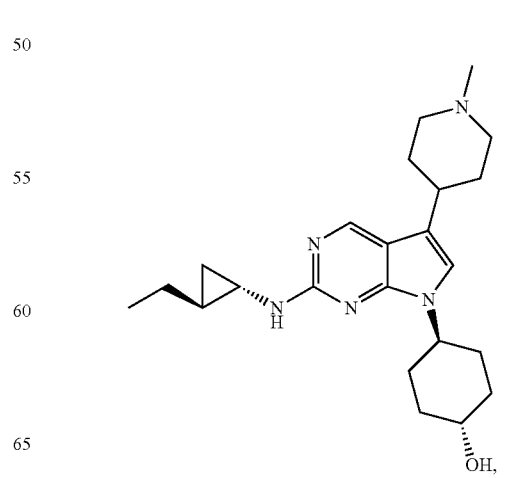
OH, and -continued

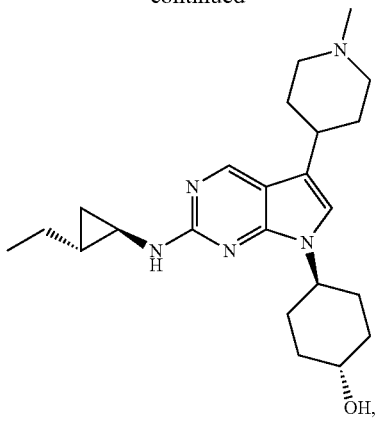

or a pharmaceutically acceptable salt thereof.

C. PHARMACEUTICAL COMPOSITIONS

In one aspect, the invention relates to pharmaceutical compositions comprising at least one disclosed compound and a pharmaceutically acceptable carrier. In a further aspect, a pharmaceutical composition can be provided comprising a therapeutically effective amount of at least one disclosed compound. In a still further aspect, a pharmaceutical composition can be provided comprising a prophylactically effective amount of at least one disclosed compound. In yet a further aspect, the invention relates to pharmaceutical compositions comprising a pharmaceutically acceptable carrier and a compound, wherein the compound is present in an effective amount.

Thus, in one aspect, disclosed are pharmaceutical compositions comprising a therapeutically effective amount of at lease one compound having a structure represented by a formula:

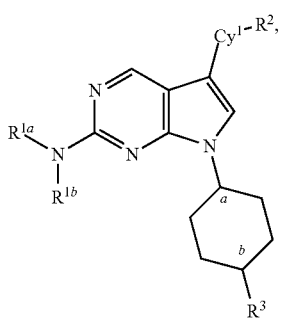

wherein Cy$^1$ is selected from C3-C8 cycloalkyl and C2-C7 heterocycloalkyl, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein R$^{1a}$ is selected from hydrogen, C1-C8 alkyl, and Cy$^2$, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein Cy$^2$, when present, is selected from C3-C9 cycloalkyl, C2-C7 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein R$^{1b}$ is selected from C1-C8 alkyl, Cy$^2$, and (C1-C4 alkyl)Cy$^2$, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein R$^2$ is selected from hydrogen, C1-C4 alkyl, —C(O)R$^{20}$, —C(O)N(R$^{22}$)R$^{20}$, —N(R$^{22}$)C(O)R$^{20}$, —SO$_2$N(R$^{22}$)R$^{21}$, —N(R$^{22}$)SO$_2$R$^{21}$, —SO$_2$R$^{21}$, and —(CH$_2$)$_n$Cy$^3$; wherein n is selected from 0, 1, 2, 3, and 4; wherein each of R$^{20}$ and R$^{21}$, when present, is selected from C1-C4 alkyl, —(CH$_2$)$_q$OR$^{30}$, and Cy$^4$; wherein q is selected from 0, 1, 2, 3, and 4; wherein R$^{30}$, when present, is selected from hydrogen and C1-C4 alkyl; wherein Cy$^4$, when present, is selected from C3-C8 cycloalkyl, C2-C7 heterocycloalkyl. C5-C6 aryl, and C3-C5 heteroaryl and substituted with 0, 1, 2, or 3 groups independently selected from halogen, —NH$_2$, C1-C4 alkyl, C1-C4 haloalkyl, C1-C4 alkoxy, C1-C4 hydroxyalkyl, C1-C4 alkylamino, (C1-C4)(C1-C4) dialkylamino, and (C1-C4 alkyl)NR$^{40a}$R$^{40b}$; wherein each of R$^{40a}$ and R$^{40b}$, when present, is independently selected from hydrogen and C1-C4 alkyl; wherein R$^{22}$, when present, is selected from hydrogen and C1-C4 alkyl; wherein Cy$^3$, when present, is selected from C3-C8 cycloalkyl, C2-C7 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; and wherein R$^3$ is selected from —(CH$_2$)$_p$OH and —(CH$_2$)$_p$NHR$^{23}$; wherein p is selected from 0, 1, and 2; and wherein R$^{23}$, when present, is selected from hydrogen and C1-C4 alkyl, provided that when R$^2$ is hydrogen or C1-C4 alkyl, then Cy$^1$ is a structure:

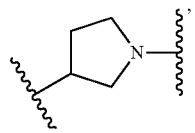

provided that when R$^2$ is C1-C4 alkyl, then R$^{1b}$ is selected from Cy$^2$ and (C1-C4 alkyl)Cy$^2$, or a pharmaceutically acceptable salt thereof, and a pharmaceutically acceptable carrier.

Thus, in one aspect, disclosed are pharmaceutical compositions comprising a therapeutically effective amount of at lease one compound having a structure represented by a formula:

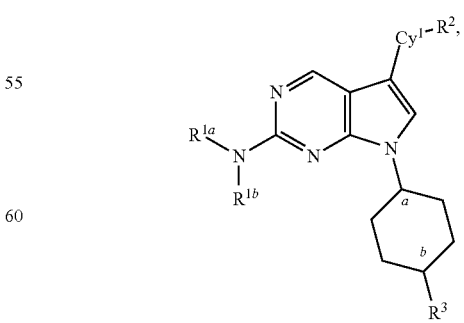

wherein Cy$^1$ is selected from C3-C8 cycloalkyl and C2-C7 heterocycloalkyl, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein $R^{1a}$ is selected from hydrogen, C1-C8 alkyl, and $Cy^2$, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein $Cy^2$, when present, is selected from C3-C8 cycloalkyl, C2-C7 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein $R^{1b}$ is selected from C1-C8 alkyl and $Cy^2$, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein $R^2$ is selected from —C(O)$R^{20}$, —C(O)N($R^{22}$)$R^{20}$, —N($R^{22}$)C(O)$R^{20}$, —SO$_2$N($R^{22}$)$R^{21}$, —N($R^{22}$)SO$_2$$R^{21}$, —SO$_2$$R^{21}$, and —(CH$_2$)$_n$$Cy^3$; wherein n is selected from 0, 1, 2, 3, and 4; wherein each of $R^{20}$ and $R^{21}$, when present, is selected from C1-C4 alkyl, —(CH$_2$)$_q$O$R^3$, and $Cy^4$; wherein q is selected from 0, 1, 2, 3, and 4; wherein $R^{30}$, when present, is selected from hydrogen and C1-C4 alkyl; wherein $Cy^4$, when present, is selected from C3-C8 cycloalkyl, C2-C7 heterocycloalkyl, C5-C6 aryl, and C4-C5 heteroaryl and substituted with 0, 1, 2, or 3 groups independently selected from halogen, C1-C4 alkyl. C1-C4 haloalkyl, C1-C4 alkoxy, C1-C4 hydroxyalkyl, C1-C4 alkylamino, and (C1-C4)(C1-C4) dialkylamino; wherein $R^{22}$, when present, is selected from hydrogen and C1-C4 alkyl; wherein $Cy^3$, when present, is selected from C3-C8 cycloalkyl, C2-C7 heterocycloalkyl. C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; and wherein $R^3$ is selected from —(CH$_2$)$_p$OH and —(CH$_2$)$_p$NH$R^{23}$; wherein p is selected from 0, 1, or 2; and wherein $R^{23}$, when present, is selected from hydrogen and C1-C4 alkyl, or a pharmaceutically acceptable salt thereof, and a pharmaceutically acceptable carrier.

The compounds are active against Mer tyrosine kinase, and generally have IC$_{50}$ values against Mer tyrosine kinase ranging from 0.01 nM to 30 µM. IC$_{50}$ refers to the concentration of the compound that is required for 50% antagonism or inhibition of Mer tyrosine kinase. IC$_{50}$ also refers to the concentration of a substance that is required for 50% antagonism or inhibition of Mer tyrosine kinase in vivo. The activity of the compounds, including IC$_{50}$, is determined according to the procedures discussed below in the Examples section.

The compounds are active against Tyro3 tyrosine kinase, and generally have IC$_{50}$ values against Tyro3 tyrosine kinase ranging from 0.01 nM to 30 µM. IC$_{50}$ refers to the concentration of the compound that is required for 50% antagonism or inhibition of Tyro3 tyrosine kinase. IC$_{50}$ also refers to the concentration of a substance that is required for 50% antagonism or inhibition of Tyro3 tyrosine kinase in vivo. The activity of the compounds, including IC$_{50}$, is determined according to the procedures discussed below in the Examples section.

Pharmaceutically acceptable salts of the compounds are conventional acid-addition salts or base-addition salts that retain the biological effectiveness and properties of the compounds and are formed from suitable non-toxic organic or inorganic acids or organic or inorganic bases. Exemplary acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Example base-addition salts include those derived from ammonium, potassium, sodium and, quaternary ammonium hydroxides, such as for example, tetramethylammonium hydroxide. Chemical modification of a pharmaceutical compound into a salt is a known technique to obtain improved physical and chemical stability, hygroscopicity, flowability and solubility of compounds. See, e.g., H. Ansel et, al., Pharmaceutical Dosage Forms and Drug Delivery Systems (6th Ed. 1995) at pp. 196 and 1456-1457.

The pharmaceutical compositions comprise the compounds in a pharmaceutically acceptable carrier. A pharmaceutically acceptable carrier refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. The compounds can be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

In a further aspect, the pharmaceutical composition is administered to a mammal. In a still further aspect, the mammal is a human. In an even further aspect, the human is a patient.

In a further aspect, the pharmaceutical composition is administered following identification of the mammal in need of treatment of an infection. In a still further aspect, the mammal has been diagnosed with a need for treatment of an infection prior to the administering step. In yet a further aspect, the infection is a viral infection or a bacterial infection. In an even further aspect, the infection is a bacterial infection. In a still further aspect, the infection is a viral infection. In yet a further aspect, the viral infection has a virion envelope phosphatidyl serine.

In a further aspect, the pharmaceutical composition is administered following identification of the mammal in need of treatment of a thrombotic disorder or a clotting disorder. In a still further aspect, the mammal has been diagnosed with a need for treatment of a thrombotic disorder or a clotting disorder prior to the administering step.

In a further aspect, the pharmaceutical composition is administered following identification of the mammal in need of treatment of a disorder of uncontrolled cellular proliferation. In a still further aspect, the mammal has been diagnosed with a need for treatment of a disorder of uncontrolled cellular proliferation prior to the administering step.

In various aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

The choice of carrier will be determined in part by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, intraperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granule; (c) powders; (d) suspensions in an appropriate liquid; and (e) suitable emulsions. Liquid formulations may include diluents, such as water, cyclodextrin, dimethyl sulfoxide and alcohols, for example, ethanol, benzyl alcohol, propylene glycol, glycerin, and the polyethylene alcohols including polyethylene glycol, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, the addition to the active ingredient in an inert base, such as gelatin and glycerin, or sucrose and acadia, emulsions, and gels containing, in addition to the active ingredient, such carriers as are known in the art.

The compounds of the present disclosure alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1, 3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present disclosure. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See *Pharmaceutics and Pharmacy Practice*, J.B. Lippincott Co., Philadelphia, Pa., Banker and Chalmers, Eds., 238-250 (1982) and *ASHP Handbook on Injectable Drugs*, Toissel, 4$^{th}$ ed., 622-630 (1986).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, and gels containing, in addition to the active ingredient, such carriers as are known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

One skilled in the art will appreciate that suitable methods of exogenously administering a compound of the present disclosure to an animal are available, and, although more than one route can be used to administer a particular compound, a particular route can provide a more immediate and more effective reaction than another route.

As regards these applications, the present method includes the administration to an animal, particularly a mammal, and more particularly a human, of a therapeutically effective amount of the compound effective in the inhibition of Mer tyrosine kinase and/or Tyro3 tyrosine kinase. The method also includes the administration of a therapeutically effect amount of the compound for the treatment of patient having a predisposition for being afflicted with a disorder associated Mer tyrosine kinase dysfunction or Tyro3 tyrosine kinase dysfunction, or an infectious disease. The dose administered to an animal, particularly a human, in the context of the present invention should be sufficient to affect a therapeutic response in the animal over a reasonable time frame. One skilled in the art will recognize that dosage will depend upon a variety of factors including the condition of the animal, the body weight of the animal, as well as the severity and stage of the disorder or infectious disease.

The total amount of the compound of the present disclosure administered in a typical treatment is preferably between about 10 mg/kg and about 1000 mg/kg of body weight for mice, and between about 100 mg/kg and about 500 mg/kg of body weight, and more preferably between 200 mg/kg and about 400 mg/kg of body weight for humans per daily dose. This total amount is typically, but not necessarily, administered as a series of smaller doses over a period of about one time per day to about three times per day for about 24 months, and preferably over a period of twice per day for about 12 months.

The size of the dose also will be determined by the route, timing and frequency of administration as well as the existence, nature and extent of any adverse side effects that might accompany the administration of the compound and the desired physiological effect. It will be appreciated by one of skill in the art that various conditions or disease states, in particular chronic conditions or disease states, may require prolonged treatment involving multiple administrations.

In a further aspect, the composition further comprises at least one agent known to treat a viral infection. Examples of viral infections include, but are not limited to, human immunodeficiency virus (HIV), human papillomavirus (HPV), influenza, chicken pox, infectious mononucleosis, mumps, measles, rubella, shingles, ebola, viral gastroenteritis, viral hepatitis, viral meningitis, human metapneumovirus, human parainfluenza virus type 1, parainfluenza virus type 2, parainfluenza virus type 3, respiratory syncytial virus, viral pneumonia, chikungunya, Venezuelan equine encephalitis, dengue, influenza, and zika. In yet a further aspect, the composition further comprises at least one agent known to have a side effect of increasing the risk of a viral infection.

In a further aspect, the composition further comprises at least one agent known to treat a bacterial infection. Examples of bacterial infections include, but are not limited to, *M. tuberculosis, M. bovis, M. bovis* strain BCG, BCG substrains, *M. avium, M. intracellulare, M. africanumn, M. kansasii, M. marinum, M. ulcerans, P. avium* subspecies paratuberculosis, *Nocardia asteroides*, other *Nocardia* species, *Legionella pneumophila*, other *Legionella* species, *Salmonella typhi*, other *Salmonella* species, *Shigella* species, *Yersinia pestis, Pasteurella haemolvtica, Pasteurella multocida*, other *Pasteurella* species, *Actinobacillus pleuropneumoniae, Listeria monocytogenes, Listeria ivanovii, Brucella abortus*, other *Brucella* species, *Cowdria ruminantium, Chlamydia pneumoniae, Chlamydia trachomatis, Chlamydia psittaci, Coxiella burnetti*, other *Rickettsial* species, *Ehrlichia* species, *Staphylococcus aureus, Staphylococcus epidermidis, Streptococcus pneumoniae, Streptococcus pyogenes, Streptococcus agalactiae, Bacillus anthracis, Escherichia coli, Vibrio cholerae, Campylobacter* species, *Neiserria meningitidis, Neiserria gonorrhea, Pseudomonas aeruginosa*, other *Pseudomonas* species, *Haemophilus influenzae, Haemophilus ducreyi*, other *Hemophilus* species, *Clostridium tetani*, other *Clostridium* species, *Yersinia enterolitica*, and other *Yersinia* species. In yet a further aspect, the composition further comprises at least one agent known to have a side effect of increasing the risk of a bacterial infection.

In a further aspect, the composition further comprises at least one agent known to treat a thrombotic disorder or a clotting disorder. In a still further aspect, the thrombotic disorder or the clotting disorder is selected from myocardial infarction, deep vein thrombosis, pulmonary embolism, and stroke. In yet a further aspect, the composition further comprises at least one agent known to have a side effect of increasing the risk of a thrombotic disorder or a clotting disorder.

In a further aspect, the composition further comprises at least one agent known to treat a disorder of uncontrolled cellular proliferation. In a still further aspect, the disorder of uncontrolled cellular proliferation is a cancer. Examples of cancers include, but are not limited to, leukemias, lymphomas, and solid tumors. In one aspect, the cancer can be a cancer selected from cancers of the gastrointestinal tract, hematologic, colon, rectum, liver, omentum, breast, kidney, lymphatic system, stomach, lung, pancreas, liver and skin. In a further aspect, the cancer is selected from leukemia and gastrointestinal stroma tumor. In a further aspect, the composition further comprises at least one agent known to have a side effect of increasing the risk of a disorder of uncontrolled cellular proliferation.

It is understood that the disclosed compositions can be prepared from the disclosed compounds. It is also understood that the disclosed compositions can be employed in the disclosed methods of using.

D. METHODS OF MAKING THE COMPOUNDS

In one aspect, disclosed are methods of making a compound having a structure represented by a formula:

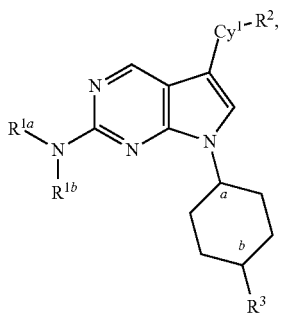

wherein Cy¹ is selected from C3-C8 cycloalkyl and C2-C7 heterocycloalkyl, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein $R^a$ is selected from hydrogen, C1-C8 alkyl, and Cy², and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein Cy², when present, is selected from C3-C9 cycloalkyl, C2-C7 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein $R^{1b}$ is selected from C1-C8 alkyl, Cy², and (C1-C4 alkyl)Cy², and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein $R^2$ is selected from hydrogen, C1-C4 alkyl, —C(O)$R^{20}$, —C(O)N($R^{22}$)$R^{20}$, —N($R^{22}$)C(O)$R^{20}$, —SO$_2$N($R^{22}$)$R^{20}$, —N($R^{22}$)SO$_2R^{21}$, —SO$_2R^{21}$, and —(CH$_2$)$_n$Cy³; wherein n is selected from 0, 1, 2, 3, and 4; wherein each of $R^{20}$ and $R^{21}$, when present, is selected from C1-C4 alkyl, —(CH$_2$)$_q$OR$^{30}$, and Cy⁴; wherein q is selected from 0, 1, 2, 3, and 4; wherein $R^{30}$, when present, is selected from hydrogen and C1-C4 alkyl; wherein Cy⁴, when present, is selected from C3-C8 cycloalkyl, C2-C7 heterocycloalkyl, C5-C6 aryl, and C3-C5 heteroaryl and substituted with 0, 1, 2, or 3 groups independently selected from halogen, —NH$_2$, C1-C4 alkyl, C1-C4 haloalkyl, C1-C4 alkoxy, C1-C4 hydroxyalkyl, C1-C4 alkylamino, (C1-C4)(C1-C4) dialkylamino, and (C1-C4 alkyl)NR$^{40a}$R$^{40b}$; wherein each of $R^{40a}$ and $R^{40b}$, when present, is independently selected from hydrogen and C1-C4 alkyl; wherein $R^{22}$, when present, is selected from hydrogen and C1-C4 alkyl; wherein Cy³, when present, is selected from C3-C8 cycloalkyl, C2-C7 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; and wherein $R^3$ is selected from —(CH$_2$)$_p$OH and —(CH$_2$)$_p$NHR$^{23}$; wherein p is selected from 0, 1, and 2; and wherein $R^{23}$, when present, is selected from hydrogen and C1-C4 alkyl, provided that when $R^2$ is hydrogen or C1-C4 alkyl, then Cy¹ is a structure:

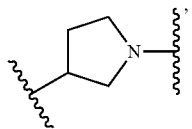

or provided that when $R^2$ is C1-C4 alkyl, then $R^{1b}$ is selected from Cy² and (C1-C4 alkyl)Cy², or a pharmaceutically acceptable salt thereof.

In one aspect, disclosed are methods of making a compound having a structure represented by a formula:

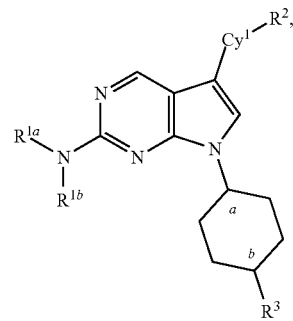

wherein Cy¹ is selected from C3-C8 cycloalkyl and C2-C7 heterocycloalkyl, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein $R^{1a}$ is selected from hydrogen, C1-C8 alkyl, and Cy², and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein Cy², when present, is selected from C3-C8 cycloalkyl, C2-C7 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein $R^{1b}$ is selected from C1-C8 alkyl and Cy², and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein R" is selected from —C(O)$R^2$, —C(O)N(R")$R^{20}$, —N($R^{22}$)C(O)$R^{20}$, —SO$_2$N($R^{22}$)$R^{21}$, —N($R^{22}$)SO$_2R^{21}$, —SO$_2R^{21}$, and —(CH$_2$)$_n$Cy³; wherein n is selected from 0, 1, 2, 3, and 4; wherein each of $R^{20}$ and $R^{21}$, when present, is selected from C1-C4 alkyl, —(CH$_2$)$_q$OR$^3$, and Cy⁴; wherein q is selected from 0, 1, 2, 3, and 4; wherein $R^{30}$, when present, is selected from hydrogen and C1-C4 alkyl; wherein Cy⁴, when present, is selected from C3-C8 cycloalkyl, C2-C7 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein $R^{22}$, when present, is selected from hydrogen and C1-C4 alkyl; wherein Cy³, when present, is selected from C3-C8 cycloalkyl, C2-C7 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; and wherein $R^3$ is selected from —$(CH_2)_pOH$ and —$(CH_2)_pNHR^{20}$; wherein p is selected from 0, 1, or 2; and wherein $R^{23}$, when present, is selected from hydrogen and C1-C4 alkyl, or a pharmaceutically acceptable salt thereof.

In one aspect, disclosed are methods of making a compound having a structure selected from:

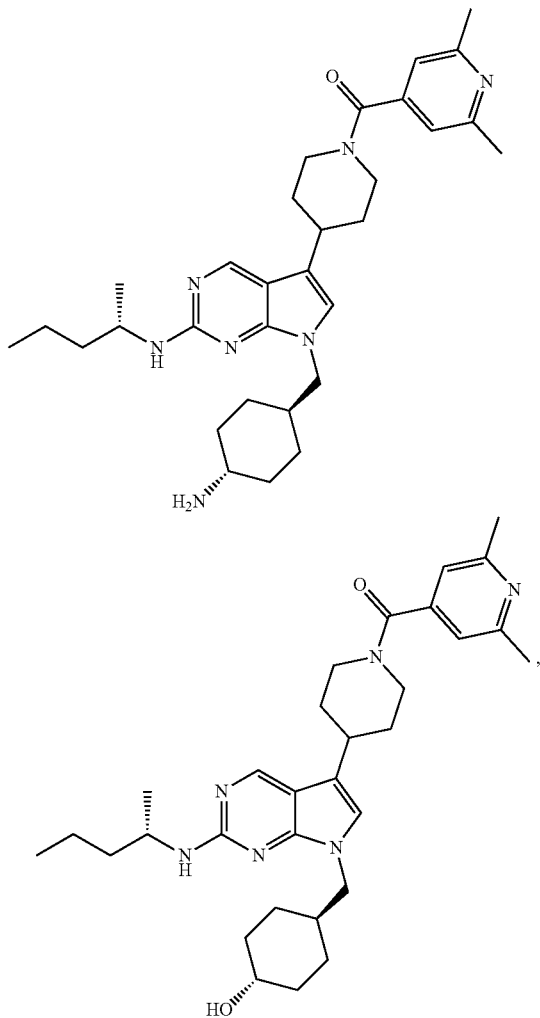

or a pharmaceutically acceptable salt thereof.

In various aspects, disclosed are methods of making compounds useful to treat a disorder of uncontrolled cellular proliferation, in particular, a cancer. In a further aspect, disclosed are methods of making compounds useful to treat an infection, in particular a viral or bacterial infection. In a still further aspect, disclosed are methods of making compounds useful to treat a thrombotic disorder or a clotting disorder. Thus, in one aspect, disclosed are methods of making a disclosed compound.

Compounds according to the present disclosure can, for example, be prepared by the several methods outlined below. A practitioner skilled in the art will understand the appropriate use of protecting groups [see: Greene and Wuts, *Protective Groups in Organic Synthesis*] and the preparation of known compounds found in the literature using the standard methods of organic synthesis. There may come from time to time the need to rearrange the order of the recommended synthetic steps, however this will be apparent to the judgment of a chemist skilled in the art of organic synthesis. The following examples are provided so that the invention might be more fully understood, are illustrative only, and should not be construed as limiting.

In one aspect, the disclosed compounds comprise the products of the synthetic methods described herein. In a further aspect, the disclosed compounds comprise a compound produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one compound of any of disclosed compounds or at least one product of the disclosed methods with a pharmaceutically acceptable carrier or diluent.

1. Route I

In one aspect, alkyl pyrrolopyrimidine analogs can be prepared as shown below.

SCHEME 1A.

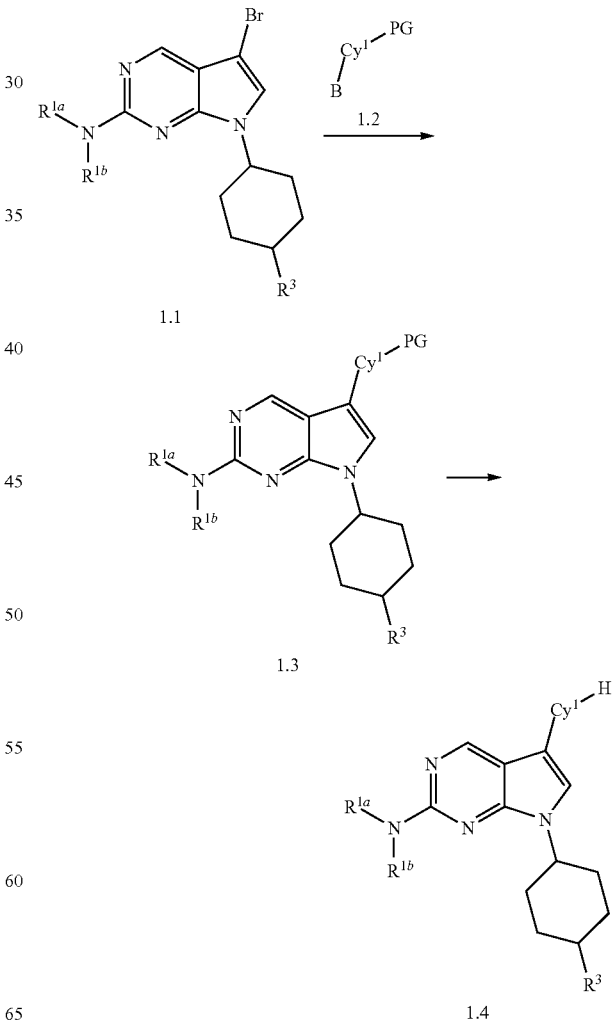

Compounds are represented in generic form, with substituents as noted in compound descriptions elsewhere herein, wherein PG is a protecting group, and B is a boron coupling agent. A more specific example is set forth below.

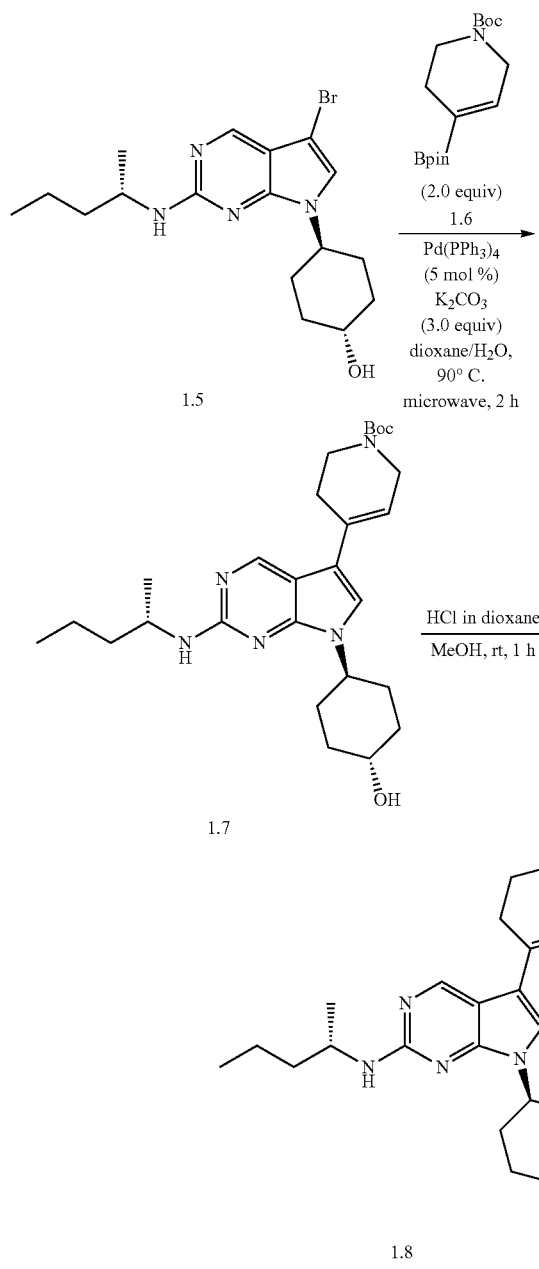

in an appropriate solvent system, e.g., dioxane and water, at an appropriate temperature, e.g., 90° C., for an appropriate period of time, e.g., 2 hours. Compounds of type 1.8 can be prepared by deprotection of an appropriate amine, e.g., 1.7 as shown above. The deprotection is carried out in the presence of an appropriate acid, e.g., hydrochloric acid, in an appropriate solvent, e.g., methanol, for an appropriate period of time, e.g., 1 hour. As can be appreciated by one skilled in the art, the above reaction provides an example of a generalized approach wherein compounds similar in structure to the specific reactants above (compounds similar to compounds of type 1.1, 1.2, and 1.3), can be substituted in the reaction to provide substituted alkyl pyrrolopyrimidine analogs similar to Formula 1.4.

2. Route II

In one aspect, alkyl pyrrolopyrimidine analogs can be prepared as shown below.

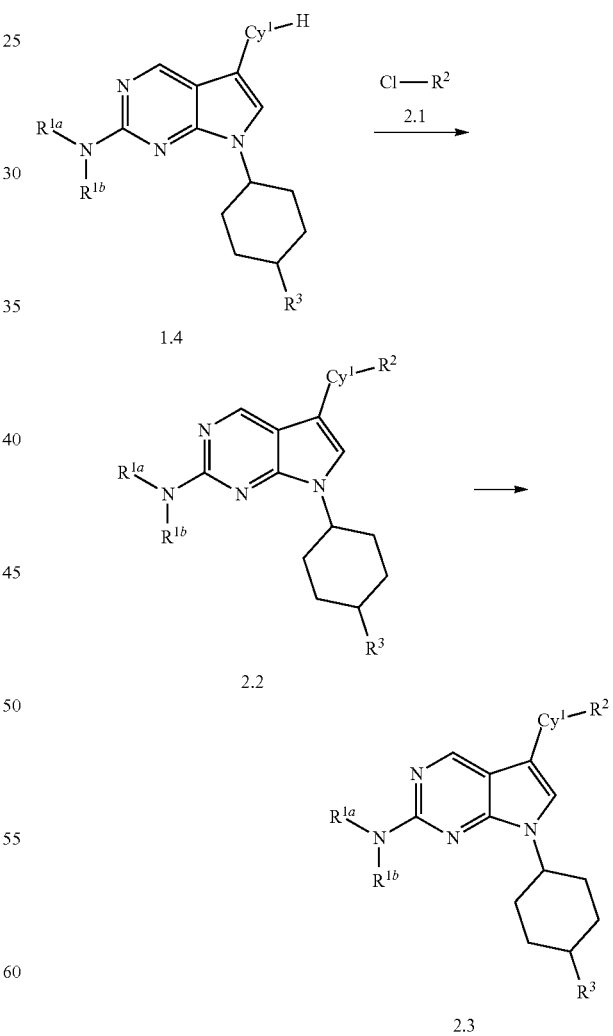

In one aspect, compounds of type 1.4, and similar compounds, can be prepared according to reaction Scheme 1B above. Thus, compounds of type 1.7 can be prepared by a coupling reaction of an appropriate alkenyl halide, e.g., 1.5 as shown above, and an appropriate boron compound, e.g., 1.6 as shown above. Appropriate alkenyl halides and appropriate boron compounds are commercially available or prepared by methods known to one skilled in the art. The coupling reaction is carried out in the presence of an appropriate catalyst, e.g., tetrakis(triphenylphosphine)palladium (0), and an appropriate base, e.g., potassium carbonate, Compounds are represented in generic form, with substituents as noted in compound descriptions elsewhere herein. A more specific example is set forth below.

SCHEME 2B.

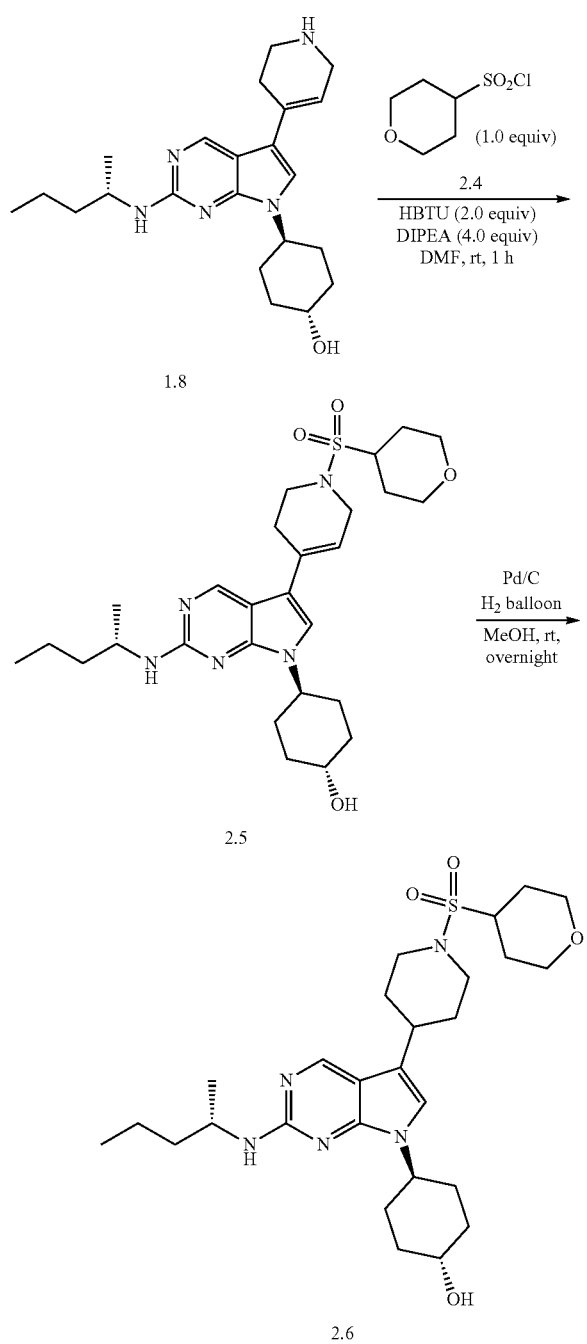

In one aspect, compounds of type 2.3, and similar compounds, can be prepared according to reaction Scheme 2B above. Thus, compounds of type 2.5 can be prepared by a coupling reaction of an appropriate amine, e.g., 1.8 as shown above, and an appropriate acyl halide or sulfonyl halide, e.g., 2.4 as shown above. Appropriate acyl halides and appropriate sulfonyl halides are commercially available or prepared by methods known to one skilled in the art. The coupling reaction is carried out in the presence of an appropriate catalyst, e.g., 2-(1H-benzotriazol-1-yl)-1,1,3,3-tetramethyluronium hexafluorophosphate (HBTU), and an appropriate base, e.g., diisopropylethylamine (DIPEA), in an appropriate solvent, e.g., dimethylformamide (DMF), for an appropriate period of time, e.g., 1 hour. Compounds of type 2.6 can be prepared by hydrogenation of an appropriate alkene, e.g., 2.5 as shown above. The hydrogenation is carried out in the presence of an appropriate hydrogen source, e.g., hydrogen gas, and an appropriate catalyst, e.g., palladium on Carbon, in an appropriate solvent, e.g., methanol. As can be appreciated by one skilled in the art, the above reaction provides an example of a generalized approach wherein compounds similar in structure to the specific reactants above (compounds similar to compounds of type 1.4, 2.1, and 2.2), can be substituted in the reaction to provide substituted alkyl pyrrolopyrimidine analogs similar to Formula 23.

3. Route III

In one aspect, alkyl pyrrolopyrimidine analogs can be prepared as shown below.

SCHEME 3A.

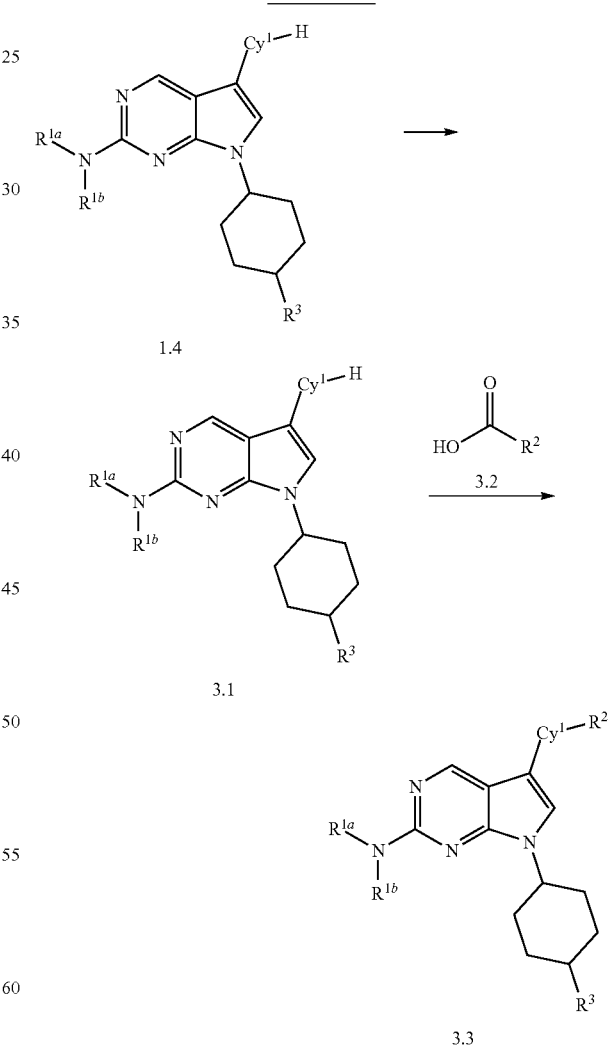

Compounds are represented in generic form, with substituents as noted in compound descriptions elsewhere herein. A more specific example is set forth below.

SCHEME 3B.

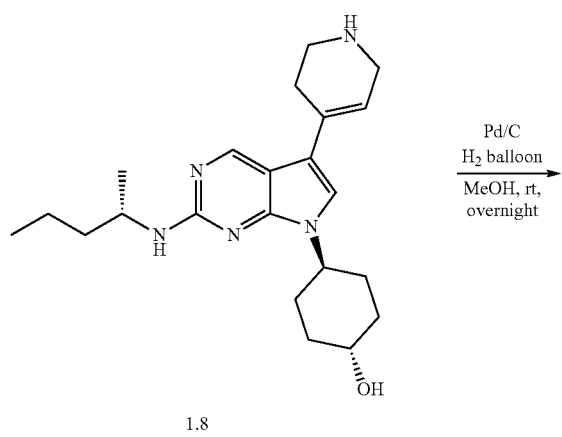

1.8

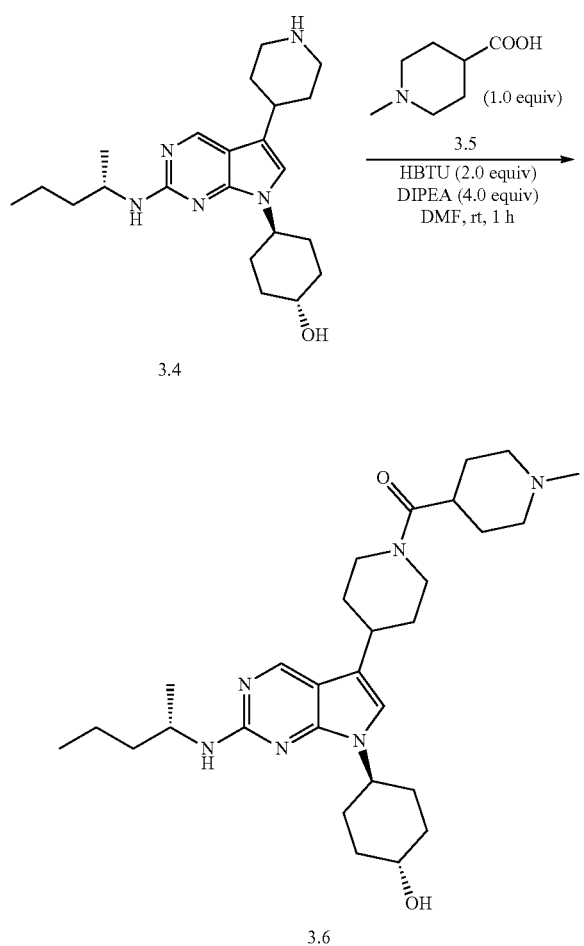

3.4

3.6

In one aspect, compounds of type 3.3, and similar compounds, can be prepared according to reaction Scheme 3B above. Thus, compounds of type 3.4 can be prepared by hydrogenation of an appropriate alkene, e.g., 1.8 as shown above. The hydrogenation is carried out in the presence of an appropriate hydrogen source, e.g., hydrogen gas, and an appropriate catalyst, e.g., palladium on Carbon, in an appropriate solvent, e.g., methanol. Compounds of type 3.6 can be prepared by a coupling reaction of an appropriate amine, e.g., 3.4 as shown above, and an appropriate carboxylic acid, e.g., 3.5 as shown above. Appropriate carboxylic acids are commercially available or prepared by methods known to one skilled in the art. The coupling reaction is carried out in the presence of an appropriate catalyst, e.g., 2-(1H-benzotriazol-1-yl)-1,1,3,3-tetramethyluronium hexafluorophosphate (HBTU), and an appropriate base, e.g., diisopropylethylamine (DIPEA), in an appropriate solvent, e.g., dimethylformamide (DMF), for an appropriate period of time, e.g., 1 hour. As can be appreciated by one skilled in the art, the above reaction provides an example of a generalized approach wherein compounds similar in structure to the specific reactants above (compounds similar to compounds of type 1.4, 3.1, and 3.2), can be substituted in the reaction to provide substituted alkyl pyrrolopyrimidine analogs similar to Formula 3.3.

4. Route IV

In one aspect, alkyl pyrrolopyrimidine analogs can be prepared as shown below.

SCHEME 4A.

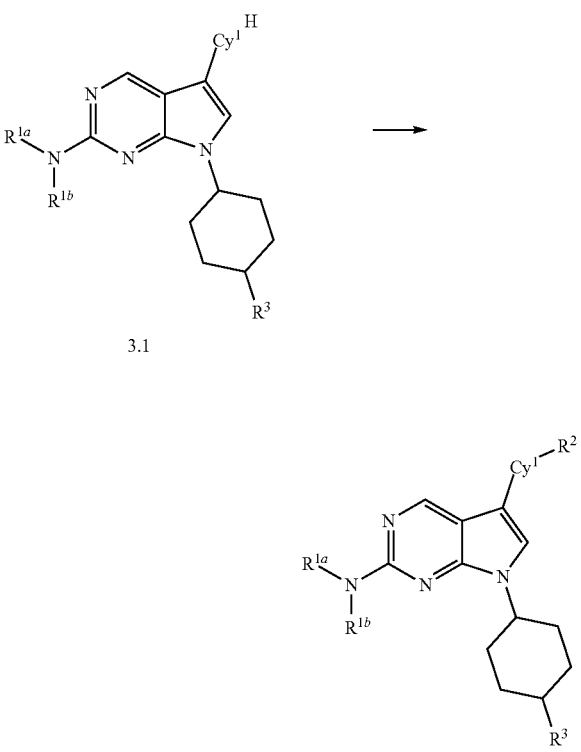

Compounds are represented in generic form, with substituents as noted in compound descriptions elsewhere herein. A more specific example is set forth below.

SCHEME 4B.

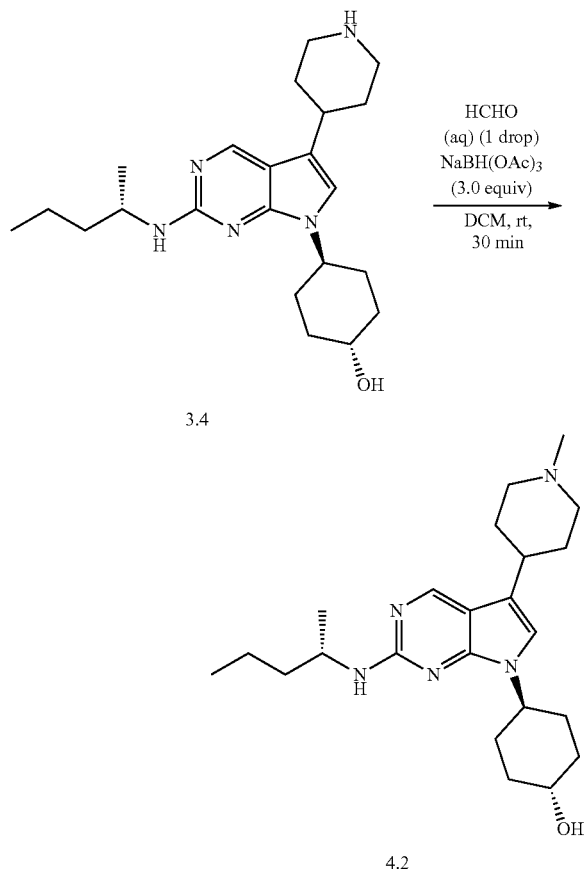

In one aspect, compounds of type 4.1, and similar compounds, can be prepared according to reaction Scheme 4B above. Thus, compounds of type 4.2 can be prepared by reductive amination of an appropriate amine, e.g., 3.4 as shown above, with an appropriate aldehyde, e.g., formaldehyde as shown above. Appropriate aldehydes are commercially available or prepared by methods known to one skilled in the art. The reductive amination is carried out in the presence of an appropriate catalyst, e.g., sodium triacetoxyborohydride, in an appropriate solvent, e.g., dichloromethane, for an appropriate period of time, e.g., 30 minutes. As can be appreciated by one skilled in the art, the above reaction provides an example of a generalized approach wherein compounds similar in structure to the specific reactants above (compound similar to compounds of type 3.1), can be substituted in the reaction to provide substituted alkyl pyrrolopyrimidine analogs similar to Formula 4.2.

E. METHODS OF USING THE COMPOUNDS

The compounds and pharmaceutical compositions of the invention are useful in treating or controlling a variety of disorders including, but not limited to, disorders of uncontrolled cellular proliferation such as, for example, cancer, infections such as, for example, a viral infection and a bacterial infection, and thrombotic disorders.

Examples of disorders of uncontrolled cellular proliferation include, but are not limited to, cancer.

Examples of viral infections for which the compounds and compositions can be useful in treating, include, but are not limited to, human immunodeficiency virus (HIV), human papillomavirus (HPV), influenza, chicken pox, infectious mononucleosis, mumps, measles, rubella, shingles, ebola, viral gastroenteritis, viral hepatitis, viral meningitis, human metapneumovirus, human parainfluenza virus type 1, parainfluenza virus type 2, parainfluenza virus type 3, respiratory syncytial virus, viral pneumonia, chikungunya. Venezuelan equine encephalitis, dengue, influenza, and zika.

Examples of bacterial infections include, but are not limited to, Gram-negative bacilli (GNB) (e.g., *Escherichia coli*, Gram-positive cocci (GPC), *Staphylococcus aureus*, *Enterococcus faecalis*, *Streptococcus pneumoniae*) and Gram-positive bacilli (e.g., species from *Bacillus, Listeria, Staphylococcus, Enterococcus, Lactobacillus, Lactococcus, Leuconostoc, Pediococcus, Streptococcus, Acetobacterium, Clostridium, Eubacterium, Heliobacterium, Heliospirillum, Megasphaera, Pectinatus, Selenomonas, Zymophilus, Sporomusa, Mycoplasma, Spiroplasma, Ureaplasma,* or *Erysipelothrix*).

Examples of thrombotic disorders include, but are not limited to, myocardial infarction, deep vein thrombosis, pulmonary embolism, and stroke.

To treat or control the disorder, the compounds and pharmaceutical compositions comprising the compounds are administered to a subject in need thereof, such as a vertebrate, e.g., a mammal, a fish, a bird, a reptile, or an amphibian. The subject can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. The subject is preferably a mammal, such as a human. Prior to administering the compounds or compositions, the subject can be diagnosed with a need for treatment of a disorder or infection.

The compounds or compositions can be administered to the subject according to any method. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration and parenteral administration, including injectable such as intravenous administration, intra-arterial administration, intramuscular administration, and subcutaneous administration. Administration can be continuous or intermittent. A preparation can be administered therapeutically; that is, administered to treat an existing disease or condition. A preparation can also be administered prophylactically; that is, administered for prevention of a disorder or infection.

The therapeutically effective amount or dosage of the compound can vary within wide limits. Such a dosage is adjusted to the individual requirements in each particular case including the specific compound(s) being administered, the route of administration, the condition being treated, as well as the patient being treated. In general, in the case of oral or parenteral administration to adult humans weighing approximately 70 Kg or more, a daily dosage of about 10 mg to about 10,000 mg, preferably from about 200 mg to about 1,000 mg, should be appropriate, although the upper limit may be exceeded. The daily dosage can be administered as a single dose or in divided doses, or for parenteral administration, as a continuous infusion. Single dose compositions can contain such amounts or submultiples thereof of the compound or composition to make up the daily dose. The dosage can be adjusted by the individual physician in the event of any contraindications. Dosage can vary, and can be administered in one or more dose administrations daily, for one or several days.

1. Treatment Methods

The compounds disclosed herein are useful for treating or controlling disorders of uncontrolled cellular proliferation, infections, and/or thrombotic or clotting disorders. Thus, provided is a method comprising administering a therapeutically effective amount of a disclosed compound or a composition comprising a disclosed compound to a subject.

The compounds disclosed herein are also useful as immunomodulatory or immunostimulatory agents.

a. Use as an Antitumor Agent

In one aspect, a disclosed compound or composition is capable of direct anti-cancer effects by inhibiting Mer tyrosine kinase within tumor cells. In one aspect, the cancer treated overexpresses MerTK. In one aspect, the cancer which overexpresses MerTK is selected from the group consisting of acute myeloid leukemia, T-cell acute lymphoid leukemia, B-cell acute lymphoid leukemia, lung cancer, glioma, melanoma, prostate cancer, schwannoma, mantle cell lymphoma, and rhabdomyosarcoma. In an alternative aspect, the cancer ectopically expresses MerTK.

In one aspect, the cancer treated has a mutation in the amino acid sequence of the MerTK extracellular or transmembrane domain selected from P40S (melanoma), S 159F (lung), E204K (urinary tract) S428G (gastric), 143 IF (lung), A446G (kidney), N454S (liver), W485S/C (lymphoma), and V4861 (melanoma). In one aspect the cancer treated has a mutation in the amino acid sequence of the MerTK cytosolic domain mutation selected from L586F (urinary tract), G594R (breast), S626C (urinary tract), P672S (lung), L688M (colon), A708S (head and neck), N718Y (lung), R722stop (colon), M790V (lung), P802S (melanoma), V8731 Giver), S905F (lung), K923R (melanoma), P958L (kidney), D983N (liver), and D990N (colon). In one aspect, the compound administered is selected from UNC381 OA and U C4202A.

In one aspect, a disclosed compound or composition is administered to a host with a cancer in combination with one or more additional chemotherapeutic agents, resulting in a synergistic anti-cancer effect and the prolonged survival of a host compared to treatment with either a compound described herein or chemotherapeutic agent alone. In one aspect, the use of a Mer TKI compound described herein in combination with a chemotherapeutic agent provides for increased antitumor effects without an increase in the standard of care dosage of the chemotherapeutic agent. In one aspect, the use of a Mer TKI compound described herein in combination with a chemotherapeutic provides for equivalent or increased anti-tumor effects utilizing a lower dosage of a chemotherapeutic agent than the standard of care dosage.

In one aspect, a disclosed compound or composition is provided for use in treating a non-small cell lung carcinoma (NSCLC). In one aspect, a method is provided to treat a host with non-small cell lung carcinoma (NSCLC) comprising administering to the host an effective amount of a disclosed compound or composition in combination with one or more additional chemotherapeutic agents. In one aspect of the invention, a method is provided to treat a host with cancer comprising administering to the host an effective amount of a Mer TKI including active compounds of the present invention in combination with another tyrosine kinase inhibitor. In one aspect, the tyrosine kinase inhibitor is a fibroblast growth factor receptor (FGFR) inhibitor. In one aspect, the FGFR inhibitor is AZD-4547. In one aspect, the cancer is non-small cell lung carcinoma (NSCLC). In some aspects of the invention, a method is provided to treat a host with non-small cell lung carcinoma (NSCLC) comprising administering to the host an effective amount of a Mer TKI including active compounds of the present invention in combination with an additional tyrosine kinase inhibitor, wherein the additional tyrosine kinase inhibitor is selected from the group consisting of gefitinib and crizotinib.

In one aspect, a disclosed compound or composition is provided for use in treating a melanoma. In one aspect, the administration of the Mer TKI compound described herein is combined with a chemotherapeutic agent. In one aspect, the chemotherapeutic agent is an anti-programmed cell death-1 (PD-1) agent. In one aspect, the chemotherapeutic agent is a B-RAF inhibitor. In one aspect, the B-RAF inhibitor is vemurafenib. In one aspect, the host does not have a melanoma with a B-RAF mutation. In one aspect, the host has a melanoma with a B-RAF mutation. In one aspect, the host has a melanoma with a RAS mutation. In one aspect, the melanoma over-expresses MerT. In one aspect, the melanoma has metastasized.

In one aspect, a disclosed compound or composition is provided for use in treating Acute Lymphoblastic Leukemia (ALL). In one aspect, a method is provided to, treat a host with ALL comprising administering to the host an effective amount of a disclosed compound or composition in combination with methotrexate.

In one aspect, a disclosed compound or composition is provided for use in treating Acute Myeloid Leukemia (AML). In one aspect, the AML contains a wild type FLT3 protein. In one aspect, the replication of the AML cells are dependent on FLT3 expression. In one aspect, the AML contains a FLT3-ITD mutation. In one aspect, the AML contains a FLT3-TKD mutation. In one aspect, the AML contains both a FLT3-ITD and FLT3-TKD mutation. In one aspect, a FLT3 or dual MER/FLT3 inhibitor described herein is administered to a host suffering from AML, wherein the AML contains a mutation within the FLT3-TKD at amino acid F691 or D835.

In one aspect, a tumor survival-signal inhibiting amount (for example 0.5 to 150 mg dose) of Mer TKI including compounds of the present invention is administered to a host alone or in combination with a chemotherapeutic agent and/or anti-cancer targeted agent. In an alternative aspect, a tumor survival-signal inhibiting amount (for example, at least 150 mg/dose, and in some aspects, at least 200, 250, 300, 350, 400, 450, or 500 mg/dosage or more) of Mer TKI including active compounds of the present invention is administered to a host alone or in combination with a chemotherapeutic agent and/or anticancer targeted agent. In one aspect, the Mer TKI and the chemotherapeutic agent act synergistically. In one aspect, the use of a Mer TKI in combination with a chemotherapeutic agent provides for increased anti-tumor effects without an increase in the standard of care dosage of the chemotherapeutic agent.

In one aspect, the use of a Mer TKI including compounds of the present invention in combination with a chemotherapeutic provides for equivalent or increased antitumor effects utilizing a lower dosage of a chemotherapeutic agent than the standard of care dosage.

In one aspect of the invention, the Mer TKI including compounds of the present invention can be administered to a host with a cancer prior to, during, or after administration with a chemotherapeutic agent or exposure to ionizing radiation. In one aspect, a host is administered an effective amount of a chemotherapeutic agent or ionizing radiation and subsequently administered a Mer TKI.

In one aspect, a method is provided to treat a host with cancer comprising administering to the host an effective amount of a disclosed compound or composition in combination with an immunomodulatory agent. In one aspect, the immunomodulatory agent is selected from the group consisting of a CTLA-4 inhibitor, PD-1 or anti-PD-1 ligand, IFN-alpha, IFN-beta, and a vaccine, for example, a cancer vaccine. In one aspect, a method is provided to treat a host with cancer comprising administering to the host an effective amount of a Mer TKI including active compounds of the present invention in combination with Keytruda® (pembrolizumab). In one aspect, a method is provided to treat a host with cancer comprising administering to the host an effective amount of a Mer TKI including active compounds of the present invention in combination with Opdivo (nivolumab). In one aspect, a method is provided to treat a host with cancer comprising administering to the host an effective amount of a Mer TKI including active compounds of the present invention in combination with Yervoy® (ipilimumab). In some aspects, a method is provided to treat a host with cancer comprising administering to the host an effective amount of a Mer TKI including active compounds of the present invention in combination with an immunomodulatory agent selected from the group consisting of pembrolizumab and ipilimumab, wherein the cancer is melanoma. In one aspect, the Mer T Is useful in the present invention, including active compounds of the present invention, are dual MER/Tyro3 TKIs. In one aspect, the Mer TKIs are dual MER Ax1 TKIs. In one aspect, the Mer TKIs are dual MER/FLT-3 TKIs. In one aspect, the Mer TKIs are MER-specific TKIs. In one aspect, the Mer TKIs are Tyro3-specific TKIs.

(i) Tumors

The active compounds and methods described herein are useful for the treatment of tumors. As contemplated herein, the cancer treated can be a primary tumor or a metastatic tumor. In one aspect, the methods described herein are used to treat a solid tumor, for example, melanoma, lung cancer (including lung adenocarcinoma, basal cell carcinoma, squamous cell carcinoma, large cell carcinoma, bronchioloalveolar carcinoma, bronchiogenic carcinoma, non-small-cell carcinoma, small cell carcinoma, mesothelioma); breast cancer (including ductal carcinoma, lobular carcinoma, inflammatory breast cancer, clear cell carcinoma, mucinous carcinoma, serosal cavities breast carcinoma); colorectal cancer (colon cancer, rectal cancer, colorectal adenocarcinoma); anal cancer; pancreatic cancer (including pancreatic adenocarcinoma, islet cell carcinoma, neuroendocrine tumors); prostate cancer; prostate adenocarcinoma; ovarian carcinoma (ovarian epithelial carcinoma or surface epithelial-stromal tumor including serous tumor, endometrioid tumor and mucinous cystadenocarcinoma, sex-cprd-stromal tumor); liver and bile duct carcinoma (including hepatocellular carcinoma, cholangiocarcinoma, hemangioma); esophageal carcinoma (including esophageal adenocarcinoma and squamous cell carcinoma); oral and oropharyngeal squamous cell carcinoma; salivary gland adenoid cystic carcinoma; bladder cancer; gastric cancer; bladder carcinoma; carcinoma of the uterus (including endometrial adenocarcinoma, ocular, uterine papillary serous carcinoma, uterine clear-cell carcinoma, uterine sarcomas and leiomyosarcomas, mixed mullerian tumors); glioma, glioblastoma, medulloblastotna, and other tumors of the brain; kidney cancers (including renal cell carcinoma, clear cell carcinoma, Wilm's tumor); cancer of the head and neck (including squamous cell carcinomas); cancer of the stomach (gastric cancers, stomach adenocarcinoma, gastrointestinal stromal tumor); testicular cancer; germ cell tumor; neuroendocrine tumor; cervical cancer; carcinoids of the gastrointestinal tract, breast, and other organs; signet ring cell carcinoma; mesenchymal tumors including sarcomas, fibrosarcomas, haemangioma, angiomatosis, haemangiopericytoma, pseudoangiomatous stromal hyperplasia, myofibroblastoma, fibromatosis, inflammatory myofibroblastic rumor, lipoma, angiolipoma, granular cell tumor, neurofibroma, schwannoma, angiosarcoma, liposarcoma, rhabdomyosarcoma, osteosarcoma, leiomyoma, leiomvsarcoma, skin, including melanoma, cervical, retinoblastoma, head and neck cancer, pancreatic, brain, thyroid, testicular, renal, bladder, soft tissue, adenal gland, urethra, cancers of the penis, rryxosarcoma, chondrosarcoma, osteosarcoma, chordoma, malignant fibrous histiocytoma, lymphangiosarcoma, mesothelioma, squamous cell carcinoma; epidermoid carcinoma, malignant skin adnexal tumors, adenocarcinoma, hepatoma, hepatocellular carcinoma, renal cell carcinoma, hypemephroma, cholangiocarcinoma, transitional cell carcinoma, choriocarcinoma, seminoma, embryonal cell carcinoma, glioma anaplastic; glioblastoma multiforme, neuroblastoma, medulloblastoma, malignant meningioma, malignant schwannoma, neurofibrosarcoma, parathyroid carcinoma, medullary carcinoma of thyroid, bronchial carcinoid, pheochromocytoma, Islet cell carcinoma, malignant carcinoid, malignant paraganglioma, melanoma, Merkel cell neoplasm, cystosarcoma phylloide, salivary cancers, thymic carcinomas, and cancers of the vagina among others.

In some aspects, a method is provided to treat a host with a glioblastoma comprising administering to the host an effective amount of a Mer TKI including active compounds of the present invention in combination with temozolomide. In some aspects, a method is provided to treat a host with a breast cancer comprising administering to the host an effective amount of a Mer TKI including active compounds of the present invention in combination with trastuzumab.

In one aspect, the cancer is NSCLC. In one aspect, the cancer is a melanoma. In one aspect, the cancer is breast cancer. In one aspect, the cancer is a glioblastoma. In one aspect, the cancer is a bone cancer. In one aspect, the cancer is a brain cancer. In one aspect, the cancer is a colon cancer. In one aspect, the cancer is a rectal cancer. In one aspect, the cancer is an endometrial cancer. In one aspect, the cancer is an esophageal cancer. In one aspect, the cancer is a cancer of the gastrointestinal tract. In one aspect, the cancer is a kidney cancer. In one aspect, the cancer is a liver cancer. In one aspect, the cancer is a lung cancer. In one aspect, the cancer is a mantle cell lymphoma. In one aspect, the cancer is an ovarian cancer. In one aspect, the cancer is a pancreatic cancer. In one aspect, the cancer is a pituitary cancer. In one aspect, the cancer is a prostate cancer. In one aspect, the cancer is a skeletal muscle cancer. In one aspect, the cancer is a skin cancer. In one aspect, the cancer is a stomach cancer. In one aspect, the cancer is a thyroid cancer. In one aspect, the cancer is a neuroendocrine cancer. In one aspect, the cancer is a gastroesophageal cancer. In one aspect, the cancer is a renal cell cancer. In one aspect, the cancer is a head and neck cancer. In some aspects, the Mer TKI used to treat a host having a cancer is selected from the group consisting of UNC381 OA and UNC4202A.

In one aspect, the methods described herein are useful for treating a host suffering from a lymphoma or lymphocytic or myelocytic proliferation disorder or abnormality. For example, the Mer TKIs as described herein can be administered to a subject suffering from a Hodgkin Lymphoma of a Non-Hodgkin Lymphoma. For example, the subject can be suffering from a Non-Hodgkin Lymphoma such as, but not limited to: an AIDS-Related Lymphoma; Anaplastic Large-Cell Lymphoma; Angioimmunoblastic Lymphoma; Blastic NK-Cell Lymphoma; Burkitt's Lymphoma; Burkitt-like Lymphoma (Small Non-Cleaved Cell Lymphoma); Chronic Lymphocytic Leukemia/Small Lymphocytic Lymphoma; Cutaneous T-Cell Lymphoma; Diffuse Large B-Cell Lymphoma; Enteropathy-Type T-Cell Lymphoma; Follicular Lymphoma; Hepatosplenic Gamma-Delta T-Cell Lymphoma Lymphoblastic Lymphoma; Mantle Cell Lymphoma; Marginal Zone Lymphoma; Nasal T-Cell Lymphoma; Pediatric Lymphoma; Peripheral T-Cell Lymphomas; Primary Central Nervous System Lymphoma; T-Cell Leukemias; Transformed Lymphomas; Treatment-Related T-Cell Lymphomas; or Waldenstrom's Macroglobulinemia.

Alternatively, the subject may be suffering from a Hodgkin Lymphoma, such as, but not limited to: Nodular Sclerosis Classical Hodgkin's Lymphoma (CHL); Mixed Cellularity CHL; Lymphocyte-depletion CHL; Lymphocyte-rich CHL; Lymphocyte Predominant Hodgkin Lymphoma; or Nodular Lymphocyte Predominant HL.

In one aspect, the methods as described herein may be useful to treat a host suffering from a specific T-cell, a B-cell, or a NK-cell based lymphoma, proliferative disorder, or abnormality. For example, the subject can be suffering from a specific T-cell or NK-cell lymphoma, for example, but not limited to: Peripheral T-cell lymphoma, for example, peripheral T-cell lymphoma and peripheral T-cell lymphoma not otherwise specified (PTCL-NOS); anaplastic large cell lymphoma, for example anaplastic lymphoma kinase (ALK) positive, ALK negative anaplastic large cell lymphoma, or primary cutaneous anaplastic large cell lymphoma; angioimmunoblastic lymphoma; cutaneous T-cell lymphoma, for example mycosis fungoides, S zary syndrome, primary cutaneous anaplastic large cell lymphoma, primary cutaneous CD30+ T-cell lymphoproliferative disorder; primary cutaneous aggressive epidermotropic CD8+ cytotoxic T-cell lymphoma; primary cutaneous gamma-delta T-cell lymphoma; primary cutaneous small/medium CD4+ T-cell lymphoma, and lymphomatoid papulosis; Adult T-cell Leukemia Lymphoma (ATLL); Blastic NK-cell Lymphoma; Enteropathy-type T-cell lymphoma; Hematosplenic gamma-delta T-cell Lymphoma; Lymphoblastic Lymphoma; Nasal NK T-cell Lymphomas; Treatment-related T-cell lymphomas; for example lymphomas that appear after solid organ or bone marrow transplantation; T-cell prolymphocyte leukemia; T-cell large granular lymphocytic leukemia; Chronic lymphoproliferative disorder of NK-cells; Aggressive NK cell leukemia; Systemic EBV+ T-cell lymphoproliferative disease of childhood (associated with chronic active EBV infection); Hydroa vacciniforme-like lymphoma; Adult T-cell leukemia/lymphoma; Enteropathy-associated T-cell lymphoma; Hepatosplenic T-cell lymphoma; or Subcutaneous panniculitis-like T-cell lymphoma.

Alternatively, the subject may be suffering from a specific B-cell lymphoma or proliferative disorder such as, but not limited to: multiple myeloma; Diffuse large B cell lymphoma; Follicular lymphoma; Mucosa-Associated Lymphatic Tissue lymphoma (MALT); Small cell lymphocytic lymphoma; Mantle cell lymphoma (MCL); Burkitt lymphoma; Mediastinal large B cell lymphoma; Waldenstrom macroglobulinemia; Nodal marginal zone B cell lymphoma (NMZL); Splenic marginal zone lymphoma (SMZL); Intravascular large B-cell lymphoma; Primary effusion lymphoma; or Lymphomatoid granulomatosis; Chronic lymphocytic leukemia/small lymphocytic lymphoma; B-cell prolymphocyte leukemia; Hairy cell leukemia Splenic lymphoma/leukemia, unclassifiable; Splenic diffuse red pulp small B-cell lymphoma; Hairy cell leukemia-variant; Lymphoplasmacytic lymphoma; Heavy chain diseases, for example, Alpha heavy chain disease, Gamma heavy chain disease. Mu heavy chain disease; Plasma cell myeloma; Solitary plasmacytoma of bone; Extraosseous plasmacytoma; Primary cutaneous follicle center lymphoma; T cell/histiocyte rich large B-cell lymphoma; DLBCL associated with chronic inflammation; Epstein-Barr virus (EBV)+ DLBCL of—the elderly; Primary mediastinal (thymic) large B-cell lymphoma; Primary cutaneous DLBCL, leg type; ALK+ large B-cell lymphoma; Plasmablastic lymphoma; Large B-cell lymphoma arising in HHV8-associated multicentric; Castleman disease; B-cell lymphoma, unclassifiable, with features intermediate between diffuse large B-cell lymphoma and Burkitt lymphoma; B-cell lymphoma, unclassifiable, with features intermediate between diffuse large B-cell lymphoma and classical Hodgkin lymphoma; Nodular sclerosis classical Hodgkin lymphoma; Lymphocyte-rich classical Hodgkin lymphoma; Mixed cellularity classical Hodgkin lymphoma; or Lymphocyte-depleted classical Hodgkin lymphoma. In one aspect, the methods described herein can be used to a subject suffering from a leukemia. For example, the subject may be suffering from an acute or chronic leukemia of a lymphocytic or myelogenous origin, such as, but not limited to: Acute lymphoblastic leukemia (ALL); Acute myelogenous leukemia (A L); Chronic lymphocytic leukemia (CLL); Chronic myelogenous leukemia (CML); juvenile myelomonocytic leukemia (JMML); hairy cell leukemia (HCL); acute promyelocytic leukemia (a subtype of AML); T-cell prolymphocyte leukemia (TPLL); large granular lymphocytic leukemia; or Adult T-cell chronic leukemia; large granular lymphocytic leukemia (LGL). In one aspect, the patient suffers from an acute myelogenous leukemia, for example an undifferentiated AML (MO); myeloblastic leukemia (M1; with/without minimal cell maturation); myeloblastic leukemia (M2; with cell maturation); promyelocytic leukemia (M3 or M3 variant [M3V]); myelomonocytic leukemia (M4 or M4 variant with eosinophilia [M4E]); monocytic leukemia (M5); erythroleukemia (M6); or megakaryoblastic leukemia (M7).

(ii) Acute Myeloid Leukemia

In one aspect, the methods described herein can be used to treat a host suffering from Acute Myeloid Leukemia (AML). In one aspect, the AML contains a wild type FLT3 protein. In one aspect, the replication of the AML cells are dependent on FLT3 expression. In one aspect, the AML contains a FLT3-ITD mutation. In one aspect, the AML contains a FLT3-T D mutation. In one aspect, the AML contains both a FLT3-ITD and FLT3-TKD mutation.

FLT3-ITD mutations are well known in the art. FLT3-TKD mutations are also well known in the art. In one aspect, a FLT3 or dual MER/FLT3 inhibitor is administered to a host suffering from AML, wherein the AML contains a mutation within the FLT3-TKD at amino acid F691 or D835. In one aspect, the FLT3-TKD mutation is selected from D835H. D835N, D835Y, D835A, D835V. D835V. D835E, I836F, I836L, 1836V, 1836D, 1836H, 1836M, and F691L. In one aspect, the host is suffering from the FLT3-TKD mutation D835Y. In one aspect, the host is suffering from the FLT3-TKD mutation F691L.

In one aspect, the host is suffering from acute promyelocytic leukemia (a subtype of AML); a minimally differentiated AML (MO); myeloblastic leukemia (M1; with/without minimal cell maturation); myeloblastic leukemia (M2; with cell maturation); promyelocytic leukemia (M3 or M3 variant [M3V]); myelomonocytic leukemia (M4 or M4 variant with eosinophilia [M4E]); monocytic leukemia (M5); erythroleukemia (M6); or megakaryocyte leukemia (M7). In one aspect, the host is suffering from AML that has relapsed or become refractory to previous treatments. In one aspect, the host has previously been treated with a FLT3 inhibitor or other chemotherapeutic agent.

In one aspect, the FLT3 inhibitors are efficacious against AML having both FLT3-ITD and FLT3-TKD mutations, wherein resistance to other FLT3 inhibitors, for example, AC220, has been established.

In one aspect, the host has an Acute Myeloid Leukemia (AML) comprising a FLT3 mutation, wherein the mutation confers resistance to a FLT3 inhibitor other than the FLT3 inhibitors described herein. In one aspect, the host has an AML comprising a FLT3 mutation, wherein the mutation has conferred resistance to quizartinib (AC220) or other FLT3 inhibitor selected from lestaurtinib, sunitinib, sorafenib, tandutinib, midostaurin, amuvatinib crenolanib, dovitinib, ENMD-2076 (EntreMed), or KW-2449 (Kyowa Hakko Kirin), or a combination thereof.

(iii) Chemotherapeutic Agents

In one aspect, an active compound or Mer TKI as described herein is used in combination or alternation with a chemotherapeutic agent. Such agents may include, but are not limited to, tamoxifen, midazolam, letrozole, bortezomib, anastrozole, goserelin, an mTOR inhibitor, a P13 kinase inhibitors, dual mTOR-PBK inhibitors, MEK inhibitors, RAS inhibitors, ALK inhibitors, HSP inhibitors (for example, HSP70 and HSP 90 inhibitors, or a combination thereof). Examples of mTOR inhibitors include but are not limited to rapamycin and its analogs, everolimus (Afinitor), temsirolimus, ridaforolimus, sirolimus, and deforolimus. Examples of P13 kinase inhibitors include but are not limited to Wortmannin, demethoxyviridin, perifosine, idelalisib, PX-866, IPI-145, BAY 80-6946, BEZ235, RP6503, TGR 1202 (RP5264), MLN 1117 (FNK1117), Pictilisib, Buparlisib, SAR245408 (XL147), SAR245409 (XL765), Palomid 529, ZSTK474, PWT33597, RP6530, CUDC-907, and AEZS-136. Examples of MEK inhibitors include but are not limited to Trametinib, Selumetinib, MEK162, GDC-0973 (XL518), and PD0325901. Examples of RAS inhibitors include but are not limited to Reolysin and siG12D LODER. Examples of ALK inhibitors include but are not limited to Crizotinib, AP261 13, and LDK378. HSP inhibitors include but are not limited to Geldanamcin or 17-N-Allylamino-17-demethoxygeldanamycin (17AAG), and Radicicol. In one aspect, the chemotherapeutic agent is an anti-programmed cell death-1 (PD-1) agent, for example, nivolumab, pembrolizumab, BMS936559, lambrolizumab, MPDL3280A, pidilizumab, AMP-244, and MED 14736. In one aspect, the chemotherapeutic agent is a B-RAF inhibitor, for example, vemurafenib or sorafenib. In one aspect, the chemotherapeutic agent is a FGFR inhibitor, for example, but not limited to, AZD4547, dovitinib, BGJ398, LY2874455, and ponatinib. In one aspect, an active compound or Mer TKI as described herein is used in combination with crizotinib.

In certain aspects, the additional therapeutic agent is an anti-inflammatory agent, a chemotherapeutic agent, a radiotherapeutic, an additional therapeutic agent, or an immunosuppressive agent.

Suitable chemotherapeutic agents include, but are not limited to, radioactive molecules, toxins, also referred to as cytotoxins or cytotoxic agents, which includes any agent that is detrimental to the viability of cells, agents, and liposomes or other vesicles containing chemotherapeutic compounds. General anticancer pharmaceutical agents include: Vincristine (Oncovin®) or liposomal vincristine (Marqibo®), Daunorubicin (daunomycin or Cerubidine®) or doxorubicin (Adriamycin®), Cytarabine (cytosine arabinoside, ara-C, or Cytosar®), L-asparaginase (Elspar®) or PEG-L-asparaginase (pegaspargase or Oncaspar®), Etoposide (VP-16), Teniposide (Vumon®), 6-mercaptopurine (6-MP or Purinethol®), Methotrexate, Cyclophosphamide (Cytoxan®), Prednisone, Dexamethasone (Decadron), imatinib (Gleevec®), dasatinib (Sprycel®), nilotinib (Tasigna®), bosutinib (Bosulif®), and ponatinib (Iclusig™). Examples of additional suitable chemotherapeutic agents include but are not limited to 1-dehydrotestosterone, 5-fluorouracil decarbazine, 6-mercaptopurine, 6-thioguanine, actinomycin D, adriamycin, aldesleukin, alkylating agents, allopurinol sodium, altretamine, amifostine, anastrozole, anthramycin (AMC)), anti-mitotic agents, cis-dichlorodiamine platinum (IT) (DDP) cisplatin), diamino-dichloroplatinum, anthracyclines, antibiotics, antimetabolites, asparaginase, BCG live (intravesical), betamethasone sodium phosphate and betamethasone acetate, bicalutamide, bleomycin sulfate, busulfan, calcium leucovorin, calicheamicin, capecitabine, carboplatin, lomustine (CCNU), carmustine (BSNU), Chlorambucil, Cisplatin, Cladribine, Colchicine, conjugated estrogens, Cyclophosphamide. Cyclophosphamide, Cytarabine, Cytarabine, cytochalasin B, Cytoxan, Dacarbazine, Dactinomycin, dactinomycin (formerly actinomvcin), Daunorubicin HCl, Daunorubicin citrate, denileukin diftitox, Dexrazoxane, Dibromomannitol, dihydroxy anthracin dione, Docetaxel, dolasetron mesylate, doxorubicin HCl, dronabinol, *E, coli* L-asparaginase, emetine, epoetin-a, *Erwinia* L-asparaginase, esterified estrogens, estradiol, estramustine phosphate sodium, ethidium bromide, ethinyl estradiol, etidronate, etoposide citrovorum factor, etoposide phosphate, filgrastim, floxuridine, fluconazole, fludarabine phosphate, fluorouracil, fiutamide, folic acid, gemcitabine HC 1, glucocorticoids, goserelin acetate, gramicidin D, granisetron HCl, hydroxyurea, idarubicin HCl, ifosfamide, interferon a-2b, irinotecan HCl, letrozole, leucovorin calcium, leuprolide acetate, levamisole HCl, lidocaine, lomustine, maytansinoid, mecbJorethamine HC 1, medroxyprogesterone acetate, megestrol acetate, melphalan HC 1, mercaptopurine, mesna, methotrexate, methyltestosterone, mithramycin, mitomycin C, mitotane, mitoxantrone, nilutamide, octreotide acetate, oligomycin A, ondansetron HCl, paclitaxel, pamidronate disodium, pentostatin, pilocarpine HC 1, plimycin, polifeprosan 20 with carmustine implant, porfimer sodium, procaine, procarbazine HC 1, propranolol, rituximab, sargramostim, streptozotocin, tamoxifen, taxol, teniposide, tenoposide, testolactone, tetracaine, thioepa chlorambucil, tMoguanine, thiotepa, topotecan HC 1, toremifene citrate, trastuzumab, tretinoin, valrubicin, vinblastine sulfate, vincristine sulfate, and vinorelbine tartrate. In one aspect, an active compound or Mer TKI as described herein is used in combination with oligomycin A.

Additional therapeutic agents that can be administered in combination with a compound disclosed herein can include bevacizumab, sutinib, sorafenib, 2-methoxyestradiol or 2ME2, finasunate, vatalanib, vandetanib, aflibercept, volociximab, etaracizumab (MEDI-522), cilengitide, erlotinib, cetuximab, panitumumab, gefitinib, icotinib, trastuzumab, dovitinib, figitumumab, atacicept, rituximab, alemtuzumab, aldesleukine, atlizumab, tocilizumab, temsirolimus, everolimus, lucatumumab, dacetuzumab, HLL1, huN901-DMI, atiprimod, natalizumab, bortezomib, carfilzomib, marizomib, tanespimycin, saquinavir mesylate, ritonavir, nelfinavir mesylate, indinavir sulfate, belinostat, panobinostat, mapatumumab, lexatumumab, dulanermin, ABT-737, oblimersen, plitidepsin, talmapimod, P276-00, enzastaurin, tipifarnib, perifosine, imatinib, dasatinib, lenalidomide, thalidomide, simvastatin, ABT-888, temozolomide, erlotinib, lapatinib, sunitinib, FTS. AZD6244, BEZ235, and celecoxib. In one aspect, an active compound or Mer TKI as described herein is used in combination with gefitinib.

In one aspect, a FLT3 or dual MER/FLT3 inhibitor described herein is used in combination with a chemotherapeutic agent for the treatment of AML. Such agents may include, but are not limited to, cytarabine (ara-C), anthracycline drugs including but not limited to, daunorubicin, idarubicin; cladribine, fludarabine, Gleevec® (imatinib), Sprycel® (dasatinib), adriamycin, arsenic trioxide, cerubidine, clafen, cyclophosphamide, cytarabine, daunorubicin, doxorubicin, vincristine, and topotecan. Some of the other chemo drugs that may be used to treat AML include: etoposide (VP-16), 6-thioguanine (6-TG), hydroxyurea (Hydrea®), Corticosteroid drugs, such as prednisone or dexamethasone (Decadron®), methotrexate (MTX), 6-mercaptopurine (6-MP), azacitidine (Vidaza®), and decitabine (Dacogen®). In one aspect, a FLT3 or dual MER/FLT3 inhibitor described herein is used in combination with cytarabine. In one aspect, a FLT3 or dual MER/FLT3 inhibitor described herein is used in combination with an additional FLT3 inhibitor to treat with a host suffering from AML. Additional FLT3 inhibitors for use in combination with the FLT3 or dual MER/FLT3 inhibitors described herein include lestaurtinib, sunitinib, sorafenib, tandutinib, midostaurin, crenolanib, dovitinib, ENMD-2076 (Entremed), amuvatinib, or KW-2449 (Kyowa Hakko Kirin).

In one aspect, a FLT3 or dual MER/FLT3 inhibitor described herein is used in combination with a Ras inhibitor. Examples of RAS inhibitors include but are not limited to Reolysin, FusOn-H2, and siG 12D LODER.

In one aspect, a FLT3 or dual MER/FLT3 inhibitor described herein is used in combination with a Phosphoinositide 3-kinase inhibitor (P13K inhibitor). P13K inhibitors that may be used in the present invention are well known. Examples of P13K inhibitors include but are not limited to Wortmannin, demethoxyviridin, perifosine, idelalisib, Pictilisib, Palomid 529, ZSTK474, PWT33597, CUDC-907, AEZS-136, PX-866, IPI-145, RP6503, SAR245408 (XL 147), duvelisib, GS-9820, GDC-0032 (2-[4-[2-(2-Isopropyl-5-methyl-1,2,4-triazol-3-yl)-5,6-dmydroimidazo[1,2-d][1,4]benzoxazepin-9-yl]pyrazol-1-yl]-2-methylpropanamide), MLN-I 1 17 ((2R)-1-Phenoxy-2-butanyl hydrogen (S)-methylphosphonate; or Methyl(oxo){[(2R)-1-phenoxy-2-butanyl]oxy}phosphonium)), BYL-719 ((2S)—N1-[4-Methyl-5-[2-(2,2,2-trifluoro-1, 1-dimethylethyl)-4-pyridinyl]-2-thiazolyl]-1,2-pyrroUdinedicarboxamide), GSK2126458 (2,4-Difluoro-N-{2-(methyloxy)-5-[4-(4-pyrida5dnyl)-6-quinolinyl]-3-pyridinyl}benzenesulfonamide), TGX-221 ((±)-7-Methyl-2-(moφholm-4-yl)-9-(1-henylan moethyl-pydo[1,2-a]-yrimidin-4-one)) GSK2636771 (2-Memyl-1-(2-memyl-3-(trifluoromemyl)benzycarboxylic acid dihydrochloride), KTN-193 ((R)-2-((I-(7-methyl-2-morpholino-4-oxo-4H-pyrido[1,2-a]pyrimidin-9-yl)ethyl)amino)benzoic acid), TGR-1202/RP5264, GS-9820 ((S)-1-(4-((2-(2-aminopyrimidin-5-yl)-7-methyl-4-mohydroxypropan-1-one), GS-1101 (5-fluoro-3-phenyl-2-([S)]-1-[9H-purin-6-ylammo]-propyl)-3H-quinazolin-4-one), AMG-319, GSK-2269557. SAR245409 (N-(4-(N-(3-((3,5-dimethoxyphenyl)amino)quinoxaUn-2-yl)sulfamoyl)phenyl)-3-methoxy-4 methylbenzamide), BAY80-6946 (2-amino-N-(7-memoxy-8-(3-mo holinopro oxy)-2,3-dihydroi idazo[1,2-c]quinaz), AS 252424 (5-[1-[5-(4-Fluoro-2-hydroxy-phenyl)-furan-2-yl]-meth-(Z)-ylidene]-thiazolidine-2,4-dione). CZ 24832 (5-(2-amino-8-fluoro-[1,2,4]triazolo[1,5-a]pyridin-6-yl)-N-tert-butylpyridme-3-sulfona Buparlisib (5-[2,6-Di(4-morpholinyl)-4-pyrimidinyl]-4-(txifluoromemyl)-2-pyridmanune), GDC-0941 (2-(1H-Indazol-4-yl)-6-[[4-(methylsulfonyl)-1-piperazinyl]methyl]-4-(4-morpholmyl) thieno[3,2-d]pyrimidine), GDC-0980 ((S)-1-(4 (2-(2-aminopyrimidin-5-yl)-7-meth 1-4-mo holmotrueno[3,2-d] pyriInidin-6 yl)methyl)piperazin-1-yl)-2-hydroxypropan-1-one (also known as RG7422)), SF1126 ((8S,14S,17S)-14-(carboxymethyl)-8-(3-gnarddinopropyl)-17-(hydroxymethyl)-3, 6,9,12,15-pentaoxo-1-(4-(4-oxo-8-phenyl-4H-chromen-2-yl)morpholino-4-ium)-2-oxa-7, 10, 13, 16-tetraazaoctadecan-18-oate), PF-05212384 (N-[4-[[4-(Dimethylamino)-1-piperidinyl]carbonyl]phenyl]-N'-[4-(4, 6-di-4-morpholinyl-1,3,5-triazin-2-yl)phenyl]urea), LY3023414, BEZ235 (2-Methyl-2-{4-[3-methyl-2-oxo-8-(quinolin-3-yl)-2,3-dmydro-1H-imidazo[4,5-c]qumolm-1-yl]phenyl}propanem XL-765 (N-(3-(N-(3-(3,5-dimemoxy-phenylammo)quinoxalin-2-yl)sulfamoyl)phenyl)-3-methoxy-4-methylbenzamide), and GSK1059615 (5-[[4-(4-Pyridinyl)-6-quinolinyl]methylene]-2,4-thiazolidenedione), PX886 ([(3aR,6E,9S,9aR,10R,11aS)-6-[[bisˆrop-2-enyl) ammo]memylidene]-5-hydxoxy-9-(methoxymelhyl)-9a, 11a-ditrioxo-2,3,3a,9,10,11-hexahydroindeno[4.5h]isochromen-10-yl] acetate (also known as sonolisib)), and the structure described in WO2014/071109 having the formula:

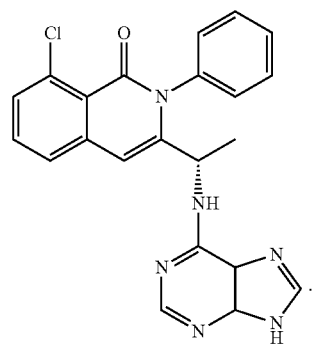 [SMILES: C[C@H](NC1=NC=NC2NC=NC12)c1cc2cccc(Cl)c2c(=O)n1-c1ccccc1]

In one aspect, a FLT3 or dual MER/FLT3 inhibitor described herein is used in combination with a modulator of the STAT5 pathway. Compounds which modulate the Janus Kinase 2 (JAK2)—Signal Transducer and Activator of Transcription 5 (STATS) pathway include but are not limited to Lestaurtinib, Ruxolitinib, SB1518, CYT387, LY3009104, INC424, LY2784544, BMS-91 1543, NS-018, and TG101348.

In one aspect, a FLT3 or dual MER/FLT3 inhibitor described herein is used in combination with an AKT inhibitor, including but not limited to, MK-2206, GSK690693, Perifosine, (KRX-0401), GDC-0068, Triciribine, AZD5363, Honokiol, PF-04691502, and Miltefosine.

(iv) Immunomodulatory Combination Agents

Active compounds as described herein used in a dosage for direct effect on the diseased cell can be used in combination with one or more immunotherapy agents for additive or synergistic efficacy against solid tumors. In one aspect, a tumor associated macrophage MerT inhibiting amount of a Mer T J is used in combination or alternation with the immunomodulatory agent. In another aspect, a host tumor survival-signal inhibiting, antiviral or antibacterial amount of a Mer T I is used in combination or alternation with the immunomodulatory agent.

Immunomodulators are small molecules or biologic agents that treat a disease by inducing, enhancing or suppressing the host's immune system. In the present application, one or more immunomodulators are selected that induce or enhance the host's immune system. Some immunomodulators boost the host's immune system and others help train the host's immune system to better attack tumor cells. Other immunomodulators target proteins that help cancer grow.

Three general categories of immunotherapies are antibodies, cancer vaccines, and non-specific immunotherapies. Antibodies are typically administered as monoclonals, although that is not required. "Naked monoclonal antibodies" work by attaching to antigens on tumor cells. Some antibodies can act as a marker for the body's immune system to destroy the tumor cells. Others block signaling agents for tumor cells. Antibodies can generally be used to bind to any signaling or metabolic agent that directly or indirectly facilitates tumor growth. Examples are alemtuzumab (Campath) which binds to CD52 antigen, and trastuzumab (Herceptin), which binds to the HER2 protein.

In another aspect, an antibody can be used that is conjugated to another moiety that increases it delivery or efficacy. For example, the antibody can be connected to a cytotoxic drug or a radiolabel. Conjugated antibodies are sometimes referred to as "tagged, labeled or loaded". Radiolabeled antibodies have small radioactive particles attached to them. Examples are Zevalin, which is an antibody against CD20 used to treat lymphoma. Chemolabeled antibodies are antibodies that have cytotoxic agents attached to them. Examples are Adcetris, which targets CD30, and Kadcyla, which targets HER2. Ontak, while not an antibody, is similar in that it is interleukin-2 attached to a toxin from diphtheria Another category of immunotherapy that can be used in the present invention is a cancer vaccine. Most cancer vaccines are prepared from tumor cells, parts of tumor cells or pure antigens. The vaccine can be used with an adjuvant to help boost the immune response. An example is Provenge, which is the first cancer vaccine approved by the US FDA. The vaccine can for example be a dendritic cell vaccine or a vector-based vaccine Nonspecific tumor immunotherapies and adjuvants include compounds that stimulate the immune system to do a better job at attacking the tumor cells. Such immunotherapies include cytokines, interleukins, interferons (a primarily but can be also 3 or y). Specific agents include granulocyte-macrophage colony-stimulating factor (GM-CSF), IL-12, IL-7, IL-21, drugs that target CTLA-4 (such as Yervoy, which is Ipilimumab) and drugs that target PD-1 or PDL-1 (such as for example, nivolumab (BMS), pembrolizumab (Merck), pidilizumab (CureTechTeva), AMP-244 (Amplimmune/GSK), BMS-936559 (BMS), and MEDI4736 (Roche/Genentech)).

Other drugs that boost the immune system are thalidomide, lenalidomide, pomalidomide, the Bacille Calmette-Gurin bacteria and Imiquimod. Additional therapeutic agents that can be used in combination with the MerTK inhibitor include bispecific antibodies, chimeric antigen receptor (CAR) T-cell therapy and tumor-infiltrating lymphocytes.

In one aspect of the present invention, a compound described herein can be combined with at least one immunosuppressive agent. The immunosuppressive agent is preferably selected from the group consisting of a calcineurin inhibitor, e.g. a cyclosporin or an ascomycin, e.g. Cyclosporin A (NEORAL®), FK506 (tacrolimus), pimecrolimus, a mTOR inhibitor, e.g. rapamycin or a derivative thereof, e.g. Sirolimus (RAPAMUNE®), Everolimus (Certican®), temsirolimus, zotarolimus, biolimus-7, biolimus-9, a rapalog, e.g. ridaforolimus, azathioprine, campath 1H, a SIP receptor modulator, e.g. fingolimod or an analogue thereof, an anti IL-8 antibody, mycophenolic acid or a salt thereof, e.g. sodium salt, or a prodrug thereof, e.g. Mycophenolate Mofetil (CELLCEPT®), OKT3 (ORTHOCLONE OKT3®), Prednisone, ATGAM®, THYMOGLOBULIN®, Brequinar Sodium, OKT4, T10B9.A-3A, 33B3.1, 15-deoxyspergualin, tresperimus, Leflunomide ARAVA®, CTLAI-Ig, anti-CD25, anti-IL2R, Basiliximab (SIMULECT®), Daclizumab (ZENAPAX®), mizorbine, methotrexate, dexamethasone, ISAtx-247, SDZ ASM 981 (pimecrolimus, Elidel®), CTLA41g (Abatacept), belatacept, LFA31g, etanercept (sold as Enbrel® by Immunex), adalimumab (Humira®), infliximab (Remicade@), an anti-LFA-1 antibody, natalizumab (Antegren®), Enlimomab, gavilimomab, antithymocyte immunoglobulin, siphzumab, Alefacept efalizumab, pentasa, mesalazine, asacol, codeine phosphate, benorylate, fenbufen, naprosyn, diclofenac, etodolac and indomethacin, aspirin and ibuprofen.

b. Use as an Immunomodulatory or Immunostimulatory Agent

In various aspects, the compounds described herein can be used as immunomodulatory agents that reverse the MerTK-induced suppression of proimflammatory cytokines such as wound healing cytokines (IL-10 and GAS6) and enhance the expression of acute inflammatory cytokines (IL-12 and IL-6). In this way, the pyrrolopyrimidine compounds can "re-normalize" or "re-program" the host microenvironment in the diseased tissue area to attack the diseased cells. This immunostimulatory activity can be used therapeutically to treat a host with a tumor, cancer or other neoplasm, or alternatively, to treat a host with an infection, for example, a viral or bacterial infection.

Taking advantage of the immunomostimulatory activity of the compounds described herein, or a pharmaceutically acceptable composition, salt, isotopic analog, or prodrug thereof, may be used for the treatment of a MERTK-negative (−/−) tumor or cancer. In one aspect, the cancer is a MERTK-negative (−/−) breast cancer.

Therefore, as part of the invention, one or more of the compounds disclosed herein can be used as adjunctive therapy for its immunostimulatory effect as a means to increase the efficacy of the antineoplastic standard of care therapies, such as chemotherapeutic compounds or radiation.

In another aspect of the invention, one or more of the compounds disclosed herein can be used as adjunctive therapy for its immunostimulatory effect as a means to increase the efficacy of the antiviral or antibacterial standard of care therapies.

For example, a disclosed compound or composition is administered to a host in an immunomodulatory effective amount to inhibit Mer tyrosine kinase activity in the host's tumor associated macrophage to suppress tumor immunity. In one aspect, the dosage of the Mer TKI administered as an immunomodulatory agent to stimulate innate anti-tumor immunity is lower than a dosage of a Mer TKI administered to a host as a direct anti-cancer agent. In one aspect, the Mer TKI is administered at a dosage which exhibits immunomodulatory but not direct cytotoxic effect.

In one aspect, the cancer is a MERTK-negative (−/−) cancer.

Without wanting to be bound by any particular theory, it is believed that the administration of a chemotherapeutic agent results in the apoptosis of tumor cells, exposing antigenic tumor proteins. The host's innate immune system is thus stimulated to recognize the antigenic apoptotic components from the tumor cells after chemotherapy or ionizing radiation and mount an immune response. In one aspect, the administration of a chemotherapeutic agent or ionizing radiation, before, with or subsequently followed by the administration of a Mer TKI is carried out using the normal standard of care chemotherapeutic protocol. In another aspect, the standard of care protocol of the chemotherapeutic is changed in a manner that causes less toxicity to the host due to the adjunctive or synergistic activity of the Mer TKI.

In one aspect, a method for the treatment of a tumor is provided that includes administering an effective amount of a Mer TKI to inhibit TK signaling in a tumor associated macrophage, without inhibiting the survival signal in the tumor itself. In this way, the Mer TKI can be used to ramp up the immune response to the tumor by inhibiting macrophage tumorogenic tolerance during normal tumor chemotherapeutic agent. The immunomodulatory dosage of the Mer TKI can be given prior to, with or after chemotherapeutic therapy and can be used simultaneously with or intermittently with the chemotherapeutic therapy. In one aspect, less chemotherapeutic therapy is needed than the normal standard of care defined for that chemotherapeutic agent, due to the increased efficacy of the immune response in the surrounding tumor microenvironment. In one aspect, a dose of Mer TKI including active compounds of the present invention (for example 0.5 to 150 mg/dose) is given as a type of adjunctive therapy with the chemotherapeutic agent.

In one aspect of the invention, a Mer TKI is administered to a host having a cancer as an immunomodulatory agent to inhibit Mer tyrosine kinase activity in a tumor associated macrophage in order to suppress tumor immunity. In one aspect, the dosage of the Mer TKI administered as an immunomodulatory agent to stimulate innate anti-tumor immunity is lower than a dosage of a Mer TKI administered to a host as a direct anti-cancer agent. In one aspect, the Mer TKI is administered at a dosage which exhibits immunomodulatory but not direct cytotoxic effects on the cancer.

In one aspect, the dose associated with the immunomodulatory effect of an active compound of the present invention is about 2-fold, about 3-fold, about 4-fold, about 5-fold, about 6-fold, about 7-fold, about 8-fold, about 9-fold, about 10-fold or greater lower than the dose associated with a direct survival-signal inhibiting anti-tumor or cytotoxic effect, or the direct antiviral or antibacterial effect. In one aspect, the dose used to induce an immunomodulatory effect in a host is between about 0.5 mg and about 150 mg. In one aspect, the dose is about 1 mg, about 2 mg, about 3 mg, about 4 mg, about 5 mg, about 10 mg, about 12 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 125 mg, about 140 mg, or about 150 mg.

c. Use as an Anti-Infective Agent

In various aspects, an effective amount of a disclosed compound or composition can be administered as an immunomodulatory agent to stimulate the innate immune system. This immunostimulatory activity can be used therapeutically to treat a host with an infection. In one aspect, the infection is a viral infection. In one aspect, the infection is a bacterial infection. In an alternative aspect, an effective amount of a disclosed compound or composition can be used to treat a host bearing any virus-related infection where the virus has a virion envelope phosphatidyl serine that complexes with MerTK to achieve viral entry or is otherwise facilitated by MerTK in the infectious process or maintenance.

(i) Viral Infections

The virus may be an enveloped virus or a non-enveloped virus. In one aspect, the host is infected or threatened to become infected with a virus selected from, for example, Flaviviridae viruses, including Flavivirus (such as Yellow Fever, West Nile and Dengue), Hepacivirus (Hepatitis C virus, "HCV"), Pegivirus and Pestivirus (Bovine viral diarrhea virus); Filoviridae viruses, including Ebola viruses; Togaviridae viruses, including Chikungunya virus; Coronaviruses, such as SARS (Severe acute respiratory syndrome) and MERS (Middle East respiratory syndrome); Orthomyxoviridae viruses, for example influenza; Paramyxoviridae viruses, for example Respiratory syncytial virus (RSV), measles and mumps; and Caliciviridae viruses, including Lagovirus, Vesivirus, and Sapovirus and Norovirus (Norwalk-like virus), and Lentiviruses, for example, HIV. In one aspect, an active compound disclosed herein is administered in combination or alternation with another anti-viral agent for combination therapy. In one aspect, the compound administered is selected from UNC3810A and UNC4202A.

More broadly, the host to be treated may be infected with an enveloped virus including, but not limited to, viruses of the following families; Bomaviridae, Bunyaviridae, Coronaviridae, Filoviridae, Flaviridae, Hepadnaviridae, Herpesviridae, Nyamiviridae, Orthomyxoviridae, Paramyxoviridae, Poxyiridae, Retroviridae, Rhabdoviridae, and Togaviridae. Examples of viruses form the Bunyaviridae family include, but are not limited to, bunya viruses such as La Crosse virus and Hantaan. Examples of viruses from the Coronaviridae family include, but are not limited to, coronaviruses such as SARS virus or Toroviruses. Examples of viruses from the Filoviradae family include, but are not limited to, Ebola and Marburg. Examples of viruses from the Flaviridae family include, but are not limited to, dengue, encephalitis viruses including West Nile virus, Japanese encephalitis virus and yellow fever virus and Hepatitis C virus. Examples of viruses from the Hepadnaviridae family include, but are not limited to, Hepatitis B. Examples of viruses from the Herpesviridae family include, but are not limited to, cytomegalovirus, herpes simplex viruses 1 and 2, HHV-6, HHV-7, HHV-8, pseudorabies virus, and varicella zoster virus. Examples of viruses from the Orthomvxoviridae family include, but are not limited to, influenza virus. Examples of viruses from the Paramyxoviridae family include, but are not limited to, measles, metapneumovirus, mumps, parainfluenza, respiratory syncytial virus, and sendai. Examples of viruses from the Poxyiridae family include, but are not limited to, pox viruses such as smallpox, monkey pox, and MoUuscum contagiosum virus, variola viruses, vaccinia virus, and yatapox viruses such as Tanapox and Yabapox. Examples of viruses from the Retroviridae family include, but are not limited to, Coltiviruses such as CTFV and Banna virus, human immunodeficiency viruses such as HIV-1 and HTV-2, murine leukemia virus, simian immunodeficiency virus, feline immunodeficiency virus, human T-cell leukemia viruses 1 and 2, and XMRV. Examples of viruses from the Rhabdoviridae family include, but are not limited to, vesicular stomatitis and rabies. Examples of viruses from the Togaviridae family include, but are not limited to, rubella viruses or alpha viruses such as Chikungunya virus, Eastern equine encephalitis virus, O'nyong'nyong virus, Ross River virus, Semliki Forest virus, Sindbis, Venezuelan equine encephalitis or Western equine encephalitis virus.

In one aspect, the host is infected with Chikungunya virus. In one aspect, the host is infected with Ebola virus. In one aspect, an active compound or Mer TKI as described herein is used in combination with brincidofovir (CMXOOI).

In another particular aspect, the host is infected with a non-enveloped virus, such as, but not limited to, viruses of the following families; Adenoviridae, Arenaviridae, Bimaviridae. Calciviridae, Iridoviridae, Ophioviridae Parvoviradae, Papillomaviridae. Papovaviridae, Picornaviridae, and Reoviridae. Examples of viruses from the Adenoviridae family include, but are not limited to adenoviruses. Examples of viruses from the Arenaviradae family include, but are not limited to, hemorrhagic fever viruses such as Guanarito, LCMV, Lassa, Junin, and Machupo. Examples of viruses from the Iridoviridae family include, but are not limited to, African swine fever virus. Examples of viruses from the Papillomavirus family include, but are not limited to, papillomaviruses. Examples of viruses from the Papovaviridae family include, but are not limited to, polyoma viruses such as BK virus and JC virus. Examples of viruses from the Parvoviridae family include, but are not limited to, parvoviruses such as human bocavirus and adeno-associated virus. Examples of viruses from the Picomaviridae family include, but are not limited to, aptoviruses, cardioviruses, coxsackieviruses, echoviruses, enteric viruses, enteroviruses, foot and mouth disease virus, hepatitis A virus, hepatoviruses, Poliovirus, and rhinovirus. Examples of viruses from the Reoviradae family include, but are not limited to, orbiviruses, reoviruses and rotaviruses.

In another aspect, a host is infected with a virus such as an astroviruses, caliciviruses including but not limited to, Norovirus and Norwalk, and Hepeviruses including, but not limited to, Hepatitis E.

As described above, a compound described herein can be administered to a host suffering from a viral infection in combination with another anti-viral or anti-infective compound. Antiviral compounds that can be used in combination with the compounds described herein include, but are not limited to, abacavir, acyclovir, adefovir, amantadine, amprenavir, ampligen, arbitol, atazanavir, balavir, boceprevir, boceprevirertet, cidofovir, dolutegravir, darunavir, delavirdine, didanosine, docosanol, edoxudine, efavirenz, emtricitabine, epivir, enfuvirtide, entecavir, famciclovir, fomivirsen, fosamprenavir, foscarnet, fosfonet, ganciclovir, ibacitabine, imunovir, idoxuridine, imiquimod, indinavir, lamivudine, lopinavir, loviride, maraviroc, moroxydine, neJ-finavir, nevirapine, nexavir, oseltamivir, penciclovir, peramivir, pleconaril, podophyllotoxin, raltegravir, ribavirin, rilpivirine, rimantadine, pyramidine, saquinavir, simeprevir, sofosbuvir, stavudine, telaprevir, tenofovir, tipranavir, trifluridine, trizivir, tromantadine, traporved, truvada, valaciclovir, valganciclovir, vicriviroc, vidarabine, viramidine, zalcitabine, zanamivir, and zidovudine.

In one aspect, a host is infected with a human immunodeficiency virus and is administered a compound described herein in combination with the anti-HIV combination drug, such as AtriplaV or other drug that includes emtricitabine. In another aspect, the patient with the human immunodeficiency virus can be treated with atazanavir, ritonavir, or Truvada®, in combination with a compound described herein. In another aspect, the patient infected with human immunodeficiencv virus can be treated with the combination of dolutegravir, Truvada, and a compound described herein. In another aspect, human immunodeficiency virus can be treated with the combination dolutegravir, Epzicom® and a compound described herein. In another aspect, a host infected with human immunodeficiency virus can be treated with a combination of raltegravir, Truvada® and a compound described herein. In another aspect, a host infected with human immunodeficiency virus can be treated with the combination of Complera® and a compound described herein. It will be appreciated by one skilled in the art that a host infected with HIV can be treated with a number of combinations of drugs depending on the mutation pattern of the virus. The patient can be treated with an appropriate combination of drugs in combination with a compound described herein.

In one aspect, the host is infected with a hepatitis C virus and is treated with an anti-hepatitis C drug in addition to the active compound described herein. For example, the patient can be treated with a combination of Sovaldi™, Harvoni®, ribavirin, and/or a pegylated interferon and a compound described herein. In one aspect the pegylated interferon is Peglntron®. In another aspect, the pegylated interferon is Pegasys®. In one aspect, the host infected with hepatitis C virus is treated with Sovaldi™, ribavirin and a compound described herein. In one aspect, the host infected with hepatitis C virus is treated with Harvoni®, ribavirin and a compound described herein. In one aspect, a host infected with hepatitis C virus is treated with a combination of Olysio™, ribavirin, a pegylated interferon and a compound described herein. In one aspect the pegylated interferon is Peglntron®. In another aspect, the pegylated interferon is Pegasys™. In one aspect, the host is infected with a hepatitis C virus and is treated with a combination of ABT-267, ABT-333 and ABT-450/ritonavir, in addition to an active compound described herein. In one aspect, the host is infected with a hepatitis C virus and is treated with a combination of MK-5172 and MK-8742, in addition to an active compound described herein.

In one aspect, a host infected with hepatitis C genotype 1 is treated with a combination of Sovaldi™, ribavirin, a pegylated interferon and a compound described herein for 12 weeks. In another aspect, a host infected with hepatitis C genotype 1 is treated with Sovaldi™ and a compound described herein for 12 weeks followed by ribavirin, pegylated interferon and a compound described herein for 24 weeks. In one aspect, a host infected with hepatitis C genotype 2 is treated with Sovaldi™, ribavirin, and a compound described herein for 12 weeks. In one aspect, a host infected with hepatitis C genotype 3 is treated with Sovaldi™, ribavirin, and a compound described herein for 24 weeks. In another aspect, a host infected with hepatitis C genotype 3 is treated with Sovaldi™, ribavirin, pegylated interferon, and a compound described herein for 12 weeks. In one aspect, a host infected with hepatitis C genotype 4 is treated with Sovaldi™, ribavirin, pegylated interferon, and a compound described herein for 12 weeks. In another aspect, a host infected with hepatitis C genotype 4 is treated with a combination of Olysio™, and a compound described herein for 12 weeks followed by ribavirin, pegylated interferon and a compound described herein for 24-28 weeks. In one aspect, a host infected with hepatitis C genotype 5 is treated with Sovaldi™, ribavirin, pegylated interferon, and a compound described herein for 12 weeks. In one aspect, a host infected with hepatitis C genotype 5 is treated with ribavirin, pegylated interferon, and a compound described herein for 48 weeks. In one aspect, a host infected with hepatitis C genotype 6 is treated with Sovaldi™, ribavirin, pegylated interferon, and a compound described herein for 12 weeks. In one aspect, a host infected with hepatitis C genotype 6 is treated with ribavirin, pegylated interferon, and a compound described herein for 48 weeks.

In one aspect, a host infected with hepatitis C genotype 1 is treated with Sovaldi™, Olysio, ribavirin, and a compound described herein for 12 weeks. In another aspect, a host infected with hepatitis C genotype 1 is treated with Sovaldi™, ribavirin, and a compound described herein for 24 weeks. In one aspect, a host infected with hepatitis C genotype 2 is treated with Sovaldi™, ribavirin, and a compound described herein for 12 weeks. In one aspect, a host infected with hepatitis C genotype 3 is treated with Sovaldi™, ribavirin, and a compound described herein for 24 weeks. In one aspect, a patient infected with hepatitis C genotype 4 is treated with Sovaldi™, ribavirin, and a compound described herein for 24 weeks.

In one aspect, a host infected with papilloma virus is treated with imiquimod and a compound described herein. In another aspect, a host infected with papilloma virus is treated with cryotherapy and a compound described herein. In another aspect, papilloma virus is surgically removed from a host and the host is treated with a compound described herein. In one aspect, the host receives a compound described herein prior to, during, and post-surgery. In one aspect, the patient receives a compound described herein post-surgery.

In one aspect a host infected with herpes simplex type 2 is treated with Famvir® and a compound described herein. In one aspect a host infected with herpes simplex type 1 is treated with acyclovir and a compound described herein. In another aspect, a host infected with herpes simplex type 2 is treated with acyclovir and a compound described herein. In one aspect, a host infected with herpes simplex type 1 is treated with Valtrex® and a compound described herein. In another aspect, a host infected with herpes simplex type 2 is treated with Valtrex® and a compound described herein. In one aspect, a host infected with herpes simplex type 1 virus receives a compound described herein for 7 days prior to treatment with acyclovir. In one aspect, a host infected with herpes simplex type 2 virus receives a compound described herein for 7 days prior to treatment with acyclovir. In one aspect, a host infected with herpes simplex type 1 virus receives a compound described herein for 7 days prior to treatment with Valtrex®. In one aspect, a host infected with herpes simplex type 2 virus receives a compound described herein for 7 days prior to treatment with Valtrex®.

In one aspect a host infected with varicella zoster virus, VZV, is treated with acyclovir and a compound described herein. In another aspect a host infected with varicella zoster virus, VZV, is treated with Valtrex® and a compound described herein. In one aspect a host infected with varicella zoster virus. VZV, is treated with famciclovir and a compound described herein. In another aspect a host infected with varicella zoster virus, VZV, is treated with foscamet and a compound described herein. In one aspect, a host infected with varicella zoster virus is treated with a compound described herein prior to vaccination with Zostavax. In another aspect, a host infected with varicella zoster virus is treated with a compound described herein prior to and post vaccination with Zostavax®.

In one aspect a host infected with influenza virus is treated with Relenza® and a compound described herein. In another aspect a host infected with influenza virus is treated with Tamiflu® and a compound described herein. In another aspect a host is infected with influenza virus and is treated with amantadine and a compound described herein. In another aspect, a host infected with influenza virus is treated with rimantadine and a compound described herein.

In one aspect, a host infected with cytomegalovirus is treated with valganciclovir and a compound described herein. In another aspect, a host infected with cytomegalovirus is treated with ganciclovir and a compound described herein. In one aspect, a host infected with cytomegalovirus is treated with foscarnet and a compound described herein. In another aspect, a host infected with cytomegalovirus is treated with cidofovir and a compound described herein.

In one aspect, a host infected with hepatitis B virus is treated with lamivudine and a compound described herein. In another aspect, a host infected with hepatitis B virus is treated with adefovir and a compound described herein.

In one aspect, a host infected with hepatitis B virus is treated with tenofovir and a compound described herein. In another aspect, a host infected with hepatitis B virus is treated with telbivudine and a compound described herein.

(v) Bacterial Infections

In one aspect, a disclosed compound or composition is used in an effective amount to treat a host infected with a bacterial infection. In one aspect, the bacteria treated is, for example, a Gram-negative bacilli (GNB), especially *Escherichia coli*. Gram-positive cocci (GPC), *Staphylococcus aureus, Enterococcus faecalis*, or *Streptococcus pneumoniae*. In one aspect, the bacterial infection may be caused, for example, by a Gram-negative bacteria, including, but not limited to *Escherichia coli, Salmonella*, and other Enterobacteriaceae, *Pseudomonas, Moraxella, Helicobacter, Stenotrophomonas, Bdellovibrio*, acetic acid bacteria, *Legionella, Staphylococcus aureus, Hemophilus influenzae, Klebsiella pneumoniae, Legionella pneumophila, Pseudomonas aeruginosa, Vibrio cholerae, Proteus mirabilis, Enterobacter cloacae, Serratia marcescens, Clostridium tetani, Helicobacter pylori, Salmonella enteritidis, Salmonella tvphi, Shigella flexneri*, or *Acinetobacter baumanii*. In one aspect, the bacterial infection may be caused, for example, by a Gram-positive species from the following genera; *Bacillus, Listeria, Staphylococcus, Enterococcus, Lactobacillus, Lactococcus, Leuconostoc, Pedicoccus, Streptococcus, Acetobacterium, Clostridium, Eubacterium, Heliobacterium. Heliospirillum, Megasphaera, Pectinatus, Selenomonas, Zymophilus, Sporomusa, Mycoplasma, Spiroplasma, Ureaplasma*, or *Erysipelothrix*.

In one aspect, the bacterial infection is associated with liver failure. In one aspect, an active compound disclosed herein is administered in combination with an antibiotic or another anti-bacterial agent.

In one aspect, the bacterial infection is associated with liver failure. In one aspect, an active compound disclosed herein is administered in combination with an antibiotic or another anti-bacterial agent.

In one aspect, a patient is suffering from acute-on-chronic liver failure (ACLF). In one aspect, a patient is suffering from acute liver failure. In one aspect, a patient is suffering from chronic liver failure. In one aspect, the liver failure is caused by a disease or condition selected from alcoholic liver disease, chronic viral hepatitis type C, chronic viral hepatitis type B, chronic bile duct blockage, Wilson's disease, hemochromatosis, exposure to drug and toxins, autoimmune hepatitis, cystic fibrosis, alpha antitrypsin deficiency, obesity or schistosomiasis.

In one aspect, an active compound disclosed herein is administered in combination with an antibiotic for the prevention or treatment of bacterial infections. Examples of antibiotics include, but are not limited to, cefotaxime (Claforan), ofloxacin (Floxin), norfloxacin (Noroxin) or trimethoprim sulfamethoxazole (Bactrim, Septra).

d. Use as an Anti-Platelet Agent

In another aspect, a compound described herein is used in the treatment of blot clot (thrombus) formation in a host in need thereof. In one aspect, the host is suffering from coronary artery disease, peripheral vascular disease, or cerebrovascular disease. In one aspect, a compound described herein is administered to a host prior to any medical or surgical procedure in which diminished coagulation potential is desirable. In one aspect, an active compound disclosed herein is administered in combination with another anti-thrombotic or anti-clotting agent.

In one aspect, a disclosed compound or composition as described herein, is provided for use in treating blot clot (thrombus) formation in a subject in need thereof, comprising administering an active compound as described herein, or a pharmaceutically acceptable composition, salt, isotopic analog, or prodrug thereof.

In one aspect, the treatment of blood clot formation is in, for example, a subject with coronary artery disease, peripheral vascular disease, or cerebrovascular disease, or the treatment is given prior to any medical or surgical procedure in which diminished coagulation potential is desirable. Coronary artery disease includes, for example, any coronary dysfunction (pathological state) resulting from coronary artherosclerosis, i.e. partial or total occlusion of coronary vessels. The term also includes a range of various acute and chronical pathological states comprising stable and unstable angina pectoris (SAP and UAP, respectively), left ventricular dysfunction LVD, (congestive) heart failure CHF, myocardial death. Peripheral vascular disease includes, for example, occlusive or functional peripheral arterial disease (PAD). Examples of occlusive PAD include peripheral arterial occlusion, which may be acute, and Buerger's disease (thomboangiitis obliterans). Examples of functional PAD include Raynaud's disease, Raynaud's phenomenon, and acrocyanosis. Cerebrovascular disease includes, for example, any abnormality of the brain resulting from a pathologic process of a blood vessel. In one aspect, the cerebrovascular disease is selected from cerebral ischemia, cerebral hemorrhage, ischemic stroke, hemorrhagic stroke, or ischemic reperfusion injury resulting from reintroduction of blood flow following cerebral ischemia or ischemic stroke. In one non-limiting aspect, the medical or surgical procedure is pulmonary vein ablation.

In one aspect, the treatment of blood clot formation is in a host having thrombi in blood vessels from pathologies or treatments including, for example, myocardial infarction, unstable angina, atrial fibrillation, stroke, renal damage, percutaneous transluminal coronary angioplasty, atherosclerosis, disseminated intravascular coagulation, sepsis, endotoxemia (i.e., the presence of endotoxins in the blood); pulmonary embolism and deep vein thrombosis. In one aspect, the compounds described herein are administered to a host having blood clots on the surfaces of artificial organs, shunts and prostheses (for example, artificial heart valves that are implanted into a patient), and in patients that have received an intracoronary stent. In one aspect, a host is administered an effective amount of a compound described herein due to the formation of clots resulting from some pathological conditions (for example, genetic mutation of VWF cleaving protease, ADAMT13), which may cause spontaneous binding of VWF to platelets resulting in formation of microthrombi in blood vessels leading to thrombotic thrombocytopenic purpura and other microangiopathy. Microangiopathy is a disease of blood vessels in which the walls of very small blood vessels (capillaries) become so thick and weak that they bleed, leak protein, and slow the flow of blood. In one aspect, the treatment is in a patient with hemolytic uremic syndrome.

In one aspect, an active compound disclosed herein is administered in combination with an additional anti-platelet agent. Examples of anti-platelet agents include, but are not limited to, aspirin, tirofiban (Aggrastat), Aggrenox, Agrylin, triflusal (Disgren), Flolan, eptifibatide (Integrilin), dipyridamole (Presantine), cilostazol (Pletal), abciximab (ReoPro), and Terutroban. In one aspect, a compound selected from UNC3810A and U C4202A is administered in combination with an additional anti-platelet agent. In one aspect, the Mer TKI and the additional anti-platelet agent act synergistically. In one aspect, the use of a Mer TKI in combination with an additional anti-platelet agent provides for increased anti-thrombotic or anti-clotting effects without an increase in the standard of care dosage.

In one aspect, the additional anti-platelet agent is an adenosine diphosphate (ADP) receptor inhibitor. Examples of ADP receptor inhibitors include, but are not limited to, clopidogrel (Plavix), prasugrel (Effient), ticagrelor (Brilinta), ticlopidine (Ticlid), N6-methyl-2'-deoxyadenosine-3', 5'-bisphosphate (MRS2179; $P_2Y1$ inhibitor), and 2-methylthioadenosine 5'-monophosphate triethylammonium salt (2-Me-SAMP; $P_2Y$ 12 inhibitor).

In one aspect, an active compound disclosed herein is administered in combination with multiple anti-platelet agents. In one non-limiting aspect, an active compound disclosed herein is administered in combination with N6-methyl-2'-deoxyadenosine-3',5'-bisphosphate and 2-methylthioadenosine 5'-monophosphate triethylammonium salt.

In one aspect, an active compound disclosed herein is administered in combination with an anti-coagulant. In one aspect, the anti-coagulant is a heparin composition. In one aspect, the heparin composition is a low molecular weight heparin composition. Low molecular weight heparin compositions are well known to those of skill in the art and include, but are not limited to, tinzaparin, certoparin, pamaparin, nadroparin, ardeparin, enoxaparin, reviparin, dalteparin, and fraxiparin. Additional examples of anticoagulants include, but are not limited to, warfarin (Coumadin), Fragmin, Hep-Lock, Lovenox, and Miradon. In one aspect, a compound selected from U C3810A and UNC4202A is administered in combination with an anti-coagulant.

e. Use as Nanoparticle Compositions or Carriers

In one aspect, an effective amount of an active compound as described herein is incorporated into nanoparticles, e.g. for convenience of delivery and/or extended release delivery. The use of materials in nanoscale provides one the ability to modify fundamental physical properties such as solubility, diffusivity, blood circulation half-life, drug release characteristics, and immunogenicity. In the last two decades, a number of nanoparticle-based therapeutic and diagnostic agents have been developed for the treatment of cancer, diabetes, pain, asthma, allergy, and infections. These nanoscale agents can provide more effective and/or more convenient routes of administration, lower therapeutic toxicity, extend the product life cycle, and ultimately reduce health-care costs. As therapeutic delivery systems, nanoparticles allow targeted delivery and controlled release.

In addition, nanoparticle-based drug delivery can be used to release drugs at a sustained rate and thus lower the frequency of administration, deliver drugs in a target manner to minimize systemic side effects, or deliver two or more drugs simultaneously for combination therapy to generate a synergistic effect and suppress drug resistance. To date, a number of nanotechnology-based therapeutic products have been approved for clinical use. Among these products, liposomal drugs and polymer-based conjugates account for more than 80% of the products. See. Zhang. L., et al., Nanoparticles in Medicine: Therapeutic Applications and Developments, Clin. Pharm. and Ther., 83(5):761-769, 2008.

Optimal solid lipid nanoparticles (SLN) can be produced in a controlled fashion when a fraction of lipid in the crystalline alpha form can be created and preserved. By doing this, the SLN carrier has a built in trigger mechanism as lipids transform from the alpha to beta form and consequently control drug release. Drug release profiles can be modified according to the composition of the lipid matrix, surfactant concentration and production parameters. See, Muller, R. H., et al., Solid lipid nanoparticles (SLN) for controlled drug delivery—a review of the state of the art, Eur. H. Pharm. Biopharm., 50:161-177, 2000. Consien et al, have recently disclosed lipid nanoparticles having novel amino-lipids that form lipid nanoparticles and their use for the intracellular delivery of biologically active compounds, e.g., nucleic acids. See. U.S. Pat. No. 8,691,750 to Consien et al.

In regard to controlled release, Kanwar has recently disclosed alginate adsorbed chitosan adsorbed lactoferrin adsorbed calcium phosphate nanoparticles and the controlled release of lactoferrin from the nanoparticles. See, WO 2012/145801 to Kanwar. In addition, Armes et al, have recently disclosed polymer-templated core-shell nanoparticles adapted to facilitate controlled release of at least one active agent into a system in response to controlled changes in the pH of the system. See, U.S. Pat. No. 8,580,311 to Armes, S, et al, incorporated by reference herein.

Petros and DeSimone have recently reviewed strategies in the design of nanoparticles. In addition, the authors reviewed their PRINT (particle replication in non-wetting templates) technology for generating microparticles and nanoparticles. See, Petros, R. A, and DeSimone, I. M., Strategies in the design of nanoparticles for therapeutic applications, Nature Reviews/Drug Discovery, vol. 9:615-627, 2010. Importantly, the authors disclosed the production of nanoparticles in which a single parameter (shape or size) can be altered independently of all other particle attributes. The authors concluded their paper by outlining several particle characteristics that have emerged as being central to the function of engineered nanoparticles. These parameters include particle size, particle shape, surface characteristics and the ability to release therapeutics. Additional nanoparticle fabrication methods can also be found in U.S. Pat. Nos. 8,465,775, 8,444,899, 8,420,124, 8,263,129, 8,158,728 and 8,268,446 all hereby incorporated by reference.

Nanoparticles may be prepared using a wide variety of methods known in the art. For example, nanoparticles can be formed by methods as nanoprecipitation, flow focusing fluidic channels, spray drying, single and double emulsion solvent evaporation, solvent extraction, phase separation, milling, microemulsion procedures, microfabrication, nanofabrication, sacrificial layers, simple and complex coacervation, and other methods well known to those of ordinary skill in the art. Alternatively or additionally, aqueous and organic solvent syntheses for monodisperse semiconductor, conductive, magnetic, organic, and other nanomaterials have been described (Pellegrino et al., 2005, Small, 1:48; Murray et al., 2000, Ann. Rev. Mat. Sci., 30:545; and Trindade et al., 2001, Chem. Mat., 13:3843). Additional methods have been described in the literature (see, e.g., Doubrow, Ed., "Microcapsules and Nanoparticles in Medicine and Pharmacy." CRC Press. Boca Raton, 1992; Mathiowitz et al., 1987, J. Control. Release, 5:13; Mathiowitz et al., 1987, Reactive Polymers, 6:275; and Mathiowitz et al., 1988, J. Appl. Polymer Sci., 35:755; U.S. Pat. Nos. 5,578,325 and 6,007, 845; P. Paolicelli et al., "Surface-modified PLGA-based Nanoparticles that can Efficiently Associate and Deliver Virus-like Particles" Nanomedicine. 5(6):843-853 (2010)).

In some aspects, the compounds described herein are associated with a nanoparticle, such as a polymeric nanoparticle. Nanoparticles may comprise natural polymers, including but not limited to chitosan, alginate, dextran, gelatin, and albumin, and synthetic polymers such as, but not limited to, poly(lactide-co-glycolide) (PLGA), (3-hydroxybutyrate-co-3-hydroxyvalerate) (PHBV), poly(sebacic anhydride), poly(e-caprolactone), polystyrene, thermoresponsive (i.e., NIPAAm and CMCTS-g-PDEA) and pH-responsive (i.e., Eudragit LI 00, Eudragit S and AQOAT AS-MG) polymers.

In one aspect, the polymeric particle is between about 0.1 nm to about 10000 nm, between about 1 nm to about 1000 nm, between about 10 nm and 1000 nm, between about 100 nm and 800 nm, between about 400 nm and 600 nm, or about 500 nm. In one aspect, the micro-particles are about 0.1 nm, 0.5 nm, 1.0 nm, 5.0 nm, 10 nm, 25 nm, 50 nm, 75 nm, 100 nm, 150 nm, 200 nm, 250 nm, 300 nm, 400 nm, 450 nm, 500 nm, 550 nm, 600 nm, 650 nm, 700 nm, 750 nm, 800 nm, 850 nm, 900 nm, 950 nm, 1000 nm, 1250 nm, 1500 nm, 1750 nm, or 2000 nm. In one aspect, the compounds described herein are covalently coupled to a polystyrene particle, PLGA particle, PLA particle, or other nanoparticle.

In some aspects, the nanoparticle can be solid or hollow and can comprise one or more layers. In some aspects, each layer has a unique composition and unique properties relative to the other layer(s). To give but one example, the nanoparticle may have a core/shell structure, wherein the core is one layer (e.g. a polymeric core) and the shell is a second layer (e.g. a lipid bilayer or monolayer). In some aspects, the nanoparticle may comprise a plurality of different layers. In some aspects, the compounds described herein can be incorporated into or surrounded by one or more layers.

In some aspects, the nanoparticles comprising the compounds described herein may optionally comprise one or more lipids. In some aspects, a nanoparticle may comprise a liposome. In some aspects, a nanoparticle may comprise a lipid bilayer. In some aspects, a nanoparticle may comprise a lipid monolayer. In some aspects, a nanoparticle may comprise a micelle. In some aspects, a nanoparticle may comprise a core comprising a polymeric matrix surrounded by a lipid layer (e.g., lipid bilayer, lipid monolayer, etc.). In some aspects, a nanoparticle may comprise a non-polymeric core (e.g., metal particle, quantum dot, ceramic particle, bone particle, viral particle, proteins, nucleic acids, carbohydrates, etc.) surrounded by a lipid layer (e.g., lipid bilayer, lipid monolayer, etc.).

In other aspects, the nanoparticle may comprise metal particles, quantum dots, ceramic particles, etc. In some aspects, a non-polymeric nanoparticle is an aggregate of non-polymeric components, such as an aggregate of metal atoms (e.g., gold atoms).

In some aspects, nanoparticles may optionally comprise one or more amphiphilic entities. In some aspects, an amphiphilic entity can promote the production of nanoparticles with increased stability, improved uniformity, or increased viscosity. In some aspects, amphiphilic entities can be associated with the interior surface of a lipid membrane (e.g., lipid bilayer, lipid monolayer, etc.). Many amphiphilic entities known in the art are suitable for use in making nanoparticles useful in the present invention. Such amphiphilic entities include, but are not limited to, phosphoglycerides; phosphatidylcholines; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohols such as polyethylene glycol (PEG); polyoxyethylene-9-lauryl ether; a surface active fatty acid, such as palmitic acid or oleic acid; fatty acids; fatty acid monoglycerides; fatty acid diglycerides; fatty acid amides; sorbitan trioleate (Span® 85) glycocholate; sorbitan monolaurate (Span® 20); polysorbate 20 (Tween® 20); polysorbate 60 (Tween® 60); polysorbate 65 (Tween® 65); polysorbate 80 (Tween® 80); polysorbate 85 (Tween® 85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatide acid; cerebrosides; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol)5000-phosphatidylethanolamine; poly(ethylene glycol)400-monostearate; phospholipids; synthetic and/or natural detergents having high surfactant properties; deoxycholates; cyclodextrins; chaotropic salts; ion pairing agents; and combinations thereof. An amphiphilic entity component may be a mixture of different amphiphilic entities. Those skilled in the art will recognize that this is an exemplary, not comprehensive, list of substances with surfactant activity. Any amphiphilic entity may be used in the production of nanoparticles to be used in accordance with the present invention.

In some aspects, a nanoparticle may optionally comprise one or more carbohydrates. Carbohydrates may be natural or synthetic. A carbohydrate may be a derivatized natural carbohydrate. In certain aspects, a carbohydrate comprises monosaccharide or disaccharide, including but not limited to glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid. In certain aspects, a carbohydrate is a polysaccharide, including but not limited to pullulan, cellulose, microcrystalline cellulose, hydroxypropyl methylcellulose (HPMC), hydroxycellulose (HC), methylcellulose (C), dextran, cyclodextran, glycogen, hydroxyethylstarch, carageenan, glycon, amylose, chitosan, N,0-carboxylmethylchitosan, algin and alginic acid, starch, chitin, inulin, konjac, glucommannan, pustulan, heparin, hyaluronic acid, curdlan, and xanthan. In some aspects, the nanoparticle does not comprise (or specifically exclude) carbohydrates, such as a polysaccharide. In certain aspects, the carbohydrate may comprise a carbohydrate derivative such as a sugar alcohol, including but not limited to mannitol, sorbitol, xylitol, erythritol, maltitol, and -lactitol.

In some aspects, the associated nanoparticle can comprise one or more polymers. In some aspects, the nanoparticle comprises one or more polymers that are a non-methoxy-terminated, pluronic polymer. In some aspects, at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 97%, or 99% (weight/weight) of the polymers that make up the nanoparticles are non-methoxy-terminated, pluronic polymers. In some aspects, all of the polymers that make up the nanoparticle are non-methoxy-terminated, pluronic polymers. In some aspects, the nanoparticle comprises one or more polymers that are a non-methoxy-terminated polymer. In some aspects, at least 1%, 2%, 3%., 4%, 5%, 10%, 15%, 2⁰%, 25%, 30%, 35%, 40%, 45%, 50%, 55%, 60%, 65%, 70%, 75%, 80%, 85%, 90%, 95%, 97%, or 99% (weight/weight) of the polymers that make up the nanoparticles are non-methoxy-terminated polymers. In some aspects, all of the polymers that make up the nanoparticle are non-methoxy-terminated polymers. In some aspects, the nanoparticle comprises one or more polymers that do not comprise pluronic polymer. In some aspects, at least 1°, 2%, 3%, 4%, 5%, 10%0, 15%, 20%, 25%, 30%, 35%, 40%, 45%, 50%, 55%, 60%, 65%, 70%, 75%, 80%, 85%0, 90%, 95%, 97%, or 99% (weight/weight) of the polymers that make up the nanoparticle do not comprise pluronic polymer. In some aspects, all of the polymers that make up the nanoparticles do not comprise pluronic polymer. In some aspects, such a polymer can be surrounded by a coating layer (e.g., liposome, lipid monolayer, micelle, etc.). In some aspects, various elements of the nanoparticle can be coupled with the polymer.

Other examples of polymers include, but are not limited to polyethylenes, polycarbonates (e.g. poly(1,3-dioxan-2one)), polyanhydrides (e.g. poly(sebacic anhydride)), polypropylfumerates, polyamides (e.g. polycaprolactam), polyacetals, polyethers, polyesters (e.g., polylactide, polyglycolide, polylactide-co-glycolide, polycaprolactone, polyhydroxyacid (e.g. poly((P-hydroxyalkanoate))), poly (orthoesters), polycyanoacrylates, polyvinyl alcohols, polyurethanes, polyphosphazenes, polyacrylates, polymethacrylates, polyureas, polystyrenes, and polyamines, polylysine, polylysine-PEG copolymers, and poly(ethyleneimine), poly (ethylene imine)-PEG copolymers.

In some aspects, nanoparticles include polymers which have been approved for use in humans by the U.S. Food and Drug Administration (FDA) under 21 C.F.R. § 177.2600, including but not limited to polyesters (e.g., polylactic acid, poly(lactic-co-glycolic acid), polycaprolactone, polyvalerolactone, poly(1,3-dioxan-2one)); polyanhydrides (e.g., poly(sebacic anhydride)); polyethers (e.g., polyethylene glycol); polyurethanes; polymethacrylates; polyacrylates; and polycyanoacrylates.

In some aspects, polymers can be hydrophilic. For example, polymers may comprise anionic groups (e.g., phosphate group, sulphate group, carboxylate group); cationic groups (e.g., quaternary amine group); or polar groups (e.g., hydroxyl group, thiol group, amine group). In some aspects, a nanoparticles comprising a hydrophilic polymeric matrix generates a hydrophilic environment within the nanoparticle. In some aspects, polymers can be hydrophobic. In some aspects, a nanoparticles comprising a hydrophobic polymeric matrix generates a hydrophobic environment within the nanoparticle. Selection of the hydrophilicity or hydrophobicity of the polymer may have an impact on the nature of materials that are incorporated (e.g., coupled) within the nanoparticle.

In some aspects, polymers may be modified with one or more moieties and/or functional groups. A variety of moieties or functional groups can be used in accordance with the present invention. In some aspects, polymers may be modified with polyethylene glycol (PEG), with a carbohydrate, and/or with acyclic polyacetals derived from polysaccharides (Papisov, 2001, ACS Symposium Series, 786:301). Certain aspects may be made using the general teachings of U.S. Pat. No. 5,543,158 to Gref et al., or WO publication WO2009/051837 by Von Andrian et al.

In some aspects, polymers may be modified with a lipid or fatty acid group. In some aspects, a fatty acid group may be one or more of butyric, caproic, caprylic, capric, lauric, myristic, palmitic, stearic, arachidic, behenic, or lignoceric acid. In some aspects, a fatty acid group may be one or more of palmitoleic, oleic, vaccenic, linoleic, alpha-linoleic, gamma-linoleic, arachidonic, gadoleic, arachidonic, eicosapentaenoic, docosahexaenoic, or erucic acid.

In some aspects, polymers may be one or more acrylic polymers. In certain aspects, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, polycyanoacrylates, and combinations comprising one or more of the foregoing polymers. The acrylic polymer may comprise fully-polymerized copolymers of acrylic and methacrylic acid esters with a low content of quaternary ammonium groups.

In some aspects, polymers can be cationic polymers. In general, cationic polymers are able to condense and/or protect negatively charged strands of nucleic acids (e.g. DNA, or derivatives thereof). Amine-containing polymers such as poly(lysine) (Zauner et al., 1998, Adv. Drug Del. Rev., 30:97; and Kabanov et al., 1995, Bioconjugate Chem., 6:7), polyethylene imine) (PEI; Boussif et al., 1995, Proc. Natl. Acad. Sci., USA, 1995, 92:7297), and poly(amidoamine) dendrimers (Kukowska-Latallo et al., 1996, Proc. Natl. Acad. Sci., USA, 93:4897; Tang et al., 1996, Bioconjugate Chem., 7:703; and Haensler et al., 1993, Bioconjugate Chem., 4:372) are positively-charged at physiological pH, form ion pairs with nucleic acids, and mediate transfection in a variety of cell lines. In aspects, the nanoparticles may not comprise (or may exclude) cationic polymers.

In some aspects, polymers can be degradable polyesters bearing cationic side chains (Putnam et al., 1999, acromolecules, 32:3658; Barrera et al., 1993. J. Am. Chem. Soc, 115:11010; Kwon et al., 1989. Macromolecules, 22:3250; Lim et al., 1999. J. Am. Chem. Soc, 121:5633; and Zhou et al., 1990. Macromolecules, 23:3399). Examples of these polyesters include poly(L-lactide-co-L-lysine) (Barrera et al., 1993, J. Am. Chem. Soc, 115:11010), poly(serine ester) (Zhou et al., 1990, Macromolecules, 23:3399), poly(4-hydroxy-L-proline ester) (Putnam et al., 1999, Macromolecules, 32:3658; and Lim et al., 1999, J. Am. Chem. Soc, 121:5633), and poly(4-hydroxy-L-proline ester) (Putnam et al., 1999, Macromolecules, 32:3658; and Lim et al., 1999, J. Am. Chem. Soc, 121:5633).

The properties of these and other polymers and methods for preparing them are well known in the art (see, for example, U.S. Pat. Nos. 6,123,727; 5,804,178; 5,770,417; 5,736,372; 5,716,404; 6,095,148; 5,837,752; 5,902,599; 5,696,175; 5,514,378; 5,512,600: 5,399,665; 5,019,379; 5,010,167; 4,806,621; 4,638,045; and 4,946,929; Wang et al., 2001, J. Am. Chem. Soc, 123:9480; Lim et al., 2001, J. Am. Chem. Soc, 123:2460; Langer, 2000, Acc. Chem. Res., 33:94; Langer, 1999, J. Control. Release, 62:7; and Uhrich et al., 1999, Chem. Rev., 99:3181). More generally, a variety of methods for synthesizing certain suitable polymers are described in Concise Encyclopedia of Polymer Science and Polymeric Amines and Ammonium Salts, Ed, by Goethals, Pergamon Press, 1980; Principles of Polymerization by Odian, John Wiley & Sons, Fourth Edition, 2004; Contemporary Polymer Chemistry by Allcock et al., Prentice-Hall, 1981; Deming et al., 1997, Nature, 390:386; and in U.S. Pat. Nos. 6,506,577, 6,632,922, 6,686,446, and 6,818,732.

Polymers can be linear or branched polymers. In some aspects, polymers can be dendrimers. In some aspects, polymers can be substantially cross-linked to one another. In some aspects, polymers can be substantially free of cross-links. In some aspects, polymers can be used without undergoing a cross-linking step. It is further to be understood that a nanoparticle may comprise block copolymers, graft copolymers, blends, mixtures, and/or adducts of any of the foregoing and other polymers. Those skilled in the art will recognize that the polymers listed herein represent an exemplary, not comprehensive, list of polymers that can be of use in accordance with the present invention.

The compounds of the present invention can be coupled to a nanoparticle by any of a number of methods. Generally, the coupling can be a result of bonding between the compound and the nanoparticle. This bonding can result in the compound being attached to the surface of the nanoparticle and/or contained within (encapsulated) the nanoparticle. In some aspects, however, the compounds are encapsulated by the nanoparticle as a result of the structure of the nanoparticle rather than bonding to the nanoparticle. In some aspects, the nanoparticle comprises a polymer as provided herein, and the compounds described herein are coupled to the nanoparticle. The compounds described herein may be encapsulated into nanoparticles as desirable using a variety of methods including but not limited to C. Astete et al., "Synthesis and characterization of PLGA nanoparticles" J. Biomater. Sci. Polymer Edn, Vol. 17, No. 3, pp. 247-289 (2006); K. Avgoustakis "Pegylated Poly(Lactide) and Poly(Lactide-Co-Glycolide) Nanoparticles: Preparation, Properties and Possible Applications in Drug Delivery" Current Drug Delivery 1:321-333 (2004); C. Reis et al., "Nanoencapsulation I. Methods for preparation of drug-loaded polymeric nanoparticles" Nanomedicine 2:8-21 (2006); P. Paolicelli et al., "Surface-modified PLGA-based Nanoparticles that can Efficiently Associate and Deliver Virus-like Particles" Nanomedicine. 5(6):843-853 (2010). Other methods suitable for encapsulating the compounds described herein may be used, including without limitation methods disclosed in U.S. Pat. No. 6,632,671 to Unger Oct. 14, 2003.

In certain aspects, nanoparticles are prepared by a nano-precipitation process or spray drying. Conditions used in preparing nanoparticles may be altered to yield particles of a desired size or property (e.g., hydrophobicity, hydrophilicity, external morphology, "stickiness." shape, etc.). The method of preparing the nanoparticles and the conditions (e.g., solvent, temperature, concentration, air flow rate, etc.) used may depend on the materials to be coupled to the nanoparticles and/or the composition of the polymer matrix. If particles prepared by any of the above methods have a size range outside of the desired range, particles can be sized, for example, using a sieve.

In one aspect of the present invention, PRINT technology is used to manufacture nanoparticles comprising a compound described herein.

In another aspect, provided herein are liposome based nanoparticles comprising a compound described herein. In another aspect, a liposome based nanoparticle comprises a compound described herein formulated for controlled-release.

In one aspect, provided herein are polymer based nanoparticles comprising a compound described herein. In another aspect, provided herein are polymer based nanoparticles comprising a compound described herein formulated for controlled-release.

In one aspect, nanoparticles are comprised of albumin and a compound described herein. In another aspect, nanoparticles are comprised of a polysaccharide and a compound described herein. In one aspect, nanoparticles are comprised of a metal and a compound described herein. In another aspect, nanoparticles are comprised of gold and a compound described herein. In another aspect, nanoparticles are comprised of iron oxide and a compound described herein. In one aspect, nanoparticles are comprised of silicon and a compound described herein.

In regard to polymers used for the production of nanoparticles, several reviews are available. See, for example. Soppimath, S., et al., Biodegradable polymeric nanoparticles as drug delivery devices, J. Controlled Release, 70:1-20, 2001. Agnihotri, S. A., et al., Recent advances on chitosan-based micro- and nanoparticle delivery, J. Controlled Release, 100(1):5-28, 2004, Ganta, S, et al., A review of stimuli-responsive nanocarriers for drug and gene delivery, J. Controlled Release, 126(3): 187-204, 2008, Danhier, F, et al., PLGA-based nanoparticles: An overview of biomedical applications. J. Controlled Release, 161(2):505-522, 2012, In one aspect, nanoparticles are comprised of L-glutamic acid copolymers and a compound described herein. In another aspect, nanoparticles are comprised of L-alanine copolymers and a compound described herein. In one aspect, nanoparticles are comprised of L-lysine copolymers and a compound described herein. In another aspect, nanoparticles are comprised of L-tyrosine copolymers and a compound described herein. In other aspect, nanoparticles are comprised of poly(lactic-co-glycolic acid) and a compound described herein. In another aspect, nanoparticles are comprised of methoxy-PEG-poly(D,L-lactide) and a compound described herein. In another aspect, nanoparticles are comprised of HPMA copolymer and a compound described herein. In one aspect, nanoparticles are comprised of polycyclodextran and a compound described herein. In one aspect, nanoparticles are comprised of polyglutamate and a compound described herein. In another aspect, nanoparticles are comprised of poly(iso-hexyl-cyanoacrylate) and a compound described herein. In one aspect, nanoparticles are comprised of poly-L-lysine and a compound described herein. In another aspect, nanoparticles are comprised of PEG and a compound described herein. In one aspect, nanoparticles are made of combinations of polymers and a compound described herein.

In one aspect, a compound described herein is released from a nanoparticle over a period of between about 1 and about 90 days. In one aspect, the compound is released over a period of about 3 to 28 days. In one aspect, the compound is released over a period of about 5 to 21 days.

2. Methods of Treating a Disorder

In one aspect, disclosed are methods for the treatment of a disorder associated with Mer tyrosine kinase and/or Tyro3 tyrosine kinase in a subject, the method comprising the step of administering to the subject an effective amount of at least one disclosed compound, thereby treating the disorder. In a further aspect, the disorder is associated with Mer tyrosine kinase. In a still further aspect, the disorder is associated with Tyro3 tyrosine kinase. In yet a further aspect, the disorder is associated with Mer tyrosine kinase dysfunction and Tyro3 kinase.

Thus, in one aspect, disclosed are methods for the treatment of a disorder associated with Mer tyrosine kinase and/or Tyro3 tyrosine kinase in a subject, the method comprising the step of administering to the subject an effective amount of at least one compound having a structure represented by a formula:

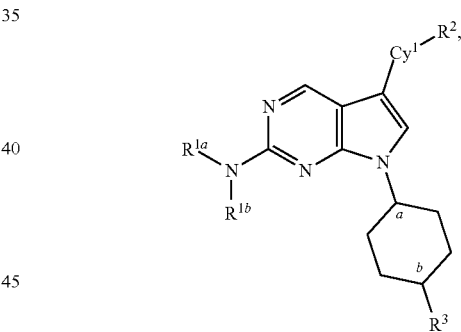

wherein $Cy^1$ is selected from C3-C8 cycloalkyl and C2-C7 heterocycloalkyl, and substituted with 0, 1, 2, or 3 groups independently selected from halogen, C1-C4 alkyl, C1-C4 haloalkyl. C1-C4 alkoxy, C1-C4 hydroxyalkyl, C1-C4 alkylamino, and (C1-C4)(C1-C4) dialkylamino; wherein $R^{1a}$ is selected from hydrogen, C1-C8 alkyl, and $Cy^2$, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein $Cy^2$, when present, is selected from C3-C9 cycloalkyl, C2-C7 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein $R^{1b}$ is selected from C1-C8 alkyl, $Cy^2$, and (C1-C4 alkyl)$Cy^2$, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein R² is selected from hydrogen. C1-C4 alkyl, —C(O)R²⁰, —C(O)N(R²²)R²⁰, —N(R²²)C(O)R²⁰, —SO₂N(R²²)R²¹, —N(R²²)SO₂R²¹, —SO₂R²¹, and —(CH₂)ₙCy³; wherein n is selected from 0, 1, 2, 3, and 4; wherein each of R² and R²¹, when present, is selected from C1-C4 alkyl, —(CH₂)qOR³⁰, and Cy⁴; wherein q is selected from 0, 1, 2, 3, and 4; wherein R³⁰, when present, is selected from hydrogen and C1-C4 alkyl; wherein Cy⁴, when present, is selected from C3-C8 cycloalkyl, C2-C7 heterocycloalkyl. C5-C6 aryl, and C3-C5 heteroaryl and substituted with 0, 1, 2, or 3 groups independently selected from halogen, —NH₂, C1-C4 alkyl, C1-C4 haloalkyl, C1-C4 alkoxy, C1-C4 hydroxyalkyl, C1-C4 alkylamino, (C1-C4)(C1-C4) dialkylamino, and (C1-C4 alkyl)NR⁴⁰ᵃR⁴⁰ᵇ; wherein each of R⁴⁰ᵃ and R⁴⁰ᵇ, when present, is independently selected from hydrogen and C1-C4 alkyl; wherein R²², when present, is selected from hydrogen and C1-C4 alkyl; wherein Cy³, when present, is selected from C3-C8 cycloalkyl, C2-C7 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; and wherein R³ is selected from —(CH₂)ₚOH and —(CH₂)ₚNHR²³; wherein p is selected from 0, 1, and 2; and wherein R²³, when present, is selected from hydrogen and C1-C4 alkyl, provided that when R² is hydrogen or C1-C4 alkyl, then Cy¹ is a structure:

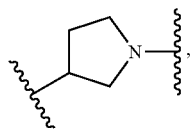

or
provided that when R² is C1-C4 alkyl, then R¹ᵇ is selected from Cy² and (C1-C4 alkyl)Cy², or a pharmaceutically acceptable salt thereof, thereby treating the disorder.

Thus, one aspect, disclosed are methods for the treatment of a disorder associated with Mer tyrosine kinase dysfunction and/or Tyro3 tyrosine kinase dysfunction in a subject, the method comprising the step of administering to the subject an effective amount of at least one compound having a structure represented by a formula:

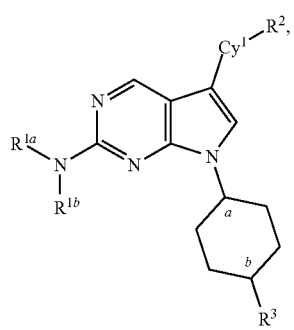

wherein Cy¹ is selected from C3-C8 cycloalkyl and C2-C7 heterocycloalkyl, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein R¹ᵃ is selected from hydrogen, C1-C8 alkyl, and Cy², and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein Cy², when present, is selected from C3-C8 cycloalkyl, C2-C7 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein R¹ᵇ is selected from C1-C8 alkyl and Cy², and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein R² is selected from —C(O)R²⁰, —C(O)N(R²²)R²⁰, —N(R²²)C(O)R²⁰, —SO₂N(R²²)R²¹, —N(R²²)SO₂R²¹, —SO₂R²¹, and —(CH₂)ₙCy³; wherein n is selected from 0, 1, 2, 3, and 4; wherein each of R²⁰ and R²¹, when present, is selected from C1-C4 alkyl, —(CH₂)qOR³⁰, and Cy⁴; wherein q is selected from 0, 1, 2, 3, and 4; wherein R³⁰, when present, is selected from hydrogen and C1-C4 alkyl; wherein Cy⁴, when present, is selected from C3-C8 cycloalkyl, C2-C7 heterocycloalkyl, C5-C6 aryl, and C4-C5 heteroaryl and substituted with 0, 1, 2, or 3 groups independently selected from halogen, C1-C4 alkyl. C1-C4 haloalkyl, C1-C4 alkoxy, C1-C4 hydroxyalkyl, C1-C4 alkylamino, and (C1-C4)(C1-C4) dialkylamino; wherein R²², when present, is selected from hydrogen and C1-C4 alkyl; wherein Cy³, when present, is selected from C3-C8 cycloalkyl, C2-C7 heterocycloalkyl. C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; and wherein R³ is selected from —(CH₂)ₚOH and —(CH₂)ₚNHR²³; wherein p is selected from 0, 1, or 2; and wherein R²³, when present, is selected from hydrogen and C1-C4 alkyl, or a pharmaceutically acceptable salt thereof, thereby treating the disorder.

Also disclosed are methods of treating a tumor in a subject, the method comprising administering to the subject an effective amount of a disclosed compound or composition. In a further aspect, the subject has been diagnosed with a need for treatment of the tumor prior to the administering step. In a still further aspect, the method further comprises the step of identifying a subject in need of treatment of the tumor.

In a further aspect, the tumor is MerTK+/+. In a still further aspect, the tumor is MerTK–/–.

Also disclosed are methods of treating a cancer in a subject, the method comprising administering to the subject an effective amount of a disclosed compound or composition. In a further aspect, the subject has been diagnosed with a need for treatment of the cancer prior to the administering step. In a still further aspect, the method further comprises the step of identifying a subject in need of treatment of the cancer.

In a further aspect, the cancer is MerTK+/+. In a still further aspect, the cancer is MerTK–/–.

Also disclosed are methods of treating an immunosuppressed microenvironment surrounding diseased tissue in a subject, the method comprising administering to the subject an effective amount of a disclosed compound or composition. In a further aspect, the subject has been diagnosed with a need for treatment of the immunosuppressed microenvironment prior to the administering step. In a still further aspect, the method further comprises the step of identifying a subject in need of treatment of the immunosuppressed microenvironment.

Also disclosed are methods of treating a thrombotic disorder in a subject, the method comprising administering to the subject an effective amount of a disclosed compound or composition. In a further aspect, the subject has been diagnosed with a need for anti-thrombotic therapy prior to the administering step. In a still further aspect, the method further comprises the step of identifying a subject in need of anti-thrombotic therapy.

In a further aspect, the subject is a mammal. In a still further aspect, the mammal is a human.

In a further aspect, the subject has been diagnosed with a need for treatment of the disorder prior to the administering step. In a still further aspect, the method further comprises the step of identifying a subject in need of treatment of the disorder.

In a further aspect, the subject has been diagnosed with a need for treatment of an immunosuppressed microenvironment surrounding diseased tissue. In a still further aspect, the method further comprises the step of identifying a subject in need of treatment of an immunosuppressed microenvironment surrounding diseased tissue.

In a further aspect, the effective amount is a therapeutically effective amount. In a still further aspect, the effective amount is a prophylactically effective amount.

In a further aspect, the disorder is a cancer, an infection, a fibrosis, a thrombotic disorder, or a clotting disorder.

In a further aspect, the disorder is an infection. In a still further aspect, the infection is a bacterial infection. In yet a further aspect, the infection is a viral infection. In an even further aspect, the viral infection has a virion envelope phosphatidyl serine.

In a further aspect, the disorder is associated with an immunosuppressed microenvironment surrounding diseased tissue.

In a further aspect, the disorder is a disorder of uncontrolled cellular proliferation. In a still further aspect, the disorder of uncontrolled cellular proliferation is cancer. In yet a further aspect, the cancer is selected from breast cancer, cervical cancer, gastrointestinal cancer, colorectal cancer, brain cancer, skin cancer, prostate cancer, ovarian cancer, thyroid cancer, testicular cancer, pancreatic cancer, endometrial cancer, melanoma, glioma, leukemia, lymphoma, chronic myeloproliferative disorder, myelodysplastic syndrome, myeloproliferative neoplasm, and plasma cell neoplasm (myeloma). In an even further aspect, the cancer is MerTK+/+. In a still further aspect, the cancer is MerTK−/−.

In a further aspect, the disorder is a thrombotic disorder or a clotting disorder. Examples of thrombotic disorders include, but are not limited to, myocardial infarction, deep vein thrombosis, pulmonary embolism, and stroke.

In a further aspect, the disorder is a liver disorder. Examples of liver disorders include, but are not limited to, alcohol-related liver diseases, cirrhosis, non-alcoholic fatty liver disease, hepatitis, haemochromatosis, and primary biliary cirrhosis.

In a further aspect, the disorder is associated with Mer tyrosine kinase dysfunction. In a still further aspect, the disorder is associated with Tyro3 tyrosine kinase dysfunction.

3. Methods of Treating an Infection

In one aspect, disclosed are methods for the treatment of an infection in a subject, the method comprising the step of administering to the subject an effective amount of at least one disclosed compound, or a pharmaceutically acceptable salt thereof, thereby treating the infection.

Thus, in one aspect, disclosed are methods for the treatment of an infection associated with Mer tyrosine kinase and/or Tyro3 tyrosine kinase in a subject, the method comprising the step of administering to the subject an effective amount of at least one compound having a structure represented by a formula:

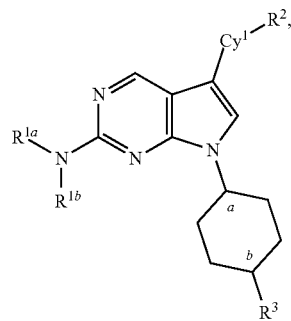

wherein $Cy^1$ is selected from C3-C8 cycloalkyl and C2-C7 heterocycloalkyl, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein $R^{1a}$ is selected from hydrogen, C1-C8 alkyl, and $Cy^2$, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein $Cy^2$, when present, is selected from C3-C9 cycloalkyl, C2-C7 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein $R^{1b}$ is selected from C1-C8 alkyl, $Cy^2$, and (C1-C4 alkyl)$Cy^2$, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein $R^2$ is selected from hydrogen, C1-C4 alkyl, —C(O)$R^{20}$, —C(O)N(R)$R^{20}$, —N($R^{22}$)C(O)$R^{20}$, —SO$_2$N($R^{22}$)$R^{21}$, —N($R^{22}$)SO$_2$$R^{21}$, —SO$_2$$R^{21}$, and —(CH$_2$)$Cy^3$; wherein n is selected from 0, 1, 2, 3, and 4; wherein each of $R^{20}$ and $R^{21}$, when present, is selected from C1-C4 alkyl, —(CH$_2$)$_q$OR$^{30}$, and $Cy^4$; wherein q is selected from 0, 1, 2, 3, and 4; wherein $R^{30}$, when present, is selected from hydrogen and C1-C4 alkyl; wherein $Cy^4$, when present, is selected from C3-C8 cycloalkyl, C2-C7 heterocycloalkyl, C5-C6 aryl, and C3-C5 heteroaryl and substituted with 0, 1, 2, or 3 groups independently selected from halogen, —NH$_2$, C1-C4 alkyl, C1-C4 haloalkyl, C1-C4 alkoxy, C1-C4 hydroxyalkyl, C1-C4 alkylamino, (C1-C4)(C1-C4) dialkylamino, and (C1-C4 alkyl)NR$^{40a}$R$^{40b}$; wherein each of $R^{40a}$ and $R^{40b}$, when present, is independently selected from hydrogen and C1-C4 alkyl; wherein $R^{22}$, when present, is selected from hydrogen and C1-C4 alkyl; wherein $Cy^3$, when present, is selected from C3-C8 cycloalkyl, C2-C7 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; and wherein R³ is selected from —(CH₂)ₚOH and —(CH₂)ₚNHR³; wherein p is selected from 0, 1, and 2; and wherein R²³, when present, is selected from hydrogen and C1-C4 alkyl, provided that when R² is hydrogen or C1-C4 alkyl, then Cy¹ is a structure:

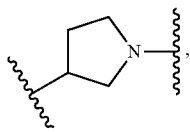

or
provided that when R² is C1-C4 alkyl, then R¹ᵇ is selected from Cy² and (C1-C4 alkyl)Cy², or a pharmaceutically acceptable salt thereof, thereby treating the infection.

Thus, in one aspect, disclosed are methods for the treatment of an infection in a subject, the method comprising the step of administering to the subject an effective amount of at least one compound having a structure represented by a formula:

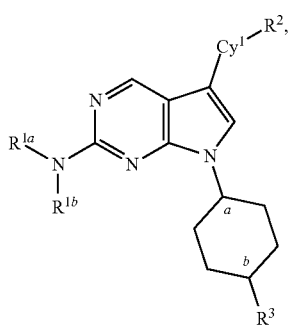

wherein Cy¹ is selected from C3-C8 cycloalkyl and C2-C7 heterocycloalkyl, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein R¹ᵃ is selected from hydrogen, C1-C8 alkyl, and Cy², and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein Cy², when present, is selected from C3-C8 cycloalkyl, C2-C7 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein R¹ᵇ is selected from C1-C8 alkyl and Cy², and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein R² is selected from —C(O)R²⁰, —C(O)N(R²²)R²⁰, —N(R²²)C(O)R²⁰, —SO₂N(R²²)R²¹, —N(R²²)SO₂R²¹, —SO₂R²¹, and —(CH₂)ₙCy³; wherein n is selected from 0, 1, 2, 3, and 4; wherein each of R²⁰ and R²¹, when present, is selected from C1-C4 alkyl, —(CH₂)qOR³⁰, and Cy⁴; wherein q is selected from 0, 1, 2, 3, and 4; wherein R³⁰, when present, is selected from hydrogen and C1-C4 alkyl; wherein Cy⁴, when present, is selected from C3-C8 cycloalkyl, C2-C7 heterocycloalkyl. C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein R²², when present, is selected from hydrogen and C1-C4 alkyl; wherein Cy³, when present, is selected from C3-C8 cycloalkyl, C2-C7 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl. C1-C4 alkylamino, and (C1-C4)(C1-C4) dialkylamino; and wherein R³ is selected from —(CH₂)ₚOH and —(CH₂)ₚNHR²³; wherein p is selected from 0, 1, or 2; and wherein R²³, when present, is selected from hydrogen and C1-C4 alkyl, or a pharmaceutically acceptable salt thereof.

Thus, in one aspect, disclosed are methods for the treatment of an infection in a subject, the method comprising the step of administering to the subject an effective amount of at least one compound having a structure selected from:

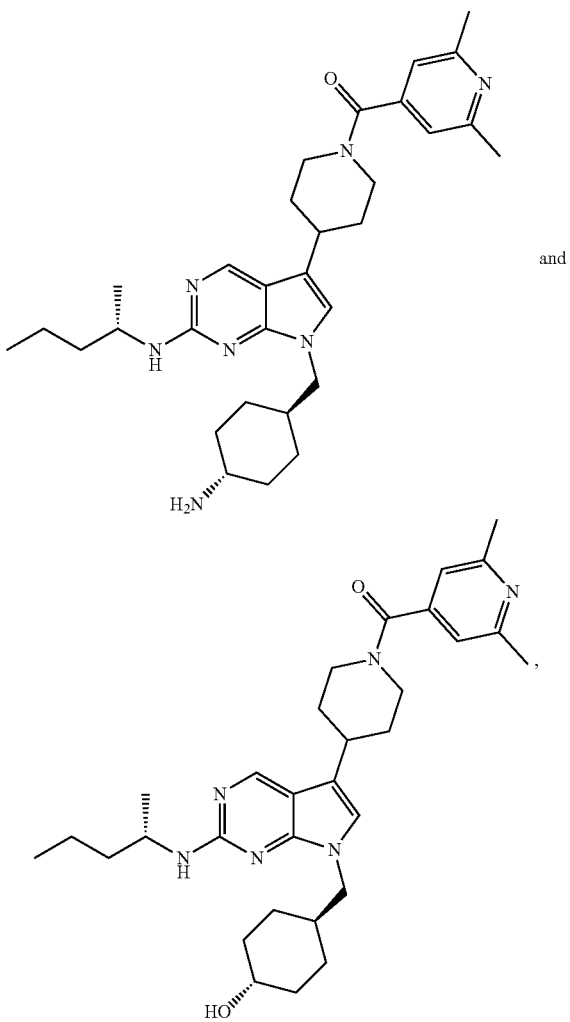

and or a pharmaceutically acceptable salt thereof.

In a further aspect, the infection is a viral infection or a bacterial infection. In a still further aspect, the infection is a bacterial infection. In yet a further aspect, the infection is a viral infection. In an even further aspect, the viral infection has a virion envelope phosphatidyl serine.

In a further aspect, the subject is a mammal. In a still further aspect, the mammal is a human.

In a further aspect, the subject has been diagnosed with a need for treatment of the infection prior to the administering step. In a still further aspect, the method further comprises the step of identifying a subject in need of treatment of the infection.

In a further aspect, the method further comprises administering an effective amount of an antiviral agent to the subject.

In a further aspect, the effective amount is a therapeutically effective amount. In a still further aspect, the effective amount is a prophylactically effective amount.

In a further aspect, the infection is associated with Mer tyrosine kinase dysfunction and/or Tyro3 tyrosine kinase dysfunction. In a still further aspect, the infection is associated with Mer tyrosine kinase dysfunction. In yet a further aspect, the infection is associated with Tyro3 tyrosine kinase dysfunction. In an even further aspect, the infection is associated with Mer tyrosine kinase dysfunction and Tyro3 tyrosine kinase dysfunction.

4. Methods of Inhibiting a Mer Tyrosine Kinase in at Least One Cell

In one aspect, disclosed are methods for inhibiting a Mer tyrosine kinase in at least one cell, the method comprising the step of contacting the at least one cell with an effective amount of at least one disclosed compound, thereby treating the infection.

Thus, in one aspect, disclosed are methods of inhibiting a Mer tyrosine kinase in at least one cell, the method comprising the step of contacting the at least one cell with an effective amount of at least one compound having a structure represented by a formula:

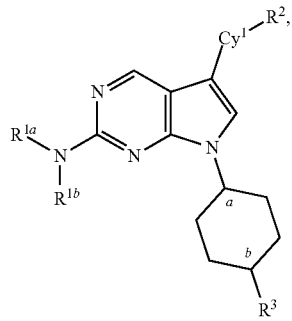

wherein $Cy^1$ is selected from C3-C8 cycloalkyl and C2-C7 heterocycloalkyl, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein $R^{1a}$ is selected from hydrogen, C1-C8 alkyl, and $Cy^2$, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein $Cy^2$, when present, is selected from C3-C8 cycloalkyl, C2-C7 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein $R^{1b}$ is selected from C1-C8 alkyl and $Cy^2$, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein R" is selected from —C(O)R³, —C(O)N(R")R²⁰, —N(R²²)C(O)R²⁰, —SO₂N(R²²)R²¹, —N(R²)SO₂R²¹, —SO₂R²¹, and —(CH₂)$_n$Cy³; wherein n is selected from 0, 1, 2, 3, and 4; wherein each of $R^{20}$ and $R^{21}$, when present, is selected from C1-C4 alkyl, —(CH₂)$_q$OR⁰, and $Cy^4$; wherein q is selected from 0, 1, 2, 3, and 4; wherein $R^{30}$, when present, is selected from hydrogen and C1-C4 alkyl; wherein $Cy^4$, when present, is selected from C3-C8 cycloalkyl, C2-C7 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein $R^{22}$, when present, is selected from hydrogen and C1-C4 alkyl; wherein $Cy^3$, when present, is selected from C3-C8 cycloalkyl, C2-C7 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; and wherein $R^3$ is selected from —(CH₂)$_p$OH and —(CH₂)$_p$NHR²³ wherein p is selected from 0, 1, or 2; and wherein $R^{23}$, when present, is selected from hydrogen and C1-C4 alkyl, or a pharmaceutically acceptable salt thereof, thereby treating the infection.

Thus, in one aspect, disclosed are methods of inhibiting a Mer tyrosine kinase in at least one cell, the method comprising the step of contacting the at least one cell with an effective amount of at least one compound having a structure selected from:

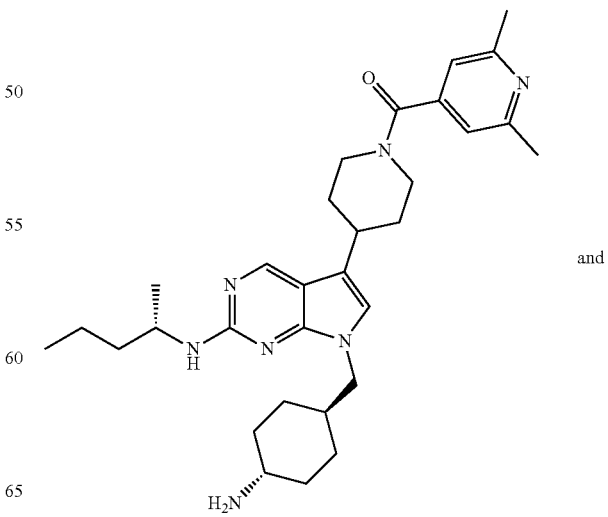

and

-continued

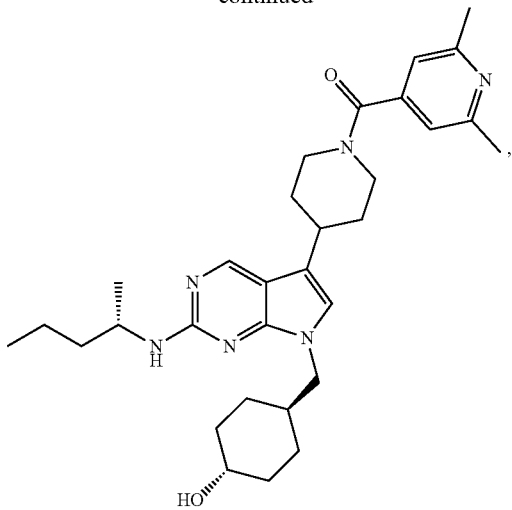

or a pharmaceutically acceptable salt thereof.

In a further aspect, the cell is mammalian. In a still further aspect, the cell is human. In yet a further aspect, the cell has been isolated from a mammal prior to the contacting step.

In a further aspect, contacting is via administration to a mammal. In a still further aspect, the mammal has been diagnosed with a need for inhibiting a Mer tyrosine kinase prior to the administering step. In yet a further aspect, the mammal has been diagnosed with a need for treatment of a disorder related to dysfunction of a Mer tyrosine kinase prior to the administering step.

In a further aspect, inhibiting a Mer tyrosine kinase is associated with treating a cancer.

In a further aspect, the compound exhibits inhibition of MerTK with an $IC_{50}$ of less than about 30 μM. In a still further aspect, the compound exhibits inhibition of MerTK with an $IC_{50}$ of less than about 25 μM. In yet a further aspect, the compound exhibits inhibition of MerTK with an $IC_{50}$ of less than about 20 μM. In an even further aspect, the compound exhibits inhibition of MerTK with an $IC_{50}$ of less than about 15 μM. In a still further aspect, the compound exhibits inhibition of MerTK with an $IC_{50}$ of less than about 10 μM. In yet a further aspect, the compound exhibits inhibition of MerTK with an $IC_{50}$ of less than about 5 μM. In an even further aspect, the compound exhibits inhibition of MerTK with an $IC_{50}$ of less than about 1 μM. In a still further aspect, the compound exhibits inhibition of MerTK with an $IC_{50}$ of less than about 0.5 μM.

5. Methods of Inhibiting a Tyro3 Tyrosine Kinase in at Least One Cell

In one aspect, disclosed are methods method for inhibiting a Tyro3 tyrosine kinase in at least one cell, the method comprising the step of contacting the at least one cell with an effective amount of at least one disclosed compound, thereby treating the infection.

Thus, in one aspect, disclosed are methods of inhibiting a Tyro3 tyrosine kinase in at least one cell, the method comprising the step of contacting the at least one cell with an effective amount of at least one compound having a structure represented by a formula:

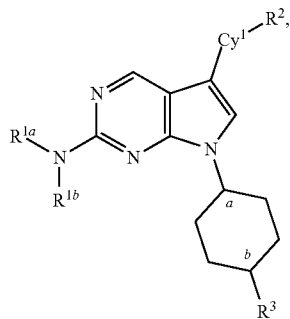

wherein $Cy^1$ is selected from C3-C8 cycloalkyl and C2-C7 heterocycloalkyl, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein $R^{1a}$ is selected from hydrogen, C1-C8 alkyl, and $Cy^2$, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein $Cy^2$, when present, is selected from C3-C8 cycloalkyl, C2-C7 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein $R^{1b}$ is selected from C1-C8 alkyl and $Cy^2$, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; wherein $R^2$ is selected from —C(O)$R^{20}$, —C(O)N($R^{22}$)$R^{20}$, —N($R^{22}$)C(O)$R^{20}$, —SO$_2$N($R^{22}$)$R^{21}$, —N($R^{22}$)SO$_2R^{21}$, —SO$_2R^{21}$, and —(CH$_2$)$_n$Cy$^3$; wherein n is selected from 0, 1, 2, 3, and 4; wherein each of $R^{20}$ and $R^{21}$, when present, is selected from C1-C4 alkyl, —(CH$_2$)$_q$OR$^3$, and $Cy^4$; wherein q is selected from 0, 1, 2, 3, and 4; wherein $R^{30}$, when present, is selected from hydrogen and C1-C4 alkyl; wherein $Cy^4$, when present, is selected from C3-C8 cycloalkyl, C2-C7 heterocycloalkyl, C5-C6 aryl, and C4-C5 heteroaryl and substituted with 0, 1, 2, or 3 groups independently selected from halogen, C1-C4 alkyl. C1-C4 haloalkyl, C1-C4 alkoxy, C1-C4 hydroxyalkyl, C1-C4 alkylamino, and (C1-C4)(C1-C4) dialkylamino; wherein $R^{22}$, when present, is selected from hydrogen and C1-C4 alkyl; wherein $Cy^3$, when present, is selected from C3-C8 cycloalkyl, C2-C7 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; and wherein $R^3$ is selected from —(CH$_2$)$_p$OH and —(CH$_2$)$_p$NHR$^{23}$; wherein p is selected from 0, 1, or 2; and wherein $R^{23}$, when present, is selected from hydrogen and C1-C4 alkyl, or a pharmaceutically acceptable salt thereof, thereby treating the infection.

Thus, in one aspect, disclosed are methods of inhibiting a Tyro3 tyrosine kinase in at least one cell, the method comprising the step of contacting the at least one cell with an effective amount of at least one compound having a structure selected from:

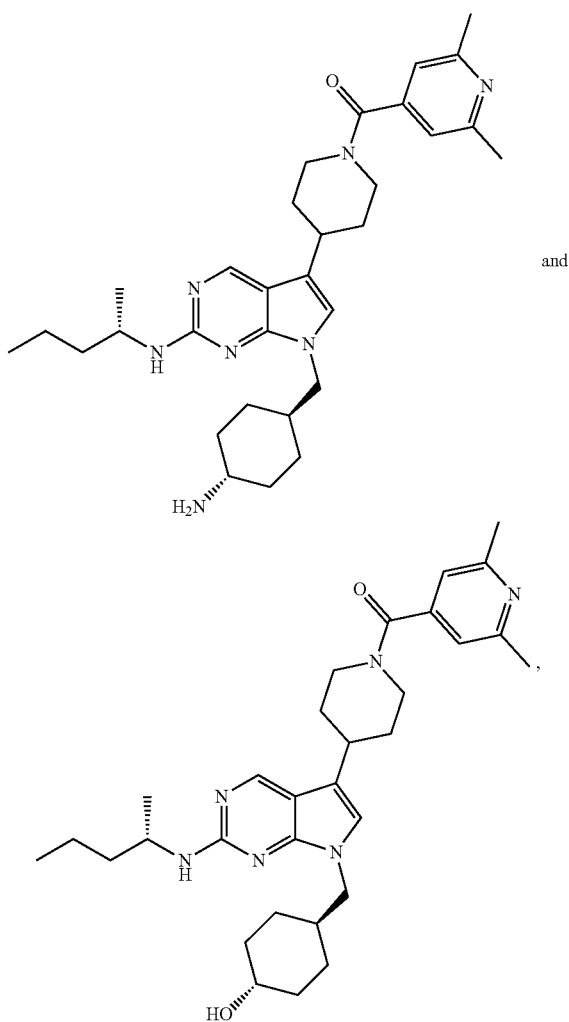

and or a pharmaceutically acceptable salt thereof.

In a further aspect, the cell is mammalian. In a still further aspect, the cell is human. In yet a further aspect, the cell has been isolated from a mammal prior to the contacting step.

In a further aspect, contacting is via administration to a mammal. In a still further aspect, the mammal has been diagnosed with a need for inhibiting a Tyro3 tyrosine kinase prior to the administering step. In yet a further aspect, the mammal has been diagnosed with a need for treatment of a disorder related to dysfunction of a Tyro3 tyrosine kinase prior to the administering step.

In a further aspect, the compound exhibits inhibition of Tyro3TK with an $IC_{50}$ of less than about 30 µM. In a still further aspect, the compound exhibits inhibition of Tyro3TK with an $IC_{50}$ of less than about 25 µM. In yet a further aspect, the compound exhibits inhibition of Tyro3TK with an $IC_{50}$ of less than about 20 µM. In an even further aspect, the compound exhibits inhibition of Tyro3TK with an $IC_{5}$ of less than about 15 µM. In a still further aspect, the compound exhibits inhibition of Tyro3TK with an $IC_{50}$ of less than about 10 µM. In yet a further aspect, the compound exhibits inhibition of Tyro3TK with an $IC_{50}$ of less than about 5 µM. In an even further aspect, the compound exhibits inhibition of Tyro3TK with an $IC_{50}$ of less than about 1 µM. In a still further aspect, the compound exhibits inhibition of Tyro3TK with an $IC_{50}$ of less than about 0.5 µM.

In a further aspect, inhibiting a Tyro3 tyrosine kinase is associated with treating a cancer.

6. Use of Compounds

In one aspect, the invention relates to the use of a disclosed compound or a product of a disclosed method.

In a further aspect, a use relates to the manufacture of a medicament for the treatment of a disorder in a mammal. In a still further aspect, the disorder is associated with Mer tyrosine kinase dysfunction. In yet a further aspect, the disorder is associated with Tyro3 tyrosine kinase dysfunction.

In a further aspect, the invention relates to the use of a disclosed compound or a product of a disclosed method in immunostimulatory therapy.

In a further aspect, the invention relates to the use of a disclosed compound or a product of a disclosed method in immunomodulatory therapy.

In a further aspect, a use relates to the manufacture of a medicament for the treatment of an infection in a mammal. In a still further aspect, the infection is associated with Mer tyrosine kinase dysfunction. In yet a further aspect, the infection is associated with Tyro3 tyrosine kinase dysfunction.

Also provided are the uses of the disclosed compounds and products. In one aspect, the invention relates to use of at least one disclosed compound; or a pharmaceutically acceptable salt, hydrate, solvate, or polymorph thereof. In a further aspect, the compound used is a product of a disclosed method of making.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, for use as a medicament.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, wherein a pharmaceutically acceptable carrier is intimately mixed with a therapeutically effective amount of the compound or the product of a disclosed method of making.

It is understood that the disclosed uses can be employed in connection with the disclosed compounds, products of disclosed methods of making, methods, compositions, and kits.

7. Manufacture of a Medicament

In one aspect, the invention relates to a method for the manufacture of a medicament for treating a disorder in a subject, the method comprising combining an effective amount of a disclosed compound or product of a disclosed method with a pharmaceutically acceptable carrier or diluent.

In one aspect, the invention relates to a method for the manufacture of a medicament for treating an infection in a subject, the method comprising combining an effective amount of a disclosed compound or product of a disclosed method with a pharmaceutically acceptable carrier or diluent.

As regards these applications, the present method includes the administration to an animal, particularly a mammal, and more particularly a human, of a therapeutically effective amount of the compound effective in the inhibition of MerTK and/or Tyro3TK. The dose administered to an animal, particularly a human, in the context of the present invention should be sufficient to affect a therapeutic response in the animal over a reasonable time frame. One skilled in the art will recognize that dosage will depend upon a variety of factors including the condition of the animal and the body weight of the animal.

The total amount of the compound of the present disclosure administered in a typical treatment is preferably between about 10 mg/kg and about 1000 mg/kg of body weight for mice, and between about 100 mg/kg and about 500 mg/kg of body weight, and more preferably between 200 mg/kg and about 400 mg/kg of body weight for humans per daily dose. This total amount is typically, but not necessarily, administered as a series of smaller doses over a period of about one time per day to about three times per day for about 24 months, and preferably over a period of twice per day for about 12 months.

The size of the dose also will be determined by the route, timing and frequency of administration as well as the existence, nature and extent of any adverse side effects that might accompany the administration of the compound and the desired physiological effect. It will be appreciated by one of skill in the art that various conditions or disease states, in particular chronic conditions or disease states, may require prolonged treatment involving multiple administrations.

Thus, in one aspect, the invention relates to the manufacture of a medicament comprising combining a disclosed compound or a product of a disclosed method of making, or a pharmaceutically acceptable salt, solvate, or polymorph thereof, with a pharmaceutically acceptable carrier or diluent.

8. Kits

In one aspect, disclosed are kits comprising at least one compound of claim 1 and one or more of: (a) at least one agent known to increase Mer tyrosine kinase activity; (b) at least one agent known to increase Tyro3 tyrosine kinase activity; (c) at least one agent known to treat a disorder of uncontrolled cellular proliferation; (d) at least one antibacterial agent; (e) at least one antiviral agent; (f) instructions for treating a disorder associated with Mer tyrosine kinase dysfunction (g) instructions for treating a disorder associated with Tyro3 tyrosine kinase dysfunction (h) instructions for treating a disorder of uncontrolled cellular proliferation; or (i) instructions for treating an infection.

In a further aspect, the disorder is an infection. In a still further aspect, the disorder is a viral infection. Examples of viral infections include, but are not limited to, human immunodeficiency virus (HIV), human papillomavirus (HPV), influenza, chicken pox, infectious mononucleosis, mumps, measles, rubella, shingles, ebola, viral gastroenteritis, viral hepatitis, viral meningitis, human metapneumovirus, human parainfluenza virus type 1, parainfluenza virus type 2, parainfluenza virus type 3, respiratory syncytial virus, viral pneumonia, chikungunya, Venezuelan equine encephalitis, dengue, influenza, and zika. In yet a further aspect, the infection is a bacterial infection. Examples of bacterial infections include, but are not limited to, *M, tuberculosis. M, bovis. M, bovis* strain BCG, BCG substrains, *M, avium, M, intracellulare, M. africanum, M. kansasii., M. marinum, M. ulcerans, M. avium* subspecies paratuberculosis, *Nocardia asteroides*, other *Nocardia* species, *Legionella pneumophila*, other *Legionella* species, *Salmonella typhi*, other *Salmonella* species, *Shigella* species, *Yersinia pestis, Pasteurella haemolytica, Pasteurella multocida*, other *Pasteurella* species, *Actinobacillus pleuropneumoniae, Listeria monocytogenes, Listeria ivanovii, Brucella abortus*, other *Brucella* species, *Cowdria ruminantium, Chlamydia pneumoniae, Chlamydia trachomatis, Chlamydia psittaci, Coxiella burnetti*, other *Rickettsial* species, *Ehrlichia* species, *Staphylococcus aureus, Staphylococcus epidermidis, Streptococcus pneumoniae, Streptococcus pyogenes, Streptococcus agalactiae, Bacillus anthracis, Escherichia coli, Vibrio cholerae, Campylobacter* species. *Neiserria meningitidis, Neiserria gonorrhea, Pseudomonas aeruginosa*, other *Pseudomonas* species, *Haemophilus influenzae, Haemophilus ducreyi*, other *Hemophilus* species, *Clostridium tetani*, other *Clostridium* species, *Yersinia enterolitica*, and other *Yersinia* species. In yet a further aspect, the composition further comprises at least one agent known to have a side effect of increasing the risk of a bacterial infection.

In a further aspect, the disorder is a thrombotic disorder or a clotting disorder. Examples of thrombotic disorders include, but are not limited to, myocardial infarction, deep vein thrombosis, pulmonary embolism, and stroke.

In a further aspect, the disorder is a disorder of uncontrolled cellular proliferation. In a still further aspect, the disorder of uncontrolled cellular proliferation is a cancer. Examples of cancers include, but are not limited to, leukemias, lymphomas, and solid tumors. In one aspect, the cancer can be a cancer selected from cancers of the gastrointestinal tract, hematologic, colon, rectum, liver, omentum, breast, kidney, lymphatic system, stomach, lung, pancreas, liver and skin. In a further aspect, the cancer is selected from leukemia and gastrointestinal stroma tumor.

In a further aspect, the agent known to treat a disorder of uncontrolled cellular proliferation is a chemotherapeutic agent. Examples of chemotherapeutic agents include, but are not limited to, alkylating agents such as busulfan, cis-platin, mitomycin C, and carboplatin; antimitotic agents such as colchicine, vinblastine, paclitaxel (e.g., TAXOL®), and docetaxel; topoisomerase I inhibitors such as camptothecin and topotecan; topoisomerase II inhibitors such as doxorubicin and etoposide; RNA/DNA antimetabolites such as 5-azacytidine, 5-fluorouracil and methotrexate; DNA antimetabolites such as 5-fluoro-2'-deoxy-uridine, ara-C, hydroxyurea, gemcitabine, capecitabine and thioguanine; antibodies such as HERCEPTIN® and RITUXAN®, as well as other known chemotherapeutics such as photofrin, melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen and alanosine.

In a further aspect, the antibacterial agent is selected from erythromycin, azithronmycin, clarithromycin, telithromycin, penicillin, cephalosporin, carbapenem, imipenem, meropenem, penicillin G, penicillin V, methicillin, oxacillin, cloxacillin, dicloxacillin, nafcillin, ampicillin, amoxicillin, carbenicillin, ticarcillin, meziocillin, piperacillin, azlocillin, temocillin, cepalothin, cephapirin, cephradine, cephaloridine, cefazolin, cefamandole, cefuroxime, cephalexin, cefprozil, cefaclor, loracarbef, cefoxitin, cefmetazole, cefotaxime, ceftizoxime, ceftriaxone, cefoperazone, ceftazidime, cefixime, cefpodoxime, ceftibuten, cefdinir, cefpirome, cefepime, astreonam, gentamycin, chloroquine, cetyl pyridinium chloride, nalidixic acid, oxolinic acid, norfloxacin, pefloxacin, enoxacin, ofloxacin, levofloxacin, ciprofloxacin, temafloxacin, lomefloxacin, fleroxacin, grepafloxacin, sparfloxacin, trovafloxacin, clinafloxacin, gatifloxacin, moxifloxacin, sitafloxacin, ganefloxacin, gemifloxacin, pazufloxacin, para-aminobenzoic acid, sulfadiazine, sulfisoxazole, sulfamethoxazole, sulfathalidine, streptomycin, neomycin, kanamycin, paromycin, gentamicin, tobramycin, amikacin, netilmicin, spectinomycin, sisomicin, dibekalin, sepamicin, tetracycline, chlortetracycline, demeclocycline, minocycline, oxytetracycline, methacycline, doxycycline, rifampicin (also called rifampin), rifapentine, rifabutin, bezoxazinorifamycin, rifaximin, lincomycin, clindamycin, vancomycin, teicoplanin, quinupristin, daflopristin, linezolid, polymyxin, colistin, colymycin, trimethoprim, bacitracin, triclosan, ascorbyl stearate, oleoyl sarcosine, dioctyl sulfosuccinate, vidarabine, and phosphonomycin.

In a further aspect, the antiviral agent is selected from selected from acemannan, acyclovir, acyclovir sodium, adamantanamine, adefovir, adenine arabinoside, alovudine, alvircept sudotox, amantadine hydrochloride, aranotin, arildone, atevirdine mesylate, avridine, cidofovir, cipamfylline, cytarabine hydrochloride, BMS 806, C31G, carrageenan, cellulose sulfate, cyclodextrins, dapivirine, delavirdine mesylate, desciclovir, dextrin 2-sulfate, didanosine, disoxaril, dolutegravir, edoxudine, enviradene, envirozime, etravirine, famciclovir, famotine hydrochloride, fiacitabine, fialuridine, fosarilate, foscarnet sodium, fosfonet sodium, FTC, ganciclovir, ganciclovir sodium, GSK 1265744, 9-2-hydroxy-ethoxy methylguanine, ibalizumab, idoxuridine, interferon, 5-iodo-2'-deoxyuridine, IQP-0528, kethoxal, lamivudine, lobucavir, maraviroc, memotine pirodavir, penciclovir, raltegravir, ribavirin, rimantadine hydrochloride, rilpivirine (TMC-278), saquinavir mesylate, SCH—C, SCH-D, somantadine hydrochloride, sorivudine, statolon, stavudine, T20, tilorone hydrochloride, TMC 120, TMC 125, trifluridine, trifluorothymidine, tenofovir, tenofovir alefenamide, tenofovir disoproxyl fumarate, prodrugs of tenofovir, UC-781, UK-427, UK-857, valacyclovir, valacyclovir hydrochloride, vidarabine, vidarabine phosphate, vidarabine sodium phosphate, viroxime, zalcitabene, zidovudine, and zinviroxime.

In a further aspect, the at least one compound and the at least one agent are co-formulated. In a further aspect, the at least one compound and the at least one agent are co-packaged.

The kits can also comprise compounds and/or products co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is understood that the disclosed kits can be prepared from the disclosed compounds, products, and pharmaceutical compositions. It is also understood that the disclosed kits can be employed in connection with the disclosed methods of using.

The foregoing description illustrates and describes the disclosure. Additionally, the disclosure shows and describes only the preferred aspects but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The aspects described herein above are further intended to explain best modes known by applicant and to enable others skilled in the art to utilize the disclosure in such, or other, aspects and with the various modifications required by the particular applications or uses thereof. Accordingly, the description is not intended to limit the invention to the form disclosed herein. Also, it is intended to the appended claims be construed to include alternative aspects.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

F. EXAMPLES

The following preparations and examples are given to enable those skilled in the art to more clearly understand and to practice the present invention. They should not be considered as limiting the scope of the invention, but merely as being illustrative and representative.

1. General Experimental Methods

All solvents were purchased from Sigma-Aldrich (anhydrous grade), VWR International, or Fisher Scientific. All non-aqueous reactions were performed in flame-dried or oven dried round-bottomed flasks under an atmosphere of nitrogen or argon. Reaction temperatures were controlled using a thermocouple thermometer and analog hotplate stirrer. Reactions were conducted at room temperature (r.t., approximately 23° C.) unless otherwise noted. Analytical thin-layer chromatography (TLC) was performed on E. Merck silica gel 60 F254 plates and visualized using UV, ceric ammonium molybdate, potassium permanganate, and anisaldehyde stains. Yields were reported as isolated, spectroscopically pure compounds.

$^1$H NMR spectra were recorded on Varian 400 MHz spectrometers and are reported relative to deuterated solvent signals. Data for $^1$H NMR spectra are reported as follows: chemical shift (δ ppm), multiplicity (s=singlet, d=doublet, t=triplet, dd=double of doublets, dt=doublet of triplets, q=quartet, m=multiplet, br=broad, app=apparent), coupling constants (Hz), and integration. LC/MS was conducted and recorded on an Agilent Technologies 6110 Quadrupole instrument.

2. Chemistry Experimentals a. General Synthesis of Amine

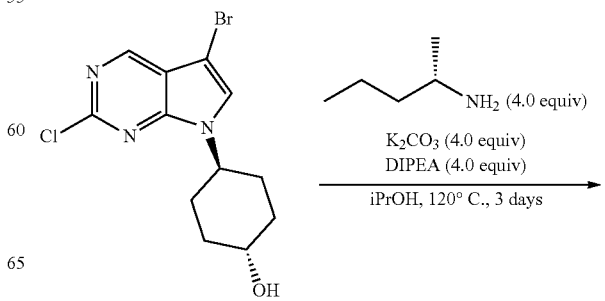

215
-continued

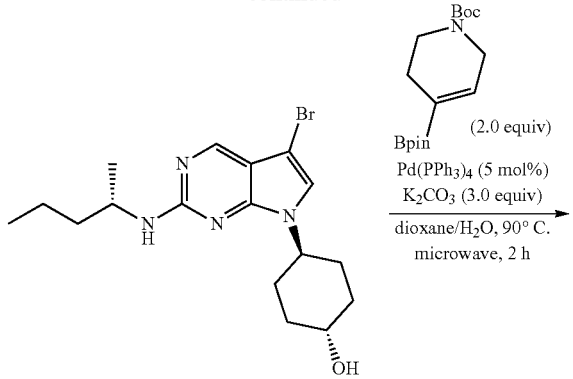

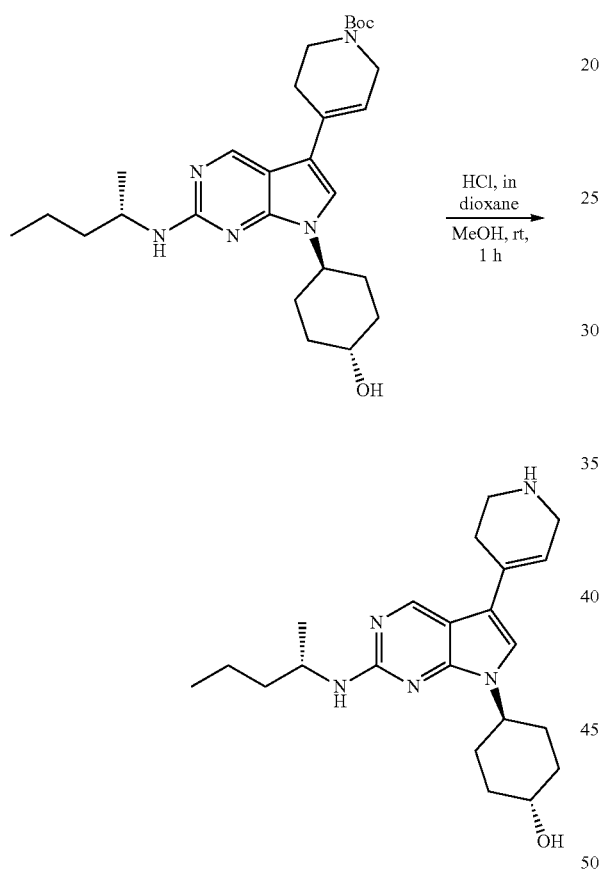

(i) General Palladium-Coupling Procedure

A mixture of (1r,4r)-4-(5-bromo-2-chloro-7H-pyrrolo[2,3-d]pyrimidin-7-yl)cyclohexan-1-ol (3.30 g, 10.0 mmol), (S)-pentan-2-amine (3.48 g, 40.0 mmol), potassium carbonate (5.52 g, 40.0 mmol), and N,N-diisopropylethylamine (6.97 mL, 40.0 mmol) in iPrOH (80 mL) was heated at 120° C., for 3 days. The reaction mixture was allowed to cool to room temperature and the solvent was removed under the reduced pressure. The residue was purified by column chromatography with ISCO system to afford the desired product (1S,4r)-4-(5-bromo-2-(((S)-pentan-2-yl)amino)-7H-pyrrolo[2,3-d]pyrimidin-7-yl)cyclohexan-1-ol as a pale yellow solid (2.82 g, 74%). Halide (381 mg, 1.0 mmol, 1.0 equiv), Pd(PPh₃)₄ (58 mg, 0.05 mmol, 0.05 equiv), 3,6-

216 dihydro-2H-pyridine-1-N-Boc-4-boronic acid, pinacol ester (618 mg, 2.0 mmol, 2.0 equiv) and potassium carbonate (415 mg, 3.0 mmol, 3.0 equiv) in a mixture of dioxane and H₂O (4:1, 10 mL) was heated at 90° C., under microwave radiation for 2 h. The reaction mixture was allowed to cool to room temperature and the solvent was removed under the reduced pressure. The residue was purified by column chromatography with ISCO system to afford the desired product.

a. Tert-butyl 4-(7-((1R,4S)-4-hydroxycyclohexyl)-2-(((S)-pentan-2-yl)amino)-7H-pyrrolo[2,3-d]pyrimidin-5-yl)-3,6-dihydropyridine-1(2H)-carboxylate

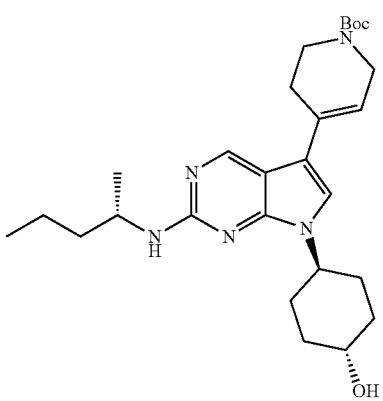 [SMILES: CCC[C@H](C)Nc1ncc2c(C3=CCN(C(=O)OC(C)(C)C)CC3)cn([C@H]3CC[C@H](O)CC3)c2n1]

Pale yellow solid (350 mg, 72% yield).

(ii) General Deprotection Procedure

To a solution of Boc-protected amine (350 mg, 0.72 mmol, 1.0 equiv) in methanol (2.0 mL) was added a hydrogen chloride solution (4 M in dioxane, 2.0 mL, 11.1 equiv) at room temperature. The resulting solution was stirred at room temperature for 1 h. The solvent was removed under the reduced pressure to provide the crude product, which was used in the next step without any further purification.

b. General Procedure A

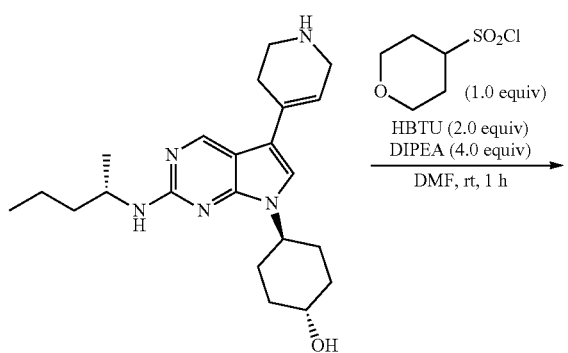

217

-continued

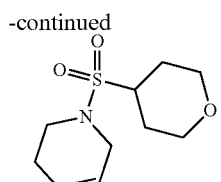

Pd/C
H₂ balloon
————————→
MeOH, rt,
overnight

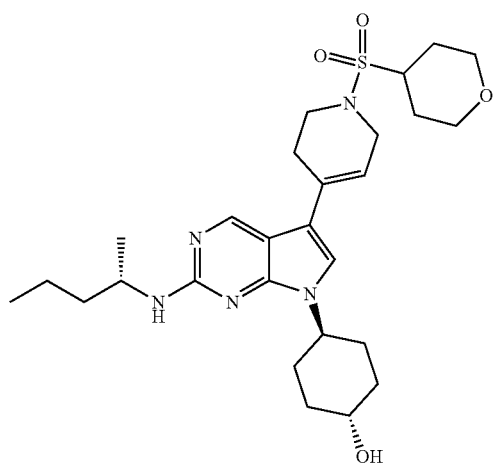 [SMILES: CCC[C@H](C)Nc1ncc2c(C3=CCN(S(=O)(=O)C4CCOCC4)CC3)cn([C@H]3CC[C@H](O)CC3)c2n1]

(i) General Coupling Procedure

To a solution of amine (71 mg, 0.185 mmol, 1.0 equiv) and N,N-diisopropylethylamine (0.2 mL) in dichloromethane (10 mL) at −78° C. was added tetrahydro-2H-pyran-4-sulfonyl chloride (34 mg, 0.185 mmol, 1.0 equiv). The reaction solution was allowed to warm to room temperature and stirred at room temperature overnight. Upon evaporation of solvent, the residue was purified by HPLC to afford the desired product.

a. (1S,4R)-4-(2-(((S)-pentan-2-yl)amino)-5-(1-((tetrahydro-2H-pyran-4-yl)sulfonyl)-1,2,3,6-tetrahydropyridin-4-yl)-7H-pyrrolo[2,3-d]pyrimidin-7-yl)cyclohexan-1-ol

218

Pale yellow solid (78 mg, 78% yield). ¹H NMR (400 MHz, CD₃OD) δ 8.71 (s, 1H), 7.56 (s, 1H), 6.16 (s, 1H), 4.52 (quint, J=7.3 Hz, 1H), 4.23-4.13 (m, 1H), 4.11-4.06 (m, 2H), 4.04-3.98 (m, 2H), 3.75-3.55 (m, 4H), 3.46-3.38 (m, 2H), 2.62-2.54 (m, 2H), 2.15-1.92 (m, 8H), 1.88-1.40 (m, 8H), 1.31 (d, J=6.6 Hz, 3H), 0.99 (t, J=7.3 Hz, 3H). MS m/z 532.30 [M+H]⁺.

(iii) General Hydrogenation Procedure

A suspension of alkene (53 mg, 0.1 mmol) and palladium on carbon (10% Pd basis, 50 mg) in MeOH was stirred under hydrogen atmosphere at room temperature overnight. The resulting mixture was filtered through a pad of Celite and the solvent was removed under the reduced pressure. The residue was purified by HPLC to afford the desired compound.

a. (1S,4R)-4-(5-(1-((1-methylpiperidin-4-yl)sulfonyl)piperidin-4-yl)-2-(((S)-pentan-2-yl)amino)-7H-pyrrolo[2,3-d]pyrimidin-7-yl)cyclohexan-1-ol (1)

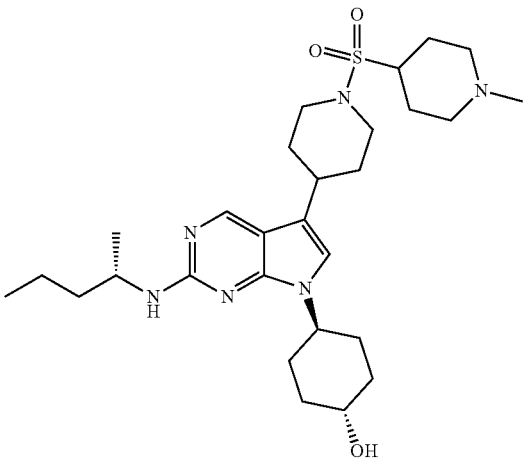 [SMILES: CCC[C@H](C)Nc1ncc2c(C3CCN(S(=O)(=O)C4CCN(C)CC4)CC3)cn([C@H]3CC[C@H](O)CC3)c2n1]

¹H NMR (400 MHz, CD₃OD) δ 8.60 (s, 1H), 7.33 (s, 1H), 4.55-4.43 (m, 1H), 4.20-4.10 (m, 1H), 3.95-3.85 (m, 2H), 3.75-3.60 (m, 3H), 3.52-3.40 (m, 1H), 3.18-3.02 (m, 4H), 3.00-2.90 (m, 1H), 2.89 (s, 3H), 2.40-2.32 (m, 2H), 2.15-1.90 (m, 10H), 1.80-1.40 (m, 8H), 1.30 (d, J=6.6 Hz, 3H), 0.98 (t, J=7.2 Hz, 3H). MS m/z 547.34 [M+H]⁺.

b. (1S,4R)-4-(2-(((S)-pentan-2-yl)amino)-5-(1-((tetrahydro-2H-pyran-4-yl)sulfonyl)piperidin-4-yl)-7H-pyrrolo[2,3-d]pyrimidin-7-yl)cyclohexan-1-ol (2)

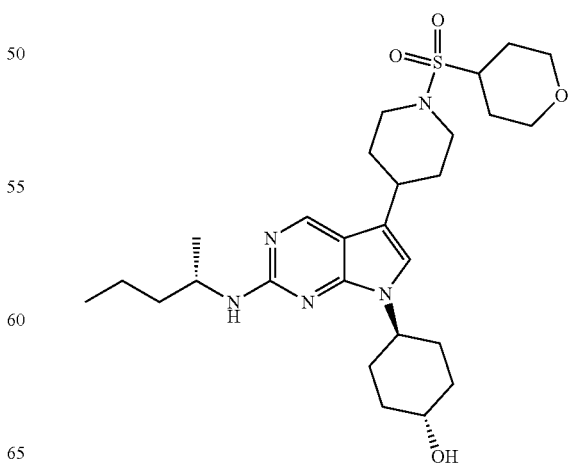

A white solid (43 mg, 78% yield). ¹H NMR (400 MHz, CD₃OD) δ 8.57 (s, 1H), 7.30 (s, 1H), 4.53-4.43 (m, 1H), 4.20-4.00 (m, 3H), 3.93-3.86 (m, 2H), 3.71-3.61 (m, 1H), 3.47-3.34 (m, 3H), 3.14-3.05 (m, 2H), 2.98-2.88 (m, 1H), 2.15-1.90 (m, 10H), 1.85-1.40 (m, 10H), 1.30 (d, J=6.6 Hz, 3H), 0.98 (t, J=7.2 Hz, 3H). MS m/z 534.31 [M+H]⁺.

c. (1S,4R)-4-(2-(((S)-pentan-2-yl)amino)-5-(1-(piperidin-4-ylsulfonyl)piperidin-4-yl)-7H-pyrrolo[2,3-d]pyrimidin-7-yl)cyclohexan-1-ol (3)

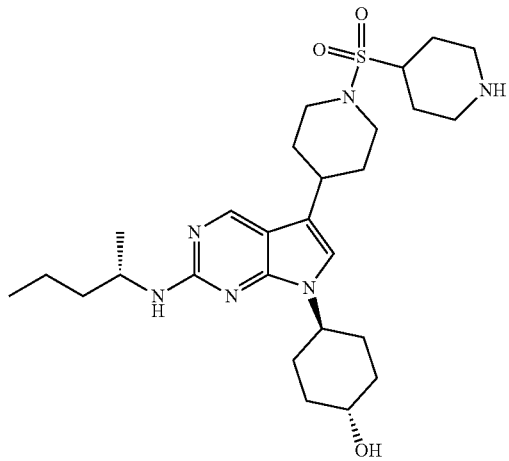 [SMILES: CCC[C@H](C)Nc1ncc2c(C3CCN(S(=O)(=O)C4CCNCC4)CC3)cn([C@H]3CC[C@H](O)CC3)c2n1]

¹H NMR (400 MHz, CD₃OD) δ 8.60 (s, 1H), 7.33 (s, 1H), 4.55-4.43 (m, 1H), 4.20-4.08 (m, 1H), 3.94-3.86 (m, 2H), 3.71-3.61 (m, 1H), 3.55-3.45 (m, 3H), 3.20-3.05 (m, 4H), 3.00-2.87 (m, 1H), 2.35-2.27 (m, 2H), 2.15-1.92 (m, 10H), 1.80-1.40 (m, 8H), 1.30 (d, J=6.6 Hz, 3H), 0.98 (t, J=7.2 Hz, 3H). MS m/z 533.33 [M+H]⁺.

d. (1S,4R)-4-(5-((2-methoxyethyl)sulfonyl)piperidin-4-yl)-2-(((S)-pentan-2-yl)amino)-7H-pyrrolo[2,3-d]pyrimidin-7-yl)cyclohexan-1-ol (4)

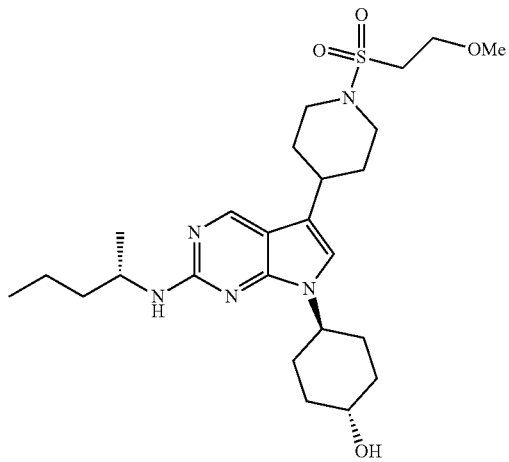 [SMILES: CCC[C@H](C)Nc1ncc2c(C3CCN(S(=O)(=O)CCOC)CC3)cn([C@H]3CC[C@H](O)CC3)c2n1]

¹H NMR (400 MHz, CD₃OD) δ 8.59 (s, 1H), 7.31 (s, 1H), 4.53-4.43 (m, 1H), 4.20-4.13 (m, 1H), 3.85-3.78 (m, 2H), 3.77-3.55 (m, 5H), 3.37 (s, 3H), 3.05-2.85 (m, 3H), 2.15-1.92 (m, 8H), 1.80-1.40 (m, 8H), 1.30 (d, J=6.6 Hz, 3H), 0.98 (t, J=7.2 Hz, 3H). MS mz 508.30 [M+H]⁺.

e. (1S,4R)-4-(5-(1-(methylsulphonyl)piperidin-4-yl)-2-(((S)-pentan-2-yl)amino)-7H-pyrrolo[2,3-d]pyrimidin-7-yl)cyclohexan-1-ol (5)

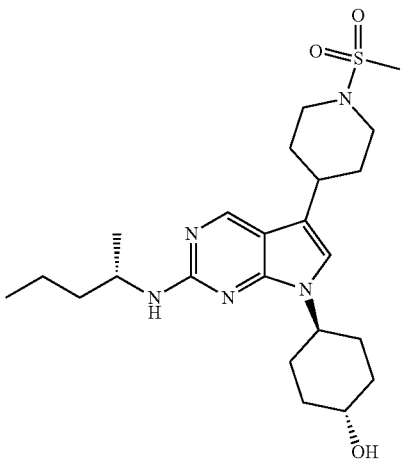 [SMILES: CCC[C@H](C)Nc1ncc2c(C3CCN(S(C)(=O)=O)CC3)cn([C@H]3CC[C@H](O)CC3)c2n1]

¹H NMR (400 MHz, CD₃OD) δ 8.58 (s, 1H), 7.33 (s, 1H), 4.54-4.42 (m, 1H), 4.20-4.10 (m, 1H), 3.87-3.80 (m, 2H), 3.75-3.55 (m, 2H), 2.94-2.84 (m, 5H), 2.15-1.93 (m, 8H), 1.85-1.40 (m, 8H), 1.30 (d, J=6.6 Hz, 3H), 0.98 (t, J=7.2 Hz, 3H). MS m/z 464.27 [M+H]⁺.

c. General Procedure B

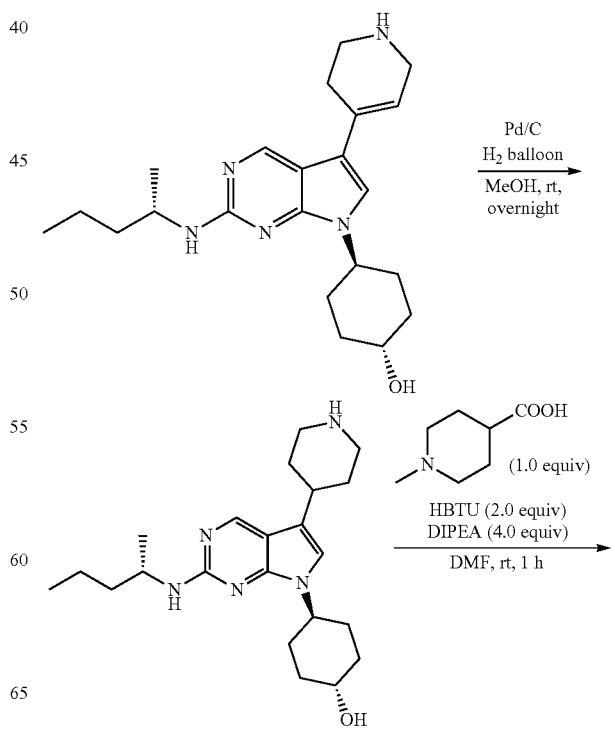

-continued

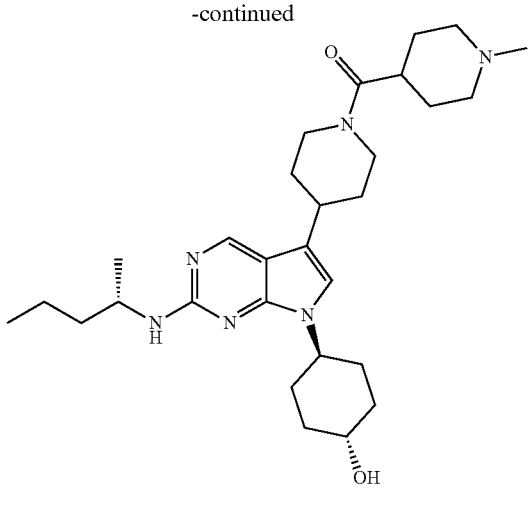

(i) General Hydrogenation Procedure

A suspension of alkene (383 mg, 1.0 mmol) and palladium on carbon (10% Pd basis, 50 mg) in MeOH was stirred under hydrogen balloon at room temperature overnight. The resulting mixture was filtered through a pad of Celite and the solvent was removed under the reduced pressure to provide the crude (1S,4r)-4-(2-(((S)-pentan-2-yl)amino)-5-(piperidin-4-yl)-7H-pyrrolo[2,3-d]pyrimidin-7-yl)cyclohexan-1-ol, which was used in the next step without further purification.

(ii) General Coupling Procedure

A solution of crude amine (30 mg, 0.0656 mmol, 1.0 equiv), 1-methylpiperidine-4-carboxylic acid (12 mg, 0.0656 mmol, 1.0 equiv), HBTU (50 mg, 0.13 mmol, 2.0 equiv) and N,N-diisopropylethylamine (0.1 mL) in DMF (0.50 mL) was stirred at room temperature for 1 h. Upon evaporation of solvent, the residue was purified by HPLC to afford the desired product.

a. (4-(7-((1R,4S)-4-hydroxycyclohexyl)-2-(((S)-pentan-2-yl)amino)-7H-pyrrolo[2,3-d]pyrimidin-5-yl)piperidin-1-yl)(piperidin-4-yl)methanone (8)

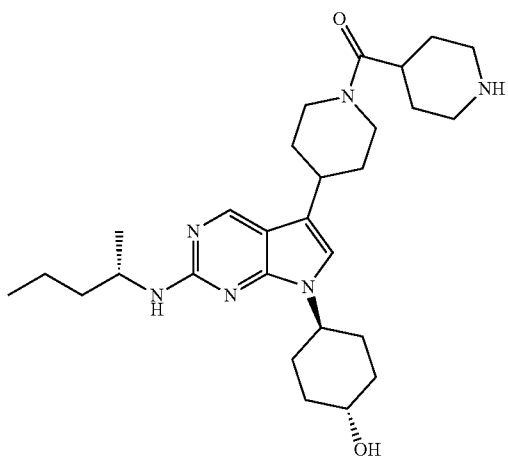 [SMILES: CCC[C@H](C)Nc1ncc2c(C3CCN(C(=O)C4CCNCC4)CC3)cn([C@H]3CC[C@H](O)CC3)c2n1]

$^1$H NMR (400 MHz, CD$_3$OD) δ 8.62 (s, 1H), 7.30 (s, 1H), 4.68-4.60 (m, 1H), 4.53-4.43 (m, 1H), 4.23-4.13 (m, 2H), 3.75-3.60 (m, 2H), 3.50-3.40 (m, 2H), 3.20-3.00 (m, 4H), 2.85-2.75 (m, 1H), 2.15-1.85 (m, 12H), 1.70-1.40 (m, 8H), 1.30 (d, J=6.6 Hz, 3H), 0.98 (t, J=7.2 Hz, 3H). MS m/z 497.36 [M+H]$^+$.

b. 1-(4-(7-((1R,4S)-4-hydroxycyclohexyl)-2-(((S)-pentan-2-yl)amino)-7H-pyrrolo[2,3-d]pyrimidin-5-yl)piperidin-1-yl)-3-methoxypropan-1-one (9)

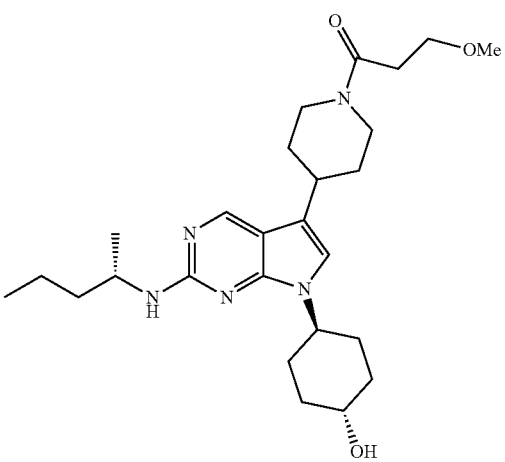 [SMILES: CCC[C@H](C)Nc1ncc2c(C3CCN(C(=O)CCOC)CC3)cn([C@H]3CC[C@H](O)CC3)c2n1]

$^1$H NMR (400 MHz CD$_3$OD) δ 8.59 (s, 1H), 7.30 (s, 1H), 4.70-4.62 (m, 1H), 4.53-4.43 (m, 1H), 4.20-4.07 (m, 2H), 3.75-3.55 (m, 3H), 3.34 (s, 3H), 3.29-3.19 (m, 1H), 3.07-2.97 (m, 1H), 2.82-2.62 (m, 3H), 2.15-1.92 (m, 8H), 1.73-1.40 (m, 8H), 1.30 (d, J=6.6 Hz, 3H), 0.98 (t, J=7.2 Hz, 3H). MS m/472.33 [M+H]$^+$.

c. (4-(7-((1R,4S)-4-hydroxycyclohexyl)-2-(((S)-pentan-2-yl)amino)-7H-pyrrolo[2,3-d]pyrimidin-5-yl)piperidin-1-yl)(tetrahydro-2H-pyran-4-yl)methanone (10)

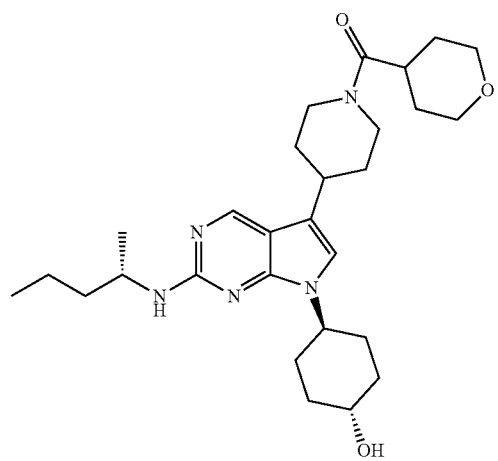 [SMILES: CCC[C@H](C)Nc1ncc2c(C3CCN(C(=O)C4CCOCC4)CC3)cn([C@H]3CC[C@H](O)CC3)c2n1]

$^1$H NMR (400 MHz, CD$_3$OD) δ 8.58 (s, 1H), 7.30 (s, 1H), 4.70-4.62 (m, 1H), 4.53-4.43 (m, 1H), 4.25-4.10 (m, 2H), 3.99-3.93 (m, 2H), 3.71-3.61 (m, 1H), 3.55-3.47 (m, 2H), 3.28-3.22 (m, 1H), 3.10-2.94 (m, 2H), 2.81-2.71 (m, 1H), 2.15-1.92 (m, 8H), 1.85-1.40 (m, 12H), 1.30 (d, J=6.6 Hz, 3H), 0.98 (t, J=7.2 Hz, 3H). MS m/z 498.34 [M+H]⁺.

d. (4-(7-((1R,4S)-4-hydroxycyclohexyl)-2-(((S)-pentan-2-yl)amino)-7H-pyrrolo[2,3-d]pyrimidin-5-yl)piperidin-1-yl)(1-methylpiperidin-4-yl)methanone (11)

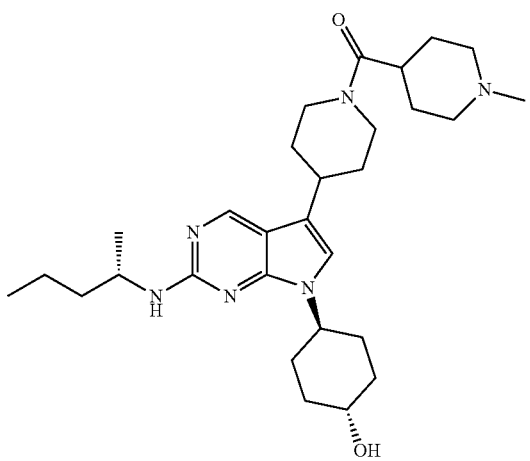 [SMILES: CCC[C@H](C)Nc1ncc2c(C3CCN(C(=O)C4CCN(C)CC4)CC3)cn([C@H]3CC[C@H](O)CC3)c2n1]

A white solid (30 mg, 90% yield). ¹H NMR (400 MHz, CD₃OD) δ 8.62 (s, 1H), 7.30 (s, 1H), 4.70-4.60 (m, 1H), 4.53-4.43 (m, 1H), 4.25-4.10 (m, 2H), 3.75-3.64 (m, 2H), 3.60-3.53 (m, 2H), 3.45-3.35 (m, 1H), 3.15-3.02 (m, 3H), 2.88 (s, 3H), 2.85-2.75 (m, 1H), 2.15-1.90 (m, 12H), 1.73-1.40 (m, 8H), 1.30 (d, J=6.6 Hz, 3H), 0.98 (t, J=7.2 Hz, 3H). MS m/z 511.38 [M+H]⁺.

e. (1R,4R)-4-(5-((1R,3S,5S)-8-azabicyclo[3.2.1]octan-3-yl)-2-(butylamino)-7H-pyrrolo[2,3-d]pyrimidin-7-yl)cyclohexan-1-ol (12)

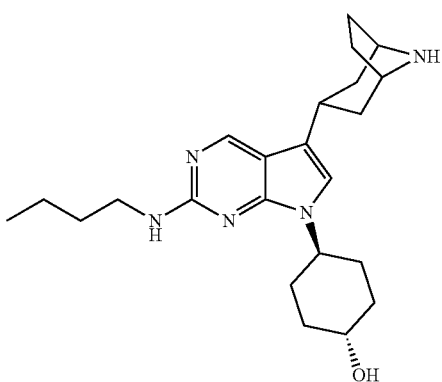 [SMILES: CCCCNc1ncc2c(C3CC4CCC(C3)N4)cn([C@H]3CC[C@H](O)CC3)c2n1]

¹H NMR (400 MHz, CD₃OD) δ 8.55 (d, J=6.7 Hz, 1H), 7.61-7.55 (m, 1H), 4.59-4.41 (m, 2H), 4.11-4.00 (m, 2H), 3.72-3.62 (m, 1H), 3.54-3.45 (m, 2H), 3.44-3.34 (m, 1H), 2.55-2.44 (m, 1H), 2.40-2.34 (m, 1H), 2.34-2.28 (m, 1H), 2.15-2.06 (m, 2H), 2.05-1.93 (m, 4H), 1.92-1.82 (m, 2H), 1.72-1.62 (m, 2H), 1.58-1.35 (m, 4H), 1.27 (s, 1H), 0.99 (t, J=7.4 Hz, 3H); MS m/z 398.20 [M+H]⁺.

f. Azetidin-3-yl(4-(7-((1R,4S)-4-hydroxycyclohexyl)-2-(((S)-pentan-2-yl)amino)-7H-pyrrolo[2,3-d]pyrimidin-5-yl)piperidin-1-yl)methanone (13)

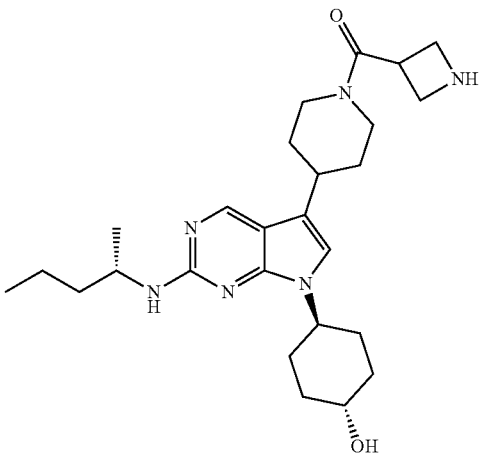 [SMILES: CCC[C@H](C)Nc1ncc2c(C3CCN(C(=O)C4CNC4)CC3)cn([C@H]3CC[C@H](O)CC3)c2n1]

¹H NMR (400 MHz. CD₃OD) δ 8.62 (s, 1H), 7.29 (s, 1H), 4.67-4.58 (m, 1H), 4.53-4.43 (m, 1H), 4.40-4.23 (m, 4H), 4.20-4.05 (m, 2H), 3.76-3.64 (m, 2H), 3.28-3.20 (m, 1H), 3.09-2.98 (m, 1H), 2.92-2.81 (m, 1H), 2.15-1.90 (m, 8H), 1.75-1.40 (m, 8H), 1.30 (d, J=6.6 Hz, 3H), 0.98 (t, J=7.3 Hz, 3H); MS m/z 470.33 [M+H]⁺.

g. (4-(7-((1R,4S)-4-hydroxycyclohexyl)-2-(((S)-pentan-2-yl)amino)-7H-pyrrolo[2,3-d]pyrimidin-5-yl)piperidin-1-yl)(1-methylazetidin-3-yl)methanone (14)

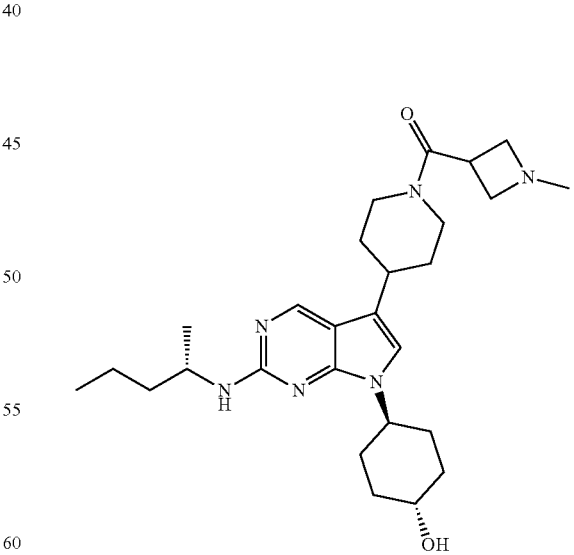

¹H NMR (400 MHz, CD₃OD) δ 8.63 (s, 1H), 7.30 (s, 1H), 4.70-4.41 (m, 4H), 4.26-4.01 (m, 4H), 3.78-3.63 (m, 2H), 3.30-3.20 (m, 1H), 3.10-3.00 (m, 1H), 2.97-2.82 (m, 4H), 2.15-1.92 (m, 8H), 1.72-1.39 (m, 8H), 1.30 (d, J=6.6 Hz, 3H), 0.98 (t, J=7.3 Hz, 3H); MS m/z 484.34 [M+H]⁺.

h. 7-((1R,4S)-4-hydroxycyclohexyl)-2-(((S)-pentan-2-yl)amino)-5-(1-prolylpiperidin-4-yl)-7H-pyrrolo[2,3-d]pyrimidine (15)

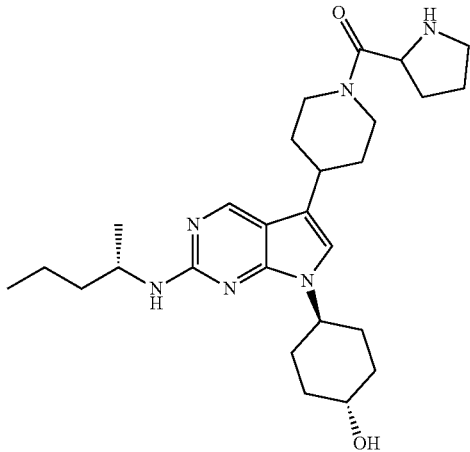 [SMILES: CCC[C@H](C)Nc1ncc2c(C3CCN(C(=O)C4CCCN4)CC3)cn([C@H]3CC[C@H](O)CC3)c2n1]

$^1$H NMR (400 MHz, CD$_3$OD) δ 8.65 (s, 1H), 7.32 (s, 1H), 4.80-4.57 (m, 2H), 4.53-4.43 (m, 1H), 4.20-4.10 (m, 1H), 4.03-3.93 (m, 1H), 3.75-3.65 (m, 2H), 3.50-3.40 (m, 1H), 3.40-3.30 (m, 1H), 3.15-3.05 (m, 1H), 2.97-2.87 (m, 1H), 2.60-2.47 (m, 1H), 2.20-1.90 (m, 12H), 1.70-1.40 (m, 8H), 1.30 (d, J=6.6 Hz, 3H), 0.98 (t, J=7.3 Hz, 3H); MS m/z 483.34 [M+H]$^+$.

i. 7-((1R,4S)-4-hydroxycyclohexyl)-5-(1-(methylpropyl)piperidin-4-yl)-2-(((S)-pentan-2-yl)amino)-7H-pyrrolo[2,3-d]pyrimidine (16)

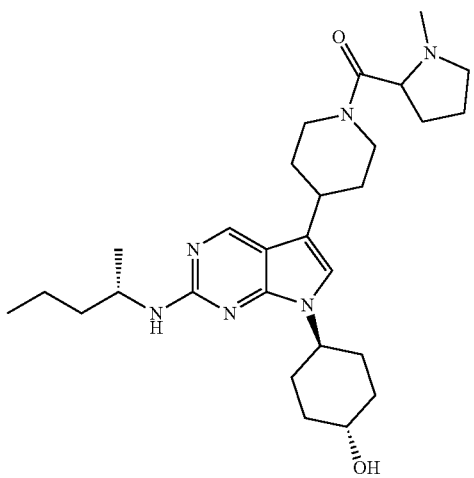 [SMILES: CCC[C@H](C)Nc1ncc2c(C3CCN(C(=O)C4CCCN4C)CC3)cn([C@H]3CC[C@H](O)CC3)c2n1]

$^1$H NMR (400 MHz. CD$_3$OD) δ 8.64 (s, 1H), 7.32 (s, 1H), 4.70-4.45 (m, 3H), 4.20-4.10 (m, 1H), 3.95-3.85 (m, 1H), 3.77-3.67 (m, 2H), 3.30-3.17 (m, 1H), 3.15-3.04 (m, 1H), 3.00-2.87 (m, 4H), 2.75-2.60 (m, 1H), 2.30-1.90 (m, 12H), 1.70-1.40 (m, 8H), 1.30 (d, J=6.6 Hz, 3H), 0.98 (t J=7.3 Hz, 3H); MS m/z 497.36 [M+H]$^+$.

j. (4-(7-((1R,4S)-4-hydroxycyclohexyl)-2-(((S)-pentan-2-yl)amino)-7H-pyrrolo[2,3-d]pyrimidin-5-yl)piperidin-1-yl)(pyrrolidin-3-yl)methanone (17)

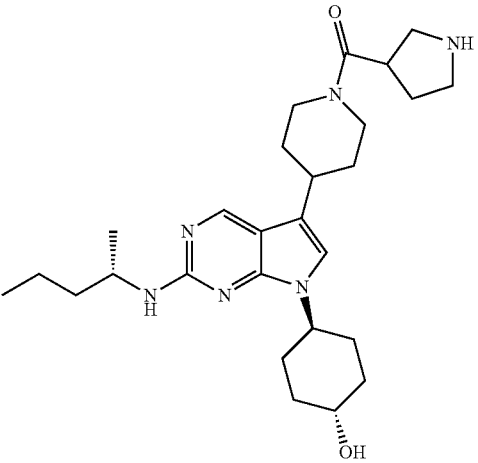 [SMILES: CCC[C@H](C)Nc1ncc2c(C3CCN(C(=O)C4CCNC4)CC3)cn([C@H]3CC[C@H](O)CC3)c2n1]

$^1$H NMR (400 MHz, CD$_3$OD) δ 8.62 (s, 1H), 7.30 (s, 1H), 4.68-4.60 (m, 1H), 4.54-4.43 (m, 1H), 4.20-4.10 (m, 2H), 3.77-3.67 (m, 4H), 3.40-3.30 (m, 3H), 3.15-3.00 (m, 1H), 2.98-2.78 (m, 1H), 2.45-2.35 (m, 1H), 2.20-1.90 (m, 9H), 1.75-1.40 (m, 8H), 1.30 (d, J=6.6 Hz, 3H), 0.98 (t, J=7.3 Hz, 3H); MS m/z 483.34 [M+H]$^+$.

k. (4-(7-((1R,4S)-4-hydroxycyclohexyl)-2-(((S)-pentan-2-yl)amino)-7H-pyrrolo[2,3-d]pyrimidin-5-yl)piperidin-1-yl)(1-methylpyrrolidin-3-yl)methanone (18)

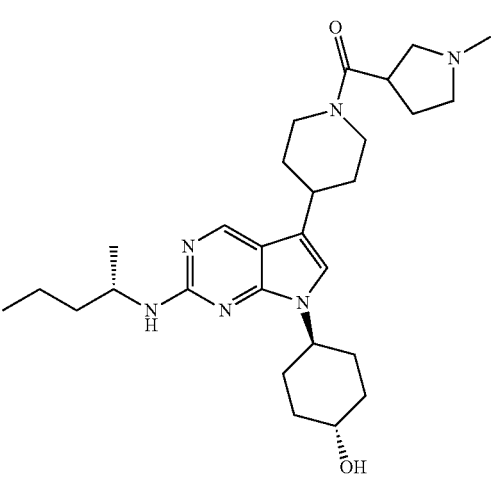 [SMILES: CCC[C@H](C)Nc1ncc2c(C3CCN(C(=O)C4CCN(C)C4)CC3)cn([C@H]3CC[C@H](O)CC3)c2n1]

$^1$H NMR (400 MHz, CD$_3$OD) δ 8.64 (s, 1H), 7.31 (s, 1H), 4.68-4.59 (m, 1H), 4.53-4.43 (m, 1H), 4.25-4.05 (m, 2H), 4.03-3.65 (m, 5H), 3.25-2.95 (m, 6H), 2.90-2.77 (m, 1H), 2.70-2.37 (m, 1H), 2.30-1.90 (m, 9H), 1.75-1.40 (m, 8H), 1.30 (d, J=6.6 Hz, 3H), 0.98 (t, J=7.3 Hz, 3H); MS m/z 497.36 [M+H]$^+$.

l. (4-(7-((1R,4S)-4-hydroxycyclohexyl)-2-(((S)-pentan-2-yl)amino)-7H-pyrrolo[2,3-d]pyrimidin-5-yl)piperidin-1-yl)((S)-piperidin-2-yl)methanone (19)

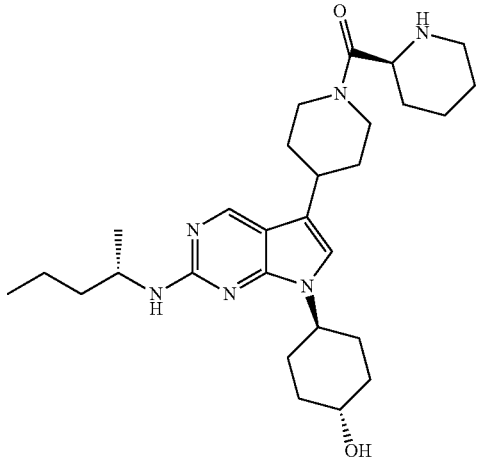 [SMILES: CCC[C@H](C)Nc1ncc2c(C3CCN(C(=O)[C@@H]4CCCCN4)CC3)cn([C@H]3CC[C@H](O)CC3)c2n1]

¹H NMR (400 MHz, CD₃OD) δ 8.64 (s, 1H), 7.31 (s, 1H), 4.65-4.30 (m, 3H), 4.20-4.10 (m, 1H), 4.00-3.93 (m, 1H), 3.75-3.65 (m, 2H), 3.45-3.35 (m, 1H), 3.15-3.05 (m, 2H), 2.95-2.80 (m, 1H), 2.20-1.85 (m, 11H), 1.80-1.40 (m, 11H), 1.30 (d, J=6.6 Hz, 3H), 0.98 (t, J=7.3 Hz, 3H); MS m/z 497.36 [M+H]⁺.

m. (4-(7-((1R,4S)-4-hydroxycyclohexyl)-2-(((S)-pentan-2-yl)amino)-7H-pyrrolo[2,3-d]pyrimidin-5-yl)piperidin-1-yl)((R)-piperidin-2-yl)methanone (20)

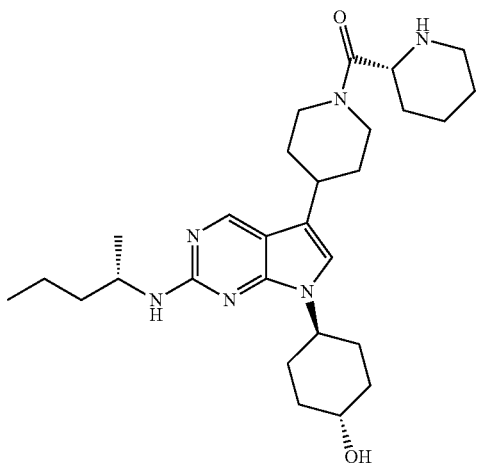 [SMILES: CCC[C@H](C)Nc1ncc2c(C3CCN(C(=O)[C@H]4CCCCN4)CC3)cn([C@H]3CC[C@H](O)CC3)c2n1]

¹H NMR (400 MHz, CD₃OD) δ 8.64 (s, 1H), 7.31 (s, 1H), 4.65-4.30 (m, 3H), 4.20-4.10 (m, 1H), 4.00-3.93 (m, 1H), 3.75-3.65 (m, 2H), 3.45-3.35 (m, 1H), 3.15-3.05 (m, 2H), 2.95-2.80 (m, 1H), 2.20-1.85 (m, 11H), 1.80-1.40 (m, 11H), 1.30 (d, J=6.6 Hz, 3H), 0.98 (t, J=7.3 Hz, 3H); MS m/z 497.36 [M+H]⁺.

n. (4-(7-((1R,4S)-4-hydroxycyclohexyl)-2-(((S)-pentan-2-yl)amino)-7H-pyrrolo[2,3-d]pyrimidin-5-yl)piperidin-1-yl)(1-methylpiperidin-2-yl)methanone (21)

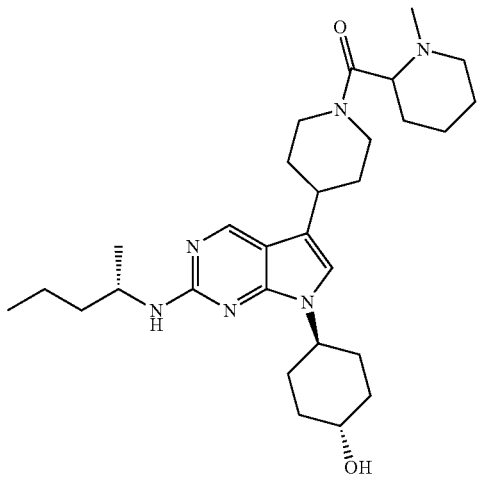 [SMILES: CCC[C@H](C)Nc1ncc2c(C3CCN(C(=O)C4CCCCN4C)CC3)cn([C@H]3CC[C@H](O)CC3)c2n1]

¹H NMR (400 MHz, CD₃OD) δ 8.62 (s, 1H), 7.32 (s, 1H), 4.70-4.63 (m, 1H), 4.55-4.40 (m, 2H), 4.20-4.10 (m, 1H), 4.07-3.95 (m, 1H), 3.75-3.65 (m, 2H), 3.55-3.45 (m, 1H), 3.20-3.05 (m, 2H), 2.97-2.79 (m, 4H), 2.70-1.90 (m, 11H), 1.85-1.40 (m, 11H), 1.30 (d, J=6.6 Hz, 3H), 0.98 (t, J=7.3 Hz, 3H); MS m/z 511.38 [M+H]⁺.

o. (4-(7-((1R,4S)-4-hydroxycyclohexyl)-2-(((S)-pentan-2-yl)amino)-7H-pyrrolo[2,3-d]pyrimidin-5-yl)piperidin-1-yl)((S)-1-methylpiperidin-2-yl)methanone (22)

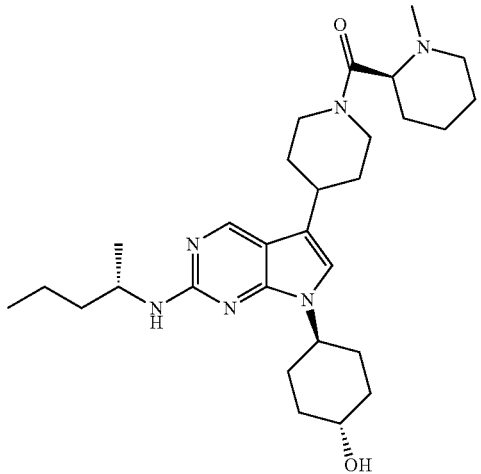 [SMILES: CCC[C@H](C)Nc1ncc2c(C3CCN(C(=O)[C@@H]4CCCCN4C)CC3)cn([C@H]3CC[C@H](O)CC3)c2n1]

¹H NMR (400 MHz, CD₃OD) δ 8.62 (s, 1H), 7.32 (s, 1H), 4.70-4.63 (m, 1H), 4.55-4.40 (m, 2H), 4.20-4.10 (m, 1H), 4.07-3.95 (m, 1H), 3.75-3.65 (m, 2H), 3.55-3.45 (m, 1H), 3.20-3.05 (m, 2H), 2.97-2.79 (m, 4H), 2.70-1.90 (m, 11H), 1.85-1.40 (m, 11H), 1.30 (d, J=6.6 Hz, 3H), 0.98 (t, J=7.3 Hz, 3H); MS m/z 511.38 [M+H]⁺.

p. (4-(7-((1R,4S)-4-hydroxycyclohexyl)-2-(((S)-pentan-2-yl)amino)-7H-pyrrolo[2,3-d]pyrimidin-5-yl)piperidin-1-yl)((R)-piperidin-3-yl)methanone (23)

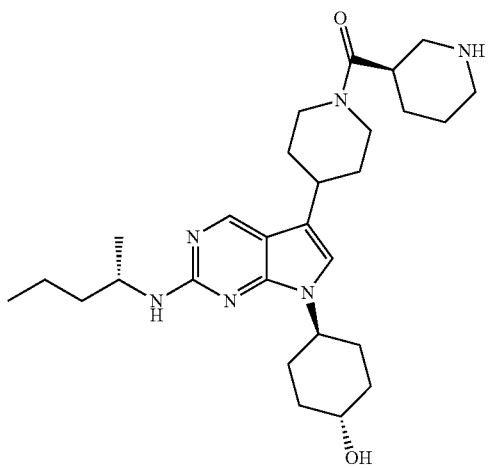 [SMILES: CCC[C@H](C)Nc1ncc2c(C3CCN(C(=O)[C@@H]4CCCNC4)CC3)cn([C@H]3CC[C@H](O)CC3)c2n1]

$^1$H NMR (400 MHz, CD$_3$OD) δ 8.63 (s, 1H), 7.31 (s, 1H), 4.70-4.62 (m, 1H), 4.54-4.42 (m, 1H), 4.20-4.00 (m, 2H), 3.75-3.65 (m, 2H), 3.30-3.10 (m, 4H), 3.10-3.00 (m, 2H), 2.90-2.75 (m, 1H), 2.20-1.40 (m, 20H), 1.30 (d, J=6.6 Hz, 3H), 0.98 (t, J=7.3 Hz, 3H); MS m/z 497.36 [M+H]$^+$.

q. (4-(7-((1R,4S)-4-hydroxycyclohexyl)-2-(((S)-pentan-2-yl)amino)-7H-pyrrolo[2,3-d]pyrimidin-5-yl)piperidin-1-yl)((S)-piperidin-3-yl)methanone (24)

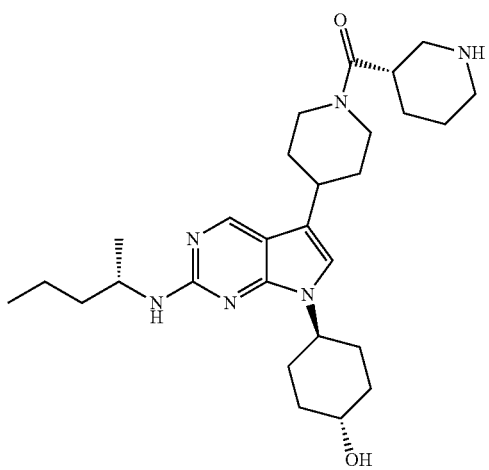 [SMILES: CCC[C@H](C)Nc1ncc2c(C3CCN(C(=O)[C@H]4CCCNC4)CC3)cn([C@H]3CC[C@H](O)CC3)c2n1]

$^1$H NMR (400 MHz, CD$_3$OD) δ 8.63 (s, 1H), 7.31 (s, 1H), 4.70-4.62 (m, 1H), 4.54-4.42 (m, 1H), 4.20-4.00 (m, 2H), 3.75-3.65 (m, 2H), 3.30-3.10 (m, 4H), 3.10-3.00 (m, 2H), 2.90-2.75 (m, 1H), 2.20-1.40 (m, 20H), 1.30 (d, J=6.6 Hz, 3H), 0.98 (t, J=7.3 Hz, 3H); MS m/z 497.36 [M+H]$^+$.

r. (4-(7-((1R,4S)-4-hydroxycyclohexyl)-2-(((S)-pentan-2-yl)amino)-7H-pyrrolo[2,3-d]pyrimidin-5-yl)piperidin-1-yl)(1-methylpiperidin-3-yl)methanone (25)

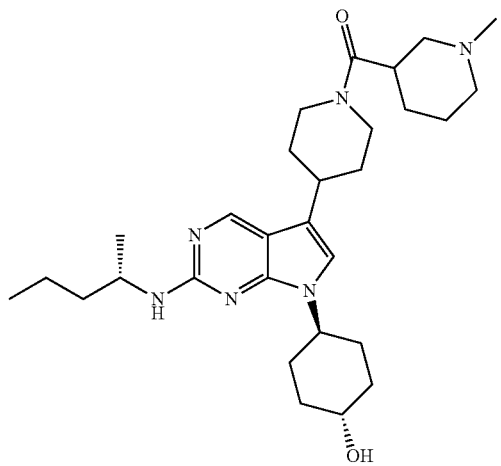 [SMILES: CCC[C@H](C)Nc1ncc2c(C3CCN(C(=O)C4CCCN(C)C4)CC3)cn([C@H]3CC[C@H](O)CC3)c2n1]

$^1$H NMR (400 MHz, CD$_3$OD) δ 8.63 (s, 1H), 7.31 (s, 1H), 4.75-4.40 (m, 2H), 4.20-3.95 (m, 2H), 3.75-3.65 (m, 2H), 3.55-3.45 (m, 2H), 3.45-3.25 (m, 1H), 3.20-2.75 (m, 7H), 2.20-1.40 (m, 20H), 1.30 (d, J=6.6 Hz, 3H), 0.98 (t, J=7.3 Hz, 3H); MS m/z 511.38 [M+H]$^+$.

s. (4-(7-((1R,4S)-4-hydroxycyclohexyl)-2-(((S)-pentan-2-yl)amino)-7H-pyrrolo[2,3-d]pyrimidin-5-yl)piperidin-1-yl)((S)-1-methylpiperidin-3-yl)methanone (26)

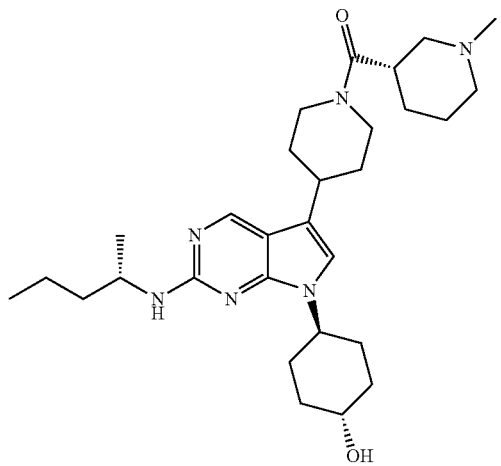 [SMILES: CCC[C@H](C)Nc1ncc2c(C3CCN(C(=O)[C@H]4CCCN(C)C4)CC3)cn([C@H]3CC[C@H](O)CC3)c2n1]

$^1$H NMR (400 MHz, CD$_3$OD) δ 8.63 (s, 1H), 7.31 (s, 1H), 4.75-4.40 (m, 2H), 4.20-3.95 (m, 2H), 3.75-3.65 (m, 2H), 3.55-3.45 (m, 2H), 3.45-3.25 (m, 1H), 3.20-2.75 (m, 7H), 2.20-1.40 (m, 20H), 1.30 (d, J=6.6 Hz, 3H), 0.98 (t, J=7.3 Hz, 3H). MS m/z 511.38 [M+H]$^+$.

t. (4-(7-((1R,4S)-4-hydroxycyclohexyl)-2-(((S)-pentan-2-yl)amino)-7H-pyrrolo[2,3-d]pyrimidin-5-yl)piperidin-1-yl)(pyridin-4-yl)methanone (27)

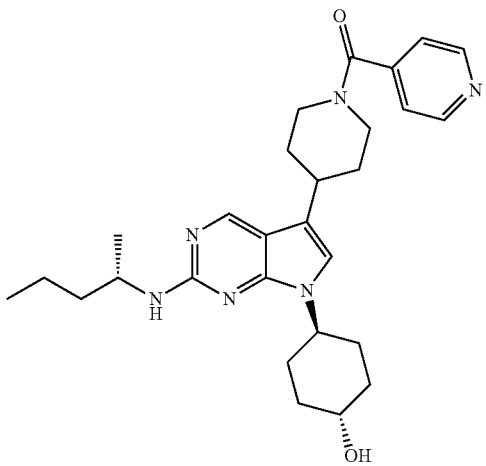 [SMILES: CCC[C@H](C)Nc1ncc2c(C3CCN(C(=O)c4ccncc4)CC3)cn([C@H]3CC[C@H](O)CC3)c2n1]

$^1$H NMR (400 MHz, CD$_3$OD) δ 8.97 (d, J=6.4 Hz, 2H), 8.66 (s, 1H), 8.13 (d, J=6.5 Hz, 2H), 7.34 (s, 1H), 4.80-4.73 (m, 1H), 4.55-4.43 (m, 1H), 4.25-4.10 (m, 1H), 3.75-3.65 (m, 2H), 3.43-3.30 (m, 1H), 3.20-3.03 (m, 2H), 2.20-1.92 (m, 8H), 1.85-1.40 (m, 8H), 1.30 (d, J=6.6 Hz, 3H), 0.98 (t, J=7.3 Hz, 3H); MS m/z 491.31 [M+H]$^+$.

u. (4-(7-((1R,4S)-4-hydroxycyclohexyl)-2-(((S)-pentan-2-yl)amino)-7H-pyrrolo[2,3-d]pyrimidin-5-yl)piperidin-1-yl)(pyridin-3-yl)methanone (28)

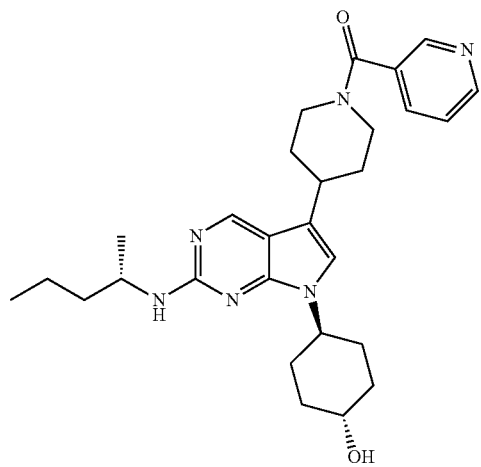 [SMILES: CCC[C@H](C)Nc1ncc2c(C3CCN(C(=O)c4cccnc4)CC3)cn([C@H]3CC[C@H](O)CC3)c2n1]

$^1$H NMR (400 MHz, CD$_3$OD) δ 9.03 (s, 1H), 8.93 (s, 1H), 8.77-8.63 (m, 2H), 8.17-8.09 (m, 1H), 7.33 (s, 1H), 4.80-4.70 (m, 1H), 4.55-4.43 (m, 1H), 4.22-4.10 (m, 1H), 3.75-3.65 (m, 2H), 3.50-3.35 (m, 1H), 3.20-3.04 (m, 2H), 2.20-1.92 (m, 8H), 1.85-1.40 (m, 8H), 1.30 (d, J=6.6 Hz, 3H), 0.98 (t, J=7.3 Hz, 3H); MS m/z 491.31 [M+H]$^+$.

v. (4-(7-((1R,4S)-4-hydroxycyclohexyl)-2-(((S)-pentan-2-yl)amino)-7H-pyrrolo[2,3-d]pyrimidin-5-yl)piperidin-1-yl)(pyridin-2-yl)methanone (29)

$^1$H NMR (400 MHz, CD$_3$OD) δ 8.80 (s, 1H), 8.67 (s, 1H), 8.42-8.35 (m, 1H), 8.05-7.85 (m, 2H), 7.34 (s, 1H), 4.80-4.70 (m, 1H), 4.55-4.43 (m, 1H), 4.20-4.10 (m, 1H), 3.80-3.65 (m, 2H), 3.50-3.35 (m, 1H), 3.20-3.04 (m, 2H), 2.20-1.92 (m, 8H), 1.85-1.40 (m, 8H), 1.30 (d, J=6.6 Hz, 3H), 0.98 (1t, J=7.3 Hz, 3H); MS m/z 491.31 [M+H]$^+$.

w. (4-(7-((1R,4S)-4-hydroxycyclohexyl)-2-(((S)-pentan-2-yl)amino)-7H-pyrrolo[2,3-d]pyrimidin-5-yl)piperidin-1-yl)(phenyl)methanone (30)

$^1$H NMR (400 MHz, CD$_3$OD) δ 8.60 (s, 1H), 7.52-7.40 (m, 5H), 7.33 (s, 1H), 4.80-4.70 (m, 1H), 4.55-4.43 (m, 1H), 4.20-4.10 (m, 1H), 3.90-3.80 (m, 1H), 3.75-3.65 (m, 1H), 3.35-3.25 (m, 1H), 3.20-3.04 (m, 2H), 2.20-1.92 (m, 8H), 1.85-1.40 (m, 8H), 1.30 (d, J=6.6 Hz, 3H), 0.98 (t, J=7.3 Hz, 3H); MS m/z 490.32 [M+H]$^+$.

x. (4-(7-((1R,4S)-4-hydroxycyclohexyl)-2-(((S)-pentan-2-yl)amino)-7H-pyrrolo[2,3-d]pyrimidin-5-yl)piperidin-1-yl)(4-methoxyphenyl)methanone (31)

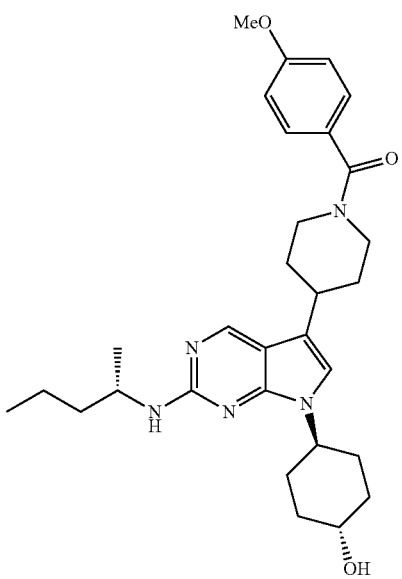 [SMILES: CCC[C@H](C)Nc1ncc2c(C3CCN(C(=O)c4ccc(OC)cc4)CC3)cn([C@H]3CC[C@H](O)CC3)c2n1]

$^1$H NMR (400 MHz, CD$_3$OD) δ 8.60 (s, 1H), 7.44-7.39 (m, 2H), 7.33 (s, 1H), 7.03-6.97 (m, 2H), 4.80-4.70 (m, 1H), 4.55-4.43 (m, 1H), 4.20-4.10 (m, 1H), 3.83 (s, 3H), 3.75-3.65 (m, 2H), 3.35-3.25 (m, 1H), 3.14-3.02 (m, 2H), 2.20-1.92 (m, 8H), 1.85-1.40 (m, 8H), 1.30 (d, J=6.6 Hz, 3H), 0.98 (t, J=7.3 Hz, 3H); MS m/z 520.33 [M+H]$^+$.

y. (4-(7-((1R,4S)-4-hydroxycyclohexyl)-2-(((S)-pentan-2-yl)amino)-7H-pyrrolo[2,3-d]pyrimidin-5-yl)piperidin-1-yl)(3-methoxyphenyl)methanone (32)

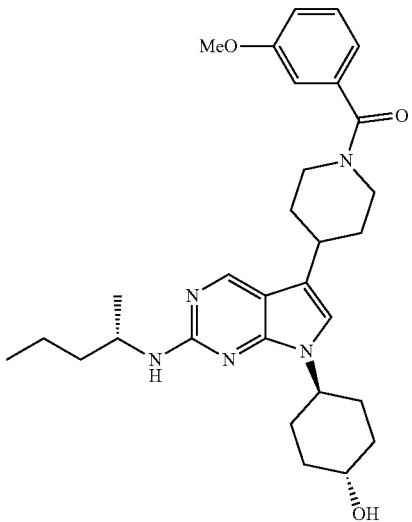 [SMILES: CCC[C@H](C)Nc1ncc2c(C3CCN(C(=O)c4cccc(OC)c4)CC3)cn([C@H]3CC[C@H](O)CC3)c2n1]

$^1$H NMR (400 MHz, CD$_3$OD) δ 8.60 (s, 1H), 7.44-7.39 (m, 2H), 7.07-6.95 (m, 3H), 4.80-4.70 (m, 1H), 4.55-4.43 (m, 1H), 4.20-4.10 (m, 1H), 3.82 (s, 3H), 3.75-3.65 (m, 2H), 3.35-3.25 (m, 1H), 3.15-2.95 (m, 2H), 2.20-1.92 (m, 8H), 1.85-1.40 (m, 8H), 1.30 (d, J=6.6 Hz, 3H), 0.98 (t, J=7.3 Hz, 3H); MS m/z 520.33 [M+H]$^+$.

z. (4-(7-((1R,4S)-4-hydroxycyclohexyl)-2-(((S)-pentan-2-yl)amino)-7H-pyrrolo[2,3-d]pyrimidin-5-yl)piperidin-1-yl)(2-methoxyphenyl)methanone (33)

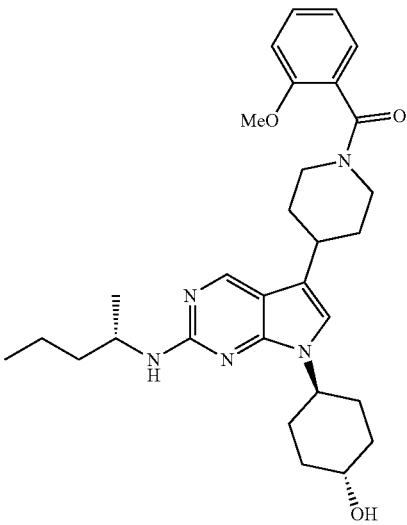 [SMILES: CCC[C@H](C)Nc1ncc2c(C3CCN(C(=O)c4ccccc4OC)CC3)cn([C@H]3CC[C@H](O)CC3)c2n1]

$^1$H NMR (400 MHz CD$_3$OD) δ 8.58 (s, 1H), 7.45-7.37 (m, 1H), 7.32 (s, 1H), 7.28-7.17 (m, 1H), 7.10-7.00 (m, 2H), 4.85-4.75 (m, 1H), 4.55-4.43 (m, 1H), 4.20-4.10 (m, 1H), 3.86 (s, 3H), 3.75-3.65 (m, 2H), 3.30-2.85 (m, 3H), 2.20-1.92 (m, 8H), 1.85-1.40 (m, 8H), 1.30 (d, J=6.6 Hz, 3H), 0.98 (t, J=7.3 Hz, 3H); MS m/z 520.33 [M+H]$^+$.

aa. (2,6-dimethylpyridin-4-yl)(4-(7-((1R,4S)-4-hydroxycyclohexyl)-2-(((S)-pentan-2-yl)amino)-7H-pyrrolo[2,3-d]pyrimidin-5-yl)piperidin-1-yl)methanone (34)

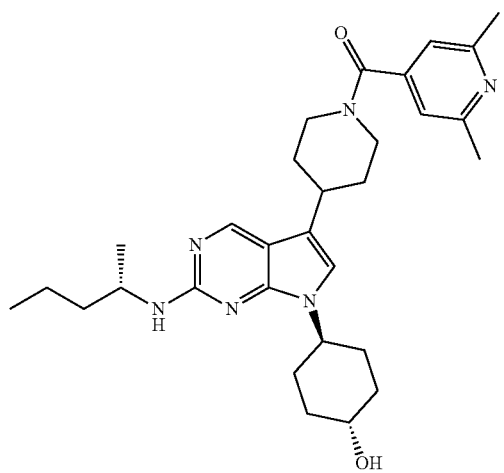 [SMILES: CCC[C@H](C)Nc1ncc2c(C3CCN(C(=O)c4cc(C)nc(C)c4)CC3)cn([C@H]3CC[C@H](O)CC3)c2n1]

$^1$H NMR (400 MHz, CD$_3$OD) δ 8.61 (s, 1H), 7.69 (s, 2H), 7.32 (s, 1H), 4.80-4.73 (m, 1H), 4.55-4.43 (m, 1H), 4.25-4.10 (m, 1H), 3.75-3.65 (m, 2H), 3.43-3.30 (m, 1H), 3.20-

3.03 (m, 2H), 2.75 (s, 6H), 2.20-1.92 (m, 8H), 1.85-1.40 (m, 8H), 1.30 (d, J=6.6 Hz, 3H), 0.98 (t, J=7.3 Hz, 3H); MS m/z 519.34 [M+H]⁺.

bb. (4-(7-((1R,4S)-4-hydroxycyclohexyl)-2-(((S)-pentan-2-yl)amino)-7H-pyrrolo[2,3-d]pyrimidin-5-yl)piperidin-1-yl)(2-methylpyridin-4-yl)methanone (35)

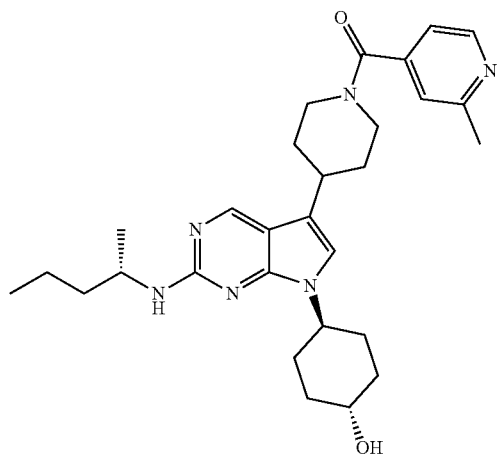 [SMILES: CCC[C@H](C)Nc1ncc2c(C3CCN(C(=O)c4ccnc(C)c4)CC3)cn([C@H]3CC[C@H](O)CC3)c2n1]

¹H NMR (400 MHz, CD₃OD) δ 8.74 (d, J=5.6 Hz, 1H), 8.63 (s, 1H), 7.90 (s, 1H), 7.83 (d, J=5.8 Hz, 1H), 7.32 (s, 1H), 4.80-4.73 (m, 1H), 4.55-4.43 (m, 1H), 4.25-4.10 (m, 1H), 3.75-3.65 (m, 2H), 3.43-3.30 (m, 1H), 3.20-3.03 (m, 2H), 2.79 (s, 3H), 2.20-1.92 (m, 8H), 1.85-1.40 (m, 8H), 1.30 (d, J=6.6 Hz, 3H), 0.98 (t, J=7.3 Hz, 3H); MS m/z 505.33 [M+H]⁺.

cc. (1-(2-fluoroethyl)piperidin-4-yl)(4-(7-((1R,4S)-4-hydroxycyclohexyl)-2-(((S)-pentan-2-yl)amino)-7H-pyrrolo[2,3-d]pyrimidin-5-yl)piperidin-1-yl)methanone (36)

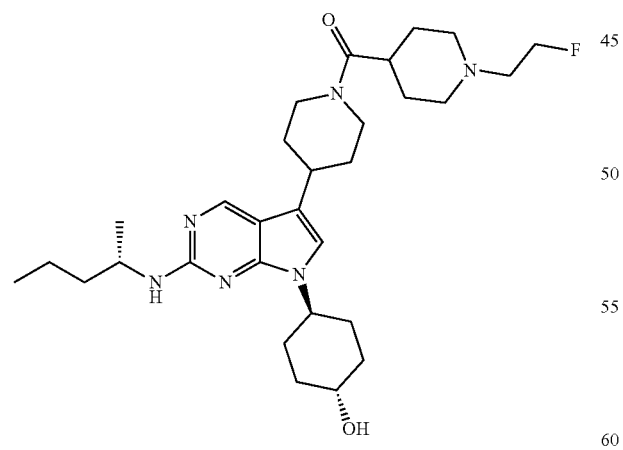

¹H NMR (400 MHz, CD₃OD) δ 8.60 (s, 1H), 7.29 (s, 1H), 4.93-4.75 (m, 2H), 4.68-4.60 (m, 1H), 4.53-4.43 (m, 1H), 4.23-4.13 (m, 1H), 3.74-3.46 (m, 6H), 3.20-3.00 (m, 4H), 2.85-2.75 (m, 1H), 2.15-1.85 (m, 12H), 1.70-1.40 (m, 8H), 1.30 (d, J=6.6 Hz, 3H), 0.98 (t, J=7.2 Hz, 3H). MS m/z 543.38 [M+H]⁺.

dd. (4-(2-(((S,2S)-2-ethylcyclopropyl)amino)-7-((1R,4S)-4-hydroxycyclohexyl)-7H-pyrrolo[2,3-d]pyrimidin-5-yl)piperidin-1-yl)(pyridin-4-yl)methanone (42)

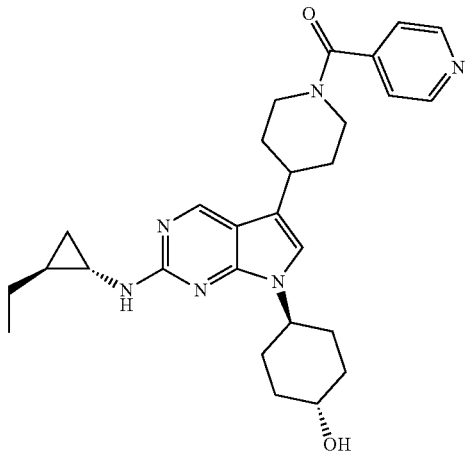 [SMILES: CC[C@H]1C[C@@H]1Nc1ncc2c(C3CCN(C(=O)c4ccncc4)CC3)cn([C@H]3CC[C@H](O)CC3)c2n1]

¹H NMR (400 MHz, CD₃OD) δ 8.88 (s, 2H), 8.64 (d, J=1.6 Hz, 1H), 7.91 (s, 2H), 7.34 (s, 1H), 4.74 (d, J=13.3 Hz, 1H), 4.55 (dt, J=11.4, 6.2 Hz, 1H), 3.66 (ddd, J=27.1, 15.4, 9.8 Hz, 2H), 3.35 (d, J=12.5 Hz, 1H), 3.08 (dt, J=23.6, 11.7 Hz, 2H), 2.50 (dd, J=6.6, 3.2 Hz, 1H), 2.21-1.85 (m, 8H), 1.75 (dt, J=23.3, 10.0 Hz, 2H), 1.54-1.31 (m, 4H), 1.10 (t, J=7.4 Hz, 3H), 1.01 (dd, J=11.7, 6.6 Hz, 1H), 0.85-0.77 (m, 1H), 0.73 (dd, J=12.4, 6.1 Hz, 1H). MS m/Z 489.30 [M+H]⁺.

ee. (4-(2-(((1R,2R)-2-ethylcyclopropyl)amino)-7-((1R,4R)-4-hydroxycyclohexyl)-7H-pyrrolo[2,3-d]pyrimidin-5-yl)piperidin-1-yl)(pyridin-4-yl)methanone (43)

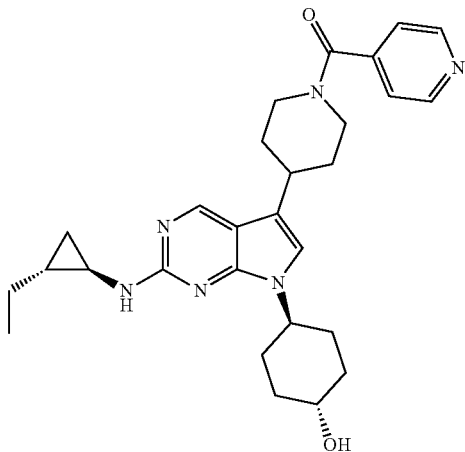 [SMILES: CC[C@@H]1C[C@H]1Nc1ncc2c(C3CCN(C(=O)c4ccncc4)CC3)cn([C@H]3CC[C@H](O)CC3)c2n1]

¹H NMR (400 MHz, CD₃OD) δ 8.88 (s, 2H), 8.64 (d, J=1.6 Hz, 1H), 7.91 (s, 2H), 7.34 (s, 1H), 4.74 (d, J=13.3 Hz, 1H), 4.55 (dt, J=11.4, 6.2 Hz, 1H), 3.66 (ddd, J=27.1, 15.4, 9.8 Hz, 2H), 3.35 (d, J=12.5 Hz, 1H), 3.08 (dt, J=23.6, 11.7 Hz, 2H), 2.50 (dd, J=6.6, 3.2 Hz, 1H), 2.21-1.85 (m, 8H), 1.75 (dt, J=23.3, 10.0 Hz, 2H), 1.54-1.31 (m, 4H), 1.10 (t, J=7.4 Hz, 3H), 1.01 (dd, J=11.7, 6.6 Hz, 1H), 0.85-0.77 (m, 1H), 0.73 (dd, J=12.4, 6.1 Hz, 1H). MS m/z 489.30 [M+H]⁺.

ff. (2,6-dimethylpyridin-4-yl)(4-(2-(((1S,2S)-2-ethylcyclopropyl)amino)-7-((1R,4S)-4-hydroxycyclohexyl)-7H-pyrrolo[2,3-d]pyrimidin-5-yl)piperidin-1-yl)methanone (55)

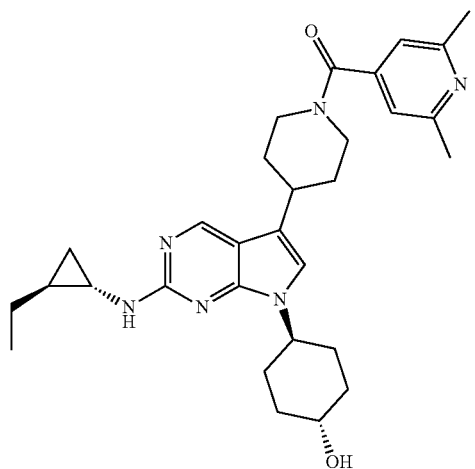 [SMILES: CC[C@H]1C[C@@H]1Nc1ncc2c(C3CCN(C(=O)c4cc(C)nc(C)c4)CC3)cn([C@H]3CC[C@H](O)CC3)c2n1]

¹H NMR (400 MHz. CD₃OD) δ 8.64 (s, 1H), 7.71 (s, 2H), 7.34 (s, 1H), 4.71 (d, J=13.3 Hz, 1H), 4.55 (dd, J=14.2, 7.3 Hz, 1H), 3.68 (ddd, J=15.1, 10.9, 4.2 Hz, 1H), 3.60 (d, J=13.8 Hz, 1H), 3.38-3.29 (m, 1H), 3.17-2.97 (m, 2H), 2.78 (d, J=11.0 Hz, 6H), 2.50 (dt, J=6.8, 3.3 Hz, 1H), 2.23-1.86 (m, 8H), 1.81-1.66 (m, 2H), 1.54-1.32 (m, 4H), 1.10 (t, J=7.4 Hz, 3H), 1.01 (dd, J=12.4, 6.8 Hz, 1H), 0.84-0.77 (m, 1H), 0.74 (dd, J=12.4, 6.1 Hz, 1H). MS m/z 517.41 [M+H]⁺.

gg. (2,6-dimethylpyridin-4-yl)(4-(2-(((R,2R)-2-ethylcyclopropyl)amino)-7-((1R,4R)-4-hydroxycyclohexyl)-7H-pyrrolo[2,3-d]pyrimidin-5-yl)piperidin-1-yl)methanone (56)

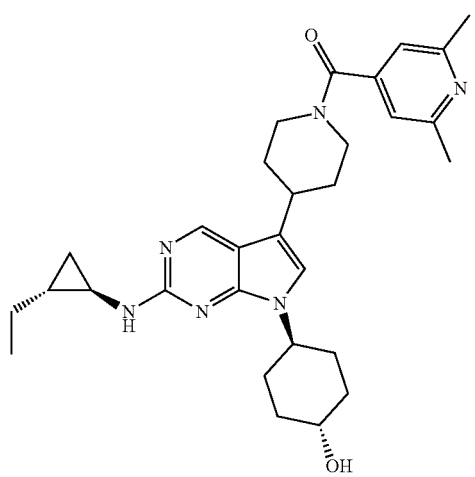 [SMILES: CC[C@@H]1C[C@H]1Nc1ncc2c(C3CCN(C(=O)c4cc(C)nc(C)c4)CC3)cn([C@H]3CC[C@H](O)CC3)c2n1]

¹H NMR (400 MHz. CD₃OD) δ 8.64 (s, 1H), 7.71 (s, 2H), 7.34 (s, 1H), 4.71 (d, J=13.3 Hz, 1H), 4.55 (dd, J=14.2, 7.3 Hz, 1H), 3.68 (ddd, J=15.1, 10.9, 4.2 Hz, 1H), 3.60 (d, J=13.8 Hz, 1H), 3.38-3.29 (m, 1H), 3.17-2.97 (m, 2H), 2.78 (d, J=11.0 Hz, 6H), 2.50 (dt, J=6.8, 3.3 Hz, 1H), 2.23-1.86 (m, 8H), 1.81-1.66 (m, 2H), 1.54-1.32 (m, 4H), 1.10 (t, J=7.4 Hz, 3H), 1.01 (dd, J=12.4, 6.8 Hz, 1H), 0.84-0.77 (m, 1H), 0.74 (dd, J=12.4, 6.1 Hz, 1H). MS m/z 517.42 [M+H]⁺.

hh. (4-(7-((1R,4S)-4-hydroxycyclohexyl)-2-(((S)-pentan-2-yl)amino)-7H-pyrrolo[2,3-d]pyrimidin-5-yl)piperidin-1-yl)(thiazol-2-yl)methanone (57)

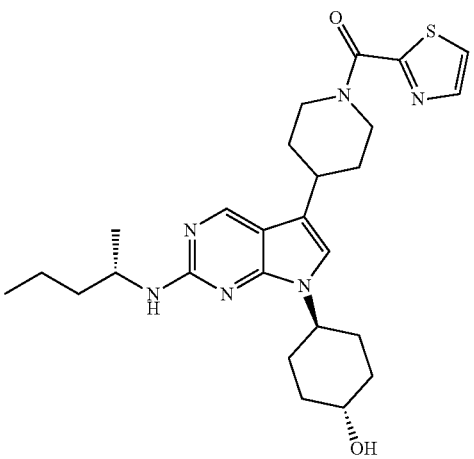 [SMILES: CCC[C@H](C)Nc1ncc2c(C3CCN(C(=O)c4nccs4)CC3)cn([C@H]3CC[C@H](O)CC3)c2n1]

¹H NMR (400 MHz. CD₃OD) δ 8.60 (s, 1H), 7.94 (d, J=3.1 Hz, 1H), 7.82 (d, J=3.0 Hz, 1H), 7.31 (s, 1H), 5.45-5.37 (m, 1H), 4.75-4.65 (m, 1H), 4.55-4.43 (m, 1H), 4.25-4.10 (m, 1H), 3.75-3.65 (m, 1H), 3.43-3.30 (m, 1H), 3.20-3.03 (m, 2H), 2.20-1.92 (m, 8H), 1.85-1.40 (m, 8H), 1.30 (d, J=6.6 Hz, 3H), 0.98 (t, J=7.3 Hz, 3H); MS m/z 497.27 [M+H]⁺.

ii. (4-(7-((1R,4S)-4-hydroxycyclohexyl)-2-(((S)-pentan-2-yl)amino)-7H-pyrrolo[2,3-d]pyrimidin-5-yl)piperidin-1-yl)(thiazol-4-yl)methanone (58)

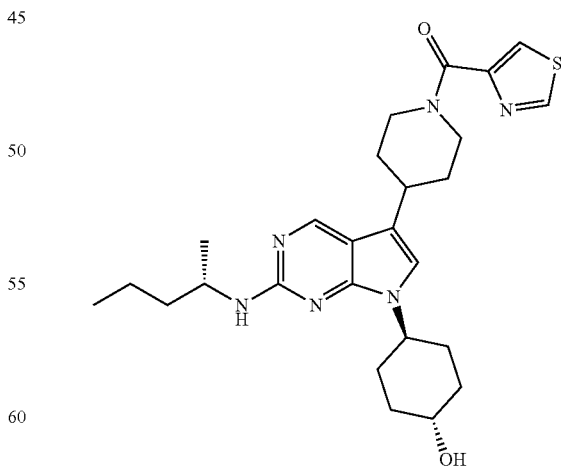

¹H NMR (400 MHz, CD₃OD) δ 9.05 (s, 1H), 8.60 (s, 1H), 8.04 (s, 1H), 7.31 (s, 1H), 4.80-4.70 (m, 1H), 4.52-4.43 (m, 1H), 4.35-4.25 (m, 1H), 4.20-4.05 (m, 1H), 3.75-3.65 (m, 1H), 3.43-3.30 (m, 18H), 3.20-3.03 (m, 2H), 2.20-1.92 (m,

8H), 1.85-1.40 (m, 8H), 1.30 (d, J=6.6 Hz, 3H), 0.98 (t, J=7.3 Hz, 3H); MS m/z 497.27 [M+H]⁺.

jj. (4-(7-((1R,4S)-4-hydroxycyclohexyl)-2-(((S)-pentan-2-yl)amino)-7H-pyrrolo[2,3-d]pyrimidin-5-yl)piperidin-1-yl)(thiazol-5-yl)methanone (59)

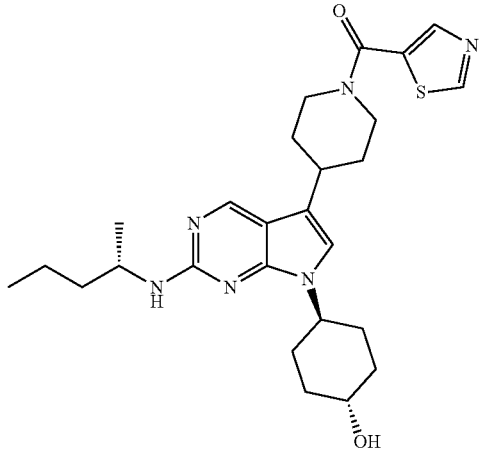 [SMILES: CCC[C@H](C)Nc1ncc2c(C3CCN(C(=O)c4cncs4)CC3)cn([C@H]3CC[C@H](O)CC3)c2n1]

$^1$H NMR (400 MHz. CD$_3$OD) δ 9.14 (s, 1H), 8.60 (s, 1H), 8.16 (s, 1H), 7.33 (s, 1H), 4.90-4.80 (m, 2H), 4.52-4.43 (m, 1H), 4.20-4.05 (m, 1H), 3.75-3.65 (m, 1H), 3.43-3.30 (m, 1H), 3.20-3.03 (m, 2H), 2.20-1.92 (m, 8H), 1.85-1.40 (m, 8H), 1.30 (d, J=6.6 Hz, 3H), 0.98 (t, J=7.3 Hz, 3H); MS m/z 497.27 [M+H]⁺.

kk. (4-(7-((1R,4S)-4-hydroxycyclohexyl)-2-(((S)-pentan-2-yl)amino)-7H-pyrrolo[2,3-d]pyrimidin-5-yl)piperidin-1-yl)(1H-pyrrol-2-yl)methanone (60)

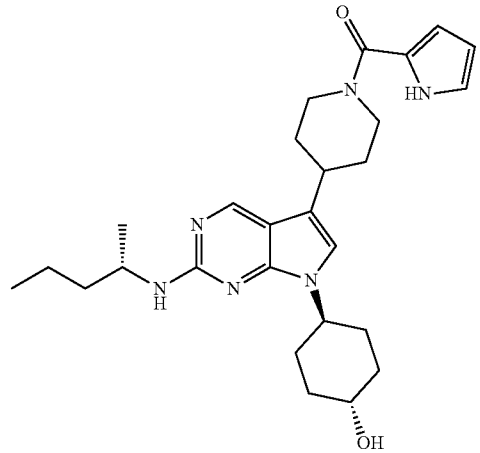 [SMILES: CCC[C@H](C)Nc1ncc2c(C3CCN(C(=O)c4ccc[nH]4)CC3)cn([C@H]3CC[C@H](O)CC3)c2n1]

$^1$H NMR (400 MHz, CD$_3$OD) δ 8.58 (s, 1H), 7.31 (s, 1H), 6.93-6.87 (m, 1H), 6.60-6.56 (m, 1H), 6.20-6.17 (m, 1H), 4.70-4.60 (m, 2H), 4.52-4.41 (m, 1H), 4.20-4.05 (m, 1H), 3.75-3.65 (m, 1H), 3.30-3.05 (m, 3H), 2.20-1.92 (m, 8H), 1.85-1.40 (m, 8H), 1.30 (d, J=6.6 Hz, 3H), 0.98 (t, J=7.3 Hz, 3H); MS m/z 479.31 [M+H]⁺.

ll. (4-(7-((1R,4S)-4-hydroxycyclohexyl)-2-(((S)-pentan-2-yl)amino)-7H-pyrrolo[2,3-d]pyrimidin-5-yl)piperidin-1-yl)(1H-pyrrol-3-yl)methanone (61)

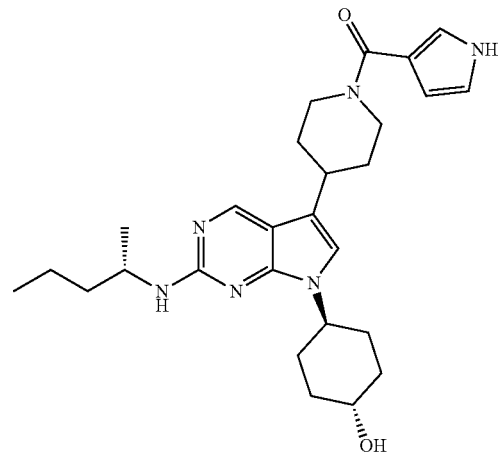 [SMILES: CCC[C@H](C)Nc1ncc2c(C3CCN(C(=O)c4cc[nH]c4)CC3)cn([C@H]3CC[C@H](O)CC3)c2n1]

$^1$H NMR (400 MHz. CD$_3$OD) δ 8.58 (s, 1H), 7.31 (s, 1H), 7.17-7.14 (m, 1H), 6.80-6.75 (m, 1H), 6.37-6.33 (m, 1H), 4.66-4.40 (m, 3H), 4.20-4.05 (m, 1H), 3.75-3.65 (m, 1H), 3.30-3.05 (m, 3H), 2.20-1.92 (m, 8H), 1.85-1.40 (m, 8H), 1.30 (d, J=6.6 Hz, 3H), 0.98 (t, J=7.3 Hz, 3H); MS m/z 479.31 [M+H]⁺.

mm. (4-(7-((1R,4S)-4-hydroxycyclohexyl)-2-(((S)-pentan-2-yl)amino-7H-pyrrolo[2,3-d]pyrimidin-5-yl)piperidin-1-yl)(1H-imidazol-2-yl)methanone (62)

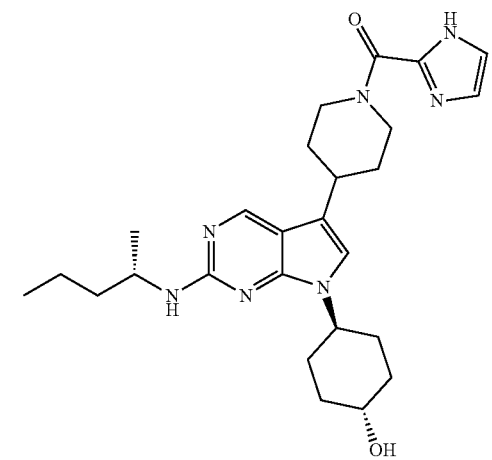 [SMILES: CCC[C@H](C)Nc1ncc2c(C3CCN(C(=O)c4ncc[nH]4)CC3)cn([C@H]3CC[C@H](O)CC3)c2n1]

$^1$H NMR (400 MHz, CD$_3$OD) δ 8.61 (s, 1H), 7.59 (s, 2H), 7.29 (s, 1H), 4.75-4.40 (m, 2H), 4.20-4.05 (m, 2H), 3.75-3.65 (m, 1H), 3.30-3.05 (m, 3H), 2.20-1.92 (m, 8H), 1.85-1.40 (m, 8H), 1.30 (d, J=6.6 Hz, 3H), 0.98 (t, J=7.3 Hz, 3H); MS m/z 480.31 [M+H]⁺.

nn. (4-(7-((1R,4S)-4-hydroxycyclohexyl)-2-(((S)-pentan-2-yl)amino)-7H-pyrrolo[2,3-d]pyrimidin-5-yl)piperidin-1-yl)(pyridazin-3-yl)methanone (63)

pp. (4-(7-((1R,4S)-4-hydroxycyclohexyl)-2-(((S)-pentan-2-yl)amino)-7H-pyrrolo[2,3-d]pyrimidin-5-yl)piperidin-1-yl)(pyrimidin-2-yl)methanone (65)

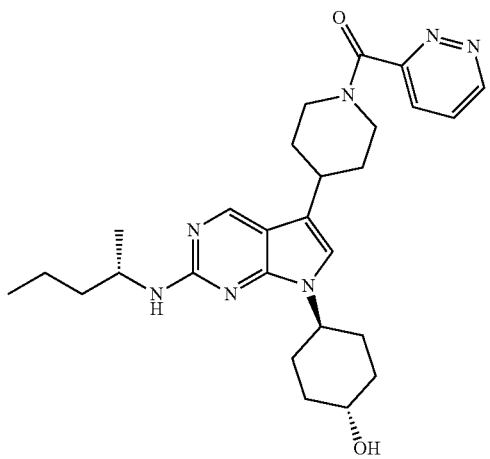 [SMILES: CCC[C@H](C)Nc1ncc2c(C3CCN(C(=O)c4cccnn4)CC3)cn([C@H]3CC[C@H](O)CC3)c2n1]

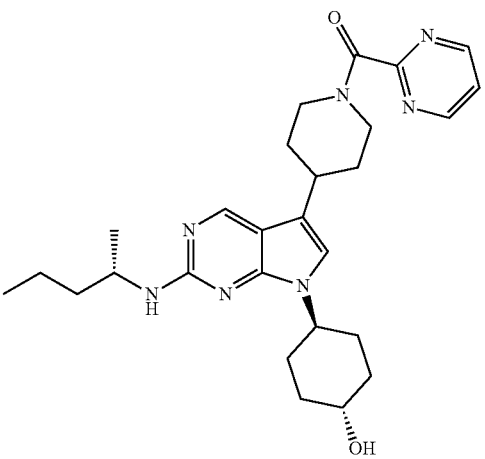

$^1$H NMR (400 MHz. CD$_3$OD) δ 9.38 (dd, J=5.1, 1.8 Hz, 1H), 8.64 (s, 1H), 8.13-8.03 (m, 2H), 7.33 (s, 1H), 4.83-4.75 (m, 1H), 4.53-4.43 (m, 1H), 4.18-4.10 (m, 1H), 3.90-3.80 (m, 1H), 3.75-3.65 (m, 1H), 3.40-3.30 (m, 1H), 3.17-3.05 (m, 2H), 2.20-1.90 (m, 8H), 1.88-1.40 (m, 8H), 1.29 (d, J=6.6 Hz, 3H), 0.97 (t, J=7.3 Hz, 3H); MS m/z 492.31 [M+H]$^+$.

$^1$H NMR (400 MHz. CD$_3$OD) δ 8.88 (d, J=5.0 Hz, 2H), 8.62 (s, 1H), 7.57 (t, J=5.0 Hz, 1H), 7.32 (s, 1H), 4.80-4.70 (m, 1H), 4.52-4.42 (m, 1H), 4.20-4.10 (m, 1H), 3.70-3.50 (m, 2H), 3.33-3.23 (m, 1H), 3.15-3.00 (m, 2H), 2.17-1.87 (m, 8H), 1.82-1.40 (m, 8H), 1.29 (d, J=6.6 Hz, 3H), 0.97 (t, J=7.3 Hz, 3H); MS m/z 492.31 [M+H]$^+$.

oo. (4-(7-((1R,4S)-4-hydroxycyclohexyl)-2-(((S)-pentan-2-yl)amino)-7H-pyrrolo[2,3-d]pyrimidin-5-yl)piperidin-1-yl)(pyridazin-4-yl)methanone (64)

qq. (4-(7-((1R,4S)-4-hydroxycyclohexyl)-2-(((S)-pentan-2-yl)amino)-7H-pyrrolo[2,3-d]pyrimidin-5-yl)piperidin-1-yl)(pyrimidin-4-yl)methanone (66)

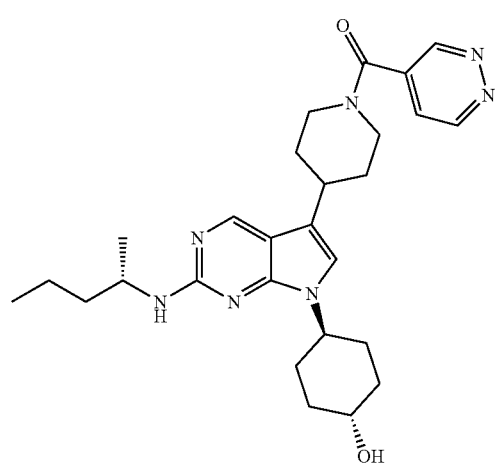 [SMILES: CCC[C@H](C)Nc1ncc2c(C3CCN(C(=O)c4ccnnc4)CC3)cn([C@H]3CC[C@H](O)CC3)c2n1]

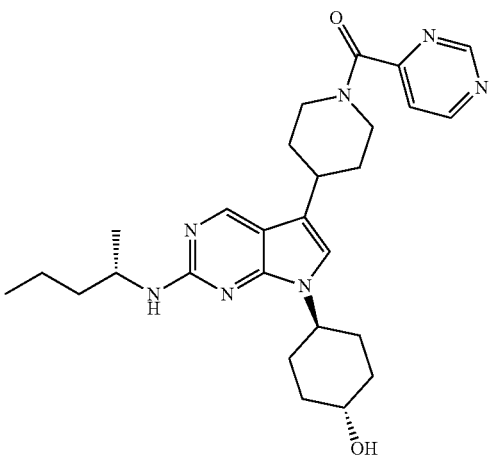 [SMILES: CCC[C@H](C)Nc1ncc2c(C3CCN(C(=O)c4ccncn4)CC3)cn([C@H]3CC[C@H](O)CC3)c2n1]

$^1$H NMR (400 MHz, CD$_3$OD) δ 9.45-9.35 (m, 2H), 8.62 (s, 1H), 7.99 (dd, J=5.3, 2.1 Hz, 1H), 7.32 (s, 1H), 4.77-4.69 (m, 1H), 4.53-4.43 (m, 1H), 4.18-4.10 (m, 1H), 3.70-3.60 (m, 2H), 3.42-3.30 (m, 1H), 3.16-3.01 (m, 2H), 2.20-1.90 (m, 8H), 1.82-1.40 (m, 8H), 1.29 (d, J=6.6 Hz, 3H), 0.97 (t, J=7.3 Hz, 3H); MS m/z 492.31 [M+H]$^+$.

$^1$H NMR (400 MHz, CD$_3$OD) δ 9.21 (d, J=1.4 Hz, 1H), 8.94 (d, J=5.1 Hz, 1H), 8.60 (s, 1H), 7.66 (dd, J=5.1, 1.4 Hz, 1H), 7.32 (s, 1H), 4.80-4.70 (m, 1H), 4.52-4.42 (m, 1H), 4.20-4.10 (m, 1H), 3.83-3.75 (m, 1H), 3.70-3.60 (m, 1H), 3.33-3.23 (m, 1H), 3.15-2.97 (m, 2H), 2.20-1.90 (m, 8H), 1.83-1.40 (m, 8H), 1.29 (d, J=6.6 Hz, 3H), 0.97 (t, J=7.3 Hz, 3H); MS m/z 492.31 [M+H]$^+$.

243 rr. (4-(7-((1R,4S)-4-hydroxycyclohexyl)-2-(((S)-pentan-2-yl)amino)-7H-pyrrolo[2,3-d]pyrimidin-5-yl)piperidin-1-yl)(pyrimidin-5-yl)methanone (67)

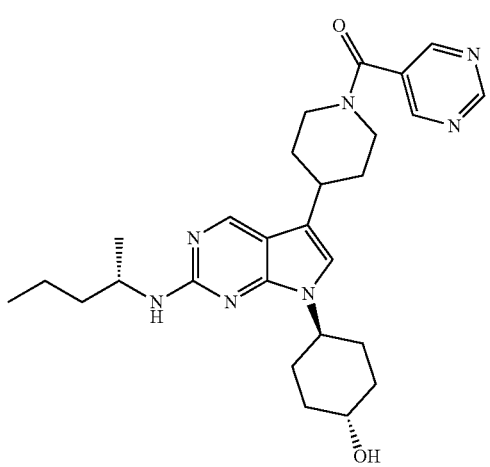 [SMILES: CCC[C@H](C)Nc1ncc2c(C3CCN(C(=O)c4cncnc4)CC3)cn([C@H]3CC[C@H](O)CC3)c2n1]

$^1$H NMR (400 MHz, CD$_3$OD) δ 9.23 (s, 1H), 8.88 (s, 2H), 8.61 (s, 1H), 7.32 (s, 1H), 4.80-4.70 (m, 1H), 4.52-4.42 (m, 1H), 4.20-4.10 (m, 1H), 3.83-3.60 (m, 2H), 3.43-3.31 (m, 1H), 3.15-2.97 (m, 2H), 2.20-1.90 (m, 8H), 1.80-1.40 (m, 8H), 1.29 (d, J=6.6 Hz, 3H), 0.97 (t, J=7.3 Hz, 3H); MS m/z 492.31 [M+H]$^+$.

ss. (4-(7-((1R,4S)-4-hydroxycyclohexyl)-2-(((S)-pentan-2-yl)amino-7H-pyrrolo[2,3-d]pyrimidin-5-yl)piperidin-1-yl)(pyrazin-2-yl)methanone (68)

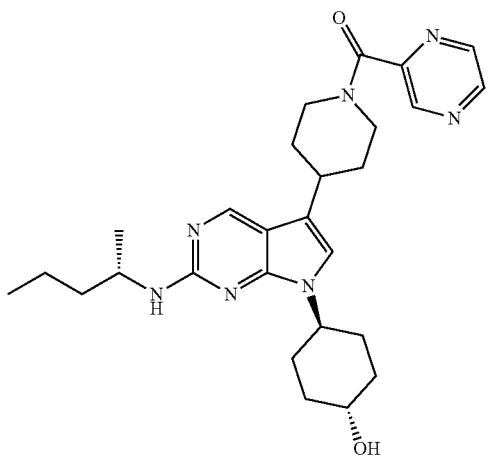 [SMILES: CCC[C@H](C)Nc1ncc2c(C3CCN(C(=O)c4cnccn4)CC3)cn([C@H]3CC[C@H](O)CC3)c2n1]

$^1$H NMR (400 MHz. CD$_3$OD) δ 8.84 (d, J=1.4 Hz, 1H), 8.69 (d, J=2.6 Hz, 1H), 8.64-8.61 (m, 2H), 7.32 (s, 1H), 4.80-4.70 (m, 1H), 4.52-4.42 (m, 1H), 4.20-4.10 (m, 1H), 3.97-3.90 (m, 1H), 3.70-3.63 (m, 1H), 3.36-3.30 (m, 1H), 3.15-3.00 (m, 2H), 2.20-1.90 (m, 8H), 1.83-1.40 (m, 8H), 1.29 (d, J=6.6 Hz, 3H), 0.97 (t, J=7.3 Hz, 3H); MS m/z 492.31 [M+H]$^+$.

244 tt. (2,6-dimethylpyridin-4Y)(4-(2-((2-ethylbutyl)amino)-7-((1R,4R)-4-hydroxycyclohexyl)-7H-pyrrolo[2,3-d]pyrimidin-5-yl)piperidin-1-yl)methanone (69)

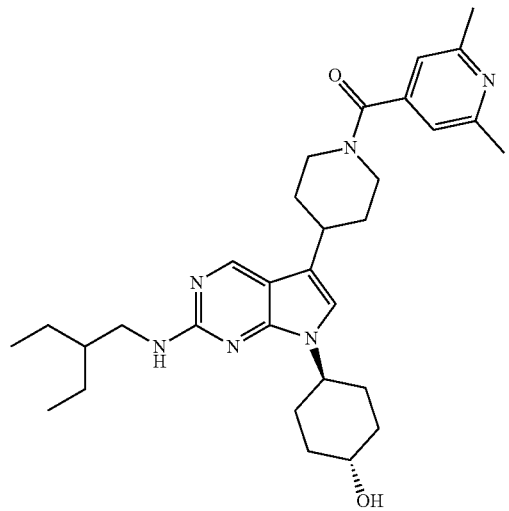 [SMILES: CCC(CC)CNc1ncc2c(C3CCN(C(=O)c4cc(C)nc(C)c4)CC3)cn([C@H]3CC[C@H](O)CC3)c2n1]

$^1$H NMR (400 MHz, CD$_3$OD) δ 8.68 (s, 1H), 7.74 (s, 2H), 7.34 (s, 1H), 4.73 (d, J=13.4 Hz, 1H), 4.56-4.48 (m, 1H), 3.72-3.58 (m, 2H), 3.47 (d, J=6.2 Hz, 2H), 3.39-3.32 (m, 1H), 3.16-3.01 (m, 2H), 2.78 (s, 6H), 2.20-2.06 (m, 3H), 2.04-1.91 (m, 5H), 1.81-1.70 (m, 2H), 1.65-1.57 (m, 1H), 1.54-1.39 (m, 6H), 0.99 (t, J=7.4 Hz, 6H). MS m/z 533.40 [M+H]$^+$.

uu. (4-(2-(butylamino)-7-((1R,4R)-4-hydroxycyclohexyl)-7H-pyrrolo[2,3-d]pyrimidin-5-yl)piperidin-1-yl)(2,6-dimethylpyridin-4-yl)methanone (70)

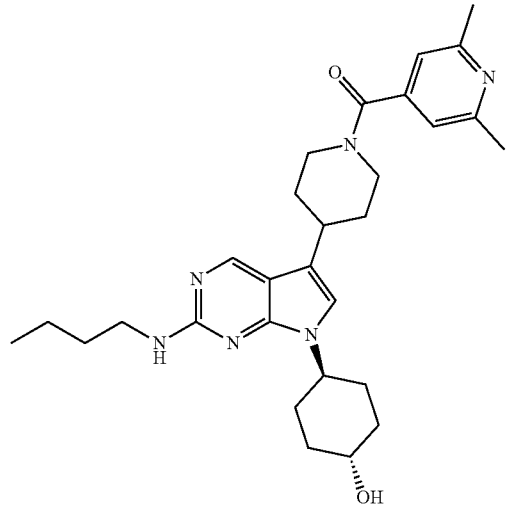 [SMILES: CCCCNc1ncc2c(C3CCN(C(=O)c4cc(C)nc(C)c4)CC3)cn([C@H]3CC[C@H](O)CC3)c2n1]

$^1$H NMR (400 MHz, CD$_3$OD) δ 8.66 (s, 1H), 7.71 (s, 2H), 7.33 (s, 1H), 4.77-4.69 (m, 1H), 4.55-4.45 (m, 1H), 3.69-3.66 (m, 1H), 3.54-3.46 (m, 2H), 3.38-3.31 (m, 2H), 3.12-3.01 (m, 2H), 2.77 (s, 6H), 2.18-2.07 (m, 3H), 2.04-1.92 (m,

5H), 1.82-1.62 (m, 4H), 1.55-1.41 (m, 4H), 1.00 (t, J=7.4 Hz, 3H). MS m/z 505.40 [M+H]⁺.

vv. (3,5-dimethylphenyl)(4-(7-((1R,4S)-4-hydroxy-cyclohexyl)-2-(((S)-pentan-2-yl)amino)-7H-pyrrolo l[2,3-d]pyrimidin-5-yl)piperidin-1-yl)methanone (71)

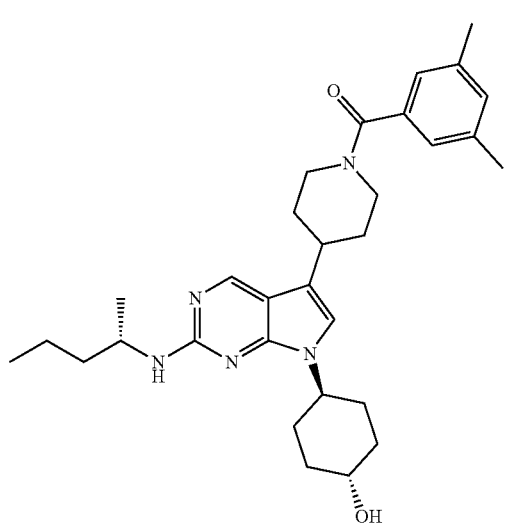 [SMILES: CCC[C@H](C)Nc1ncc2c(C3CCN(C(=O)c4cc(C)cc(C)c4)CC3)cn([C@H]3CC[C@H](O)CC3)c2n1]

$^1$H NMR (400 MHz, CD$_3$OD) δ 8.60 (s, 1H), 7.33 (s, 1H), 7.12 (s, 1H), 7.02 (s, 2H), 4.77-4.68 (m, 1H), 4.54-4.44 (m, 1H), 4.22-4.12 (m, 1H), 3.88-3.80 (m, 1H), 3.74-3.65 (m, 1H), 3.25 (s, 1H), 3.13-2.93 (m, 2H), 2.34 (s, 6H), 2.19-1.90 (m, 8H), 1.77-1.38 (m, 8H), 1.30 (d, J=6.6 Hz, 3H), 0.98 (t, J=7.3 Hz, 3H). MS m/z 518.40 [M+H]⁺.

ww. (4-(2-((2-cyclopropylethyl)amino)-7-((1R,4R)-4-hydroxycyclohexyl)-7H-pyrrolo[2,3-d]pyrimidin-5-yl)piperidin-1-yl)(2,6-dimethylpyridin-4-yl)methanone (72)

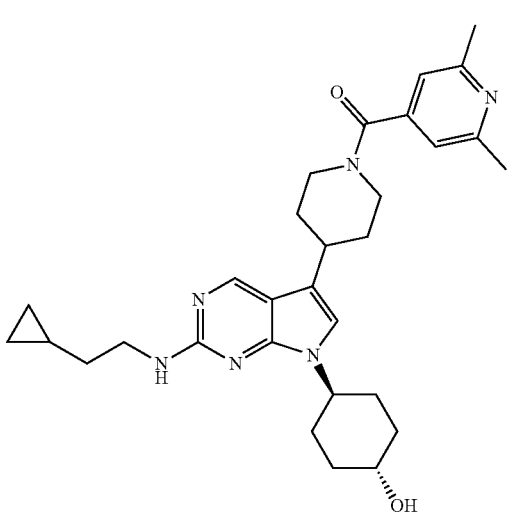 [SMILES: Cc1cc(C(=O)N2CCC(c3cn([C@H]4CC[C@H](O)CC4)c4nc(NCCC5CC5)ncc34)CC2)cc(C)n1]

$^1$H NMR (400 MHz, CD$_3$OD) δ 8.69 (s, 1H), 7.76 (s, 2H), 7.34 (s, 1H), 4.73 (d, J=13.2 Hz, 1H), 4.57-4.45 (m, 1H), 3.73-3.54 (m, 4H), 3.42-3.32 (m, 1H), 3.20-3.00 (m, 2H), 2.79 (s, 6H), 2.13 (t, J=12.8 Hz, 3H), 2.06-1.92 (m, 5H), 1.82-1.68 (m, 2H), 1.65-1.39 (m, 4H), 0.86-0.75 (m, 1H), 0.55-0.43 (m, 2H), 0.14 (q, J=4.9 Hz, 2H). MS m/z 517.40 [M+H]⁺.

xx. (4-(2-(benzylamino)-7-((1R,4R)-4-hydroxycyclohexyl)-7H-pyrrolo[2,3-d]pyrimidin-5-yl)piperidin-1-yl)(2,6-dimethylpyridin-4-yl)methanone (73)

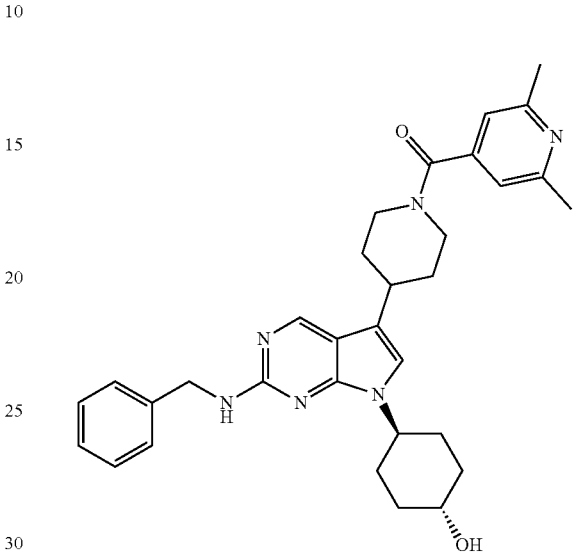

$^1$H NMR (400 MHz, CD$_3$OD) δ 8.72 (s, 1H), 7.74 (s, 2H), 7.43 (d, J=7.4 Hz, 2H), 7.33 (dd, J=12.6, 4.6 Hz, 3H), 7.27 (d, J=7.3 Hz, 1H), 4.76-4.63 (m, 3H), 4.47-4.37 (m, 1H), 3.69-3.57 (m, 2H), 3.38-3.32 (m, 1H), 3.16-3.02 (m, 2H), 2.78 (s, 6H), 2.17-2.04 (m, 3H), 2.01-1.81 (m, 5H), 1.80-1.67 (m, 2H), 1.53-1.41 (m, 2H). MS m/z 539.30 [M+H]⁺.

yy. (2,6-dimethylpyridin-4-yl)(4-(7-((1R,4S)-4-hydroxycyclohexyl)-2-(((S)-1-phenylethyl)amino)-7H-pyrrolo[2,3-d]pyrimidin-5-yl)piperidin-1-yl)methanone (74)

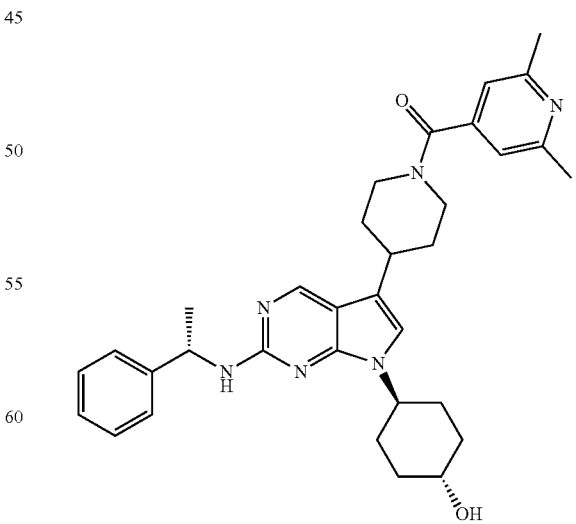

$^1$H NMR (400 MHz, CD$_3$OD) δ 8.69 (s, 1H), 7.73 (s, 2H), 7.43 (d, J=7.5 Hz, 2H), 7.34 (t, J=7.6 Hz, 2H), 7.27 (s, 2H), 5.15-5.05 (m, 1H), 4.75-4.67 (m, 1H), 4.34-4.27 (m, 1H), 3.71-3.55 (m, 2H), 3.40-3.32 (m, 1H), 3.14-3.00 (m, 2H), 2.78 (s, 6H), 2.16-1.66 (m, 10H), 1.63 (d, J=7.0 Hz, 3H), 1.52-1.38 (m, 2H). MS m/z 553.35 [M+H]+.

zz. (2,6-dimethylpyridin-4-yl)(4-(2-(((S)-1-(4-fluorophenyl)ethyl)amino)-7-((1R,4S)-4-hydroxycyclohexyl)-7H-pyrrolo[2,3-d]pyrimidin-5-yl)piperidin-1-yl)methanone (75)

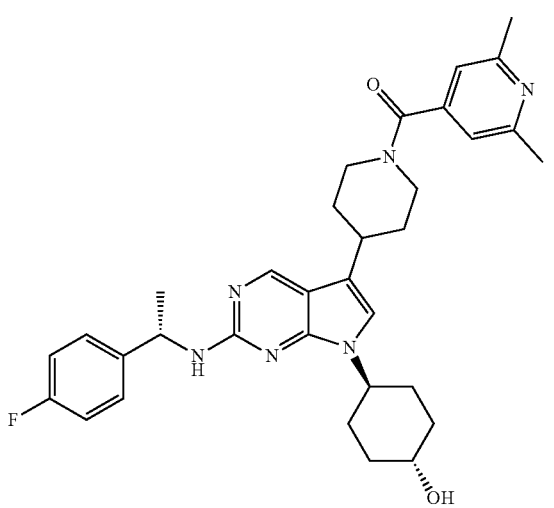 [SMILES: Cc1cc(C(=O)N2CCC(c3cn([C@H]4CC[C@H](O)CC4)c4nc(N[C@@H](C)c5ccc(F)cc5)ncc34)CC2)cc(C)n1]

¹H NMR (400 MHz, CD₃OD) δ 8.69 (s, 1H), 7.71 (s, 2H), 7.46 (dd, J=8.6, 5.3 Hz, 2H), 7.28 (s, 1H), 7.07 (t, J=8.7 Hz, 2H), 5.12-5.07 (m, 1H), 4.71 (d, J=13.9 Hz, 1H), 4.34-4.27 (m, 1H), 3.68-3.57 (m, 2H), 3.41-3.33 (m, 1H), 3.12-3.02 (m, 2H), 2.77 (s, 6H), 2.14-1.70 (m, 10H), 1.62 (d, J=7.0 Hz, 3H), 1.52-1.40 (m, 2H). MS m/z 571.35 [M+H]+.

aaa. (4-(2-((cyclohexylmethyl)amino)-7-((1R,4R)-4-hydroxycyclohexyl)-7H-pyrrolo[2,3-d]pyrimidin-5-yl)piperidin-1-yl)(2,6-dimethylpyridin-4-yl)methanone (76)

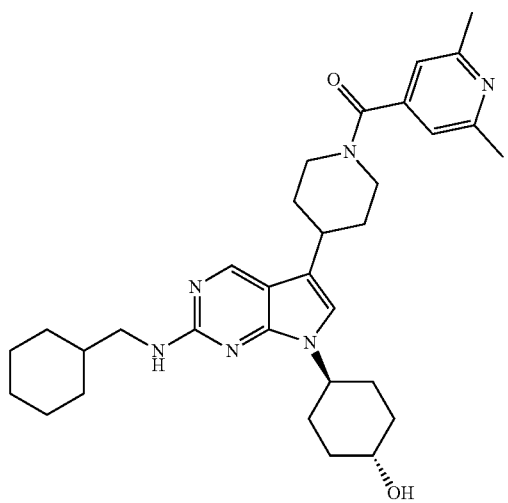 [SMILES: Cc1cc(C(=O)N2CCC(c3cn([C@H]4CC[C@H](O)CC4)c4nc(NCC5CCCCC5)ncc34)CC2)cc(C)n1]

¹H NMR (400 MHz, CD₃OD) δ 8.67 (s, 1H), 7.74 (s, 2H), 7.33 (s, 1H), 4.73 (d, J=13.2 Hz, 1H), 4.54-4.43 (m, 1H), 3.74-3.58 (m, 2H), 3.35 (d, J=6.8 Hz, 3H), 3.16-3.02 (m, 2H), 2.78 (s, 6H), 2.20-1.90 (m, 8H), 1.90-1.64 (m, 8H), 1.57-1.43 (m, 2H), 1.36-1.19 (m, 3H), 1.13-1.00 (m, 2H). MS m/z 545.40. [M+H]+.

bbb. (4-(2-(((R)-2,3-dihydro-1H-inden-1-yl)amino)-7-((1R,4R)-4-hydroxycyclohexyl)-7H-pyrrolo[2,3-d]pyrimidin-5-yl)piperidin-1-yl)(2,6-dimethylpyridin-4-yl)methanone (77)

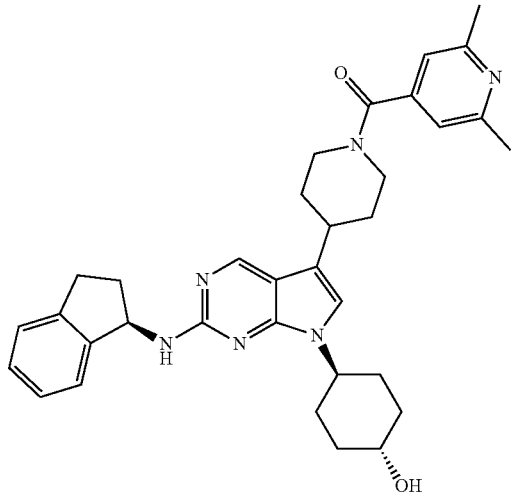 [SMILES: Cc1cc(C(=O)N2CCC(c3cn([C@H]4CC[C@H](O)CC4)c4nc(N[C@@H]5CCc6ccccc65)ncc34)CC2)cc(C)n1]

¹H NMR (400 MHz, CD₃OD) δ 8.72 (s, 1H), 7.72 (s, 2H), 7.39-7.30 (m, 3H), 7.26 (t, J=7.3 Hz, 1H), 7.19 (t, J=7.4 Hz, 1H), 5.60 (t, J=7.4 Hz, 1H), 4.74 (d, J=13.1 Hz, 1H), 4.49-4.42 (m, 1H), 3.70-3.60 (m, 2H), 3.40-3.33 (m, 1H), 3.18-3.08 (m, 2H), 3.06-2.93 (m, 1H), 2.78 (s, 6H), 2.71-2.63 (m, 1H), 2.20-2.12 (m, 2H), 2.12-1.86 (m, 8H), 1.77 (dd, J=21.2, 12.4 Hz, 2H), 1.48 (dd, J=15.7, 7.9 Hz, 2H). MS [M+H]+ m/z 565.30.

ccc. (4-(2-(((S)-2,3-dihydro-1H-inden-1-yl)amino)-7-((1R,4S)-4-hydroxycyclohexyl)-7H-pyrrolo[2,3-d]pyrimidin-5-yl)piperidin-1-yl)(2,6-dimethylpyridin-4-yl)methanone (78)

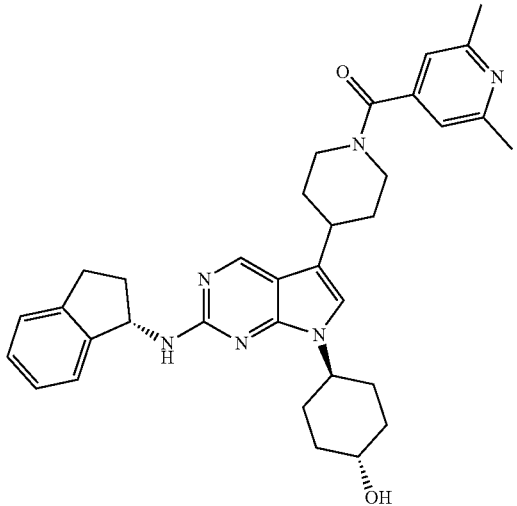 [SMILES: Cc1cc(C(=O)N2CCC(c3cn([C@H]4CC[C@H](O)CC4)c4nc(N[C@H]5CCc6ccccc65)ncc34)CC2)cc(C)n1]

¹H NMR (400 MHz, CD₃OD) δ 8.73 (s, 1H), 7.75 (s, 2H), 7.38-7.30 (m, 3H), 7.26 (t, J=7.3 Hz, 1H), 7.19 (1, J=7.4 Hz, 1H), 5.60 (t, J=7.4 Hz, 1H), 4.74 (d, J=13.5 Hz, 1H), 4.52-4.41 (m, 1H), 3.73-3.57 (m, 2H), 3.40-3.34 (m, 1H), 3.17-3.06 (m, 2H), 3.05-2.94 (m, 1H), 2.79 (s, 6H), 2.72-2.62 (m, 1H), 2.19-1.87 (m, 10H), 1.82-1.70 (m, 2H), 1.53-1.41 (m, 2H). MS [M+H]⁺ m/z 565.35.

ddd. (4-(dimethylamino)phenyl)(4-(7-((1R,4S)-4-hydroxycyclohexyl)-2-(((S)-pentan-2-yl)amino)-7H-pyrrolo[2,3-d]pyrimidin-5-yl)piperidin-1-yl)methanone (79)

¹H NMR (400 MHz, CD₃OD) δ 8.60 (s, 1H), 7.33 (s, 1H), 6.58 (d, J=2.2 Hz, 1H), 6.54 (d, J=2.3 Hz, 2H), 4.78-4.67 (m, 1H), 4.53-4.44 (m, 1H), 4.21-4.11 (m, 1H), 3.93-3.74 (m, 7H), 3.73-3.63 (m, 1H), 3.25 (d, J=12.1 Hz, 1H), 3.11-2.93 (m, 2H), 2.17-1.92 (m, 8H), 1.78-1.41 (m, 8H), 1.30 (d, J=6.6 Hz, 3H), 0.99 (t, J=7.3 Hz, 3H). MS [M+H]⁺ m/z 549.35.

fff. (3,5-difluorophenyl)(4-(7-((1R,4S)-4-hydroxycyclohexyl)-2-(((S)-pentan-2-yl)amino)-7H-pyrrolo[2,3-d]pyrimidin-5-yl)piperidin-1-yl)methanone (81)

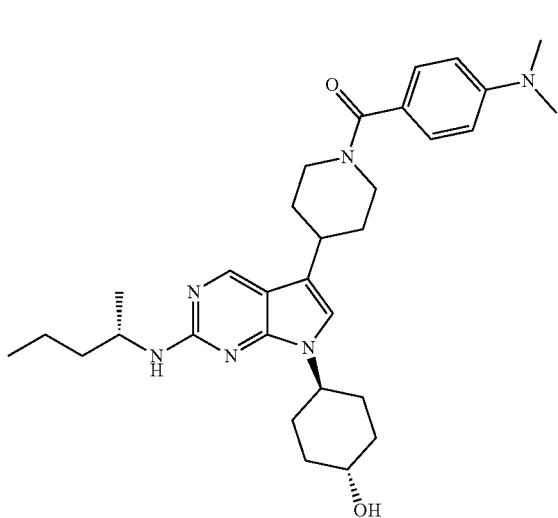 [SMILES: CCC[C@H](C)Nc1ncc2c(C3CCN(C(=O)c4ccc(N(C)C)cc4)CC3)cn([C@H]3CC[C@H](O)CC3)c2n1]

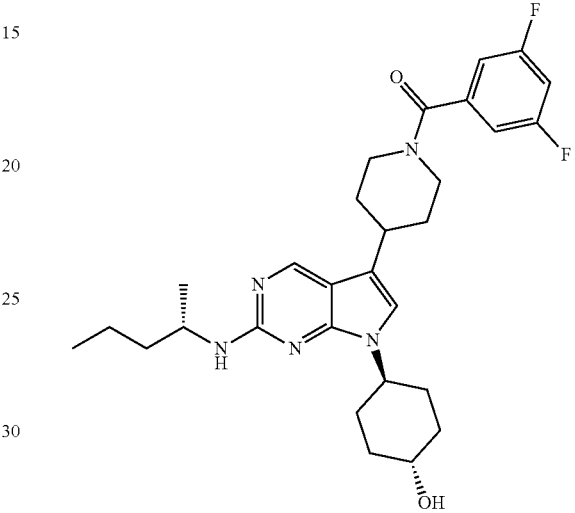

¹H NMR (400 MHz, CD₃OD) δ 8.64 (s, 1H), 7.57 (d, J=8.5 Hz, 2H), 7.41 (d, J=8.0 Hz, 2H), 7.33 (s, 1H), 4.53-4.45 (m, 1H), 4.20-4.12 (m, 1H), 3.74-3.64 (m, 1H), 3.30-3.16 (m, 9H), 3.16-3.04 (m, 2H), 2.16-1.91 (m, 8H), 1.78-1.40 (m, 8H), 1.30 (d, J=6.6 Hz, 3H), 0.98 (t, J=7.3 Hz, 3H). MS [M+H]⁺ m/z 533.40.

eee. (3,5-dimethoxyphenyl)(4-(7-((1R,4S)-4-hydroxycyclohexyl)-2-(((S)-pentan-2-yl)amino)-7H-pyrrolo[2,3-d]pyrimidin-5-yl)piperidin-1-yl)methanone (80)

¹H NMR (400 MHz, CD₃OD) δ 8.61 (s, 1H), 7.33 (s, 1H), 7.18-6.99 (m, 3H), 4.71 (d, J=9.6 Hz, 1H), 4.53-4.42 (m, 1H), 4.23-4.11 (m, 1H), 3.81-3.63 (m, 2H), 3.18-2.96 (m, 3H), 2.20-1.89 (m, 8H), 1.77-1.38 (m, 8H), 1.30 (d, J=6.6 Hz, 3H), 0.99 (s, 3H). MS [M+H]⁺ m/z 526.30.

ggg. (4-aminophenyl)(4-(7-((1R,4S)-4-hydroxycyclohexyl)-2-(((S)-pentan-2-yl)amino)-7H-pyrrolo[2,3-d]pyrimidin-5-yl)piperidin-1-yl)methanone (82)

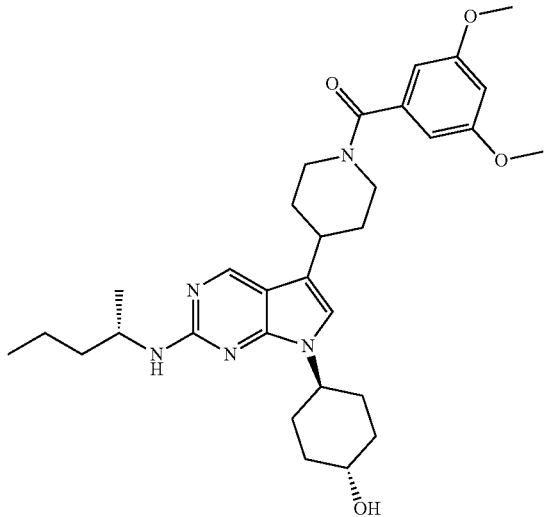 [SMILES: CCC[C@H](C)Nc1ncc2c(C3CCN(C(=O)c4cc(OC)cc(OC)c4)CC3)cn([C@H]3CC[C@H](O)CC3)c2n1]

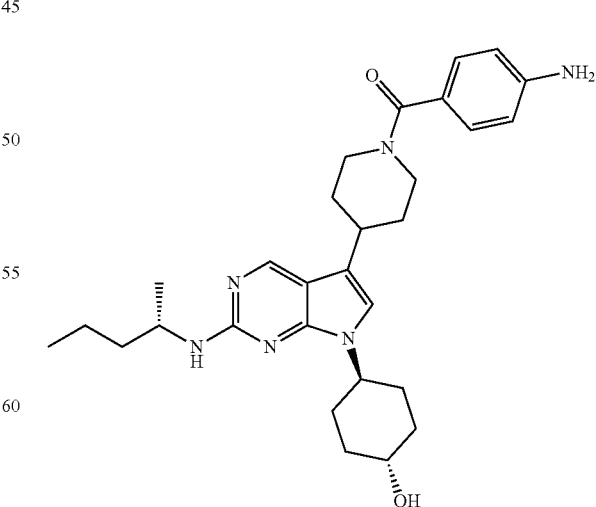

¹H NMR (400 MHz, CD₃OD) δ 8.61 (s, 1H), 7.48-7.42 (m, 2H), 7.33 (s, 1H), 7.14 (d, J=8.4 Hz, 2H), 4.54-4.46 (m,

1H), 4.21-4.13 (m, 1H), 3.71-3.65 (m, 1H), 3.26-3.00 (m, 5H), 2.17-1.94 (m, 8H), 1.76-1.38 (m, 8H), 1.30 (d, J=6.6 Hz, 3H), 0.99 (t, J=7.3 Hz, 3H). MS [M+H]$^+$ m/z 504.35.

hhh. (4-(7-((1R,4S)-4-hydroxycyclohexyl)-2-(((S)-pentan-2-yl)amino)-7H-pyrrolo[2,3-d]pyrimidin-5-yl)piperidin-1-yl)(4-(methylamino)phenyl)methanone (83)

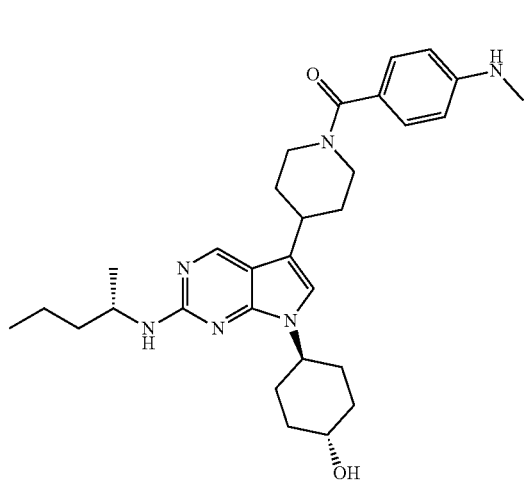 [SMILES: CCC[C@H](C)Nc1ncc2c(C3CCN(C(=O)c4ccc(NC)cc4)CC3)cn([C@H]3CC[C@H](O)CC3)c2n1]

$^1$H NMR (400 MHz, CD$_3$OD) δ 8.61 (s, 1H), 7.53-7.41 (m, 2H), 7.33 (s, 1H), 7.08 (s, 2H), 4.54-4.43 (m, 1H), 4.21-4.10 (m, 1H), 3.73-3.62 (m, 1H), 3.27-3.01 (m, 5H), 2.94 (s, 3H), 2.16-1.90 (m, 8H), 1.78-1.39 (m, 8H), 1.30 (d, J=6.5 Hz, 3H), 0.99 (1t, J=7.3 Hz, 3H). MS (ESI) for [M+H]+(C$_{30}$H$_{42}$N$_6$O$_2$$^+$): calcd. m/z 519.34; found m/z 519.35. LC-MS: >95% purity.

iii. (4-chlorophenyl)(4-(7-((1R,4S)-4-hydroxycyclohexyl)-2-(((S)-pentan-2-yl)amino)-7H-pyrrolo[2,3-d]pyrimidin-5-yl)piperidin-1-yl)methanone (84)

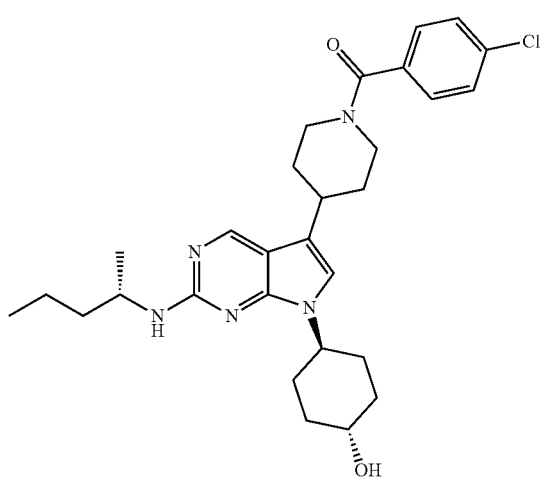 [SMILES: CCC[C@H](C)Nc1ncc2c(C3CCN(C(=O)c4ccc(Cl)cc4)CC3)cn([C@H]3CC[C@H](O)CC3)c2n1]

$^1$H NMR (400 MHz, CD$_3$OD) δ 8.60 (s, 1H), 7.52-7.43 (m, 3H), 7.36 (dt, J=7.0, 1.4 Hz; 1H), 7.32 (s, 1H), 4.78-4.68 (m, 1H), 4.53-4.44 (m, 1H), 4.20-4.12 (m, 1H), 3.84-3.74 (m, 1H), 3.73-3.61 (m, 1H), 3.14-2.96 (m, 3H), 2.18-1.91 (m, 8H), 1.79-1.39 (m, 8H), 1.30 (d, J=6.6 Hz, 3H), 0.98 (t, J=7.3 Hz, 3H). MS [M+H]$^+$ m/z 524.30.

jjj. (4-(7-((1R,4S)-4-hydroxycyclohexyl)-2-(((S)-pentan-2-yl)amino)-7H-pyrrolo[2,3-d]pyrimidin-5-yl)piperidin-1-yl)(4-((methylamino)methyl)phenyl)methanone (85)

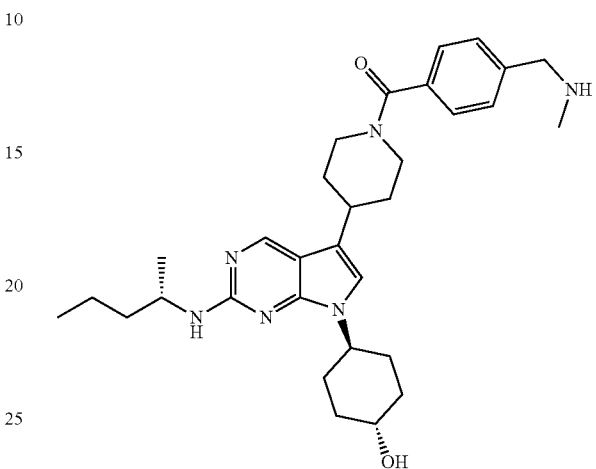

$^1$H NMR (400 MHz, CD$_3$OD) δ 8.62 (s, 1H), 7.57 (dd, J=20.2, 8.3 Hz, 4H), 7.32 (s, 1H), 4.80-4.69 (m, 1H), 4.53-4.42 (m, 1H), 4.24 (s, 2H), 4.22-4.11 (m, 1H), 3.84-3.74 (m, 1H), 3.73-3.62 (m, 1H), 3.34 (s, 1H), 3.29-3.25 (m, 1H), 3.07 (dd, J=25.8, 13.8 Hz, 2H), 2.74 (s, 3H), 2.19-1.87 (m, 8H), 1.79-1.40 (m, 8H), 1.30 (d, J=6.5 Hz, 3H), 0.98 (t, J=7.3 Hz, 3H). MS [M+H]$^+$ m/z 532.40.

kkk. (2,6-dimethylpyridin-4-yl(4-(7-((R,4S)-4-(hydroxymethyl)cyclohexyl)-2-(((S)-pentan-2-yl)amino)-7H-pyrrolo[2,3-d]pyrimidin-5-yl)piperidin-7-yl)methanone (86)

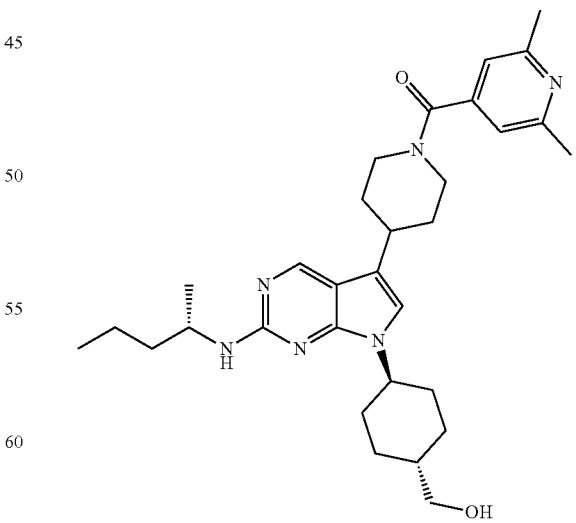

$^1$H NMR (400 MHz, CD$_3$OD) δ 8.67 (d, J=2.0 Hz, 1H), 7.71 (s, 2H), 7.35 (s, 1H), 4.77-4.69 (m, 1H), 4.53-4.43 (m, 1H), 4.20-4.12 (m, 1H), 3.66-3.57 (m, 1H), 3.44 (d, J=6.2

Hz, 2H), 3.35 (t, J=9.6 Hz, 1H), 3.19-2.99 (m, 3H), 2.77 (s, 5H), 2.15 (d, J=12.9 Hz, 1H), 2.04-1.89 (m, 6H), 1.81-1.53 (m, 6H), 1.50-1.40 (m, 2H), 1.29 (d, J=6.5 Hz, 3H), 1.27-1.17 (m, 2H), 0.97 (t, J=7.3 Hz, 3H). MS [M+H]$^+$ m/z 532.40.

lll. (4-((dimethylamino)methyl)phenyl)(4-(7-((1R,4S)-4-hydroxycyclohexyl)-2-(((S)-pentan-2-yl)amino)-7H-pyrrolo[2,3-d]pyrimidin-5-yl)piperidin-1-yl)methanone (87)

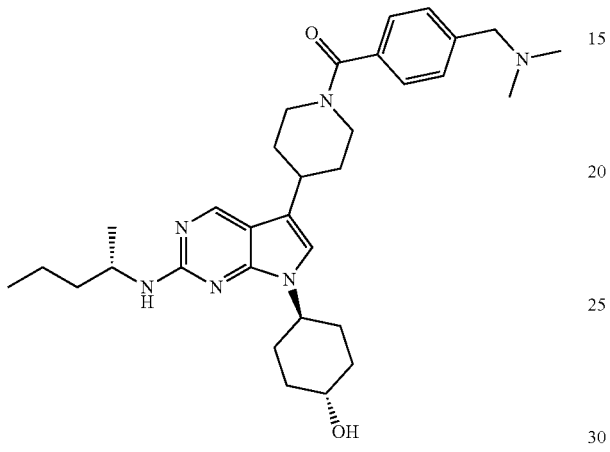

$^1$H NMR (400 MHz, CD$_3$OD) δ 8.63 (s, 1H), 7.64 (d, J=8.1 Hz, 2H), 7.57 (d, J=8.1 Hz, 2H), 7.33 (s, 1H), 4.81-4.72 (m, 1H), 4.54-4.43 (m, 1H), 4.39 (d, J=5.6 Hz, 2H), 4.21-4.09 (m, 1H), 3.79 (d, J=13.2 Hz, 1H), 3.74-3.63 (m, 1H), 3.31 (s, 1H), 3.17-2.96 (m, 2H), 2.88 (s, 6H), 2.18-1.90 (m, 8H), 1.79-1.39 (m, 8H), 1.30 (d, J=6.6 Hz, 3H), 0.98 (t, J=7.3 Hz, 3H). MS [M+H]$^+$ m/z 547.40.

mmm. (4-(7-((1R,4S)-4-(difluoromethyl)cyclohexyl)-2-(((S)-pentan-2-yl)amino)-7H-pyrrolo[2,3-d]pyrimidin-5-yl)piperidin-1-yl)(2,6-dimethylpyridin-4-yl)methanone (88)

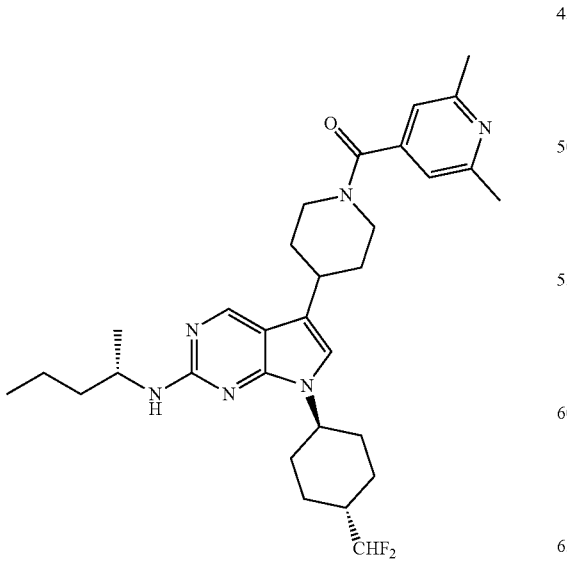

$^1$H NMR (400 MHz, CD$_3$OD) δ 8.65 (s, 1H), 7.63 (s, 2H), 7.35 (s, 1H), 5.73 (td, J=56.7, 4.2 Hz, 2H), 4.73 (d, J=13.7 Hz, 1H), 4.56-4.46 (m, 1H), 4.20-4.12 (m, 1H), 3.65-3.58 (m, 1H), 3.35 (d, J=12.4 Hz, 1H), 3.16-3.01 (m, 2H), 2.74 (s, 5H), 2.19-1.86 (m, 8H), 1.80-1.56 (m, 4H), 1.53-1.37 (m, 4H), 1.30 (d, J=6.6 Hz, 3H), 0.98 (t, J=7.3 Hz, 3H). MS [M+H]$^+$ m/z 553.35.

nnn. (4-fluorophenyl)(4-(7-((1R,4S)-4-hydroxycyclohexyl)-2-(((S)-pentan-2-yl)amino)-7H-pyrrolo[2,3-d]pyrimidin-5-yl)piperidin-1-yl)methanone (89)

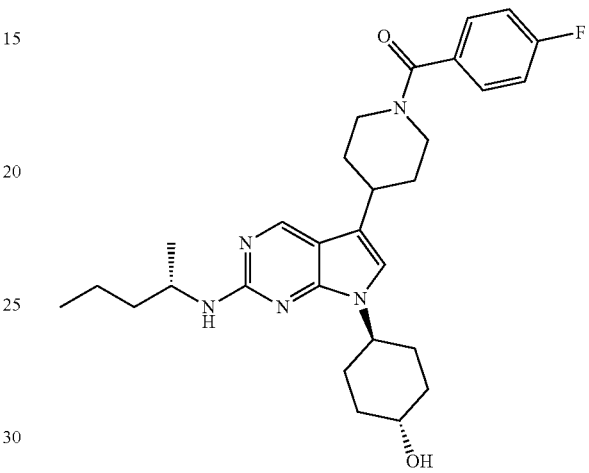

$^1$H NMR (400 MHz, CD$_3$OD), 8.60 (s, 1H), 7.53-7.44 (m, 2H), 7.31 (s, 1H), 7.25-7.17 (m, 2H), 4.79-4.69 (m, 1H), 4.53-4.44 (m, 1H), 4.22-4.06 (m, 1H), 3.84 (s, 1H), 3.74-3.60 (m, 1H), 3.16-2.93 (m, 3H), 2.15-1.92 (m, 8H), 1.73-1.40 (m, 8H), 1.29 (d, J=6.6 Hz, 3H), 0.98 (t, J=7.3 Hz, 3H). MS [M+H]$^+$ m/z 508.30.

ooo. (4-(7-(((1R,4S)-4-aminocyclohexyl)methyl)-2-(((S)-pentan-2-yl)amino)-7H-pyrrolo[2,3-d]pyrimidin-5-yl)piperidin-1-yl)(2,6-dimethylpyridin-4-yl)methanone (102)

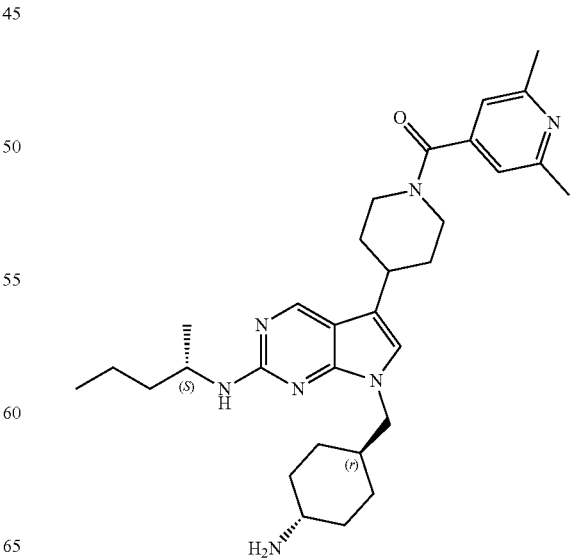

¹H NMR (400 MHz, CD₃OD) δ 8.73 (s, 1H), 7.79 (s, 2H), 7.29 (s, 1H), 4.74 (d, J=13.3 Hz, 1H), 4.23-4.11 (m, 1H), 4.10-3.94 (m, 2H), 3.63 (d, J=13.2 Hz, 1H), 3.43-3.32 (m, 1H), 3.21-3.01 (m, 3H), 2.81 (s, 6H), 2.17 (d, J=12.8 Hz, 1H), 2.11-1.87 (m, 4H), 1.86-1.71 (m, 4H), 1.71-1.53 (m, 2H), 1.52-1.33 (m, 4H), 1.30 (d, J=6.5 Hz, 3H), 1.28-1.16 (m, 2H), 0.98 (t, J=7.3 Hz, 3H). MS [M+H]⁺ m/z 532.30.

ppp. (2,6-dimethylpyridin-4-yl)(4-(7-(((1R,4S)-4-hydroxycyclohexyl)methyl)-2-(((S)-pentan-2-yl)amino)-7H-pyrrolo[2,3-d]pyrimidin-5-yl)piperidin-1-yl)methanone (103)

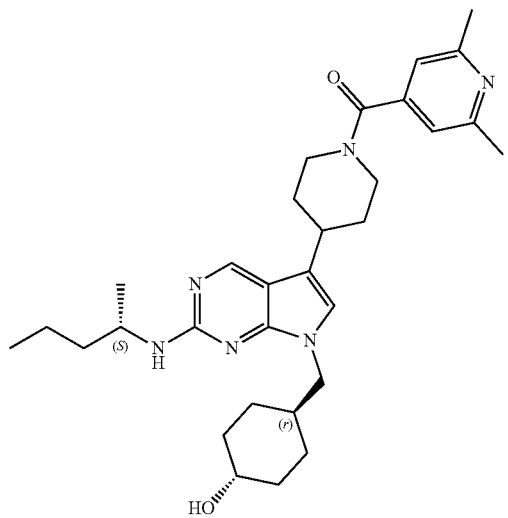

¹H NMR (400 MHz, CD₃OD) δ 8.66 (s, 1H), 7.75 (s, 2H), 7.23 (s, 1H), 4.74 (d, J=13.6 Hz, 1H), 4.22-4.11 (m, 1H), 4.03-3.89 (m, 2H), 3.66-3.57 (m, 1H), 3.53-3.44 (m, 1H), 3.40-3.34 (m, 1H), 3.18-3.02 (m, 2H), 2.79 (s, 6H), 2.18 (d, J=12.3 Hz., 1H), 2.05-1.91 (m, 3H), 1.89-1.79 (m, 1H), 1.79-1.69 (m, 2H), 1.69-1.52 (m, 4H), 1.51-1.41 (m, 2H), 1.30 (d, J=6.6 Hz, 3H), 1.24-1.10 (m, 4H), 0.98 (t, J=7.3 Hz, 3H). MS [M+H]⁺ m/z 533.30.

d. General Procedure C

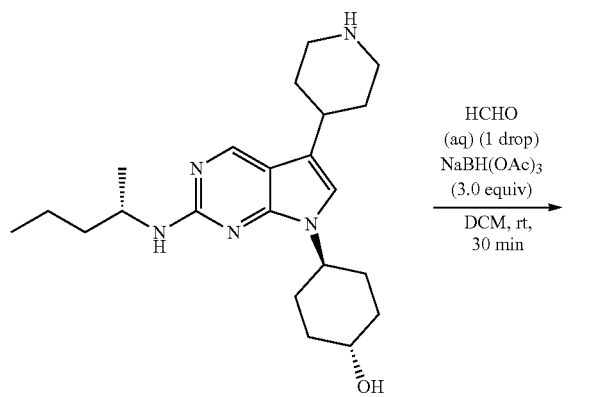

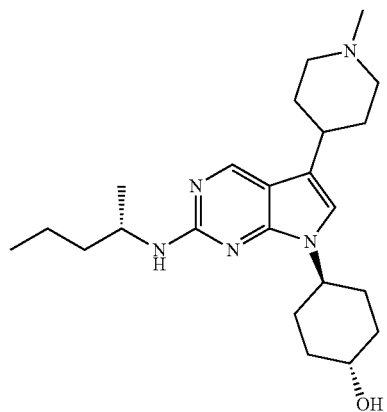

To a solution of crude amine (39 mg, 0.1 mmol, 1.0 equiv) in dichloromethane (1 mL) at room temperature was added a drop of formaldehyde solution (37 wt % in water) and sodium triacetoxyborohydride (64 mg, 0.3 mmol, 3.0 equiv). The resulting mixture was stirred at room temperature for 30 minutes. Upon evaporation of solvent, the residue was purified by HPLC to afford the desired compound.

(i) (1S,4R)-4-(5-([1,4'-bipiperidin]-4-yl)-2-(((S)-pentan-2-yl)amino)-7H-pyrrolo[2,3-d]pyrimidin-7-yl)cyclohexan-1-ol (51)

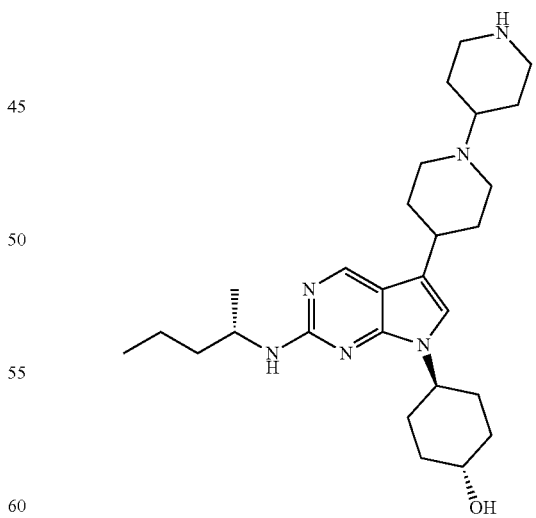

¹H NMR (400 MHz, CD₃OD) δ 8.80 (s, 1H), 7.40 (s, 1H), 4.55-4.45 (m, 1H), 4.20-4.10 (m, 1H), 3.75-3.60 (m, 7H), 3.30-3.20 (m, 1H), 3.20-3.10 (m, 3H), 2.55-2.43 (m, 2H), 2.15-1.90 (m, 10H), 1.70-1.40 (m, 6H), 1.35-1.25 (m, 5H), 0.99 (t, J=7.2 Hz, 3H). MS m/z 469.37 [M+H]⁺.

257

(ii) (1S,4R)-4-(5-(1'-methyl-[1,4'-bipiperidin]-4-yl)-2-(((S)-pentan-2-yl)amino)-7H-pyrrolo[2,3-d]pyrimidin-7-yl)cyclohexan-1-ol (52)

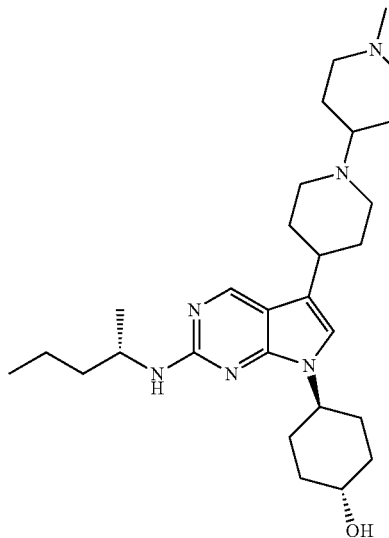

¹H NMR (400 MHz, CD₃OD) δ 8.80 (s, 1H), 7.40 (s, 1H), 4.55-4.45 (m, 1H), 4.20-4.10 (m, 1H), 3.75-3.60 (m, 7H), 3.30-3.20 (m, 1H), 3.20-3.10 (m, 3H), 2.91 (s, 3H), 2.55-2.43 (m, 2H), 2.15-1.90 (m, 1OH), 1.70-1.40 (m, 6H), 1.35-1.25 (m, 5H), 0.99 (t, J=7.2 Hz, 3H). MS m/z 483.38 [M+H]⁺.

(iii) (1S,4R)-4-(2-(((S)-pentan-2-yl)amino)-5-(1-(piperidin-4-ylmethyl)piperidin-4-yl)-7H-pyrrolo[2,3-d]pyrimidin-7-yl)cyclohexan-1-ol (53)

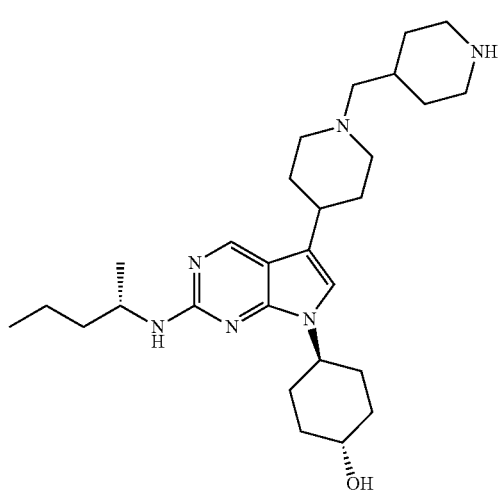 [SMILES: CCC[C@H](C)Nc1ncc2c(C3CCN(CC4CCNCC4)CC3)cn([C@H]3CC[C@H](O)CC3)c2n1]

¹H NMR (400 MHz. CD₃OD) δ 8.84 (s, 1H), 7.40 (s, 1H), 4.55-4.45 (m, 1H), 4.20-4.10 (m, 1H), 3.80-3.60 (m, 4H), 3.50-3.40 (m, 2H), 3.20-3.00 (m, 6H), 2.40-1.92 (m, 12H), 1.71-1.40 (m, 8H), 1.35-1.28 (m, 4H), 0.98 (t, J=7.2 Hz, 3H). MS m/z 483.38 [M+H]⁺.

258

(iv) (1S,4R)-4-(5-(1-((l-methylpiperidin-4-yl)methyl)piperidin-4-yl)-2-(((S)-pentan-2-yl)amino)-7H-pyrrolo[2,3-d]pyrimidin-7-yl)cyclohexan-1-ol (54)

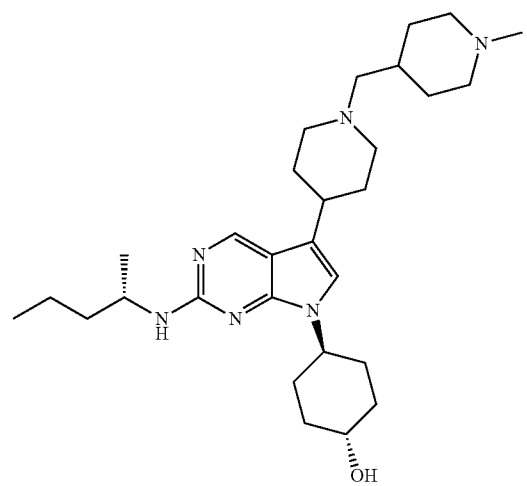 [SMILES: CCC[C@H](C)Nc1ncc2c(C3CCN(CC4CCN(C)CC4)CC3)cn([C@H]3CC[C@H](O)CC3)c2n1]

¹H NMR (400 MHz, CD₃OD) δ 8.84 (s, 1H), 7.40 (s, 1H), 4.55-4.45 (m, 1H), 4.20-4.10 (m, 1H), 3.80-3.60 (m, 4H), 3.50-3.40 (m, 2H), 3.20-3.00 (m, 6H), 2.88 (s, 3H), 2.40-1.92 (m, 12H), 1.71-1.40 (m, 8H), 1.35-1.28 (m, 4H), 0.98 (t, J=7.2 Hz; 3H). MS m/z 497.40 [M+H]⁺.

(iii) (1S,4R)-4-(5-(1-((2,6-dimethylpyridin-4-yl)methyl)piperidin-4-yl)-2-(((S)-pentan-2-yl)amino)-7H-pyrrolo[2,3-d]pyrimidin-7-yl)cyclohexan-1-ol (90)

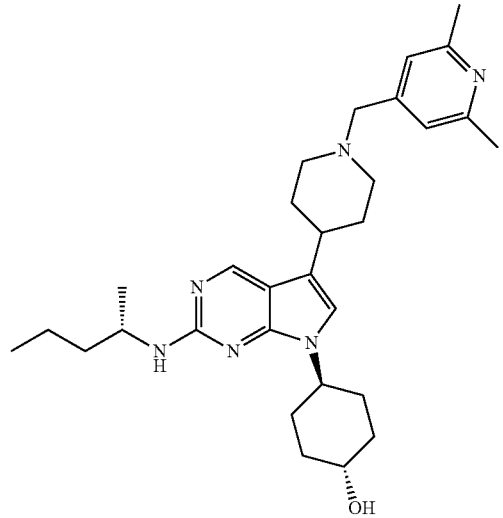 [SMILES: CCC[C@H](C)Nc1ncc2c(C3CCN(Cc4cc(C)nc(C)c4)CC3)cn([C@H]3CC[C@H](O)CC3)c2n1]

¹H NMR (400 MHz, CD₃OD) 8.68 (d, J=7.8 Hz, 1H), 7.85 (d, J=4.5 Hz, 2H), 7.47 (d, J=12.2 Hz, 1H), 4.57-4.43 (m, 1H), 4.23-4.11 (m, 1.5H), 3.95-3.85 (m, 1H), 3.79-3.53 (m, 4.5H), 2.81 (d, J=7.6 Hz, 6H), 2.55-2.38 (m, 1H), 2.25-2.07 (m, 3H), 2.06-1.91 (m, 4H), 1.77-1.54 (m, 2H), 1.54-1.39 (m, 4H), 1.31 (dd, J=8.0, 6.7 Hz, 3H), 0.99 (q, J=7.0 Hz, 3H). MS [M+H]⁺ m/z 505.30; d.r.=1:1.

(iv) (1S,4R)-4-(5-(1-((2,6-dimethylpyridin-4-yl)methyl)piperidin-4-yl)-2-(((S)-1-phenylethyl)amino)-7H-pyrrolo[2,3-d]pyrimidin-7-yl)cyclohexan-1-ol (91)

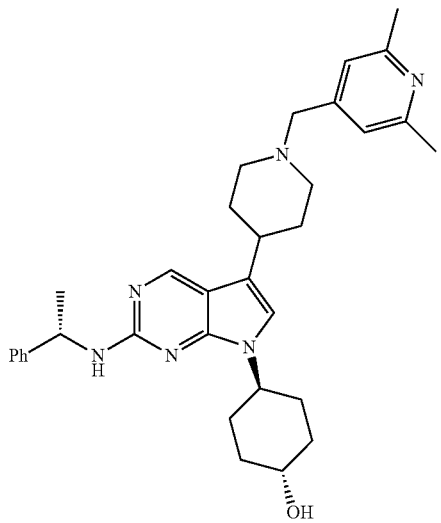 [SMILES: Cc1cc(CN2CCC(c3cn([C@H]4CC[C@H](O)CC4)c4nc(N[C@@H](C)c5ccccc5)ncc34)CC2)cc(C)n1]

¹H NMR (400 MHz. CD₃OD) δ 8.72-8.65 (m, 1H), 7.83-7.75 (m, 2H), 7.47-7.30 (m, 5H), 7.28-7.20 (m, 1H), 5.17-5.03 (m, 1H), 4.38-4.23 (m, 1H), 4.15 (dd, J=11.7, 7.7 Hz, 0.5H), 3.94-3.80 (m, 1H), 3.78-3.46 (m, 4.5H), 2.85-2.73 (m, 6H), 2.52-2.35 (m, 1H), 2.22-1.97 (m, 3H), 1.93-1.74 (m, 3H), 1.73-1.66 (m, 1H), 1.64 (t, J=7.1 Hz, 3H), 1.53-1.36 (m, 2H). MS [M+H]⁺ m/z 539.30, d.r.=1:1.

(v) (1S,4R)-4-(5-(1-(cyclohexylmethyl)piperidin-4-yl)-2-(((S)-1-phenylethyl)amino)-7H-pyrrolo[2,3-d]pyrimidin-7-yl)cyclohexan-1-ol (92)

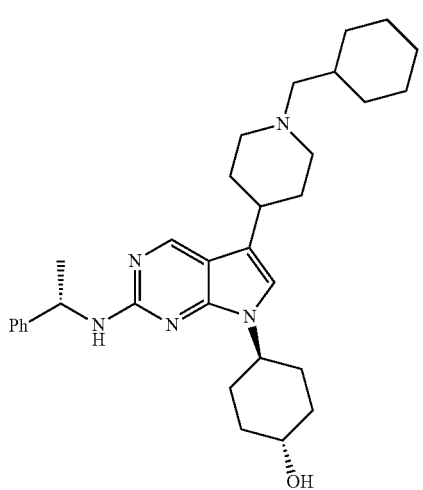 [SMILES: C[C@H](Nc1ncc2c(C3CCN(CC4CCCCC4)CC3)cn([C@H]3CC[C@H](O)CC3)c2n1)c1ccccc1]

¹H NMR (400 MHz, CD₃OD) δ 8.80 (s, 1H), 7.48-7.42 (m, 2H), 7.40-7.33 (m, 3H), 7.29-7.24 (m, 1H), 5.12 (q, J=6.9 Hz, 1H), 4.39-4.26 (m, 1H), 3.75-3.62 (m, 3H), 3.18-3.06 (m, 3H), 3.03 (d, J=6.7 Hz, 2H), 2.25-2.01 (m, 6H), 1.91-1.80 (m, 7H), 1.78-1.68 (m, 2H), 1.66 (d, J=7.0 Hz, 3H), 1.56-1.23 (m, 6H), 1.17-1.05 (m, 2H). MS m/z 516.40 [M+H]⁺.

(vi) (1S,4R)-4-(5-(1-ethylpiperidin-4-yl)-2-(((S)-1-phenylethyl)amino)-7H-pyrrolo[2,3-d]pyrimidin-7-yl)cyclohexan-1-ol (93)

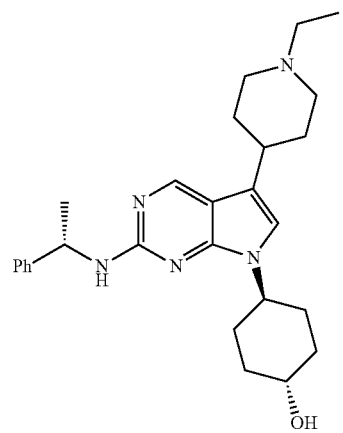 [SMILES: CCN1CCC(c2cn([C@H]3CC[C@H](O)CC3)c3nc(N[C@@H](C)c4ccccc4)ncc23)CC1]

¹H NMR (400 MHz. CD₃OD) δ 8.73 (s, 1H), 7.47-7.41 (m, 2H), 7.37-7.30 (m, 3H), 7.27-7.21 (m, 1H), 5.10 (q, J=6.8 Hz, 1H), 4.37-4.25 (m, 1H), 3.73-3.61 (m, 3H), 3.23 (q, J=7.3 Hz, 2H), 3.17-3.01 (m, 3H), 2.29-2.19 (m, 2H), 2.11-1.94 (m, 4H), 1.91-1.75 (m, 3H), 1.71-1.62 (m, 4H), 1.50-1.44 (m, 1H), 1.40 (t, J=7.3 Hz, 3H), 1.36-1.28 (m, 1H). MS m/z 448.30 [M+H]⁺.

(vii) (1S,4R)-4-(5-(1-isopropylpiperidin-4-yl)-2-(((S)-1-phenylethyl)amino)-7H-pyrrolo[2,3-d]pyrimidin-7-yl)cyclohexan-1-ol (94)

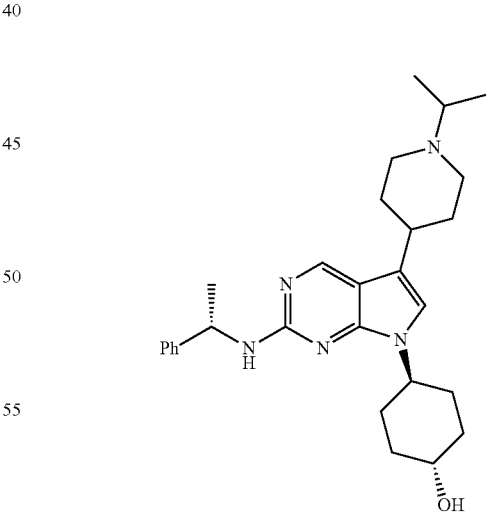

¹H NMR (400 MHz, CD₃OD) δ 8.77 (s, 1H), 7.47-7.40 (m, 2H), 7.38-7.28 (m, 3H), 7.27-7.21 (m, 1H), 5.10 (q, J=6.8 Hz, 1H), 4.37-4.25 (m, 1H), 3.71-3.59 (m, 1H), 3.59-3.49 (m, 3H), 3.25-3.14 (m, 2H), 3.13-3.03 (m, 1H), 2.28-2.20 (m, 2H), 2.15-1.99 (m, 4H), 1.91-1.76 (m, 3H), 1.71-1.65 (m, 1H), 1.63 (d, J=7.0 Hz, 3H), 1.53-1.43 (m, 2H), 1.41 (d, J=6.7 Hz, 6H). MS m/z 462.40 [M+H]⁺.

(viii) (4-(7-((1R,4S)-4-aminocyclohexyl)-2-(((S)-pentan-2-yl)amino)-7H-pyrrolo[2,3-d]pyrimidin-5-yl)piperidin-1-yl)(2,6-dimethylpyridin-4-yl)methanone (95)

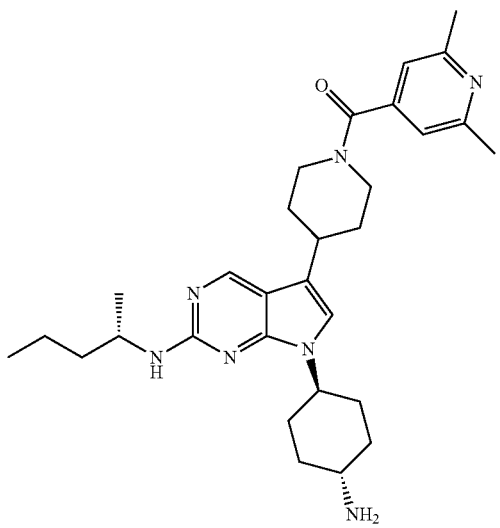 [SMILES: CCC[C@H](C)Nc1ncc2c(C3CCN(C(=O)c4cc(C)nc(C)c4)CC3)cn([C@H]3CC[C@H](N)CC3)c2n1]

¹H NMR (400 MHz, CD₃OD) δ 8.70 (s, 1H), 7.77 (s, 2H), 7.41 (s, 1H), 4.74 (d, J=13.5 Hz, 1H), 4.63-4.51 (m, 1H), 4.24-4.12 (m, 1H), 3.68-3.55 (m, 1H), 3.40-3.33 (m, 1H), 3.30-3.24 (m, 1H), 3.19-3.01 (m, 2H), 2.80 (s, 6H), 2.28-2.20 (m, 2H), 2.19-2.05 (m, 5H), 2.02-1.95 (m, 1H), 1.84-1.53 (m, 6H), 1.52-1.40 (m, 2H), 1.31 (d, J=6.5 Hz, 3H), 0.99 (t, J=7.3 Hz, 3H). MS [M+H]⁺ m/z 518.30.

(ix) (2,6-dimethylpyridin-4-yl)(3-(7-((1R,4S)-4-hydroxycyclohexyl)-2-(((S)-pentan-2-yl)amino)-7H-pyrrolo[2,3-d]pyrimidin-5-yl)pyrrolidin-1-yl)methanone (96)

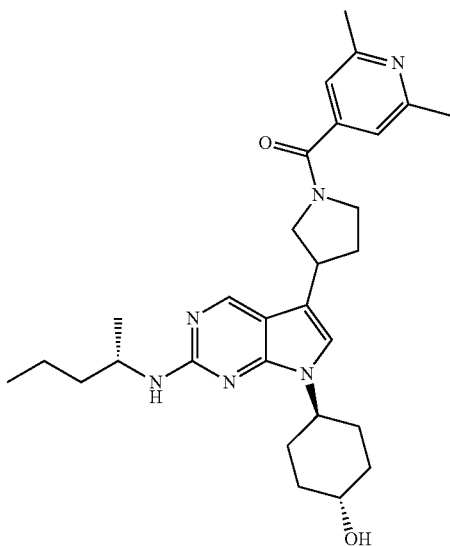 [SMILES: CCC[C@H](C)Nc1ncc2c(C3CCN(C(=O)c4cc(C)nc(C)c4)C3)cn([C@H]3CC[C@H](O)CC3)c2n1]

¹H NMR (400 MHz, CD₃OD) δ 8.68 (d, J=7.8 Hz, 1H), 7.85 (d, J=4.5 Hz, 2H), 7.47 (d, J=12.2 Hz, 1H), 4.57-4.43 (m, 1H) 4.23-4.11 (m, 1.5H) 3.95-3.85 (m, 1H), 3.79-3.53 (m, 4.5H), 2.81 (d, J=7.6 Hz, 6H), 2.55-2.38 (m, 1H), 2.25-2.07 (m, 3H), 2.06-1.91 (m, 4H), 1.77-1.54 (m, 2H), 1.54-1.39 (m, 4H), 1.31 (dd, J=8.0, 6.7 Hz, 3H), 0.99 (q, J=7.0 Hz, 3H). MS [M+H]⁺ m/z 505.30, d.r.=1:1.

(x) (2,6-dimethylpyridin-4-yl)(3-(7-((1R,4S)-4-hydroxycyclohexyl)-2-(((S)-1-phenylethyl)amino)-7H-pyrrolo[2,3-d]pyrimidin-5-yl)pyrrolidin-1-yl)methanone (97)

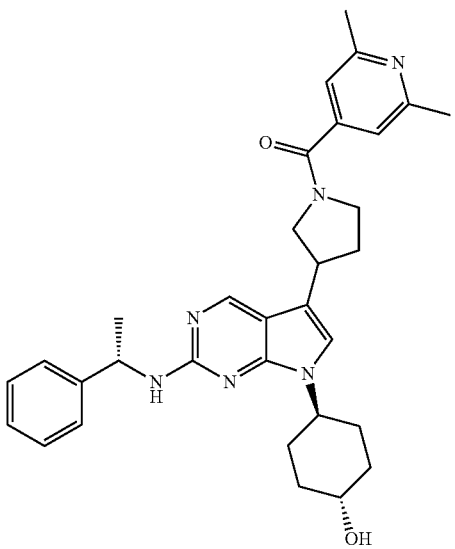 [SMILES: Cc1cc(C(=O)N2CCC(c3cn([C@H]4CC[C@H](O)CC4)c4nc(N[C@@H](C)c5ccccc5)ncc34)C2)cc(C)n1]

¹H NMR (400 MHz, CD₃OD) δ 8.72-8.65 (m, 1H), 7.83-7.75 (m, 2H), 7.47-7.30 (m, 5H), 7.28-7.20 (m, 1H), 5.17-5.03 (m, 1H), 4.38-4.23 (m, 1H), 4.15 (dd, J=11.7, 7.7 Hz, 0.5H), 3.94-3.80 (m, 1H), 3.78-3.46 (m, 4.5H), 2.85-2.73 (m, 6H), 2.52-2.35 (m, 1H), 2.22-1.97 (m, 3H), 1.93-1.74 (m, 3H), 1.73-1.66 (m, 1H), 1.64 (t, J=7.1 Hz, 3H), 1.53-1.36 (m, 2H). MS [M+H]⁺ m/z 539.30, d.r.=1:1.

(xi) (1S,4R-4-(2-(((S)-pentan-2-yl)amino)-5-(pyrrolidin-3-yl)-7H-pyrrolo[2,3-d]pyrimidin-7-yl)cyclohexan-1-ol (98)

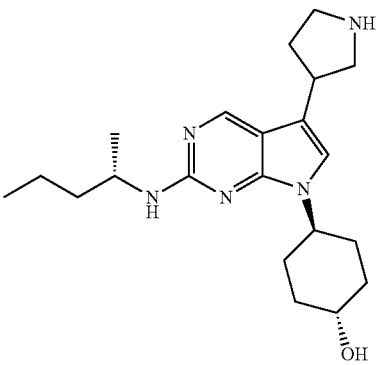 [SMILES: CCC[C@H](C)Nc1ncc2c(C3CCNC3)cn([C@H]3CC[C@H](O)CC3)c2n1]

¹H NMR (400 MHz, CD₃OD) δ 8.74 (s, 1H), 7.55 (s, 1H), 4.57-4.43 (m, 1H), 4.25-4.09 (m, 1H), 3.80-3.65 (m, 3H), 3.57 (ddd, J=11.9, 8.3, 3.9 Hz, 1H), 3.47-3.37 (m, 1H), 3.37-3.32 (m, 1H), 2.59-2.45 (m, 1H), 2.25-2.07 (m, 3H), 2.06-1.94 (m, 4H), 1.74-1.63 (m, 1H), 1.63-1.54 (m, 1H), 1.54-1.40 (m, 4H), 1.31 (d, J=6.5 Hz, 3H), 0.99 (t, J=7.3 Hz, 3H). MS m/z 372.30 [M+H]$^+$.

(xii) (1S,4R)-4-(5-(1-methylpyrrolidin-3-yl)-2-(((S)-pentan-2-yl)amino)-7H-pyrrolo[2,3-d]pyrimidin-7-yl)cyclohexan-1-ol (99)

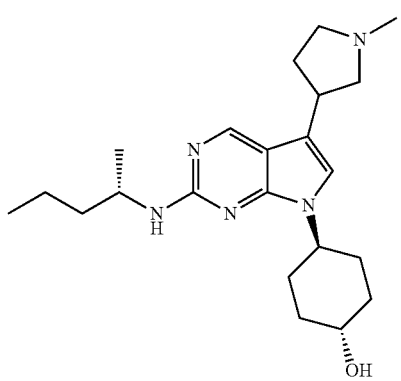 [SMILES: CCC[C@H](C)Nc1ncc2c(C3CCN(C)C3)cn([C@H]3CC[C@H](O)CC3)c2n1]

$^1$H NMR (400 MHz, CD$_3$OD) δ 8.76 (d, J=18.7 Hz, 1H), 7.56 (s, 1H), 4.56-4.45 (m, 1H), 4.22-4.12 (m, 1H), 4.08-3.92 (m, 1H), 3.91-3.65 (m, 3H), 3.63-3.35 (m, 1H), 3.29-3.20 (m, 1H), 3.03 (d, J=11.9 Hz, 3H), 2.69-2.52 (m, 1H), 2.40-2.19 (m, 1H), 2.18-2.06 (m, 2H), 2.06-1.94 (m, 4H), 1.74-1.54 (m, 2H), 1.54-1.40 (m, 4H), 1.31 (d, J=6.5 Hz, 3H), 0.99 (t, J=7.3 Hz, 3H). MS m/z 386.30 [M+H]$^+$.

e. General Procedure D

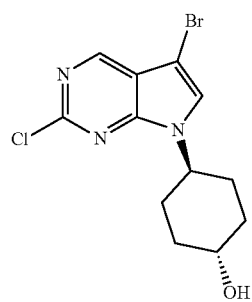

+

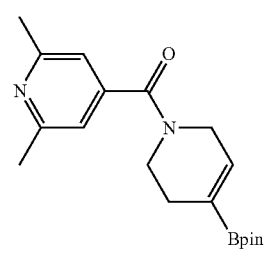

Pd$_2$(dba)$_3$, Na$_2$CO$_3$, ethanol/water (3:1), 90° C., 3 h
71%
→

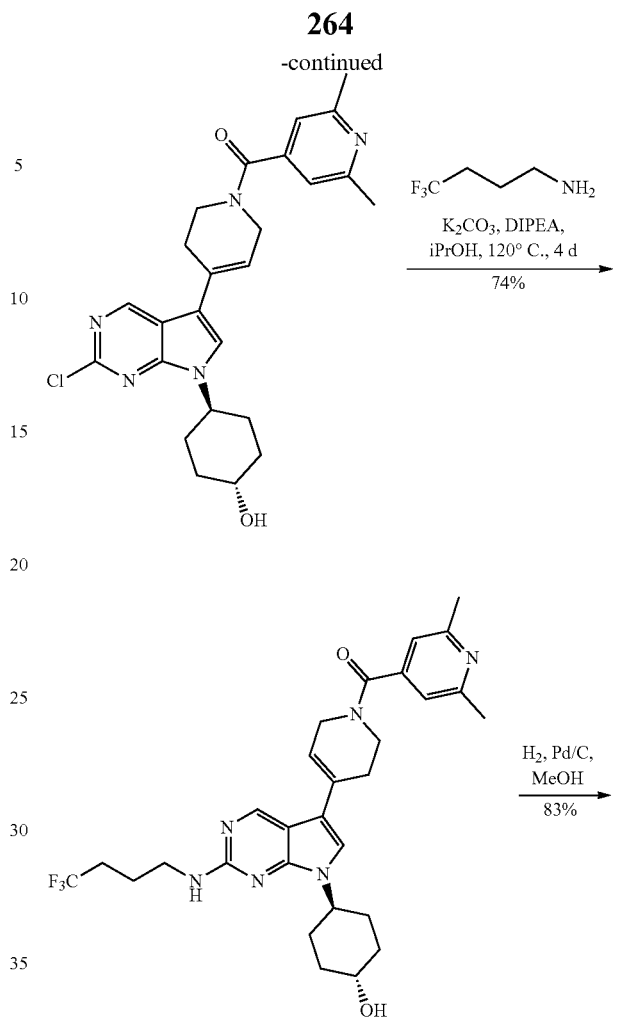

(i) General Palladium-Coupling Procedure

To a solution of trans-4-(5-bromo-2-chloro-7H-pyrrolo[2,3-d]pyrimidin-7-yl)cyclohexan-1-ol (1 g, 3.024 mmol) in ethanol (23.67 g, 30 mL, 513.794 mmol) and water (30.000 g, 30 mL, 1.665 mol) was added (2,6-dimethylpyridin-4-yl)

(4-(4,4,5,5-tetramethyl-1,3,2-dioxaborolan-2-yl)-3,6-dihydropyridin-1(2H)-yl)methanone (1.035 g, 3.024 mmol) and sodium carbonate (0.641 g, 6.049 mmol) and Pd$_2$(dba)$_3$ (0.276 g, 0.302 mmol). The system was degassed and refilled by N$_2$ 3 times and heated 90° C. for 3 h. Extraction with ethyl acetate for 3 times. The organic phase was combined and washed with brine, dried over sodium sulfate. After removal of the solvent under reduced pressure, the residue was purified by ISCO to give (4-(2-chloro-7-(trans-4-hydroxycyclohexyl)-7H-pyrrolo[2,3-d]pyrimidin-5-yl)-3,6-dihydropyridin-1(2H)-yl)(2,6-dimethylpyridin-4-yl)methanone (1 g, 70.95%) as a yellow solid.

(ii) General Amination Procedure

To a solution of (4-(2-chloro-7-(trans-4-hydroxycyclohexyl)-7H-pyrrolo[2,3-d]pyrimidin-5-yl)-3,6-dihydropyridin-1 (2H)-yl)(2,6-dimethylpyridin-4-yl)methanone (100 mg, 0.214 mmol) and N-ethyl-N-isopropylpropan-2-amine (0.055 g, 0.074 mL, 0.429 mmol) in propan-2-ol (1.571 g, 2 mL, 26.158 mmol) was added potassium carbonate (0.029 g, 0.214 mmol) (powder) and 4,4,4-trifluorobutan-1-amine (0.054 g, 0.049 mL, 0.429 mmol). The mixture was blowed by N$_2$ and then sealed in a sealed tube and heated at 120° C., for 4 days. Water was added and the mixture was extracted by ethyl acetate for 3 times and the combined organic phases were washed with brine and dried over sodium sulfate. After removal of the solvent under reduced pressure, the residue was purified by ISCO to give (2,6-dimethylpyridin-4-yl)(4-(7-(trans-4-hydroxycyclohexyl)-2-((4,4,4-trifluorobutyl)amino)-7H-pyrrolo[2,3-d]pyrimidin-5-yl)-3,6-dihydropyridin-1(2H)-yl)methanone (88 mg, 73.67%).

(iii) General Hydrogenation Procedure

To a solution of (2,6-dimethylpyridin-4-yl)(4-(7-(trans-4-hydroxycyclohexyl)-2-((4,4,4-trifluorobutyl)amino)-7H-pyrrolo[23-d]pyrimidin-5-yl)-3,6-dihydropyridin-1(2H)-yl)methanone (88 mg, 0.16 mmol) in methanol (71 g, 90 mL, 2.2 mol) was added palladium on carbon (88 mg, 0.83 mmol). The system was degassed and filled with H$_2$ for 3 times. The mixture was stirred overnight for 12h. Filtration and evaporation gave a residue which was purified by HPLC (0~100% MeCN in water+0.1% trifluoroacetic acid) to afford the title compound as TFA salt, which was converted to HCl salt with 4 N HCl in 1,4-dioxane and lyophilized to give (2,6-dimethylpyridin-4-yl)(4-(7-(trans-4-hydroxycyclohexyl)-2-((4,4,4-trifluorobutyl)amino)-7H-pyrrolo[2,3-d]pyrimidin-5-yl)piperidin-1-yl)methanone as yellow solid (73 mg, 83%). $^1$H NMR (400 MHz, CD$_3$OD) δ 8.75 (s, 1H), 7.79 (s, 2H), 7.39 (s, 1H), 4.74 (d, J=13.6 Hz, 1H), 4.59-4.47 (m, 1H), 3.75-3.57 (m, 4H), 3.42-3.32 (m, 1H), 3.21-3.02 (m, 2H), 2.81 (s, 6H), 2.40-2.26 (m, 2H), 2.21-2.07 (m, 3H), 2.05-1.93 (m, 7H), 1.87-1.68 (m, 2H), 1.59-1.42 (m, 2H); MS (ESI) for [M+H]$^+$ (C$_{29}$H$_{38}$F$_3$N$_6$O$_2^+$): calcd. m/z 559.30; found m/z 559.30, LC-MS: >95% purity.

a. (2,6-dimethylpyridin-4-Y)(4-(2-((4-hydroxybutyl)amino)-7-((1R,4R)-4-hydroxycyclohexyl)-7H-pyrrolo[2,3-d]pyrimidin-5-yl)piperidin-1-yl)methanone (100)

$^1$H NMR (400 MHz, CD$_3$OD) δ 8.70 (s, 1H), 7.78 (s, 2H), 7.36 (s, 1H), 4.74 (d, J=12.6 Hz, 1H), 4.58-4.46 (m, 1H), 3.76-3.60 (m, 4H), 3.55 (t, J=6.9 Hz, 2H), 3.40-3.33 (m, 1H), 3.20-3.02 (m, 2H), 2.81 (s, 6H), 2.20-2.07 (m, 3H), 2.06-1.93 (m, 5H), 1.78 (dt, J=12.0, 6.6 Hz, 4H), 1.70-1.61 (m, 2H), 1.57-1.44 (m, 2H). MS [M+H]$^+$ m/z 521.30.

b. (2,6-dimethylpyridin-4-yl)(4-(7-((1R,4R)-4-hydroxycyclohexyl)-2-((4,4,4-trifluorobutyl)amino)-7H-pyrrolo[2,3-d]pyrimidin-5-Y L)piperidin-1-yl)methanone (101)

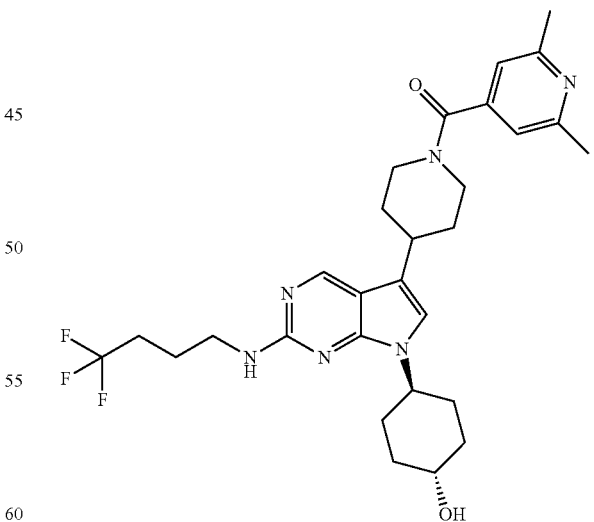

$^1$H NMR (400 MHz, CD$_3$OD) δ 8.75 (s, 1H), 7.79 (s, 2H), 7.39 (s, 1H), 4.74 (d, J=13.6 Hz, 1H), 4.59-4.47 (m, 1H), 3.75-3.57 (m, 4H), 3.42-3.32 (m, 1H), 3.21-3.02 (m, 2H), 2.81 (s, 6H), 2.40-2.26 (m, 2H), 2.21-2.07 (m, 3H), 2.05-1.93 (m, 7H), 1.87-1.68 (m, 2H), 1.59-1.42 (m, 2H). MS [M+H]$^+$ m/z 559.30.

f. Synthesis of Chiral 2-ethylcyclopropanamine

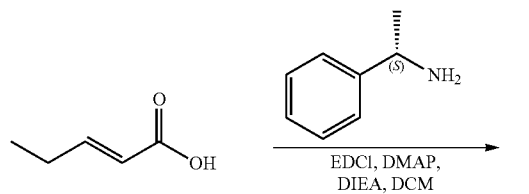

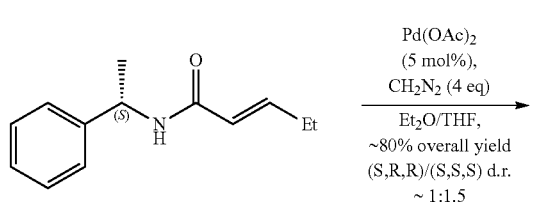

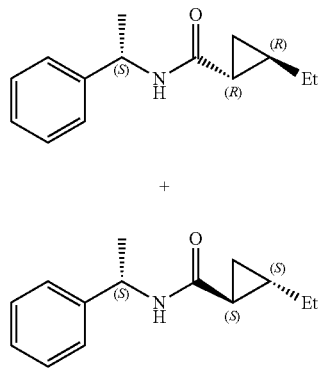

(i) Synthesis of (S,E)-N-(1-phenylethyl)pent-2-enamide

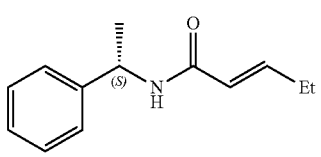

To a solution of (E)-pent-2-enoic acid (2.00 g, 20.0 mmol, 1 equiv.), (S)-1-phenylethanamine (2.42 g, 20.0 mmol, 1 equiv.) in 50 mL DCM at 0° C., was added N,N-dimethylpyridin-4-amine (246 mg, 2.00 mmol, 0.1 equiv.), N-(3-Dimethylaminopropyl)-N'-ethylcarbodiimide hydrochloride (4.20 g, 22.0 mmol, 1.1 equiv.) and N,N-Diisopropylethylamine (3.80 mL, 22.0 mmol, 1.1 equiv.). The reaction mixture was stirred at 0° C., for 1 h, and then moved to room temperature and stirred overnight. The reaction mixture was concentrated and diluted with ethyl acetate. The organic layer was washed with H$_2$O, brine, dried over Na$_2$SO$_4$ and concentrated. The crude residue was purified by ISCO system on silica gel (EA in PE: 0%~50%) to afford the desired product (S,E)-N-(1-phenylethyl)pent-2-enamide 3 (3.22 g, 79%) as white solid. $^1$H NMR (400 MHz, CDCl$_3$) δ 7.25 (dd, J=28.2, 4.0 Hz, 5H), 6.85 (d, J=15.3 Hz, 1H), 5.70 (dt, J=15.3, 1.6 Hz, 1H), 5.60 (s, 1H), 5.20-5.10 (m, 1H), 2.20-2.09 (m, 2H), 1.47 (d, J=6.9 Hz, 3H), 1.00 (t, J=7.4 Hz, 3H).

(iv) Synthesis of (1R,2R)-2-ethyl-N—((S)-1-phenylethyl)cyclopropanecarboxamide/(1S,2S)-2-ethyl-N—((S)-1-phenylethyl)cyclopropanecarboxamide

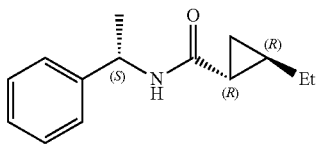

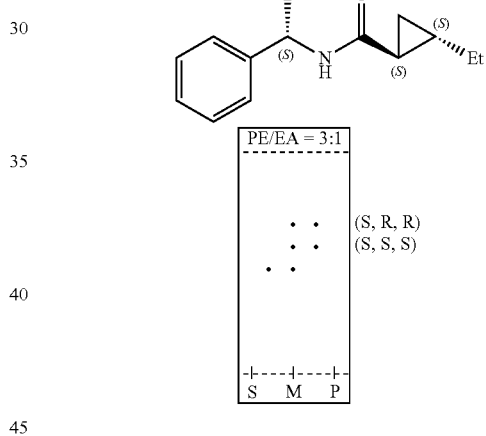

To a solution of (S,E)-N-(1-phenylethyl)pent-2-enamide (500 mg, 2.46 mmol, 1 equiv.) and Pd(OAc)$_2$ (27.5 mg, 0.12 mmol, 0.05 equiv.) in tetrahydrofuran and diethyl ether (1:2, 15 mL) at 0° C., was added CH$_2$N$_2$ solution (10.6 mmol, 4 equiv., freshly prepared from 1-methyl-1-nitrosourea and potassium hydroxide) in 30 mL diethyl ether. The mixture was stirred at 0° C., for 0.5 h and then stirred at room temperature for another 0.5 h. The mixture was filtered through a pad of Celite and purified by ISCO system on silica gel (EA in PE: 0%~10%) to afford the desired products: less polar (1R,2R)-2-ethyl-N—((S)-1-phenylethyl)cyclopropanecarboxamide (181 mg, 34%), more polar (1S, 2S)-2-ethyl-N—((S)-1-phenylethyl) cyclopropanecarboxamide (270 mg, 51%) as white foam.

(1R,2R)-2-ethyl-N—((S)-1-phenylethyl)cyclopropanecarboxamide: $^1$H NMR (400 MHz, CdCl$_3$) δ 7.26-7.22 (m, 5H), 5.70 (s, 1H), 5.09-4.98 (m, 1H), 1.40 (d, J=6.9 Hz, 3H), 1.31-1.15 (m, 3H), 0.98 (ddd, J=15.8, 8.2, 4.1 Hz, 2H), 0.88 (t, J=7.1 Hz, 3H), 0.50-0.43 (m, 1H). MS m/z 218 [M+H]$^+$.

(1S,2S)-2-ethyl-N—((S)-1-phenylethyl)cyclopropanecarboxamide: $^1$H NMR (400 MHz, CDCl$_3$) δ 7.38-7.10 (m, 5H), 5.71 (s, 1H), 5.17-4.97 (m, 1H), 1.43 (d, J=6.9 Hz, 3H), 1.32-1.22 (m, 2H), 1.22-1.13 (m, 1H), 1.08 (dt, J=8.7, 4.4 Hz, 1H), 1.05-0.98 (m, 1H), 0.88 (t, J=7.1 Hz, 3H), 0.56-0.50 (m, 1H). MS m/z 218 [M+H]$^+$.

g. Synthesis of (1R,2R)-2-ethylcyclopropan-1-amine

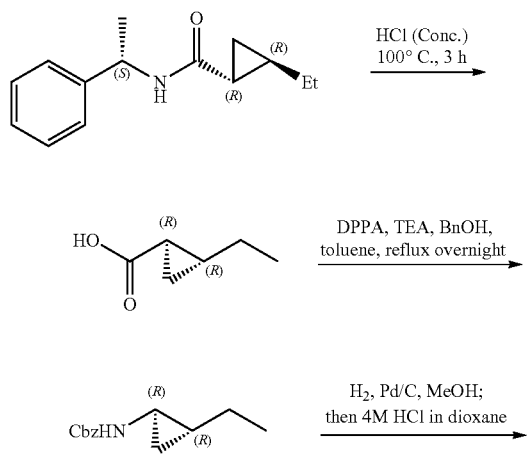

(i) Synthesis of (1R,2R)-2-ETHYLCYCLOPROPANECARBOXYMC ACID

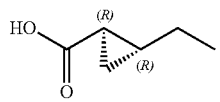

(1R,2R)-2-ethyl-N—((S)-1-phenylethyl)cyclopropanecarboxamide (2.0 g, 9.2 mmol, 1 equiv.) was dissolved in cone, hydrochloric acid (35.0 mL). The mixture was heated to reflux for 5 h and was allowed to cool to 0° C. The mixture was basified by slow addition of sodium hydroxide to pH 10-12. The water phase was extracted by diethyl ether (×2) and the organic phase was discarded. The water phase was acidified to pH 1 by 1M hydrochloric acid aqueous solution. The mixture was extracted by diethyl ether (×3). The organic layer was combined and washed with brine, dried over Na$_2$SO$_4$ and concentrated at 10-15° C., to afford the desired product (1R,2R)-2-ethylcyclopropanecarboxylic acid (1.02 mg, 97%). [α]$_D^{20}$-61.7 (c 1.40, CHCl3); $^1$H NMR (400 MHz, cdcl$_3$) δ 1.45-1.39 (m, 1H), 1.39-1.30 (m, 2H), 1.24-1.18 (m, 2H), 0.98 (t, J=7.3 Hz, 3H), 0.78 (ddd, J=8.1, 6.3, 4.2 Hz, 1H).

(ii) Synthesis of Benzyl ((1R,2R)-2-ethylcyclopropyl)carbamate

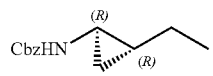

To a solution of (1R,2R)-2-ethylcyclopropanecarboxylic acid (500 mg, 4.40 mmol, 1 equiv.), trimethylamine (737 μL, 5.30 mmol, 1.2 equiv.), benzyl alcohol (1.37 mL, 13.2 mmol, 3 equiv.) in toluene (40.0 mL) was added diphenyl phosphoryl azide (1.04 mL, 4.84 mmol, 1.1 equiv.). The mixture was heated to reflux overnight. Solvent was removed in vacuo and the resulting mixture was purified by ISCO system on silica gel (EA in PE: 0%~15%) to afford the desired products benzyl ((1R,2R)-2-ethylcyclopropyl)carbamate (500 mg, 52%). $^1$H NMR (400 MHz, CDCl$_3$) δ 7.42-7.25 (m, 5H), 5.10 (s, 2H), 4.88 (s, 1H), 2.30 (s, 1H), 1.40-1.15 (m, 3H), 0.98 (s, 3H), 0.85 (s, 1H), 0.70-0.58 (m, 1H), 0.57-0.48 (m, J=6.0 Hz, 1H).

(iii) Synthesis of (1R,2R)-2-ethylcyclopropanamine Hydrochloride

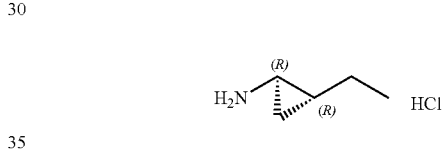

To a solution of Benzyl ((1R,2R)-2-ethylcyclopropyl)carbamate (480 mg, 2.20 mmol) in methanol (25 mL) was added Pd/C (10 wt %, 100 mg). The mixture was stirred at room temperature under hydrogen atmosphere (1 atm) for 2 h. The reaction mixture was filtered through a pad of Celite and 3M HCl in methanol (3 mL) was added. After 5 mins' ultra-sonication, the residue was concentrated in vacuo to give the desired product (1R,2R)-2-ethylcyclopropanamine hydrochloride (282 mg, >95%). %). [α]$_D^{20}$-38.1 (c 1.05, CH$_3$OH); $^1$H NMR (400 MHz, CD$_3$OD) δ 2.35 (dt. J=7.3, 3.5 Hz, 1H), 1.42-1.24 (m, 2H), 1.16-1.06 (m, 1H), 1.01 (t, J=7.4 Hz, 3H), 0.88 (ddd, J=9.9, 6.3, 3.8 Hz, 1H), 0.67 (dd, J=13.8, 6.3 Hz, 1H).

h. Synthesis of (1S,2S)-2-ethylcyclopropan-1-amine

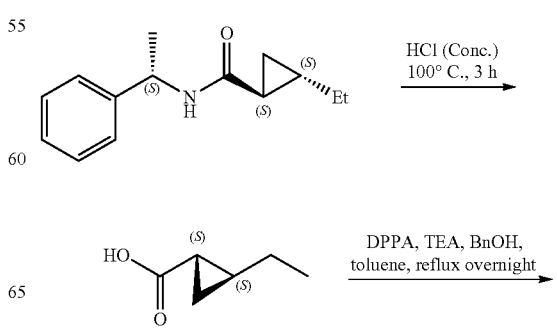

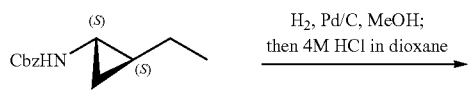

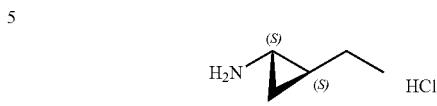

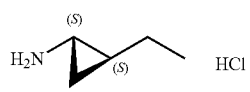

(i) Synthesis of (1S,2S)-2-ethylcyclopropanecarboxylic Acid

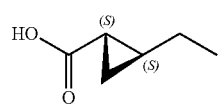

(1S,2S)-2-ethyl-N—((S)-1-phenylethyl)cyclopropanecarboxamide (217 mg, 1.0 mmol, 1 equiv.) was dissolved in Conc. hydrochloric acid (7.0 mL). The mixture was heated to reflux for 5 h and was allowed to cool to 0° C. The mixture was basified by slow addition of sodium hydroxide to pH 10~12. The water phase was extracted by diethyl ether (×2) and the organic phase was discarded. The water phase was acidified to pH ~1 by 1M hydrochloric acid aqueous solution. The mixture was extracted by diethyl ether (×3). The organic layer was combined and washed with brine, dried over $Na_2SO_4$ and concentrated at 10~15° C., to afford the desired product (1S,2S)-2-ethylcyclopropanecarboxylic acid (87 mg, 76%). $[\alpha]_D^{20}$+58.1 (c 1.08, CHCl3); $^1$H NMR (400 MHz. CDCl$_3$) δ 1.46-1.39 (m, 1H), 1.38-1.27 (m, 2H), 1.25-1.18 (m, 2H), 0.98 (t, J=7.3 Hz, 3H), 0.78 (ddd, J=8.1, 6.3, 4.2 Hz, 1H).

(ii) Synthesis of Benzyl ((1S,2S)-2-ethylcyclopropyl)carbamate

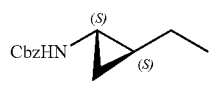

To a solution of (1S,2S)-2-ethylcyclopropanecarboxylic acid (228 mg, 2.00 mmol, 1 equiv.), trimethylamine (334 μL, 2.40 mmol, 1.2 equiv.), benzyl alcohol (1.04 mL, 10.0 mmol, 5 equiv.) in toluene (20.0 mL) was added diphenyl phosphoryl azide (473 μL, 2.20 mmol, 1.1 equiv.). The mixture was heated to reflux overnight. Solvent was removed in vacuo and the resulting mixture was purified by ISCO system on silica gel (EA in PE: 0%~15%) to afford the desired products benzyl ((1S,2S)-2-ethylcyclopropyl)carbamate (226 mg, 52%). $^1$H NMR (400 MHz, CDCl$_3$) δ 7.41-7.28 (m, 5H), 5.10 (s, 2H), 4.88 (s, 1H), 2.30 (s, 1H), 1.40-1.15 (m, 3H), 0.95 (d, J=25.0 Hr, 3H), 0.88-0.80 (m, 1H), 0.68-0.60 (m, 1H), 0.56-0.49 (m, 1H).

(iii) Synthesis of (1S,2S)-2-ethylcyclopropanamine Hydrochloride

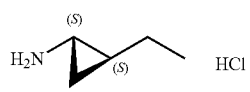

To a solution of Benzyl ((1S,2S)-2-ethylcyclopropyl)carbamate (160 mg, 0.73 mmol, 1 equiv.) in methanol (10 mL) was added Pd/C (10 wt %., 90 mg). The mixture was stirred at room temperature under hydrogen atmosphere (1 atm) for 2 h. The reaction mixture was filtered through a pad of Celite and 3M HCl in methanol (1 mL) was added. After 5 mins' ultra-sonication, the residue was concentrated in vacuo to give the desired product (1S,2S)-2-ethylcyclopropanamine hydrochloride (66 mg, 74%). $[\alpha]_D^{20}$+35.2 (c 1.01, $CH_3OH$); $^1$H NMR (400 MHz, $CD_3OD$) δ 2.35 (dt, J=7.3, 3.5 Hz, 1H), 1.33 (tq, J=14.0, 7.0 Hz, 2H), 1.10 (ddd, J=9.7, 6.4, 3.1 Hz, 1H), 1.01 (t, J=7.4 Hz., 3H), 0.87 (ddd, J=9.9, 6.3, 3.8 Hz, 1H), 0.68 (dd, J=13.8, 6.4 Hz, 1H).

i. Determination of Absolute Chemistry

To a solution of (1R,2R)-2-ethylcyclopropanecarboxylic acid (37.6 mg, 0.33 mmol, 1.1 equiv.) and N,N-dimethylpyridin-4-amine (3.66 mg, 0.030 mmol, 0.1 equiv.) in dichloromethane (3.0 mL) was added ethanethiol (21.6 mL, 0.30 mmol, 1 equiv.) and N,N'-Dicyclohexylcarbodiimide (68 mg, 0.033 mmol, 1.1 equiv.). The resulting mixture was stirred at room temperature overnight. The solid was filtered and the filtrate was concentrated and purified by ISCO system on silica gel (EA in PE: 0%~10%) to afford the desired product (1R,2R)—S-ethyl 2-ethylcyclopropanecarbothioate (35 mg, 66%). $[\alpha]_D^{20}$-102.8 (c 1.4, $CH_2Cl_2$), {lit.[1]: $[\alpha]_D^{20}$-109.1 (c 1.0, $CH_2Cl_2$)}; $^1$H NMR (400 MHz, CDCl$_3$) δ 2.88 (qd, J=7.4, 1.5 Hz, 2H), 1.75 (dt, J=8.2, 4.3 Hz; 1H), 1.52-1.45 (m, 1H), 1.39-1.29 (m, 3H), 1.24 (t, J=7.4 Hz, 3H), 0.97 (t, J=7.3 Hz, 3H), 0.79 (ddd, J=7.9, 6.5, 4.0 Hz, 1H).

3. Characterization of Exemplary Compounds

The compounds below in Table 1 were synthesized with methods identical or analogous to those described herein. The requisite starting materials were commercially available, described in the literature, or readily synthesized by one skilled in the art of organic synthesis.

TABLE 1

| No. | Structure | MW | Name |
|---|---|---|---|
| 1 | 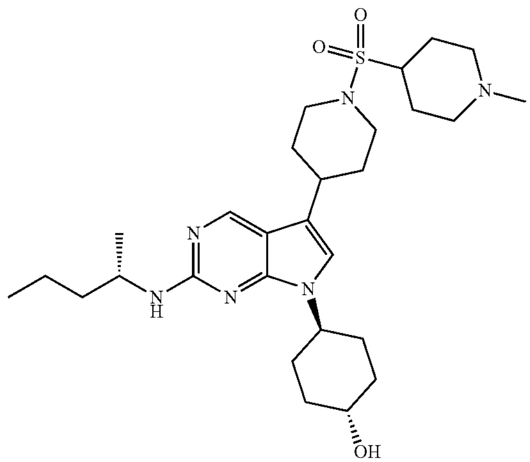 [SMILES: CCC[C@H](C)Nc1ncc2c(C3CCN(S(=O)(=O)C4CCN(C)CC4)CC3)cn([C@H]3CC[C@H](O)CC3)c2n1] | 531.7 | (1S,4R)-4-(5-(1-((1-methylpiperidin-4-yl)sulfonyl)piperidin-4-yl)-2-(((S)-pentan-2-yl)amino)-7H-pyrrolo[2,3-d]pyrimidin-7-yl)cyclohexan-1-ol |
| 2 | 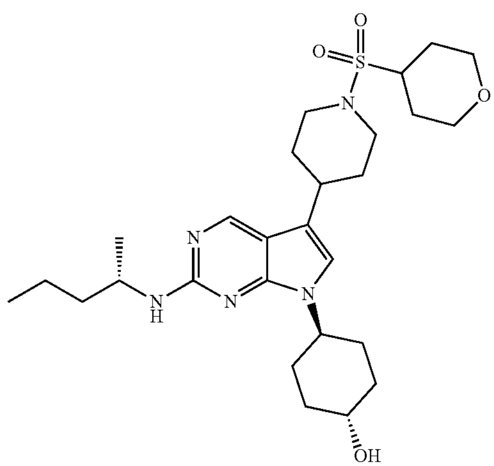 [SMILES: CCC[C@H](C)Nc1ncc2c(C3CCN(S(=O)(=O)C4CCOCC4)CC3)cn([C@H]3CC[C@H](O)CC3)c2n1] | 533.7 | (1S,4R)-4-(2-(((S)-pentan-2-yl)amino)-5-(1-((tetrahydro-2H-pyran-4-yl)sulfonyl)piperidin-4-yl)-7H-pyrrolo[2,3-d]pyrimidin-7-yl)cyclohexan-1-ol |
| 3 | 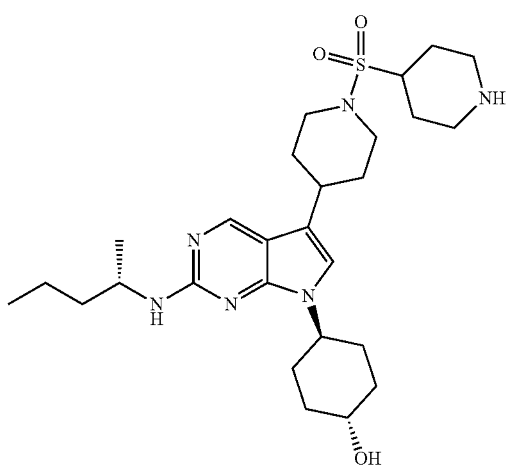 [SMILES: CCC[C@H](C)Nc1ncc2c(C3CCN(S(=O)(=O)C4CCNCC4)CC3)cn([C@H]3CC[C@H](O)CC3)c2n1] | 532.8 | (1S,4R)-4-(2-(((S)-pentan-2-yl)amino)-5-(1-(piperidin-4-ylsulfonyl)piperidin-4-yl)-7H-pyrrolo[2,3-d]pyrimidin-7-yl)cyclohexan-1-ol |

TABLE 1-continued

| No. | Structure | MW | Name |
|---|---|---|---|
| 4 | 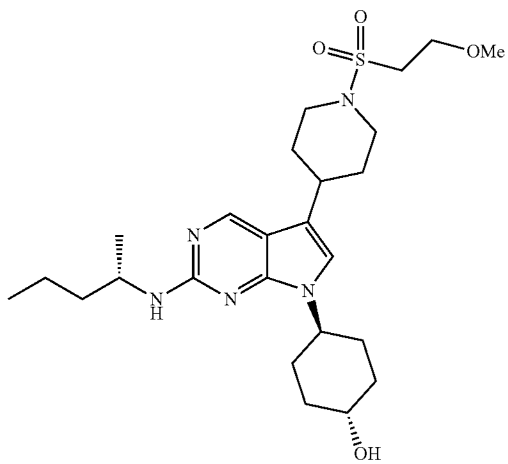 [SMILES: CCC[C@H](C)Nc1ncc2c(C3CCN(S(=O)(=O)CCOC)CC3)cn([C@H]3CC[C@H](O)CC3)c2n1] | 507.7 | (1S,4R)-4-(5-(1-((2-methoxyethyl)sulfonyl)piperidin-4-yl)-2-(((S)-pentan-2-yl)amino)-7H-pyrrolo[2,3-d]pyrimidin-7-yl)cyclohexan-1-ol |
| 5 | 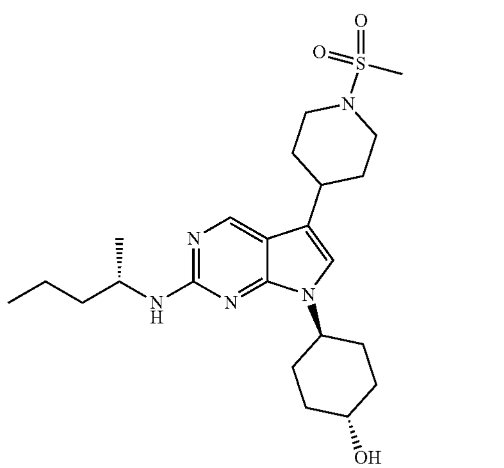 [SMILES: CCC[C@H](C)Nc1ncc2c(C3CCN(S(C)(=O)=O)CC3)cn([C@H]3CC[C@H](O)CC3)c2n1] | 463.6 | (1S,4R)-4-(5-(1-(methylsulfonyl)piperidin-4-yl)-2-(((S)-pentan-2-yl)amino)-7H-pyrrolo[2,3-d]pyrimidin-7-yl)cyclohexan-1-ol |
| 8 | 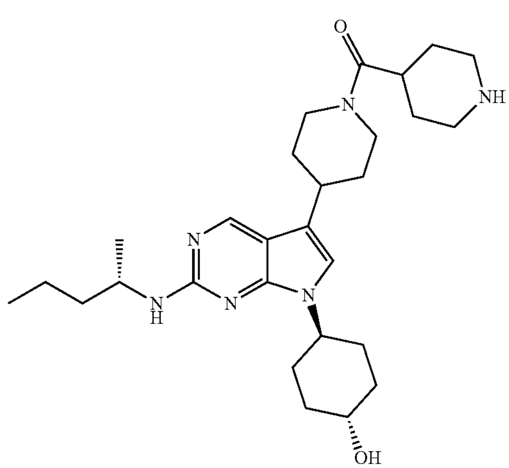 [SMILES: CCC[C@H](C)Nc1ncc2c(C3CCN(C(=O)C4CCNCC4)CC3)cn([C@H]3CC[C@H](O)CC3)c2n1] | 496.7 | (4-(7-((1R,4S)-4-hydroxycyclohexyl)-2-(((S)-pentan-2-yl)amino)-7H-pyrrolo[2,3-d]pyrimidin-5-yl)piperidin-1-yl)(piperidin-4-yl)methanone |

TABLE 1-continued

| No. | Structure | MW | Name |
|---|---|---|---|
| 9 | 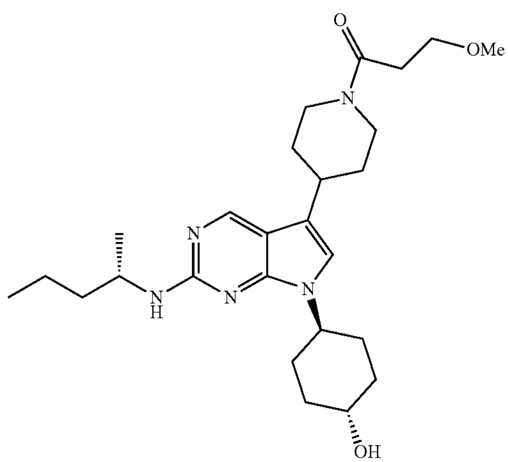 [SMILES: CCC[C@H](C)Nc1ncc2c(C3CCN(C(=O)CCOC)CC3)cn([C@H]3CC[C@H](O)CC3)c2n1] | 471.7 | 1-(4-(7-((1R,4S)-4-hydroxycyclohexyl)-2-(((S)-pentan-2-yl)amino)-7H-pyrrolo[2,3-d]pyrimidin-5-yl)piperidin-1-yl)-3-methoxypropan-1-one |
| 10 | 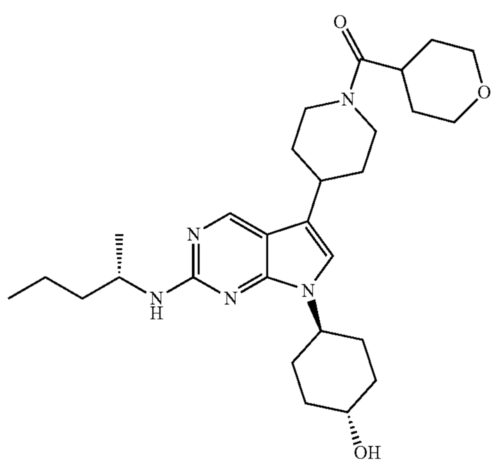 [SMILES: CCC[C@H](C)Nc1ncc2c(C3CCN(C(=O)C4CCOCC4)CC3)cn([C@H]3CC[C@H](O)CC3)c2n1] | 497.7 | (4-(7-((1R,4S)-4-hydroxycyclohexyl)-2-(((S)-pentan-2-yl)amino)-7H-pyrrolo[2,3-d]pyrimidin-5-yl)piperidin-1-yl)(tetrahydro-2H-pyran-4-yl)methanone |
| 11 | 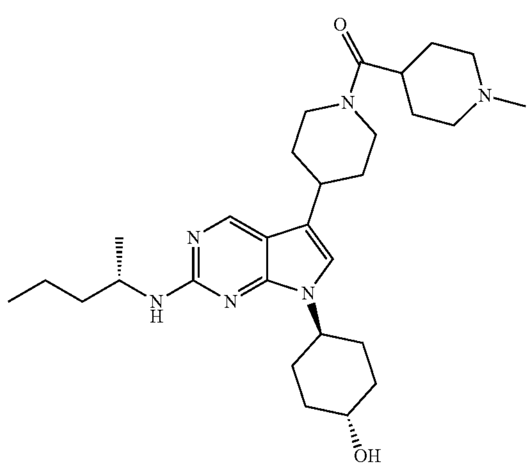 [SMILES: CCC[C@H](C)Nc1ncc2c(C3CCN(C(=O)C4CCN(C)CC4)CC3)cn([C@H]3CC[C@H](O)CC3)c2n1] | 510.7 | (4-(7-((1R,4S)-4-hydroxycyclohexyl)-2-(((S)-pentan-2-yl)amino)-7H-pyrrolo[2,3-d]pyrimidin-5-yl)piperidin-1-yl)(1-methylpiperidin-4-yl)methanone |

TABLE 1-continued

| No. | Structure | MW | Name |
|---|---|---|---|
| 12 | 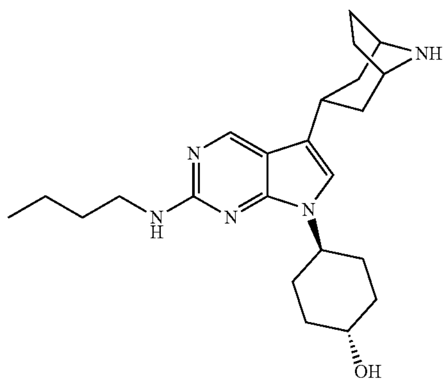 [SMILES: CCCCNc1ncc2c(C3CC4CCC(C3)N4)cn([C@H]3CC[C@H](O)CC3)c2n1] | 397.6 | (1R,4R)-4-(5-((1R,3S,5S)-8-azabicyclo[3.2.1]octan-3-yl)-2-(butylamino)-7H-pyrrolo[2,3-d]pyrimidin-7-yl)cyclohexan-1-ol |
| 13 | 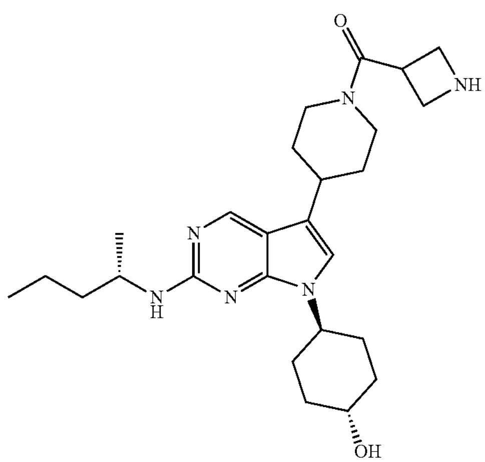 [SMILES: CCC[C@H](C)Nc1ncc2c(C3CCN(C(=O)C4CNC4)CC3)cn([C@H]3CC[C@H](O)CC3)c2n1] | 468.7 | Azetidin-3-yl(4-(7-((1R,4S)-4-hydroxycyclohexyl)-2-(((S)-pentan-2-yl)amino)-7H-pyrrolo[2,3-d]pyrimidin-5-yl)piperidin-1-yl)methanone |
| 14 | 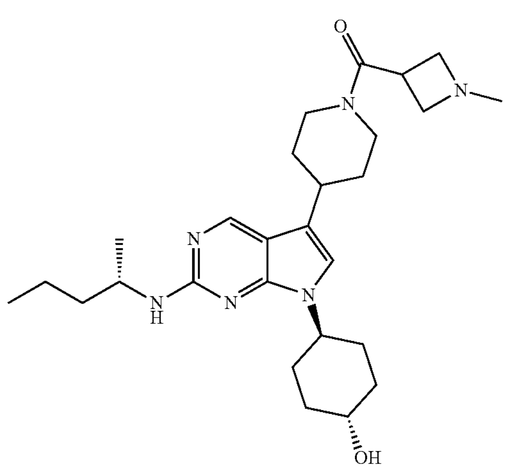 [SMILES: CCC[C@H](C)Nc1ncc2c(C3CCN(C(=O)C4CN(C)C4)CC3)cn([C@H]3CC[C@H](O)CC3)c2n1] | 482.7 | (4-(7-((1R,4S)-4-hydroxycyclohexyl)-2-(((S)-pentan-2-yl)amino)-7H-pyrrolo[2,3-d]pyrimidin-5-yl)piperidin-1-yl)(1-methylazetidin-3-yl)methanone |

TABLE 1-continued
| No. | Structure | MW | Name |
|---|---|---|---|
| 15 | 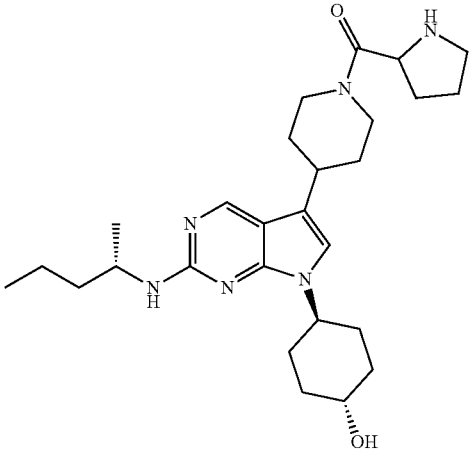 [SMILES: CCC[C@H](C)Nc1ncc2c(C3CCN(C(=O)C4CCCN4)CC3)cn([C@H]3CC[C@H](O)CC3)c2n1] | 482.7 | 7-((1R,4S)-4-hydroxycyclohexyl)-2-(((S)-pentan-2-yl)amino)-5-(1-prolylpiperidin-4-yl)-7H-pyrrolo[2,3-d]pyrimidine |
| 16 | 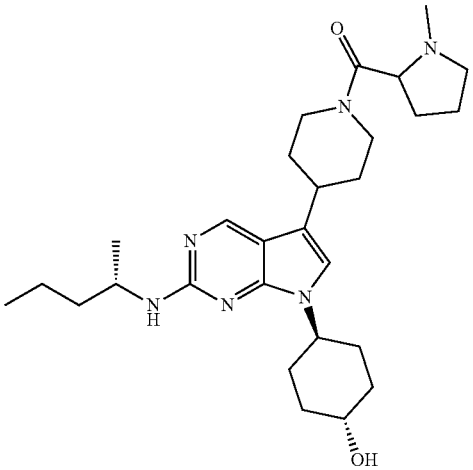 [SMILES: CCC[C@H](C)Nc1ncc2c(C3CCN(C(=O)C4CCCN4C)CC3)cn([C@H]3CC[C@H](O)CC3)c2n1] | 496.7 | 7-((1R,4S)-4-hydroxycyclohexyl)-5-(1-(methylprolyl)piperidin-4-yl)-2-(((S)-pentan-2-yl)amino)-7H-pyrrolo[2,3-d]pyrimidine |
| 17 | 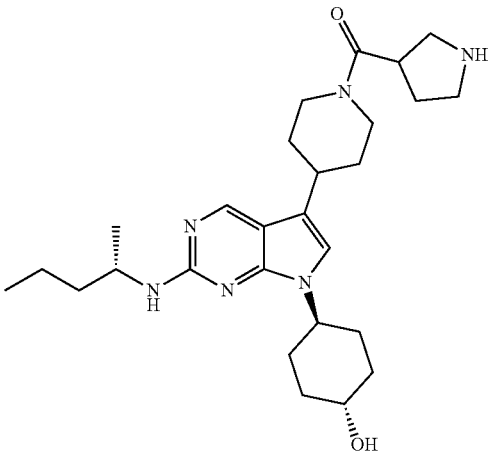 [SMILES: CCC[C@H](C)Nc1ncc2c(C3CCN(C(=O)C4CCNC4)CC3)cn([C@H]3CC[C@H](O)CC3)c2n1] | 482.7 | (4-(7-((1R,4S)-4-hydroxycyclohexyl)-2-(((S)-pentan-2-yl)amino)-7H-pyrrolo[2,3-d]pyrimidin-5-yl)piperidin-1-yl)(pyrrolidin-3-yl)methanone |

TABLE 1-continued

| No. | Structure | MW | Name |
|---|---|---|---|
| 18 | 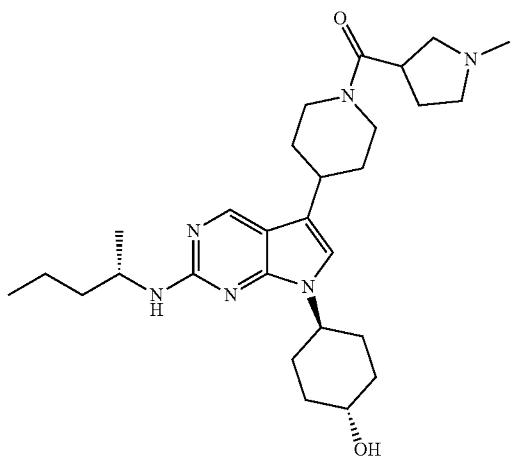 [SMILES: CCC[C@H](C)Nc1ncc2c(C3CCN(C(=O)C4CCN(C)C4)CC3)cn([C@H]3CC[C@H](O)CC3)c2n1] | 496.7 | (4-(7-((1R,4S)-4-hydroxycyclohexyl)-2-(((S)-pentan-2-yl)amino)-7H-pyrrolo[2,3-d]pyrimidin-5-yl)piperidin-1-yl)(1-methylpyrrolidin-3-yl)methanone |
| 19 | 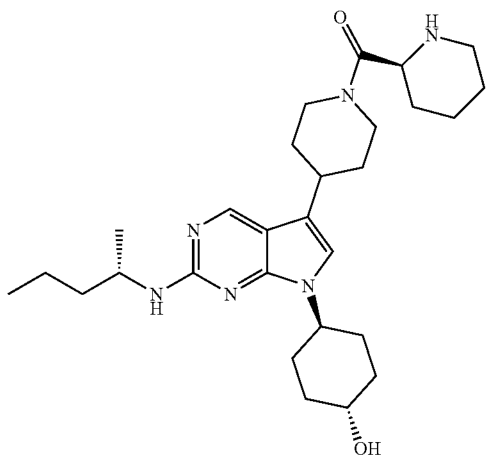 [SMILES: CCC[C@H](C)Nc1ncc2c(C3CCN(C(=O)[C@@H]4CCCCN4)CC3)cn([C@H]3CC[C@H](O)CC3)c2n1] | 496.7 | (4-(7-((1R,4S)-4-hydroxycyclohexyl)-2-(((S)-pentan-2-yl)amino)-7H-pyrrolo[2,3-d]pyrimidin-5-yl)piperidin-1-yl)((S)-piperidin-2-yl)methanone |
| 20 | 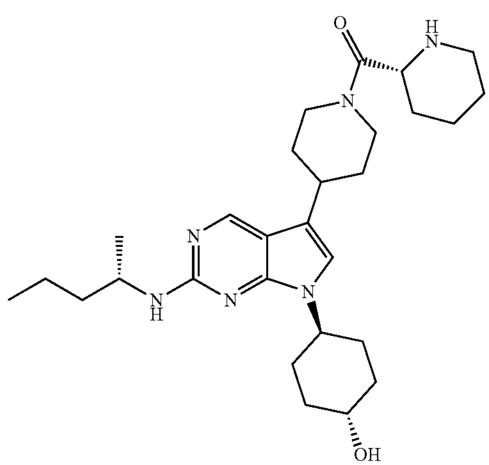 [SMILES: CCC[C@H](C)Nc1ncc2c(C3CCN(C(=O)[C@H]4CCCCN4)CC3)cn([C@H]3CC[C@H](O)CC3)c2n1] | 496.7 | (4-(7-((1R,4S)-4-hydroxycyclohexyl)-2-(((S)-pentan-2-yl)amino)-7H-pyrrolo[2,3-d]pyrimidin-5-yl)piperidin-1-yl)((R)-piperidin-2-yl)methanone |

TABLE 1-continued

| No. | Structure | MW | Name |
|---|---|---|---|
| 21 | 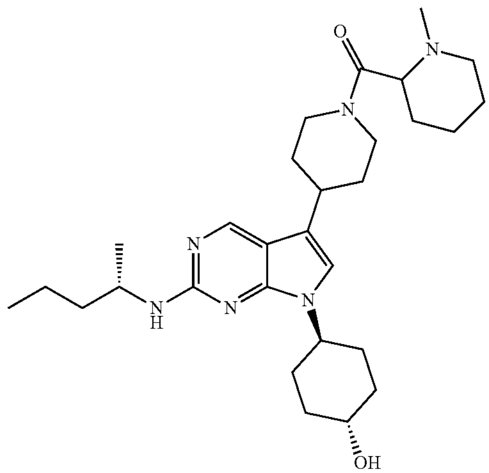 [SMILES: CCC[C@H](C)Nc1ncc2c(C3CCN(C(=O)C4CCCCN4C)CC3)cn([C@H]3CC[C@H](O)CC3)c2n1] | 510.7 | (4-(7-((1R,4S)-4-hydroxycyclohexyl)-2-(((S)-pentan-2-yl)amino)-7H-pyrrolo[2,3-d]pyrimidin-5-yl)piperidin-1-yl)(1-methylpyrrolidin-2-yl)methanone |
| 22 | 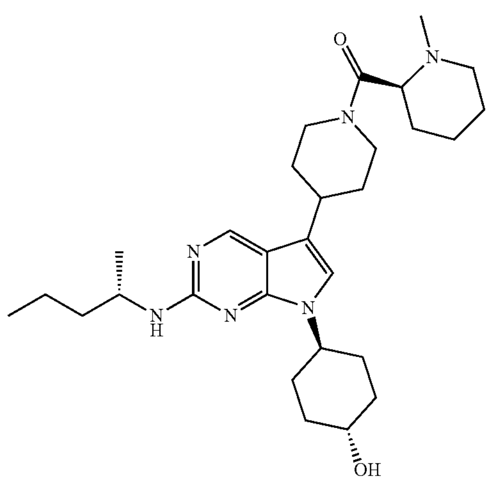 [SMILES: CCC[C@H](C)Nc1ncc2c(C3CCN(C(=O)[C@@H]4CCCCN4C)CC3)cn([C@H]3CC[C@H](O)CC3)c2n1] | 510.7 | (4-(7-((1R,4S)-4-hydroxycyclohexyl)-2-(((S)-pentan-2-yl)amino)-7H-pyrrolo[2,3-d]pyrimidin-5-yl)piperidin-1-yl)((S)-1-methylpiperidin-2-yl)methanone |
| 23 | 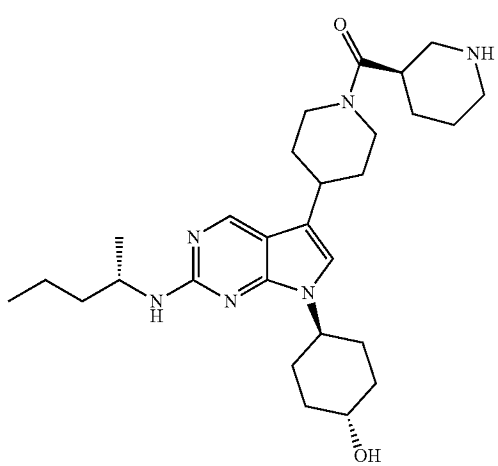 [SMILES: CCC[C@H](C)Nc1ncc2c(C3CCN(C(=O)[C@@H]4CCCNC4)CC3)cn([C@H]3CC[C@H](O)CC3)c2n1] | 496.7 | (4-(7-((1R,4S)-4-hydroxycyclohexyl)-2-(((S)-pentan-2-yl)amino)-7H-pyrrolo[2,3-d]pyrimidin-5-yl)piperidin-1-yl)((R)-piperidin-3-yl)methanone |

US 11,001,586 B2
TABLE 1-continued
| No. | Structure | MW | Name |
|---|---|---|---|
| 24 | 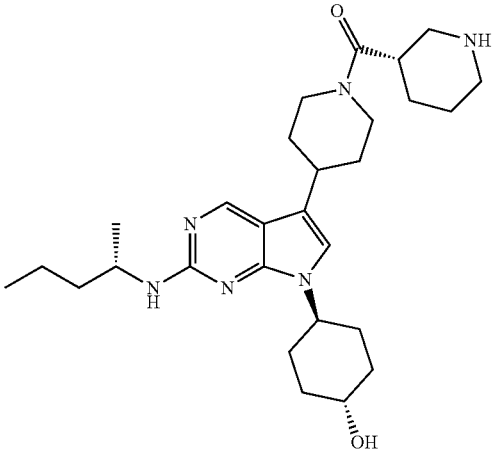 [SMILES: CCC[C@H](C)Nc1ncc2c(C3CCN(C(=O)[C@H]4CCCNC4)CC3)cn([C@H]3CC[C@H](O)CC3)c2n1] | 496.7 | (4-(7-((1R,4S)-4-hydroxycyclohexyl)-2-(((S)-pentan-2-yl)amino)-7H-pyrrolo[2,3-d]pyrimidin-5-yl)piperidin-1-yl)((S)-piperidin-3-yl)methanone |
| 25 | 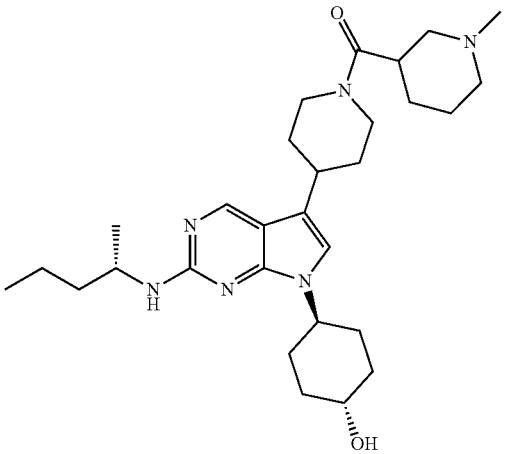 [SMILES: CCC[C@H](C)Nc1ncc2c(C3CCN(C(=O)C4CCCN(C)C4)CC3)cn([C@H]3CC[C@H](O)CC3)c2n1] | 510.7 | (4-(7-((1r,4S)-4-hydroxycyclohexyl)-2-(((S)-pentan-2-yl)amino)-7H-pyrrolo[2,3-d]pyrimidin-5-yl)piperidin-1-yl)(1-methylpiperidin-3-yl)methanone |
| 26 | 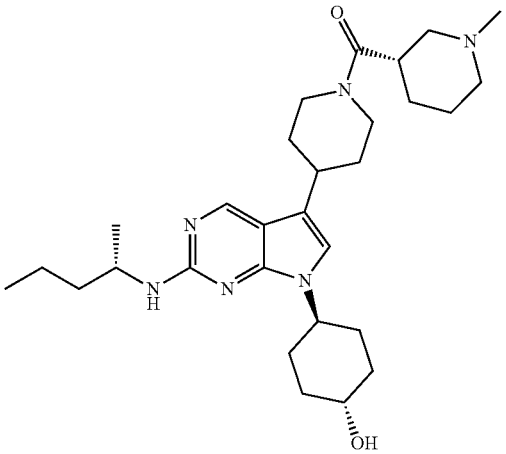 [SMILES: CCC[C@H](C)Nc1ncc2c(C3CCN(C(=O)[C@H]4CCCN(C)C4)CC3)cn([C@H]3CC[C@H](O)CC3)c2n1] | 510.7 | (4-(7-((1R,4S)-4-hydroxycyclohexyl)-2-(((S)-pentan-2-yl)amino)-7H-pyrrolo[2,3-d]pyrimidin-5-yl)piperidin-1-yl)((S)-1-methylpiperidin-3-yl)methanone |

TABLE 1-continued

| No. | Structure | MW | Name |
|---|---|---|---|
| 27 | 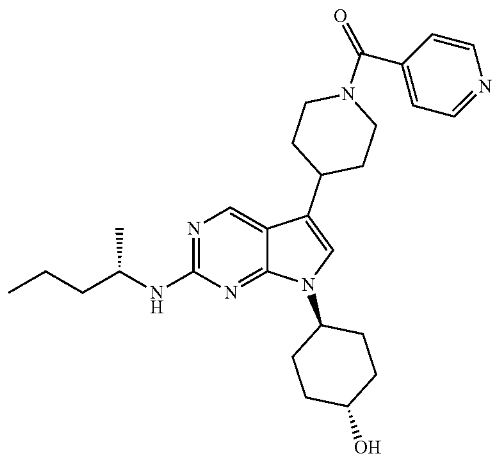 [SMILES: CCC[C@H](C)Nc1ncc2c(C3CCN(C(=O)c4ccncc4)CC3)cn([C@H]3CC[C@H](O)CC3)c2n1] | 490.7 | (4-(7-((1R,4S)-4-hydroxycyclohexyl)-2-(((S)-pentan-2-yl)amino)-7H-pyrrolo[2,3-d]pyrimidin-5-yl)piperidin-1-yl)(pyridin-4-yl)methanone |
| 28 | 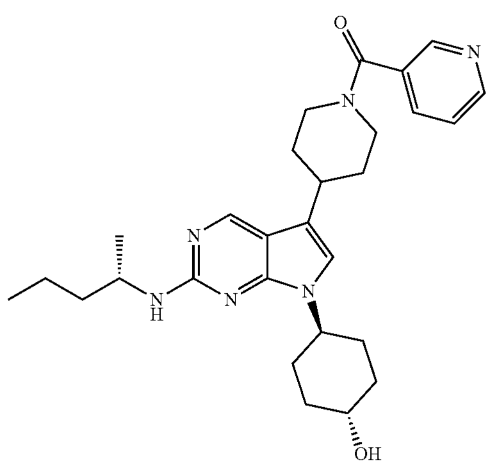 [SMILES: CCC[C@H](C)Nc1ncc2c(C3CCN(C(=O)c4cccnc4)CC3)cn([C@H]3CC[C@H](O)CC3)c2n1] | 490.7 | (4-(7-((1R,4S)-4-hydroxycyclohexyl)-2-(((S)-pentan-2-yl)amino)-7H-pyrrolo[2,3-d]pyrimidin-5-yl)piperidin-1-yl)(pyridin-3-yl)methanone |
| 29 | 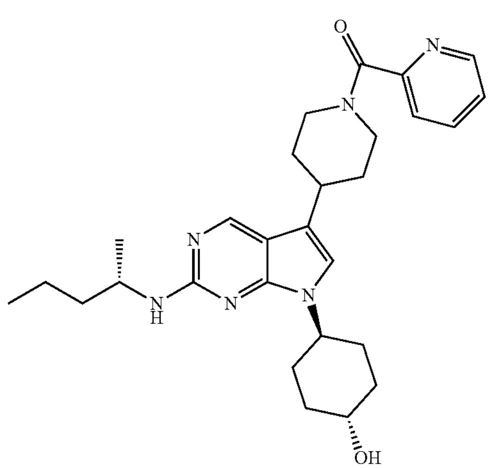 [SMILES: CCC[C@H](C)Nc1ncc2c(C3CCN(C(=O)c4ccccn4)CC3)cn([C@H]3CC[C@H](O)CC3)c2n1] | 490.7 | (4-(7-((1R,4S)-4-hydroxycyclohexyl)-2-(((S)-pentan-2-yl)amino)-7H-pyrrolo[2,3-d]pyrimidin-5-yl)piperidin-1-yl)(pyridin-2-yl)methanone |

TABLE 1-continued

| No. | Structure | MW | Name |
|---|---|---|---|
| 30 | 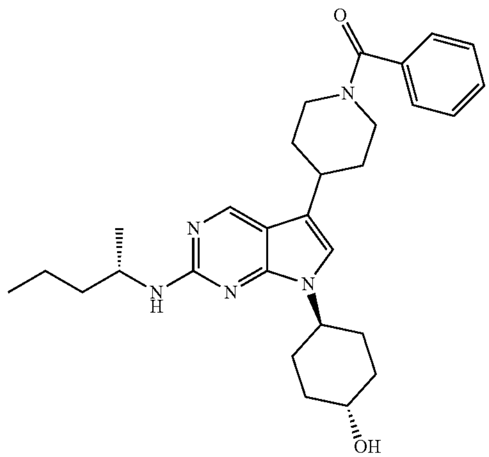 [SMILES: CCC[C@H](C)Nc1ncc2c(C3CCN(C(=O)c4ccccc4)CC3)cn([C@H]3CC[C@H](O)CC3)c2n1] | 489.7 | (4-(7-((1R,4S)-4-hydroxycyclohexyl)-2-(((S)-pentan-2-yl)amino)-7H-pyrrolo[2,3-d]pyrimidin-5-yl)piperidin-1-yl)(phenyl)methanone |
| 31 | 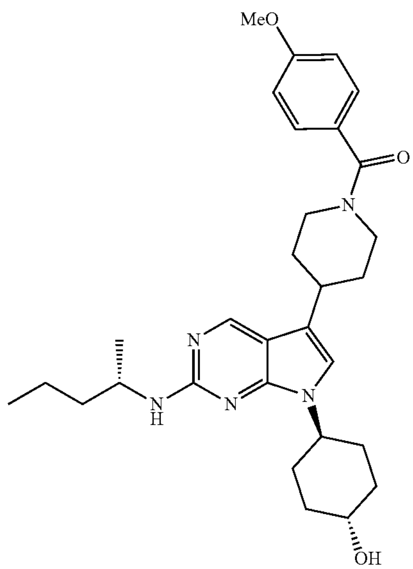 [SMILES: CCC[C@H](C)Nc1ncc2c(C3CCN(C(=O)c4ccc(OC)cc4)CC3)cn([C@H]3CC[C@H](O)CC3)c2n1] | 519.7 | (4-(7-((1R,4S)-4-hydroxycyclohexyl)-2-(((S)-pentan-2-yl)amino)-7H-pyrrolo[2,3-d]pyrimidin-5-yl)piperidin-1-yl)(4-methoxyphenyl)methanone |
| 32 | 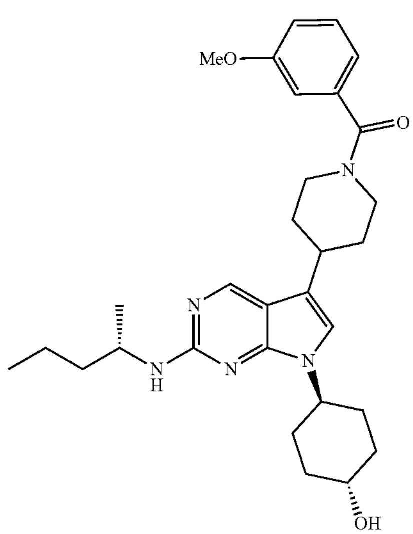 [SMILES: CCC[C@H](C)Nc1ncc2c(C3CCN(C(=O)c4cccc(OC)c4)CC3)cn([C@H]3CC[C@H](O)CC3)c2n1] | 519.7 | (4-(7-((1R,4S)-4-hydroxycyclohexyl)-2-(((S)-pentan-2-yl)amino)-7H-pyrrolo[2,3-d]pyrimidin-5-yl)piperidin-1-yl)(3-methoxyphenyl)methanone |

TABLE 1-continued

| No. | Structure | MW | Name |
|---|---|---|---|
| 33 | 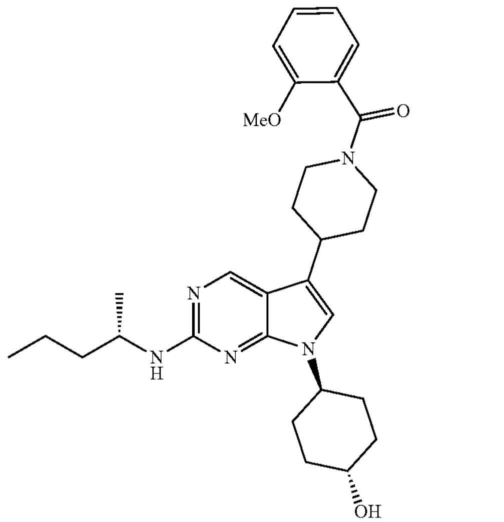 [SMILES: CCC[C@H](C)Nc1ncc2c(C3CCN(C(=O)c4ccccc4OC)CC3)cn([C@H]3CC[C@H](O)CC3)c2n1] | 519.7 | (4-(7-((1R,4S)-4-hydroxycyclohexyl)-2-(((S)-pentan-2-yl)amino)-7H-pyrrolo[2,3-d]pyrimidin-5-yl)piperidin-1-yl)(2-methoxyphenyl)methanone |
| 34 | 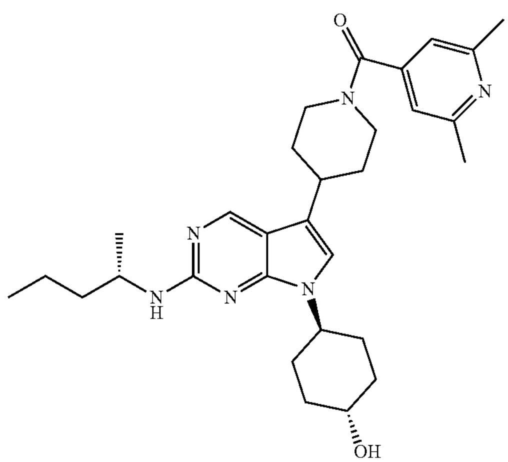 [SMILES: CCC[C@H](C)Nc1ncc2c(C3CCN(C(=O)c4cc(C)nc(C)c4)CC3)cn([C@H]3CC[C@H](O)CC3)c2n1] | 518.7 | (2,6-dimethylpyridin-4-yl)(4-(7-((1R,4S)-4-hydroxycyclohexyl)-2-(((S)-pentan-2-yl)amino)-7H-pyrrolo[2,3-d]pyrimidin-5-yl)piperidin-1-yl)methanone |
| 35 | 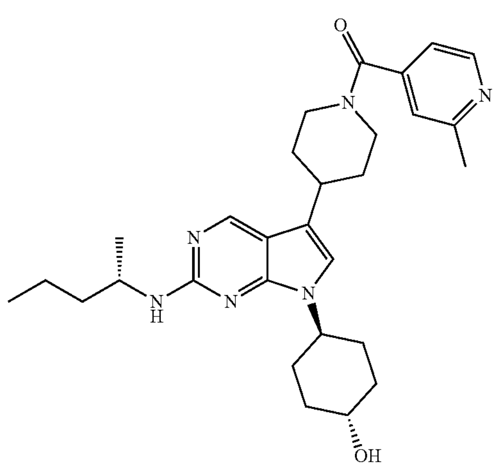 [SMILES: CCC[C@H](C)Nc1ncc2c(C3CCN(C(=O)c4ccnc(C)c4)CC3)cn([C@H]3CC[C@H](O)CC3)c2n1] | 504.7 | (4-(7-((1R,4S)-4-hydroxycyclohexyl)-2-(((S)-pentan-2-yl)amino)-7H-pyrrolo[2,3-d]pyrimidin-5-yl)piperidin-1-yl)(2-methylpyridin-4-yl)methanone |

TABLE 1-continued

| No. | Structure | MW | Name |
|---|---|---|---|
| 36 | 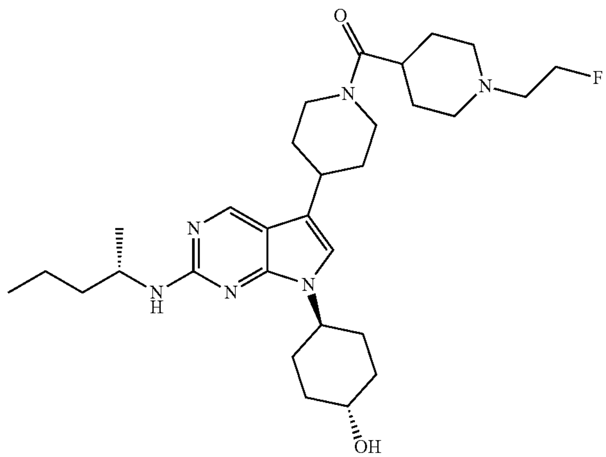 [SMILES: CCC[C@H](C)Nc1ncc2c(C3CCN(C(=O)C4CCN(CCF)CC4)CC3)cn([C@H]3CC[C@H](O)CC3)c2n1] | 542.7 | (1-(2-fluoroethyl)piperidin-4-yl)(4-(7-((1R,4S)-4-hydroxycyclohexyl)-2-(((S)-pentan-2-yl)amino)-7H-pyrrolo[2,3-d]pyrimidin-5-yl)piperidin-1-yl)methanone |
| 37 | 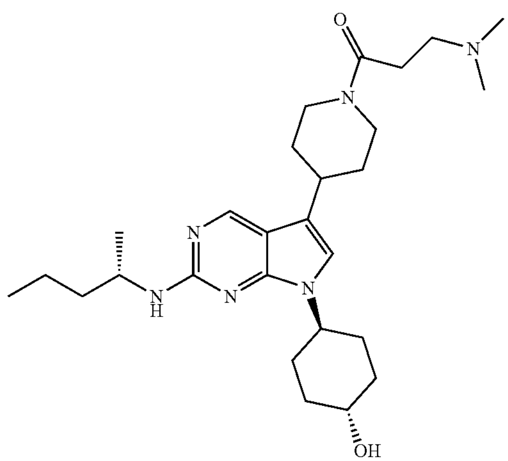 [SMILES: CCC[C@H](C)Nc1ncc2c(C3CCN(C(=O)CCN(C)C)CC3)cn([C@H]3CC[C@H](O)CC3)c2n1] | 584.7 | 3-(dimethylamino)-1-(4-(7-((1R,4S)-4-hydroxycyclohexyl)-2-(((S)-pentan-2-yl)amino)-7H-pyrrolo[2,3-d]pyrimidin-5-yl)piperidin-1-yl)propan-1-one |
| 38 | 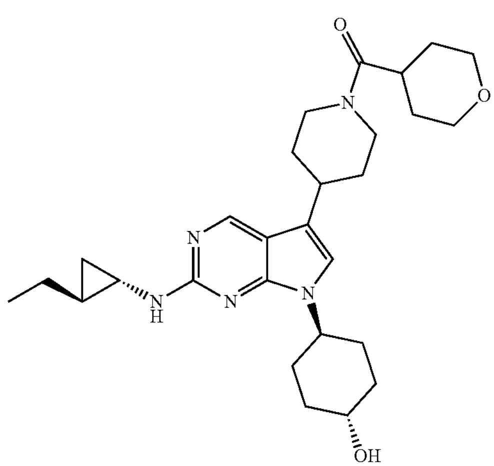 [SMILES: CC[C@H]1C[C@@H]1Nc1ncc2c(C3CCN(C(=O)C4CCOCC4)CC3)cn([C@H]3CC[C@H](O)CC3)c2n1] | 495.7 | (4-(2-(((1S,2S)-2-ethylcyclopropyl)amino)-7-((1R,4S)-4-hydroxycyclohexyl)-7H-pyrrolo[2,3-d]pyrimidin-5-yl)piperidin-1-yl)(tetrahydro-2H-pyran-4-yl)methanone |

TABLE 1-continued

| No. | Structure | MW | Name |
|---|---|---|---|
| 39 | 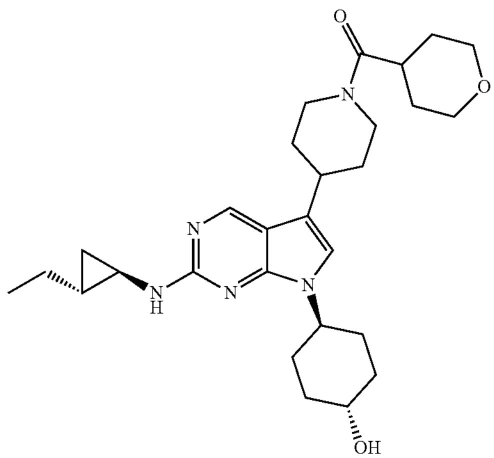 [SMILES: CC[C@@H]1C[C@H]1Nc1ncc2c(C3CCN(C(=O)C4CCOCC4)CC3)cn([C@H]3CC[C@H](O)CC3)c2n1] | 495.7 | (4-(2-(((1R,2R)-2-ethylcyclopropyl)amino)-7-((1R,4R)-4-hydroxycyclohexyl)-7H-pyrrolo[2,3-d]pyrimidin-5-yl)piperidin-1-yl)(tetrahydro-2H-pyran-4-yl)methanone |
| 42 | 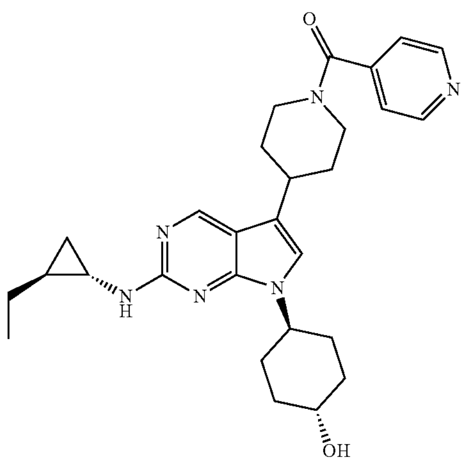 [SMILES: CC[C@H]1C[C@@H]1Nc1ncc2c(C3CCN(C(=O)c4ccncc4)CC3)cn([C@H]3CC[C@H](O)CC3)c2n1] | 488.6 | (4-(2-(((1S,2S)-2-ethylcyclopropyl)amino)-7-((1R,4S)-4-hydroxycyclohexyl)-7H-pyrrolo[2,3-d]pyrimidin-5-yl)piperidin-1-yl)(pyridin-4-yl)methanone |
| 43 | 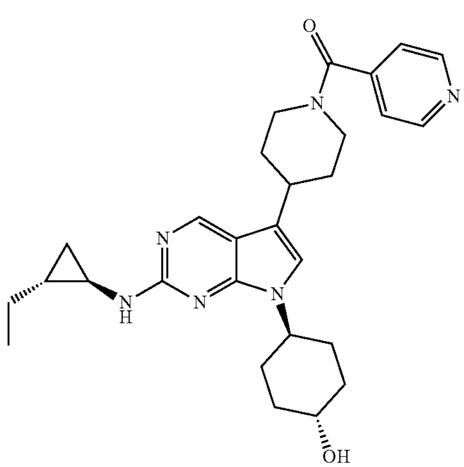 [SMILES: CC[C@@H]1C[C@H]1Nc1ncc2c(C3CCN(C(=O)c4ccncc4)CC3)cn([C@H]3CC[C@H](O)CC3)c2n1] | 488.6 | (4-(2-(((1R,2R)-2-ethylcyclopropyl)amino)-7-((1R,4R)-4-hydroxycyclohexyl)-7H-pyrrolo[2,3-d]pyrimidin-5-yl)piperidin-1-yl)(pyridin-4-yl)methanone |

TABLE 1-continued

| No. | Structure | MW | Name |
|---|---|---|---|
| 51 | 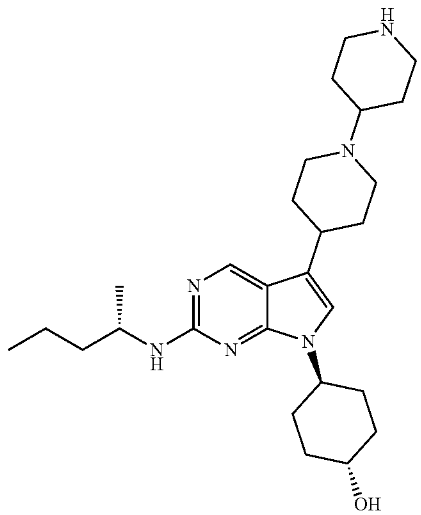 [SMILES: CCC[C@H](C)Nc1ncc2c(C3CCN(C4CCNCC4)CC3)cn([C@H]3CC[C@H](O)CC3)c2n1] | 468.7 | (1S,4R)-4-(5-([1,4'-bipiperidin]-4-yl)-2-(((S)-pentan-2-yl)amino)-7H-pyrrolo[2,3-d]pyrimidin-7-yl)cyclohexan-1-ol |
| 52 | 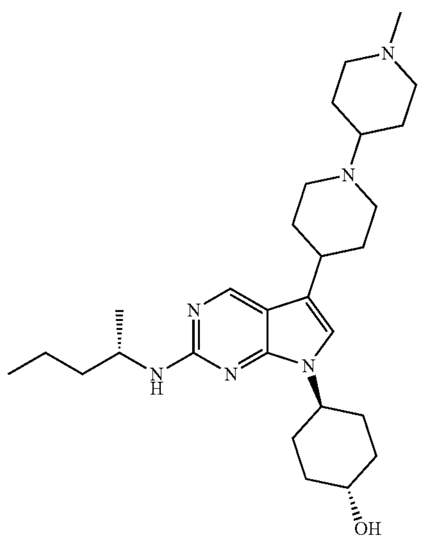 [SMILES: CCC[C@H](C)Nc1ncc2c(C3CCN(C4CCN(C)CC4)CC3)cn([C@H]3CC[C@H](O)CC3)c2n1] | 482.7 | (1S,4R)-4-(5-(1'-methyl-[1,4'-bipiperidin]-4-yl)-2-(((S)-pentan-2-yl)amino)-7H-pyrrolo[2,3-d]pyrimidin-7-yl)cyclohexan-1-ol |
| 53 | 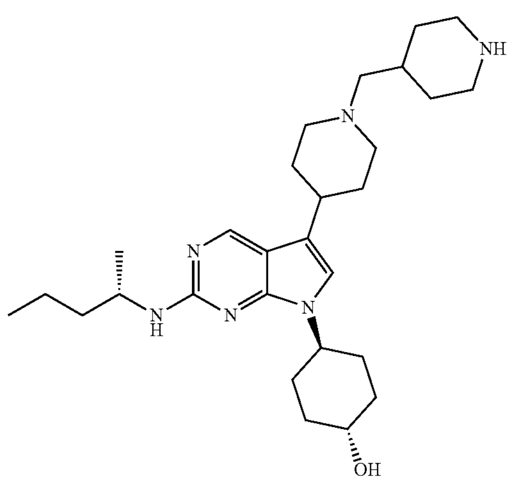 [SMILES: CCC[C@H](C)Nc1ncc2c(C3CCN(CC4CCNCC4)CC3)cn([C@H]3CC[C@H](O)CC3)c2n1] | 482.7 | (1S,4R)-4-(2-(((S)-pentan-2-yl)amino)-5-(1-(piperidin-4-ylmethyl)piperidin-4-yl)-7H-pyrrolo[2,3-d]pyrimidin-7-yl)cyclohexan-1-ol |

TABLE 1-continued

| No. | Structure | MW | Name |
|---|---|---|---|
| 54 | 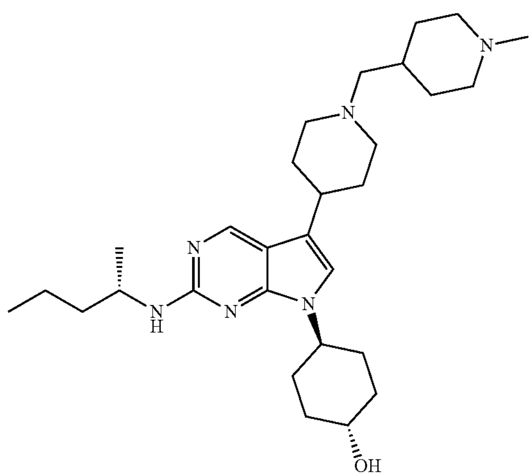 [SMILES: CCC[C@H](C)Nc1ncc2c(C3CCN(CC4CCN(C)CC4)CC3)cn([C@H]3CC[C@H](O)CC3)c2n1] | 496.7 | (1S,4R)-4-(5-(1-((1-methylpiperidin-4-yl)methyl)piperidin-4-yl)-2-(((S)-pentan-2-yl)amino)-7H-pyrrolo[2,3-d]pyrimidin-7-yl)cyclohexan-1-ol |
| 55 | 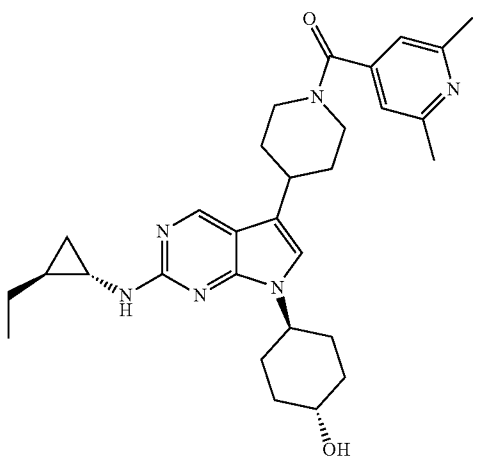 [SMILES: CC[C@H]1C[C@@H]1Nc1ncc2c(C3CCN(C(=O)c4cc(C)nc(C)c4)CC3)cn([C@H]3CC[C@H](O)CC3)c2n1] | 516.7 | (2,6-dimethylpyridin-4-yl)(4-(2-(((1S,2S)-2-ethylcyclopropyl)amino)-7-((1r,4S)-4-hydroxycyclohexyl)-7H-pyrrolo[2,3-d]pyrimidin-5-yl)piperidin-1-yl)methanone |
| 56 | 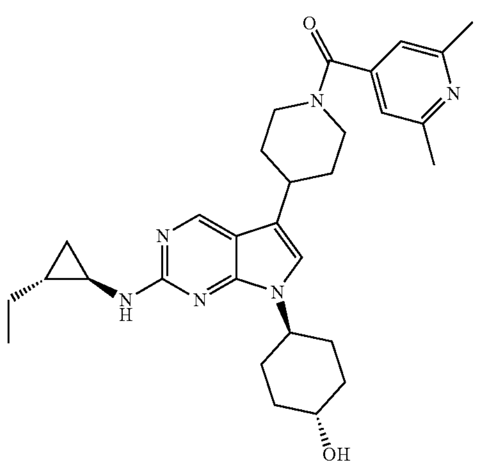 [SMILES: CC[C@@H]1C[C@H]1Nc1ncc2c(C3CCN(C(=O)c4cc(C)nc(C)c4)CC3)cn([C@H]3CC[C@H](O)CC3)c2n1] | 516.7 | (2,6-dimethylpyridin-4-yl)(4-(2-(((1R,2R)-2-ethylcyclopropyl)amino)-7-((1r,4R)-4-hydroxycyclohexyl)-7H-pyrrolo[2,3-d]pyrimidin-5-yl)piperidin-1-yl)methanone |

TABLE 1-continued

| No. | Structure | MW | Name |
|---|---|---|---|
| 57 | 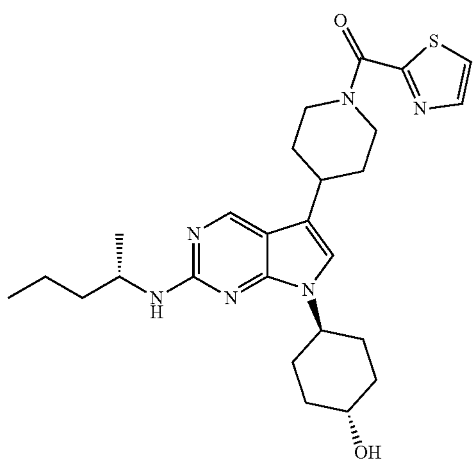 [SMILES: CCC[C@H](C)Nc1ncc2c(C3CCN(C(=O)c4nccs4)CC3)cn([C@H]3CC[C@H](O)CC3)c2n1] | 496.7 | (4-(7-((1r,4S)-4-hydroxycyclohexyl)-2-(((S)-pentan-2-yl)amino)-7H-pyrrolo[2,3-d]pyrimidin-5-yl)piperidin-1-yl)(thiazol-2-yl)methanone |
| 58 | 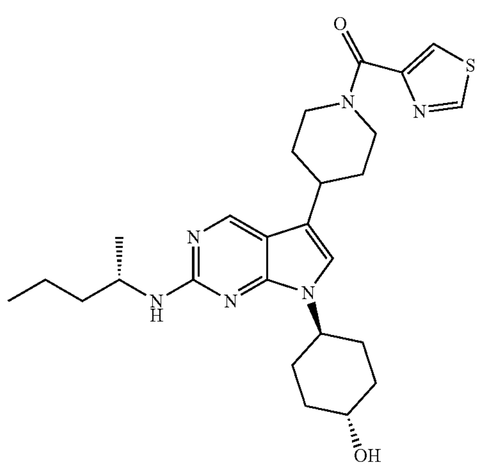 [SMILES: CCC[C@H](C)Nc1ncc2c(C3CCN(C(=O)c4cscn4)CC3)cn([C@H]3CC[C@H](O)CC3)c2n1] | 496.7 | (4-(7-((1r,4S)-4-hydroxycyclohexyl)-2-(((S)-pentan-2-yl)amino)-7H-pyrrolo[2,3-d]pyrimidin-5-yl)piperidin-1-yl)(thiazol-4-yl)methanone |
| 59 | 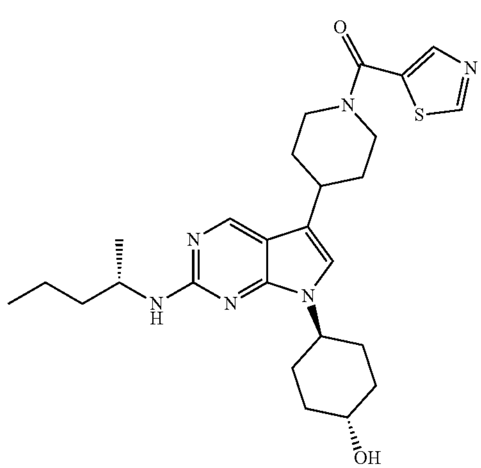 [SMILES: CCC[C@H](C)Nc1ncc2c(C3CCN(C(=O)c4cncs4)CC3)cn([C@H]3CC[C@H](O)CC3)c2n1] | 496.7 | (4-(7-((1r,4S)-4-hydroxycyclohexyl)-2-(((S)-pentan-2-yl)amino)-7H-pyrrolo[2,3-d]pyrimidin-5-yl)piperidin-1-yl)(thiazol-5-yl)methanone |

TABLE 1-continued

| No. | Structure | MW | Name |
|---|---|---|---|
| 60 | 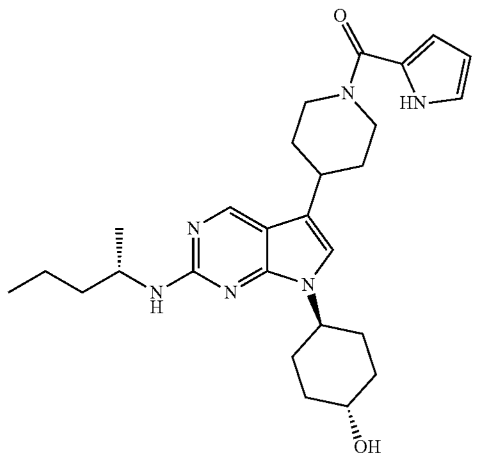 [SMILES: CCC[C@H](C)Nc1ncc2c(C3CCN(C(=O)c4ccc[nH]4)CC3)cn([C@H]3CC[C@H](O)CC3)c2n1] | 478.6 | (4-(7-((1r,4S)-4-hydroxycyclohexyl)-2-(((S)-pentan-2-yl)amino)-7H-pyrrolo[2,3-d]pyrimidin-5-yl)piperidin-1-yl)(1H-pyrrol-2-yl)methanone |
| 61 | 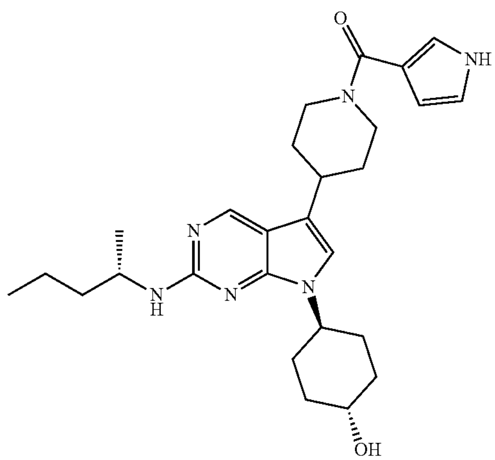 [SMILES: CCC[C@H](C)Nc1ncc2c(C3CCN(C(=O)c4cc[nH]c4)CC3)cn([C@H]3CC[C@H](O)CC3)c2n1] | 478.6 | (4-(7-((1r,4S)-4-hydroxycyclohexyl)-2-(((S)-pentan-2-yl)amino)-7H-pyrrolo[2,3-d]pyrimidin-5-yl)piperidin-1-yl)(1H-pyrrol-3-yl)methanone |
| 62 | 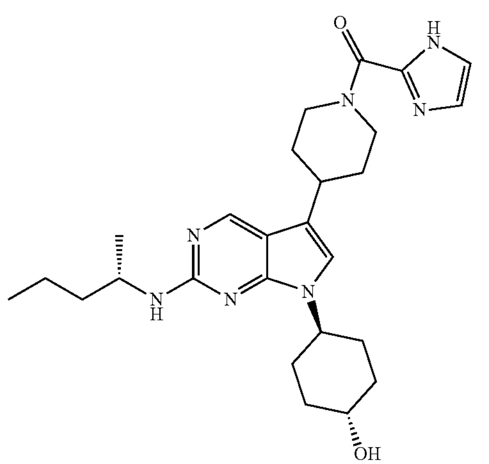 [SMILES: CCC[C@H](C)Nc1ncc2c(C3CCN(C(=O)c4ncc[nH]4)CC3)cn([C@H]3CC[C@H](O)CC3)c2n1] | 479.6 | (4-(7-((1r,4S)-4-hydroxycyclohexyl)-2-(((S)-pentan-2-yl)amino)-7H-pyrrolo[2,3-d]pyrimidin-5-yl)piperidin-1-yl)(1H-imidazol-2-yl)methanone |

TABLE 1-continued

| No. | Structure | MW | Name |
|---|---|---|---|
| 63 | 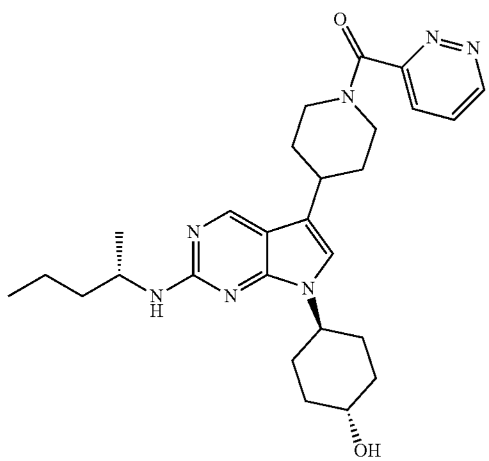 [SMILES: CCC[C@H](C)Nc1ncc2c(C3CCN(C(=O)c4cccnn4)CC3)cn([C@H]3CC[C@H](O)CC3)c2n1] | 491.6 | (4-(7-((1r,4S)-4-hydroxycyclohexyl)-2-(((S)-pentan-2-yl)amino)-7H-pyrrolo[2,3-d]pyrimidin-5-yl)piperidin-1-yl)(pyridazin-3-yl)methanone |
| 64 | 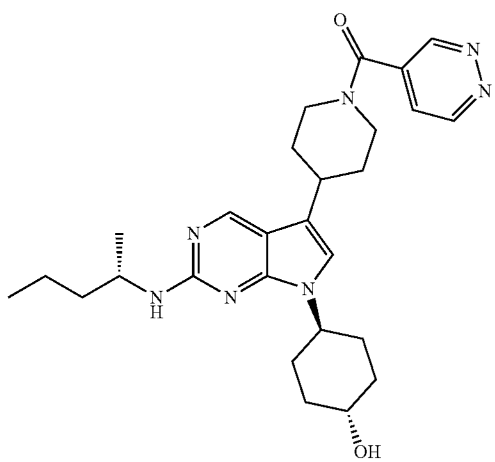 [SMILES: CCC[C@H](C)Nc1ncc2c(C3CCN(C(=O)c4ccnnc4)CC3)cn([C@H]3CC[C@H](O)CC3)c2n1] | 491.6 | (4-(7-((1r,4S)-4-hydroxycyclohexyl)-2-(((S)-pentan-2-yl)amino)-7H-pyrrolo[2,3-d]pyrimidin-5-yl)piperidin-1-yl)(pyridazin-4-yl)methanone |
| 65 | 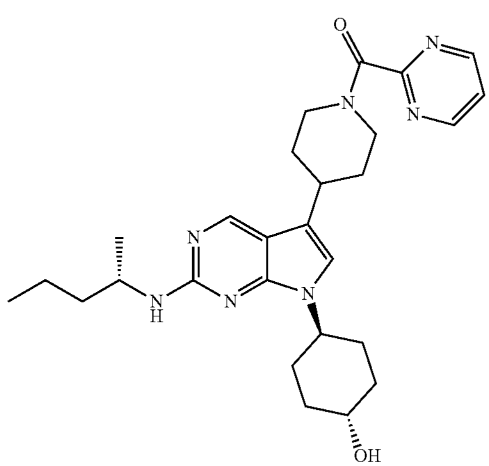 [SMILES: CCC[C@H](C)Nc1ncc2c(C3CCN(C(=O)c4ncccn4)CC3)cn([C@H]3CC[C@H](O)CC3)c2n1] | 491.6 | (4-(7-((1r,4S)-4-hydroxycyclohexyl)-2-(((S)-pentan-2-yl)amino)-7H-pyrrolo[2,3-d]pyrimidin-5-yl)piperidin-1-yl)(pyrimidin-2-yl)methanone |

TABLE 1-continued

| No. | Structure | MW | Name |
|---|---|---|---|
| 66 | 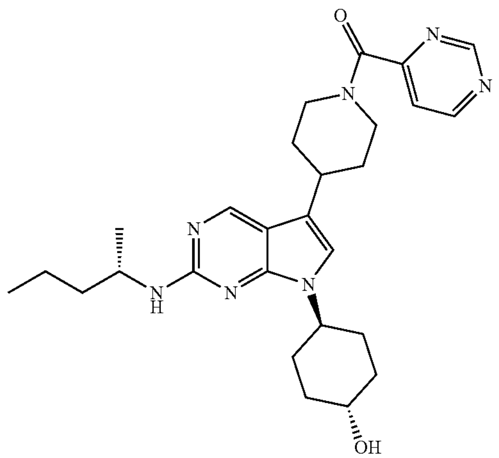 [SMILES: CCC[C@H](C)Nc1ncc2c(C3CCN(C(=O)c4ccncn4)CC3)cn([C@H]3CC[C@H](O)CC3)c2n1] | 491.6 | (4-(7-((1r,4S)-4-hydroxycyclohexyl)-2-(((S)-pentan-2-yl)amino)-7H-pyrrolo[2,3-d]pyrimidin-5-yl)piperidin-1-yl)(pyrimidin-4-yl)methanone |
| 67 | 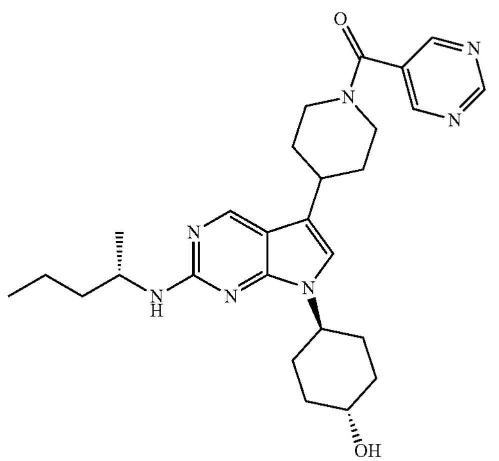 [SMILES: CCC[C@H](C)Nc1ncc2c(C3CCN(C(=O)c4cncnc4)CC3)cn([C@H]3CC[C@H](O)CC3)c2n1] | 491.6 | (4-(7-((1r,4S)-4-hydroxycyclohexyl)-2-(((S)-pentan-2-yl)amino)-7H-pyrrolo[2,3-d]pyrimidin-5-yl)piperidin-1-yl)(pyrimidin-5-yl)methanone |
| 68 | 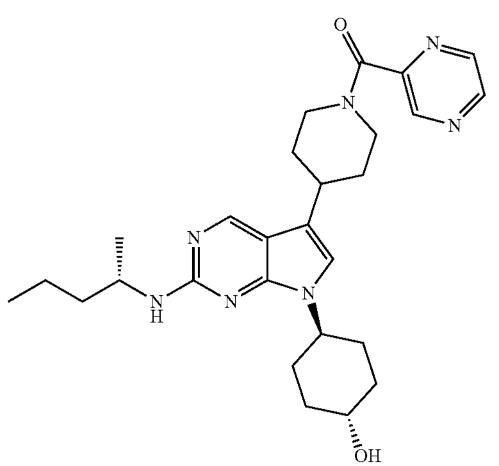 [SMILES: CCC[C@H](C)Nc1ncc2c(C3CCN(C(=O)c4cnccn4)CC3)cn([C@H]3CC[C@H](O)CC3)c2n1] | 491.6 | (4-(7-((1r,4S)-4-hydroxycyclohexyl)-2-(((S)-pentan-2-yl)amino)-7H-pyrrolo[2,3-d]pyrimidin-5-yl)piperidin-1-yl)(pyrazin-2-yl)methanone |

TABLE 1-continued

| No. | Structure | MW | Name |
|-----|-----------|-----|------|
| 69 | 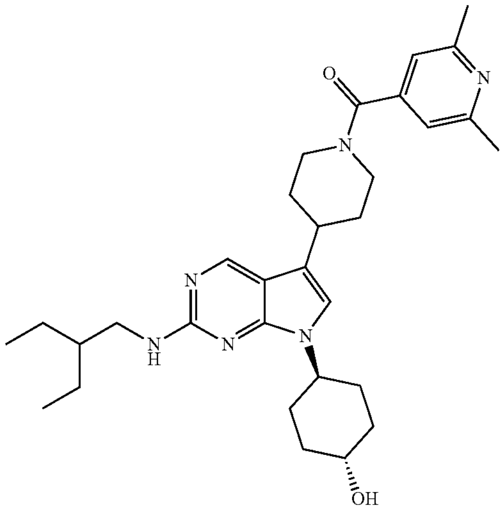 [SMILES: CCC(CC)CNc1ncc2c(C3CCN(C(=O)c4cc(C)nc(C)c4)CC3)cn([C@H]3CC[C@H](O)CC3)c2n1] | 532.7 | (2,6-dimethylpyridin-4-yl)(4-(2-((2-ethylbutyl)amino)-7-((1r,4r)-4-hydroxycyclohexyl)-7H-pyrrolo[2,3-d]pyrimidin-5-yl)piperidin-1-yl)methanone |
| 70 | 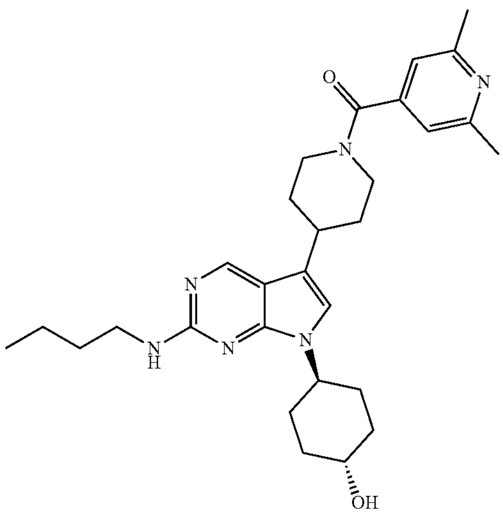 [SMILES: CCCCNc1ncc2c(C3CCN(C(=O)c4cc(C)nc(C)c4)CC3)cn([C@H]3CC[C@H](O)CC3)c2n1] | 504.7 | (4-(2-(butylamino)-7-((1r,4r)-4-hydroxycyclohexyl)-7H-pyrrolo[2,3-d]pyrimidin-5-yl)piperidin-1-yl)(2,6-dimethylpyridin-4-yl)methanone |
| 71 | 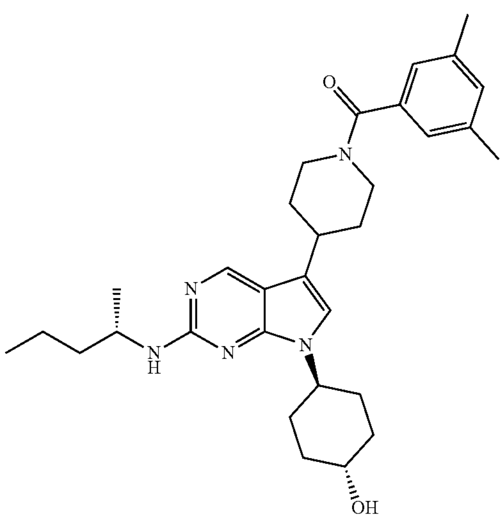 [SMILES: CCC[C@H](C)Nc1ncc2c(C3CCN(C(=O)c4cc(C)cc(C)c4)CC3)cn([C@H]3CC[C@H](O)CC3)c2n1] | 517.7 | (3,5-dimethylphenyl)(4-(7-((1r,4S)-4-hydroxycyclohexyl)-2-(((S)-pentan-2-yl)amino)-7H-pyrrolo[2,3-d]pyrimidin-5-yl)piperidin-1-yl)methanone |

TABLE 1-continued

| No. | Structure | MW | Name |
|---|---|---|---|
| 72 | 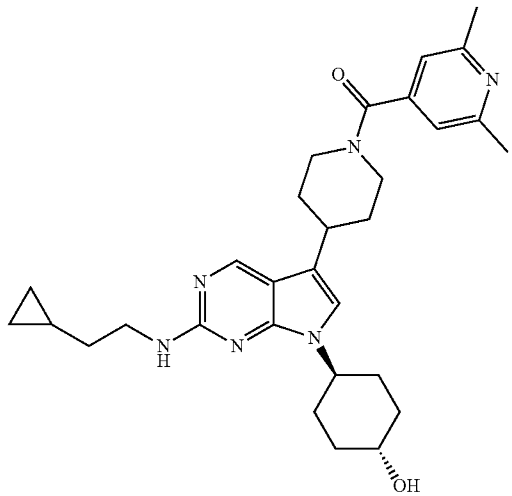 [SMILES: Cc1cc(C(=O)N2CCC(c3cn([C@H]4CC[C@H](O)CC4)c4nc(NCCC5CC5)ncc34)CC2)cc(C)n1] | 516.7 | (4-(2-((2-cyclopropylethyl)amino)-7-((1r,4r)-4-hydroxycyclohexyl)-7H-pyrrolo[2,3-d]pyrimidin-5-yl)piperidin-1-yl)(2,6-dimethylpyridin-4-yl)methanone |
| 73 | 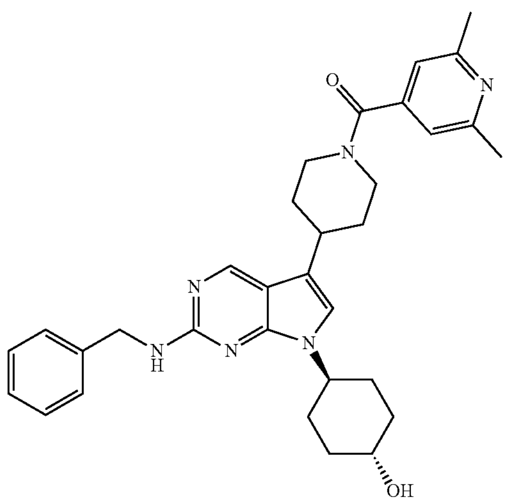 [SMILES: Cc1cc(C(=O)N2CCC(c3cn([C@H]4CC[C@H](O)CC4)c4nc(NCc5ccccc5)ncc34)CC2)cc(C)n1] | 538.7 | (4-(2-(benzylamino)-7-((1r,4r)-4-hydroxycyclohexyl)-7H-pyrrolo[2,3-d]pyrimidin-5-yl)piperidin-1-yl)(2,6-dimethylpyridin-4-yl)methanone |
| 74 | 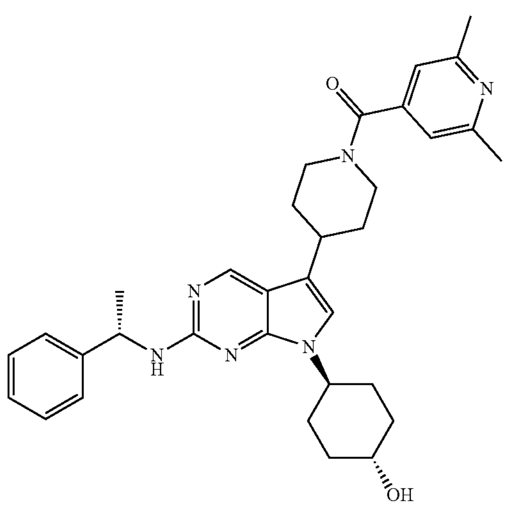 [SMILES: Cc1cc(C(=O)N2CCC(c3cn([C@H]4CC[C@H](O)CC4)c4nc(N[C@@H](C)c5ccccc5)ncc34)CC2)cc(C)n1] | 552.7 | (2,6-dimethylpyridin-4-yl)(4-(7-((1r,4S)-4-hydroxycyclohexyl)-2-(((S)-1-phenylethyl)amino)-7H-pyrrolo[2,3-d]pyrimidin-5-yl)piperidin-1-yl)methanone |

TABLE 1-continued

| No. | Structure | MW | Name |
|---|---|---|---|
| 75 | 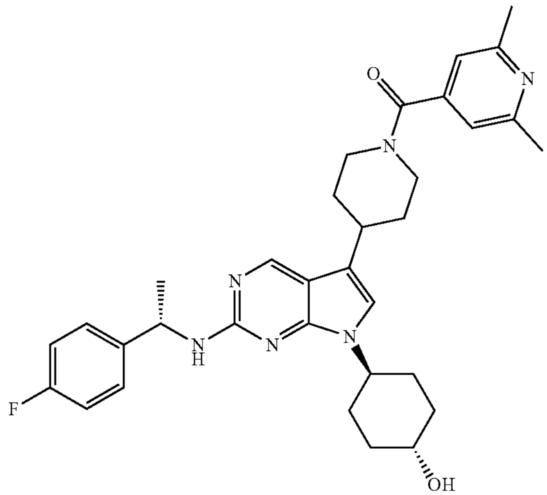 [SMILES: Cc1cc(C(=O)N2CCC(c3cn([C@H]4CC[C@H](O)CC4)c4nc(N[C@@H](C)c5ccc(F)cc5)ncc34)CC2)cc(C)n1] | 570.7 | (2,6-dimethylpyridin-4-yl)(4-(2-(((S)-1-(4-fluorophenyl)ethyl)amino)-7-((1r,4S)-4-hydroxycyclohexyl)-7H-pyrrolo[2,3-d]pyrimidin-5-yl)piperidin-1-yl)methanone |
| 76 | 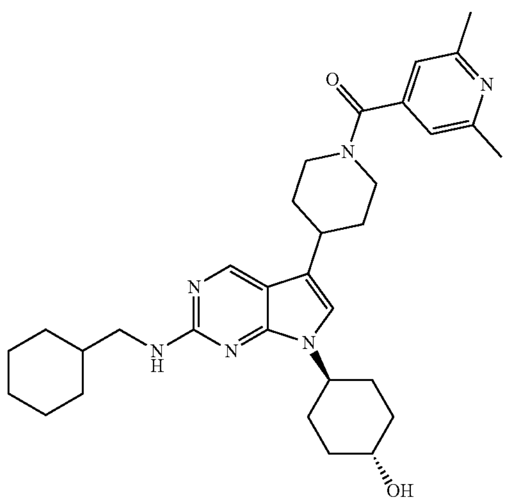 [SMILES: Cc1cc(C(=O)N2CCC(c3cn([C@H]4CC[C@H](O)CC4)c4nc(NCC5CCCCC5)ncc34)CC2)cc(C)n1] | 544.7 | (4-(2-((cyclohexylmethyl)amino)-7-((1r,4r)-4-hydroxycyclohexyl)-7H-pyrrolo[2,3-d]pyrimidin-5-yl)piperidin-1-yl)(2,6-dimethylpyridin-4-yl)methanone |
| 77 | 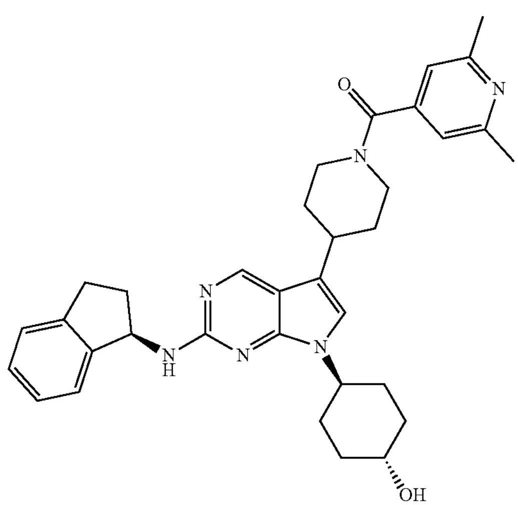 [SMILES: Cc1cc(C(=O)N2CCC(c3cn([C@H]4CC[C@H](O)CC4)c4nc(N[C@@H]5CCc6ccccc65)ncc34)CC2)cc(C)n1] | 564.7 | (4-(2-(((R)-2,3-dihydro-1H-inden-1-yl)amino)-7-((1r,4R)-4-hydroxycyclohexyl)-7H-pyrrolo[2,3-d]pyrimidin-5-yl)piperidin-1-yl)(2,6-dimethylpyridin-4-yl)methanone |

TABLE 1-continued

| No. | Structure | MW | Name |
|---|---|---|---|
| 78 | 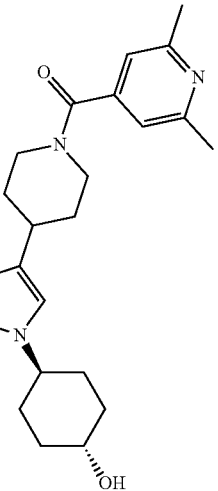 | 564.7 | (4-(2-(((S)-2,3-dihydro-1H-inden-1-yl)amino)-7-((1r,4S)-4-hydroxycyclohexyl)-7H-pyrrolo[2,3-d]pyrimidin-5-yl)piperidin-1-yl)(2,6-dimethylpyridin-4-yl)methanone |
| 79 | 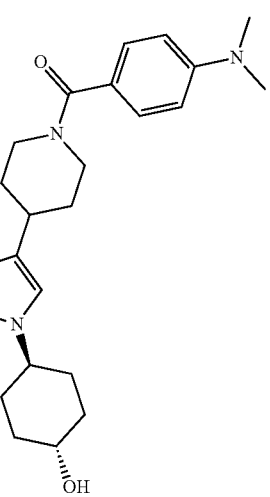 | 532.7 | (4-(dimethylamino)phenyl)(4-(7-((1r,4S)-4-hydroxycyclohexyl)-2-(((S)-pentan-2-yl)amino)-7H-pyrrolo[2,3-d]pyrimidin-5-yl)piperidin-1-yl)methanone |
| 80 | 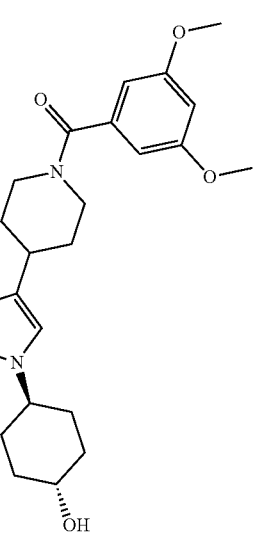 | 549.7 | (3,5-dimethoxyphenyl)(4-(7-((1r,4S)-4-hydroxycyclohexyl)-2-(((S)-pentan-2-yl)amino)-7H-pyrrolo[2,3-d]pyrimidin-5-yl)piperidin-1-yl)methanone |

TABLE 1-continued

| No. | Structure | MW | Name |
|---|---|---|---|
| 81 | 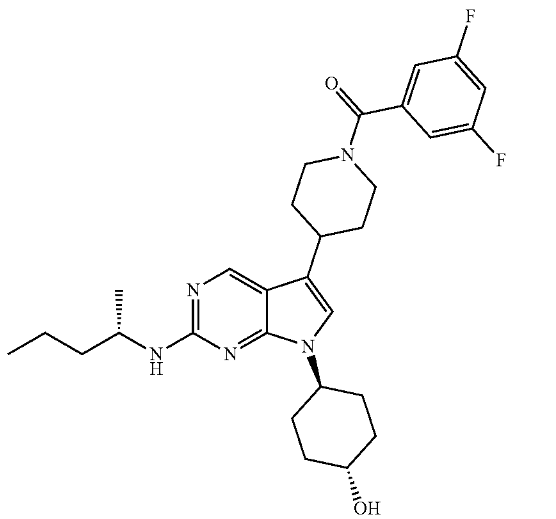 [SMILES: CCC[C@H](C)Nc1ncc2c(C3CCN(C(=O)c4cc(F)cc(F)c4)CC3)cn([C@H]3CC[C@H](O)CC3)c2n1] | 525.6 | (3,5-difluorophenyl)(4-(7-((1r,4S)-4-hydroxycyclohexyl)-2-(((S)-pentan-2-yl)amino)-7H-pyrrolo[2,3-d]pyrimidin-5-yl)piperidin-1-yl)methanone |
| 82 | 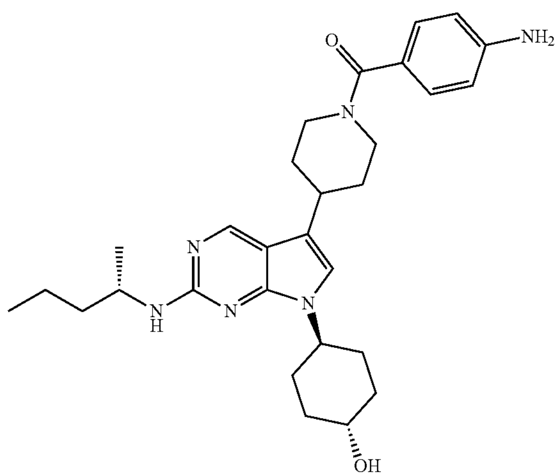 [SMILES: CCC[C@H](C)Nc1ncc2c(C3CCN(C(=O)c4ccc(N)cc4)CC3)cn([C@H]3CC[C@H](O)CC3)c2n1] | 504.7 | (4-aminophenyl)(4-(7-((1r,4S)-4-hydroxycyclohexyl)-2-(((S)-pentan-2-yl)amino)-7H-pyrrolo[2,3-d]pyrimidin-5-yl)piperidin-1-yl)methanone |
| 83 | 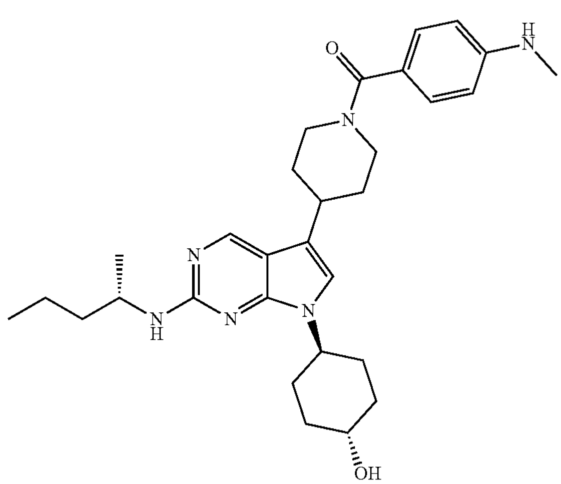 [SMILES: CCC[C@H](C)Nc1ncc2c(C3CCN(C(=O)c4ccc(NC)cc4)CC3)cn([C@H]3CC[C@H](O)CC3)c2n1] | 518.7 | (4-(7-((1r,4S)-4-hydroxycyclohexyl)-2-(((S)-pentan-2-yl)amino)-7H-pyrrolo[2,3-d]pyrimidin-5-yl)piperidin-1-yl)(4-(methylamino)phenyl)methanone |

TABLE 1-continued

| No. | Structure | MW | Name |
|---|---|---|---|
| 84 | 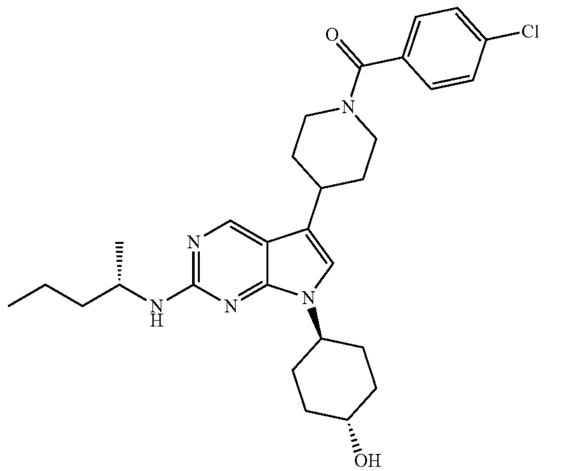 [SMILES: CCC[C@H](C)Nc1ncc2c(C3CCN(C(=O)c4ccc(Cl)cc4)CC3)cn([C@H]3CC[C@H](O)CC3)c2n1] | 524.1 | (4-chlorophenyl)(4-(7-((1r,4S)-4-hydroxycyclohexyl)-2-(((S)-pentan-2-yl)amino)-7H-pyrrolo[2,3-d]pyrimidin-5-yl)piperidin-1-yl)methanone |
| 85 | 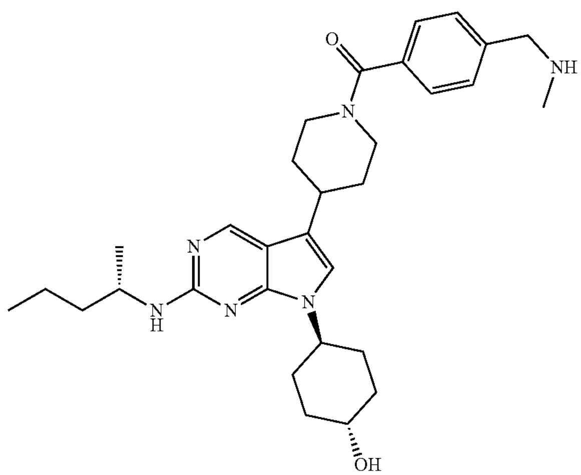 [SMILES: CCC[C@H](C)Nc1ncc2c(C3CCN(C(=O)c4ccc(CNC)cc4)CC3)cn([C@H]3CC[C@H](O)CC3)c2n1] | 532.7 | (4-(7-((1r,4S)-4-hydroxycyclohexyl)-2-(((S)-pentan-2-yl)amino)-7H-pyrrolo[2,3-d]pyrimidin-5-yl)piperidin-1-yl)(4-((methylamino)methyl)phenyl)methanone |
| 86 | 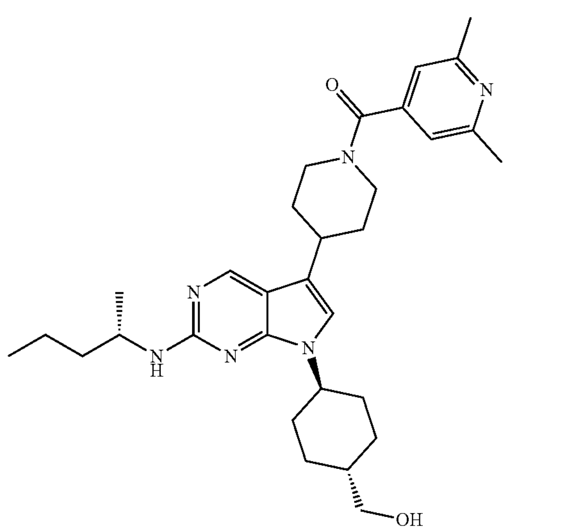 [SMILES: CCC[C@H](C)Nc1ncc2c(C3CCN(C(=O)c4cc(C)nc(C)c4)CC3)cn([C@H]3CC[C@H](CO)CC3)c2n1] | 532.7 | (2,6-dimethylpyridin-4-yl)(4-(7-((1r,4S)-4-hydroxymethyl)cyclohexyl)-2-(((S)-pentan-2-yl)amino)-7H-pyrrolo[2,3-d]pyrimidin-5-yl)piperidin-1-yl)methanone |

TABLE 1-continued

| No. | Structure | MW | Name |
|---|---|---|---|
| 87 | 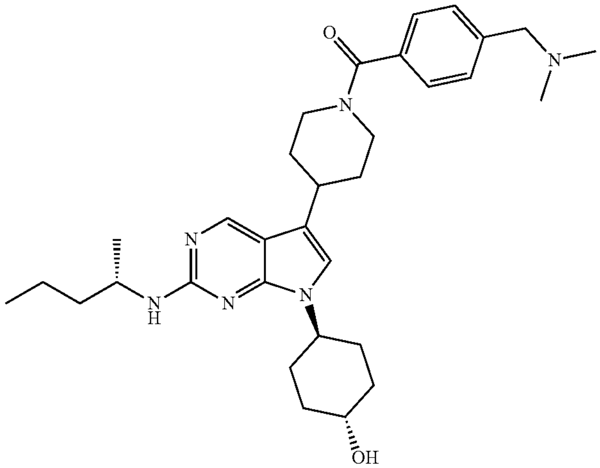 [SMILES: CCC[C@H](C)Nc1ncc2c(C3CCN(C(=O)c4ccc(CN(C)C)cc4)CC3)cn([C@H]3CC[C@H](O)CC3)c2n1] | 546.8 | (4-(((dimethylamino)methyl)phenyl)(4-(7-((1r,4S)-4-hydroxycyclohexyl)-2-(((S)-pentan-2-yl)amino)-7H-pyrrolo[2,3-d]pyrimidin-5-yl)piperidin-1-yl)methanone |
| 88 | 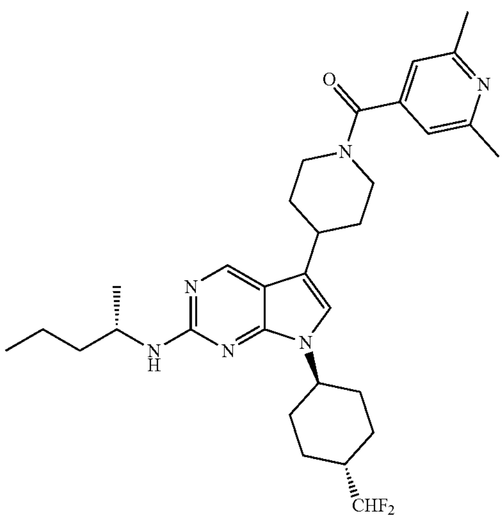 [SMILES: CCC[C@H](C)Nc1ncc2c(C3CCN(C(=O)c4cc(C)nc(C)c4)CC3)cn([C@H]3CC[C@H](C(F)F)CC3)c2n1] | 552.7 | (4-(7-((1r,4S)-4-(difluoromethyl)cyclohexyl)-2-(((S)-pentan-2-yl)amino)-7H-pyrrolo[2,3-d]pyrimidin-5-yl)piperidin-1-yl)(2,6-dimethylpyridin-4-yl)methanone |
| 89 | 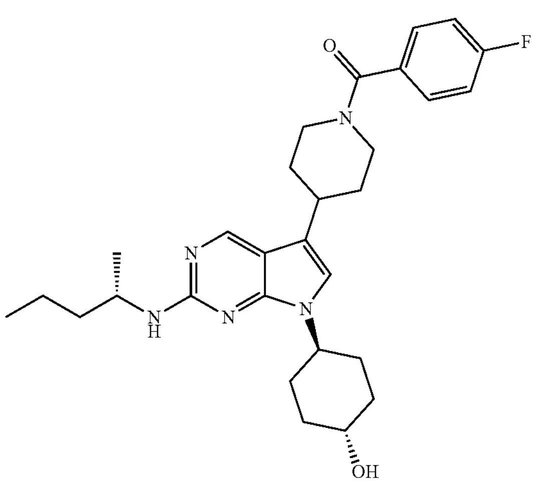 [SMILES: CCC[C@H](C)Nc1ncc2c(C3CCN(C(=O)c4ccc(F)cc4)CC3)cn([C@H]3CC[C@H](O)CC3)c2n1] | 507.7 | (4-fluorophenyl)(4-(7-((1r,4S)-4-hydroxycyclohexyl)-2-(((S)-pentan-2-yl)amino)-7H-pyrrolo[2,3-d]pyrimidin-5-yl)piperidin-1-yl)methanone |

TABLE 1-continued

| No. | Structure | MW | Name |
|---|---|---|---|
| 90 | 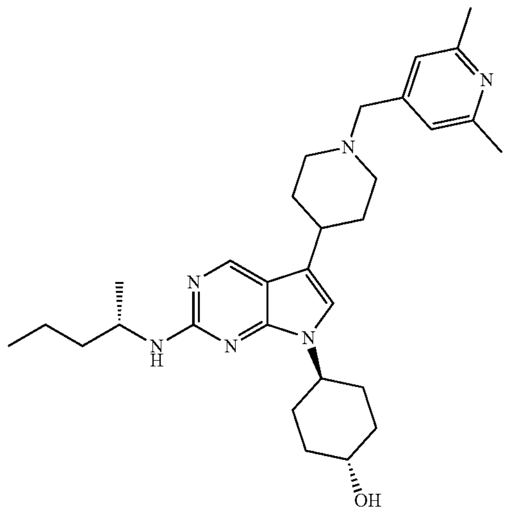 [SMILES: CCC[C@H](C)Nc1ncc2c(C3CCN(Cc4cc(C)nc(C)c4)CC3)cn([C@H]3CC[C@H](O)CC3)c2n1] | 504.7 | (1S,4r)-4-(5-(1-((2,6-dimethylpyridin-4-yl)methyl)piperidin-4-yl)-2-(((S)-pentan-2-yl)amino)-7H-pyrrolo[2,3-d]pyrimidin-7-yl)cyclohexan-1-ol |
| 91 | 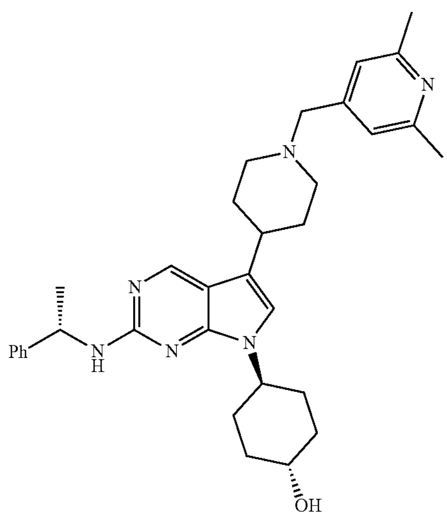 [SMILES: Cc1cc(CN2CCC(c3cn([C@H]4CC[C@H](O)CC4)c4nc(N[C@@H](C)c5ccccc5)ncc34)CC2)cc(C)n1] | 538.7 | (1S,4r)-4-(5-(1-((2,6-dimethylpyridin-4-yl)methyl)piperidin-4-yl)-2-(((S)-1-phenylethyl)amino)-7H-pyrrolo[2,3-d]pyrimidin-7-yl)cyclohexan-1-ol |
| 92 | 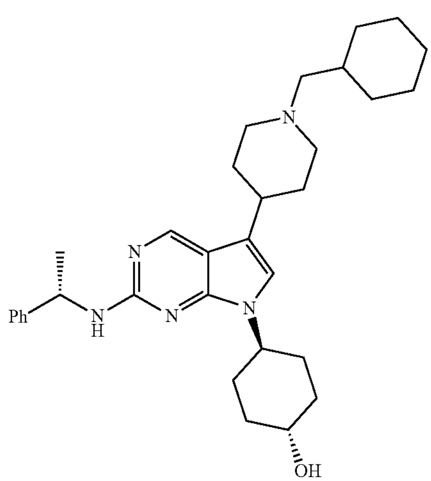 [SMILES: C[C@H](Nc1ncc2c(C3CCN(CC4CCCCC4)CC3)cn([C@H]3CC[C@H](O)CC3)c2n1)c1ccccc1] | 515.8 | (1S,4r)-4-(5-(1-(cyclohexylmethyl)piperidin-4-yl)-2-(((S)-1-phenylethyl)amino)-7H-pyrrolo[2,3-d]pyrimidin-7-yl)cyclohexan-1-ol |

TABLE 1-continued

| No. | Structure | MW | Name |
|---|---|---|---|
| 93 | 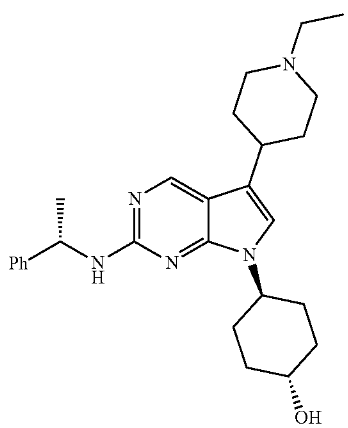 [SMILES: CCN1CCC(c2cn([C@H]3CC[C@H](O)CC3)c3nc(N[C@@H](C)c4ccccc4)ncc23)CC1] | 447.6 | (1S,4r)-4-(5-(1-ethylpiperidin-4-yl)-2-(((S)-1-phenylethyl)amino)-7H-pyrrolo[2,3-d]pyrimidin-7-yl)cyclohexan-1-ol |
| 94 | 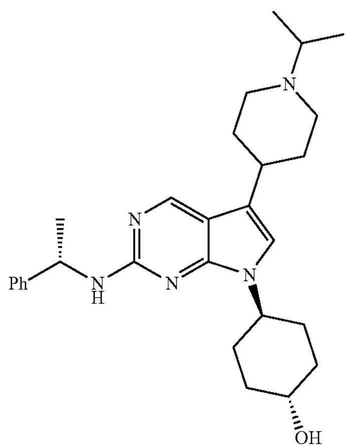 [SMILES: CC(C)N1CCC(c2cn([C@H]3CC[C@H](O)CC3)c3nc(N[C@@H](C)c4ccccc4)ncc23)CC1] | 461.7 | (1S,4r)-4-(5-(1-isopropylpiperidin-4-yl)-2-(((S)-1-phenylethyl)amino)-7H-pyrrolo[2,3-d]pyrimidin-7-yl)cyclohexan-1-ol |
| 95 | 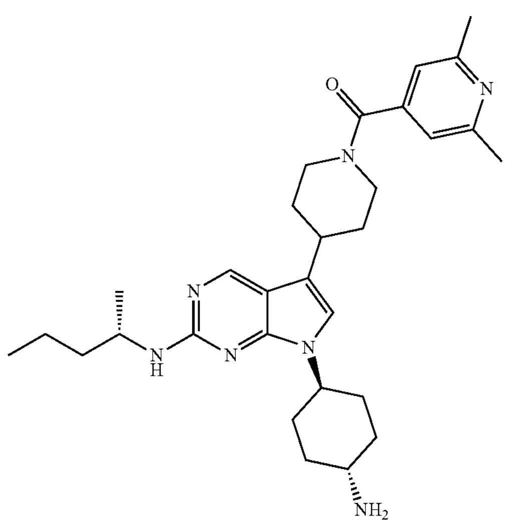 [SMILES: CCC[C@H](C)Nc1ncc2c(C3CCN(C(=O)c4cc(C)nc(C)c4)CC3)cn([C@H]3CC[C@H](N)CC3)c2n1] | 517.7 | (4-(7-((1r,4S)-4-aminocyclohexyl)-2-(((S)-pentan-2-yl)amino)-7H-pyrrolo[2,3-d]pyrimidin-5-yl)piperidin-1-yl)(2,6-dimethylpyridin-4-yl)methanone |

TABLE 1-continued

| No. | Structure | MW | Name |
|---|---|---|---|
| 96 | 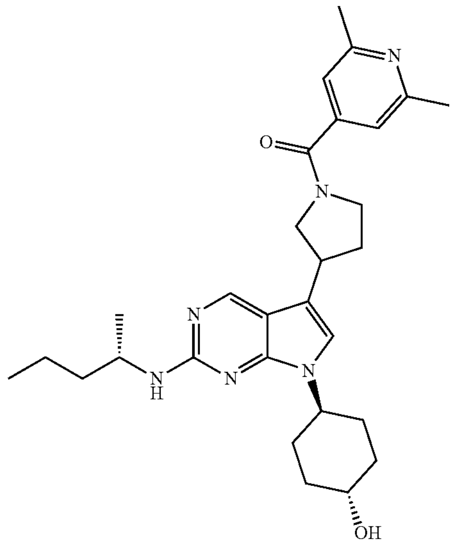 [SMILES: CCC[C@H](C)Nc1ncc2c(C3CCN(C(=O)c4cc(C)nc(C)c4)C3)cn([C@H]3CC[C@H](O)CC3)c2n1] | 504.7 | (2,6-dimethylpyridin-4-yl)(3-(7-((1r,4S)-4-hydroxycyclohexyl)-2-(((S)-pentan-2-yl)amino)-7H-pyrrolo[2,3-d]pyrimidin-5-yl)pyrrolidin-1-yl)methanone |
| 97 | 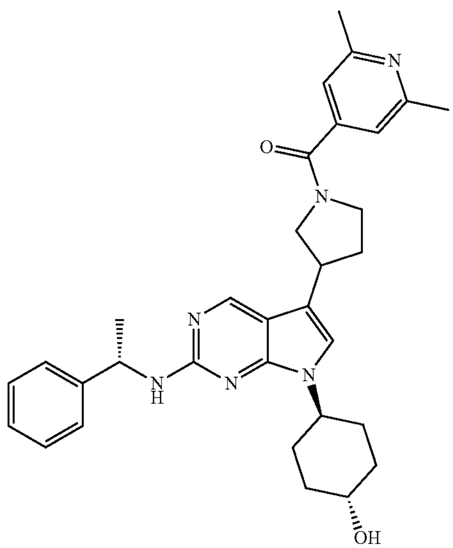 [SMILES: Cc1cc(C(=O)N2CCC(c3cn([C@H]4CC[C@H](O)CC4)c4nc(N[C@@H](C)c5ccccc5)ncc34)C2)cc(C)n1] | 538.7 | (2,6-dimethylpyridin-4-yl)(3-(7-((1r,4S)-4-hydroxycyclohexyl)-2-(((S)-1-phenylethyl)amino)-7H-pyrrolo[2,3-d]pyrimidin-5-yl)pyrrolidin-1-yl)methanone |
| 98 | 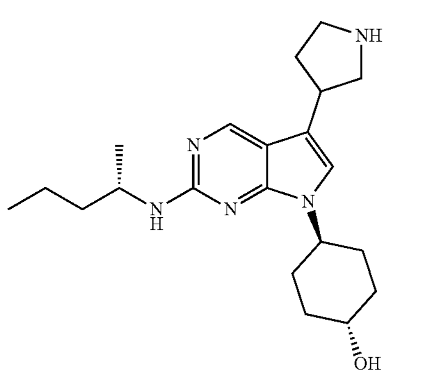 [SMILES: CCC[C@H](C)Nc1ncc2c(C3CCNC3)cn([C@H]3CC[C@H](O)CC3)c2n1] | 371.5 | (1S,4r)-4-(2-(((S)-pentan-2-yl)amino)-5-(pyrrolidin-3-yl)-7H-pyrrolo[2,3-d]pyrimidin-7-yl)cyclohexan-1-ol |

TABLE 1-continued

| No. | Structure | MW | Name |
|---|---|---|---|
| 99 | 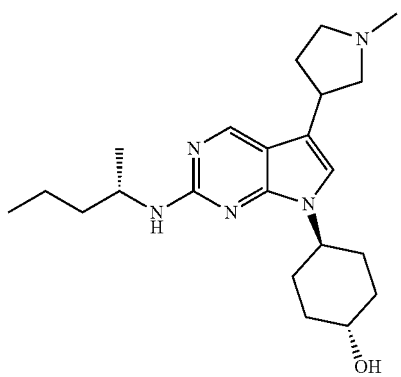 [SMILES: CCC[C@H](C)Nc1ncc2c(C3CCN(C)C3)cn([C@H]3CC[C@H](O)CC3)c2n1] | 385.6 | (1S,4r)-4-(5-(1-methylpyrrolidin-3-yl)-2-(((S)-pentan-2-yl)amino)-7H-pyrrolo[2,3-d]pyrimidin-7-yl)cyclohexan-1-ol |
| 100 | 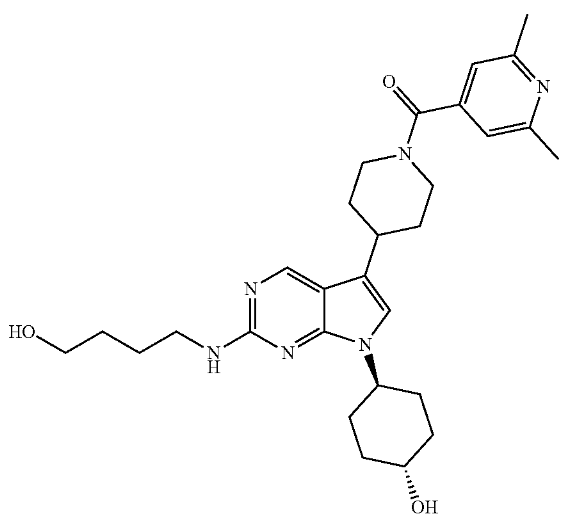 [SMILES: Cc1cc(C(=O)N2CCC(c3cn([C@H]4CC[C@H](O)CC4)c4nc(NCCCCO)ncc34)CC2)cc(C)n1] | 520.7 | (2,6-dimethylpyridin-4-yl)(4-(2-((4-hydroxybutyl)amino)-7-((1r,4r)-4-hydroxycyclohexyl)-7H-pyrrolo[2,3-d]pyrimidin-5-yl)piperidin-1-yl)methanone |
| 101 | 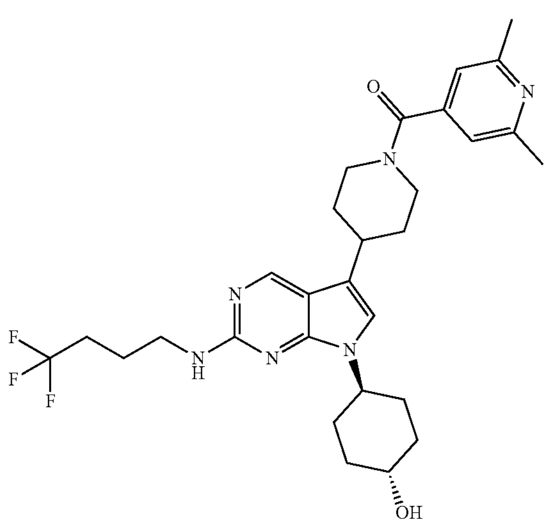 [SMILES: Cc1cc(C(=O)N2CCC(c3cn([C@H]4CC[C@H](O)CC4)c4nc(NCCCC(F)(F)F)ncc34)CC2)cc(C)n1] | 558.7 | (2,6-dimethylpyridin-4-yl)(4-(7-((1r,4r)-4-hydroxycyclohexyl)-2-((4,4,4-trifluorobutyl)amino)-7H-pyrrolo[2,3-d]pyrimidin-5-yl)piperidin-1-yl)methanone |

TABLE 1-continued

| No. | Structure | MW | Name |
|---|---|---|---|
| 102 | 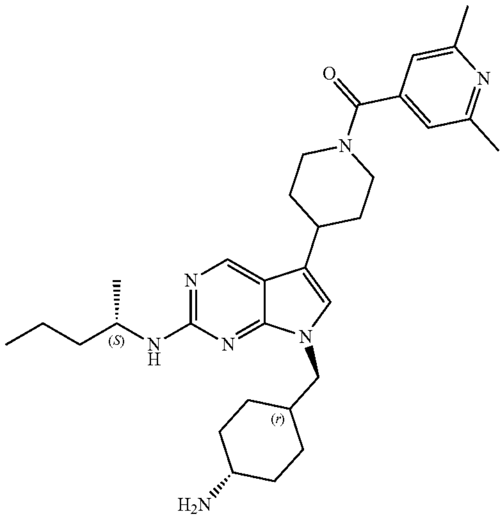 | 531.8 | (4-(7-(((1r,4S)-4-aminocyclohexyl)methyl)-2-(((S)-pentan-2-yl)amino)-7H-pyrrolo[2,3-d]pyrimidin-5-yl)piperidin-1-yl)(2,6-dimethylpyridin-4-yl)methanone |
| 103 | 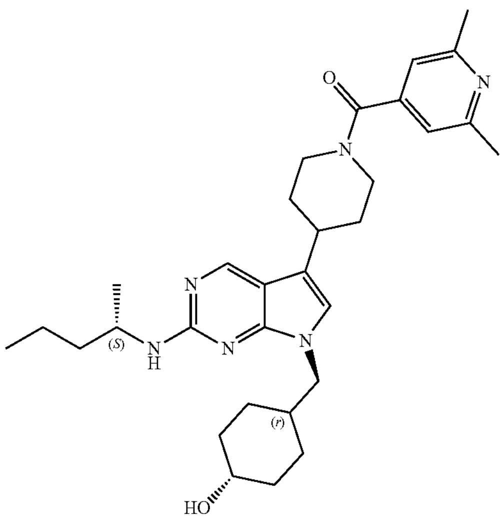 | 532.7 | (2,6-dimethylpyridin-4-yl)(4-(7-(((1r,4S)-4-hydroxycyclohexyl)methyl)-2-(((S)-pentan-2-yl)amino)-7H-pyrrolo[2,3-d]pyrimidin-5-yl)piperidin-1-yl)methanone |

4. Evaluation of Activity Against Mer Tyrosine Kinase

Table 2 below illustrates the effects of the disclosed compounds on Mer tyrosine kinase and Tyro3 tyrosine kinase. NOTE: ++++ means <10 nM; +++ means between 10-100 nM; ++ means between 100 nM-1 μM; + means between 1-30 μM; − means inactive.

TABLE 2

| No. | Mer IC$_{50}$ | Tyro3 IC$_{50}$ |
|---|---|---|
| 1 | ++++ | +++ |
| 2 | ++++ | ++ |
| 3 | ++++ | +++ |
| 4 | ++++ | ++ |
| 5 | ++++ | ++ |
| 8 | ++++ | +++ |
| 9 | ++++ | ++ |
| 10 | ++++ | +++ |
| 11 | ++++ | +++ |
| 12 | +++ | + |
| 13 | ++++ | +++ |
| 14 | ++++ | +++ |
| 15 | ++++ | +++ |
| 16 | ++++ | +++ |
| 17 | ++++ | +++ |
| 18 | ++++ | +++ |
| 19 | ++++ | +++ |
| 20 | ++++ | ++ |
| 21 | ++++ | +++ |
| 22 | ++++ | +++ |
| 23 | ++++ | +++ |
| 24 | ++++ | +++ |
| 25 | ++++ | +++ |
| 26 | ++++ | +++ |
| 27 | ++++ | +++ |
| 28 | ++++ | ++ |
| 29 | ++++ | ++ |
| 30 | ++++ | +++ |
| 31 | ++++ | ++ |
| 32 | ++++ | ++ |
| 33 | ++++ | ++ |

TABLE 2-continued

| No. | Mer IC$_{50}$ | Tyro3 IC$_{50}$ |
|---|---|---|
| 34 | ++++ | +++ |
| 35 | ++++ | +++ |
| 36 | ++++ | +++ |
| 42 | ++++ | ++ |
| 43 | ++++ | ++ |
| 51 | ++++ | +++ |
| 52 | ++++ | +++ |
| 53 | ++++ | +++ |
| 54 | ++++ | +++ |
| 55 | ++++ | +++ |
| 56 | ++++ | +++ |
| 57 | ++++ | ++ |
| 58 | ++++ | +++ |
| 59 | ++++ | +++ |
| 60 | ++++ | ++ |
| 61 | ++++ | ++ |
| 62 | ++++ | ++ |
| 63 | ++++ | ++ |
| 64 | ++++ | +++ |
| 65 | ++++ | +++ |
| 66 | ++++ | +++ |
| 67 | ++++ | +++ |
| 68 | ++++ | ++ |
| 69 | ++++ | +++ |
| 70 | ++++ | ++ |
| 71 | ++++ | ++ |
| 72 | ++++ | ++ |
| 73 | ++++ | ++ |
| 74 | ++++ | ++ |
| 75 | ++++ | +++ |
| 76 | ++++ | + |
| 77 | +++ | ++ |
| 78 | +++ | + |
| 79 | ++++ | ++ |
| 80 | ++++ | ++ |
| 81 | ++++ | ++ |
| 82 | ++++ | ++ |
| 83 | ++++ | +++ |
| 84 | ++++ | ++ |
| 85 | ++++ | +++ |
| 86 | ++++ | +++ |
| 87 | ++++ | +++ |
| 88 | ++++ | ++ |
| 89 | ++++ | ++ |
| 90 | ++++ | ++ |
| 91 | +++ | ++ |
| 92 | ++++ | ++ |
| 93 | +++ | ++ |
| 94 | +++ | ++ |
| 95 | ++++ | +++ |
| 96 | +++ | ++ |
| 97 | ++ | ++ |
| 98 | ++++ | +++ |
| 99 | ++++ | ++ |
| 100 | ++++ | + |
| 101 | ++++ | + |
| 102 | ++++ | ++ |
| 103 | +++ | ++ |

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula:

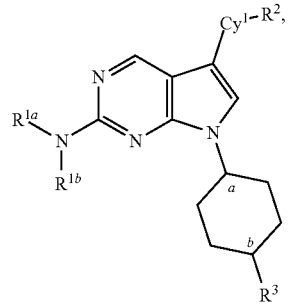

wherein $Cy^1$ is selected from C3-C8 cycloalkyl and C2-C7 heterocycloalkyl, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino;

wherein $R^{1a}$ is selected from hydrogen, C1-C8 alkyl, and $Cy^2$, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino;

wherein $Cy^2$, when present, is selected from C3-C9 cycloalkyl, C2-C7 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino;

wherein $R^{1b}$ bis selected from C1-C8 alkyl, $Cy^2$, and (C1-C4 alkyl)$Cy^2$, and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino;

wherein $R^2$ is selected from —C(O)$R^{20}$, —C(O)N($R^{22}$)$R^{20}$, —N($R^{22}$)C(O)$R^{20}$, —SO$_2$N($R^{22}$)$R^{21}$, —N($R^{22}$)SO$_2$$R^{21}$, —SO$_2$$R^{21}$, and —(CH2)$_n$$Cy^3$;

wherein n is selected from 0, 1, 2, 3, and 4;

wherein each of $R^{20}$ and $R^{21}$, when present, is selected from C1-C4 alkyl, —(CH$_2$)$_q$OR$^{30}$, and $Cy^4$;

wherein q is selected from 0, 1, 2, 3, and 4;

wherein $R^{30}$, when present, is selected from hydrogen and C1-C4 alkyl;

wherein $Cy^4$, when present, is selected from C3-C8 cycloalkyl, C2-C7 heterocycloalkyl, C5-C6 aryl, and C3-C5 heteroaryl and substituted with 0, 1, 2, or 3 groups independently selected from halogen, —NH$_2$, C1-C4 alkyl, C1-C4 haloalkyl, C1-C4 alkoxy, C1-C4 hydroxyalkyl, C1-C4 alkylamino, (C1-C4)(C1-C4) dialkylamino, and (C1-C4 alkyl)NR$^{40a}$R$^{40b}$;

wherein each of $R^{40a}$ and $R^{40b}$, when present, is independently selected from hydrogen and C1-C4 alkyl;

wherein $R^{22}$, when present, is selected from hydrogen and C1-C4 alkyl;

wherein $Cy^3$, when present, is selected from C3-C8 cycloalkyl, C2-C7 heterocycloalkyl, C5-C6 aryl, and C4-C5 heteroaryl and substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino; and wherein R³ is selected from —(CH₂)ₚOH and —(CH₂)ₚNHR²³;
  wherein p is selected from 0, 1, and 2; and
  wherein R²³, when present, is selected from hydrogen and C1-C4 alkyl, or a pharmaceutically acceptable salt thereof.

2. The compound of claim 1, wherein the substituents on the carbons marked "a" and "b" are in a trans configuration.

3. The compound of claim 1, wherein Cy¹ is a structure selected from:

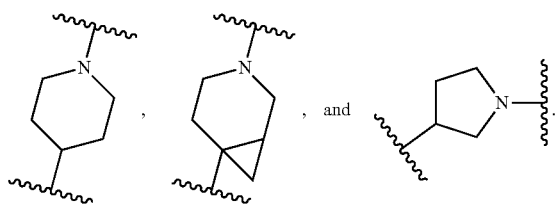 [SMILES: *C1CCN(*)CC1 ; *N1CCC2(*)CC2C1 ; *C1CCN(*)C1]

4. The compound of claim 1, wherein R¹ᵃ is hydrogen.
5. The compound of claim 1, wherein R¹ᵇ bis C1-C8 alkyl.
6. The compound of claim 1, wherein R¹ᵇ bis a structure:

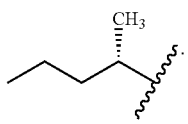

7. The compound of claim 5, wherein R¹ᵇ is selected from Cy² and (C1-C4 alkyl)Cy² substituted with 0, 1, 2, or 3 groups independently selected from halogen, C1-C4 alkyl, C1-C4 haloalkyl, C1-C4 alkoxy, C1-C4 hydroxyalkyl, C1-C4 alkylamino, and (C1-C4)(C1-C4) dialkylamino.

8. The compound of claim 1, wherein R¹ᵇ is a structure selected from:

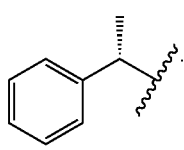

9. The compound of claim 1, wherein R² is —C(O)R²⁰.
10. The compound of claim 1, wherein R³ is —OH.
11. The compound of claim 1, wherein the compound has a structure:

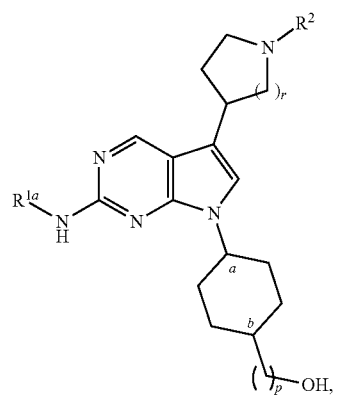

wherein r is selected from 1 and 2.

12. The compound of claim 1, wherein the compound is selected from:

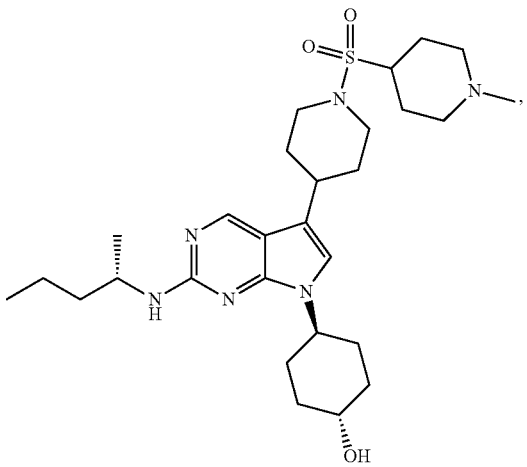

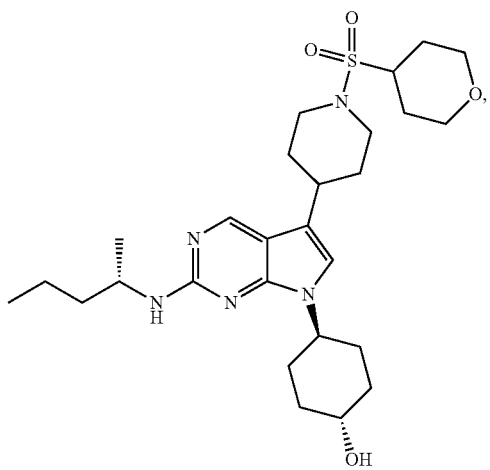

339
-continued
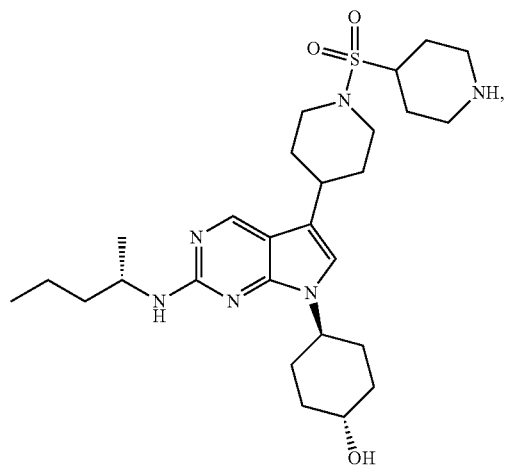
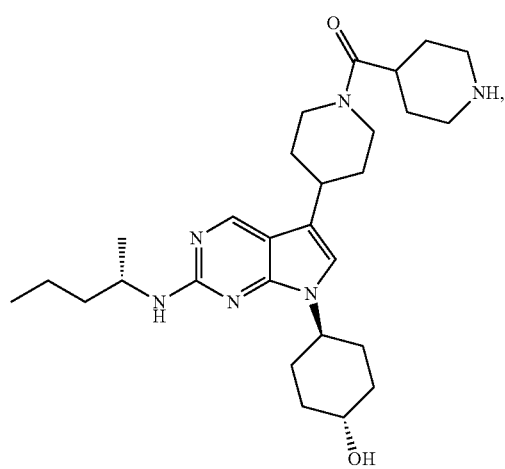
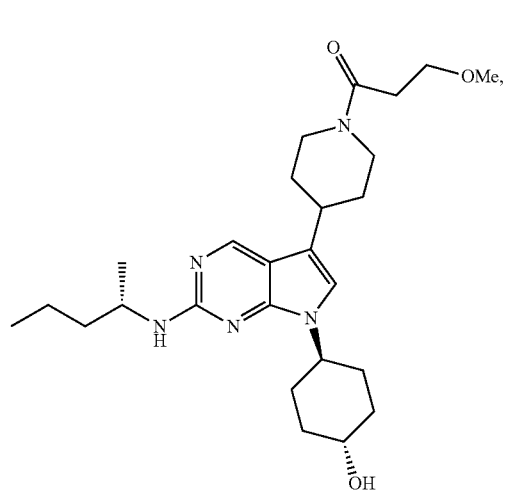
340
-continued
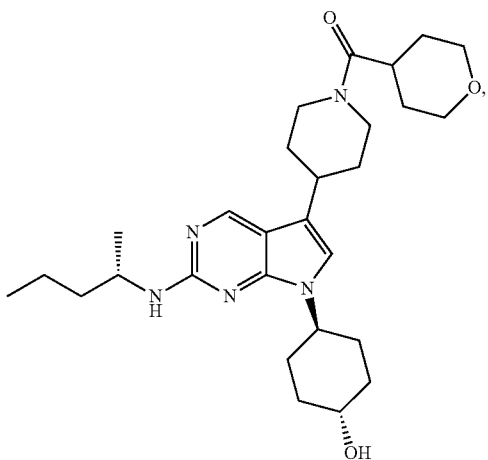
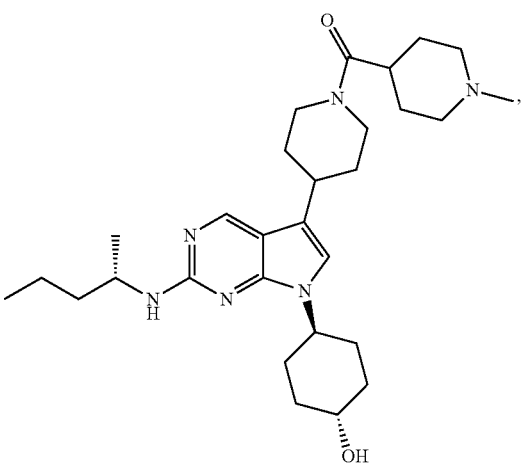
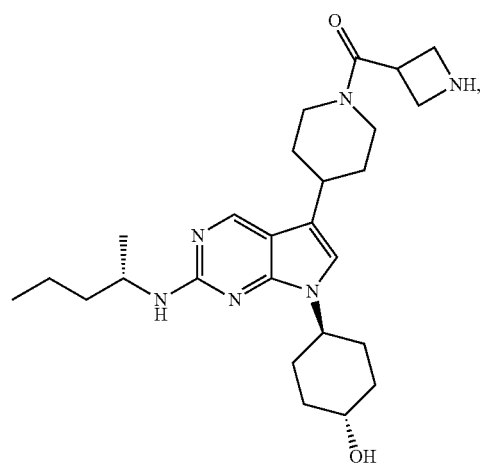

341 342
-continued -continued
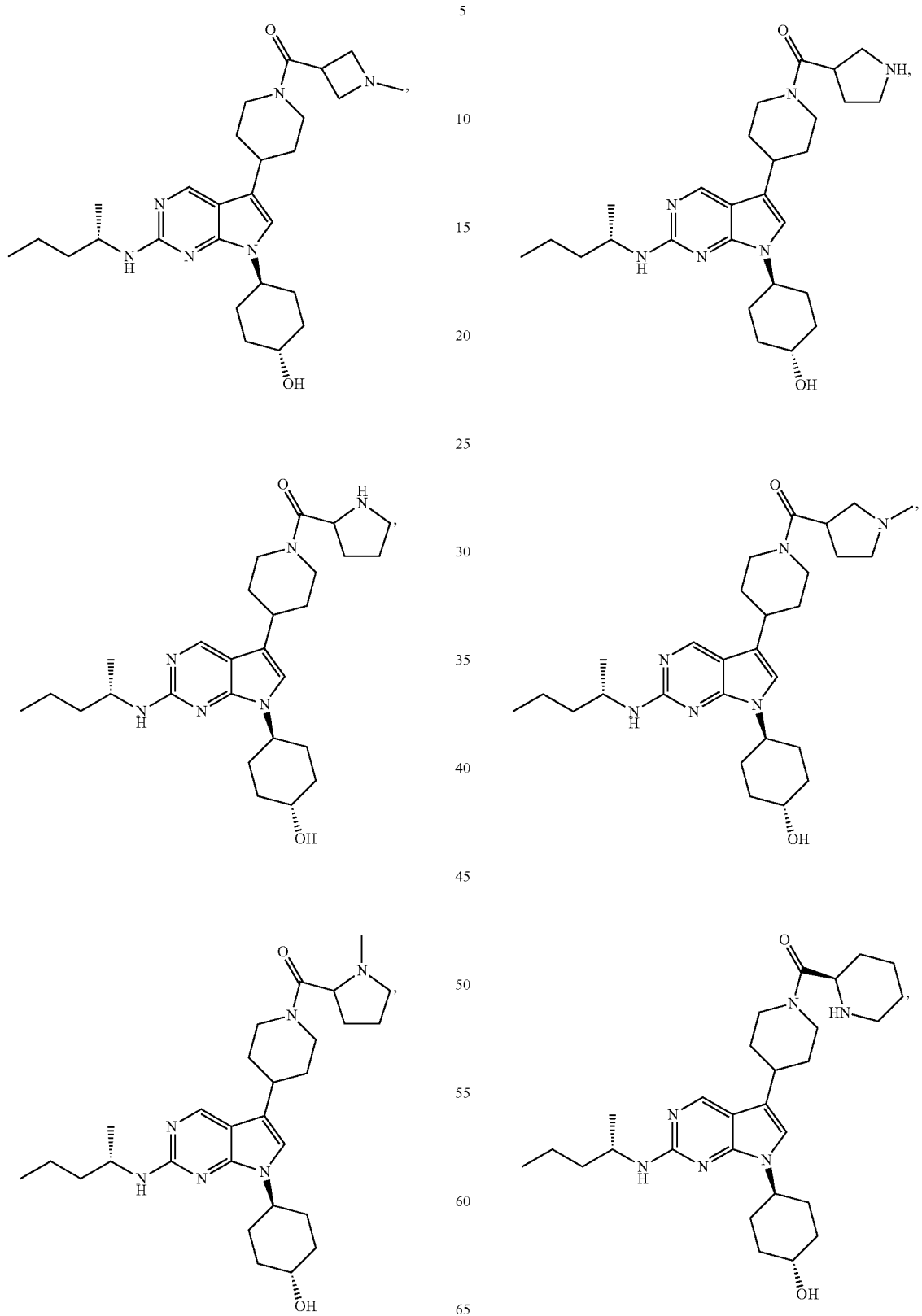

343
-continued
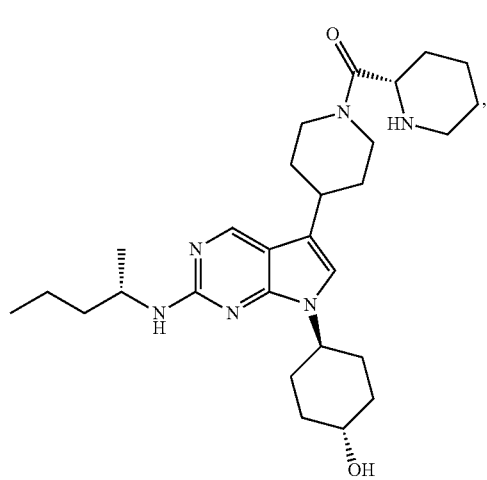
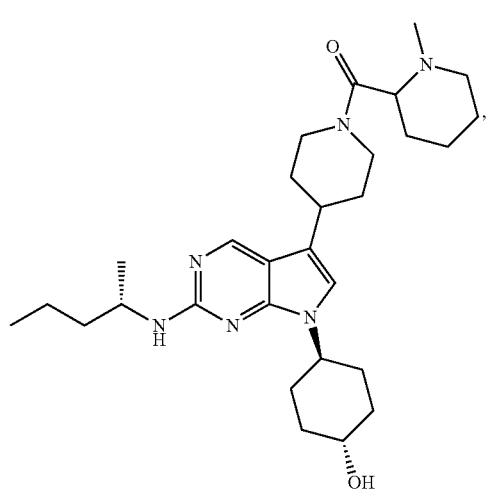
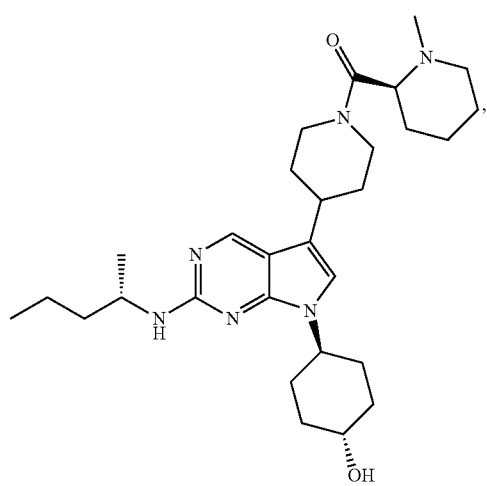
344
-continued
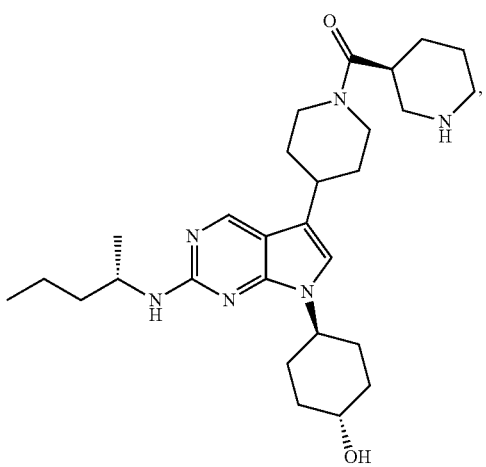
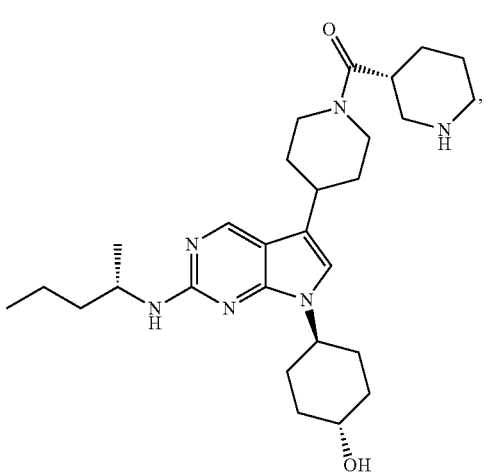
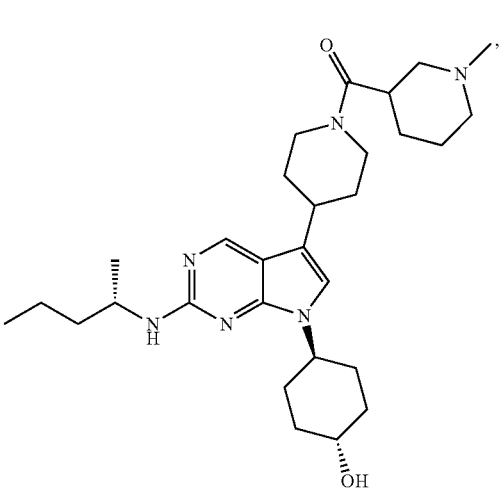

345
-continued
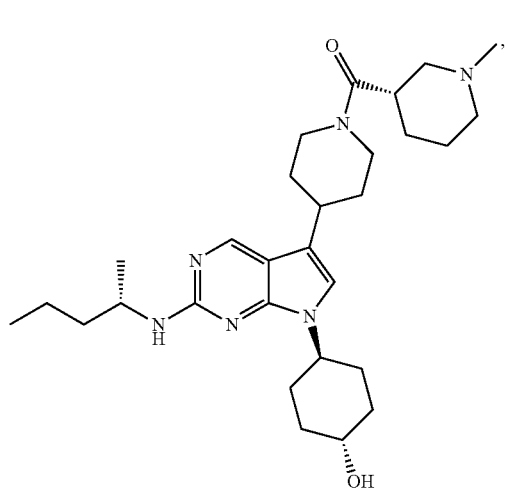
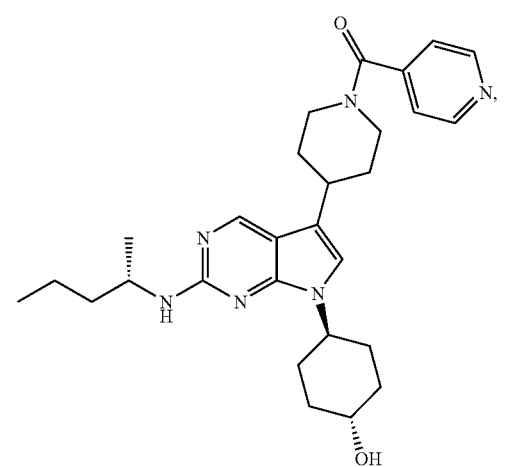
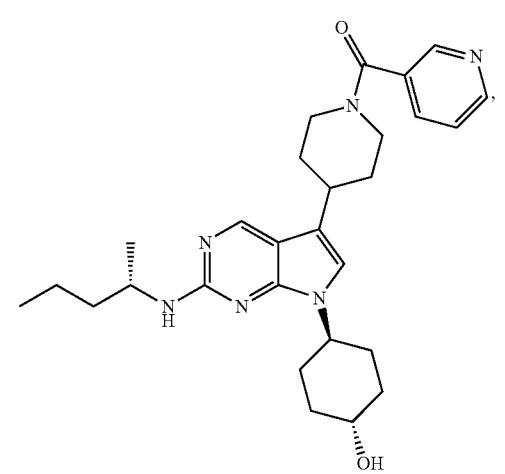
346
-continued
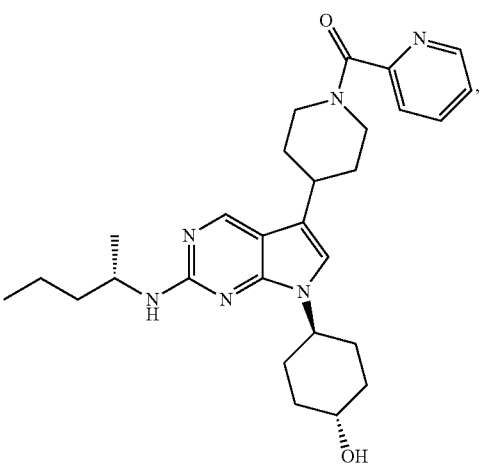
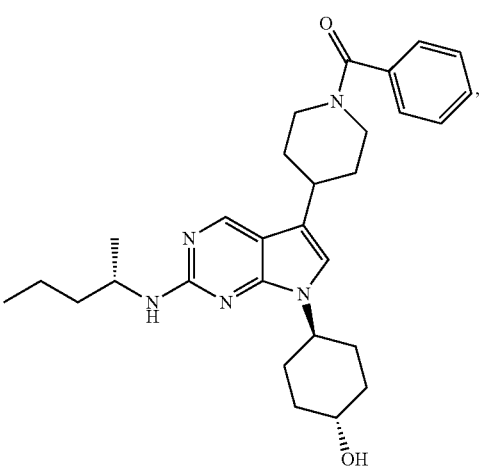
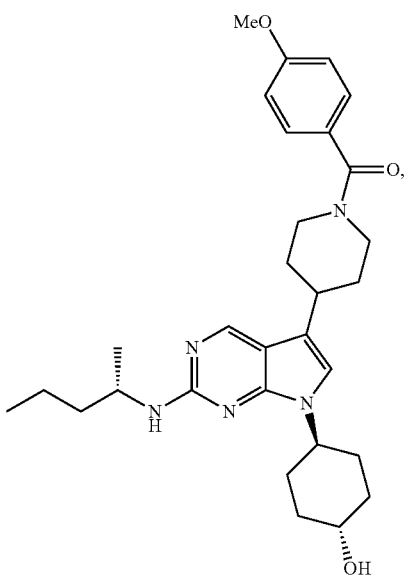

347
-continued
348
-continued
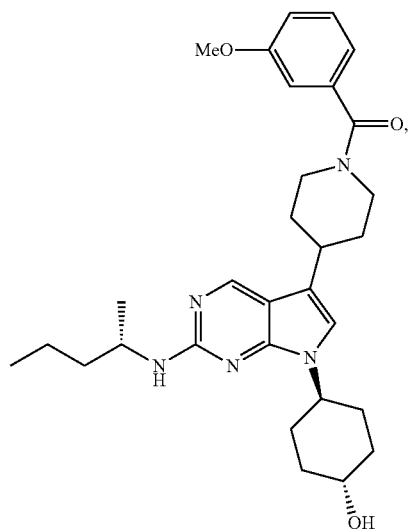
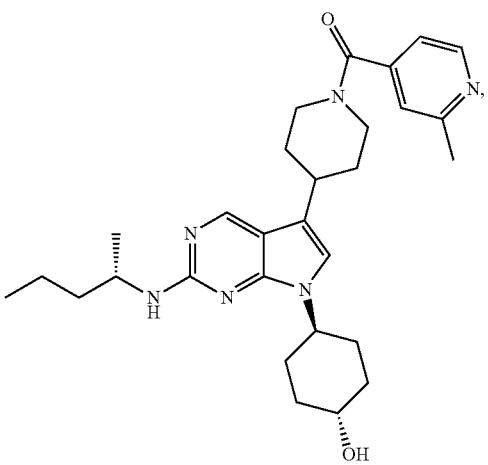
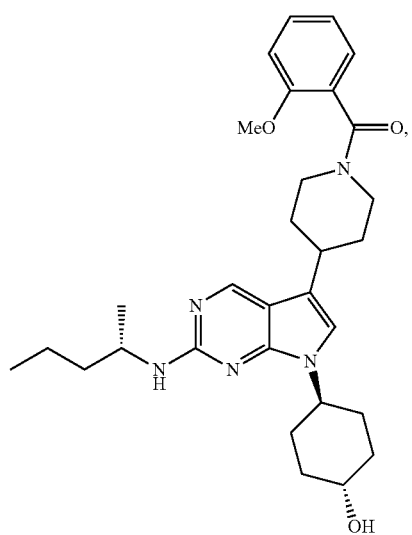
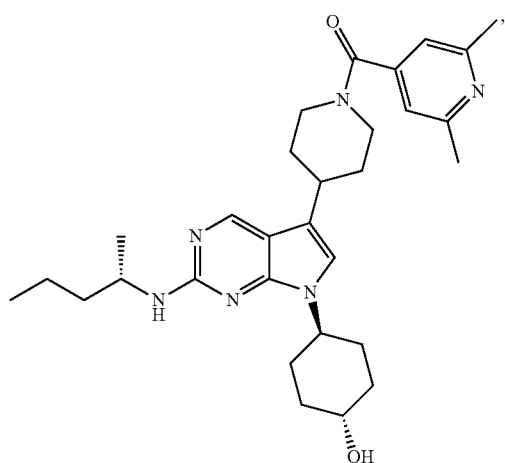
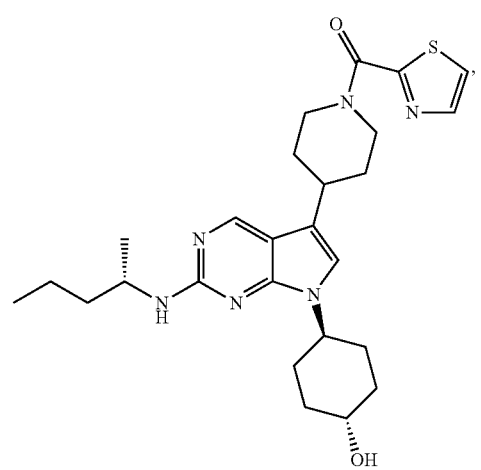

349
-continued
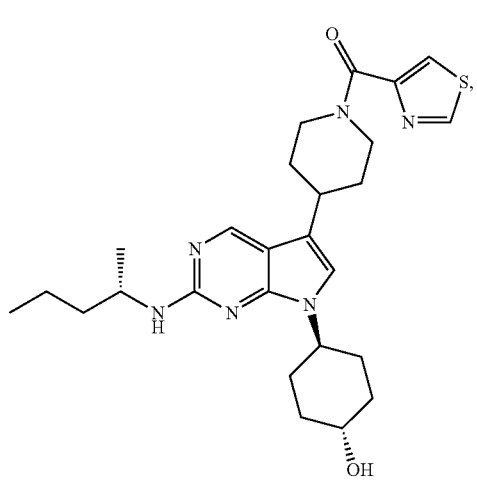
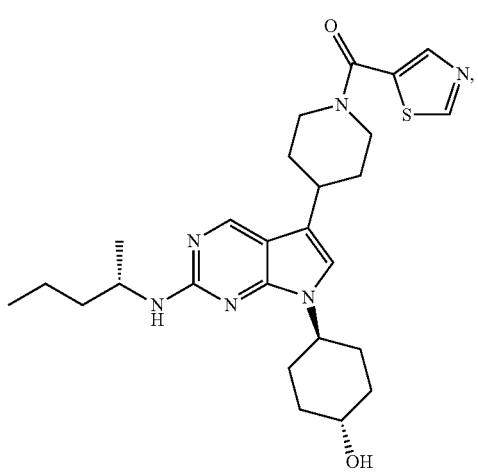
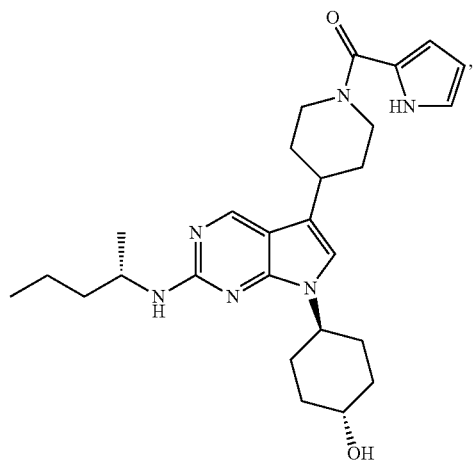
350
-continued
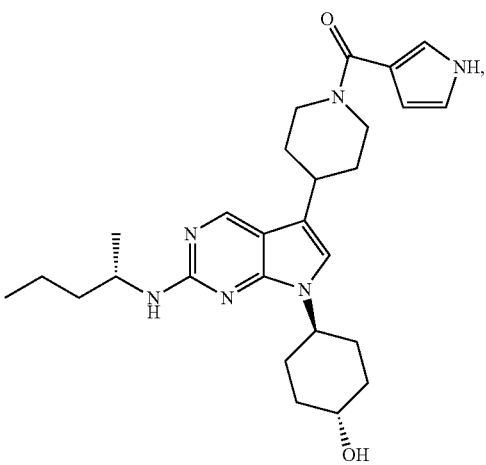
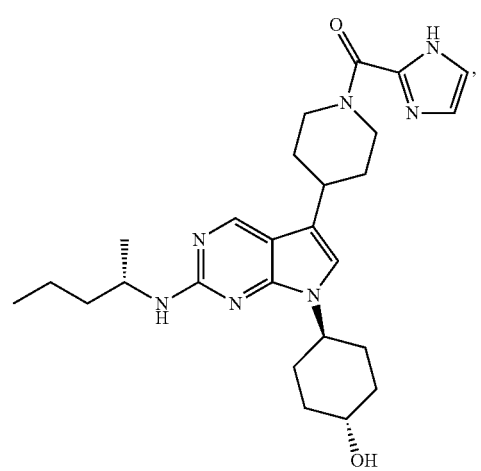
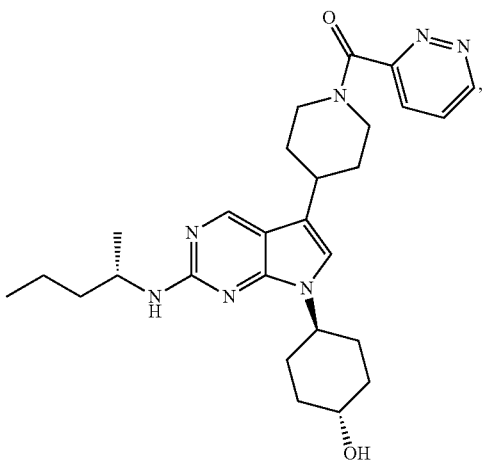

351
-continued
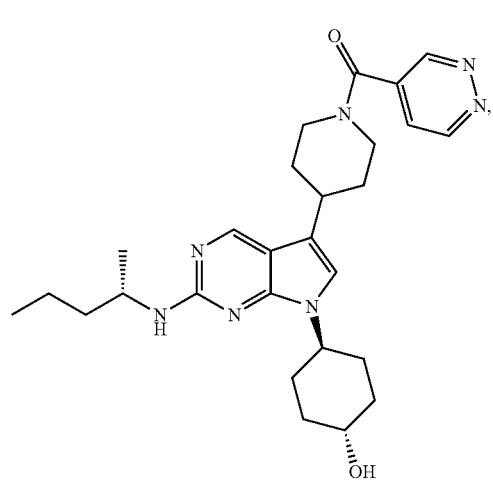
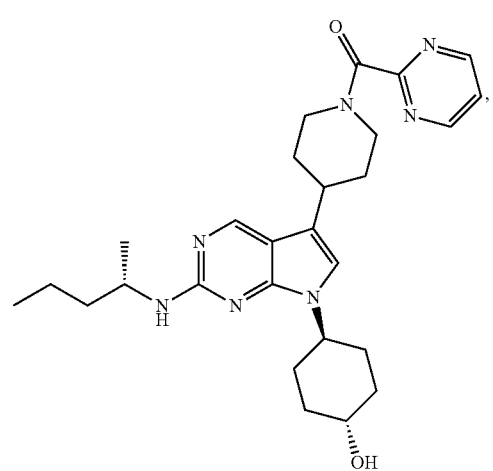
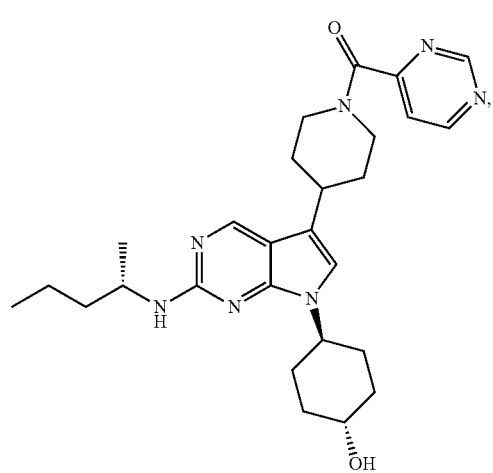
352
-continued
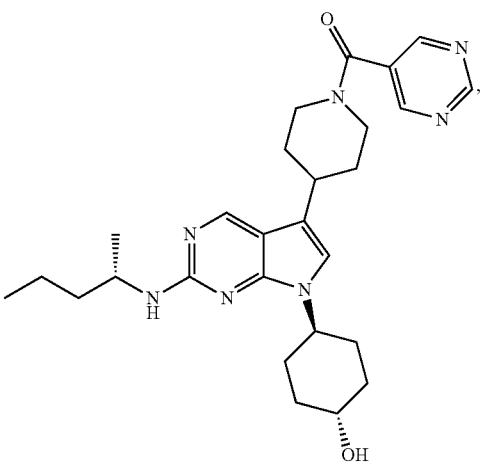
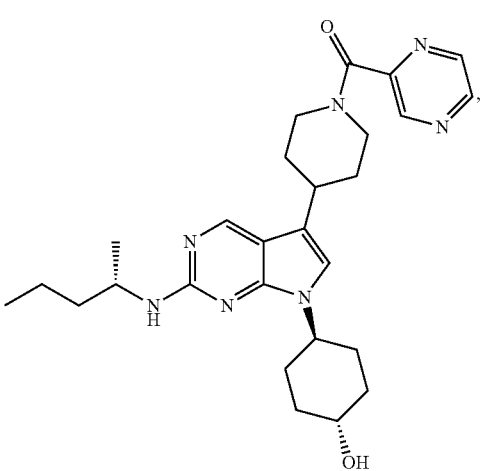
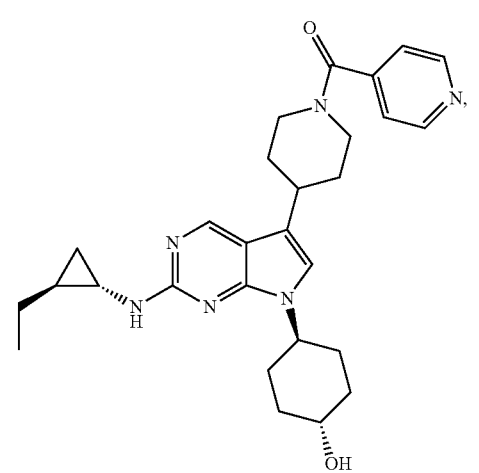

353
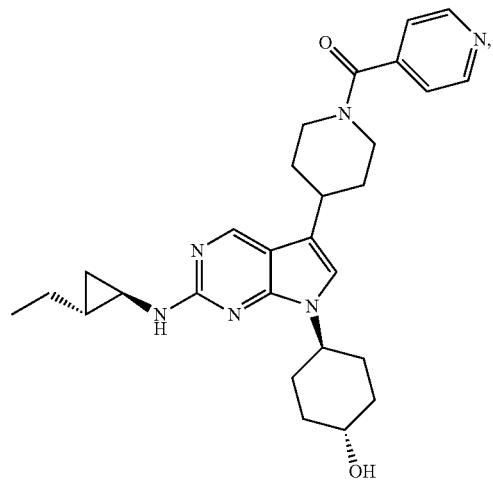
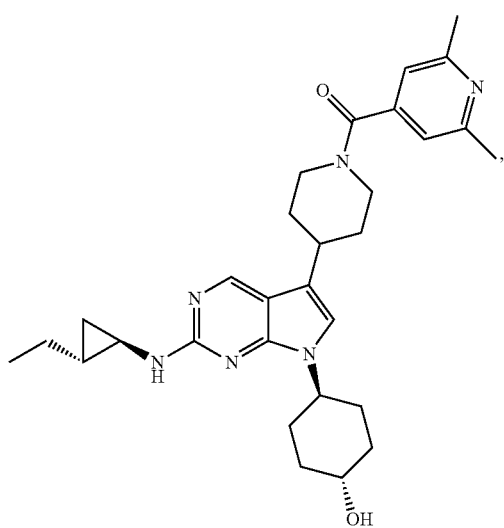
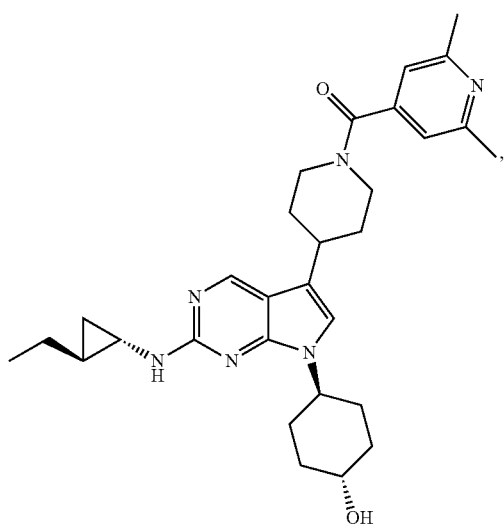
354
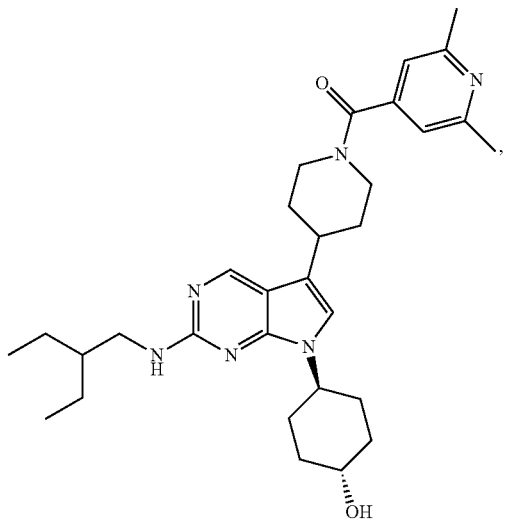
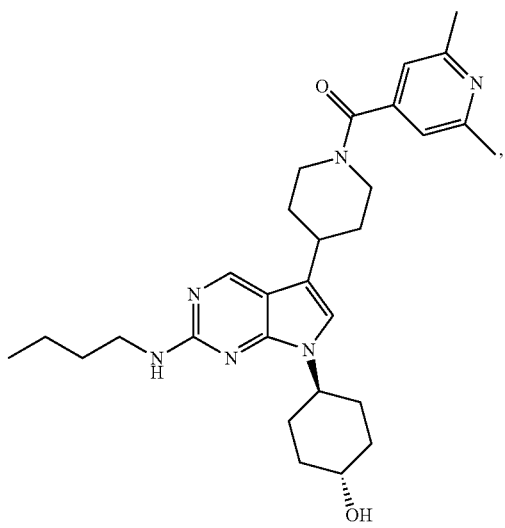
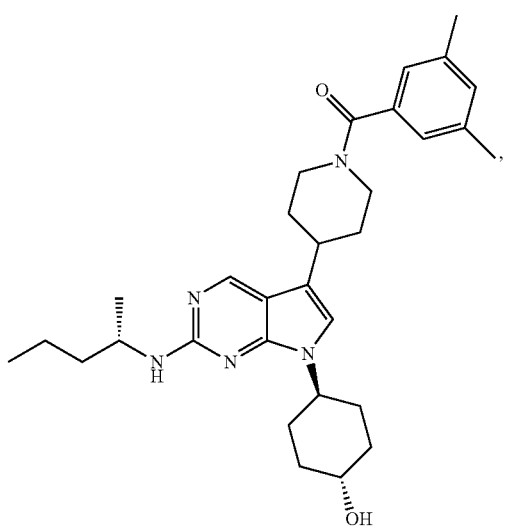

355
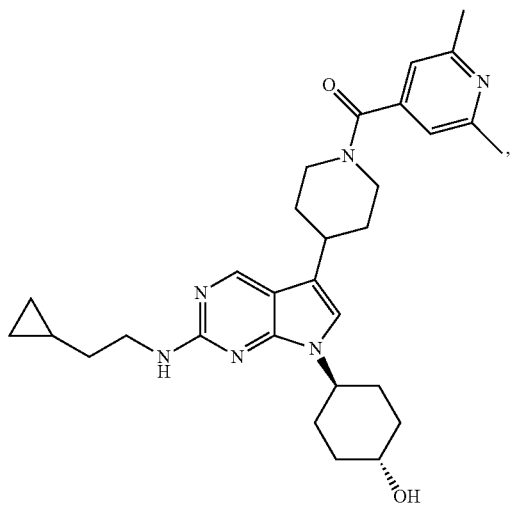
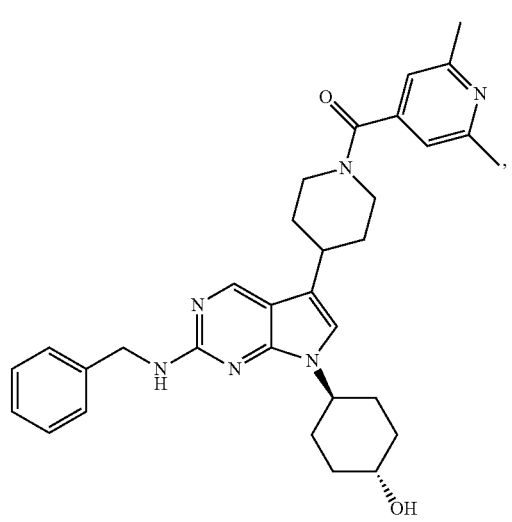
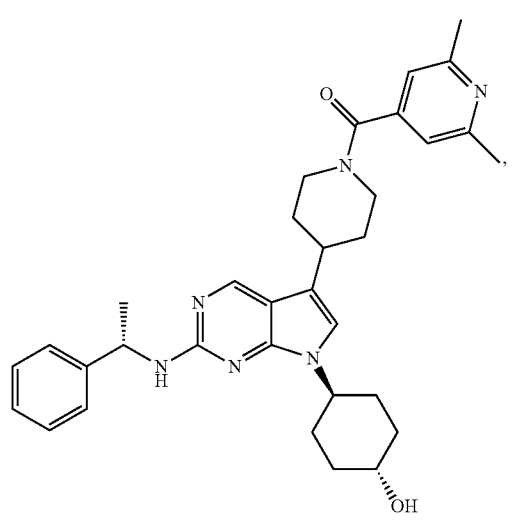 [SMILES: Cc1cc(C(=O)N2CCC(c3cn([C@H]4CC[C@H](O)CC4)c4nc(N[C@@H](C)c5ccccc5)ncc34)CC2)cc(C)n1]
356
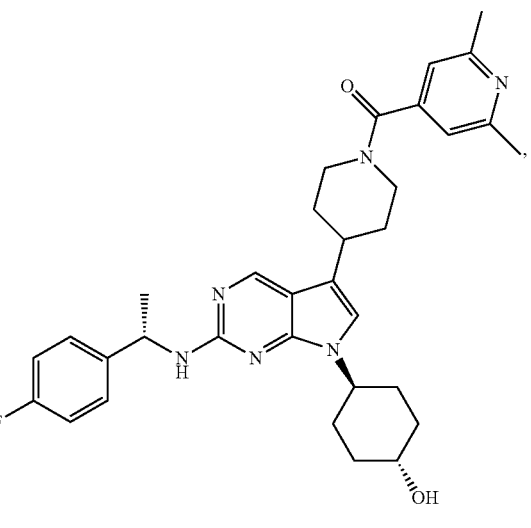
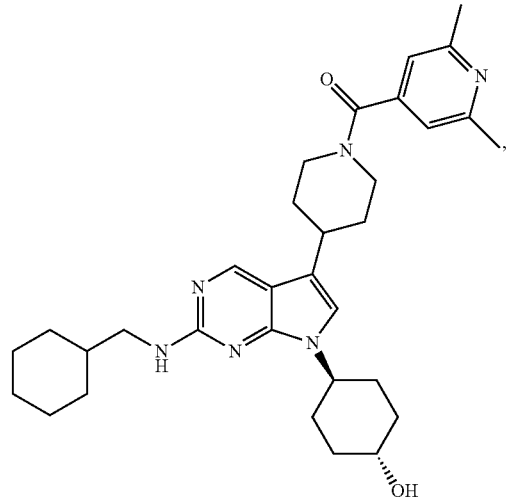
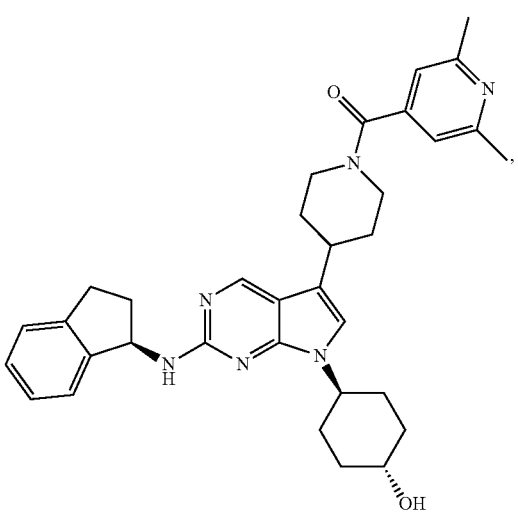

357
-continued
358
-continued
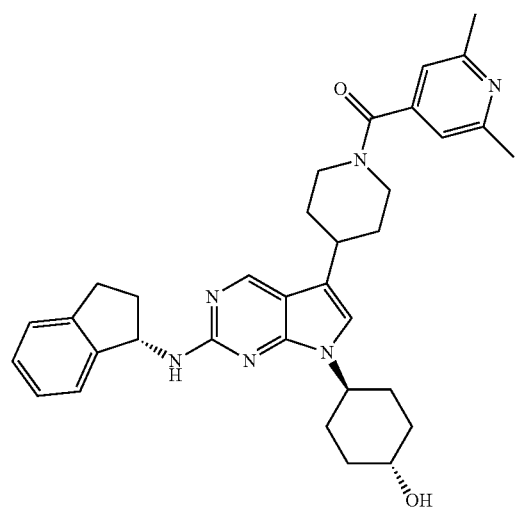
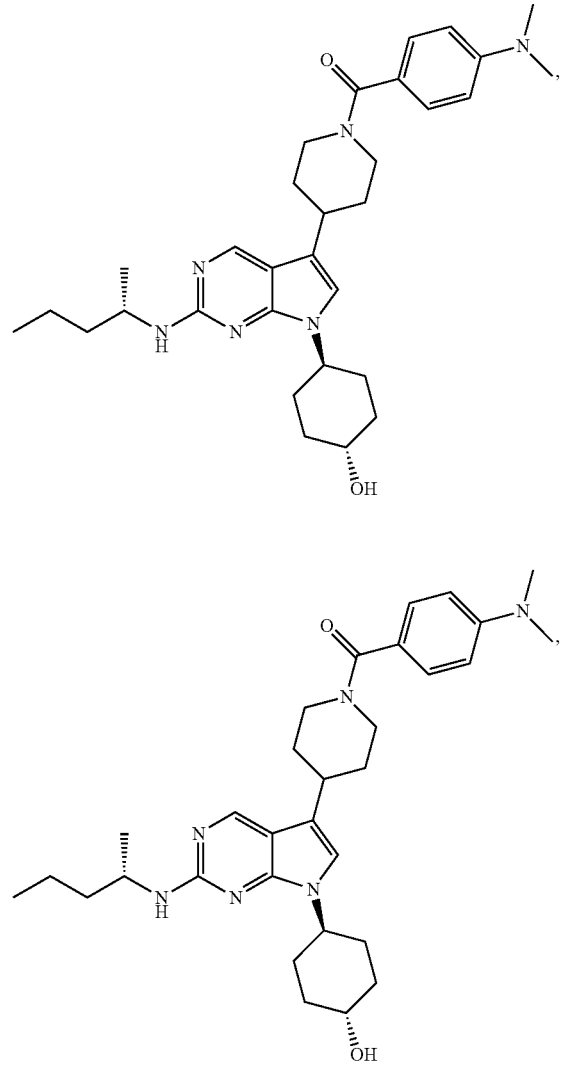
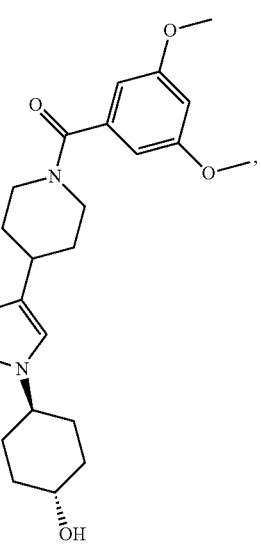

359
-continued
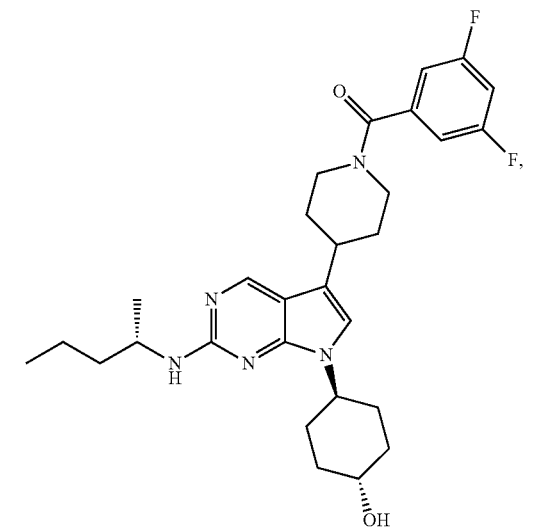
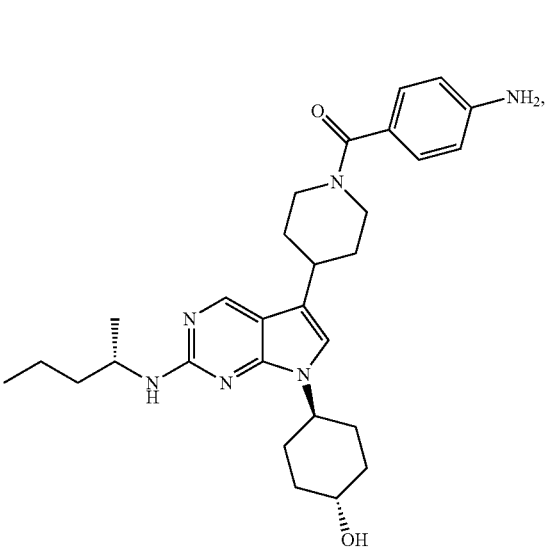
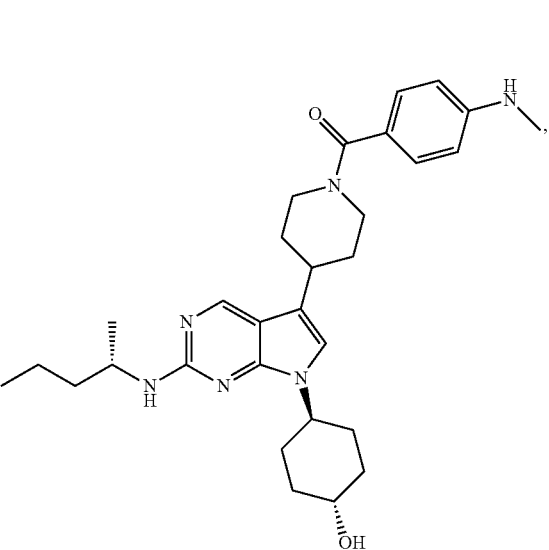
360
-continued
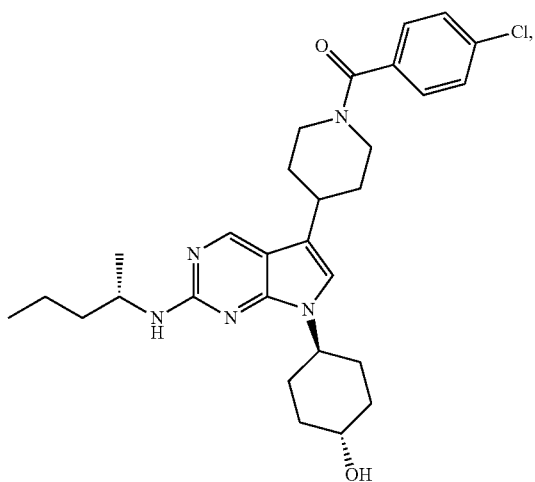
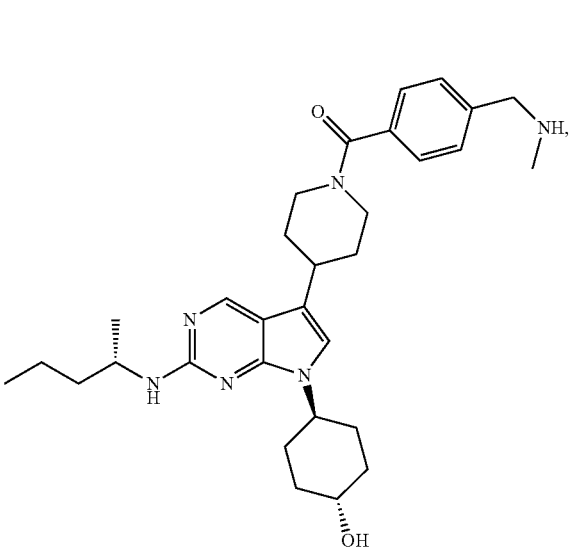
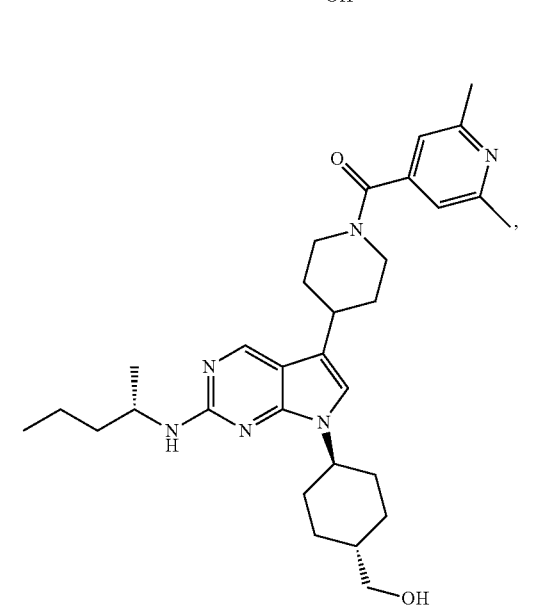

361
-continued
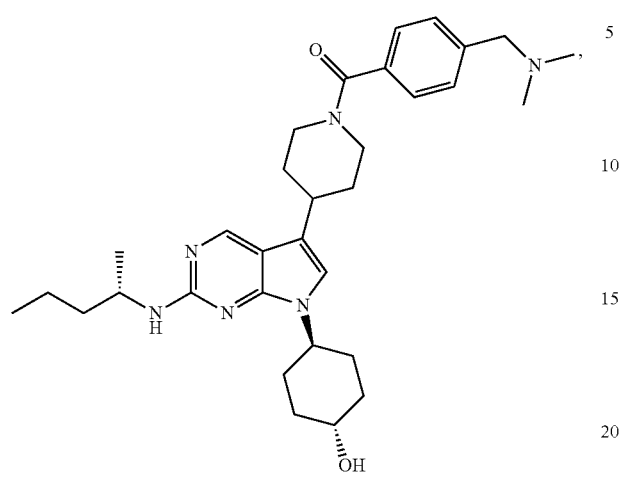
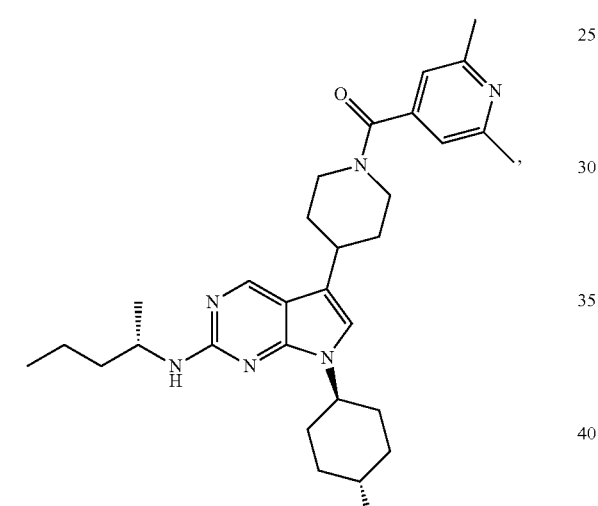
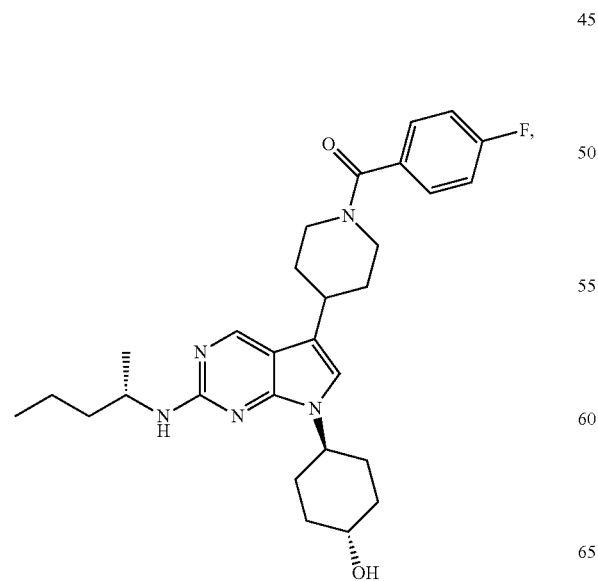
362
-continued
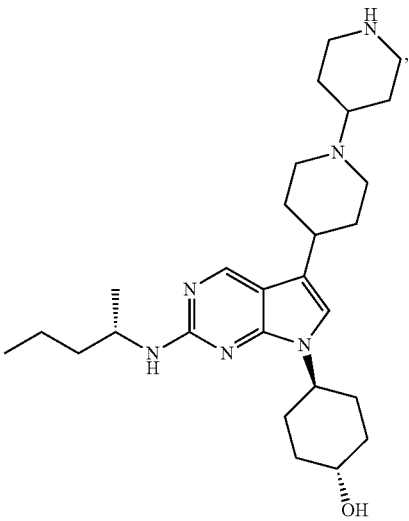 [SMILES: CCC[C@H](C)Nc1ncc2c(C3CCN(C4CCNCC4)CC3)cn([C@H]3CC[C@H](O)CC3)c2n1]
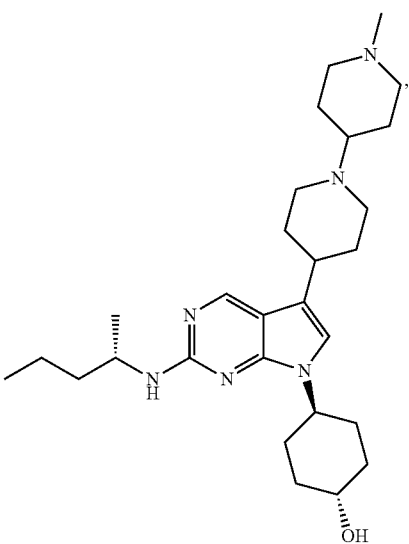
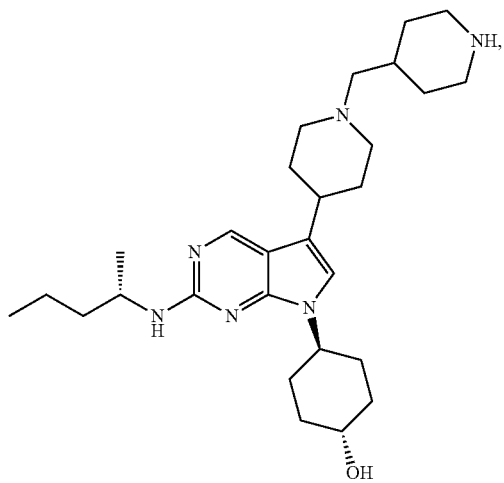

363
-continued
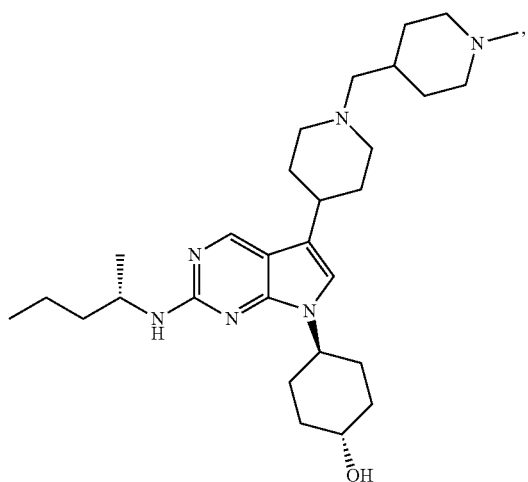
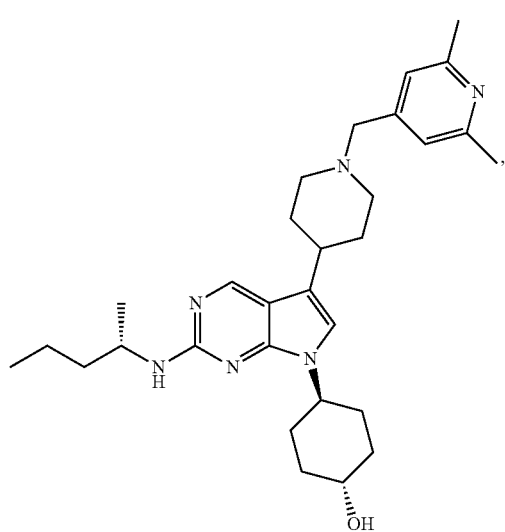
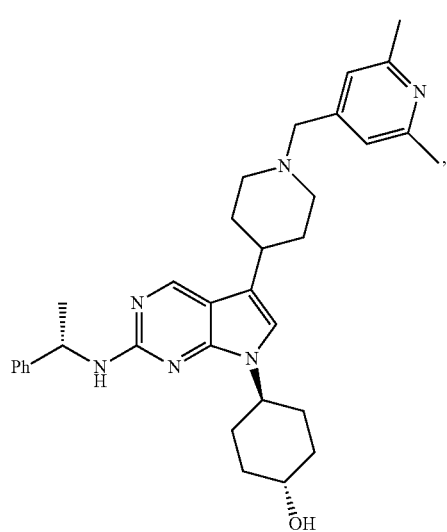
364
-continued
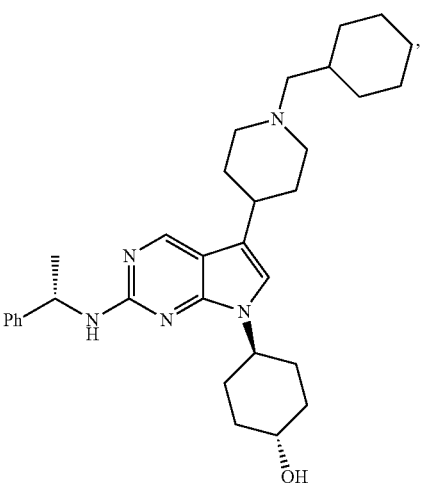
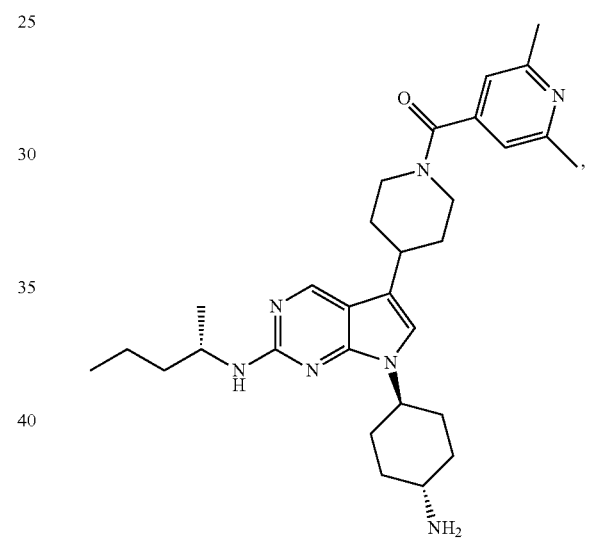
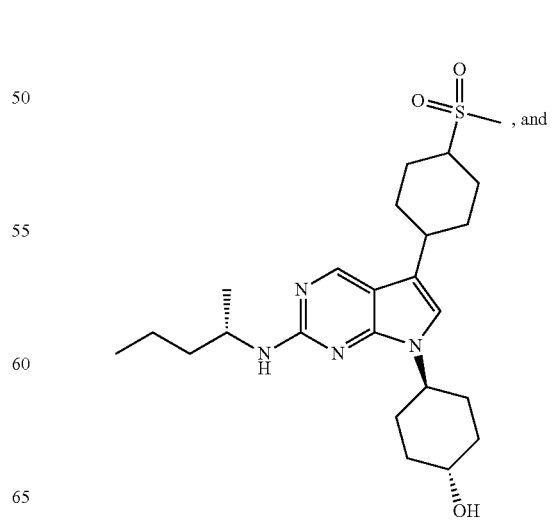

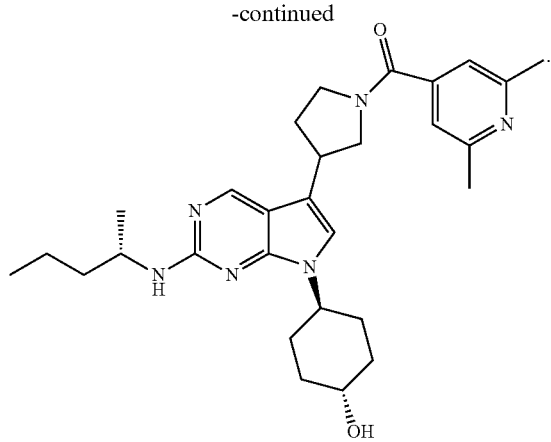

13. The compound of claim 1, wherein the compound is:

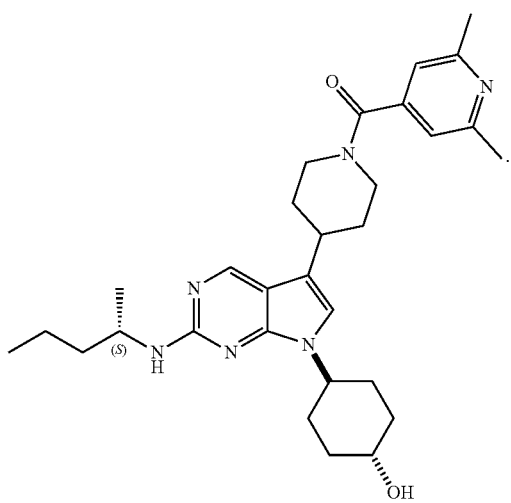

14. A pharmaceutical composition comprising a therapeutically effective amount of at least one compound of claim 1, and a pharmaceutically acceptable carrier.

15. A method for the treatment of acute myeloid leukemia in a subject, the method comprising the step of administering to the subject an effective amount of at least one compound of claim 1, thereby treating the disorder.

16. The method of claim 15, wherein the compound has a structure:

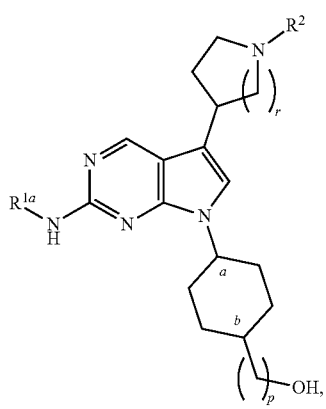

wherein r is selected from 1 and 2.

17. The method of claim 15, wherein the compound is selected from:

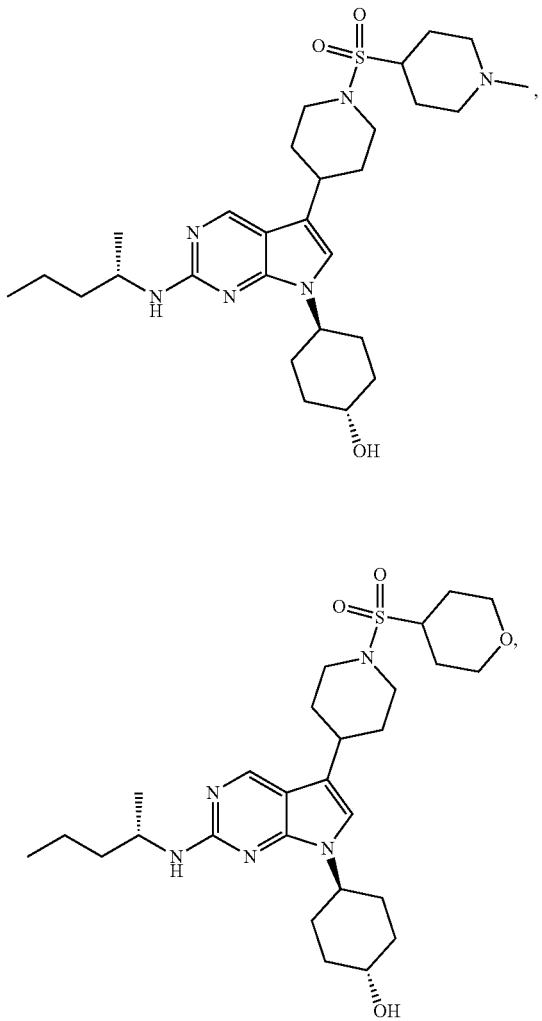

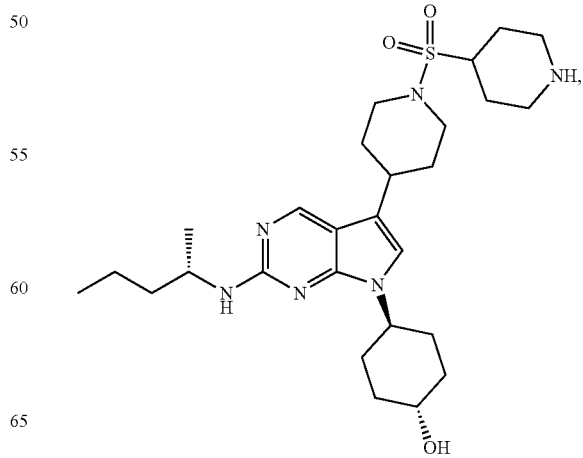

367 368
-continued -continued
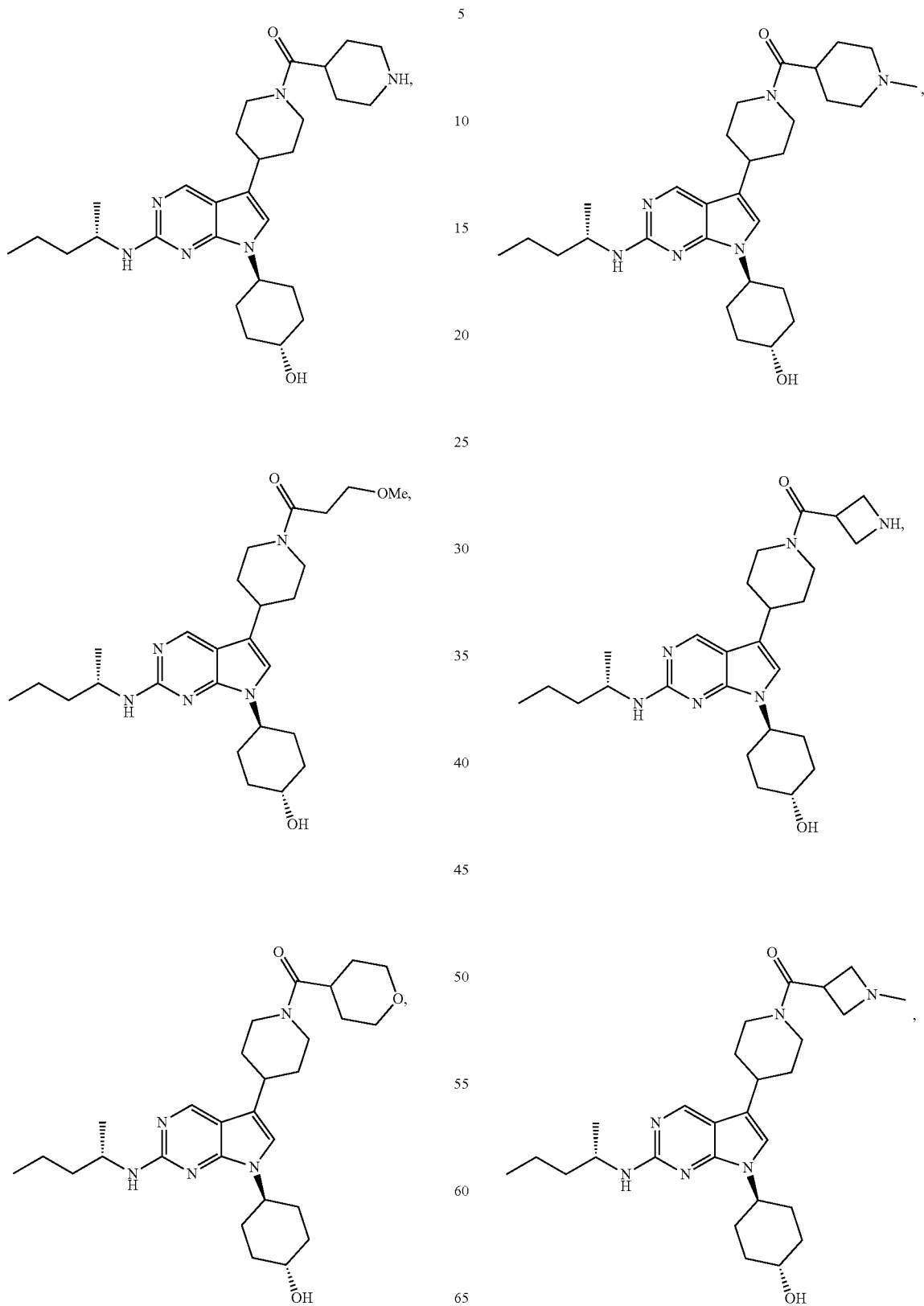

369
-continued
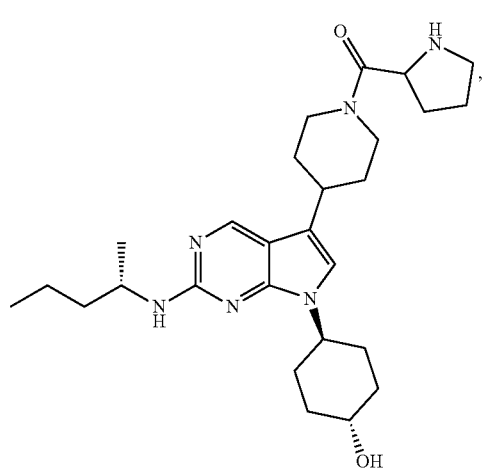
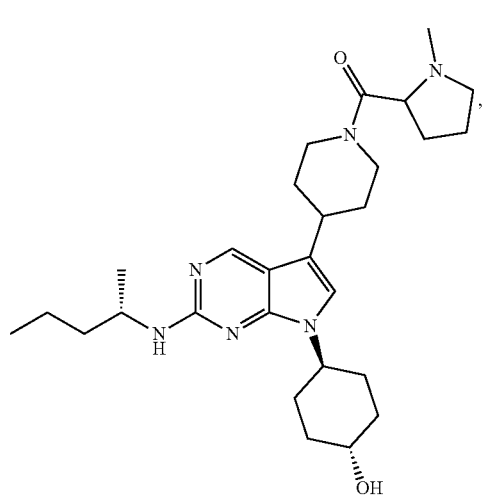
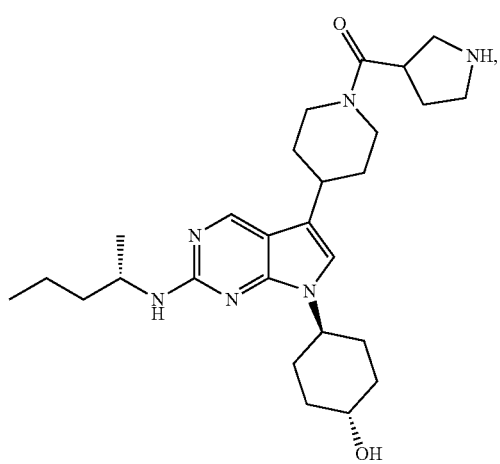
370
-continued
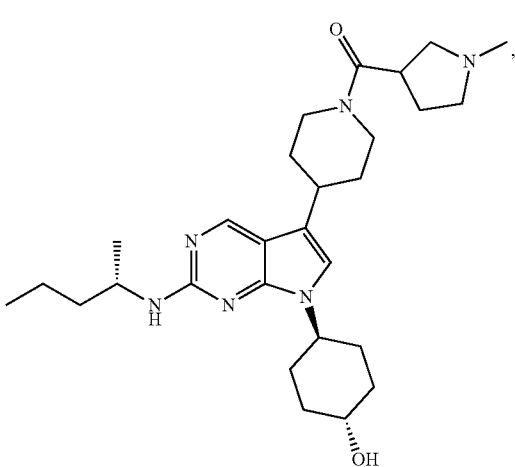
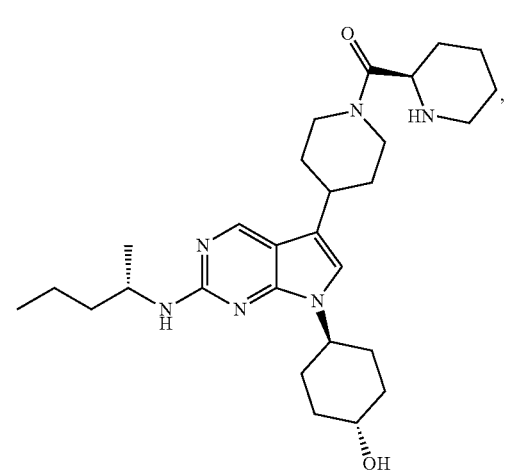
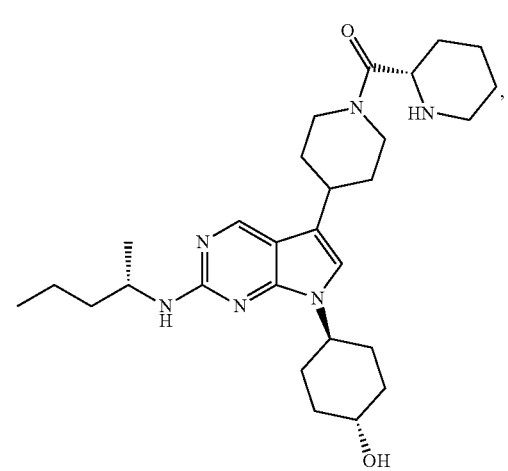

371
-continued
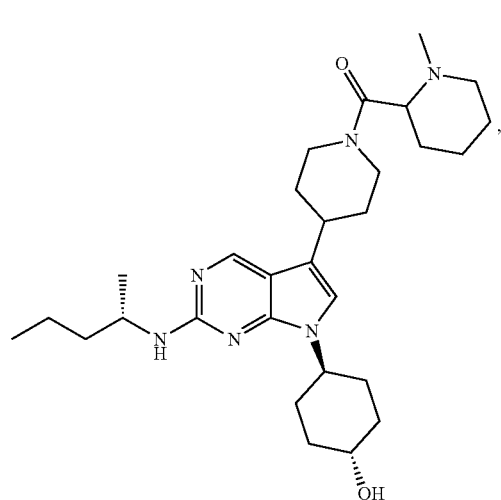
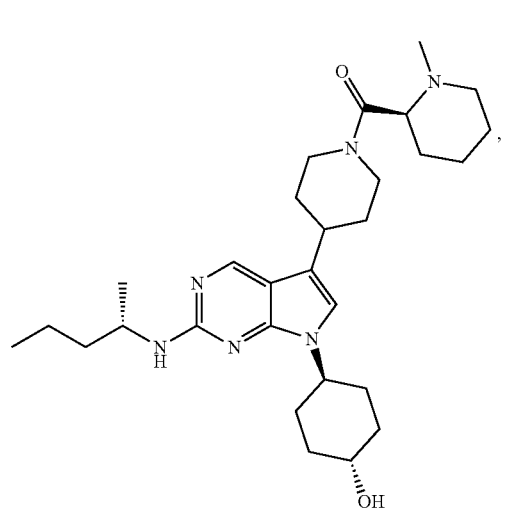
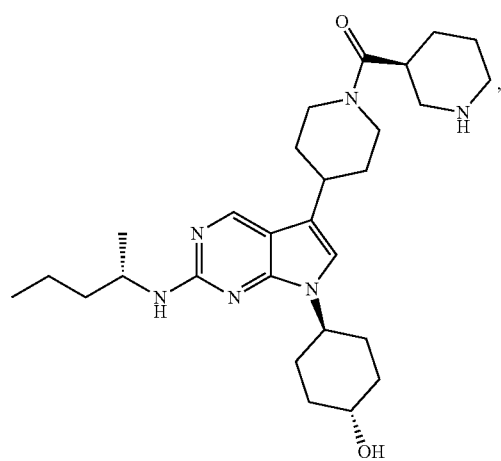
372
-continued
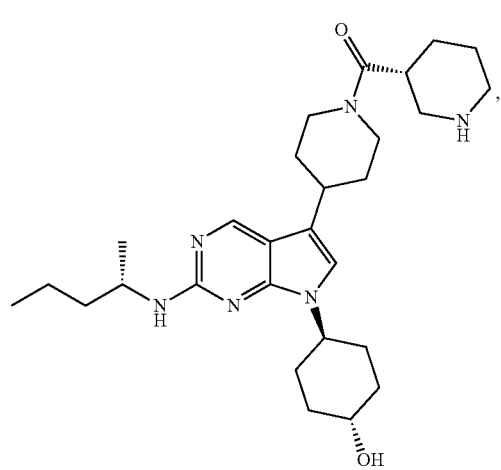
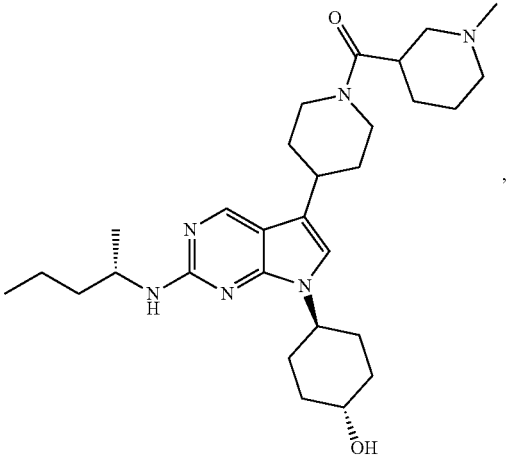
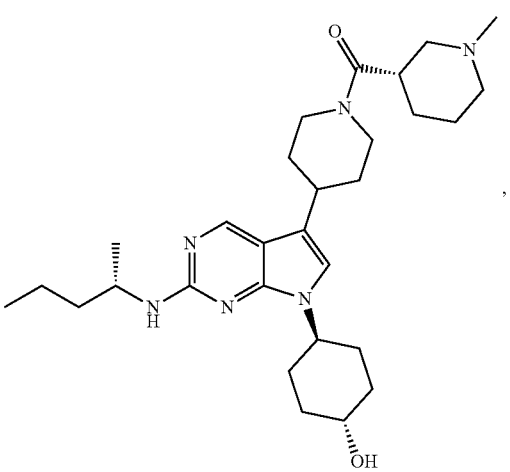

373
-continued
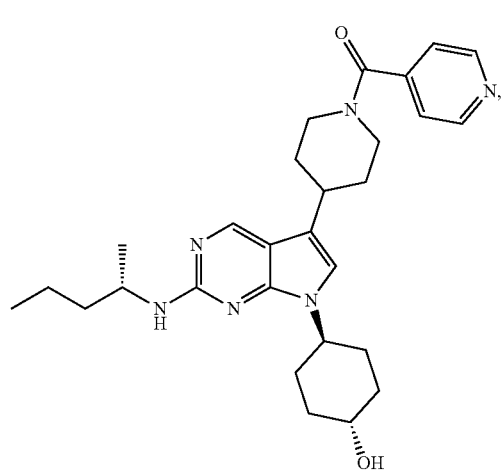
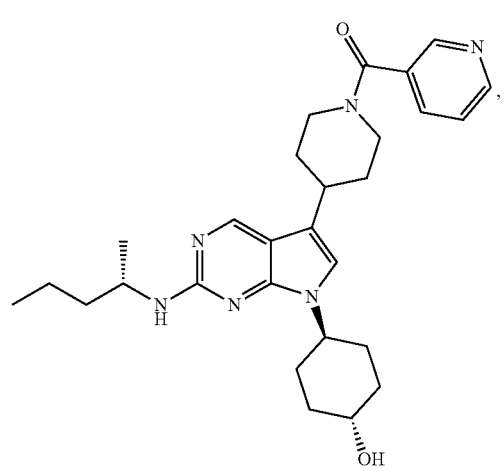
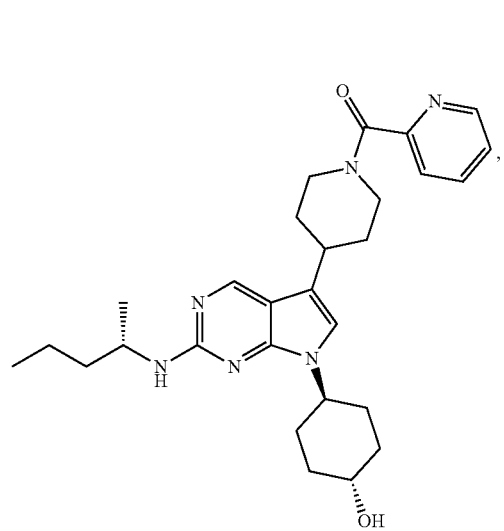
374
-continued
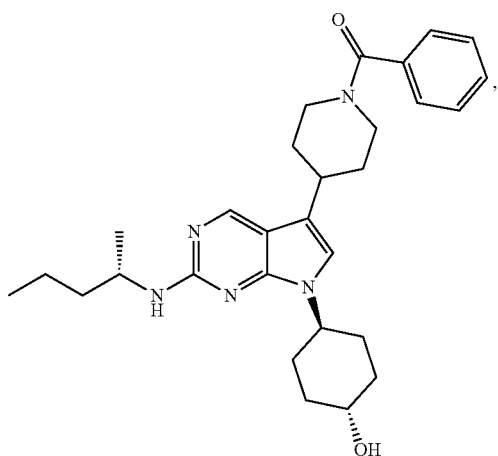
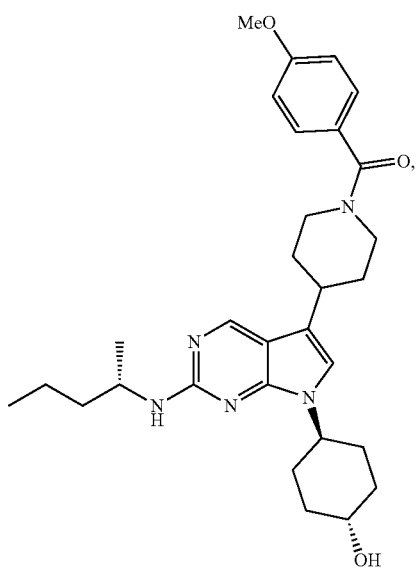
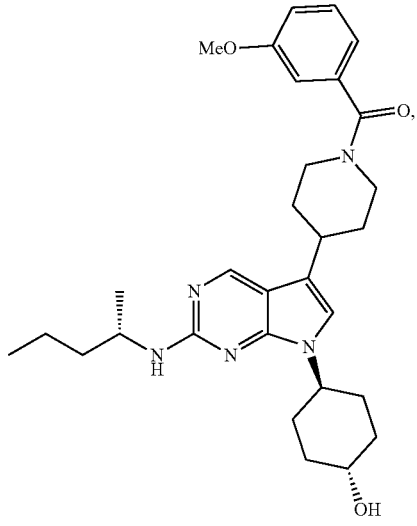

375
-continued
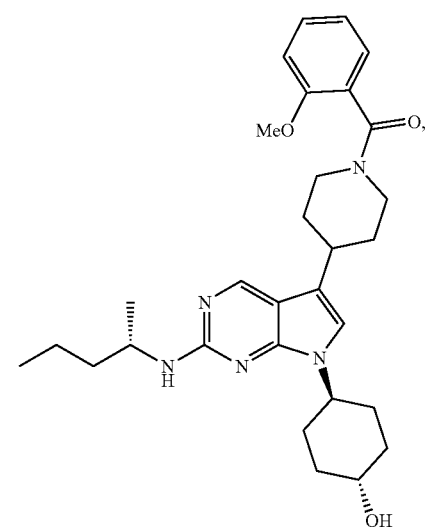
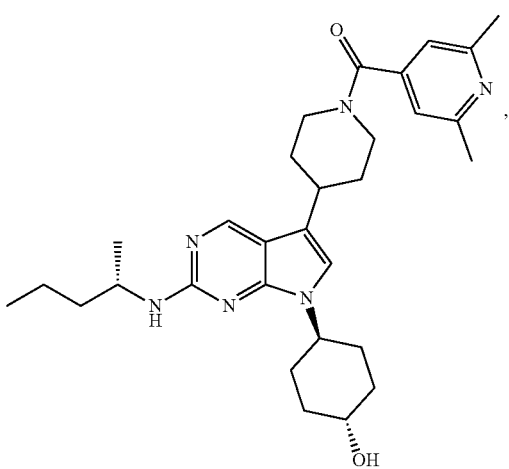
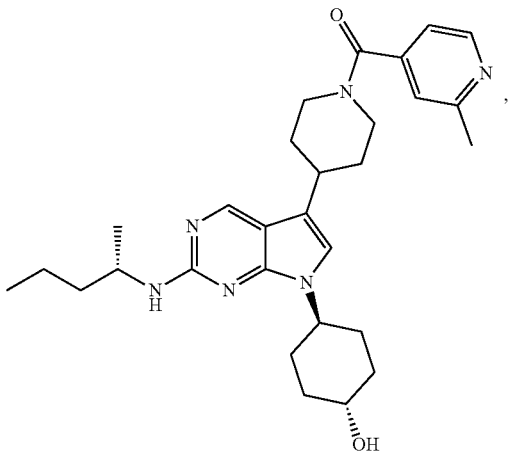
376
-continued
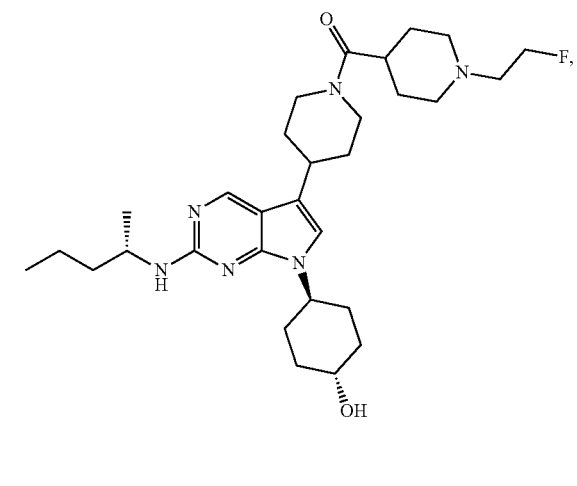
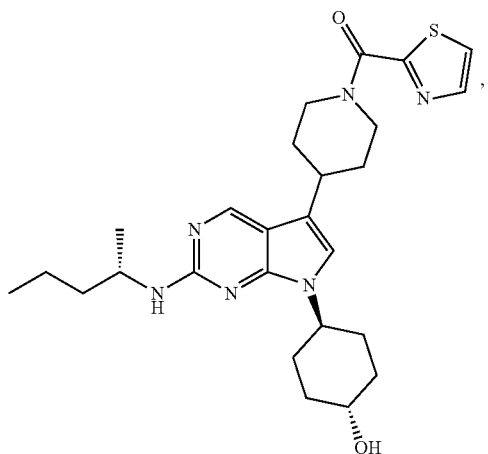
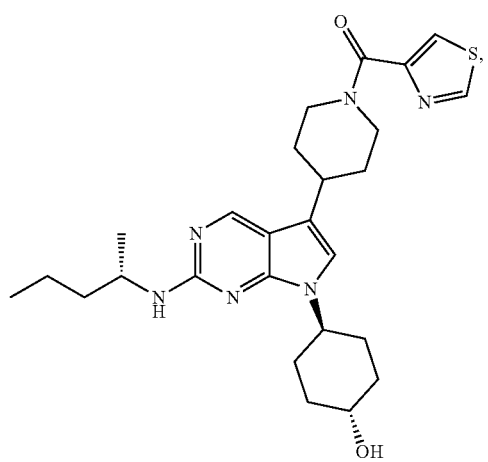

377
-continued
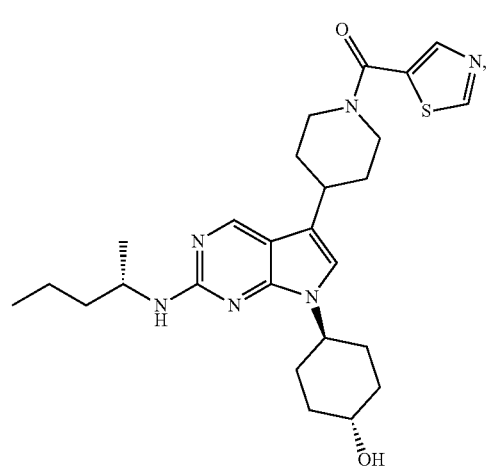
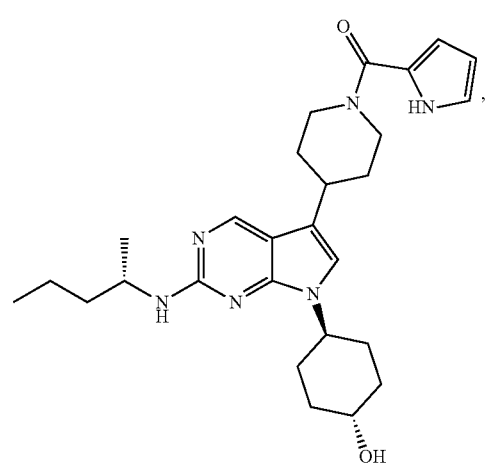
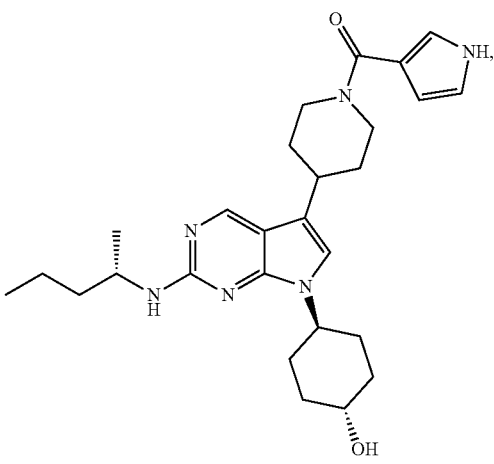
378
-continued
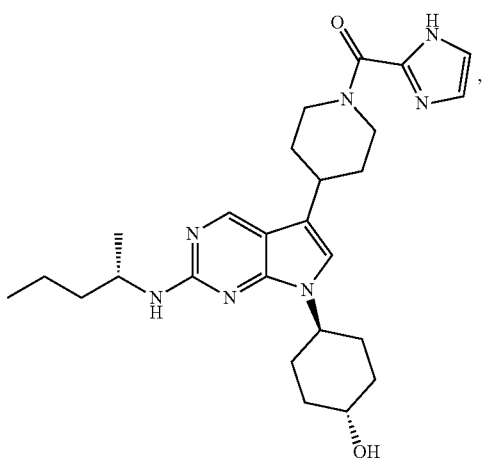
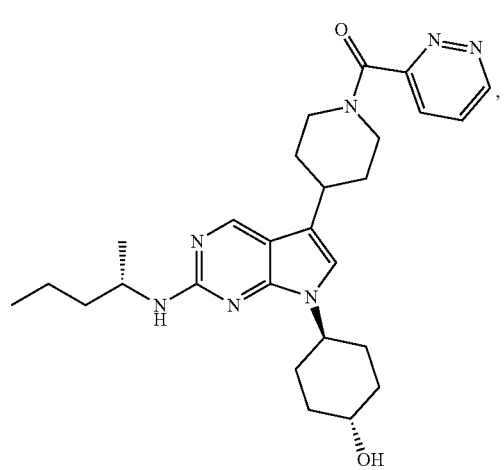
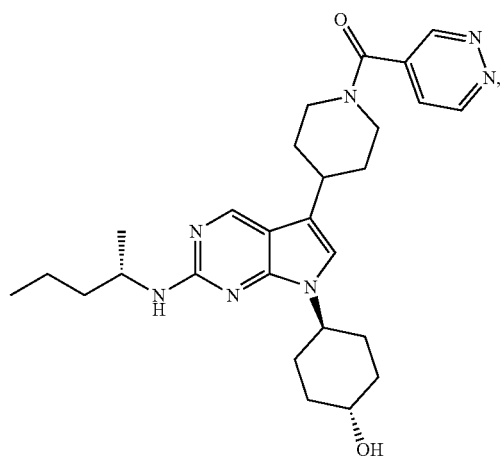

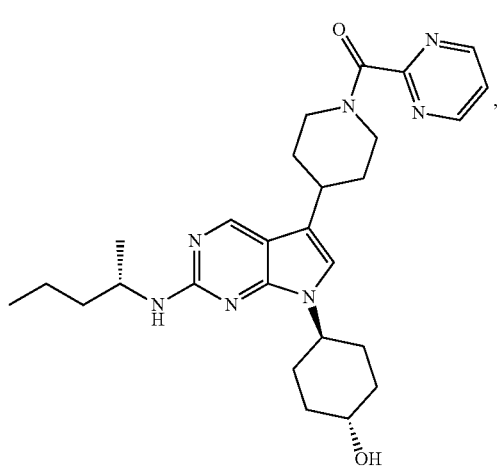
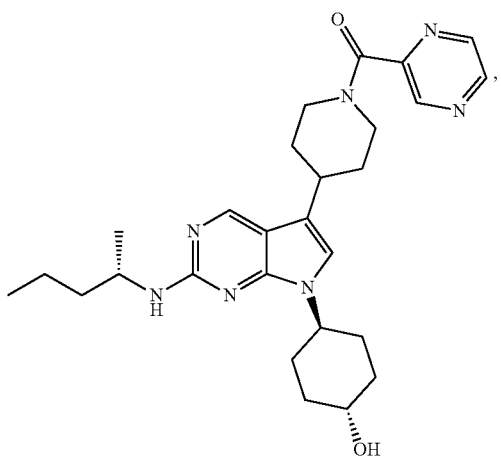
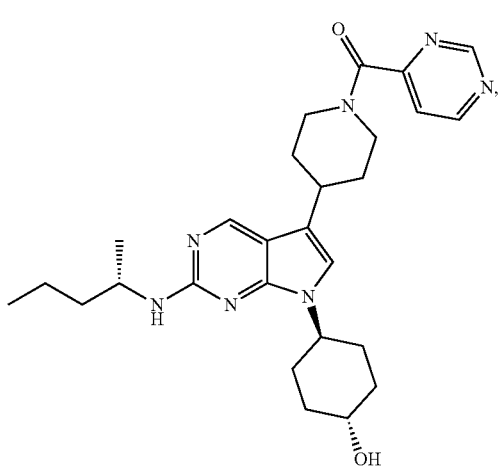
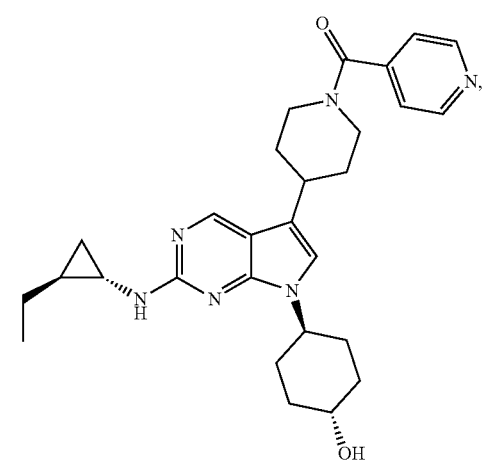
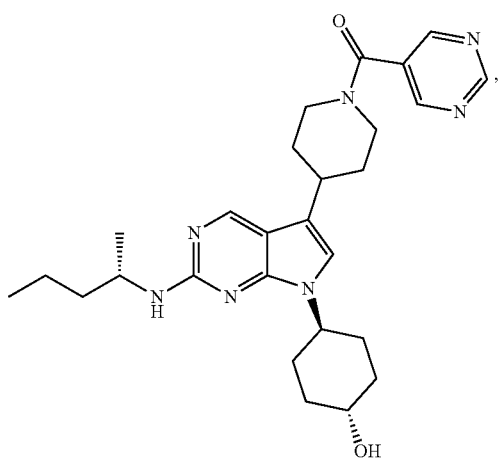
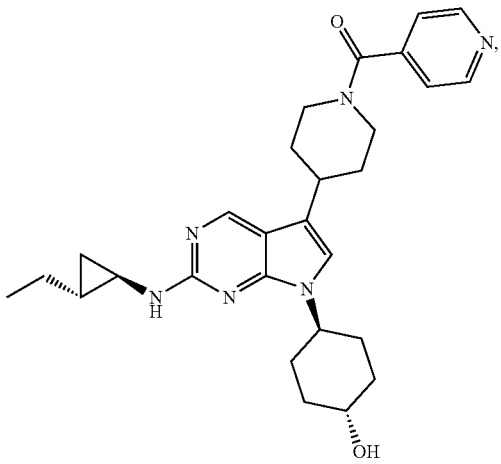

381
-continued
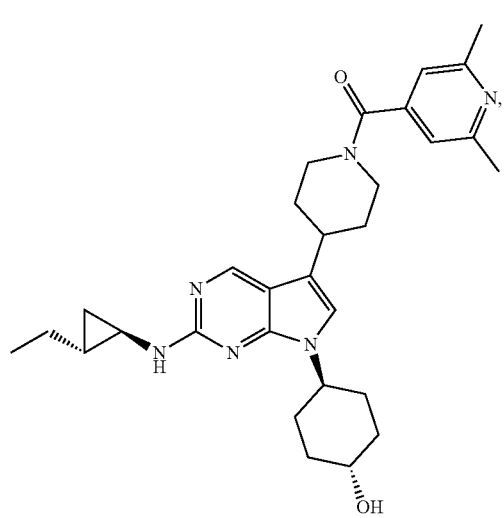
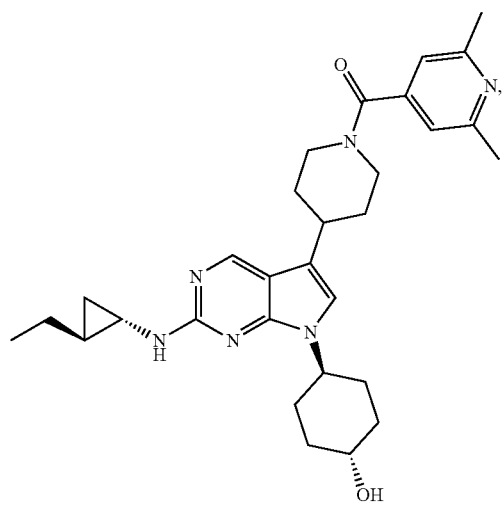
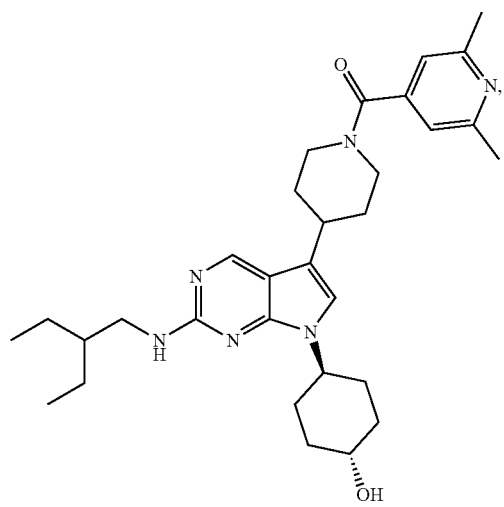
382
-continued
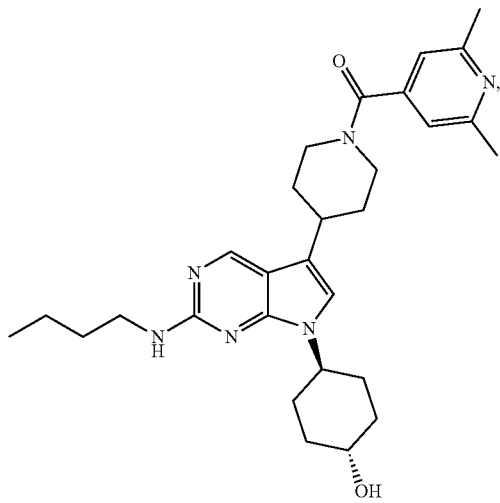
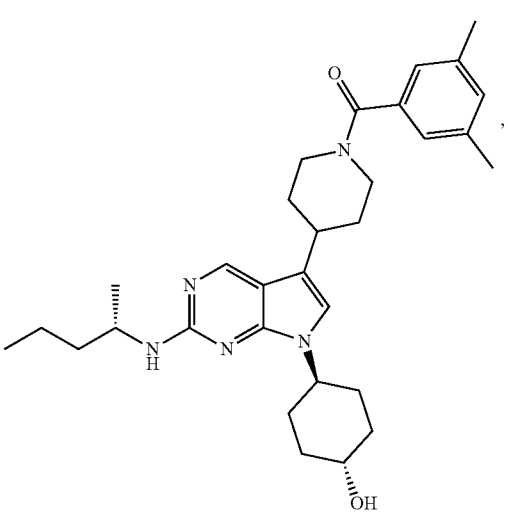
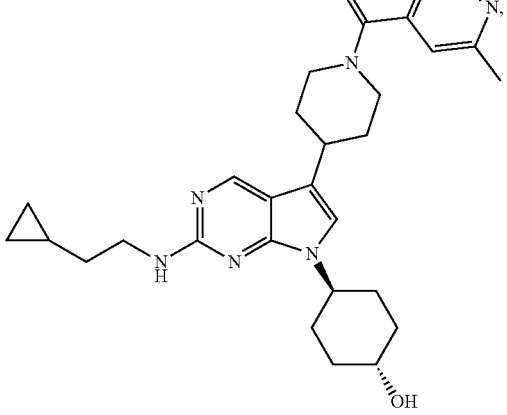

383
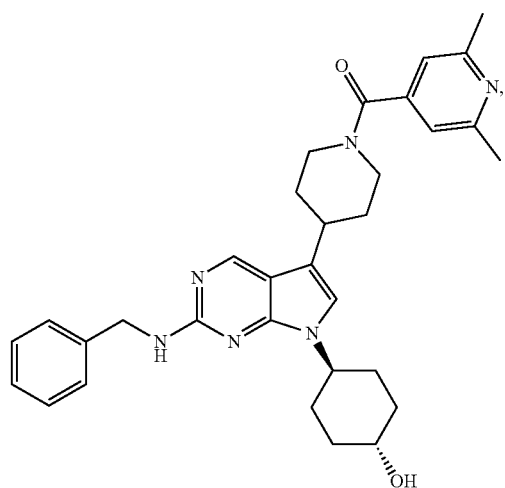
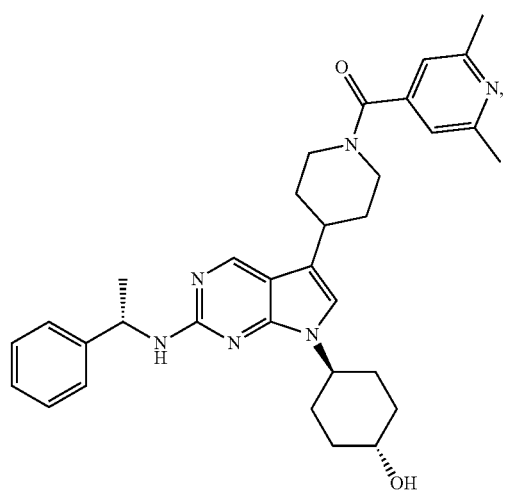
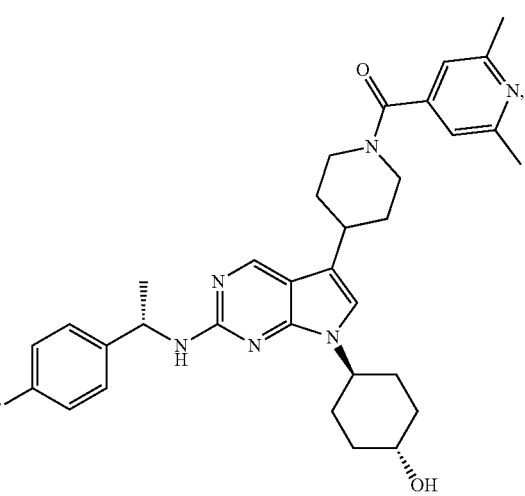
384
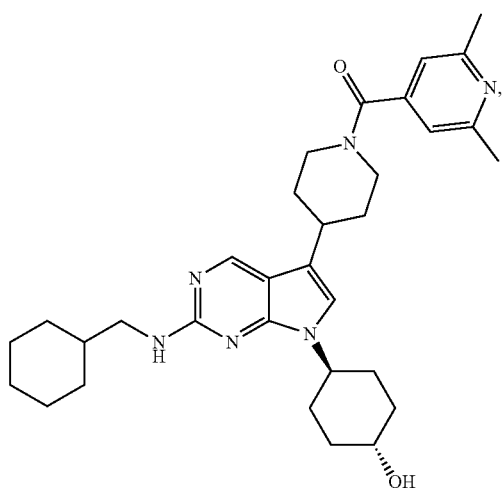
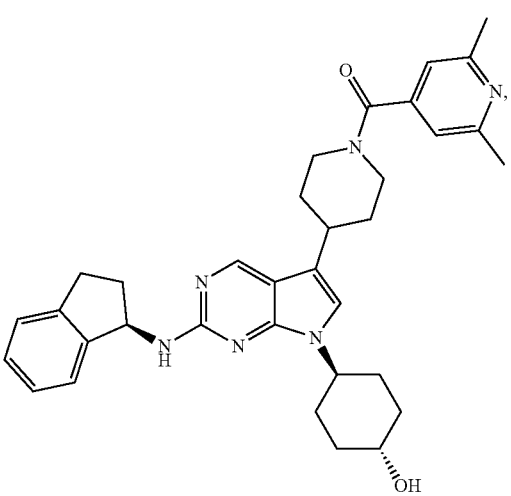
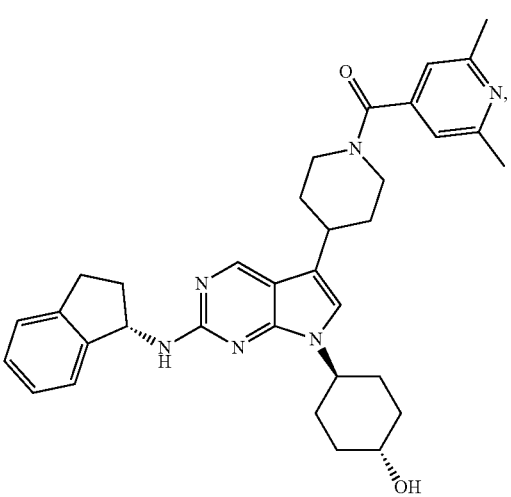

385
-continued
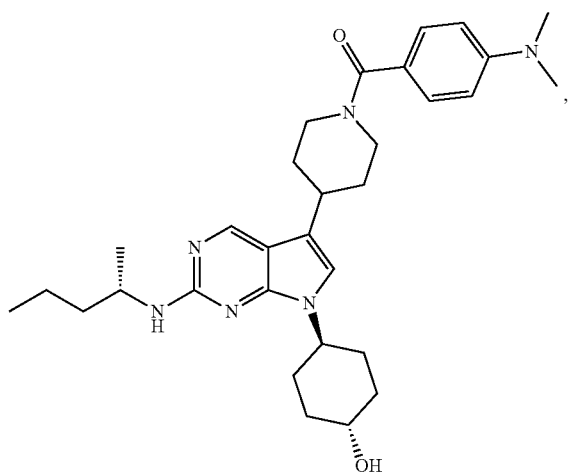
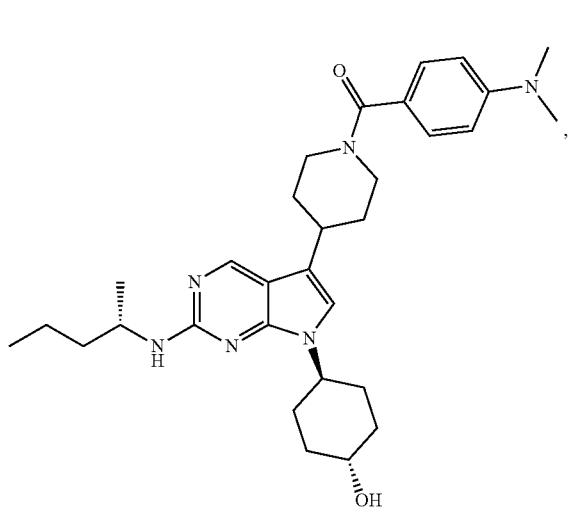
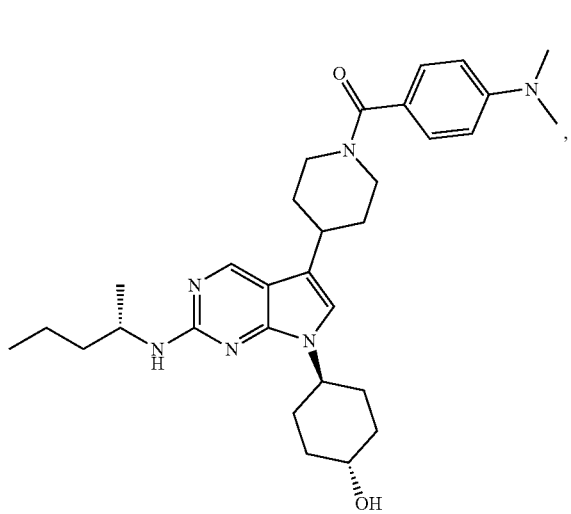
386
-continued
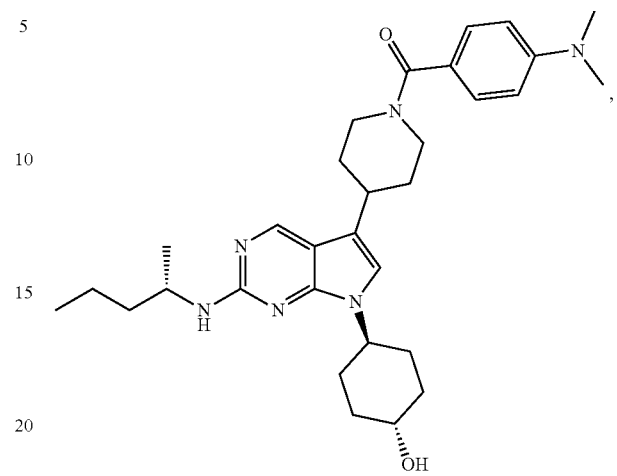
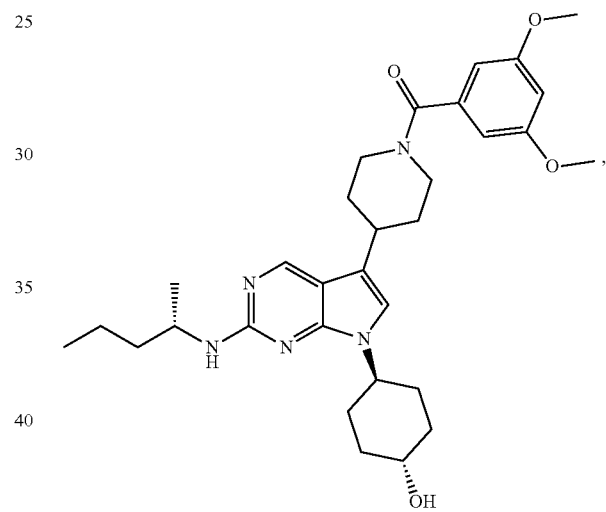
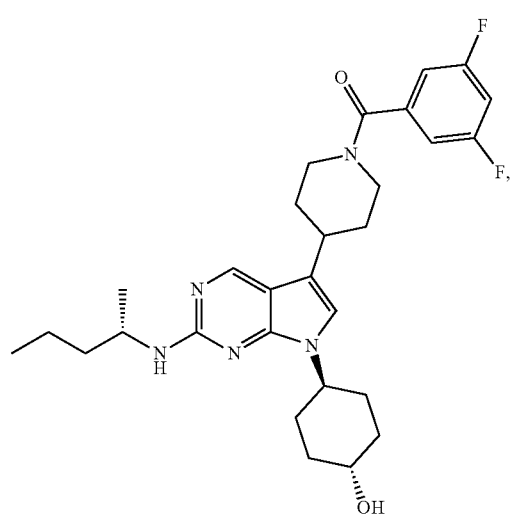

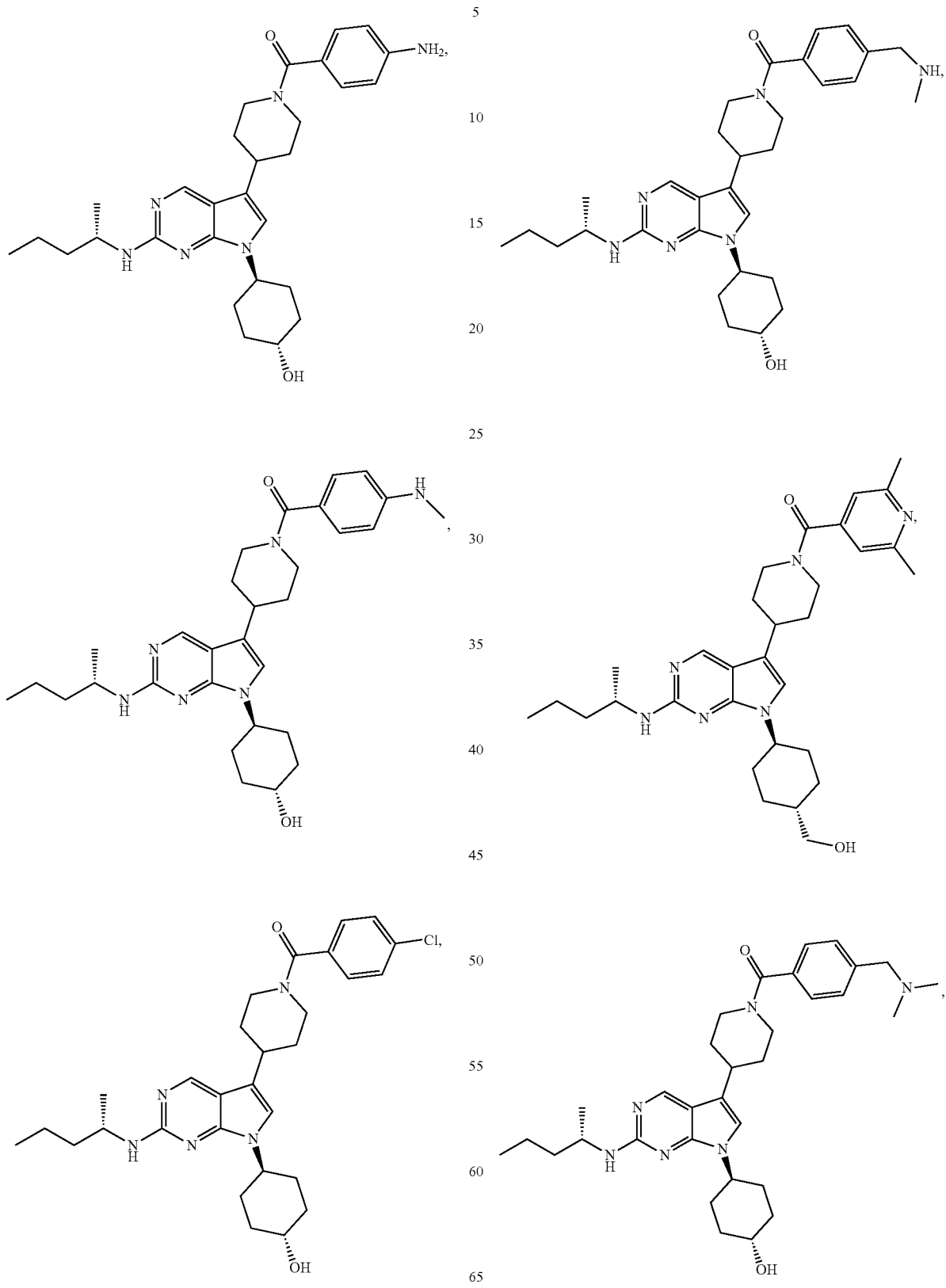

389
-continued
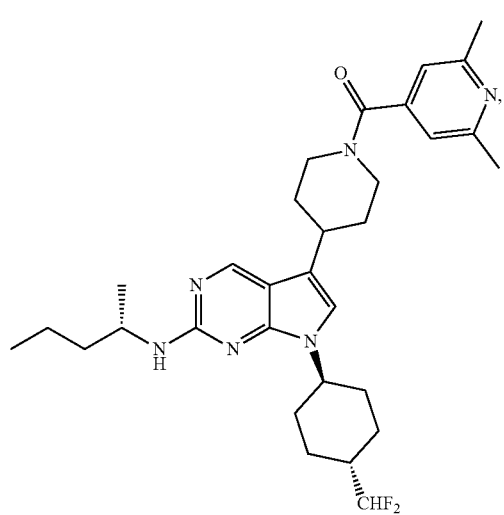
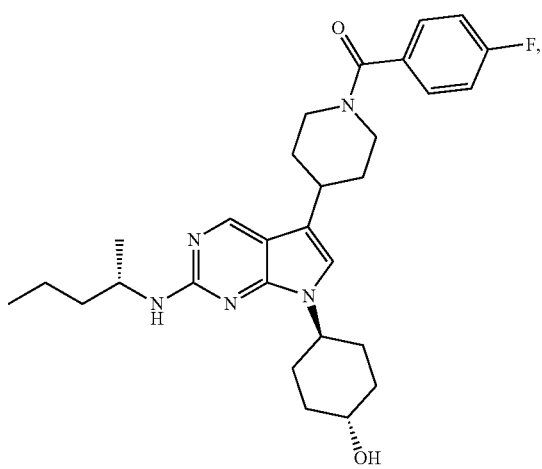
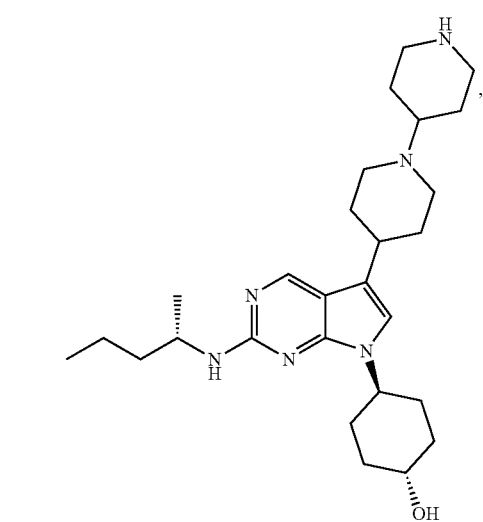
390
-continued
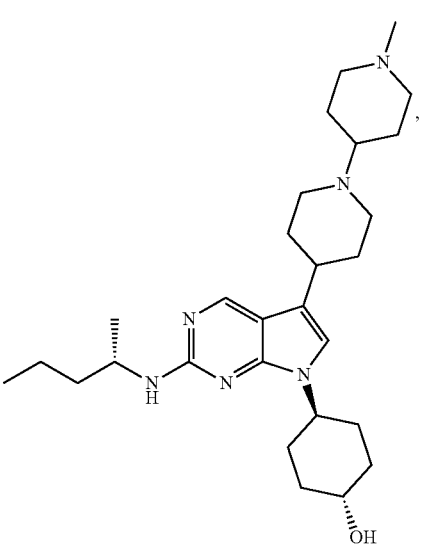
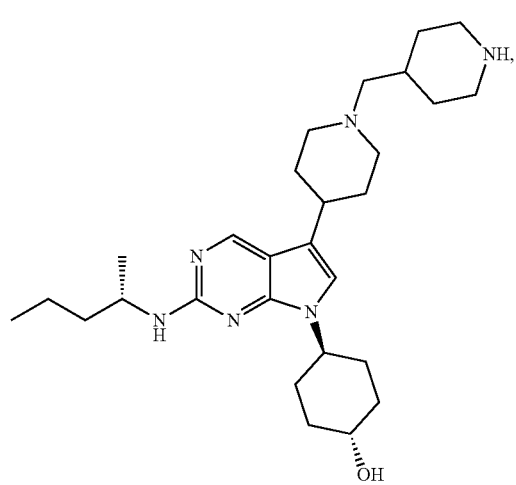
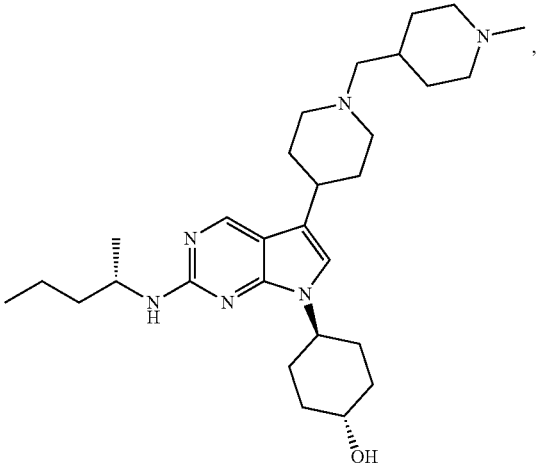

391
-continued
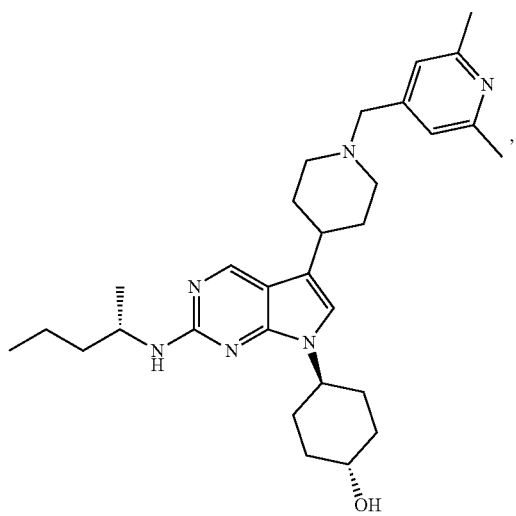
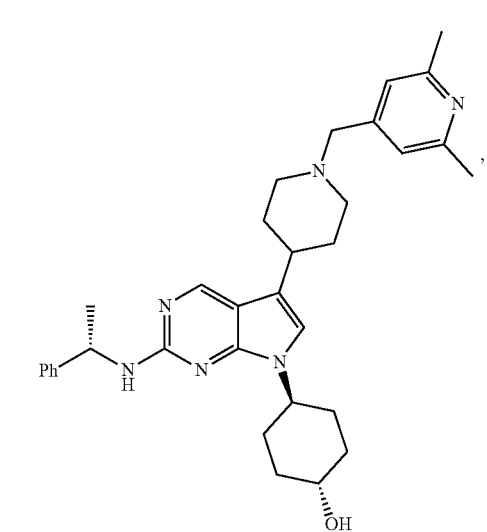
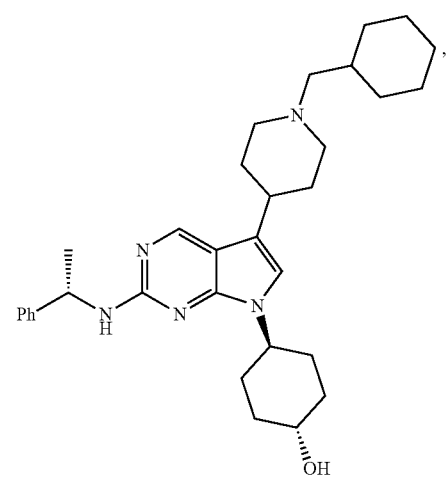
392
-continued
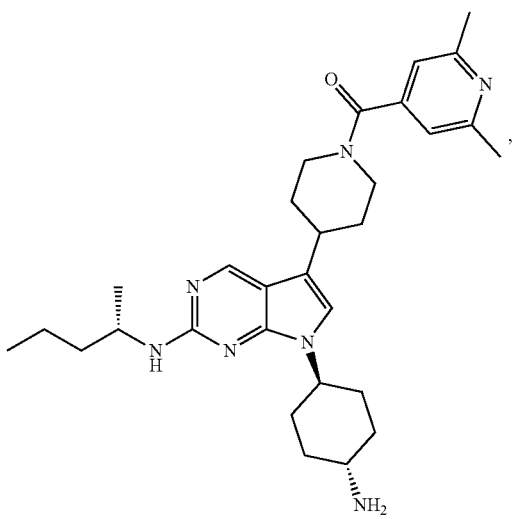
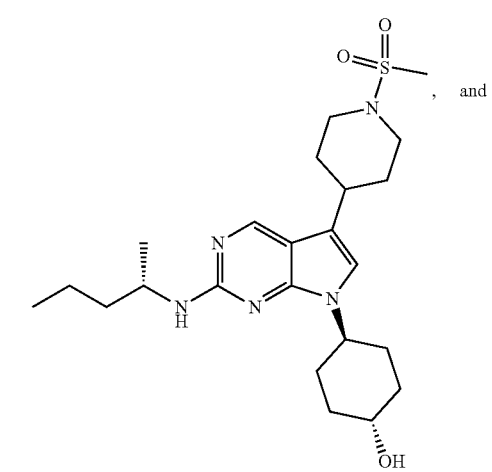, and
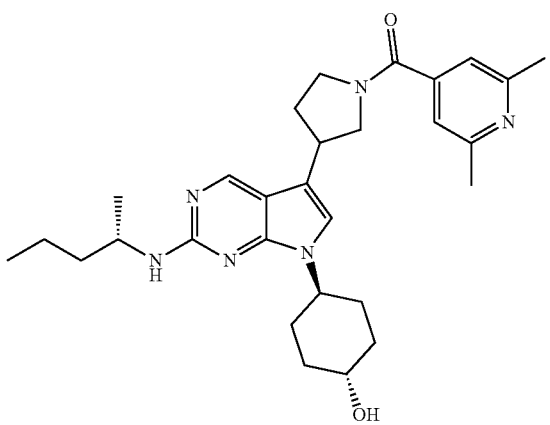

18. The method of claim 15, wherein the compound is.
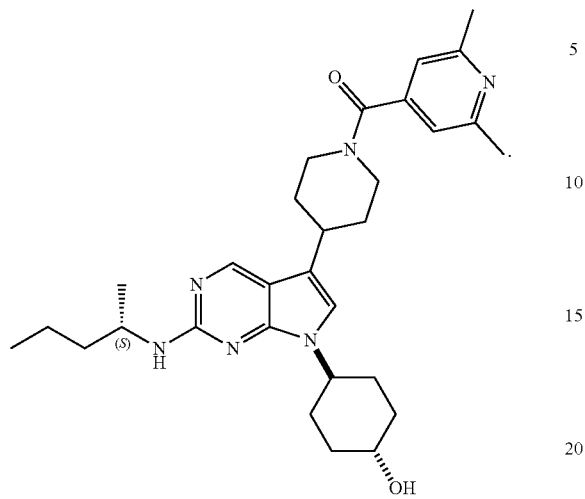
19. The method of claim 15, wherein the effective amount is a therapeutically effective amount.
20. The method of claim 15, further comprising administering an effective amount of a chemotherapeutic agent.
* * * * *